(12) United States Patent
Ng et al.

(10) Patent No.: US 9,271,970 B2
(45) Date of Patent: Mar. 1, 2016

(54) NAPHTHYRIDINE DERIVATIVES AS INHIBITORS OF HYPOXIA INDUCIBLE FACTOR (HIF) HYDROXYLASE

(71) Applicant: FibroGen, Inc., San Francisco, CA (US)

(72) Inventors: Danny Ng, Daly City, CA (US);
Michael P. Arend, Foster City, CA (US);
Lee A. Flippin, Woodside, CA (US)

(73) Assignee: FIBROGEN, INC., San Francisco, CA (US)

( * ) Notice: Subject to any disclaimer, the term of this patent is extended or adjusted under 35 U.S.C. 154(b) by 0 days.

(21) Appl. No.: 14/581,592

(22) Filed: Dec. 23, 2014

(65) Prior Publication Data
US 2015/0174110 A1    Jun. 25, 2015

Related U.S. Application Data

(62) Division of application No. 13/983,025, filed as application No. PCT/US2012/023546 on Feb. 1, 2012, now Pat. No. 8,921,389.

(60) Provisional application No. 61/438,929, filed on Feb. 2, 2011.

(51) Int. Cl.
| | |
|---|---|
| C07D 471/04 | (2006.01) |
| A61K 31/4375 | (2006.01) |
| A61K 31/444 | (2006.01) |
| A61K 31/497 | (2006.01) |
| A61K 31/501 | (2006.01) |
| A61K 31/506 | (2006.01) |
| A61K 31/5377 | (2006.01) |
| A61K 45/06 | (2006.01) |

(52) U.S. Cl.
CPC ........... *A61K 31/4375* (2013.01); *A61K 31/444* (2013.01); *A61K 31/497* (2013.01); *A61K 31/501* (2013.01); *A61K 31/506* (2013.01); *A61K 31/5377* (2013.01); *A61K 45/06* (2013.01); *C07D 471/04* (2013.01)

(58) Field of Classification Search
CPC .......................... C07D 471/04; A61K 31/4375
USPC .......................................... 546/122; 514/300
See application file for complete search history.

(56) References Cited

U.S. PATENT DOCUMENTS

| | | | |
|---|---|---|---|
| 5,620,995 A | 4/1997 | Weidmann et al. |
| 5,658,933 A | 8/1997 | Weidmann et al. |
| 7,323,475 B2 | 1/2008 | Arend et al. |
| 7,618,940 B2 | 11/2009 | Fourney et al. |
| 7,629,357 B2 | 12/2009 | Arend et al. |
| 7,696,223 B2 | 4/2010 | Deng et al. |
| 7,863,292 B2 | 1/2011 | Arend et al. |
| 7,928,120 B2 | 4/2011 | Arend et al. |
| 8,017,625 B2 | 9/2011 | Arend et al. |
| 8,124,582 B2 | 2/2012 | Guenzler-Pukall et al. |
| 8,217,043 B2 | 7/2012 | Deng et al. |
| 8,269,008 B2 | 9/2012 | Arend et al. |
| 8,278,325 B2 | 10/2012 | Arend et al. |
| 8,324,405 B2 | 12/2012 | Ho et al. |
| 8,703,795 B2 | 4/2014 | Turtle et al. |
| 8,759,373 B2 | 6/2014 | Arend et al. |
| 8,765,956 B2 | 7/2014 | Arend et al. |
| 2007/0155784 A1 | 7/2007 | Arend et al. |
| 2010/0330199 A1 | 12/2010 | Zhou et al. |
| 2011/0212959 A1 | 9/2011 | Arend et al. |
| 2011/0305776 A1 | 12/2011 | Ho et al. |
| 2013/0178417 A1 | 7/2013 | Arend et al. |
| 2014/0024675 A1 | 1/2014 | Witschi et al. |
| 2014/0024676 A1 | 1/2014 | Witschi et al. |
| 2014/0088101 A1 | 3/2014 | Ng et al. |
| 2014/0221422 A1 | 8/2014 | Turtle et al. |
| 2014/0343094 A1 | 11/2014 | Arend et al. |

FOREIGN PATENT DOCUMENTS

| | | | |
|---|---|---|---|
| WO | WO 03/049686 | | 6/2003 |
| WO | WO 03/053997 | | 7/2003 |
| WO | 2007/090068 | * | 8/2007 |
| WO | WO 2007/090068 | | 8/2007 |
| WO | WO 2007/103905 | | 9/2007 |

OTHER PUBLICATIONS

U.S. Appl. No. 14/289,573, filed May 28, 2014, Arend et al.
International Preliminary Report on Patentability from PCT/US2012/023546 mailed Aug. 6, 2013.
International Search Report and Written Opinion from PCT/US2012/023546 mailed May 4, 2012.
Warshakoon, et al. "Design and synthesis of substituted pyridine derivatives as HIF-1α prolyl hydroxylase inhibitors," Bioorganic & Meidicnal Chemistry Letters 16 (2006) 5616-5620.
Bernhardt et al., "Inhibition of Prolyl Hydroxylases Increases Erythropoietin Production in ESRD," J Am Soc Nephrol 21 (2010) 2151-2156.
Semenza, "Hydroxylation of HIF-1: Oxygen Sensing at the Molecular Level," Physiology 19 (2004) 176-182.
Hsieh, et al., "HIF—prolyl hydroxylase inhibition results in endogenous erythropoietin induction, erythrocytosis, and modest fetal hemoglobin expression in rhesus macaques," Blood 110:6 (2007) 2140-2147.

* cited by examiner

*Primary Examiner* — Niloofar Rahmani
(74) *Attorney, Agent, or Firm* — Sheppard Mullin Richter & Hampton LLP

(57) ABSTRACT

The present disclosure relates to novel compounds, methods, and compositions capable of inhibiting HIF hydroxylase enzyme activity, thereby increasing the stability and/or activity of hypoxia inducible factor (HIF).

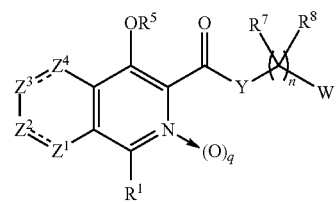

30 Claims, No Drawings

NAPHTHYRIDINE DERIVATIVES AS INHIBITORS OF HYPOXIA INDUCIBLE FACTOR (HIF) HYDROXYLASE

CROSS-REFERENCE TO RELATED APPLICATIONS

This application is a divisional application of U.S. patent application Ser. No. 13/983,025, filed on Nov. 6, 2013,which application is a National Phase application under 35 U.S.C. §371 of PCT Application PCT/US2012/023546, filed on Feb. 1, 2012, which application claims priority under 35 U.S.C. §119(e) to U.S. Provisional Patent Application No. 61/438,929, filed on Feb. 2, 2011, which applications are incorporated by reference herein in their entirety.

FIELD

The present disclosure relates to novel compounds, methods, and compositions capable of inhibiting HIF hydroxylase enzyme activity, thereby increasing the stability and/or activity of hypoxia inducible factor (HIF).

STATE OF THE ART

Hypoxia inducible factor (HIF) is a basic helix-loop-helix (bHLH) PAS (Per/Arnt/Sim) transcriptional activator that mediates changes in gene expression in response to changes in cellular oxygen concentration. HIF is a heterodimer containing an oxygen-regulated α-subunit (HIFα), and a constitutively expressed β-subunit (HIFβ/ARNT). In oxygenated (normoxic) cells, HIFα subunits are rapidly degraded by a mechanism that involves ubiquitination by the von Hippel-Lindau tumor suppressor (pVHL) E3 ligase complex. Under hypoxic conditions, HIFα is not degraded, and an active HIFα/β complex accumulates in the nucleus, and activates the expression of several genes including glycolytic enzymes, glucose transporters, erythropoietin (EPO), and vascular endothelial growth factor (VEGF). (Jiang et al. (1996) *J. Biol. Chem.* 271:17771-17778; Iliopoulus et al. (1996) *Proc. Natl. Acad. Sci. USA,* 93:10595-10599; Maxwell et al. (1999) *Nature* 399:271-275; Sutter et al. (2000) *Proc. Natl. Acad. Sci. USA* 97:4748-4753; Cockman et al. (2000) *J. Biol. Chem.* 275:25733-25741; and Tanimoto et al. (2000) *EMBO J.* 19:4298-4309.)

Levels of HIFα are elevated in most cells in response to hypoxia, and HIFα is induced in vivo when animals are subjected to anemia or hypoxia. HIFα levels rise within a few hours after the onset of hypoxia, and induce numerous beneficial cellular processes including cytoprotective effects, enhanced erythropoiesis, and physiological adaptation to ischemic or hypoxic states. Induction of HIFα is potentially beneficial in conditions such as heart attack, stroke, peripheral vascular disease, chronic ischemia, inflammation, and anemia.

HIFα levels are also increased by a number of factors that mimic hypoxia, including iron chelators such as desferrioxamine (DFO), and divalent metal salts such as $CoCl_2$. Additionally, several compounds originally identified as inhibitors of procollagen prolyl hydroxylase enzymes have been found to stabilize HIFα. Examples of such compounds can be found, e.g., in Majamaa et al. (1984) *Eur. J. Biochem.* 138:239-245; Majamaa et al. (1985) *Biochem. J.* 229:127-133; Kivirikko, and Myllyharju (1998) *Matrix Biol.* 16:357-368; Bickel et al. (1998) *Hepatology* 28:404-411; Friedman et al. (2000) *Proc. Natl. Acad. Sci. USA* 97:4736-4741; Franklin (1991) *Biochem. Soc. Trans.* 19):812-815; and Franklin et al. (2001) *Biochem. J.* 353:333-338. Additionally, compounds that inhibit HIF hydroxylases have been described in, e.g., International Publication Nos. WO 03/049686, WO 02/074981, WO 03/080566, WO 2004/108681, WO 2006/094292, WO 2007/038571, WO 2007/070359, WO 2007/090068, WO 2007/103905, WO 2007/115315, WO 2007/136990, WO 2007/150011, WO 2008/076425, WO 2008/076427, WO 2008/089051, WO 2008/089052, WO 2008/130600, WO 2008/130508, WO 2008/137084, WO 2008/137060, WO 2009/039321, WO 2009/039322, WO 2009/039323, WO 2009/049112, WO 2009/070644, WO2009/073497, WO 2009/073669, WO 2009/073669, and WO 2009/086044.

There remains a need for compounds that are effective in the treatment and prevention of conditions and disorders associated with HIF, including anemia and tissue damage caused by ischemia and/or hypoxia. The compounds provided herein inhibit HIF hydroxylase activity, thereby increasing the stability and/or activity of hypoxia inducible factor (HIF), and can be used to treat and prevent HIF-associated conditions and disorders.

SUMMARY

The present disclosure is directed to novel compounds and methods of using these compounds to inhibit HIF hydroxylase activity, thereby increasing the stability and/or activity of hypoxia inducible factor (HIF).

In one aspect, there are provided compounds of Formula I:

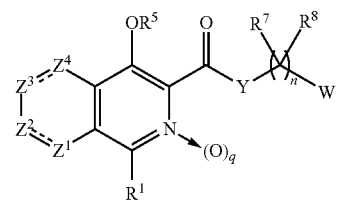

wherein
q is 0 or 1;
$R^1$ is selected from the group consisting of hydrogen, cyano, halo, hydroxy, alkoxy, amino, acyloxy, aminoacyl, alkyl, cycloalkyl, cycloalkoxy, aryl, aryloxy, heterocycloalkyl, heteroaryloxy, and heteroaryl;
$Z^1$ and $Z^4$ are each independently selected from the group consisting of —$CR^4$, —$CHR^4$, —$NR^2$— and —C(O)—; $Z^2$ and $Z^3$ are each independently selected from the group consisting of —$CR^3$, —$CHR^3$, —$NR^2$ and —C(O)—; and ═ is a single or a double bond; provided that:
a) one of $Z^1$ or $Z^2$ is —$NR^2$—, the other of $Z^1$ or $Z^2$ is —C(O)— and the bond connecting $Z^1$ and $Z^2$ is a single bond, and
$Z^3$ is —$CHR^3$ and $Z^4$ is —$CHR^4$ when the bond connecting $Z^3$ and $Z^4$ is a single bond, or $Z^3$ is —$CR^3$ and $Z^4$ is —$CR^4$ when the bond connecting $Z^3$ and $Z^4$ is a double bond; or
b) one of $Z^3$ or $Z^4$ is —$NR^2$—, the other of $Z^3$ or $Z^4$ is —C(O)— and the bond connecting $Z^3$ and $Z^4$ is a single bond, and
$Z^1$ is —$CHR^4$ and $Z^2$ is —$CHR^3$ when the bond connecting $Z^1$ and $Z^2$ is a single bond, or $Z^1$ is —$CR^4$ and $Z^2$ is —$CR^3$ when the bond connecting $Z^1$ and $Z^2$ is a double bond;

R² is selected from the group consisting of hydrogen, alkyl, cycloalkyl, aryl, heterocycloalkyl, and heteroaryl;

R³ and R⁴ are each independently selected from the group consisting of hydrogen, alkyl, alkoxy, amino, acyloxy, aminoacyl, cycloalkyl, cycloalkoxy, aryl, aryloxy, heterocycloalkyl, heteroaryloxy, and heteroaryl;

Y is —NR⁶— or —O—;

n is 1, 2, 3, 4, 5, or 6;

R⁵ is selected from the group consisting of hydrogen, acyl, sulfonyl, aminoacyl, oxycarbonyl, alkyl, cycloalkyl, aryl, heterocycloalkyl, and heteroaryl;

R⁶ is selected from the group consisting of hydrogen, alkyl, cycloalkyl, aryl, heterocycloalkyl, and heteroaryl;

R⁷ and R⁸ are each independently selected from the group consisting of hydrogen, alkyl, cycloalkyl, aryl, heterocycloalkyl, and heteroaryl; or R⁷ and R⁸ together with the carbon atom to which they are attached form a cycloalkyl, or heterocycloalkyl;

W is selected from the group consisting of R⁹, —C(O)OR⁹, —C(O)NR⁶R⁹, —NR⁶C(O)R⁹, —NR⁶C(O)OR⁹, —NR⁶C(O)NR⁶R⁹, —NR⁶S(O)₂R⁹, —S(O)₂NR⁶R⁹, —NR⁶R⁹ and —OR⁹; and R⁹ is selected from the group consisting of hydrogen, alkyl, cycloalkyl, aryl, heterocycloalkyl, and heteroaryl; and further wherein each alkyl, alkoxy, amino, acyloxy, aminoacyl, cycloalkyl, cycloalkoxy, aryl, aryloxy, heterocycloalkyl, heteroaryloxy, and heteroaryl described above for R¹, R², R³, R⁴, R⁵, R⁶, R⁷, R⁸ and R⁹ can be optionally substituted with from 1 to 3 R¹⁰, wherein each R¹⁰ is independently selected from the group consisting of alkyl, alkoxy, haloalkyl, haloalkoxy, acyl, acylamino, acyloxy, amino, aminoacyl, aminocarbonylamino, aminothiocarbonylamino, aminocarbonyloxy, aryl, aryloxy, aryloxyaryl, cyano, halogen, hydroxyl, nitro, oxo, thioxo, carboxyl, carboxyl ester, cycloalkyl, thio, alkylthio, arylthio, cycloalkylthio, heteroarylthio, heterocyclicthio, sulfonyl, heteroaryl, heterocyclic, cycloalkoxy, heteroaryloxy, heterocyclyloxy, oxycarbonylamino, oxythiocarbonylamino, —OS(O)₂-alkyl, —OS(O)₂-aryl, —OS(O)₂-heteroaryl, —OS(O)₂-heterocyclic, —OSO₂—NR⁴⁰R⁴⁰, —NR⁴⁰S(O)₂—NR⁴⁰-alkyl, —NR⁴⁰S(O)₂—NR⁴⁰-aryl, NR⁴⁰S(O)₂—N⁴⁰-heteroaryl, and —NR⁴⁰S(O)₂—NR⁴⁰-heterocyclic, where each R⁴⁰ is independently hydrogen or alkyl; and further wherein each alkyl, alkoxy, aryl, aryloxy, aryloxyaryl, cycloalkyl, alkylthio, arylthio, cycloalkylthio, heteroarylthio, heterocyclicthio, heteroaryl, heterocyclic, cycloalkoxy, heteroaryloxy, or heterocyclyloxy may be additionally substituted with from 1-3 substituents independently alkyl, alkoxy, haloalkyl, haloalkoxy, or halogen;

or a pharmaceutically acceptable salt, single stereoisomer, mixture of stereoisomers, ester, tautomer or prodrug thereof In another aspect, the disclosure is directed to compounds of Formula Ia.

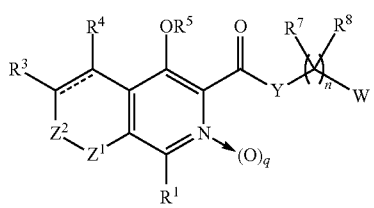

Ia

In another aspect, the disclosure is directed to compounds of Formula Ib.

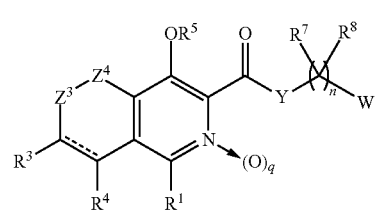

Ib

In another aspect, the disclosure is directed to compounds of Formula IIa.

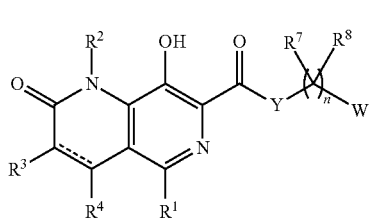

IIa

In another aspect, the disclosure is directed to compounds of Formula IIb.

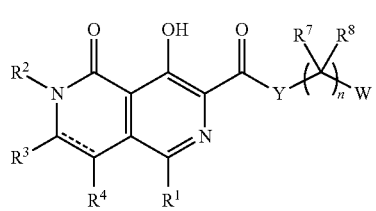

IIb

In another aspect, the disclosure is directed to compounds of Formula IIIa.

IIIa

In another aspect, the disclosure is directed to compounds of Formula IIIb.

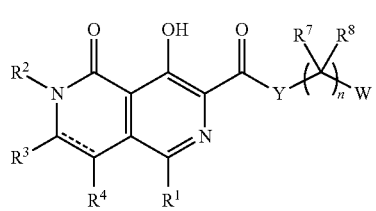

IIIb

The disclosure also provides pharmaceutical compositions comprising one or more compounds of Formula I, Ia, Ib, IIa, IIb, IIIa, or IIIb and a pharmaceutically acceptable excipient. In some embodiments, the composition further comprises or is used in combination with at least one additional therapeutic agent. In some embodiments, the agent is selected from the group consisting of vitamin $B_{12}$, folic acid, ferrous sulfate, recombinant human erythropoietin, and an erythropoiesis stimulating agent (ESA).

The disclosure is also directed to methods of treating, pretreating, or delaying onset or progression of a condition associated with or mediated, at least in part, by hypoxia inducible factor (HIF), the method comprising administering to a patient a therapeutically effective amount of a compound of Formula I, Ia, Ib, IIa, IIb, IIIa, or IIIb, or a pharmaceutical composition comprising one or more compounds of Formula I, Ia, Ib, IIa, IIb, IIIa, or IIIb. In one embodiment, the condition associated with or mediated by HIF is tissue damage associated with ischemia or hypoxia. In one aspect, the ischemia is associated with an event including, but not limited to, myocardial infarction, pulmonary embolism, intestinal infarction, ischemic stroke, renal ischemic-reperfusion injury, cardiac cirrhosis, transient ischemic attack, macular degeneration, chronic kidney failure, peripheral artery disease, and congestive heart failure.

The disclosure is also directed to methods of treating, pretreating, or delaying onset or progression of a condition associated with or mediated, at least in part, by erythropoietin (EPO), the method comprising administering to a patient a therapeutically effective amount of a compound of Formula I, Ia, Ib, IIa, IIb, IIIa, or IIIb or a pharmaceutical composition comprising one or more compounds of Formula I, Ia, Ib, IIa, IIb, IIIa, or IIIb.

The disclosure is also directed to methods of treating, pretreating, or delaying onset or progression of anemia, the method comprising administering to a patient a therapeutically effective amount of a compound of Formula I, Ia, Ib, IIa, IIb, IIIa, or IIb or a pharmaceutical composition comprising one or more compounds of Formula I, Ia, Ib, IIa, IIb, IIIa, or IIIb.

The disclosure is also directed to methods of inhibiting the activity of at least one HIF hydroxylase, the method comprising bringing into contact the HIF hydroxylase and a compound of the disclosure. In one embodiment, the HIF hydroxylase is an asparaginyl hydroxylase such as Factor Inhibiting HIF (FIH). In another embodiment, the HIF hydroxylase is a prolyl hydroxylase including, but not limited to, a HIF prolyl hydroxylase selected from the group consisting of human EGLN1, EGLN2, or EGLN3, or an orthologous enzyme from another species.

DETAILED DESCRIPTION

Before the present compositions and methods are described, it is to be understood that the disclosure is not limited to the particular compounds, compositions, methodologies, protocols, cell lines, assays, and reagents described, as these may vary. It is also to be understood that the terminology used herein is intended to describe particular embodiments of the present disclosure, and is in no way intended to limit the scope of the present disclosure as set forth in the appended claims.

1. Compounds

The disclosure is directed to compounds of Formula I:

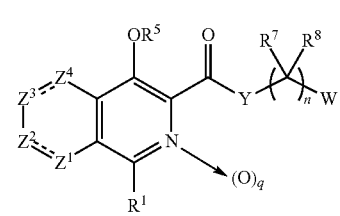

wherein
q is 0 or 1;
$R^1$ is selected from the group consisting of hydrogen, cyano, halo, hydroxy, alkoxy, amino, acyloxy, aminoacyl, alkyl, cycloalkyl, cycloalkoxy, aryl, aryloxy, heterocycloalkyl, heteroaryloxy, and heteroaryl;
$Z^1$ and $Z^4$ are each independently selected from the group consisting of —$CR^4$—, —$CHR^4$, —$NR^2$— and —C(O)—; $Z^2$ and $Z^3$ are each independently selected from the group consisting of —$CR^3$—, —$CHR^3$, —$NR^2$ and —C(O)—; and ═ is a single or a double bond; provided that:
a) one of $Z^1$ or $Z^2$ is —$NR^2$—, the other of $Z^1$ or $Z^2$ is —C(O)— and the bond connecting $Z^1$ and $Z^2$ is a single bond, and
$Z^3$ is —$CHR^3$ and $Z^4$ is —$CHR^4$ when the bond connecting $Z^3$ and $Z^4$ is a single bond, or $Z^3$ is —$CR^3$ and $Z^4$ is —$CR^4$ when the bond connecting $Z^3$ and $Z^4$ is a double bond; or
b) one of $Z^3$ or $Z^4$ is —$NR^2$—, the other of $Z^3$ or $Z^4$ is —C(O)— and the bond connecting $Z^3$ and $Z^4$ is a single bond, and
$Z^1$ is —$CHR^4$ and $Z^2$ is —$CHR^3$ when the bond connecting $Z^1$ and $Z^2$ is a single bond, or $Z^1$ is —$CR^4$ and $Z^2$ is —$CR^3$ when the bond connecting $Z^1$ and $Z^2$ is a double bond;
$R^2$ is selected from the group consisting of hydrogen, alkyl, cycloalkyl, aryl, heterocycloalkyl, and heteroaryl;
$R^3$ and $R^4$ are each independently selected from the group consisting of hydrogen, alkyl, alkoxy, amino, acyloxy, aminoacyl, cycloalkyl, cycloalkoxy, aryl, aryloxy, heterocycloalkyl, heteroaryloxy, and heteroaryl;
Y is —$NR^6$— or —O—;
n is 1, 2, 3, 4, 5, or 6;
$R^5$ is selected from the group consisting of hydrogen, acyl, sulfonyl, aminoacyl, oxycarbonyl, alkyl, cycloalkyl, aryl, heterocycloalkyl, and heteroaryl;
$R^6$ is selected from the group consisting of hydrogen, alkyl, cycloalkyl, aryl, heterocycloalkyl, and heteroaryl;
$R^7$ and $R^8$ are each independently selected from the group consisting of hydrogen, alkyl, cycloalkyl, aryl, heterocycloalkyl, and heteroaryl; or $R^7$ and $R^8$ together with the carbon atom to which they are attached form a cycloalkyl, or heterocycloalkyl;
W is selected from the group consisting of $R^9$, —C(O)$OR^9$, —C(O)$NR^6R^9$, —$NR^6$C(O)$R^9$, —$NR^6$C(O)$OR^9$, —$NR^6$C(O)$NR^6R^9$, —$NR^6$S(O)$_2R^9$, —S(O)$_2NR^6R^9$, —$NR^6R^9$ and —$OR^9$; and
$R^9$ is selected from the group consisting of hydrogen, alkyl, cycloalkyl, aryl, heterocycloalkyl, and heteroaryl; and
further wherein each alkyl, alkoxy, amino, acyloxy, aminoacyl, cycloalkyl, cycloalkoxy, aryl, aryloxy, heterocycloalkyl, heteroaryloxy, and heteroaryl described above for $R^1$, $R^2$, $R^3$, $R^4$, $R^5$, $R^6$, $R^7$, $R^8$ and $R^9$ can be optionally substituted with from 1 to 3 $R^{10}$, wherein each $R^{10}$ is independently selected from the group consisting of alkyl, alkoxy, haloalkyl, haloalkoxy, acyl, acylamino, acyloxy, amino, aminoacyl, aminocarbonylamino, aminothiocarbonylamino, aminocarbonyloxy, aryl, aryloxy, aryloxyaryl, cyano, halogen, hydroxyl, nitro, oxo, thioxo, carboxyl, carboxyl ester, cycloalkyl, thio, alkylthio, arylthio, cycloalkylthio, heteroarylthio, heterocyclicthio, sulfonyl, heteroaryl, heterocyclic, cycloalkoxy, heteroaryloxy, heterocyclyloxy, oxycarbonylamino, oxythiocarbonylamino, —OS(O)$_2$-alkyl, —OS(O)$_2$-aryl, —OS(O)$_2$-heteroaryl, —OS(O)$_2$-heterocyclic, —OSO$_2$—NR$^{40}$R$^{40}$, —NR$^{40}$S(O)$_2$—NR$^{40}$-alkyl, —NR$^{40}$S(O)$_2$—NR$^{40}$-aryl, NR$^{40}$S(O)$_2$—NR$^{40}$-heteroaryl, and —NR$^{40}$S(O)$_2$—NR$^{40}$-heterocyclic, where each $R^{40}$ is independently hydrogen or alkyl; and further wherein each alkyl, alkoxy, aryl, aryloxy, aryloxyaryl, cycloalkyl, alkylthio, arylthio, cycloalkylthio, heteroarylthio, heterocyclicthio, heteroaryl, heterocyclic, cycloalkoxy, heteroaryloxy, or heterocyclyloxy may be additionally substituted with from 1-3 substituents independently alkyl, alkoxy, haloalkyl, haloalkoxy, or halogen;

or a pharmaceutically acceptable salt, single stereoisomer, mixture of stereoisomers, ester, tautomer or prodrug thereof In another aspect, the disclosure is directed to compounds of Formula Ia or Formula Ib

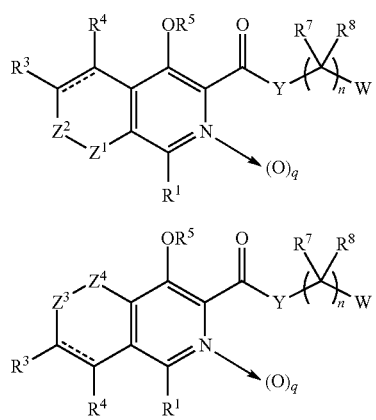

wherein
---- is a single or a double bond; and
q, $R^1$, $Z^1$, $Z^2$, $Z^3$, $Z^4$, $R^3$, $R^4$, $R^5$, Y, $R^7$, $R^8$, n, and W are as defined for Formula I;
or a pharmaceutically acceptable salt, single stereoisomer, mixture of stereoisomers, ester, tautomer or prodrug thereof In another aspect, the disclosure is directed to compounds of Formula IIa:

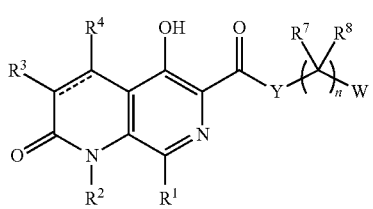

wherein
---- is a single or a double bond; and
$R^1$, $R^2$, $R^3$, $R^4$, Y, $R^7$, $R^8$, n, and W are as defined for Formula I;
or a pharmaceutically acceptable salt, single stereoisomer, mixture of stereoisomers, ester, tautomer or prodrug thereof In yet another aspect, the disclosure is directed to compounds of Formula IIb:

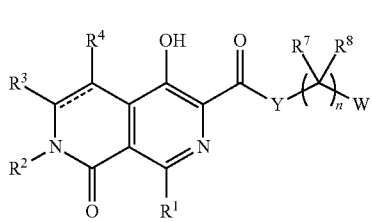

wherein
---- is a single or a double bond; and
$R^1$, $R^2$, $R^3$, $R^4$, Y, $R^7$, $R^8$, n, and W are as defined for Formula I;
or a pharmaceutically acceptable salt, single stereoisomer, mixture of stereoisomers, ester, tautomer or prodrug thereof In yet another aspect, the disclosure is directed to compounds of Formula IIIa:

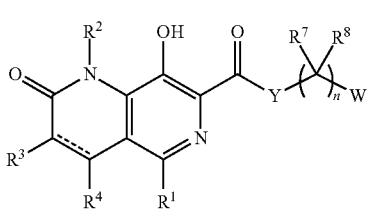

wherein
---- is a single or a double bond; and
$R^1$, $R^2$, $R^3$, $R^4$, Y, $R^7$, $R^8$, n, and W are as defined for Formula I;
or a pharmaceutically acceptable salt, single stereoisomer, mixture of stereoisomers, ester, tautomer or prodrug thereof In yet another aspect, the disclosure is directed to compounds of Formula IIIb:

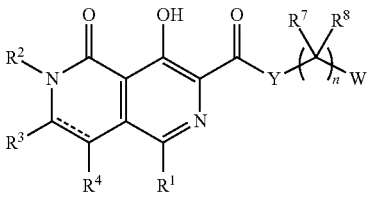

wherein
---- is a single or a double bond; and
$R^1$, $R^2$, $R^3$, $R^4$, Y, $R^7$, $R^8$, n, and W are as defined for Formula I;
or a pharmaceutically acceptable salt, single stereoisomer, mixture of stereoisomers, ester, tautomer or prodrug thereof In certain embodiments of compounds of Formula I, Ia, or Ib, q is 0.

In one embodiment of compounds of Formula I or Ia, $Z^1$ is —$NR^2$— and $Z^2$ is —C(O)—. In another embodiment of compounds of Formula I or Ia, $Z^1$ is —C(O)— and $Z^2$ is —$NR^2$—.

In one embodiment of compounds of Formula I or Ib, $Z^3$ is —$NR^2$— and $Z^4$ is —C(O)—. In another embodiment of compounds of Formula I or Ib, $Z^3$ is —C(O)— and $Z^4$ is —$NR^2$—.

In certain embodiments of compounds of Formula I, Ia, Ib, IIa, IIb, IIIa, or IIIb, $R^1$ is selected from the group consisting of hydrogen, cyano, optionally substituted alkyl, optionally substituted aryl, and optionally substituted heteroaryl. In certain embodiments of compounds of Formula I, Ia, Ib, IIa, IIb, IIIa, or IIIb, $R^1$ is selected from the group consisting of hydrogen, cyano, and optionally substituted alkyl. In certain embodiments of compounds of Formula I, Ia, Ib, IIa, IIb, IIIa, or IIIb, $R^1$ is selected from the group consisting of hydrogen, cyano, methyl, phenyl, pyridin-3-yl and (5-fluoro)pyridin-3-yl. In certain embodiments of compounds of Formula I, Ia, Ib, IIa, IIb, IIIa, or IIIb, $R^1$ is selected from the group consisting of hydrogen, cyano, methyl, phenyl, pyridin-3-yl, (5-fluoro)pyridin-3-yl, thiazol-2-yl, thiazol-4-yl, thiazol-5-yl, 1-methyl-4-pyrazol-4-yl, pyridin-4-yl, 2-methyl-pyridin-3-yl, 4-methyl-pyridin-3-yl, 4-methoxy-pyridin-3-yl, 4-trifluoromethyl-pyridin-3-yl, 5-chloro-pyridin-3-yl, 5-fluoro-pyridin-3-yl, 5-methoxy-pyridin-3-yl, pyrazin-2-yl, pyridazin-3-yl, pyridazin-4-yl, pyrimidin-5-yl, 2-ethoxy-pyramidin-5-yl, and 2-ethylthio-pyramidin-5-yl.

In certain embodiments of compounds of Formula I, Ia, Ib, IIa, IIb, IIIa, or IIIb, $R^2$ is selected from the group consisting of hydrogen and optionally substituted alkyl. In certain embodiments, the disclosure is directed to compounds of Formula I, Ia, Ib, IIa, IIb, IIIa, or IIIb, wherein $R^2$ is $(C_{1-3})$alkylene-$R^{11}$, and $R^{11}$ is selected from the group consisting of optionally substituted cycloalkyl, optionally substituted aryl, optionally substituted heterocycloalkyl, and optionally substituted heteroaryl. In certain embodiments of compounds of Formula I, Ia, Ib, IIa, IIb, IIIa, or IIIb, $R^2$ is $(C_1-C_3)$alkylene-phenyl. In certain embodiments of compounds of Formula I, Ia, Ib, IIa, IIb, IIIa, or IIIb, $R^2$ is benzyl. In certain embodiments of compounds of Formula I, Ia, Ib, IIa, IIb, IIIa, or IIIb, $R^2$ is selected from the group consisting of methyl, benzyl, cyclopentylmethyl, cyclohexylmethyl, tetrahydropyran-4-yl-methyl, 2-ethyl-butyl, 4-cyano-benzyl, 4-methoxy-benzyl, phenethyl, (R)-1-phenyl-ethyl, (S)-1-phenyl-ethyl, phenyl, and thiazol-2-yl.

In certain embodiments of compounds of Formula I, Ia, Ib, IIa, IIb, IIIa, or IIIb, ⁃⁃⁃ is a single bond. In other embodiments of compounds of Formula I, Ia, Ib, IIa, IIb, IIIa, or IIIb, ⁃⁃⁃ is a double bond.

In certain embodiments of compounds of Formula I, Ia, Ib, IIa, IIb, IIIa, or IIIb, $R^3$ and $R^4$ are each independently selected from the group consisting of hydrogen, optionally substituted alkyl, optionally substituted cycloalkyl, optionally substituted aryl, optionally substituted heterocycloalkyl, and optionally substituted heteroaryl.

In certain embodiments of compounds of Formula I, Ia, Ib, IIa, IIb, IIIa, or IIIb, $R^3$ is selected from the group consisting of hydrogen, optionally substituted alkyl, optionally substituted aryl and optionally substituted heteroaryl. In certain embodiments of compounds of Formula I, Ia, Ib, IIa, IIb, IIIa, or IIIb, $R^3$ is selected from the group consisting of hydrogen, methyl, benzyl, 2-phenyleth-1-yl, phenyl, thien-2-yl, pyridin-2-yl, pyridin-3-yl, and pyridin-4-yl. In certain embodiments of compounds of Formula I, Ia, Ib, IIa, IIb, IIIa, or IIIb, $R^3$ is selected from the group consisting of hydrogen, methyl, benzyl, 2-phenyleth-1-yl, phenyl, thien-2-yl, pyridin-2-yl, pyridin-3-yl, and pyridin-4-yl, 4-cyano-phenyl, 2-trifluoromethyl-phenyl, 3-trifluoromethyl-phenyl, 4-trifluoromethyl-phenyl, 4-trifluoromethoxy-phenyl, 3-methoxy-phenyl, 4-methoxy-phenyl, 5-fluoro-2-methoxy-phenyl, 4-methanesulfonylphenyl, 4-morpholin-4-yl-phenyl, 1-methyl-pyrazol-y-yl, thiazol-2-yl, pyridin-3-yl, pyrazin-2-yl, pyrimidin-5-yl, 2-dimethylamino-pyrimidin-5-yl, and benzo[1,2,5]oxadiazol-5-yl. In certain embodiments of compounds of Formula I, Ia, Ib, IIa, IIb, IIIa, or IIIb, $R^3$ is hydrogen.

In certain embodiments of compounds of Formula I, Ia, Ib, IIa, IIb, IIIa, or IIIb, $R^4$ is hydrogen.

In certain embodiments of compounds of Formula I, Ia, or Ib, $R^5$ is selected from the group consisting of hydrogen and optionally substituted alkyl. In certain embodiments of compounds of Formula I, Ia, or Ib, $R^5$ is hydrogen.

In certain embodiments of compounds of Formula I, Ia, Ib, IIa, IIb, IIIa, or IIIb, Y is —$NR^6$—, and $R^6$ is hydrogen or optionally substituted alkyl. In certain embodiments of compounds of Formula I, Ia, Ib, IIa, IIb, IIIa, or IIIb, Y is —NH—. In other embodiments of compounds of Formula I, Ia, Ib, IIa, IIb, IIIa, or IIIb, Y is —O—.

In certain embodiments of compounds of Formula I, Ia, Ib, IIa, IIb, IIIa, or IIIb, $R^7$ and $R^8$ are each independently selected from the group consisting of hydrogen, and optionally substituted alkyl; or $R^7$ and $R^8$ together with the carbon atom to which they are attached form an optionally substituted cycloalkyl. In certain embodiments of compounds of Formula I, Ia, Ib, IIa, IIb, IIIa, or IIIb, where $R^7$ and $R^8$ together with the carbon atom to which they are attached form an optionally substituted cycloalkyl, or optionally substituted heterocycloalkyl, the $R^7$ and $R^8$ are attached to adjacent carbon atoms. In certain embodiments of compounds of Formula I, Ia, Ib, IIa, IIb, IIIa, or IIIb, where $R^7$ and $R^8$ together with the carbon atom to which they are attached form an optionally substituted cycloalkyl, or optionally substituted heterocycloalkyl, the $R^7$ and $R^8$ are attached to the same carbon atom.

In certain embodiments of compounds of Formula I, Ia, Ib, IIa, IIb, IIIa, or IIIb, W is $R^9$, —$OR^9$, —$C(O)OR^9$, —$C(O)NR^6R^9$, —$NR^6C(O)R^9$, —$NR^6C(O)OR^9$, —$NR^6C(O)NR^6R^9$, —$NR^6S(O)_2R^9$, or —$S(O)_2NR^6R^9$. In certain embodiments of compounds of Formula I, Ia, Ib, IIa, IIb, IIIa, or IIIb, W is $R^9$, —$C(O)OR^9$, —$NR^6C(O)R^9$, —$NR^6C(O)NR^6R^9$, or —$NR^6S(O)_2R^9$. In certain embodiments of compounds of Formula I, Ia, Ib, IIa, IIb, IIIa, or IIIb, W is $R^9$, —$C(O)OR^9$, —$NR^6C(O)R^9$, —$NR^6S(O)_2R^9$, or —$S(O)_2NR^6R^9$. In certain embodiments of compounds of Formula I, Ia, Ib, IIa, IIb, IIIa, or IIIb, W is $R^9$ or —$C(O)OR^9$. In certain embodiments of compounds of Formula I, Ia, Ib, IIa, IIb, IIIa, or IIIb, W is —$C(O)OR^9$.

In certain embodiments of compounds of Formula I, Ia, Ib, IIa, IIb, IIIa, or IIIb, $R^9$ is hydrogen, optionally substituted alkyl, optionally substituted cycloalkyl, optionally substituted aryl, or optionally substituted heteroaryl. In certain embodiments of compounds of Formula I, Ia, Ib, IIa, IIb, IIIa, or IIIb, $R^9$ is hydrogen, methyl, ethyl, propyl, isopropyl, trifluoromethyl, 1-hydroxy-1-oxo-eth-2-yl, cyclopropyl, phenyl, 4-fluorophenyl, morpholinyl, -5-H-tetrazolyl, pyridin-4-yl or pyridazin-4-yl. In certain embodiments of compounds of Formula I, Ia, Ib, IIa, IIb, IIIa, or IIIb, $R^9$ is hydrogen. In certain embodiments of compounds of Formula I, Ia, Ib, IIa, IIb, IIIa, or IIIb, $R^9$ is selected from the group consisting of alkyl, cycloalkyl, aryl, heterocycloalkyl, and heteroaryl.

In certain embodiments of compounds of Formula I, Ia, Ib, IIa, IIb, IIIa, or IIIb, each optional $R^{10}$ is independently selected from the group consisting of alkyl, alkoxy, haloalkyl, haloalkoxy, acyl, acylamino, acyloxy, amino, aminoacyl, aminocarbonylamino, aminothiocarbonylamino, aminocarbonyloxy, aryl, aryloxy, aryloxyaryl, cyano, halogen, hydroxyl, nitro, oxo, thioxo, carboxyl, carboxyl ester, cycloalkyl, thio, alkylthio, arylthio, cycloalkylthio, heteroarylthio, heterocyclicthio, sulfonyl, heteroaryl, heterocyclic, cycloalkoxy, heteroaryloxy, heterocyclyloxy, oxycarbonylamino, oxythiocarbonylamino, —OS(O)$_2$-alkyl, —OS(O)$_2$-aryl, —OS(O)$_2$-heteroaryl, —OS(O)$_2$-heterocyclic, —OSO$_2$—NR$^{40}$R$^{40}$, —NR$_{40}$S(O)$_2$—NR$^{40}$-alkyl, —NR$^{40}$S(O)$_2$—NR$^{40}$-aryl, —NR$^{40}$S(O)$_2$—NR$^{40}$-heteroaryl, and —NR$^{40}$S(O)$_2$—NR$^{40}$-heterocyclic, where each R$^{40}$ is independently hydrogen or alkyl.

In certain embodiments, the group

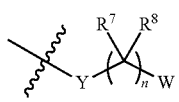

of compounds of Formula I, Ia, Ib, IIa, IIb, IIIa, or IIIb, is represented by

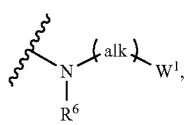

where alk is optionally substituted $C_1$-$C_6$ alkylene or optionally substituted $C_2$-$C_4$ alkylene, W$^1$ is —C(O)OR$^9$, —NR$^6$C(O)R$^9$, —NR$^6$C(O)NR$^6$R$^9$, or —NR$^6$S(O)$_2$R$^9$, and R$^6$ is hydrogen or alkyl, particularly methyl.

In certain embodiments, the group

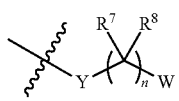

of compounds of Formula I, Ia, Ib, IIa, IIb, IIIa, or IIIb, is represented by

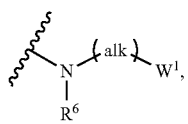

where alk is optionally substituted $C_1$-$C_6$ alkylene or optionally substituted $C_2$-$C_4$ alkylene, W$^1$ is R$^9$, and each R$^6$ is independently hydrogen or alkyl, particularly methyl. In some such embodiments, R$^9$ is selected from the group consisting of hydrogen, methyl, ethyl, propyl, isopropyl, trifluoromethyl, 1-hydroxy-1-oxo-eth-2-yl, cyclopropyl, phenyl, 4-fluorophenyl, 3-carboxyphenyl, morpholinyl, -5-H-tetrazolyl, pyridin-4-yl or pyridazin-4-yl.

In certain embodiments of compounds of Formula I, Ia, Ib, IIa, IIb, IIIa, or IIIb, the group

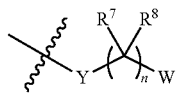

is selected from the group consisting of

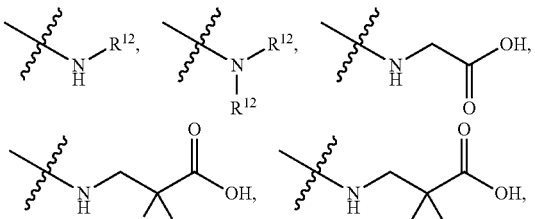

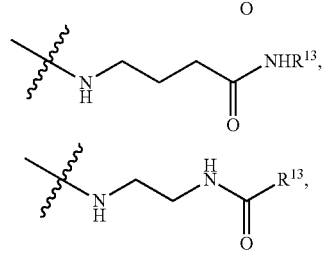

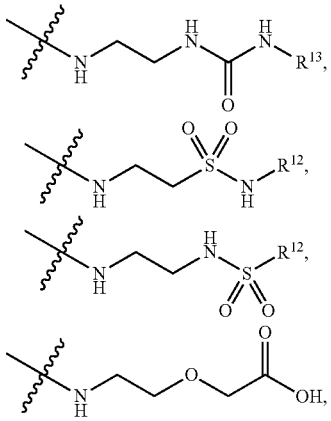

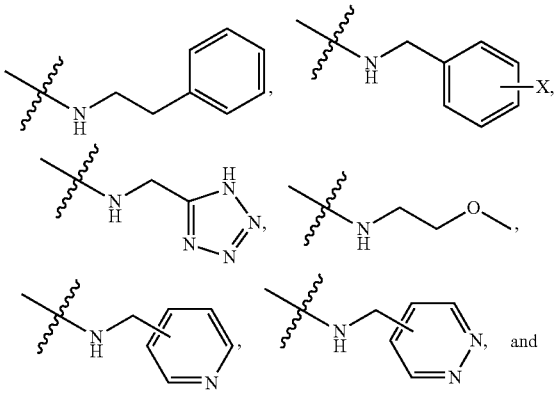

and

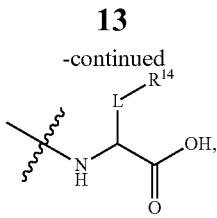

wherein $R^7$ and $R^8$ are as defined for Formula I, X is halo, m is 1, 2, 3 or 4, $R^{12}$ is selected from the group consisting of $(C_{1-3})$alkyl optionally substituted with heterocycloalkyl, or $(C_{3-7})$cycloalkyl, and $R^{13}$ is selected from the group consisting of H, $(C_{1-3})$alkyl optionally substituted with 1 to 3 halo, or $(C_{3-7})$cycloalkyl; L is optionally substituted $(C_{1-3})$alkylene, and $R^{14}$ is selected from the group consisting of optionally substituted cycloalkyl, optionally substituted aryl, optionally substituted heterocycloalkyl, and optionally substituted heteroaryl.

In certain embodiments of compounds of Formula I, Ia, Ib, IIa, IIb, IIIa, or IIIb, the group

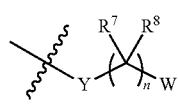

is selected from the group consisting of

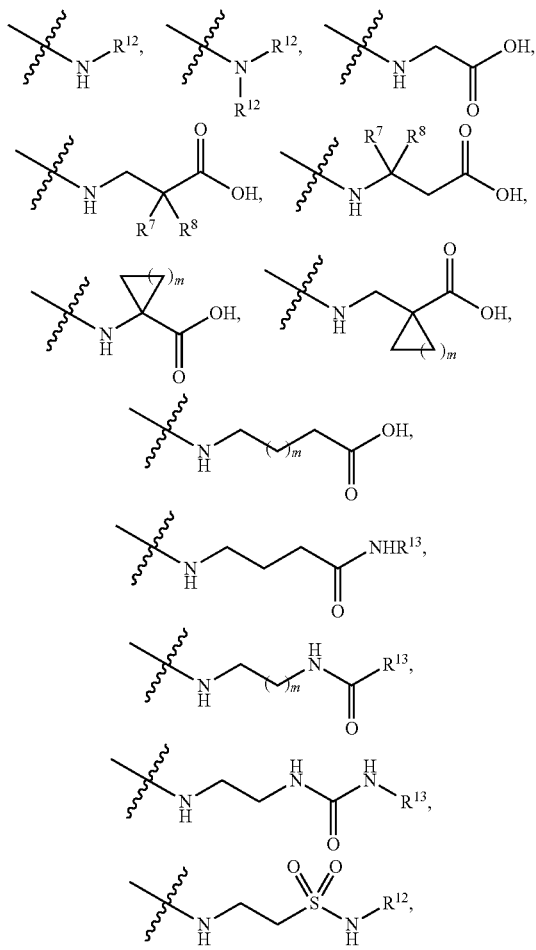

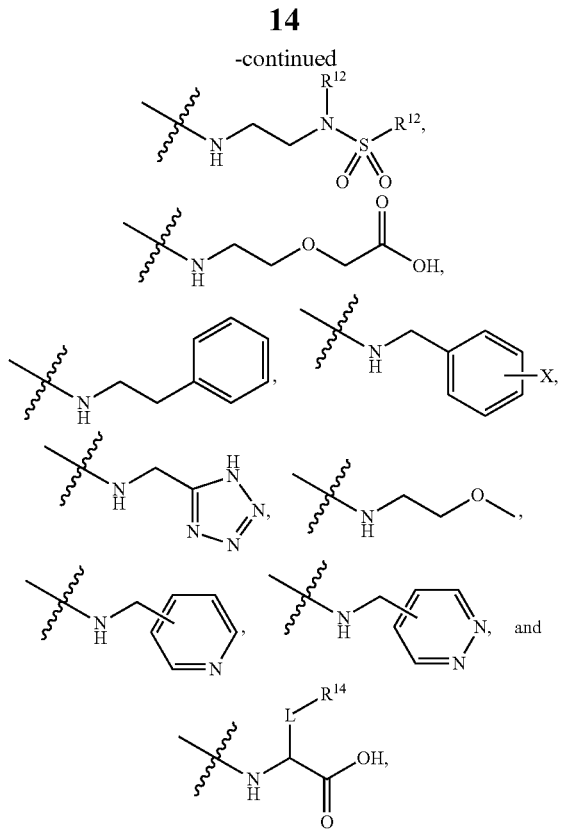

wherein $R^7$ and $R^8$ are as defined for Formula I, X is halo or carboxy, m is 1, 2, 3 or 4, $R^{12}$ is selected from the group consisting of $(C_{1-3})$alkyl optionally substituted with heterocycloalkyl, or $(C_{3-7})$cycloalkyl, and $R^{13}$ is selected from the group consisting of H, $(C_{1-3})$alkyl optionally substituted with 1 to 3 halo, or $(C_{3-7})$cycloalkyl; L is optionally substituted $(C_{1-3})$alkylene, and $R^{14}$ is selected from the group consisting of optionally substituted cycloalkyl, optionally substituted aryl, optionally substituted heterocycloalkyl, and optionally substituted heteroaryl.

In certain embodiments of compounds of Formula I, Ia, Ib, IIa, IIb, IIIa, or IIIb, the group

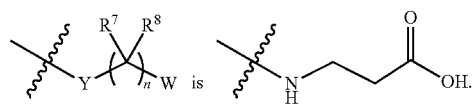

In certain embodiments of compounds of Formula I, Ia, Ib, IIa, IIb, IIIa, or IIIb,
  $R^1$ is selected from the group consisting of hydrogen, cyano, optionally substituted alkyl, optionally substituted aryl, and optionally substituted heteroaryl;
  $R^3$ and $R^4$ are each independently selected from the group consisting of hydrogen, optionally substituted alkyl, optionally substituted cycloalkyl, optionally substituted aryl, optionally substituted heterocycloalkyl, and optionally substituted heteroaryl; and
  $R^6$, when present, is selected from the group consisting of hydrogen, and optionally substituted alkyl.

In certain embodiments of compounds of Formula I, Ia, Ib, IIa, IIb, IIIa, or IIIb,
  $R^1$ is selected from the group consisting of hydrogen, cyano, and alkyl;

$R^2$ is substituted alkyl;

$R^3$ and $R^4$ are each independently selected from the group consisting of hydrogen, optionally substituted alkyl, optionally substituted cycloalkyl, optionally substituted aryl, optionally substituted heterocycloalkyl, and optionally substituted heteroaryl;

Y is —O— or —$NR^6$—; and $R^6$ is hydrogen.

In certain embodiments of compounds of Formula I, Ia, Ib, IIa, IIb, IIIa, or IIIb, $R^1$ is selected from the group consisting of hydrogen, cyano, optionally substituted alkyl, optionally substituted aryl, and optionally substituted heteroaryl;

$R^2$ is substituted alkyl;

$R^3$ and $R^4$ are each independently selected from the group consisting of hydrogen, optionally substituted alkyl, optionally substituted cycloalkyl, optionally substituted aryl, optionally substituted heterocycloalkyl, and optionally substituted heteroaryl;

Y is —O— or —$NR^6$—;

$R^6$ is hydrogen;

$R^7$ and $R^8$ are each independently selected from the group consisting of hydrogen, and optionally substituted alkyl; or $R^7$ and $R^8$ together with the carbon atom to which they are attached form an optionally substituted cycloalkyl; and W is $R^9$ or —C(O)$OR^9$.

In certain embodiments of compounds of Formula I, Ia, Ib, IIa, IIb, IIIa, or IIIb, $R^1$ is selected from the group consisting of hydrogen, cyano, optionally substituted alkyl, optionally substituted aryl, and optionally substituted heteroaryl;

$R^2$ is substituted alkyl;

$R^3$ and $R^4$ are each independently selected from the group consisting of hydrogen, optionally substituted alkyl, optionally substituted cycloalkyl, optionally substituted aryl, optionally substituted heterocycloalkyl, and optionally substituted heteroaryl;

Y is —O— or —$NR^6$—;

$R^6$ is hydrogen;

$R^7$ and $R^8$ are each independently selected from the group consisting of hydrogen, optionally substituted alkyl; or $R^7$ and $R^8$ together with the carbon atom to which they are attached form an optionally substituted cycloalkyl;

W is —C(O)$OR^9$; and $R^9$ is hydrogen.

In certain embodiments of Formula IIa, or IIIa,

Y is —NH—;

$R^1$ is hydrogen, cyano, aryl or heteroaryl;

$R^2$ is $(C_{1-3})$alkylene-$R^{11}$, and $R^{11}$ is aryl;

$R^3$ is hydrogen, alkyl, aryl, or $(C_{1-3})$alkylene-$R^{15}$, and $R^{15}$ is aryl;

$R^4$ is hydrogen;

---- is a single or double bond;

n is 1;

W is —C(O)$OR^9$; and $R^7$, $R^8$ and $R^9$ are hydrogen.

In certain embodiments of Formula IIb,

Y is —NH—;

$R^1$ is hydrogen;

$R^2$ is $(C_{1-3})$alkylene-$R^{11}$, and $R^{11}$ is optionally substituted aryl;

$R^3$ and $R^4$ are hydrogen;

---- is a single or double bond;

n is 1, 2, 3, or 4;

$R^7$ and $R^8$ are hydrogen or alkyl;

W is selected from the group consisting of $R^9$, —C(O)$OR^9$, —C(O)$NHR^9$, —NHC(O)$R^9$, —$NCH_3C(O)R^9$, —$NCH_3C(O)OR^9$, —NHC(O)$NHR^9$, —NHS(O)$_2R^9$, —S(O)$_2NHR^9$, and —$OR^9$; and $R^9$ is selected from the group consisting of hydrogen, optionally substituted alkyl, cycloalkyl, and heteroaryl.

In certain embodiments of Formula IIa, or IIIa,

Y is —NH—;

$R^1$ is hydrogen, cyano or optionally substituted heteroaryl;

$R^2$ is aryl or $(C_{1-3})$alkylene-$R^{11}$, and $R^{11}$ is aryl or cycloalkyl;

$R^3$ is optionally substituted aryl;

$R^4$ is hydrogen;

---- is a double bond;

n is 2, 3, or 4;

W is —C(O)$OR^9$; and $R^7$, $R^8$ and $R^9$ are hydrogen.

In certain embodiments of Formula IIb, or IIIb,

Y is —NH—;

$R^1$ is hydrogen, cyano or optionally substituted heteroaryl;

$R^2$ is aryl or $(C_{1-3})$alkylene-$R^{11}$, and $R^{11}$ is aryl or cycloalkyl;

$R^3$ is optionally substituted aryl;

$R^4$ is hydrogen;

---- is a double bond;

n is 2, 3, or 4;

W is —C(O)$OR^9$; and $R^7$, $R^8$ and $R^9$ are hydrogen.

In certain embodiments of Formula IIa,

Y is —NH—;

$R^1$ is hydrogen, cyano, or optionally substituted heteroaryl;

$R^2$ is $(C_{1-3})$alkylene-$R^{11}$, and $R^{11}$ is aryl;

$R^3$ is aryl;

$R^4$ is hydrogen;

---- is a double bond;

n is 2;

$R^7$ and $R^8$ are alkyl, or hydrogen;

W is —C(O)$OR^9$, —$NCH_3S(O)_2R^9$, or —NHC(O)$R^9$; and $R^9$ is hydrogen, or optionally substituted alkyl.

In certain embodiments of Formula IIb,

Y is —NH—;

$R^1$ is cyano;

$R^2$ is $(C_{1-3})$alkylene-$R^{11}$, and $R^{11}$ is aryl;

$R^3$ and $R^4$ are hydrogen;

---- is a double bond;

n is 1, or 2;

$R^7$ and $R^8$ are hydrogen;

W is $R^9$, or —$OR^9$; and $R^9$ is optionally substituted alkyl, or heteroaryl.

In certain embodiments of Formula IIb,

Y is —NH—;

$R^1$ is hydrogen;

$R^2$ is $(C_{1-3})$alkylene-$R^{11}$, and $R^{11}$ is aryl;

$R^3$ and $R^4$ are hydrogen;

---- is a double bond;

n is 2;

$R^7$ and $R^8$ are hydrogen;

W is $R^9$, —NHC(O)$R^9$, —NHS(O)$_2R^9$, or —NHC(O)$NHR^9$; and $R^9$ is hydrogen, or optionally substituted alkyl.

In certain embodiments of Formula IIa, IIIa, or IIIb,

Y is —NH—;

$R^1$ is hydrogen;

$R^2$ is $(C_{1-3})$alkylene-$R^{11}$, and $R^{11}$ is aryl;

$R^3$ is optionally substituted aryl, or optionally substituted heteroaryl;

---- is a double bond;

$R^4$ is hydrogen;
n is 2, 3, or 4;
$R^7$ and $R^8$ are hydrogen or methyl;
W is $R^9$ or —C(O)OR$^9$; and
$R^9$ is hydrogen, optionally substituted alkyl, or optionally substituted heteroaryl.
In certain embodiments of Formula IIa, IIb, IIIa, or IIIb,
$R^2$ is benzyl;
$R^3$ is hydrogen, methyl, phenyl, or benzyl; and
$R^4$ is hydrogen.
In certain embodiments of Formula IIa, IIb, IIIa, or IIIb,
$R^2$ is benzyl;
$R^3$ is hydrogen, methyl, phenyl, or benzyl;
$R^4$ is hydrogen;
---- is a double bond;
n is 1, 2, 3 or 4;
W is —C(O)OR$^9$; and
$R^7$, $R^8$ and $R^9$ are hydrogen.
In certain embodiments of Formula IIa, IIb, IIIa, or IIIb,
n is 2;
$R^7$ and $R^8$ are hydrogen or methyl; and
W is —C(O)OR$^9$.

Exemplary compounds of the present disclosure are shown in Tables I, II, III and IV, below. In the following Tables, Et is ethyl, Ph is phenyl, and Py is pyridinyl.

Exemplary compounds of Formula IIa, where Y is —NH—, and $R^4$ is hydrogen are provided in Table I.

TABLE I

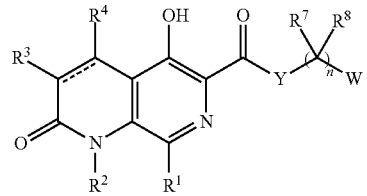

IIa

| No | $R^1$ | $R^2$ | $R^3$ | ---- | n | $R^7$ | $R^8$ | W | $R^9$ |
|---|---|---|---|---|---|---|---|---|---|
| 1 | —H | —CH$_2$Ph | —H | — | 1 | —H | —H | —C(O)OR$^9$ | —H |
| 2 | —H | —CH$_2$Ph | —CH$_3$ | = | 1 | —H | —H | —C(O)OR$^9$ | —H |
| 3 | —H | —CH$_2$Ph | —CH$_2$Ph | = | 1 | —H | —H | —C(O)OR$^9$ | —H |
| 4 | —H | —CH$_2$Ph | —Ph | = | 1 | —H | —H | —C(O)OR$^9$ | —H |
| 5 | —CH$_3$ | —CH$_2$Ph | —CH$_3$ | = | 1 | —H | —H | —C(O)OR$^9$ | —H |
| 6 | —CN | —CH$_2$Ph | —CH$_3$ | = | 1 | —H | —H | —C(O)OR$^9$ | —H |
| 7 | —H | —CH$_2$Ph | —H | = | 1 | —H | —H | —C(O)OR$^9$ | —H |
| 8 | —CH$_3$ | —CH$_2$Ph | —H | — | 1 | — | —H | —C(O)OR$^9$ | —H |
| 9 | —CN | —CH$_2$Ph | —H | — | 1 | —H | —H | —C(O)OR$^9$ | —H |
| 10 | -3-Py | —CH$_2$Ph | —CH$_3$ | = | 1 | —H | —H | —C(O)OR$^9$ | —H |
| 11 | —H | —CH$_2$Ph | —(CH$_2$)$_2$Ph | = | 1 | —H | —H | —C(O)OR$^9$ | —H |
| 12 | —CH$_3$ | —CH$_2$Ph | —Ph | = | 1 | —H | —H | —C(O)OR$^9$ | —H |
| 13 | —Ph | —CH$_2$Ph | —Ph | = | 1 | —H | —H | —C(O)OR$^9$ | —H |
| 14 | —CN | —CH$_2$Ph | —Ph | = | 1 | —H | —H | —C(O)OR$^9$ | —H |
| 15 | —CN | —CH$_2$Ph | —Ph | = | 2 | —H | —H | —C(O)OR$^9$ | —H |
| 16 | -3-Py | —CH$_2$Ph | —Ph | = | 1 | —H | —H | —C(O)OR$^9$ | —H |
| 17 | —CN | —CH$_2$Ph | —CH$_2$Ph | = | 1 | —H | —H | —C(O)OR$^9$ | —H |
| 18 | —CN | —CH$_2$Ph | —CH$_2$Ph | = | 2 | —H | —H | —C(O)OR$^9$ | —H |
| 19 | —CH$_3$ | —CH$_2$Ph | —CH$_2$Ph | = | 1 | —H | —H | —C(O)OR$^9$ | —H |
| 20 | —CH$_3$ | —CH$_2$Ph | —CH$_2$Ph | = | 2 | —H | —H | —C(O)OR$^9$ | —H |
| 21 | -3-Py | —CH$_2$Ph | —CH$_2$Ph | = | 1 | —H | —H | —C(O)OR$^9$ | —H |
| 22 | -3-Py | —CH$_2$Ph | —CH$_2$Ph | = | 2 | —H | —H | —C(O)OR$^9$ | —H |
| 23 | —CN | —CH$_2$Ph | —Ph | = | 3 | —H | —H | —C(O)OR$^9$ | —H |
| 24 | —CN | —CH$_2$Ph | —Ph | = | 4 | —H | —H | —C(O)OR$^9$ | —H |
| 25 | —CN | —CH$_2$Ph | —Ph | = | 2 | —H, —CH$_3$ | —H, —CH$_3$ | —C(O)OR$^9$ | —H |
| 40 | —CN | —CH$_2$Ph | —Ph | = | 1 | —H | —H | $R^9$ | -4-Py |
| 41 | —CN | —CH$_2$Ph | —Ph | = | 1 | —H | —H | $R^9$ | —H |
| 42 | —CN | —CH$_2$Ph | —Ph | = | 1 | —H | —CH$_2$Ph | —C(O)OR$^9$ | —H |
| 43 | —CN | —CH$_2$Ph | —Ph | = | 1 | —CH$_2$Ph | —H | —C(O)OR$^9$ | —H |
| 83 | —H | —CH$_2$Ph | —Ph | = | 1 | —H | —H | $R^9$ | —H |
| 84 | —H | —CH$_2$Ph | —Ph | = | 2 | —H | —H | —C(O)OR$^9$ | —H |
| 107 | —H | —CH$_2$Ph | —Ph | = | 2 | —H | —H | —NHC(O)OR$^9$ | —CH$_3$ |
| 108 | —H | —CH$_2$Ph | —Ph | = | 2 | —H | —H | —NCH$_3$S(O)$_2$R$^9$ | —CH$_3$ |
| 109 | —H | —CH$_2$Ph | —Ph | = | 2 | —H | —H | —NHC(O)OR$^9$ | —CF$_3$ |
| 110 | —H | —CH$_2$Ph | —Ph | = | 2 | —H | —H | —NHC(O)NHR$^9$ | —CH$_2$CH$_3$ |
| 113 | —H | —CH$_2$Ph | —Ph | = | 1 | —H | —H | $R^9$ | -5-H-tetrazolyl |
| 114 | —H | —CH$_2$Ph | —Ph | = | 2 | —H, —CH$_3$ | —H, —CH$_3$ | —C(O)OR$^9$ | —H |
| 117 | —H | —CH$_2$Ph | —Ph | = | 2 | —H | —H | —NHC(O)OR$^9$ | —H |
| 118 | -3-Py | —CH$_2$Ph | —Ph | = | 2 | —H | —H | —C(O)OR$^9$ | —H |
| 119 | —Ph | —CH$_2$Ph | —Ph | = | 2 | —H | —H | —C(O)OR$^9$ | —H |
| 120 | —CH$_3$ | —CH$_2$Ph | —Ph | = | 2 | —H | —H | —C(O)OR$^9$ | —H |
| 121 | —H | —CH$_2$Ph | —Ph | = | 2 | —H | —H | —C(O)OR$^9$ | —H |
| 122 | —H | —CH$_2$Ph | —H | = | 2 | —H | —H | —C(O)OR$^9$ | —H |
| 123 | —H | —CH$_2$Ph | —(CH$_2$)$_2$Ph | = | 2 | —H | —H | —C(O)OR$^9$ | —H |
| 124 | —H | —CH$_2$Ph | -3-Py | = | 2 | —H | —H | —C(O)OR$^9$ | —H |
| 125 | —H | —CH$_2$Ph | -2-Py | = | 2 | —H | —H | —C(O)OR$^9$ | —H |

TABLE I-continued

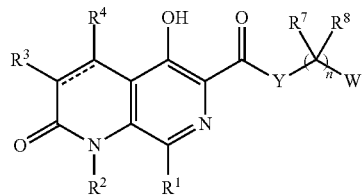

IIa

| No | $R^1$ | $R^2$ | $R^3$ | n | $R^7$ | $R^8$ | W | $R^9$ |
|---|---|---|---|---|---|---|---|---|
| 126 | —H | —CH$_2$Ph | —Ph | 3 | —H | —H | —C(O)OR$^9$ | —H |
| 127 | —H | —CH$_2$Ph | —CH$_3$ | 2 | —H | —H | —C(O)OR$^9$ | —H |
| 128 | —H | —CH$_2$Ph | 2-thienyl | 2 | —H | —H | —C(O)OR$^9$ | —H |
| 129 | —H | —CH$_2$Ph | -4-Py | 2 | —H | —H | —C(O)OR$^9$ | —H |
| 130 | —H | —CH$_2$Ph | —Ph | 2 | —H | —H | —NHS(O)$_2$R$^9$ | —CH$_3$ |
| 131 | —CN | —CH$_2$Ph | —Ph | 2 | —H | —H | —NCH$_3$S(O)$_2$R$^9$ | —CH$_3$ |
| 132 | —CH$_3$ | —CH$_2$Ph | —Ph | 2 | —H | —H | —NCH$_3$S(O)$_2$R$^9$ | —CH$_3$ |
| 133 | —Ph | —CH$_2$Ph | —Ph | 2 | —H | —H | —NCH$_3$S(O)$_2$R$^9$ | —CH$_3$ |
| 134 | -3-Py | —CH$_2$Ph | —Ph | 2 | —H | —H | —NCH$_3$S(O)$_2$R$^9$ | —H |
| 135 | —H | —(CH$_2$)$_2$Ph | —Ph | 2 | —H | —H | —C(O)OR$^9$ | —H |
| 136 | —H | —Ph | —Ph | 2 | —H | —H | —C(O)OR$^9$ | —H |
| 137 | —H | —Ph | —CH$_2$Ph | 2 | —H | —H | —C(O)OR$^9$ | —H |
| 138 | —H | —CH$_3$ | —Ph | 2 | —H | —H | —C(O)OR$^9$ | —H |
| 139 | —H | —CH$_2$Ph | 4-CN—Ph | 2 | —H | —H | —C(O)OR$^9$ | —H |
| 140 | —H | —CH$_2$Ph | 4-CH$_3$O—Ph | 2 | —H | —H | —C(O)OR$^9$ | —H |
| 141 | —H | —CH$_2$Ph | 2-thiazolyl | 2 | —H | —H | —C(O)OR$^9$ | —H |
| 142 | —H | —CH$_2$Ph | —Ph | 2 | —CH$_3$, —H | —H, —H | —C(O)OR$^9$ | —H |
| 143 | —H | —CH$_2$-4-CH$_3$O—Ph | —Ph | 2 | —H | —H | —C(O)OR$^9$ | —H |
| 144 | —H | —CH$_2$-4-CN—Ph | —Ph | 2 | —H | —H | —C(O)OR$^9$ | —H |
| 145 | —H | —CH$_2$Ph | 2-pyrazinyl | 2 | —H | —H | —C(O)OR$^9$ | —H |
| 146 | —H | —CH$_2$Ph | 4-CH$_3$S(O)$_2$—Ph | 2 | —H | —H | —C(O)OR$^9$ | —H |
| 147 | —H | —CH$_2$Ph | 3-CF$_3$—Ph | 2 | —H | —H | —C(O)OR$^9$ | —H |
| 148 | —H | —CH$_2$Ph | 4-morpholin-4-yl-Ph | 2 | —H | —H | —C(O)OR$^9$ | —H |
| 149 | —H | —CH$_2$Ph | benzo[1,2,5]oxadiazol-5-yl | 2 | —H | —H | —C(O)OR$^9$ | —H |
| 150 | —H | —CH$_2$Ph | 5-F-2-CH$_3$O—Ph | 2 | —H | —H | —C(O)OR$^9$ | —H |
| 151 | —H | —CH$_2$Ph | 4-CF$_3$O—Ph | 2 | —H | —H | —C(O)OR$^9$ | —H |
| 152 | —H | —CH$_2$Ph | —Ph | 1 | —CH$_2$Ph | —H | —C(O)OR$^9$ | —H |
| 153 | —H | —CH$_2$Ph | 1-CH$_3$-4-pyrazolyl | 2 | —H | —H | —C(O)OR$^9$ | —H |
| 154 | —H | —CH$_2$Ph | 5-pyrimidinyl | 2 | —H | —H | —C(O)OR$^9$ | —H |
| 155 | —H | —CH$_2$Ph | 2-dimethylamino-5-pyrimidinyl | 2 | —H | —H | —C(O)OR$^9$ | —H |
| 156 | —H | —CH$_2$-cyclohexyl | —Ph | 2 | —H | —H | —C(O)OR$^9$ | —H |
| 157 | —H | —CH$_2$-4-tetrahydropyranyl | —Ph | 2 | —H | —H | —C(O)OR$^9$ | —H |
| 158 | —H | —CH$_2$-2-thiazolyl | —Ph | 2 | —H | —H | —C(O)OR$^9$ | —H |
| 159 | -5-pyrimidinyl | —CH$_2$Ph | —Ph | 2 | —H | —H | —C(O)OR$^9$ | —H |
| 160 | -2-pyrazinyl | —CH$_2$Ph | —Ph | 2 | —H | —H | —C(O)OR$^9$ | —H |
| 161 | —H | —CH$_2$Ph | —Ph | 4 | —H | —H | —C(O)OR$^9$ | —H |
| 162 | -3-Py | —CH$_2$Ph | —Ph | 3 | —H | —H | —C(O)OR$^9$ | —H |
| 163 | -3-Py | —CH$_2$Ph | —Ph | 4 | —H | —H | —C(O)OR$^9$ | —H |
| 164 | -3-Py | —Ph | —Ph | 2 | —H | —H | —C(O)OR$^9$ | —H |
| 165 | -3-Py | —Me | —Ph | 2 | —H | —H | —C(O)OR$^9$ | —H |
| 166 | -3-Py | —(CH$_2$)$_2$—Ph | —Ph | 2 | —H | —H | —C(O)OR$^9$ | —H |
| 167 | -4-Py | —CH$_2$Ph | —Ph | 2 | —H | —H | —C(O)OR$^9$ | —H |
| 168 | -3-Py | —CH$_2$Ph | 3-Py | 2 | —H | —H | —C(O)OR$^9$ | —H |
| 169 | —H | (R)-1-Ph-ethyl | —Ph | 2 | —H | —H | —C(O)OR$^9$ | —H |
| 170 | —H | (R)-1-Ph-ethyl | —Ph | 3 | —H | —H | —C(O)OR$^9$ | —H |
| 171 | -5-CH$_3$O-3-Py | —CH$_2$Ph | —Ph | 2 | —H | —H | —C(O)OR$^9$ | —H |
| 172 | -5-Cl-3-Py | —CH$_2$Ph | —Ph | 2 | —H | —H | —C(O)OR$^9$ | —H |
| 173 | —H | (S)-1-phenyl-ethyl | —Ph | 2 | —H | —H | —C(O)OR$^9$ | —H |
| 174 | —H | (S)-1-phenyl-ethyl | —Ph | 3 | —H | —H | —C(O)OR$^9$ | —H |
| 175 | -3-Py | (S)-1-phenyl-ethyl | —Ph | 2 | —H | —H | —C(O)OR$^9$ | —H |

TABLE I-continued

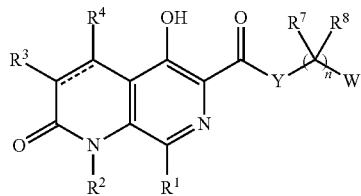

IIa

| No | R¹ | R² | R³ | | n | R⁷ | R⁸ | W | R⁹ |
|---|---|---|---|---|---|---|---|---|---|
| 176 | -3-Py | (R)-1-phenyl-ethyl | —Ph | = | 2 | —H | —H | —C(O)OR⁹ | —H |
| 177 | -5-F-3-Py | —CH₂Ph | —Ph | = | 2 | —H | —H | —C(O)OR⁹ | —H |
| 178 | -2-CH₃-3-Py | —CH₂Ph | —Ph | = | 2 | —H | —H | —C(O)OR⁹ | —H |
| 179 | -4-CH₃-3-Py | —CH₂Ph | —Ph | = | 2 | —H | —H | —C(O)OR⁹ | —H |
| 180 | -4-CF₃-3-Py | —CH₂Ph | —Ph | = | 2 | —H | —H | —C(O)OR⁹ | —H |
| 181 | -4-CH₃O-3-Py | —CH₂Ph | —Ph | = | 2 | —H | —H | —C(O)OR⁹ | —H |
| 182 | -3-Py | —CH₂-4-tetrahydropyranyl | —Ph | = | 2 | —H | —H | —C(O)OR⁹ | —H |
| 183 | -3-Py | —CH₂-cyclohexyl | —Ph | = | 2 | —H | —H | —C(O)OR⁹ | —H |
| 184 | —H | —CH₂-cyclohexyl | —Ph | = | 3 | —H | —H | —C(O)OR⁹ | —H |
| 185 | -3-Py | —CH₂Ph | 4-CH₃O—Ph | = | 2 | —H | —H | —C(O)OR⁹ | —H |
| 186 | —H | —CH₂Ph | 4-CH₃eO—Ph | = | 3 | —H | —H | —C(O)OR⁹ | —H |
| 187 | —H | —CH₂Ph | 3-CH₃O—Ph | = | 2 | —H | —H | —C(O)OR⁹ | —H |
| 188 | —H | —CH₂Ph | 3-CH₃O—Ph | = | 3 | —H | —H | —C(O)OR⁹ | —H |
| 189 | —H | —CH₂Ph | —Ph | = | 1 | R⁷/R⁸ = cyclopropyl | | —C(O)OR⁹ | —H |
| 190 | -3-Py | —CH₂Ph | —Ph | = | 1 | R⁷/R⁸ = cyclopropyl | | —C(O)OR⁹ | —H |
| 191 | -3-Py | —CH₂Ph | —Ph | = | 2 | —H, —CH₃ | —H, —CH₃ | —C(O)OR⁹ | —H |
| 192 | -2-EtO-5-pyrimidinyl | —CH₂Ph | —Ph | = | 2 | —H | —H | —C(O)OR⁹ | —H |
| 193 | -3-Py | —CH₂Ph | —Ph | = | 2 | —H | —H | —C(O)OR⁹ | —H |
| 194 | -4-pyridazinyl | —CH₂Ph | —Ph | = | 2 | —H | —H | —C(O)OR⁹ | —H |
| 195 | -2-thiazolyl | —CH₂Ph | —Ph | = | 2 | —H | —H | —C(O)OR⁹ | —H |
| 198 | -4-Py | —CH₂—cyclohexyl | —Ph | = | 2 | —H | —H | —C(O)OR⁹ | —H |
| 199 | -4-Py | —Ph | —Ph | = | 2 | —H | —H | —C(O)OR⁹ | —H |
| 200 | -1-CH₃-4-pyrazolyl | —CH₂Ph | —Ph | = | 2 | —H | —H | —C(O)OR⁹ | —H |
| 201 | -5-thiazolyl | —CH₂Ph | —Ph | = | 2 | —H | —H | —C(O)OR⁹ | —H |
| 202 | -4-thiazolyl | —CH₂Ph | —Ph | = | 2 | —H | —H | —C(O)OR⁹ | —H |
| 203 | -3-pyridazinyl | —CH₂Ph | —Ph | = | 2 | —H | —H | —C(O)OR⁹ | —H |
| 204 | -3-Py | —CH₂Ph | —(CH₂)₂Ph | = | 2 | —H | —H | —C(O)OR⁹ | —H |
| 205 | —H | —CH₂Ph | —CH₂Ph | = | 2 | —H | —H | —C(O)OR⁹ | —H |
| 207 | -2-EtO-5-pyrimidinyl | —CH₂-cyclohexyl | —Ph | = | 2 | —H | —H | —C(O)OR⁹ | —H |
| 208 | -2-EtS-5-pyrimidinyl | —CH₂Ph | —Ph | = | 2 | —H | —H | —C(O)OR⁹ | —H |
| 209 | —H | —CH₂Ph | 4-CF₃—Ph | = | 2 | —H | —H | —C(O)OR⁹ | —H |
| 210 | —H | —CH₂Ph | 2-CF₃—Ph | = | 2 | —H | —H | —C(O)OR⁹ | —H |
| 211 | —H | —CH₂Ph | 4-CF₃—Ph | = | 3 | —H | —H | —C(O)OR⁹ | —H |
| 212 | —H | —CH₂Ph | 3-CF₃—Ph | = | 3 | —H | —H | —C(O)OR⁹ | —H |
| 213 | —H | —CH₂Ph | 2-CF₃—Ph | = | 3 | —H | —H | —C(O)OR⁹ | —H |
| 214 | -3-Py | —CH₂Ph | 4-CF₃—Ph | = | 2 | —H | —H | —C(O)OR⁹ | —H |
| 215 | -3-Py | —CH₂Ph | 3-CF₃—Ph | = | 2 | —H | —H | —C(O)OR⁹ | —H |
| 216 | -3-Py | —CH₂Ph | 2-CF₃—Ph | = | 2 | —H | —H | —C(O)OR⁹ | —H |
| 217 | —H | —CH₂cyclopentyl | —Ph | = | 2 | —H | —H | —C(O)OR⁹ | —H |
| 218 | —H | —CH₂cyclopentyl | —Ph | = | 3 | —H | —H | —C(O)OR⁹ | —H |
| 219 | -3-Py | —CH₂cyclopentyl | —Ph | = | 2 | —H | —H | —C(O)OR⁹ | —H |

TABLE I-continued

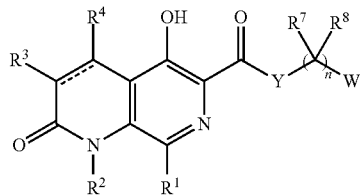

| No | R¹ | R² | R³ | n | R⁷ | R⁸ | W | R⁹ |
|---|---|---|---|---|---|---|---|---|
| 221 | —H | 2-ethyl-butyl | —Ph | 2 | —H | —H | —C(O)OR⁹ | —H |
| 222 | —H | 2-ethyl-butyl | —Ph | 3 | —H | —H | —C(O)OR⁹ | —H |
| 223 | -3-Py | 2-ethyl-butyl | —Ph | 2 | —H | —H | —C(O)OR⁹ | —H |
| 224 | -4-Py | 2-ethyl-butyl | —Ph | 2 | —H | —H | —C(O)OR⁹ | —H |
| 225 | —H | —CH₂Ph | —Ph | 1 | —H | —H | R⁹ | 3-carboxyphenyl |
| 226 | -3-Py | —CH₂Ph | —Ph | 2 | R⁷/R⁸ = cyclopropyl, —H | | —C(O)OR⁹ | —H |

Exemplary compounds of Formula IIb, where R³, and R⁴ are hydrogen are provided in Table II.

TABLE II

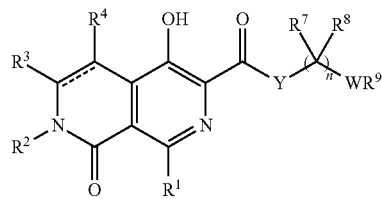

| No | R¹ | R² | Y | R⁶ | n | R⁷ | R⁸ | W | R⁹ |
|---|---|---|---|---|---|---|---|---|---|
| 26 | —H | —CH₂Ph | —NR⁶— | —H | 1 | —H | —H | —C(O)OR⁹ | —H |
| 27 | —H | —CH₂Ph | —NR⁶— | —H | 2 | —H | —H | —C(O)OR⁹ | —H |
| 28 | —H | —CH₂Ph | —NR⁶— | —H | 2 | —H, —CH₃ | —H, —CH₃ | —C(O)OR⁹ | —H |
| 29 | —H | —CH₂Ph | —NR⁶— | —H | 3 | —H | —H | —C(O)OR⁹ | —H |
| 30 | —H | —CH₂Ph | —NR⁶— | —H | 4 | —H | —H | —C(O)OR⁹ | —H |
| 31 | —H | —CH₂Ph | —NR⁶— | —H | 1 | —H | —H | R⁹ | -4-Py |
| 32 | —H | —CH₂Ph | —NR⁶— | —H | 1 | —H | —H | R⁹ | —H |
| 33 | —H | —CH₂Ph | —O— | —H | 0 | — | — | R⁹ | —H |
| 34 | —H | —CH₂Ph | —NR⁶— | —CH₃ | 1 | —H | —H | R⁹ | —H |
| 35 | —H | —CH₂Ph | —NR⁶— | —H | 0 | — | — | R⁹ | —H |
| 36 | —H | —CH₂Ph | —NR⁶— | —H | 3 | —H | —H | R⁹ | —H |
| 37 | —H | —CH₂Ph | —NR⁶— | —H | 0 | — | — | R⁹ | cyclopropyl |
| 38 | —CN | —CH₂Ph | —NR⁶— | —H | 1 | —H | —H | R⁹ | —H |
| 39 | —CN | —CH₂Ph | —NR⁶— | —H | 0 | — | — | R⁹ | cyclopropyl |
| 44 | —CH₃ | —CH₂Ph | —NR⁶— | —H | 1 | —H | —H | —C(O)OR⁹ | —H |
| 45 | -5-F-3-Py | —CH₂Ph | —NR⁶— | —H | 1 | —H | —H | —C(O)OR⁹ | —H |
| 46 | —Ph | —CH₂Ph | —NR⁶— | —H | 1 | —H | —H | —C(O)OR⁹ | —H |
| 47 | —CN | —CH₂Ph | —NR⁶— | —H | 1 | —H | —H | —C(O)OR⁹ | —H |
| 48 | —CN | —CH₂Ph | —NR⁶— | —H | 1 | —H | —H | R⁹ | -4-Py |
| 49 | —CN | —CH₂Ph | —NR⁶— | —H | 2 | —H | —H | —C(O)OR⁹ | —H |
| 50 | —CN | —CH₂Ph | —NR⁶— | —H | 2 | —H, —CH₃ | —H, —CH₃ | —C(O)OR⁹ | —H |
| 51 | —CN | —CH₂Ph | —NR⁶— | —H | 1 | —H | —CH₂Ph | —C(O)OR⁹ | —H |
| 52 | —CN | —CH₂Ph | —NR⁶— | —H | 4 | —H | —H | —C(O)OR⁹ | —H |
| 56 | —CN | —CH₂Ph | —NR⁶— | —H | 1 | —CH₂Ph | —H | —C(O)OR⁹ | —H |
| 57 | —CN | —CH₂Ph | —NR⁶— | —H | 1 | —CH₃ | —H | —C(O)OR⁹ | —H |
| 58 | —CN | —CH₂Ph | —NR⁶— | —H | 1 | —H | —CH₃ | —C(O)OR⁹ | —H |
| 59 | —CN | —CH₂Ph | —NR⁶— | —H | 2 | —H | —H | R⁹ | morpholino |
| 60 | —CN | —CH₂Ph | —NR⁶— | —H | 1 | —H | —H | R⁹ | pyridazin-4-yl |
| 61 | —CN | —CH₂Ph | —NR⁶— | —H | 2 | —H | —H | —OR⁹ | —CH₂C(O)₂H |
| 62 | —CN | —CH₂Ph | —NR⁶— | —H | 2 | —H, R⁷/R⁸ = cyclobutyl | —H | —C(O)OR⁹ | —H |

TABLE II-continued

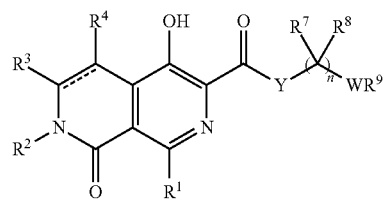

IIb

| No | R¹ | R² | Y | ----- | R⁶ | n | R⁷ | R⁸ | W | R⁹ |
|---|---|---|---|---|---|---|---|---|---|---|
| 63 | —H | —CH$_2$-2,4-(OCH$_3$)$_2$Ph | —NR⁶— | = | —H | 1 | —H | —H | R⁹ | —H |
| 64 | —H | —CH$_2$-2,4-(OCH$_3$)$_2$Ph | —NR⁶— | = | —H | 1 | —H | —H | —C(O)OR⁹ | —H |
| 65 | —H | —CH$_2$-2,4-(OCH$_3$)$_2$Ph | —NR⁶— | = | —H | 2 | —H | —H | —C(O)OR⁹ | —H |
| 66 | —H | —CH$_2$-2,4-(OCH$_3$)$_2$Ph | —NR⁶— | — | —H | 1 | —H | —H | R⁹ | —H |
| 67 | —H | —CH$_2$-2,4-(OCH$_3$)$_2$Ph | —NR⁶— | — | —H | 1 | —H | —H | —C(O)OR⁹ | —H |
| 68 | —H | —CH$_2$-2,4-(OCH$_3$)$_2$Ph | —NR⁶— | — | —H | 2 | —H | —H | —C(O)OR⁹ | —H |
| 73 | —CN | —CH$_2$Ph | —NR⁶— | = | —H | 3 | —H | —H | —C(O)NHR⁹ | —(CH$_2$)$_2$CH$_3$ |
| 74 | —H | —H | —NR⁶— | = | —H | 2 | —H | —H | —C(O)OR⁹ | —H |
| 76 | —H | —CH$_2$-2,4-(OCH$_3$)$_2$Ph | —NR⁶— | = | —H | 2 | —H | —H | R⁹ | —Ph |
| 77 | —H | —CH$_2$-2,4-(OCH$_3$)$_2$Ph | —NR⁶— | = | —H | 2 | —H | —H | —OR⁹ | —CH$_3$ |
| 78 | —H | —CH$_2$-2,4-(OCH$_3$)$_2$Ph | —NR⁶— | = | —H | 1 | —H | —H | R⁹ | -4-F—Ph |
| 85 | —H | —CH$_2$Ph | —NR⁶— | = | —H | 2 | —H | —H | —OR⁹ | —CH$_2$C(O)$_2$H |
| 86 | —H | —CH$_2$Ph | —NR⁶— | = | —H | 1 | —H | —H | R⁹ | -5-H-tetrazolyl |
| 87 | -5-F-3-Py | —CH$_2$Ph | —NR⁶— | = | —H | 2 | —H | —H | —C(O)OR⁹ | —H |
| 88 | -5-F-3-Py | —CH$_2$Ph | —NR⁶— | = | —H | 2 | —H, —CH$_3$ | —H, —CH$_3$ | —C(O)OR⁹ | —H |
| 89 | —H | —CH$_2$Ph | —NR⁶— | = | —H | 2 | —H | —H | —NHC(O)NHR⁹ | —CH(CH$_3$)$_2$ |
| 90 | —H | —CH$_2$Ph | —NR⁶— | = | —H | 2 | —H | —H | —S(O)$_2$NHR⁹ | —H |
| 91 | —H | —CH$_2$Ph | —NR⁶— | = | —H | 2 | —H | —H | —C(O)NHR⁹ | —CF$_3$ |
| 92 | —H | —CH$_2$Ph | —NR⁶— | = | —H | 2 | —H | —H | —C(O)NHR⁹ | —CH$_3$ |
| 97 | —H | —CH$_2$Ph | —NR⁶— | = | —H | 2 | —H | —H | —NCH$_3$C(O)R⁹ | —CF$_3$ |
| 98 | —H | —CH$_2$Ph | —NR⁶— | = | —H | 2 | —H | —H | —NCH$_3$C(O)NHR⁹ | —CH(CH$_3$)$_2$ |
| 99 | —H | —CH$_2$Ph | —NR⁶— | = | —H | 2 | —H | —H | —NCH$_3$C(O)OR⁹ | —CH$_3$ |
| 100 | —H | —CH$_2$Ph | —NR⁶— | = | —H | 2 | —H | —H | —NCH$_3$S(O)$_2$R⁹ | —CH$_3$ |
| 101 | —H | —CH$_2$Ph | —NR⁶— | = | —H | 2 | —H | —H | —NHS(O)$_2$R⁹ | —CH$_3$ |
| 102 | —H | —CH$_2$Ph | —NR⁶— | = | —H | 3 | —H | —H | —NHC(O)R⁹ | —CF$_3$ |
| 103 | —H | —CH$_2$Ph | —NR⁶— | = | —H | 3 | —H | —H | —NHC(O)NHR⁹ | —CH(CH$_3$)$_2$ |
| 104 | —H | —CH$_2$Ph | —NR⁶— | = | —H | 3 | —H | —H | —NHC(O)NHR⁹ | —H |
| 115 | —H | —CH$_2$Ph | —NR⁶— | = | —H | 2 | —H | —H | —NCH$_3$C(O)R⁹ | —H |
| 116 | —H | —CH$_2$Ph | —NR⁶— | = | —H | 2 | —H | —H | —NCH$_3$C(O)R⁹ | —CH$_3$ |
| 196 | —H | —CH$_2$Ph | —NR⁶— | = | —H | 3 | —H | —H | —NHC(O)R⁹ | —H |
| 197 | —H | —CH$_2$Ph | —NR⁶— | = | —H | 3 | —H | —H | —NHC(O)R⁹ | —CH$_3$ |
| 206 | -3-Py | —CH$_2$Ph | —NR⁶— | = | —H | 2 | —H | —H | —C(O)OR⁹ | —H |
| 220 | —H | —CH$_2$Ph | —NR⁶— | = | —H | 1 | R⁷/R⁸ = cyclopropyl | | —C(O)OR⁹ | —H |

Exemplary compounds of Formula Ina, where Y is —NH—, $R^3$, and $R^4$ are hydrogen are provided in Table III.

TABLE III

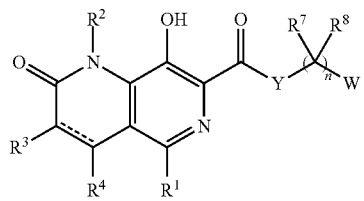

IIIa

| No | $R^1$ | $R^2$ | ----- | n | $R^7$ | $R^8$ | W | $R^9$ |
|---|---|---|---|---|---|---|---|---|
| 69 | —H | —CH$_2$Ph | = | 1 | —H | —H | —C(O)OR$^9$ | —H |
| 70 | —H | —CH$_2$Ph | = | 2 | —H | —H | —C(O)OR$^9$ | —H |
| 71 | —H | —CH$_2$Ph | = | 2 | —H, —CH$_3$ | —H, —CH$_3$ | —C(O)OR$^9$ | —H |
| 72 | —H | —CH$_2$Ph | = | 1 | —H | —H | R$^9$ | -4-Py |
| 75 | —H | —CH$_2$Ph | = | 1 | —H | —H | R$^9$ | —H |
| 79 | —CN | —CH$_2$Ph | = | 1 | —H | —H | R$^9$ | —H |
| 80 | -5-F-3-Py | —CH$_2$Ph | = | 1 | —H | —H | —C(O)OR$^9$ | —H |
| 81 | -5-F-3-Py | —CH$_2$Ph | = | 2 | —H | —H | —C(O)OR$^9$ | —H |
| 82 | —H | —CH$_2$Ph | = | 1 | —H | —H | R$^9$ | -5-H-tetrazolyl |
| 93 | —CN | —CH$_2$Ph | = | 1 | —H | —H | —C(O)OR$^9$ | —H |
| 94 | —CN | —CH$_2$Ph | = | 2 | —H | —H | —C(O)OR$^9$ | —H |
| 95 | —CN | —CH$_2$Ph | = | 2 | —H | —H | —NHC(O)R$^9$ | —CH$_3$ |
| 96 | —H | —CH$_2$Ph | = | 2 | —H | —H | —NHC(O)R$^9$ | —CH$_3$ |
| 105 | —H | —CH$_2$Ph | = | 2 | —H | —H | —NCH$_3$S(O)$_2$R$^9$ | —CH$_3$ |
| 106 | —CN | —CH$_2$Ph | = | 2 | —H | —H | —S(O)NHR$^9$ | —H |
| 111 | —H | —CH$_2$Ph | = | 2 | —H | —H | —NHS(O)$_2$R$^9$ | —CH$_3$ |
| 112 | —CH$_3$ | —CH$_2$Ph | = | 2 | —H | —H | —C(O)OR$^9$ | —H |

Exemplary compounds of Formula IIIb, where Y is —NH—, $R^3$, and $R^4$ are hydrogen are provided in Table IV.

TABLE IV

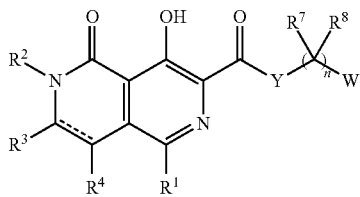

IIIb

| No | $R^1$ | $R^2$ | ----- | n | $R^7$ | $R^8$ | W | $R^9$ |
|---|---|---|---|---|---|---|---|---|
| 53 | —H | —CH$_2$Ph | = | 1 | —H | —H | —C(O)OR$^9$ | —H |
| 54 | —H | —CH$_2$Ph | = | 2 | —H | —H | —C(O)OR$^9$ | —H |
| 55 | —CN | —CH$_2$Ph | = | 1 | —H | —H | —C(O)OR$^9$ | —H |

Compounds of the disclosure include, but are not limited to, [(1-benzyl-5-hydroxy-2-oxo-1,2,3,4-tetrahydro-[1,7]naphthyridine-6-carbonyl)-amino]-acetic acid; [(1-benzyl-5-hydroxy-3-methyl-2-oxo-1,2-dihydro-[1,7]naphthyridine-6-carbonyl)-amino]-acetic acid; [(1,3-dibenzyl-5-hydroxy-2-oxo-1,2-dihydro-[1,7]naphthyridine-6-carbonyl)-amino]-acetic acid; [(1-benzyl-5-hydroxy-2-oxo-3-phenyl-1,2-dihydro-[1,7]naphthyridine-6-carbonyl)-amino]-acetic acid; [(1-benzyl-5-hydroxy-3,8-dimethyl-2-oxo-1,2-dihydro-[1,7]naphthyridine-6-carbonyl)-amino]-acetic acid; [(1-benzyl-8-cyano-5-hydroxy-3-methyl-2-oxo-1,2-dihydro-[1,7]naphthyridine-6-carbonyl)-amino]-acetic acid; [(1-benzyl-5-hydroxy-2-oxo-1,2-dihydro-[1,7]naphthyridine-6-carbonyl)-amino]-acetic acid; [(1-benzyl-5-hydroxy-8-methyl-2-oxo-1,2,3,4-tetrahydro-[1,7]naphthyridine-6-carbonyl)-amino]-acetic acid; [(1-benzyl-8-cyano-5-hydroxy-2-oxo-1,2,3,4-tetrahydro-[1,7]naphthyridine-6-carbonyl)-amino]-acetic acid; [(1-benzyl-5-hydroxy-3-methyl-2-oxo-8-pyridin-3-yl-1,2-dihydro-[1,7]naphthyridine-6-carbonyl)-amino]-acetic acid; [(1-benzyl-5-hydroxy-2-oxo-3-phenethyl-1,2-dihydro-[1,7]naphthyridine-6-carbonyl)-amino]-acetic acid; [(1-benzyl-5-hydroxy-8-methyl-2-oxo-3-phenyl-1,2-dihydro-[1,7]naphthyridine-6-carbonyl)-amino]-acetic acid; [(1-benzyl-5-hydroxy-2-oxo-3,8-diphenyl-1,2-dihydro-[1,7]naphthyridine-6-carbonyl)-amino]-acetic acid; [(1-benzyl-8-cyano-5-hydroxy-2-oxo-3-phenyl-1,2-dihydro-[1,7]naphthyridine-6-carbonyl)-amino]-acetic acid; 3-[(1-benzyl-8-cyano-5-hydroxy-2-oxo-3-phenyl-1,2-dihydro-[1,7]naphthyridine-6-carbonyl)-amino]-propionic acid; [(1-benzyl-5-hydroxy-2-oxo-3-phenyl-8-pyridin-3-yl-1,2-dihydro-[1,7]naphthyridine-6-carbonyl)-amino]-acetic acid; [(1,3-dibenzyl-8-cyano-5-hydroxy-2-oxo-1,2-dihydro-[1,7]naphthyridine-6-carbonyl)-amino]-acetic acid; 3-[(1,3-dibenzyl-8-cyano-5-hydroxy-2-oxo-1,2-dihydro-[1,7]naphthyridine-6-carbonyl)-amino]-propionic acid; [(1,3-dibenzyl-5-hydroxy-8-methyl-2-oxo-1,2-dihydro-[1,7]naphthyridine-6-carbonyl)-amino]-acetic acid; 3-[(1,3-dibenzyl-5-hydroxy-8-methyl-2-oxo-1,2-dihydro-[1,7]naphthyridine-6-carbonyl)-amino]-propionic acid; [(1,3-dibenzyl-5-hydroxy-2-oxo-8-pyridin-3-yl-1,2-dihydro-[1,7]naphthyridine-6-carbonyl)-amino]-acetic acid; 3-[(1,3-dibenzyl-5-hydroxy-2-oxo-8-pyridin-3-yl-1,2-dihydro-[1,7]naphthyridine-6-carbonyl)-amino]-propionic acid; 4-[(1-benzyl-8-cyano-5-hydroxy-2-oxo-3-phenyl-1,2-dihydro-[1,7]naphthyridine-6-carbonyl)-amino]-butyric acid; 5-[(1-benzyl-8-cyano-5-hydroxy-2-oxo-3-phenyl-1,2-dihydro-[1,7]naphthyridine-6-carbonyl)-amino]-pentanoic acid; 3-[(1-benzyl-8-cyano-5- hydroxy-2-oxo-3-phenyl-1,2-dihydro-[1,7]naphthyridine-6-carbonyl)-amino]-2,2-dimethyl-propionic acid; [(7-benzyl-4-hydroxy-8-oxo-7,8-dihydro-[2,7]naphthyridine-3-carbonyl)-amino]-acetic acid; 3-[(7-benzyl-4-hydroxy-8-oxo-7,8-dihydro-[2,7]naphthyridine-3-carbonyl)-amino]-propionic acid; 3-[(7-benzyl-4-hydroxy-8-oxo-7,8-dihydro-[2,7]naphthyridine-3-carbonyl)-amino]-2,2-dimethyl-propionic acid; 4-[(7-benzyl-4-hydroxy-8-oxo-7,8-dihydro-[2,7]naphthyridine-3-carbonyl) -amino]-butyric acid; 5-[(7-benzyl-4-hydroxy-8-oxo-7,8-dihydro-[2,7]naphthyridine-3-carbonyl)-amino]-pentanoic acid; 7-benzyl-4-hydroxy-8-oxo-7,8-dihydro-[2,7]naphthyridine-3-carboxylic acid (pyridin-4-ylmethyl)-amide; 7-benzyl-4-hydroxy-8-oxo-7,8-dihydro-[2,7]naphthyridine-3-carboxylic acid methylamide; 7-benzyl-4-hydroxy-8-oxo-7,8-dihydro-[2,7]naphthyridine-3-carboxylic acid; 7-benzyl-4-hydroxy-8-oxo-7,8-dihydro-[2,7]naphthyridine-3-carboxylic acid dimethylamide; 7-benzyl-4-hydroxy-8-oxo-7,8-dihydro-[2,7]naphthyridine-3-carboxylic acid amide; 7-benzyl-4-hydroxy-8-oxo-7,8-dihydro-[2,7]naphthyridine-3-carboxylic acid propylamide; 7-benzyl-4-hydroxy-8-oxo-7,8-dihydro-[2,7]naphthyridine-3-carboxylic acid cyclopropylamide; 1-benzyl-8-cyano-5-hydroxy-2-oxo-3-phenyl-1,2-dihydro-[1,7]naphthyridine-6-carboxylic acid (pyridin-4-ylmethyl)-amide; (R)-2-[(1-benzyl-8-cyano-5-hydroxy-2-oxo-3-phenyl-1,2-dihydro-[1,7]naphthyridine-6-carbonyl)-amino]-3-phenyl-propionic acid; (S)-2-[(1-benzyl-8-cyano-5-hydroxy-2-oxo-3-phenyl-1,2-dihydro-[1,7]naphthyridine-6-carbonyl)-amino]-3-phenyl-propionic acid; [(7-benzyl-4-hydroxy-1-methyl-8-oxo-7,8-dihydro-[2,7]naphthyridine-3-carbonyl)-amino]-acetic acid; {[7-benzyl-1-(5-fluoro-pyridin-3-yl)-4-hydroxy-8-oxo-7,8-dihydro-[2,7]naphthyridine-3-carbonyl]-amino}-acetic acid; [(7-benzyl-4-hydroxy-8-oxo-1-phenyl-7,8-dihydro-[2,7]naphthyridine-3-carbonyl)-amino]-acetic acid; [(7-benzyl-1-cyano-4-hydroxy-8-oxo-7,8-dihydro-[2,7]naphthyridine-3-carbonyl)-amino]-acetic acid; 7-benzyl-1-cyano-4-hydroxy-8-oxo-7,8-dihydro-[2,7]naphthyridine-3-carboxylic acid (pyridin-4-ylmethyl)-amide; 3-[(7-benzyl-1-cyano-4-hydroxy-8-oxo-7,8-dihydro-[2,7]naphthyridine-3-carbonyl)-amino]-propionic acid; 3-[(7-benzyl-1-cyano-4-hydroxy-8-oxo-7,8-dihydro-[2,7]naphthyridine-3-carbonyl)-amino]-2,2-dimethyl-propionic acid; (R)-2-[(7-benzyl-1-cyano-4-hydroxy-8-oxo-7,8-dihydro-[2,7]naphthyridine-3-carbonyl)-amino]-3-phenyl-propionic acid; 5-[(7-benzyl-1-cyano-4-hydroxy-8-oxo-7,8-dihydro-[2,7]naphthyridine-3-carbonyl)-amino]-pentanoic acid; [(6-benzyl-4-hydroxy-5-oxo-5,6-dihydro-[2,6]naphthyridine-3-carbonyl)-amino]-acetic acid; 3-[(6-benzyl-4-hydroxy-5-oxo-5,6-dihydro-[2,6]naphthyridine-3-carbonyl)-amino]-propionic acid; [(6-benzyl-1-cyano-4-hydroxy-5-oxo-5,6-dihydro-[2,6]naphthyridine-3-carbonyl)-amino]-acetic acid; (S)-2-[(7-benzyl-1-cyano-4-hydroxy-8-oxo-7,8-dihydro-[2,7]naphthyridine-3-carbonyl)-amino]--phenyl-propionic acid; (S)-2-[(7-benzyl-1-cyano-4-hydroxy-8-oxo-7,8-dihydro-[2,7]naphthyridine-3-carbonyl)-amino]-propionic acid; (R)-2-[(7-benzyl-1-cyano-4-hydroxy-8-oxo-7,8-dihydro-[2,7]naphthyridine-3-carbonyl)-amino]-propionic acid; 7-benzyl-1-cyano-4-hydroxy-8-oxo-7,8-dihydro-[2,7]naphthyridine-3-carboxylic acid (2-morpholin-4-yl-ethyl)-amide; 7-benzyl-1-cyano-4-hydroxy-8-oxo-7,8-dihydro-[2,7]naphthyridine-3-carboxylic acid (pyridazin-4-ylmethyl)-amide; {2-[(7-benzyl-1-cyano-4-hydroxy-8-oxo-7,8-dihydro-[2,7]naphthyridine-3-carbonyl)-amino]ethoxy}-acetic acid; 1-{[(7-benzyl-1-cyano-4-hydroxy-8-oxo-7,8-dihydro-[2,7]naphthyridine-3-carbonyl) -amino]-methyl}-cyclobutanecarboxylic acid; 7-(2,4-dimethoxy-benzyl)-4-hydroxy-8-oxo-7,8-dihydro-[2,7]naphthyridine-3-carboxylic acid methylamide; {[7-(2,4-dimethoxy-benzyl)-4-hydroxy-8-oxo-7,8-dihydro-[2,7]naphthyridine-3-carbonyl]-amino}-acetic acid; 3-{[7-(2,4-dimethoxy-benzyl)-4-hydroxy-8-oxo-7,8-dihydro-[2,7]naphthyridine-3-carbonyl]-amino}-propionic acid; 7-(2,4-dimethoxy-benzyl)-4-hydroxy-8-oxo-5,6,7,8-tetrahydro-[2,7]naphthyridine-3-carboxylic acid methylamide; {[7-(2,4-dimethoxy-benzyl)-4-hydroxy-8-oxo-5,6,7,8-tetrahydro-[2,7]naphthyridine-3-carbonyl]-amino}-acetic acid; 3-{[7-(2,4-dimethoxy-benzyl)-4-hydroxy-8-oxo-5,6,7,8-tetrahydro-[2,7]naphthyridine-3-carbonyl]-amino}-propionic acid; [(1-benzyl-8-hydroxy-2-oxo-1,2-dihydro-[1,6]naphthyridine-7-carbonyl)-amino]-acetic acid; 3-[(1-benzyl-8-hydroxy-2-oxo-1,2-dihydro-[1,6]naphthyridine-7-carbonyl)-amino]-propionic acid; 3-[(1-benzyl-8-hydroxy-2-oxo-1,2-dihydro-[1,6]naphthyridine-7-carbonyl)-amino]-2,2-dimethyl-propionic acid; 1-benzyl-8-hydroxy-2-oxo-1,2-dihydro-[1,6]naphthyridine-7-carboxylic acid (pyridin-4-ylmethyl)-amide; 7-benzyl-1-cyano-4-hydroxy-8-oxo-7,8-dihydro-[2,7]naphthyridine-3-carboxylic acid (3-propylcarbamoyl-propyl)-amide; 3-[(4-hydroxy-8-oxo-7,8-dihydro-[2,7]naphthyridine-3-carbonyl)-amino]-propionic acid; 1-benzyl-8-hydroxy-2-oxo-1,2-dihydro-[1,6]naphthyridine-7-carboxylic acid methylamide; 7-(,4-dimethoxy-benzyl)-4-hydroxy-8-oxo-7,8-dihydro-[2,7]naphthyridine-3-carboxylic acid phenethyl-amide; 7-(2,4-dimethoxy-benzyl)-4-hydroxy-8-oxo-7,8-dihydro-[2,7]naphthyridine-3-carboxylic acid (2-methoxy-ethyl)-amide; 7-(2,4-dimethoxy-benzyl)-4-hydroxy-8-oxo-7,8-dihydro-[2,7]naphthyridine-3-carboxylic acid 4-fluoro-benzylamide; 1-benzyl-5-cyano-8-hydroxy-2-oxo-1,2-dihydro-[1,6]naphthyridine-7-carboxylic acid methylamide; {[1-benzyl-5-(5-fluoro-pyridin-3-yl)-8-hydroxy-2-oxo-1,2-dihydro-[1,6]naphthyridine-7-carbonyl]-amino}-acetic acid; 3-{[1-benzyl-5-(5-fluoro-pyridin-3-yl)-8-hydroxy-2-oxo-1,2-dihydro-[1,6]naphthyridine-7-carbonyl]-amino}-propionic acid; 1-benzyl-8-hydroxy-2-oxo-1,2-dihydro-[1,6]naphthyridine-7-carboxylic acid (1H-tetrazol-5-ylmethyl)-amide; 1-benzyl-5-hydroxy-2-oxo-3-phenyl-1,2-dihydro-[1,7]naphthyridine-6-carboxylic acid methylamide; 3-[(1-benzyl-5-hydroxy-2-oxo-3-phenyl-1,2-dihydro-[1,7]naphthyridine-6-carbonyl)-amino]-propionic acid; {2-[(7-benzyl-4-hydroxy-8-oxo-7,8-dihydro-[2,7]naphthyridine-3-carbonyl)-amino]ethoxy}-acetic acid; 7-benzyl-4-hydroxy-8-oxo-7,8-dihydro-[2,7]naphthyridine-3-carboxylic acid (1H-tetrazol-5-ylmethyl)-amide; 3-{[7-benzyl-1-(5-fluoro-pyridin-3-yl)-4-hydroxy-8-oxo-7,8-dihydro-[2,7]naphthyridine-3-carbonyl]-amino}-propionic acid; 3-{[7-benzyl-1-(5-fluoro-pyridin-3-yl)-4-hydroxy-8-oxo-7,8-dihydro-[2,7]naphthyridine-3-carbonyl]-amino}-2,2-dimethyl-propionic acid; 7-benzyl-4-hydroxy-8-oxo-7,8-dihydro-[2,7]naphthyridine-3-carboxylic acid [2-(3-isopropyl-ureido)-ethyl]-amide; 7-benzyl-4-hydroxy-8-oxo-7,8-dihydro-[2,7]naphthyridine-3-carboxylic acid (2-sulfamoyl-ethyl)-amide; 7-benzyl-4-hydroxy-8-oxo-7,8-dihydro-[2,7]naphthyridine-3-carboxylic acid [2-(2,2,2-trifluoro-acetylamino)-ethyl]-amide; 7-benzyl-4-hydroxy-8-oxo-7,8-dihydro-[2,7]naphthyridine-3-carboxylic acid (2-acetylamino-ethyl)-amide; [(1-benzyl-5-cyano-8-hydroxy-2-oxo-1,2-dihydro-[1,6]naphthyridine-7-carbonyl)-amino]-acetic acid; 3-[(1-benzyl-5-cyano-8-hydroxy-2-oxo-1,2-dihydro-[1,6]naphthyridine-7-carbonyl)-amino]-propionic acid; 1-benzyl-5-cyano-8-hydroxy-2-oxo-1,2-dihydro-[1,6]naphthyridine-7-carboxylic acid (2-acetylamino-ethyl)-amide; 1-benzyl-8-hydroxy-2-oxo-1,2-dihydro-[1,6]naphthyridine-7-carboxylic acid (2-acetylamino-ethyl)-amide; 7-benzyl-4- hydroxy-8-oxo-7,8-dihydro-[2,7]naphthyridine-3-carboxylic acid {2-[methyl-(2,2,2-trifluoro-acetyl)-amino]-ethyl}-amide; 7-benzyl-4-hydroxy-8-oxo-7,8-dihydro-[2,7]naphthyridine-3-carboxylic acid [2-(3-isopropyl-1-methyl-ureido)-ethyl]-amide; {2-[(7-benzyl-4-hydroxy-8-oxo-7,8-dihydro-[2,7]naphthyridine-3-carbonyl)-amino]ethyl}-methyl-carbamic acid methyl ester; 7-benzyl-4-hydroxy-8-oxo-7,8-dihydro-[2,7]naphthyridine-3-carboxylic acid [2-(methanesulfonyl-methyl-amino)-ethyl]-amide; 7-benzyl-4-hydroxy-8-oxo-7,8-dihydro-[2,7]naphthyridine-3-carboxylic acid (2-methanesulfonylamino-ethyl)-amide; 7-benzyl-4-hydroxy-8-oxo-7,8-dihydro-[2,7]naphthyridine-3-carboxylic acid [3-(2,2,2-trifluoro-acetylamino)-propyl]-amide; 7-benzyl-4-hydroxy-8-oxo-7,8-dihydro-[2,7]naphthyridine-3-carboxylic acid [3-(3-isopropyl-ureido)-propyl]-amide; 7-benzyl-4-hydroxy-8-oxo-7,8-dihydro-[2,7]naphthyridine-3-carboxylic acid (3-ureido-propyl)-amide; 1-benzyl-8-hydroxy-2-oxo-1,2-dihydro-[1,6]naphthyridine-7-carboxylic acid [2-(methanesulfonyl-methyl-amino)-ethyl]-amide; 1-benzyl-5-cyano-8-hydroxy-2-oxo-1,2-dihydro-[1,6]naphthyridine-7-carboxylic acid (2-sulfamoyl-ethyl)-amide; 1-benzyl-5-hydroxy-2-oxo-3-phenyl-1,2-dihydro-[1,7]naphthyridine-6-carboxylic acid (2-acetylamino-ethyl)-amide; 1-benzyl-5-hydroxy-2-oxo-3-phenyl-1,2-dihydro-[1,7]naphthyridine-6-carboxylic acid [2-(methanesulfonyl-methyl-amino)-ethyl]-amide; 1-benzyl-5-hydroxy-2-oxo-3-phenyl-1,2-dihydro-[1,7]naphthyridine-6-carboxylic acid [2-(2,2,2-trifluoro-acetylamino)-ethyl]-amide; 1-benzyl-5-hydroxy-2-oxo-3-phenyl-1,2-dihydro-[1,7]naphthyridine-6-carboxylic acid [2-(3-ethyl-ureido)-ethyl]-amide; 1-benzyl-8-hydroxy-2-oxo-1,2-dihydro-[1,6]naphthyridine-7-carboxylic acid (2-methanesulfonylamino-ethyl)-amide; 3-[(1-benzyl-8-hydroxy-5-methyl-2-oxo-1,2-dihydro-[1,6]naphthyridine-7-carbonyl)-amino]-propionic acid; 1-benzyl-5-hydroxy-2-oxo-3-phenyl-1,2-dihydro-[1,7]naphthyridine-6-carboxylic acid (1H-tetrazol-5-ylmethyl)-amide; 3-[(1-benzyl-5-hydroxy-2-oxo-3-phenyl-1,2-dihydro-[1,7]naphthyridine-6-carbonyl)-amino]-2,2-dimethyl-propionic acid; 7-benzyl-4-hydroxy-8-oxo-7,8-dihydro-[2,7]naphthyridine-3-carboxylic acid [2-(formyl-methyl-amino)-ethyl]-amide; 7-benzyl-4-hydroxy-8-oxo-7,8-dihydro-[2,7]naphthyridine-3-carboxylic acid [2-(acetyl-methyl-amino)-ethyl]-amide; 1-benzyl-5-hydroxy-2-oxo-3-phenyl-1,2-dihydro-[1,7]naphthyridine-6-carboxylic acid (2-formylamino-ethyl)-amide; 3-[(1-benzyl-5-hydroxy-2-oxo-3-phenyl-8-pyridin-3-yl-1,2-dihydro-[1,7]naphthyridine-6-carbonyl)-amino]-propionic acid; 3-[(1-benzyl-5-hydroxy-2-oxo-3,8-diphenyl-1,2-dihydro-[1,7]naphthyridine-6-carbonyl)-amino]-propionic acid; 3-[(1-benzyl-5-hydroxy-8-methyl-2-oxo-3-phenyl-1,2-dihydro-[1,7]naphthyridine-6-carbonyl)-amino]-propionic acid; 3-[(1-benzyl-5-hydroxy-2-oxo-3-phenyl-1,2,3,4tetrahydro-[1,7]naphthyridine-6-carbonyl)-amino]-propionic acid; 3-[(1-benzyl-5-hydroxy-2-oxo-1,2-dihydro-[1,7]naphthyridine-6-carbonyl)-amino]-propionic acid; 3-[(1-benzyl-5-hydroxy-2-oxo-3-phenethyl-1,2-dihydro-[1,7]naphthyridine-6-carbonyl)-amino]-propionic acid; 3-[(1-benzyl-5-hydroxy-2-oxo-3-pyridin-3-yl-1,2-dihydro-[1,7]naphthyridine-6-carbonyl)-amino]-propionic acid; 3-[(1-benzyl-5-hydroxy-2-oxo-3-pyridin-2-yl-1,2-dihydro-[1,7]naphthyridine-6-carbonyl)-amino]-propionic acid; 4-[(1-benzyl-5-hydroxy-2-oxo-3-phenyl-1,2-dihydro-[1,7]naphthyridine-6-carbonyl)-amino]-butyric acid; 3-[(1-benzyl-5-hydroxy-3-methyl-2-oxo-1,2-dihydro-[1,7]naphthyridine-6-carbonyl)-amino]-propionic acid; 3-[(1-benzyl-5-hydroxy-2-oxo-3-thiophen-2-yl-1,2-dihydro-[1,7]naphthyridine-6-carbonyl)-amino]-propionic acid; 7-benzyl-1-cyano-4-hydroxy-8-oxo-7,8-dihydro-[2,7]naphthyridine-3-carboxylic acid methylamide; 7-benzyl-1-cyano-4-hydroxy-8-oxo-7,8-dihydro-[2,7]naphthyridine-3-carboxylic acid cyclopropylamide; 1-benzyl-8-cyano-5-hydroxy-2-oxo-3-phenyl-1,2-dihydro-[1,7]naphthyridine-6-carboxylic acid methylamide; 3-[(1-benzyl-5-hydroxy-2-oxo-3-pyridin-4-yl-1,2-dihydro-[1,7]naphthyridine-6-carbonyl)-amino]-propionic acid; 1-benzyl-5-hydroxy-2-oxo-3-phenyl-1,2-dihydro-[1,7]naphthyridine-6-carboxylic acid (2-methanesulfonylamino-ethyl)-amide; 1-benzyl-8-cyano-5-hydroxy-2-oxo-3-phenyl-1,2-dihydro-[1,7]naphthyridine-6-carboxylic acid [2-(methanesulfonyl-methyl-amino)-ethyl]-amide; 1-benzyl-5-hydroxy-8-methyl-2-oxo-3-phenyl-1,2-dihydro-[1,7]naphthyridine-6-carboxylic acid [2-(methanesulfonyl-methyl-amino)-ethyl]-amide; 1-benzyl-5-hydroxy-2-oxo-3,8-diphenyl-1,2-dihydro-[1,7]naphthyridine-6-carboxylic acid [2-(methanesulfonyl-methyl-amino)-ethyl]-amide; 1-benzyl-5-hydroxy-2-oxo-3-phenyl-8-pyridin-3-yl-1,2-dihydro-[1,7]naphthyridine-6-carboxylic acid [2-(methanesulfonyl-methyl-amino)-ethyl]-amide; 3-[(5-hydroxy-2-oxo-1-phenethyl-3-phenyl-1,2-dihydro-[1,7]naphthyridine-6-carbonyl)-amino]-propionic acid; 3-[(5-hydroxy-2-oxo-1,3-diphenyl-1,2-dihydro-[1,7]naphthyridine-6-carbonyl)-amino]-propionic acid; 3-[(3-benzyl-5-hydroxy-2-oxo-1-phenyl-1,2-dihydro-[1,7]naphthyridine-6-carbonyl)-amino]-propionic acid; 3-[(5-hydroxy-1-methyl-2-oxo-3-phenyl-1,2-dihydro-[1,7]naphthyridine-6-carbonyl)-amino]-propionic acid; 3-{[1-benzyl-3-(4-cyano-phenyl)-5-hydroxy-2-oxo-1,2-dihydro-[1,7]naphthyridine-6-carbonyl]-amino}-propionic acid; 3-{[1-benzyl-5-hydroxy-3-(4-methoxy-phenyl)-2-oxo-1,2-dihydro-[1,7]naphthyridine-6-carbonyl]-amino}-propionic acid; 3-[(1-benzyl-5-hydroxy-2-oxo-3-thiazol-2-yl-1,2-dihydro-[1,7]naphthyridine-6-carbonyl)-amino]-propionic acid; (R)-3-[(1-benzyl-5-hydroxy-2-oxo-3-phenyl-1,2-dihydro-[1,7]naphthyridine-6-carbonyl)-amino]-butyric acid; 3-{[5-hydroxy-1-(4-methoxy-benzyl)-2-oxo-3-phenyl-1,2-dihydro-[1,7]naphthyridine-6-carbonyl]-amino}-propionic acid; 3-{[1-(4-cyano-benzyl)-5-hydroxy-2-oxo-3-phenyl-1,2-dihydro-[1,7]naphthyridine-6-carbonyl]-amino}-propionic acid; 3-[(1-benzyl-5-hydroxy-2-oxo-3-pyrazin-2-yl-1,2-dihydro-[1,7]naphthyridine-6-carbonyl)-amino]-propionic acid; 3-{[1-benzyl-5-hydroxy-3-(4-methanesulfonyl-phenyl)-2-oxo-1,2-dihydro-[1,7]naphthyridine-6-carbonyl]-amino}-propionic acid; 3-{[1-benzyl-5-hydroxy-2-oxo-3-(3-trifluoromethyl-phenyl)-1,2-dihydro-[1,7]naphthyridine-6-carbonyl]-amino}-propionic acid; 3-{[1-benzyl-5-hydroxy-3-(4-morpholin-4-yl-phenyl)-2-oxo-1,2-dihydro-[1,7]naphthyridine-6-carbonyl]-amino}-propionic acid; 3-[(3-benzo[1,2,5]oxadiazol-5-yl-1-benzyl-5-hydroxy-2-oxo-1,2-dihydro-[1,7]naphthyridine-6-carbonyl)-amino]-propionic acid; 3-{[1-benzyl-3-(5-fluoro-2-methoxy-phenyl)-5-hydroxy-2-oxo-1,2-dihydro-[1,7]naphthyridine-6-carbonyl]-amino}-propionic acid; 3-{[1-benzyl-5-hydroxy-2-oxo-3-(4-trifluoromethoxy-phenyl)-1,2-dihydro-[1,7]naphthyridine-6-carbonyl]-amino}-propionic acid; (R)-2-[(1-benzyl-5-hydroxy-2-oxo-3-phenyl-1,2-dihydro-[1,7]naphthyridine-6-carbonyl)-amino]-3-phenyl-propionic acid; 3-{[1-benzyl-5-hydroxy-3-(1-methyl-1h-pyrazol-4-yl)-2-oxo-1,2-dihydro-[1,7]naphthyridine-6-carbonyl]-amino}-propionic acid; 3-[(1-benzyl-5-hydroxy-2-oxo-3-pyrimidin-5-yl-1,2-dihydro-[1,7]naphthyridine-6-carbonyl)-amino]-propionic acid; 3-{[1-benzyl-3-(2-dimethylamino-pyrimidin-5-yl)-5-hydroxy-2-oxo-1,2-dihydro-[1,7]naphthyridine-6-carbonyl]-amino}-propionic acid; 3-[(1-cyclohexylmethyl-5-hydroxy-2-oxo-3-phenyl-1,2-dihydro-[1,7]naphthyridine-6-carbonyl)-amino]-propionic acid; 3-{[5-hydroxy-2-oxo-3-phenyl-1-

(tetrahydro-pyran-4-ylmethyl)-1,2-dihydro-[1,7]naphthyridine-6-carbonyl]-amino}-propionic acid; 3-[(5-hydroxy-2-oxo-3-phenyl-1-thiazol-2-ylmethyl-1,2-dihydro-[1,7]naphthyridine-6-carbonyl)-amino]-propionic acid; 3-[(1-benzyl-5-hydroxy-2-oxo-3-phenyl-8-pyrimidin-5-yl-1,2-dihydro-[1,7]naphthyridine-6-carbonyl)-amino]-propionic acid; 3-[(1-benzyl-5-hydroxy-2-oxo-3-phenyl-8-pyrazin-2-yl-1,2-dihydro-[1,7]naphthyridine-6-carbonyl)-amino]-propionic acid; 5-[(1-benzyl-5-hydroxy-2-oxo-3-phenyl-1,2-dihydro-[1,7]naphthyridine-6-carbonyl)-amino]-pentanoic acid; 4-[(1-benzyl-5-hydroxy-2-oxo-3-phenyl-8-pyridin-3-yl-1,2-dihydro-[1,7]naphthyridine-6-carbonyl)-amino]-butyric acid; 5-[(1-benzyl-5-hydroxy-2-oxo-3-phenyl-8-pyridin-3-yl-1,2-dihydro-[1,7]naphthyridine-6-carbonyl)-amino]-pentanoic acid; 3-[(5-hydroxy-2-oxo-1,3-diphenyl-8-pyridin-3-yl-1,2-dihydro-[1,7]naphthyridine-6-carbonyl)-amino]-propionic acid; 3-[(5-hydroxy-1-methyl-2-oxo-3-phenyl-8-pyridin-3-yl-1,2-dihydro-[1,7]naphthyridine-6-carbonyl)-amino]-propionic acid; 3-[(5-hydroxy-2-oxo-1-phenethyl-3-phenyl-8-pyridin-3-yl-1,2-dihydro-[1,7]naphthyridine-6-carbonyl)-amino]-propionic acid; 3-[(1-benzyl-5-hydroxy-2-oxo-3-phenyl-8-pyridin-4-yl-1,2-dihydro-[1,7]naphthyridine-6-carbonyl)-amino]-propionic acid; 3-[(1-benzyl-5-hydroxy-2-oxo-3,8-di-pyridin-3-yl-1,2-dihydro-[1,7]naphthyridine-6-carbonyl)-amino]-propionic acid; (R)-3-{[5-hydroxy-2-oxo-3-phenyl-1-(1-phenyl-ethyl)-1,2-dihydro-[1,7]naphthyridine-6-carbonyl]-amino}-propionic acid; (R)-4-{[5-hydroxy-2-oxo-3-phenyl-1-(1-phenyl-ethyl)-1,2-dihydro-[1,7]naphthyridine-6-carbonyl]-amino}-butyric acid; 3-{[1-benzyl-5-hydroxy-8-(5-methoxy-pyridin-3-yl)-2-oxo-3-phenyl-1,2-dihydro-[1,7]naphthyridine-6-carbonyl]-amino}-propionic acid; 3-{[1-benzyl-8-(5-chloro-pyridin-3-yl)-5-hydroxy-2-oxo-3-phenyl-1,2-dihydro-[1,7]naphthyridine-6-carbonyl]-amino}-propionic acid; (S)-3-{[5-hydroxy-2-oxo-3-phenyl-1-(1-phenyl-ethyl)-1,2-dihydro-[1,7]naphthyridine-6-carbonyl]-amino}-propionic acid; (S)-4-{[5-hydroxy-2-oxo-3-phenyl-1-(1-phenyl-ethyl)-1,2-dihydro-[1,7]naphthyridine-6-carbonyl]-amino}-butyric acid; (S)-3-{[5-hydroxy-2-oxo-3-phenyl-1-(1-phenyl-ethyl)-8-pyridin-3-yl-1,2-dihydro-[1,7]naphthyridine-6-carbonyl]-amino}-propionic acid; (R)-3-{[5-hydroxy-2-oxo-3-phenyl-1-(1-phenyl-ethyl)-8-pyridin-3-yl-1,2-dihydro-[1,7]naphthyridine-6-carbonyl]-amino}-propionic acid; 3-{[1-benzyl-8-(5-fluoro-pyridin-3-yl)-5-hydroxy-2-oxo-3-phenyl-1,2-dihydro-[1,7]naphthyridine-6-carbonyl]-amino}-propionic acid; 3-{[1-benzyl-5-hydroxy-8-(2-methyl-pyridin-3-yl)-2-oxo-3-phenyl-1,2-dihydro-[1,7]naphthyridine-6-carbonyl]-amino}-propionic acid; 3-{[1-benzyl-5-hydroxy-8-(6-methyl-pyridin-3-yl)-2-oxo-3-phenyl-1,2-dihydro-[1,7]naphthyridine-6-carbonyl]-amino}-propionic acid; 3-{[1-benzyl-5-hydroxy-2-oxo-3-phenyl-8-(6-trifluoromethyl-pyridin-3-yl)-1,2-dihydro-[1,7]naphthyridine-6-carbonyl]-amino}-propionic acid; 3-{[1-benzyl-5-hydroxy-8-(6-methoxy-pyridin-3-yl)-2-oxo-3-phenyl-1,2-dihydro-[1,7]naphthyridine-6-carbonyl]-amino}-propionic acid; 3-{[5-hydroxy-2-oxo-3-phenyl-8-pyridin-3-yl-1-(tetrahydro-pyran-4-ylmethyl)-1,2-dihydro-[1,7]naphthyridine-6-carbonyl]-amino}-propionic acid; 3-[(1-cyclohexylmethyl-5-hydroxy-2-oxo-3-phenyl-8-pyridin-3-yl-1,2-dihydro-[1,7]naphthyridine-6-carbonyl)-amino]-propionic acid; 4-[(1-cyclohexylmethyl-5-hydroxy-2-oxo-3-phenyl-1,2-dihydro-[1,7]naphthyridine-6-carbonyl)-amino]-butyric acid; 3-{[1-benzyl-5-hydroxy-3-(4-methoxy-phenyl)-2-oxo-8-pyridin-3-yl-1,2-dihydro-[1,7]naphthyridine-6-carbonyl]-amino}-propionic acid; 4-{[1-benzyl-5-hydroxy-3-(4-methoxy-phenyl)-2-oxo-1,2-dihydro-[1,7]naphthyridine-6-carbonyl]-amino}-butyric acid; 3-{[1-benzyl-5-hydroxy-3-(3-methoxy-phenyl)-2-oxo-1,2-dihydro-[1,7]naphthyridine-6-carbonyl]-amino}-propionic acid; 4-{[1-benzyl-5-hydroxy-3-(3-methoxy-phenyl)-2-oxo-1,2-dihydro-[1,7]naphthyridine-6-carbonyl]-amino}-butyric acid; 1-[(1-benzyl-5-hydroxy-2-oxo-3-phenyl-1,2-dihydro-[1,7]naphthyridine-6-carbonyl)-amino]-cyclopropanecarboxylic acid; 1-[(1-benzyl-5-hydroxy-2-oxo-3-phenyl-8-pyridin-3-yl-1,2-dihydro-[1,7]naphthyridine-6-carbonyl)-amino]-cyclopropanecarboxylic acid; 3-[(1-benzyl-5-hydroxy-2-oxo-3-phenyl-8-pyridin-3-yl-1,2-dihydro-[1,7]naphthyridine-6-carbonyl)-amino]-2,2-dimethyl-propionic acid; 3-{[1-benzyl-8-(2-ethoxy-pyrimidin-5-yl)-5-hydroxy-2-oxo-3-phenyl-1,2-dihydro-[1,7]naphthyridine-6-carbonyl]-amino}-propionic acid; 3-[(1-benzyl-5-hydroxy-2-oxo-3-phenyl-8-pyridin-2-yl-1,2-dihydro-[1,7]naphthyridine-6-carbonyl)-amino]-propionic acid; 3-[(1-benzyl-5-hydroxy-2-oxo-3-phenyl-8-pyridazin-4-yl-1,2-dihydro-[1,7]naphthyridine-6-carbonyl)-amino]-propionic acid; 3-[(1-benzyl-5-hydroxy-2-oxo-3-phenyl-8-thiazol-2-yl-1,2-dihydro-[1,7]naphthyridine-6-carbonyl)-amino]-propionic acid; 7-benzyl-4-hydroxy-8-oxo-7,8-dihydro-[2,7]naphthyridine-3-carboxylic acid (3-formylamino-propyl)-amide; 7-benzyl-4-hydroxy-8-oxo-7,8-dihydro-[2,7]naphthyridine-3-carboxylic acid (3-acetylamino-propyl)-amide; 3-[(1-cyclohexylmethyl-5-hydroxy-2-oxo-3-phenyl-8-pyridin-4-yl-1,2-dihydro-[1,7]naphthyridine-6-carbonyl)-amino]-propionic acid; 3-[(5-hydroxy-2-oxo-1,3-diphenyl-8-pyridin-4-yl-1,2-dihydro-[1,7]naphthyridine-6-carbonyl)-amino]-propionic acid; 3-{[1-benzyl-5-hydroxy-8-(1-methyl-1h-pyrazol-4-yl)-2-oxo-3-phenyl-1,2-dihydro-[1,7]naphthyridine-6-carbonyl]-amino}-propionic acid; 3-[(1-benzyl-5-hydroxy-2-oxo-3-phenyl-8-thiazol-5-yl-1,2-dihydro-[1,7]naphthyridine-6-carbonyl)-amino]-propionic acid; 3-[(1-benzyl-5-hydroxy-2-oxo-3-phenyl-8-thiazol-4-yl-1,2-dihydro-[1,7]naphthyridine-6-carbonyl)-amino]-propionic acid; 3-[(1-benzyl-5-hydroxy-2-oxo-3-phenyl-8-pyridazin-3-yl-1,2-dihydro-[1,7]naphthyridine-6-carbonyl)-amino]-propionic acid; 3-[(1-benzyl-5-hydroxy-2-oxo-3-phenethyl-8-pyridin-3-yl-1,2-dihydro-[1,7]naphthyridine-6-carbonyl)-amino]-propionic acid; 3-[(1,3-dibenzyl-5-hydroxy-2-oxo-1,2-dihydro-[1,7]naphthyridine-6-carbonyl)-amino]-propionic acid; 3-[(7-benzyl-4-hydroxy-8-oxo-1-pyridin-3-yl-7,8-dihydro-[2,7]naphthyridine-3-carbonyl)-amino]-propionic acid; 3-{[1-cyclohexylmethyl-8-(2-ethoxy-pyrimidin-5-yl)-5-hydroxy-2-oxo-3-phenyl-1,2-dihydro-[1,7]naphthyridine-6-carbonyl]-amino}-propionic acid; 3-{[1-benzyl-5-hydroxy-8-(2-methylsulfanyl-pyrimidin-5-yl)-2-oxo-3-phenyl-1,2-dihydro-[1,7]naphthyridine-6-carbonyl]-amino}-propionic acid; 3-{[1-benzyl-5-hydroxy-2-oxo-3-(4-trifluoromethyl-phenyl)-1,2-dihydro-[1,7]naphthyridine-6-carbonyl]-amino}-propionic acid; 3-{[1-benzyl-5-hydroxy-2-oxo-3-(2-trifluoromethyl-phenyl)-1,2-dihydro-[1,7]naphthyridine-6-carbonyl]-amino}-propionic acid; 4-{[1-benzyl-5-hydroxy-2-oxo-3-(4-trifluoromethyl-phenyl)-1,2-dihydro-[1,7]naphthyridine-6-carbonyl]-amino}-butyric acid; 4-{[1-benzyl-5-hydroxy-2-oxo-3-(3-trifluoromethyl-phenyl)-1,2-dihydro-[1,7]naphthyridine-6-carbonyl]-amino}-butyric acid; 4-{[1-benzyl-5-hydroxy-2-oxo-3-(2-trifluoromethyl-phenyl)-1,2-dihydro-[1,7]naphthyridine-6-carbonyl]-amino}-butyric acid; 3-{[1-benzyl-5-hydroxy-2-oxo-8-pyridin-3-yl-3-(4-trifluoromethyl-phenyl)-1,2-dihydro-[1,7]naphthyridine-6-carbonyl]-amino}-propionic acid; 3-{[1-benzyl-5-hydroxy-2-oxo-8-pyridin-3-yl-3-(3-trifluoromethyl-phenyl)-1,2-dihydro-[1,7]naphthyridine-6-carbonyl]-amino}-propionic acid; 3-{[1-benzyl-5-hydroxy- 2-oxo-8-pyridin-3-yl-3-(2-trifluoromethyl-phenyl)-1,2-dihydro-[1,7]naphthyridine-6-carbonyl]-amino}-propionic acid; 3-[(1-cyclopentylmethyl-5-hydroxy-2-oxo-3-phenyl-1,2-dihydro-[1,7]naphthyridine-6-carbonyl)-amino]-propionic acid; 4-[(1-cyclopentylmethyl-5-hydroxy-2-oxo-3-phenyl-1,2-dihydro-[1,7]naphthyridine-6-carbonyl)-amino]-butyric acid; 3-[(1-cyclopentylmethyl-5-hydroxy-2-oxo-3-phenyl-8-pyridin-3-yl-1,2-dihydro-[1,7]naphthyridine-6-carbonyl)-amino]-propionic acid; 1-[(7-benzyl-4-hydroxy-8-oxo-7,8-dihydro-[2,7]naphthyridine-3-carbonyl)-amino]-cyclopropanecarboxylic acid; 3-{[1-(2-ethyl-butyl)-5-hydroxy-2-oxo-3-phenyl-1,2-dihydro-[1,7]naphthyridine-6-carbonyl]-amino}-propionic acid; 4-{[1-(2-ethyl-butyl)-5-hydroxy-2-oxo-3-phenyl-1,2-dihydro-[1,7]naphthyridine-6-carbonyl]-amino}-butyric acid; 3-{[1-(2-ethyl-butyl)-5-hydroxy-2-oxo-3-phenyl-8-pyridin-3-yl-1,2-dihydro-[1,7]naphthyridine-6-carbonyl]-amino}-propionic acid; 3-{[1-(2-ethyl-butyl)-5-hydroxy-2-oxo-3-phenyl-8-pyridin-4-yl-1,2-dihydro-[1,7]naphthyridine-6-carbonyl]-amino}-propionic acid; 3-{[(1-benzyl-5-hydroxy-2-oxo-3-phenyl-1,2-dihydro-[1,7]naphthyridine-6-carbonyl)-amino]-methyl}-benzoic acid; and {1-[(1-benzyl-5-hydroxy-2-oxo-3-phenyl-8-pyridin-3-yl-1,2-dihydro-[1,7]naphthyridine-6-carbonyl)-amino]-cyclopropyl}-acetic acid; or a pharmaceutically acceptable salt, single stereoisomer, mixture of stereoisomers, ester, tautomer, or prodrug thereof.

2. Compositions and Methods of the Disclosure

The disclosure provides for use of a compound of Formula I, Ia, Ib, IIa, IIb, IIIa, or Mb for the manufacture of a medicament for use in treating various conditions or disorders as described herein. In one embodiment, a pharmaceutical composition is provided comprising at least one compound of Formula I, Ia, Ib, IIa, IIb, IIIa, or Mb and a pharmaceutically acceptable excipient or carrier.

In various embodiments, the medicament or pharmaceutical composition can further comprise or be used in combination with at least one additional therapeutic agent. In one embodiment, the agent is selected from the group consisting of vitamin $B_{12}$, ferrous sulfate, folic acid, and/or recombinant erythropoietin or an erythropoiesis stimulating agent (ESA).

The compounds of the present disclosure, or medicaments or compositions comprising the compounds, can be used to inhibit HIF hydroxylase activity, thereby modulating the stability and/or activity of HIF and activating HIF-regulated gene expression. The compound, or composition or medicament thereof, can be used in methods to treat, pretreat, or delay progression or onset of conditions mediated at least in part by HIF, including, but not limited to, anemia and various aspects of ischemic and hypoxic conditions. Ischemic and hypoxic conditions may result from an event selected from, but not limited to, myocardial infarction, pulmonary embolism, intestinal infarction, ischemic stroke, acute respiratory failure, renal ischemic-reperfusion injury, cardiac cirrhosis, macular degeneration, neonatal respiratory distress syndrome, peripheral artery disease, chronic kidney failure, congestive heart failure, transient ischemic attack, etc. In yet another embodiment, the compound, or composition or medicament thereof, is administered immediately after a trauma or injury. In other embodiments, the compound, or composition or medicament thereof, can be administered to a subject based on predisposing conditions, e.g., hypertension, diabetes, occlusive arterial disease, chronic venous insufficiency, Raynaud's disease, chronic skin ulcers, cirrhosis, congestive heart failure, transient ischemic attack, and systemic sclerosis. In still other embodiments, compounds may be administered to a subject to decrease or prevent the development of tissue damage associated with ischemia or hypoxia.

The compounds of the present disclosure, or compositions or medicaments thereof, can also be used to increase endogenous erythropoietin (EPO). The compounds, or composition or medicament thereof, can be administered to prevent, pretreat, or treat EPO-associated conditions, including, e.g., conditions associated with anemia and neurological disorders. In one embodiment, the compounds of the present disclosure, or compositions or medicaments thereof, can be used to treat, pretreat, or delay onset of anemia such as anemia that may develop in association with various conditions or disorders. Conditions associated with anemia include, but are not limited to, acute or chronic kidney disease, diabetes, cancer, ulcers, infection with virus, e.g., HIV, bacteria, or parasites; inflammation, etc. Conditions can further include those associated with procedures or treatments including, e.g., radiation therapy, chemotherapy, dialysis, anesthesia, and surgery. Conditions associated with anemia additionally include abnormal hemoglobin and/or erythrocytes, such as found in disorders such as microcytic anemia, hypochromic anemia, aplastic anemia, etc.

The compounds can be used to increase endogenous EPO in a subject undergoing a specific treatment or procedure, prophylactically or concurrently, for example, an HIV-infected anemic patient being treated with azidothymidine (zidovudine) or other reverse transcriptase inhibitors, an anemic cancer patient receiving cyclic cisplatin- or non-cisplatin-containing chemotherapeutics, or an anemic or non-anemic patient scheduled to undergo surgery. Additionally, the compounds can be used to increase endogenous EPO levels in an anemic or non-anemic patient scheduled to undergo surgery to reduce the need for allogenic blood transfusions or to facilitate banking of blood prior to surgery.

The disclosure is also directed to a method of inhibiting the activity of at least one hydroxylase enzyme which modifies the alpha subunit of hypoxia inducible factor. The HIF hydroxylase enzyme may be an asparaginyl hydroxylase such as Factor Inhibiting HIF (FIH). The HIF hydroxylase enzyme may be a prolyl hydroxylase including, but not limited to, a prolyl hydroxylase selected from the group consisting of EGLN1, EGLN2, and EGLN3. In one embodiment, the method comprises contacting the hydroxylase enzyme with an effective amount of one or more compounds selected from the group comprising compounds of Formula I, Ia, Ib, Ha, IIb, IIIa, or Mb.

3. Definitions

It must be noted that as used herein, and in the appended claims, the singular forms "a," "an," and "the" include plural references unless the context clearly dictates otherwise.

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present disclosure, the preferred methods, devices, and materials are now described. All publications cited herein are incorporated herein by reference in their entirety for the purpose of describing and disclosing the methodologies, reagents, and tools reported in the publications that might be used in connection with the disclosure. Nothing herein is to be construed as an admission that the disclosure is not entitled to antedate such disclosure by virtue of prior disclosure.

The practice of the present disclosure will employ, unless otherwise indicated, conventional methods of chemistry, biochemistry, molecular biology, cell biology, genetics, immunology, and pharmacology, within the skill of the art. Such techniques are explained fully in the literature. (See, e.g., Gennaro, A. R., ed. (1990) Remington's Pharmaceutical Sciences, 18$^{th}$ ed., Mack Publishing Co.; Colowick, S. et al., eds., Methods In Enzymology, Academic Press, Inc.; D. M. Weir, and C. C. Blackwell, eds. (1986) Handbook of Experimental Immunology, Vols. I-IV, Blackwell Scientific Publications; Maniatis, T. et al., eds. (1989) Molecular Cloning: A Laboratory Manual, 2$^{nd}$ edition, Vols. I-III, Cold Spring Harbor Laboratory Press; Ausubel, F. M. et al., eds. (1999) Short Protocols in Molecular Biology, 4$^{th}$ edition, John Wiley & Sons; Ream et al., eds. (1998) Molecular Biology Techniques: An Intensive Laboratory Course, Academic Press; Newton & Graham eds. (1997) PCR (Introduction to Biotechniques Series), 2nd ed., Springer Verlag).

The term "HIFα" refers to the alpha subunit of hypoxia inducible factor protein. HIFα may be any human or other mammalian protein, or fragment thereof, including, but not limited to, human HIF-1α (Genbank Accession No. Q16665), HIF-2α (Genbank Accession No. AAB41495), and HIF-3α (Genbank Accession No. AAD22668); murine HIF-1α (Genbank Accession No. Q61221), HIF-2α (Genbank Accession No. BAA20130, and AAB41496), and HIF-3α (Genbank Accession No. AAC72734); rat HIF-1α (Genbank Accession No. CAA70701), HIF-2α (Genbank Accession No. CAB96612), and HIF-3α (Genbank Accession No. CAB96611); and bovine HIF-1α (Genbank Accession No. BAA78675), HIF-2α (GenBank Accession No. BAA78676), and HIF-3α (GenBank Accession No. NP 001098812). HIFα may also be any non-mammalian protein or fragment thereof, including *Xenopus laevis* HIF-1α (Genbank Accession No. CAB96628), *Drosophila melanogaster* HIF-1α (Genbank Accession No. JC4851), and chicken HIF-1α (Genbank Accession No. BAA34234).

A fragment of HIFα includes any fragment retaining at least one functional or structural characteristic of HIFα. Fragments of HIFα include, e.g., the regions defined by human HIF-1α from amino acids 401 to 603 (Huang et al., supra), amino acid 531 to 575 (Jiang et al. (1997) *J. Biol. Chem.* 272:19253-19260), amino acid 556 to 575 (Tanimoto et al., supra), amino acid 557 to 571 (Srinivas et al. (1999) *Biochem. Biophys. Res. Commun.* 260:557-561), and amino acid 556 to 575 (Ivan and Kaelin (2001) *Science* 292:464-468).

The terms "HIF-associated conditions" and "conditions mediated at least in part by HIF" are used inclusively and refer to any condition that can be associated with below normal, abnormal, or inappropriate modulation of HIF. HIF-associated conditions include any condition wherein an increase in HIF level would provide therapeutic benefit. HIF-associated conditions include anemic conditions and tissue damage or disorders associated with ischemic or hypoxic conditions.

The term "HIF hydroxylase" refers to any enzyme that modifies the alpha subunit of HIF by hydroxylation of one or more amino acid residues. HIF hydroxylases include Factor Inhibiting HIF (FIH) (GenBank Accession AAL27308; Mahon et al. (2001) *Genes Dev.* 15:2675-2686; Lando et al. (2002) *Science* 295:858-861; and Lando et al. (2002) *Genes Dev.* 16:1466-1471), which modifies at least one asparagine residue found within HIFα. (Also, see, Elkins et al. (2002) *J. Biol. Chem.* C200644200.) HIF hydroxylases also include HIF prolyl hydroxylases (HIF PHs), which modify proline residues found within HIFα.

The terms "HIF prolyl hydroxylase", "PHD" and "HIF PH" refer to any enzyme that modifies the alpha subunit of HIF protein by hydroxylation of one or more proline residues. HIF PH includes members of the Egl-Nine (EGLN) gene family described by Taylor (2001, Gene 275:125-132), and characterized by Aravind and Koonin (2001, Genome Biol 2: RESEARCH 0007), Epstein et al. (2001, *Cell* 107:43-54), and Bruick and McKnight (2001, *Science* 294:1337-1340). HIF PH2, as used in examplary assays described herein (infra), may be any HIF PH2, also referred to as PHD2, e.g., human EGLN1 (GenBank Accession No. AAG33965; Dupuy et al. (2000) *Genomics* 69:348-54), mouse EGLN1 (GenBank Accession No. CAC42515), rat EGLN1 (GenBank Accession No. P59722), etc. Alternatively, another HIF PH may be used in the assay. Such HIF PH enzymes include, but are not limited to HIF PH1, also referred to as PHD1, e.g., human EGLN2 isoform 1 (GenBank Accession No. CAC42510; Taylor, supra), human EGLN2 isoform 3 (GenBank Accession No. NP_542770), mouse EGLN2 (GenBank Accession No. CAC42516), and rat EGLN2 (GenBank Accession No. AA046039), etc.; and any HIF PH3, also referred to as PDH3, e.g. human EGLN3 (GenBank Accession No. CAC42511; Taylor, supra), mouse EGLN3 (GenBank Accession No. CAC42517), and rat EGLN3 (SM-20) (GenBank Accession No. AAA19321). In other embodiments of the present disclosure, EGLN may include *Caenorhabditis elegans* EGL-9 (GenBank Accession No. AAD56365) and *Drosophila melanogaster* CG1114 gene product (GenBank Accession No. AAF52050). HIF PH also includes any fragment of the foregoing full-length proteins that retains the ability to hydroxylate at least one prolyl residue in HIFα.

The term "ischemia" refers to a deficient supply of blood to a cell, tissue, organ, etc. Ischemia is associated with a reduction in nutrients, including oxygen, delivered to tissues. Ischemia may arise due to conditions such as atherosclerosis, formation of a thrombus in an artery or vein, blockage of an artery or vein by an embolus, vascular closure due to other causes, e.g., vascular spasm, etc. Such conditions may reduce blood flow, producing a state of hypoperfusion to an organ or tissue, or block blood flow completely. Other conditions that can lead to ischemia include tissue damage due to trauma or injury, such as, e.g., spinal cord injury; viral infection, which can lead to, e.g., congestive heart failure, etc. The term "ischemic condition" refers to conditions or events that are associated with or result in ischemia. Conditions associated or resulting in ischemia include, but are not limited to, an event selected from the group consisting of myocardial infarction, ischemic stroke, pulmonary embolism, perinatal hypoxia, circulatory shock including, e.g., hemorrhagic, septic, cardiogenic, etc.; mountain sickness, acute respiratory failure, etc.; intestinal infarction, acute kidney failure, renal ischemia reperfusion injury, etc.; atherosclerosis, chronic venous insufficiency, congestive heart failure, cardiac cirrhosis, diabetes, macular degeneration, sleep apnea, Raynaud's disease, systemic sclerosis, nonbacterial thrombotic endocarditis, occlusive artery disease, angina pectoris, transient ischemic attacks (TIAs), chronic alcoholic liver disease, chronic kidney failure, peripheral vascular disorders, ulcers, burns, chronic wounds etc. Ischemia can also result when individuals are placed under general anesthesia, and can cause tissue damage in organs prepared for transplant.

The terms "hypoxia" and "hypoxic" refer to an environment with levels of oxygen below normal. The term "hypoxic condition" includes, but is not limited to, ischemic conditions (ischemic hypoxia) such as those listed above, wherein hypoxia results from reduced circulation; pulmonary disorders (hypoxic hypoxia) such as COPD, severe pneumonia, pulmonary edema, pulmonary hypertension, hyaline membrane disease, and the like, wherein hypoxia results from reduced oxygenation of the blood in the lungs; anemic conditions (anemic hypoxia) such as gastric or duodenal ulcers, liver or renal disease, thrombocytopenia or blood coagulation disorders, cancer or other chronic illness, cancer chemotherapy and other therapeutic interventions that produce anemia, and the like, wherein hypoxia results from a decreased concentration of hemoglobin or red blood cells; and altitude sickness, etc.

The term "anemia" as used herein refers to any abnormality or deficiency in hemoglobin or erythrocytes that leads to reduced oxygen levels in the blood. Anemia can be associated with abnormal production, processing, or performance of erythrocytes and/or hemoglobin. The term anemia refers to any reduction in the number of red blood cells and/or in the level of hemoglobin in blood relative to normal blood levels.

The term "anemic condition" refers to any condition, disease, or disorder associated with anemia. Anemia can arise due to various conditions, for example, acute or chronic kidney disease, infections, inflammation, cancer, irradiation, toxins, diabetes, and surgery. Infections may be due to, e.g., virus, bacteria, and/or parasites, etc. Inflammation may be due to infection or autoimmune disorders, such as rheumatoid arthritis, etc. Anemia can be associated with blood loss due to, e.g., stomach ulcers, duodenal ulcers, hemorrhoids, cancer of the stomach or large intestine, trauma, injury, surgical procedures, etc. Anemia can develop in association with radiation therapy, chemotherapy, and kidney dialysis. Anemia can also develop in HIV-infected patients undergoing treatment with azidothymidine (zidovudine) or other reverse transcriptase inhibitors, and can develop in cancer patients undergoing chemotherapy, e.g., with cyclic cisplatin- or non-cisplatin-containing chemotherapeutics. Aplastic anemia and myelodysplastic syndromes are diseases associated with bone marrow failure, which results in decreased production of erythrocytes. Further, anemia can result from defective or abnormal hemoglobin or erythrocytes, such as in disorders including microcytic anemia, hypochromic anemia, etc. Anemia can result from disorders in iron transport, processing, and utilization, see, e.g., sideroblastic anemia, etc.

The terms "disorders," "diseases," and "conditions" are used inclusively herein and refer to any condition deviating from normal.

The terms "erythropoietin" and "EPO" refer to any naturally occurring, recombinant, or synthetic erythropoietin, erythropoiesis stimulating protein (ESP), or erythropoiesis stimulating agent (ESA) including, e.g., human erythropoietin (GenBank Accession No. AAA52400; Lin et al. (1985) *Proc. Nat'l. Acad. Sci. USA* 82:7580-7584), EPOETIN human recombinant erythropoietin (Amgen, Inc., Thousand Oaks Calif.), ARANESP human recombinant erythropoietin (Amgen), PROCRIT human recombinant erythropoietin (Ortho Biotech Products, L.P., Raritan N.J.), Continuous erythropoiesis receptor activator (CERA; F. Hoffmann-La Roche Ltd., Basel, Switzerland), etc.

The terms "erythropoietin-associated conditions" and "conditions mediated at least in part by erythropoietin" are used inclusively and refer to any condition that can be associated with below normal, abnormal, or inappropriate modulation of endogenous erythropoietin. EPO-associated conditions include any condition wherein an increase in EPO level would provide therapeutic benefit. Erythropoietin-associated conditions include anemic conditions such as those described above.

EPO-associated conditions further include neurological disorders and/or injuries, including cases of stroke, trauma, epilepsy, neurodegenerative disease, and the like, wherein erythropoietin may provide a neuroprotective effect. Neurodegenerative diseases contemplated by the disclosure include Alzheimer's disease, Parkinson's disease, Huntington's disease, and the like.

The terms "treating," "treatment" and the like, are used herein to mean administering a therapy to a patient in need thereof. The therapy may be administered thereby providing a prophylactic effect in terms of completely or partially preventing a disorder or sign or symptom thereof and/or the therapy may be administered thereby providing a partial or complete cure for a disorder and/or adverse effect attributable to the disorder.

It is to be realized that in some embodiments, each of the chemical moieties disclosed herein (e.g., alkyl, alkoxy, amino, aryl, aryloxy, aryloxyaryl, cycloalkyl, alkylthio, arylthio, cycloalkylthio, heteroarylthio, heterocyclicthio, sulfonyl, heteroaryl, heterocyclic, cycloalkoxy, heteroaryloxy, heterocyclyloxy, etc.) can be optionally substituted. Such substituted moieties are defined hereinbelow (e.g., substituted alkyl, substituted alkoxy, substituted aryl, substituted aryloxy, substituted aryloxyaryl, substituted cycloalkyl, substituted alkylthio, substituted arylthio, substituted cycloalkylthio, heteroarylthio, heterocyclicthio, substituted sulfonyl, substituted heteroaryl, substituted heterocyclic, substituted cycloalkoxy, substituted heteroaryloxy, substituted heterocyclyloxy, etc.). Alternatively, the phrase "optionally substituted" as used herein in connection with a group such as alkyl, alkoxy, haloalkyl, haloalkoxy, amino, acyloxy, aminoacyl, cycloalkyl, cycloalkoxy, aryl, aryloxy, heterocycloalkyl, heteroaryloxy, or heteroaryl, is intended to refer to such a group being optionally substituted with from 1 to 3 substituents independently selected from the group consisting of alkoxy, acyl, acylamino, acyloxy, amino, aminoacyl, aminocarbonylamino, aminothiocarbonylamino, aminocarbonyloxy, aryl, aryloxy, aryloxyaryl, cyano, halogen, hydroxyl, nitro, oxo, thioxo, carboxyl, carboxyl ester, cycloalkyl, thio, alkylthio, arylthio, cycloalkylthio, heteroarylthio, heterocyclicthio, sulfonyl, heteroaryl, heterocyclic, cycloalkoxy, heteroaryloxy, heterocyclyloxy, oxycarbonylamino, oxythiocarbonylamino, —OS(O)$_2$-alkyl, —OS(O)$_2$-aryl, —OS(O)$_2$-heteroaryl, —OS(O)$_2$-heterocyclic, —OSO$_2$—NR$^{40}$R$^{40}$, —NR$^{40}$S(O)$_2$—NR$^{40}$-alkyl, —NR$^{40}$S(O)$_2$—NR$^{40}$-aryl, —NR$^{40}$S(O)$_2$—NR$^{40}$-heteroaryl, and —NR$^{40}$S(O)$_2$—NR$^{40}$-heterocyclic, where each R$^{40}$ is independently hydrogen or alkyl; and further wherein each alkyl, alkoxy, aryl, aryloxy, aryloxyaryl, cycloalkyl, alkylthio, arylthio, cycloalkylthio, heteroarylthio, heterocyclicthio, heteroaryl, heterocyclic, cycloalkoxy, heteroaryloxy, or heterocyclyloxy may be additionally substituted with from 1-3 substituents independently alkyl, alkoxy, haloalkyl, haloalkoxy, or halogen.

The term "alkyl" refers to saturated monovalent hydrocarbyl groups having from 1 to 10 carbon atoms, more particularly from 1 to 5 carbon atoms, and even more particularly 1 to 3 carbon atoms. This term is exemplified by groups such as methyl, ethyl, n-propyl, iso-propyl, n-butyl, t-butyl, n-pentyl, and the like.

The term "substituted alkyl" refers to an alkyl group of from 1 to 10 carbon atoms, more particularly 1 to 5 carbon atoms, and having from 1 to 5 substituents, preferably 1 to 3 substituents, each substituent is independently selected from the group consisting of alkoxy, substituted alkoxy, acyl, acylamino, acyloxy, amino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, thioxo, carboxyl, carboxyl ester, cycloalkyl, substituted cycloalkyl, thio, alkylthio, substituted alkylthio, arylthio, substituted arylthio, cycloalkylthio, substituted cycloalkylthio, heteroarylthio, substituted heteroarylthio, heterocyclicthio, substituted heterocyclicthio, sulfonyl, substituted sulfonyl, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NR$^{40}$R$^{40}$, NR$^{40}$S(O)$_2$—NR$^{40}$-alkyl, —NR$^{40}$S(O)$_2$—NR$^{40}$-substituted alkyl, —NR$^{40}$S(O)$_2$—NR$^{40}$-aryl, —NR$^{40}$S(O)$_2$—NR$^{40}$-substituted aryl, —NR$^{40}$S(O)$_2$—NR$^{40}$-heteroaryl, —NR$^{40}$S(O)$_2$—NR$^{40}$-substituted heteroaryl, —NR$^{40}$S(O)$_2$—NR$^{40}$-heterocyclic, and —NR$^{40}$S(O)$_2$—NR$^{40}$-substituted heterocyclic, where each R$^{40}$ is independently hydrogen or alkyl. This group is exemplified by groups such as trifluoromethyl, benzyl, pyrazol-1-ylmethyl, phenethyl, 2,4-dimethoxybenzyl, 3,5-dimethoxybenzyl, etc.

The term "alkylidene" or "alkylene" refers to divalent saturated aliphatic hydrocarbyl groups preferably having from 1 to 5 and more preferably 1 to 3 carbon atoms which are either straight-chained or branched. This term is exemplified by groups such as methylene (—CH$_2$—), ethylene (—CH$_2$CH$_2$—), n-propylene (—CH$_2$CH$_2$CH$_2$—), iso-propylene (—CH$_2$CH(CH$_3$)—) and the like. "(C$_{u-v}$)alkylene" refers to alkylene groups having from u to v carbon atoms. The alkylidene or alkylene groups include branched and straight chain hydrocarbyl groups. For example "(C$_{1-3}$)alkylene" is meant to include methylene, ethylene, propylene, and the like.

The term "alkyl alcohol" refers to the group "alkyl-OH". For example, alkyl alcohol is meant to include methanol, ethanol, 2-propanol, 2-butanol, butanol, etc.

The term "substituted alkyl alcohol" refers to the group "substituted alkyl-OH".

The term "alkoxy" refers to the group "alkyl-O—," which includes, by way of example, methoxy, ethoxy, n-propoxy, iso-propoxy, n-butoxy, t-butoxy, sec-butoxy, n-pentoxy, and the like.

The term "substituted alkoxy" refers to the group "substituted alkyl-O-".

The term "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—, provided that a nitrogen atom of the heterocyclic or substituted heterocyclic is not bound to the —C(O)— group, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminoacyl" or "amide", or the prefix "carbamoyl," "carboxamide," "substituted carbamoyl" or "substituted carboxamide" refers to the group —C(O)NR$^{42}$R$^{42}$ where each R$^{42}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic; or where each R$^{42}$ is joined to form together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "alkenyl" refers to a vinyl unsaturated monovalent hydrocarbyl group having from 2 to 6 carbon atoms, and preferably 2 to 4 carbon atoms, and having at least 1, and preferably from 1 to 2 sites of vinyl (>C=C<) unsaturation. Such groups are exemplified by vinyl (ethen-1-yl), allyl, but-3-enyl and the like.

The term "substituted alkenyl" refers to alkenyl groups having from 1 to 3 substituents, and preferably 1 to 2 substituents, selected from the group consisting of alkoxy, substituted alkoxy, acyl, acylamino, acyloxy, amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic. This term includes both E (trans) and Z (cis) isomers as appropriate. It also includes mixtures of both E and Z components.

The term "alkynyl" refers to acetylenic unsaturated monovalent hydrocarbyl groups having from 2 to 6 carbon atoms, and preferably 2 to 3 carbon atoms, and having at least 1, and preferably from 1 to 2 sites of acetylenic (—C≡C—) unsaturation. This group is exemplified by ethyn-1-yl, propyn-1-yl, propyn-2-yl, and the like.

The term "substituted alkynyl" refers to alkynyl groups having from 1 to 3 substituents, and preferably 1 to 2 substituents, selected from the group consisting of alkoxy, substituted alkoxy, acyl, acylamino, acyloxy, amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic. This group is exemplified by groups such as phenylethynyl, etc.

The term "amino" refers to the group NR$^{41}$R$^{41}$, where each R$^{41}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, sulfonyl, and substituted sulfonyl, provided that both R$^{41}$ groups are not hydrogen; or the R$^{41}$ groups can be joined together with the nitrogen atom to form a heterocyclic or substituted heterocyclic ring. This group is exemplified by phenylamino, methylphenylamino, and the like. This group is exemplified by groups such as (ethanic acid-2-yl)amino, etc.

The term "acylamino" refers to the groups NR$^{45}$C(O)alkyl, —NR$^{45}$C(O)substituted alkyl, —NR$^{45}$C(O)cycloalkyl, —NR$^{45}$C(O)substituted cycloalkyl, —NR$^{45}$C(O)alkenyl, —NR$^{45}$C(O)substituted alkenyl, —NR$^{45}$C(O)alkynyl, —NR$^{45}$C(O)substituted alkynyl, —NR$^{45}$C(O)aryl, —NR$^{45}$C(O)substituted aryl, —NR$^{45}$C(O)heteroaryl, —NR$^{45}$C(O)substituted heteroaryl, —NR$^{45}$C(O)heterocyclic, and —NR$^{45}$C(O)substituted heterocyclic where R$^{45}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are defined herein.

The term "oxycarbonylamino" refers to the groups $NR^{46}C(O)O$-alkyl, $-NR^{46}C(O)O$-substituted alkyl, $-NR^{46}C(O)O$-alkenyl, $-NR^{46}C(O)O$-substituted alkenyl, $-NR^{46}C(O)O$-alkynyl, $-NR^{46}C(O)O$-substituted alkynyl, $-NR^{46}C(O)O$-cycloalkyl, $-NR^{46}C(O)O$-substituted cycloalkyl, $-NR^{46}C(O)O$-aryl, $-NR^{46}C(O)O$-substituted aryl, $-NR^{46}C(O)O$-heteroaryl, $-NR^{46}C(O)O$-substituted heteroaryl, $-NR^{46}C(O)O$-heterocyclic, and $-NR^{46}C(O)O$-substituted heterocyclic where $R^{46}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "oxythiocarbonylamino" refers to the groups $NR^{46}C(S)O$-alkyl, $-NR^{46}C(S)O$-substituted alkyl, $-NR^{46}C(S)O$-alkenyl, $-NR^{46}C(S)O$-substituted alkenyl, $-NR^{46}C(S)O$-alkynyl, $-NR^{46}C(S)O$-substituted alkynyl, $-NR^{46}C(S)O$-cycloalkyl, $-NR^{46}C(S)O$-substituted cycloalkyl, $-NR^{46}C(S)O$-aryl, $-NR^{46}C(S)O$-substituted aryl, $-NR^{46}C(S)O$-heteroaryl, $-NR^{46}C(S)O$-substituted heteroaryl, $-NR^{46}C(S)O$-heterocyclic, and $-NR^{46}C(S)O$-substituted heterocyclic where $R^{46}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonyloxy," or the prefix "carbamoyloxy" or "substituted carbamoyloxy," refers to the groups $-OC(O)NR^{47}R^{47}$ where each $R^{47}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic; or where each $R^{47}$ is joined to form, together with the nitrogen atom, a heterocyclic or substituted heterocyclic, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonylamino" refers to the group $NR^{49}C(O)N(R^{49})_2$ where each $R^{49}$ is independently selected from the group consisting of hydrogen and alkyl.

The term "aminothiocarbonylamino" refers to the group $NR^{49}C(S)N(R^{49})_2$ where each $R^{49}$ is independently selected from the group consisting of hydrogen and alkyl.

The term "aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3 (4H)-one-7-yl, and the like) provided that the point of attachment is the aryl group. Preferred aryls include phenyl and naphthyl.

The term "substituted aryl" refers to aryl groups, as defined herein, which are substituted with from 1 to 4, particularly 1 to 3, substituents selected from the group consisting of hydroxy, acyl, acylamino, acyloxy, alkyl, substituted alkyl, alkoxy, substituted alkoxy, alkenyl, substituted alkenyl, alkynyl, substituted alkynyl, amidino ($-C(=NH)$-amino), amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyl ester, cyano, thio, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, guanidino ($-NH-C(=NH)$-amino), halo, nitro, heteroaryl, substituted heteroaryl, heterocyclic, substituted heterocyclic, oxycarbonylamino, oxythiocarbonylamino, sulfonyl, substituted sulfonyl, $-OS(O)_2$-alkyl, $-OS(O)_2$-substituted alkyl, $-OS(O)_2$-aryl, $-OS(O)_2$-substituted aryl, $-OS(O)_2$-heteroaryl, $-OS(O)_2$-substituted heteroaryl, $-OS(O)_2$-heterocyclic, $-OS(O)_2$-substituted heterocyclic, $-OSO_2-NR^{51}R^{51}$, $-NR^{51}S(O)_2-NR^{51}$-alkyl, $-NR^{51}S(O)_2-NR^{51}$-substituted alkyl, $-NR^{51}S(O)_2-NR^{51}$-aryl, $-NR^{51}S(O)_2-NR^{51}$-substituted aryl, $-NR^{51}S(O)_2-NR^{51}$-hetero aryl, $-NR^{51}S(O)_2-NR^{51}$-substituted hetero aryl, $-NR^{51}S(O)_2-NR^{51}$-heterocyclic, $-NR^{51}S(O)_2-NR^{51}$-substituted heterocyclic, where each $R^{51}$ is independently selected from hydrogen or alkyl, wherein each of the terms is as defined herein. This group is exemplified by groups such as 4-fluorophenyl, 3-methoxyphenyl, 4-t-butylphenyl, 4-trifluoromethylphenyl, 2-trifluoromethoxyphenyl, 3-trifluoromethoxyphenyl, 4-trifluoromethoxyphenyl, 2-chlorophenyl, 3-chlorophenyl, 4-chlorophenyl, 2-chloro-6-fluorophenyl, 2,4-dichlorophenyl, 4-methoxyphenyl, 2,6-dimethoxyphenyl, 3-cyanophenyl, 4-cyanophenyl, 4-phenoxyphenyl, 4-methanesulfonylphenyl, biphenyl-4-yl, etc.

The term "aryloxy" refers to the group aryl-O— that includes, by way of example, phenoxy, naphthoxy, and the like.

The term "substituted aryloxy" refers to substituted aryl-O— groups.

The term "aryloxyaryl" refers to the group -aryl-O-aryl.

The term "substituted aryloxyaryl" refers to aryloxyaryl groups substituted with from 1 to 3 substituents on either or both aryl rings as defined above for substituted aryl.

The term "carboxyl" refers to —COOH or salts thereof.

The terms "carboxyl ester" and "oxycarbonyl" refer to the groups —C(O)O-alkyl, —C(O)O-substituted alkyl, —C(O)O-alkenyl, —C(O)O-substituted alkenyl, —C(O)O-alkynyl, —C(O)O— substituted alkynyl, —C(O)O-cycloalkyl, —C(O)O-substituted cycloalkyl, —C(O)O-aryl, —C(O)O— substituted aryl, —C(O)O-heteroaryl, —C(O)O-substituted heteroaryl, —C(O)O-heterocyclic, and —C(O)O-substituted heterocyclic.

The term "cyano" refers to the group —CN.

The term "cycloalkyl" refers to a saturated or an unsaturated but nonaromatic cyclic alkyl groups of from 3 to 10, 3 to 8 or 3 to 6 carbon atoms having single or multiple cyclic rings including, by way of example, adamantyl, cyclopropyl, cyclobutyl, cyclopentyl, cyclooctyl, cyclohexenyl, and the like.

The term "substituted cycloalkyl" refers to a cycloalkyl group, having from 1 to 5 substituents selected from the group consisting of oxo (=O), thioxo (=S), alkyl, substituted alkyl, alkoxy, substituted alkoxy, acyl, acylamino, acyloxy, amino, aminoacyl, aryl, substituted aryl, aryloxy, substituted aryloxy, cyano, halogen, hydroxy, nitro, carboxyl, carboxyl ester, cycloalkyl, substituted cycloalkyl, heteroaryl, substituted heteroaryl, heterocyclic, and substituted heterocyclic.

The term "cycloalkylene" and "substituted cycloalkylene" refer to divalent cycloalkyl and substituted cycloalkyl groups as defined above.

The term "cycloalkoxy" refers to —O-cycloalkyl groups.

The term "substituted cycloalkoxy" refers to —O-substituted cycloalkyl groups.

The term "halo" or "halogen" refers to fluoro, chloro, bromo, and iodo.

The term "haloalkyl" refers to an alkyl group, having from 1 to 3 substituents selected from the group consisting of fluoro, chloro, bromo, and iodo.

The term "haloalkoxy" refers to an alkoxy group, having from 1 to 3 substituents selected from the group consisting of fluoro, chloro, bromo, and iodo.

The term "hydroxy" or "hydroxyl" refers to the group —OH.

The term "heteroaryl" refers to an aromatic ring of from 1 to 15 carbon atoms, preferably from 1 to 10 carbon atoms, and 1 to 4 heteroatoms within the ring selected from the group consisting of oxygen, nitrogen, and sulfur. Such heteroaryl groups can have a single ring (e.g., pyridinyl, furyl, or thienyl) or multiple condensed rings (e.g., indolizinyl or benzothienyl) provided the point of attachment is through a ring containing the heteroatom and that ring is aromatic. The nitrogen and/or sulfur ring atoms can optionally be oxidized to provide for the N-oxide or the sulfoxide, and sulfone derivatives. Examples of heteroaryls include but are not limited to, pyridinyl, pyrimidinyl, pyrrolyl, pyrazolyl, indolyl, thiophenyl, thienyl, and furyl.

The term "substituted heteroaryl" refers to heteroaryl groups that are substituted with from 1 to 3 substituents selected from the same group of substituents defined for substituted aryl. This group is exemplified by groups such as 5-flouro-pyridin-3-yl, 1-benzyl-1H-[1,2,3]triazol-4-yl, 5-bromo-furan-2-yl, triflouromethyl-2H-pyrazol-3-yl, etc.

The term "heteroaryloxy" refers to the group —O-heteroaryl, and "substituted heteroaryloxy" refers to the group —O-substituted heteroaryl.

The term "heterocyclyl" or "heterocyclic" refers to a saturated or unsaturated (but not aromatic) group having a single ring or multiple condensed rings, from 1 to 10 carbon atoms, and from 1 to 4 hetero atoms selected from the group consisting of nitrogen, sulfur or oxygen within the ring wherein, in fused ring systems, one or more of the rings can be aryl or heteroaryl provided that the point of attachment is at the heterocycle. The nitrogen and/or sulfur ring atoms can optionally be oxidized to provide for the N-oxide or the sulfoxide, and sulfone derivatives.

The term "substituted heterocyclyl" or "substituted heterocyclic" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholine, thiomorpholine (also referred to as thiamorpholine), piperidine, pyrrolidine, tetrahydrofuran, and the like.

The term "nitro" refers to the group —NO$_2$.

The term "oxo" refers to the atom (=O) or to the atom (—O$^-$).

The term "sulfonyl" refers to the group —S(O)$_2$H.

The term "substituted sulfonyl" refers to the group —SO$_2$-alkyl, —SO$_2$-substituted alkyl, —SO$_2$-alkenyl, —SO$_2$-substituted alkenyl, —SO$_2$-alkynyl, —SO$_2$-substituted alkynyl, —SO$_2$-cycloalkyl, —SO$_2$-substituted cycloalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

The term "heterocyclyloxy" refers to the group —O-heterocyclic, and "substituted heterocyclyloxy" refers to the group —O-substituted heterocyclic.

The term "thio" or "mercapto" refers to the group —SH.

The term "alkylsulfanyl," "alkylthio," or "thioether" refers to the groups —S-alkyl where alkyl is as defined above.

The term "substituted alkylthio," "substituted alkylsulfanyl," or "substituted alkylthio" refers to the group —S-substituted alkyl where substituted alkyl is as defined above.

The term "cycloalkylthio" or "cycloalkylsulfanyl" refers to the groups —S-cycloalkyl where cycloalkyl is as defined above.

The term "substituted cycloalkylthio" refers to the group —S-substituted cycloalkyl where substituted cycloalkyl is as defined above.

The term "arylthio" or "arylsulfanyl" refers to the group —S-aryl, and "substituted arylthio" refers to the group —S-substituted aryl where aryl and substituted aryl are as defined above.

The term "heteroarylthio" or "heteroarylsulfanyl" refers to the group —S-heteroaryl, and "substituted heteroarylthio" refers to the group —S-substituted heteroaryl where heteroaryl and substituted heteroaryl are as defined above.

The term "heterocyclicthio" or "heterocyclicsulfanyl" refers to the group —S-heterocyclic, and "substituted heterocyclicthio" refers to the group —S-substituted heterocyclic where heterocyclic, and substituted heterocyclic are as defined above.

The term "ester" refers to compounds of Formula I, Ia, Ib, IIa, IIb, IIIa, or IIIb where W is —C(O)O— and R$^9$ is alkyl, substituted alkyl, aryl, substituted aryl, and the like; R$^1$ is acyloxy; R$^5$ is acyl; or W is —O— and R$^9$ has been substituted for an acyl group. In some embodiments, esters include compounds of Formula I wherein R$^1$ is acyloxy. In some embodiments, esters include compounds of Formula I wherein R$^5$ is acyl. Exemplary esters of Formula I, Ia, Ib, IIa, IIb, IIIa, or IIIb can be provided, for example, via acylation of the hydroxyl group at the C1 or C4 position of the naphthyridinone using a suitable reagent such as an acid chloride or anhydride. Other exemplary esters of Formula I, Ia, Ib, IIa, IIb, IIIa, or IIIb can be provided, for example, via esterification of the carboxylic acid moiety when W is —C(O)O— using an alkoxy, substituted alkoxy, aryloxy, substituted aryloxy, and the like. Such acylation and esterification methods are well known in the art.

The term "pharmaceutically acceptable salt" refers to pharmaceutically acceptable salts of a compound, which salts are derived from a variety of organic and inorganic counter ions well known in the art, and include, by way of example only, sodium, potassium, calcium, magnesium, ammonium, tetraalkylammonium, and the like; and, when the molecule contains a basic functionality, salts of organic or inorganic acids, such as hydrochloride, hydrobromide, tartrate, mesylate, acetate, maleate, oxalate, and the like. For example, pharmaceutically acceptable salts of the disclosure can be provided by compounds of Formula I, Ia, Ib, IIa, IIb, IIIa, or Mb when when W is —C(O)O— and the $R^9$ group has been replaced with a cation. Such pharmaceutically acceptable salts of the disclosure can be provided by methods well known in the art. The term "cation" refers to a positively charged organic and inorganic counter ion, and includes, by way of example only, sodium, potassium, calcium, magnesium, ammonium, tetraalkylammonium, and the like.

The terms "stereoisomer" or "stereoisomers" refer to compounds that differ in the chirality of one or more stereocenters. Stereoisomers include enantiomers (compounds are non-superimposable mirror images) and diastereomers (compounds having more than one stereogenic center that are non-mirror images of each other and wherein one or more stereogenic center differs between the two stereoisomers). The compounds of the disclosure can be present as a mixture of stereoisomers or as a single stereoisomer.

The term "tautomer" refers to alternate forms of a compound that differ in the position of a proton, such as enol, keto, and imine enamine tautomers, or the tautomeric forms of heteroaryl groups containing a ring atom attached to both a ring NH moiety and a ring =N moiety such as pyrazoles, imidazoles, benzimidazoles, triazoles, and tetrazoles.

The term "prodrug" as used herein, refers to compounds of Formula I, Ia, Ib, IIa, IIb, Ma, or Mb that include chemical groups which, in vivo, can be converted into the carboxylate group in embodiments when W is —C(O)OR$^9$, and/or can be split off from the $R^5$ atom to provide for the active drug, a pharmaceutically acceptable salt thereof, or a biologically active metabolite thereof. Suitable groups are well known in the art and particularly include: for the carboxylic acid moiety, a prodrug selected from, e.g., esters including, but not limited to, those derived from alkyl alcohols, substituted alkyl alcohols, hydroxy substituted aryls and heteroaryls and the like; amides, particularly amides derived from amines of the Formula HNR$^{200}$R$^{210}$ where R$^{200}$ and R$^{210}$ are independently hydrogen, alkyl, substituted alkyl, aryl, substituted aryl, and the like; hydroxymethyl, aldehyde, N-oxides, and derivatives thereof. Exemplary structures of such prodrugs can be of Formula P-1, P-2, or P-3 shown below, where R$^{300}$ is alkyl, substituted alkyl, alkoxy, substituted alkoxy, aryl, substituted aryl, aryloxy, substituted aryloxy, or amino

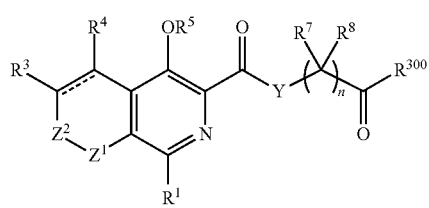

P-1

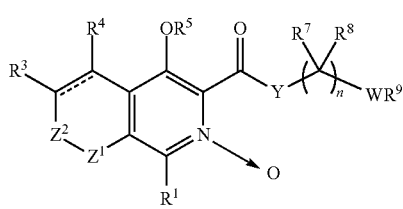

P-2

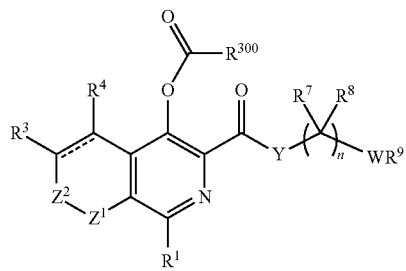

P-3

The term "pharmaceutically acceptable excipient" as used herein means an inert or inactive substance used in the production of pharmaceutical products or other tablets, including without limitation any substance used as a binder, disintegrant, coating, compression/encapsulation aid, cream or lotion, lubricant, parenteral, sweetener or flavoring, suspending/gelling agent, or wet granulation agent. Binders include, e.g., carbopol, povidone, xanthan gum, etc.; coatings include, e.g., cellulose acetate phthalate, ethylcellulose, gellan gum, maltodextrin, etc.; compression/encapsulation aids include, e.g., calcium carbonate, dextrose, fructose dc, honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams and lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; parenterals include, e.g., mannitol, povidone, etc.; plasticizers include, e.g., dibutyl sebacate, polyvinylacetate phthalate, etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

4. Compound Preparation

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

1991), March's *Advanced Organic Chemistry,* (John Wiley, and Sons, 5$^{th}$ Edition, 2001), and Larock's *Comprehensive Organic Transformations* (VCH Publishers Inc., 1989).

Synthesis of Compounds Disclosure

The compounds of this disclosure are preferably prepared by, but are not limited to, the synthetic protocols illustrated in Scheme A, wherein R is an alkyl group (e.g. methyl, ethyl, etc.), X is halo (e.g. chloro, bromo, or iodo), LG is a leaving group (e.g. halo, alkoxy, etc.) and PG is a suitable protecting group as described in T. W. Greene and G. M. Wuts (1999) *Protecting Groups in Organic Synthesis,* 3rd Edition, Wiley, New York, and references cited therein. In Scheme A, the substituents n, $Z^1$, $Z^2$, $Z^3$, $Z^4$, $R^1$, $R^5$, $R^7$, $R^8$, W, and Y are as defined herein.

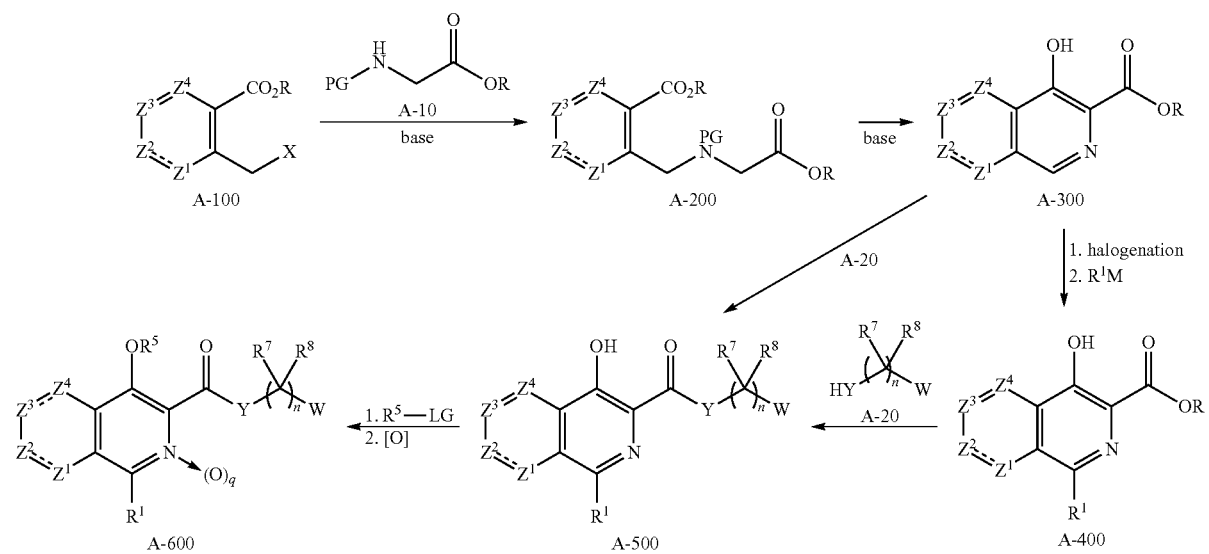

Scheme A

Furthermore, the compounds of this disclosure may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, Compounds of formula A-200 are prepared by coupling compounds A-100 wherein R is an alkyl group (e.g. methyl, ethyl, etc.) and X is halo (e.g. chloro, bromo, or iodo) with compounds A-10 wherein PG is a suitable amine protecting group (e.g. tosyl) and R is an alkyl group (e.g. methyl, ethyl, etc.). The reaction is conducted under conventional coupling conditions well known in the art. In one embodiment, the reaction is conducted in the presence of sodium iodide and potassium carbonate or another suitable base in THF, DMF or another suitable solvent at ambient temperatures. The reaction is continued until it is substantially complete which typically occurs within about 1 to 72 h. Upon reaction completion, compounds A-200 can be recovered by conventional techniques such as neutralization, extraction, precipitation, chromatography, filtration and the like, or alternatively used in the next step without isolation or purification. Compounds A-200 can then be cyclized to afford compound A-300 under basic conditions using a suitable base (e.g. alkoxide, such as methoxde, ethoxide, etc.).

Compounds A-400 (Formula I, wherein $R^1$ is halo) are prepared by contacting compounds A-300 with a halogenating reagent, such as NBS or $I_2$, in a suitable solvent such as methylene chloride, carbon tetrachloride, etc. Upon reaction completion, compounds A-400 can be recovered by conventional techniques such as neutralization, extraction, precipitation, chromatography, filtration and the like. In some embodiments of compounds A-400, R is $R^9$ as defined for Formula I. Further derivitization of compounds A-400 to provide compounds of Formula I, wherein $R^1$ is alkyl, aryl, etc., are prepared by contacting compounds A-400 wherein $R^1$ is halo with reagents $R^1M$, where M is a suitable functional group such as, but not limited to, boronic acids or their derivatives such as $C_6H_4B(OH)_2$; organozinc compounds such as benzylzinc bromide; organomagnesium compounds such as benzyl magnesium bromide; organotin compounds such as tributyl(phenylethynyl)stannane or tributylphenyltin; hydroxyl; amino; or thio, and the like. The reaction is typically conducted in the presence of suitable catalyst such as a palladium catalyst including $Pd(PPh_3)_4$, $PdCl_2(PPh_3)_2$ or tris (dibenzylideneacetone)dipalladium(0), and the like, or a copper catalyst such as CuCl, and if required suitable mediator, co-catalyst and/or base known to one skilled in the art using suitable solvents/solvent mixtures. Upon reaction completion, compounds A-400 can be recovered by conventional techniques such as neutralization, extraction, precipitation, chromatography, filtration and the like. Optionally, compounds A-400 wherein ---- is a single bond can be prepared via hydrogenation of compounds A-300 or A-400 using hydrogen gas with a catalyst such as palladium on carbon under conventional hydrogenation conditions well known in the art.

Compounds A-500 are prepared by contacting compounds A-300 or A-400 with at least a stoichiometric amount and preferably an excess of compounds A-20. The reaction is conducted under conventional coupling conditions well known in the art. In one embodiment, the reaction is conducted in the presence of sodium methoxide, sodium ethoxide or another suitable base in methanol. Upon reaction completion, compounds A-500 can be recovered by conventional techniques such as neutralization, extraction, precipitation, chromatography, filtration and the like.

Compounds A-600 are prepared by derivatization of the 4-hydroxyl group of the naphthyridinone ring using a reagent of the formula $R^5$-LG, wherein LG is a leaving group such as halo or alkoxy. Further, the nitrogen of the naphthyridinone ring of compounds A-500 or A-600 can be oxidized to afford the N-oxide (i.e., q is 1) under standard oxidation conditions known in the art.

Exemplary compounds of formula A-100 for use in the methods of Scheme A for the preparation of compounds of Formula IIa can be prepared according to the synthetic protocols illustrated in Scheme B, wherein R is an alkyl group (e.g. methyl, ethyl, etc.) and $R^2$ is as defined herein.

Scheme B

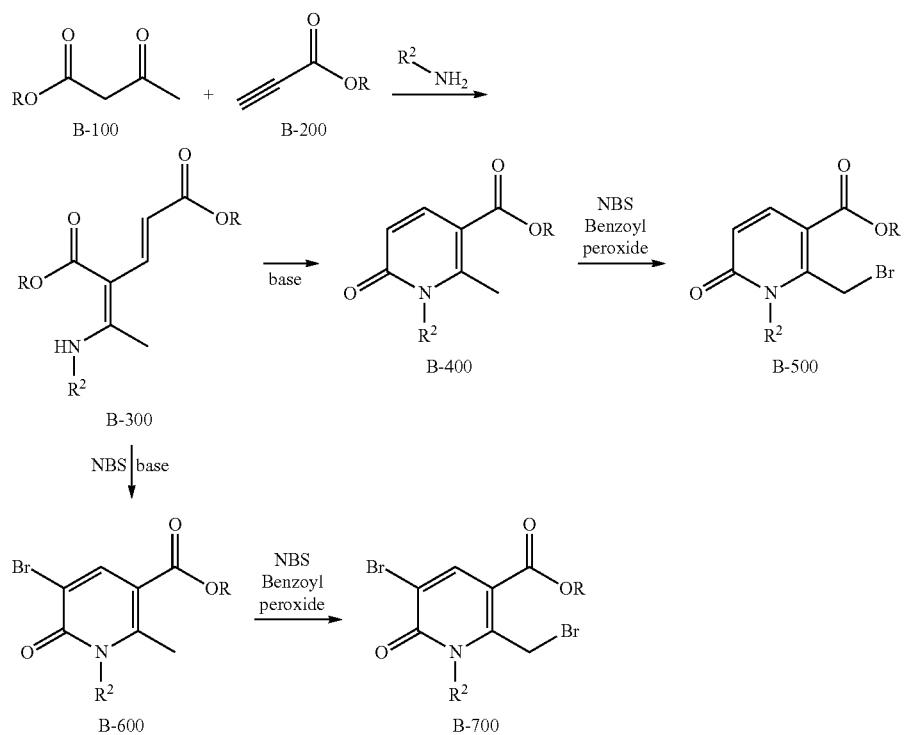

Compounds B-300 are prepared by condensing compounds B-100 and B-200 in the presence of $R^2$—$NH_2$. Compounds B-300 are cyclized in the presence of a base to provide compounds B-400 (when $R^3$ is H). Compounds B-600 can be prepared by cyclizing compounds B-300 in the presence of n-bromosuccinamide (NBS) and a base. Such compounds can then be used to further elaborate $R^3$. Reacting B-400 or B-600 with N-bromosuccinimide (NBS) in the presence of benzoyl peroxide provides compounds B-500 or B-700 for use in the methods shown in Scheme A. Upon each reaction completion, each of compounds B-300, B-400, B-500, B-600, and B-700 can be recovered by conventional techniques such as neutralization, extraction, precipitation, chromatography, filtration and the like.

Exemplary compounds of formula A-100 for use in the methods of Scheme A for the preparation of compounds of Formula IIb can be prepared according to the synthetic protocols illustrated in Scheme C, wherein R is an alkyl group (e.g. methyl, ethyl, etc.) and $R^2$ is as defined herein.

Scheme C

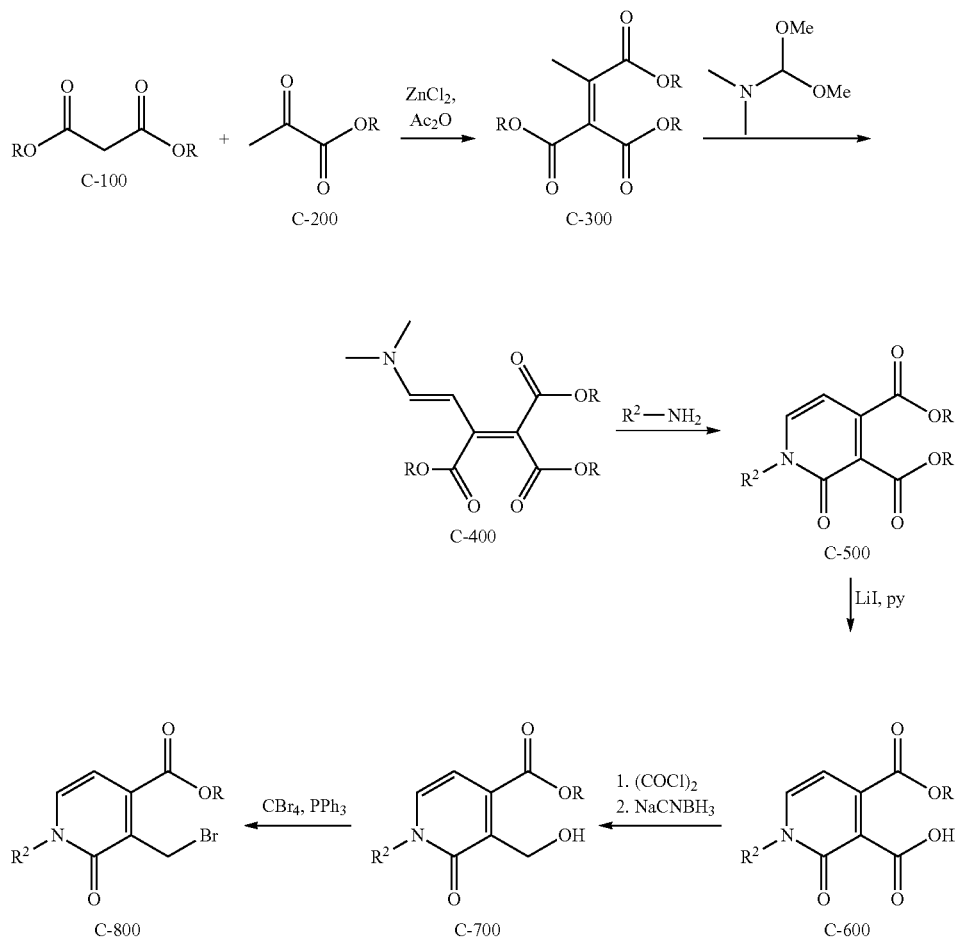

Compounds C-300 are prepared by condensing compounds C-100 and C-200 in the presence of $ZnCl_2$ and acetic anhydride ($Ac_2O$). Compounds C-400 are prepared by reacting compounds C-300 with 1,1-dimethoxy-N,N-dimethylmethanamine. Cyclization of compounds C-400 in the presence of $R^2$—$NH_2$ provides compounds C-500. Mono de-esterification of compounds C-500 with lithium iodide and pyridine (py) provides compounds C-600. Compounds C-700 are prepared via reduction of compounds C-600 using oxalyl chloride followed by sodium cyanoborohydride. Conversion of compounds C-700 to the corresponding methylbromide compounds C-800 for use in Scheme A is accomplished using carbon tetrabromide and triphenylphosphine ($PPh_3$). Upon each reaction completion, each of compounds C-300, C-400, C-500, C-600, C-700 and C-800 can be recovered by conventional techniques such as neutralization, extraction, precipitation, chromatography, filtration and the like.

Exemplary compounds of formula A-300 for use in the methods of Scheme A can be prepared from compounds B-500, B-700 and C-800 according to the synthetic protocols illustrated in Scheme D, wherein R is an alkyl group (e.g. methyl, ethyl, etc.), PG is a suitable protecting group as described in T. W. Greene and G. M. Wuts (1999) *Protecting Groups in Organic Synthesis,* 3rd Edition, Wiley, New York, and references cited therein, and $R^2$ is as defined herein.

Scheme D

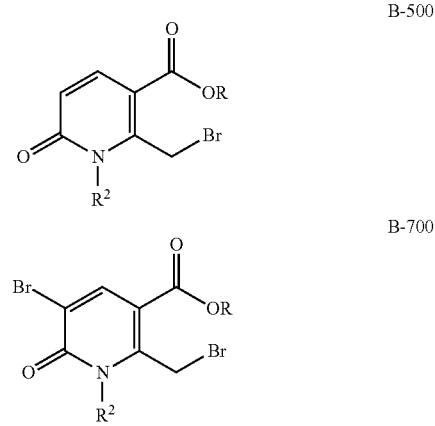

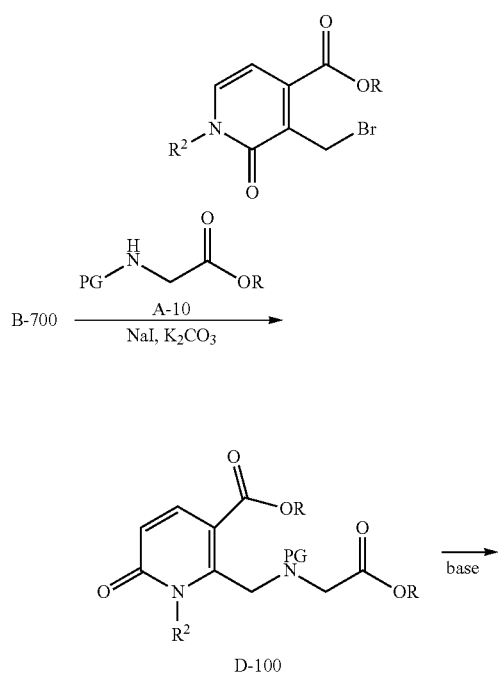

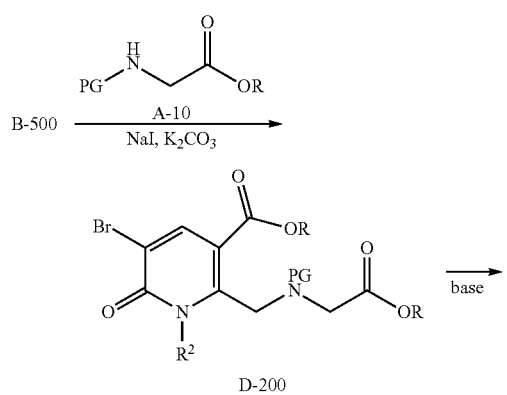

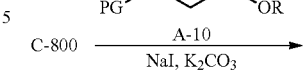

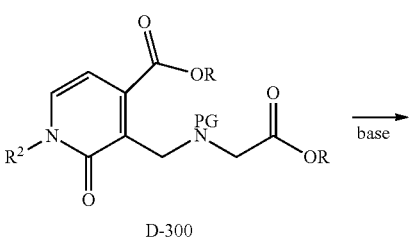

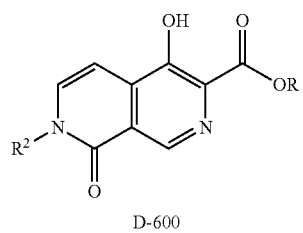

Compounds D-100, D-200 and D-300 are prepared by contacting compounds B-500, B-700 and C-800, respectively, with at least a stoichiometric amount and preferably an excess of compound A-10 in the presence of sodium iodide and potassium carbonate. The reaction is conducted under conventional substitution conditions well known in the art. Upon reaction completion, compounds D-100, D-200 and D-300 can be recovered by conventional techniques such as neutralization, extraction, precipitation, chromatography, filtration and the like, or alternatively, used in the subsequent step without purification. Compounds D-100, D-200 and D-300 can be cyclized to afford compounds D-400, D-500 and D-600, respectively, under basic conditions (e.g. alkoxide, such as methoxde, ethoxide, etc.). Upon reaction completion, compounds D-400, D-500 and D-600 can be recovered by conventional techniques such as neutralization, extraction, precipitation, chromatography, filtration and the like.

Further exemplary compounds of formula A-300 for use in the methods of Scheme A can be prepared from compound D-500 according to the synthetic protocols illustrated in Scheme E, wherein R is an alkyl group (e.g. methyl, ethyl, etc.), PG is a suitable protecting group as described in T. W. Greene and G. M. Wuts (1999) *Protecting Groups in Organic Synthesis*, 3rd Edition, Wiley, New York, and references cited therein, and $R^2$ and $R^3$ are as defined herein.

Scheme E

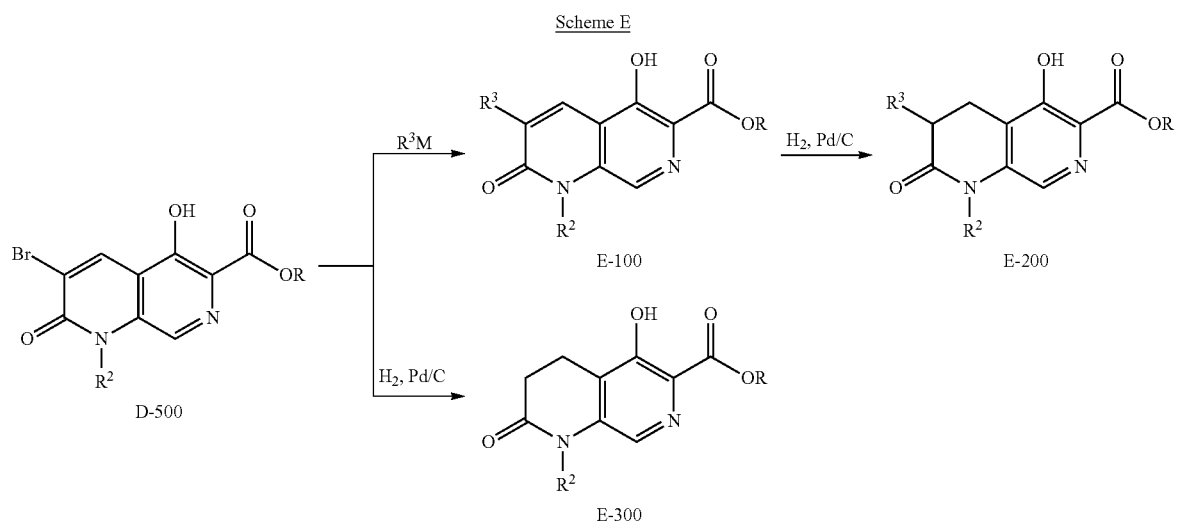

Compounds E-100 can be prepared by reacting compounds D-500 with reagents $R^3M$, where M is a suitable functional group such as, but not limited to, boronic acids or their derivatives such as $C_6H_4B(OH)_2$; organozinc compounds such as benzylzinc bromide; organomagnesium compounds such as benzyl magnesium bromide; organotin compounds such as tributyl(phenylethynyl)stannane or tributylphenyltin; hydroxyl; amino; or thio, and the like. The reaction is typically conducted in the presence of suitable catalyst such as a palladium catalyst including $Pd(PPh_3)_4$, $PdCl_2(PPh_3)_2$ or tris(dibenzylideneacetone)dipalladium(0), and the like, or a copper catalyst such as CuCl, and if required suitable mediator, co-catalyst and/or base known to one skilled in the art using suitable solvents/solvent mixtures. Upon reaction completion, E-100 can be recovered by conventional techniques such as neutralization, extraction, precipitation, chromatography, filtration, and the like; or, alternatively, used in the next step without purification and/or isolation. Compounds E-100 can be modified to E-200 using hydrogen gas with a catalyst such as palladium on carbon under conventional hydrogenation conditions well known in the art. Compounds E-300 can be prepared via hydrogenation of compounds D-500 using hydrogen gas with a catalyst such as palladium on carbon under conventional hydrogenation conditions well known in the art.

Exemplary compounds of formula A-100 for use in the methods of Scheme A for the preparation of compounds of Formula Ina can be prepared according to the synthetic protocols illustrated in Scheme F, wherein R is an alkyl group (e.g. methyl, ethyl, etc.) and $R^2$ is as defined herein and LG is a leaving group (e.g. chloro, bromo, etc.).

Scheme F

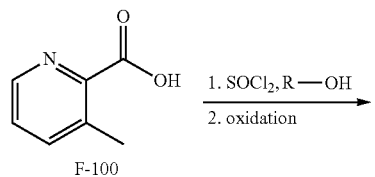

Compounds F-200 are prepared by esterifying the carboxylic acid moiety of compounds F-100 using an alcohol of formula R—OH under standard esterification methods, followed by N-oxidation (e.g. using meta-chloroperbenzoic acid). Compounds F-300 can be prepared via chlorination of F-200 using phosphoryl chloride. Compounds F-300 are hydrolysed in the presence of dichloroacetic acid to provide compounds F-400. Compounds F-500 are prepared by contacting $R^2$-LG with compounds F-400 in the presence of a base. Reacting compounds F-500 with N-bromosuccinimide (NBS) in the presence of benzoyl peroxide provides compounds F-600 for use in the methods shown in Scheme A. Upon each reaction completion, each of compounds F-200, F-300, F-400, and F-500 can be recovered and optionally purified by conventional techniques such as neutralization, extraction, precipitation, chromatography, filtration and the like.

Exemplary compounds of formula A-100 for use in the methods of Scheme A for the preparation of compounds of Formula IIIb can be prepared according to the synthetic protocols illustrated in Scheme G, wherein R is an alkyl group (e.g. methyl, ethyl, etc.) and R² is as defined herein and LG is a leaving group (e.g. chloro, bromo, etc.).

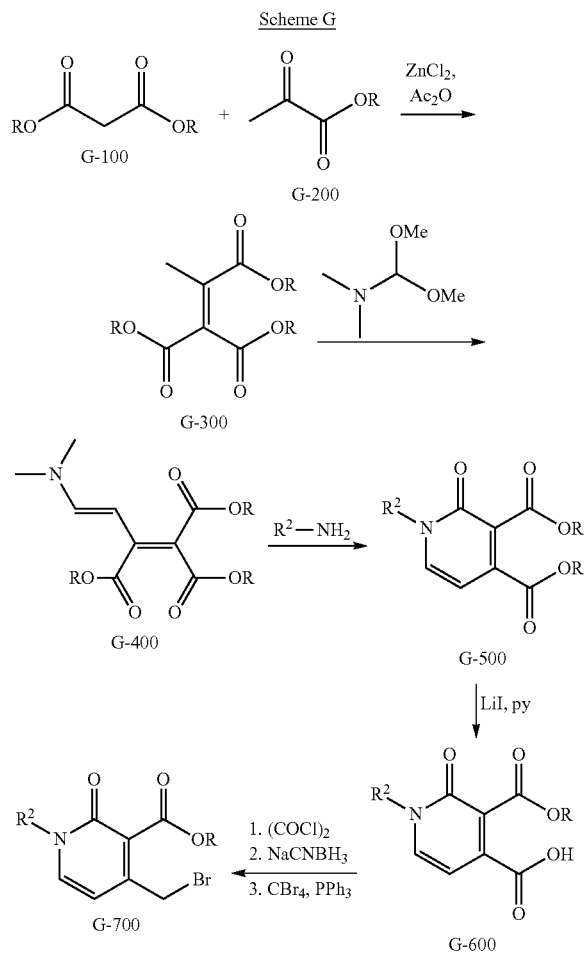

Compounds G-300 are prepared by condensing compounds G-100 and G-200 in the presence of $ZnCl_2$ and acetic anhydride ($Ac_2O$). Compounds G-400 are prepared by reacting compounds G-300 with 1,1-dimethoxy-N,N-dimethylmethanamine Cyclization of compounds G-400 in the presence of $R^2$—$NH_2$ provides compounds G-500. Selective mono de-esterification of compounds G-500 with lithium iodide and pyridine (py) provides compounds G-600. Reduction of compounds C-600 using oxalyl chloride followed by sodium cyanoborohydride provides the corresponding alcohol. Conversion of the resulting alcohol to the corresponding bromide can be accomplished using carbon tetrabromide and triphenylphosphine ($PPh_3$), thus providing compounds G-700 for use in Scheme A. Upon each reaction completion, each of compounds G-300, G-400, G-500, G-600 and G-700 can be recovered by conventional techniques such as neutralization, extraction, precipitation, chromatography, filtration and the like.

The general synthetic methods described and shown in the Schemes above can be modified by one of skill in the art to provide the compounds of the present disclosure.

The compounds A-10, A-20, B-100, B-200, C-100, C-200, F-100, G-100 and G-200 for use in the reactions depicted in the above schemes can be synthesized from commercial starting materials under reaction conditions known in the art or are available from commercial sources.

Other modifications to arrive at compounds of this disclosure are well within the skill of the art. For example, modification of the C-4 hydroxy group may be done by conventional means to corresponding ethers, acyloxy etc. to provide compounds of Formula I. In addition, the thio moiety can be oxidized to provide compounds of Formula I using methods well known to those of skill in the art.

5. Use of Compounds of the Disclosure

The compounds of the present disclosure can be used to inhibit HIF hydroxylase activity, thereby modulating the stability and/or activity of HIF and activating HIF-regulated gene expression. The compounds can be used in methods to treat, pretreat, or delay progression or onset of conditions associated with HIF including, but not limited to, anemia and various aspects of ischemic and hypoxic conditions. In various embodiments, compound administration is initiated following diagnosis of a condition associated with ischemia, e.g., myocardial infarction, pulmonary embolism, intestinal infarction, ischemic stroke, renal ischemic-reperfusion injury, cardiac cirrhosis, macular degeneration, pulmonary embolism, chronic kidney disease, transient ischemic attack, peripheral vascular disease, acute respiratory failure, neonatal respiratory distress syndrome, and congestive heart failure. In another embodiment, the compound is administered immediately after a trauma or injury. In other embodiments, the compound can be administered to a subject based on predisposing conditions, e.g., hypertension, diabetes, occlusive arterial disease, chronic venous insufficiency, Raynaud's disease, chronic skin ulcers, cirrhosis, congestive heart failure, and systemic sclerosis. In still other embodiments, compounds may be administered to pretreat a subject to decrease or prevent the development of tissue damage associated with ischemia or hypoxia.

In particular embodiments, the compounds of the present disclosure can be used to increase endogenous erythropoietin (EPO). The compounds can be administered to prevent, pretreat, or treat EPO-associated conditions, including, e.g., anemia and neurological disorders. Conditions associated with anemia include disorders such as acute or chronic kidney disease, diabetes, cancer, ulcers, infection with virus, e.g., HIV, bacteria, or parasites; inflammation, etc. Anemic conditions can further be associated with procedures or treatments including, e.g., radiation therapy, chemotherapy, dialysis, and surgery. Anemia may additionally be associated with abnormal hemoglobin and/or erythrocytes, such as found in disorders such as microcytic anemia, hypochromic anemia, aplastic anemia, etc.

The compounds can be used to increase endogenous EPO in a subject undergoing a specific treatment or procedure, prophylactically or concurrently, for example, an HIV-infected anemic patient being treated with azidothymidine (zidovudine) or other reverse transcriptase inhibitors, an anemic cancer patient receiving cyclic cisplatin- or non-cisplatin-containing chemotherapeutics, or an anemic or non-anemic patient scheduled to undergo surgery. Additionally, the compounds can be used to increase endogenous EPO levels in an anemic or non-anemic patient scheduled to undergo surgery to reduce the need for allogenic blood transfusions or to facilitate banking of blood prior to surgery.

6. Biological Testing

The biological activity of the compounds of the disclosure may be assessed using any conventionally known methods.

Suitable assay methods are well known in the art. The following assays are presented only as examples and are not intended to be limiting. The compounds of the disclosure are active in at least one of the following assays.

i. Cell-Based HIFα Stabilization Assay

Human cells derived from various tissues are separately seeded into 35 mm culture dishes, and grown at 37° C., 20% $O_2$, 5% $CO_2$ in standard culture medium, e.g., DMEM (Dulbecco's modification of Eagle's medium), 10% FBS (fetal bovine serum). When cell layers reach confluence, the media is replaced with OPTI-MEM media (Invitrogen Life Technologies, Carlsbad Calif.), and cell layers are incubated for approximately 24 hours in 20% $O_2$, 5% $CO_2$ at 37° C. Compound or 0.013% DMSO (dimethyl sulfoxide) is then added to existing medium and incubation is continued overnight.

Following incubation, the media is removed, centrifuged, and stored for analysis (see VEGF and EPO assays below). The cells are washed two times in cold phosphate buffered saline (PBS) and then lysed in 1 mL of 10 mM Tris (pH 7.4), 1 mM EDTA, 150 mM NaCl, 0.5% IGEPAL (Sigma-Aldrich, St. Louis Mo.), and a protease inhibitor mix (Roche Molecular Biochemicals) for 15 minutes on ice. Cell lysates are centrifuged at 3,000×g for 5 minutes at 4° C., and the cytosolic fractions (supernatant) are collected. The nuclei (pellet) are resuspended and lysed in 100 µL of 20 mM HEPES (pH 7.2), 400 mM NaCl, 1 mM EDTA, 1 mM dithiothreitol, and a protease mix (Roche Molecular Biochemicals), centrifuged at 13,000×g for 5 minutes at 4° C., and the nuclear protein fractions (supernatant) are collected.

Nuclear fractions are analyzed for HIF-1α using a QUANTIKINE immunoassay (R&D Systems, Inc., Minneapolis Minn.) according to the manufacturer's instructions.

ii. Cell-Based VEGF and EPO ELISA Assays

Conditioned media collected from cell cultures as described above is analyzed for vascular endothelial growth factor (VEGF) and/or erythropoietin (EPO) expression using an appropriate QUANTIKINE immunoassay (R&D Systems) according to the manufacturer's instructions.

iii. HIF-PH Assay

Ketoglutaric acid α-[1-$^{14}$C]-sodium salt, alpha-ketoglutaric acid sodium salt, and HPLC purified peptide may be obtained from commercial sources, e.g., Perkin-Elmer (Wellesley Mass.), Sigma-Aldrich, and SynPep Corp. (Dublin Calif.), respectively. Peptides for use in the assay may be fragments of HIFα as described above or as disclosed in International Publication WO 2005/118836, incorporated by reference herein. For example, a HIF peptide for use in the HIF-PH assay is [methoxycoumarin]-DLDLEALAPYIPAD-DDFQL-amide. HIF-PH, e.g., HIF-PH2 (EGLN1), can be expressed in, e.g., insect Hi5 cells, and partially purified, e.g., through a SP ion exchange chromatography column. Enzyme activity is determined by capturing $^{14}CO_2$ using an assay described by Kivirikko and Myllyla (1982, *Methods Enzymol.* 82:245-304). Assay reactions contain 50 mM HEPES (pH 7.4), 100 µM α-ketoglutaric acid sodium salt, 0.30 µCi/mL ketoglutaric acid α-[1-$^{14}$C]-sodium salt, 40 µM FeSO$_4$, 1 mM ascorbate, 1541.8 units/mL Catalase, with or without 50 µM peptide substrate and various concentrations of compound of the disclosure. Reactions are initiated by addition of HIF-PH enzyme.

The peptide-dependent percent turnover is calculated by subtracting percent turnover in the absence of peptide from percent turnover in the presence of substrate peptide. Percent inhibition and $IC_{50}$ are calculated using peptide-dependent percent turnover at given inhibitor concentrations. Calculation of $IC_{50}$ values for each inhibitor is conducted using GraFit software (Erithacus Software Ltd., Surrey UK).

Representative compounds of the disclosure were analyzed using the HIF-PH assay described above. Table V presents enzyme inhibition data for exemplary compounds against HIF-PH2, a representative HIF prolyl hydroxylase. By inhibiting HIF prolyl hydroxylase, compounds of the disclosure stabilize HIFα, which then combines with HIFβ to form an active transcription factor that increases expression of various genes involved in numerous beneficial cellular processes.

TABLE V

| No. | Name | HIF PH2 $IC_{50}$ (µM) |
|---|---|---|
| 1 | [(1-Benzyl-5-hydroxy-2-oxo-1,2,3,4-tetrahydro-[1,7]naphthyridine-6-carbonyl)-amino]-acetic acid | 2.1 |
| 2 | [(1-Benzyl-5-hydroxy-3-methyl-2-oxo-1,2-dihydro-[1,7]naphthyridine-6-carbonyl)-amino]-acetic acid | 0.63 |
| 3 | [(1,3-Dibenzyl-5-hydroxy-2-oxo-1,2-dihydro-[1,7]naphthyridine-6-carbonyl)-amino]-acetic acid | 0.23 |
| 4 | [(1-Benzyl-5-hydroxy-2-oxo-3-phenyl-1,2-dihydro-[1,7]naphthyridine-6-carbonyl)-amino]-acetic acid | 0.26 |
| 5 | [(1-Benzyl-5-hydroxy-3,8-dimethyl-2-oxo-1,2-dihydro-[1,7]naphthyridine-6-carbonyl)-amino]-acetic acid | 0.93 |
| 6 | [(1-Benzyl-8-cyano-5-hydroxy-3-methyl-2-oxo-1,2-dihydro-[1,7]naphthyridine-6-carbonyl)-amino]-acetic acid | 0.09 |
| 7 | [(1-Benzyl-5-hydroxy-2-oxo-1,2-dihydro-[1,7]naphthyridine-6-carbonyl)-amino]-acetic acid | 0.22 |
| 8 | [(1-Benzyl-5-hydroxy-8-methyl-2-oxo-1,2,3,4-tetrahydro-[1,7]naphthyridine-6-carbonyl)-amino]-acetic acid | 6.5 |
| 9 | [(1-Benzyl-8-cyano-5-hydroxy-2-oxo-1,2,3,4-tetrahydro-[1,7]naphthyridine-6-carbonyl)-amino]-acetic acid | 0.22 |
| 10 | [(1-Benzyl-5-hydroxy-3-methyl-2-oxo-8-pyridin-3-yl-1,2-dihydro-[1,7]naphthyridine-6-carbonyl)-amino]-acetic acid | 0.52 |
| 11 | [(1-Benzyl-5-hydroxy-2-oxo-3-phenethyl-1,2-dihydro-[1,7]naphthyridine-6-carbonyl)-amino]-acetic acid | 0.41 |
| 12 | [(1-Benzyl-5-hydroxy-8-methyl-2-oxo-3-phenyl-1,2-dihydro-[1,7]naphthyridine-6-carbonyl)-amino]-acetic acid | 0.23 |
| 13 | [(1-Benzyl-5-hydroxy-2-oxo-3,8-diphenyl-1,2-dihydro-[1,7]naphthyridine-6-carbonyl)-amino]-acetic acid | 0.30 |
| 14 | [(1-Benzyl-8-cyano-5-hydroxy-2-oxo-3-phenyl-1,2-dihydro-[1,7]naphthyridine-6-carbonyl)-amino]-acetic acid | 0.06 |

TABLE V-continued

| No. | Name | HIF PH2 IC$_{50}$ (μM) |
|---|---|---|
| 15 | 3-[(1-Benzyl-8-cyano-5-hydroxy-2-oxo-3-phenyl-1,2-dihydro-[1,7]naphthyridine-6-carbonyl)-amino]-propionic acid | 6.8 |
| 16 | [(1-Benzyl-5-hydroxy-2-oxo-3-phenyl-8-pyridin-3-yl-1,2-dihydro-[1,7]naphthyridine-6-carbonyl)-amino]-acetic acid | 0.21 |
| 17 | [(1,3-Dibenzyl-8-cyano-5-hydroxy-2-oxo-1,2-dihydro-[1,7]naphthyridine-6-carbonyl)-amino]-acetic acid | 0.09 |
| 18 | 3-[(1,3-Dibenzyl-8-cyano-5-hydroxy-2-oxo-1,2-dihydro-[1,7]naphthyridine-6-carbonyl)-amino]-propionic acid | 4.5 |
| 19 | [(1,3-Dibenzyl-5-hydroxy-8-methyl-2-oxo-1,2-dihydro-[1,7]naphthyridine-6-carbonyl)-amino]-acetic acid | 2.1 |
| 20 | 3-[(1,3-Dibenzyl-5-hydroxy-8-methyl-2-oxo-1,2-dihydro-[1,7]naphthyridine-6-carbonyl)-amino]-propionic acid | 35 |
| 21 | [(1,3-Dibenzyl-5-hydroxy-2-oxo-8-pyridin-3-yl-1,2-dihydro-[1,7]naphthyridine-6-carbonyl)-amino]-acetic acid | 0.61 |
| 22 | 3-[(1,3-Dibenzyl-5-hydroxy-2-oxo-8-pyridin-3-yl-1,2-dihydro-[1,7]naphthyridine-6-carbonyl)-amino]-propionic acid | 10 |
| 23 | 4-[(1-Benzyl-8-cyano-5-hydroxy-2-oxo-3-phenyl-1,2-dihydro-[1,7]naphthyridine-6-carbonyl)-amino]-butyric acid | 21 |
| 24 | 5-[(1-Benzyl-8-cyano-5-hydroxy-2-oxo-3-phenyl-1,2-dihydro-[1,7]naphthyridine-6-carbonyl)-amino]-pentanoic acid | >200 |
| 25 | 3-[(1-Benzyl-8-cyano-5-hydroxy-2-oxo-3-phenyl-1,2-dihydro-[1,7]naphthyridine-6-carbonyl)-amino]-2,2-dimethyl-propionic acid | 149 |
| 26 | [(7-Benzyl-4-hydroxy-8-oxo-7,8-dihydro-[2,7]naphthyridine-3-carbonyl)-amino]-acetic acid | 0.22 |
| 27 | 3-[(7-Benzyl-4-hydroxy-8-oxo-7,8-dihydro-[2,7]naphthyridine-3-carbonyl)-amino]-propionic acid | 0.18 |
| 28 | 3-[(7-Benzyl-4-hydroxy-8-oxo-7,8-dihydro-[2,7]naphthyridine-3-carbonyl)-amino]-2,2-dimethyl-propionic acid | 1.7 |
| 29 | 4-[(7-Benzyl-4-hydroxy-8-oxo-7,8-dihydro-[2,7]naphthyridine-3-carbonyl)-amino]-butyric acid | 0.76 |
| 30 | 5-[(7-Benzyl-4-hydroxy-8-oxo-7,8-dihydro-[2,7]naphthyridine-3-carbonyl)-amino]-pentanoic acid | 0.66 |
| 31 | 7-Benzyl-4-hydroxy-8-oxo-7,8-dihydro-[2,7]naphthyridine-3-carboxylic acid (pyridin-4-ylmethyl)-amide | 0.19 |
| 32 | 7-Benzyl-4-hydroxy-8-oxo-7,8-dihydro-[2,7]naphthyridine-3-carboxylic acid methylamide | 0.80 |
| 33 | 7-Benzyl-4-hydroxy-8-oxo-7,8-dihydro-[2,7]naphthyridine-3-carboxylic acid | 6.6 |
| 34 | 7-Benzyl-4-hydroxy-8-oxo-7,8-dihydro-[2,7]naphthyridine-3-carboxylic acid dimethylamide | 40 |
| 35 | 7-Benzyl-4-hydroxy-8-oxo-7,8-dihydro-[2,7]naphthyridine-3-carboxylic acid amide | 32 |
| 36 | 7-Benzyl-4-hydroxy-8-oxo-7,8-dihydro-[2,7]naphthyridine-3-carboxylic acid propylamide | 0.65 |
| 37 | 7-Benzyl-4-hydroxy-8-oxo-7,8-dihydro-[2,7]naphthyridine-3-carboxylic acid cyclopropylamide | 0.39 |
| 38 | 7-Benzyl-1-cyano-4-hydroxy-8-oxo-7,8-dihydro-[2,7]naphthyridine-3-carboxylic acid methylamide | >200 |
| 39 | 7-Benzyl-1-cyano-4-hydroxy-8-oxo-7,8-dihydro-[2,7]naphthyridine-3-carboxylic acid cyclopropylamide | >200 |
| 40 | 1-Benzyl-8-cyano-5-hydroxy-2-oxo-3-phenyl-1,2-dihydro-[1,7]naphthyridine-6-carboxylic acid (pyridin-4-ylmethyl)-amide | 15 |
| 41 | 1-Benzyl-8-cyano-5-hydroxy-2-oxo-3-phenyl-1,2-dihydro-[1,7]naphthyridine-6-carboxylic acid methylamide | >200 |
| 42 | (R)-2-[(1-Benzyl-8-cyano-5-hydroxy-2-oxo-3-phenyl-1,2-dihydro-[1,7]naphthyridine-6-carbonyl)-amino]-3-phenyl-propionic acid | 129 |
| 43 | (S)-2-[(1-Benzyl-8-cyano-5-hydroxy-2-oxo-3-phenyl-1,2-dihydro-[1,7]naphthyridine-6-carbonyl)-amino]-3-phenyl-propionic acid | 144 |
| 44 | [(7-Benzyl-4-hydroxy-1-methyl-8-oxo-7,8-dihydro-[2,7]naphthyridine-3-carbonyl)-amino]-acetic acid | 1.1 |
| 45 | {[7-Benzyl-1-(5-fluoro-pyridin-3-yl)-4-hydroxy-8-oxo-7,8-dihydro-[2,7]naphthyridine-3-carbonyl]-amino}-acetic acid | 0.35 |
| 46 | [(7-Benzyl-4-hydroxy-8-oxo-1-phenyl-7,8-dihydro-[2,7]naphthyridine-3-carbonyl)-amino]-acetic acid | 1.4 |
| 47 | [(7-Benzyl-1-cyano-4-hydroxy-8-oxo-7,8-dihydro-[2,7]naphthyridine-3-carbonyl)-amino]-acetic acid | 0.10 |
| 48 | 7-Benzyl-1-cyano-4-hydroxy-8-oxo-7,8-dihydro-[2,7]naphthyridine-3-carboxylic acid (pyridin-4-ylmethyl)-amide | 195 |
| 49 | 3-[(7-Benzyl-1-cyano-4-hydroxy-8-oxo-7,8-dihydro-[2,7]naphthyridine-3-carbonyl)-amino]-propionic acid | 95 |
| 50 | 3-[(7-Benzyl-1-cyano-4-hydroxy-8-oxo-7,8-dihydro-[2,7]naphthyridine-3-carbonyl)-amino]-2,2-dimethyl-propionic acid | >200 |
| 51 | (R)-2-[(7-Benzyl-1-cyano-4-hydroxy-8-oxo-7,8-dihydro-[2,7]naphthyridine-3-carbonyl)-amino]-3-phenyl-propionic acid | >200 |

TABLE V-continued

| No. | Name | HIF PH2 IC$_{50}$ (μM) |
|---|---|---|
| 52 | 5-[(7-Benzyl-1-cyano-4-hydroxy-8-oxo-7,8-dihydro-[2,7]naphthyridine-3-carbonyl)-amino]-pentanoic acid | >200 |
| 53 | [(6-Benzyl-4-hydroxy-5-oxo-5,6-dihydro-[2,6]naphthyridine-3-carbonyl)-amino]-acetic acid | 45 |
| 54 | 3-[(6-Benzyl-4-hydroxy-5-oxo-5,6-dihydro-[2,6]naphthyridine-3-carbonyl)-amino]-propionic acid | 181 |
| 55 | [(6-Benzyl-1-cyano-4-hydroxy-5-oxo-5,6-dihydro-[2,6]naphthyridine-3-carbonyl)-amino]-acetic acid | 9.3 |
| 56 | (S)-2-[(7-Benzyl-1-cyano-4-hydroxy-8-oxo-7,8-dihydro-[2,7]naphthyridine-3-carbonyl)-amino]-3-phenyl-propionic acid | >200 |
| 57 | (S)-2-[(7-Benzyl-1-cyano-4-hydroxy-8-oxo-7,8-dihydro-[2,7]naphthyridine-3-carbonyl)-amino]-propionic acid | 0.42 |
| 58 | (R)-2-[(7-Benzyl-1-cyano-4-hydroxy-8-oxo-7,8-dihydro-[2,7]naphthyridine-3-carbonyl)-amino]-propionic acid | 153 |
| 59 | 7-Benzyl-1-cyano-4-hydroxy-8-oxo-7,8-dihydro-[2,7]naphthyridine-3-carboxylic acid (2-morpholin-4-yl-ethyl)-amide | >200 |
| 60 | 7-Benzyl-1-cyano-4-hydroxy-8-oxo-7,8-dihydro-[2,7]naphthyridine-3-carboxylic acid (pyridazin-4-ylmethyl)-amide | 177 |
| 61 | {2-[(7-Benzyl-1-cyano-4-hydroxy-8-oxo-7,8-dihydro-[2,7]naphthyridine-3-carbonyl)-amino]-ethoxy}-acetic acid | 34 |
| 62 | 1-{[(7-Benzyl-1-cyano-4-hydroxy-8-oxo-7,8-dihydro-[2,7]naphthyridine-3-carbonyl)-amino]-methyl}-cyclobutanecarboxylic acid | 182 |
| 63 | 7-(2,4-Dimethoxy-benzyl)-4-hydroxy-8-oxo-7,8-dihydro-[2,7]naphthyridine-3-carboxylic acid methylamide | 0.50 |
| 64 | {[7-(2,4-Dimethoxy-benzyl)-4-hydroxy-8-oxo-7,8-dihydro-[2,7]naphthyridine-3-carbonyl]-amino}-acetic acid | 0.28 |
| 65 | 3-{[7-(2,4-Dimethoxy-benzyl)-4-hydroxy-8-oxo-7,8-dihydro-[2,7]naphthyridine-3-carbonyl]-amino}-propionic acid | 0.23 |
| 66 | 7-(2,4-Dimethoxy-benzyl)-4-hydroxy-8-oxo-5,6,7,8-tetrahydro-[2,7]naphthyridine-3-carboxylic acid methylamide | 2.4 |
| 67 | {[7-(2,4-Dimethoxy-benzyl)-4-hydroxy-8-oxo-5,6,7,8-tetrahydro-[2,7]naphthyridine-3-carbonyl]-amino}-acetic acid | 0.44 |
| 68 | 3-{[7-(2,4-Dimethoxy-benzyl)-4-hydroxy-8-oxo-5,6,7,8-tetrahydro-[2,7]naphthyridine-3-carbonyl]-amino}-propionic acid | 0.32 |
| 69 | [(1-Benzyl-8-hydroxy-2-oxo-1,2-dihydro-[1,6]naphthyridine-7-carbonyl)-amino]-acetic acid | 3.6 |
| 70 | 3-[(1-Benzyl-8-hydroxy-2-oxo-1,2-dihydro-[1,6]naphthyridine-7-carbonyl)-amino]-propionic acid | 167 |
| 71 | 3-[(1-Benzyl-8-hydroxy-2-oxo-1,2-dihydro-[1,6]naphthyridine-7-carbonyl)-amino]-2,2-dimethyl-propionic acid | >200 |
| 72 | 1-Benzyl-8-hydroxy-2-oxo-1,2-dihydro-[1,6]naphthyridine-7-carboxylic acid (pyridin-4-ylmethyl)-amide | 31 |
| 73 | 7-Benzyl-1-cyano-4-hydroxy-8-oxo-7,8-dihydro-[2,7]naphthyridine-3-carboxylic acid (3-propylcarbamoyl-propyl)-amide | >200 |
| 74 | 3-[(4-Hydroxy-8-oxo-7,8-dihydro-[2,7]naphthyridine-3-carbonyl)-amino]-propionic acid | 6.6 |
| 75 | 1-Benzyl-8-hydroxy-2-oxo-1,2-dihydro-[1,6]naphthyridine-7-carboxylic acid methylamide | >200 |
| 76 | 7-(2,4-Dimethoxy-benzyl)-4-hydroxy-8-oxo-7,8-dihydro-[2,7]naphthyridine-3-carboxylic acid phenethyl-amide | >200 |
| 77 | 7-(2,4-Dimethoxy-benzyl)-4-hydroxy-8-oxo-7,8-dihydro-[2,7]naphthyridine-3-carboxylic acid (2-methoxy-ethyl)-amide | 2.3 |
| 78 | 7-(2,4-Dimethoxy-benzyl)-4-hydroxy-8-oxo-7,8-dihydro-[2,7]naphthyridine-3-carboxylic acid 4-fluoro-benzylamide | >200 |
| 79 | 1-Benzyl-5-cyano-8-hydroxy-2-oxo-1,2-dihydro-[1,6]naphthyridine-7-carboxylic acid methylamide | >200 |
| 80 | {[1-Benzyl-5-(5-fluoro-pyridin-3-yl)-8-hydroxy-2-oxo-1,2-dihydro-[1,6]naphthyridine-7-carbonyl]-amino}-acetic acid | 1.9 |
| 81 | 3-{[1-Benzyl-5-(5-fluoro-pyridin-3-yl)-8-hydroxy-2-oxo-1,2-dihydro-[1,6]naphthyridine-7-carbonyl]-amino}-propionic acid | 51 |
| 82 | 1-Benzyl-8-hydroxy-2-oxo-1,2-dihydro-[1,6]naphthyridine-7-carboxylic acid (1H-tetrazol-5-ylmethyl)-amide | 138 |
| 83 | 1-Benzyl-5-hydroxy-2-oxo-3-phenyl-1,2-dihydro-[1,7]naphthyridine-6-carboxylic acid methylamide | >200 |
| 84 | 3-[(1-Benzyl-5-hydroxy-2-oxo-3-phenyl-1,2-dihydro-[1,7]naphthyridine-6-carbonyl)-amino]-propionic acid | 20 |
| 85 | {2-[(7-Benzyl-4-hydroxy-8-oxo-7,8-dihydro-[2,7]naphthyridine-3-carbonyl)-amino]-ethoxy}-acetic acid | 1.0 |
| 86 | 7-Benzyl-4-hydroxy-8-oxo-7,8-dihydro-[2,7]naphthyridine-3-carboxylic acid (1H-tetrazol-5-ylmethyl)-amide | 0.29 |
| 87 | 3-{[7-Benzyl-1-(5-fluoro-pyridin-3-yl)-4-hydroxy-8-oxo-7,8-dihydro-[2,7]naphthyridine-3-carbonyl]-amino}-propionic acid | 25 |
| 88 | 3-{[7-Benzyl-1-(5-fluoro-pyridin-3-yl)-4-hydroxy-8-oxo-7,8-dihydro-[2,7]naphthyridine-3-carbonyl]-amino}-2,2-dimethyl-propionic acid | >200 |
| 89 | 7-Benzyl-4-hydroxy-8-oxo-7,8-dihydro-[2,7]naphthyridine-3-carboxylic acid [2-(3-isopropyl-ureido)-ethyl]-amide | >200 |

TABLE V-continued

| No. | Name | HIF PH2 IC$_{50}$ (μM) |
|---|---|---|
| 90 | 7-Benzyl-4-hydroxy-8-oxo-7,8-dihydro-[2,7]naphthyridine-3-carboxylic acid (2-sulfamoyl-ethyl)-amide | 1.0 |
| 91 | 7-Benzyl-4-hydroxy-8-oxo-7,8-dihydro-[2,7]naphthyridine-3-carboxylic acid [2-(2,2,2-trifluoro-acetylamino)-ethyl]-amide | 0.69 |
| 92 | 7-Benzyl-4-hydroxy-8-oxo-7,8-dihydro-[2,7]naphthyridine-3-carboxylic acid (2-acetylamino-ethyl)-amide | 0.61 |
| 94 | 3-[(1-Benzyl-5-cyano-8-hydroxy-2-oxo-1,2-dihydro-[1,6]naphthyridine-7-carbonyl)-amino]-propionic acid | 65 |
| 95 | 1-Benzyl-5-cyano-8-hydroxy-2-oxo-1,2-dihydro-[1,6]naphthyridine-7-carboxylic acid (2-acetylamino-ethyl)-amide | 134 |
| 96 | 1-Benzyl-8-hydroxy-2-oxo-1,2-dihydro-[1,6]naphthyridine-7-carboxylic acid (2-acetylamino-ethyl)-amide | 137 |
| 97 | 7-Benzyl-4-hydroxy-8-oxo-7,8-dihydro-[2,7]naphthyridine-3-carboxylic acid{2-[methyl-(2,2,2-trifluoro-acetyl)-amino]-ethyl}-amide | 0.9 |
| 98 | 7-Benzyl-4-hydroxy-8-oxo-7,8-dihydro-[2,7]naphthyridine-3-carboxylic acid [2-(3-isopropyl-1-methyl-ureido)-ethyl]-amide | 3.7 |
| 99 | {2-[(7-Benzyl-4-hydroxy-8-oxo-7,8-dihydro-[2,7]naphthyridine-3-carbonyl)-amino]-ethyl}-methyl-carbamic acid methyl ester | 2.0 |
| 100 | 7-Benzyl-4-hydroxy-8-oxo-7,8-dihydro-[2,7]naphthyridine-3-carboxylic acid [2-(methanesulfonyl-methyl-amino)-ethyl]-amide | 2.2 |
| 101 | 7-Benzyl-4-hydroxy-8-oxo-7,8-dihydro-[2,7]naphthyridine-3-carboxylic acid (2-methanesulfonylamino-ethyl)-amide | 1.9 |
| 102 | 7-Benzyl-4-hydroxy-8-oxo-7,8-dihydro-[2,7]naphthyridine-3-carboxylic acid [3-(2,2,2-trifluoro-acetylamino)-propyl]-amide | 2.4 |
| 103 | 7-Benzyl-4-hydroxy-8-oxo-7,8-dihydro-[2,7]naphthyridine-3-carboxylic acid [3-(3-isopropyl-ureido)-propyl]-amide | 9.4 |
| 104 | 7-Benzyl-4-hydroxy-8-oxo-7,8-dihydro-[2,7]naphthyridine-3-carboxylic acid (3-ureido-propyl)-amide | 1.5 |
| 105 | 1-Benzyl-8-hydroxy-2-oxo-1,2-dihydro-[1,6]naphthyridine-7-carboxylic acid [2-(methanesulfonyl-methyl-amino)-ethyl]-amide | >200 |
| 106 | 1-Benzyl-5-cyano-8-hydroxy-2-oxo-1,2-dihydro-[1,6]naphthyridine-7-carboxylic acid (2-sulfamoyl-ethyl)-amide | >200 |
| 107 | 1-Benzyl-5-hydroxy-2-oxo-3-phenyl-1,2-dihydro-[1,7]naphthyridine-6-carboxylic acid (2-acetylamino-ethyl)-amide | 40 |
| 108 | 1-Benzyl-5-hydroxy-2-oxo-3-phenyl-1,2-dihydro-[1,7]naphthyridine-6-carboxylic acid [2-(methanesulfonyl-methyl-amino)-ethyl]-amide | 200 |
| 109 | 1-Benzyl-5-hydroxy-2-oxo-3-phenyl-1,2-dihydro-[1,7]naphthyridine-6-carboxylic acid [2-(2,2,2-trifluoro-acetylamino)-ethyl]-amide | >200 |
| 110 | 1-Benzyl-5-hydroxy-2-oxo-3-phenyl-1,2-dihydro-[1,7]naphthyridine-6-carboxylic acid [2-(3-ethyl-ureido)-ethyl]amide | 200 |
| 111 | 1-Benzyl-8-hydroxy-2-oxo-1,2-dihydro-[1,6]naphthyridine-7-carboxylic acid (2-methanesulfonylamino-ethyl)-amide | >200 |
| 112 | 3-[(1-Benzyl-8-hydroxy-5-methyl-2-oxo-1,2-dihydro-[1,6]naphthyridine-7-carbonyl)-amino]-propionic acid | >200 |
| 113 | 1-Benzyl-5-hydroxy-2-oxo-3-phenyl-1,2-dihydro-[1,7]naphthyridine-6-carboxylic acid (1 H-tetrazol-5-ylmethyl)-amide | 22 |
| 114 | 3-[(1-Benzyl-5-hydroxy-2-oxo-3-phenyl-1,2-dihydro-[1,7]naphthyridine-6-carbonyl)-amino]-2,2-dimethyl-propionic acid | 91 |
| 115 | 7-Benzyl-4-hydroxy-8-oxo-7,8-dihydro-[2,7]naphthyridine-3-carboxylic acid [2-(formyl-methyl-amino)-ethyl]-amide | 0.35 |
| 116 | 7-Benzyl-4-hydroxy-8-oxo-7,8-dihydro-[2,7]naphthyridine-3-carboxylic acid [2-(acetyl-methyl-amino)-ethyl]-amide | 0.44 |
| 117 | 1-Benzyl-5-hydroxy-2-oxo-3-phenyl-1,2-dihydro-[1,7]naphthyridine-6-carboxylic acid (2-formylamino-ethyl)-amide | 27 |
| 118 | 3-[(1-Benzyl-5-hydroxy-2-oxo-3-phenyl-8-pyridin-3-yl-1,2-dihydro-[1,7]naphthyridine-6-carbonyl)-amino]-propionic acid | 23 |
| 119 | 3-[(1-Benzyl-5-hydroxy-2-oxo-3,8-diphenyl-1,2-dihydro-[1,7]naphthyridine-6-carbonyl)-amino]-propionic acid | 49 |
| 120 | 3-[(1-Benzyl-5-hydroxy-8-methyl-2-oxo-3-phenyl-1,2-dihydro-[1,7]naphthyridine-6-carbonyl)-amino]-propionic acid | 88 |
| 121 | 3-[(1-Benzyl-5-hydroxy-2-oxo-3-phenyl-1,2,3,4-tetrahydro-[1,7]naphthyridine-6-carbonyl)-amino]-propionic acid | 132 |
| 122 | 3-[(1-Benzyl-5-hydroxy-2-oxo-1,2-dihydro-[1,7]naphthyridine-6-carbonyl)-amino]-propionic acid | 75 |
| 123 | 3-[(1-Benzyl-5-hydroxy-2-oxo-3-phenethyl-1,2-dihydro-[1,7]naphthyridine-6-carbonyl)-amino]-propionic acid | 16 |
| 124 | 3-[(1-Benzyl-5-hydroxy-2-oxo-3-pyridin-3-yl-1,2-dihydro-[1,7]naphthyridine-6-carbonyl)-amino]-propionic acid | 19 |
| 125 | 3-[(1-Benzyl-5-hydroxy-2-oxo-3-pyridin-2-yl-1,2-dihydro-[1,7]naphthyridine-6-carbonyl)-amino]-propionic acid | 34 |
| 126 | 4-[(1-Benzyl-5-hydroxy-2-oxo-3-phenyl-1,2-dihydro-[1,7]naphthyridine-6-carbonyl)-amino]-butyric acid | 31 |
| 127 | 3-[(1-Benzyl-5-hydroxy-3-methyl-2-oxo-1,2-dihydro-[1,7]naphthyridine-6-carbonyl)-amino]-propionic acid | 12.1 |

TABLE V-continued

| No. | Name | HIF PH2 IC$_{50}$ (μM) |
|---|---|---|
| 128 | 3-[(1-Benzyl-5-hydroxy-2-oxo-3-thiophen-2-yl-1,2-dihydro-[1,7]naphthyridine-6-carbonyl)-amino]-propionic acid | 6.7 |
| 129 | 3-[(1-Benzyl-5-hydroxy-2-oxo-3-pyridin-4-yl-1,2-dihydro-[1,7]naphthyridine-6-carbonyl)-amino]-propionic acid | 10.6 |
| 130 | 1-Benzyl-5-hydroxy-2-oxo-3-phenyl-1,2-dihydro-[1,7]naphthyridine-6-carboxylic acid (2-methanesulfonylamino-ethyl)-amide | 64.8 |
| 131 | 1-Benzyl-8-cyano-5-hydroxy-2-oxo-3-phenyl-1,2-dihydro-[1,7]naphthyridine-6-carboxylic acid [2-(methanesulfonyl-methyl-amino)-ethyl]-amide | 86.9 |
| 132 | 1-Benzyl-5-hydroxy-8-methyl-2-oxo-3-phenyl-1,2-dihydro-[1,7]naphthyridine-6-carboxylic acid [2-(methanesulfonyl-methyl-amino)-ethyl]-amide | 200 |
| 133 | 1-Benzyl-5-hydroxy-2-oxo-3,8-diphenyl-1,2-dihydro-[1,7]naphthyridine-6-carboxylic acid [2-(methanesulfonyl-methyl-amino)-ethyl]-amide | 200 |
| 134 | 1-Benzyl-5-hydroxy-2-oxo-3-phenyl-8-pyridin-3-yl-1,2-dihydro-[1,7]naphthyridine-6-carboxylic acid [2-(methanesulfonyl-methyl-amino)-ethyl]-amide | 200 |
| 135 | 3-[(5-Hydroxy-2-oxo-l-phenethyl-3-phenyl-1,2-dihydro-[1,7]naphthyridine-6-carbonyl)-amino]-propionic acid | 3.6 |
| 136 | 3-[(5-Hydroxy-2-oxo-1,3-diphenyl-1,2-dihydro-[1,7]naphthyridine-6-carbonyl)-amino]-propionic acid | 56.1 |
| 137 | 3-[(3-Benzyl-5-hydroxy-2-oxo-l-phenyl-1,2-dihydro-[1,7]naphthyridine-6-carbonyl)-amino]-propionic acid | 49.1 |
| 138 | 3-[(5-Hydroxy-l-methyl-2-oxo-3-phenyl-1,2-dihydro-[1,7]naphthyridine-6-carbonyl)-amino]-propionic acid | 5.7 |
| 139 | 3-{[1-Benzyl-3-(4-cyano-phenyl)-5-hydroxy-2-oxo-1,2-dihydro-[1,7]naphthyridine-6-carbonyl]-amino}-propionic acid | 15.8 |
| 140 | 3-{[1-Benzyl-5-hydroxy-3-(4-methoxy-phenyl)-2-oxo-1,2-dihydro-[1,7]naphthyridine-6-carbonyl]-amino}-propionic acid | 9.2 |
| 141 | 3-[(1-Benzyl-5-hydroxy-2-oxo-3-thiazol-2-yl-1,2-dihydro-[1,7]naphthyridine-6-carbonyl)-amino]-propionic acid | 10.5 |
| 142 | (R)-3-[(1-Benzyl-5-hydroxy-2-oxo-3-phenyl-1,2-dihydro-[1,7]naphthyridine-6-carbonyl)-amino]-butyric acid | 87.9 |
| 143 | 3-{[5-Hydroxy-1-(4-methoxy-benzyl)-2-oxo-3-phenyl-1,2-dihydro-[1,7]naphthyridine-6-carbonyl]-amino}-propionic acid | 7.7 |
| 144 | 3-{[1-(4-Cyano-benzyl)-5-hydroxy-2-oxo-3-phenyl-1,2-dihydro-[1,7]naphthyridine-6-carbonyl]-amino}-propionic acid | 4.7 |
| 145 | 3-[(1-Benzyl-5-hydroxy-2-oxo-3-pyrazin-2-yl-1,2-dihydro-[1,7]naphthyridine-6-carbonyl)-amino]-propionic acid | 9.2 |
| 146 | 3-{[1-Benzyl-5-hydroxy-3-(4-methanesulfonyl-phenyl)-2-oxo-1,2-dihydro-[1,7]naphthyridine-6-carbonyl]-amino}-propionic acid | 6.9 |
| 147 | 3-{[1-Benzyl-5-hydroxy-2-oxo-3-(3-trifluoromethyl-phenyl)-1,2-dihydro-[1,7]naphthyridine-6-carbonyl]-amino}-propionic acid | 12.3 |
| 148 | 3-{[1-Benzyl-5-hydroxy-3-(4-morpholin-4-yl-phenyl)-2-oxo-1,2-dihydro-[1,7]naphthyridine-6-carbonyl]-amino}-propionic acid | 9.0 |
| 149 | 3-[(3-Benzo[1,2,5]oxadiazol-5-yl-1-benzyl-5-hydroxy-2-oxo-1,2-dihydro-[1,7]naphthyridine-6-carbonyl)-amino]-propionic acid | 4.9 |
| 150 | 3-{[1-Benzyl-3-(5-fluoro-2-methoxy-phenyl)-5-hydroxy-2-oxo-1,2-dihydro-[1,7]naphthyridine-6-carbonyl]-amino}-propionic acid | 15.4 |
| 151 | 3-{[1-Benzyl-5-hydroxy-2-oxo-3-(4-trifluoromethoxy-phenyl)-1,2-dihydro-[1,7]naphthyridine-6-carbonyl]-amino}-propionic acid | 12.6 |
| 152 | (R)-2-[(1-Benzyl-5-hydroxy-2-oxo-3-phenyl-1,2-dihydro-[1,7]naphthyridine-6-carbonyl)-amino]-3-phenyl-propionic acid | 102.7 |
| 153 | 3-{[1-Benzyl-5-hydroxy-3-(1-methyl-1H-pyrazol-4-yl)-2-oxo-1,2-dihydro-[1,7]naphthyridine-6-carbonyl]-amino}-propionic acid | 17.4 |
| 154 | 3-[(1-Benzyl-5-hydroxy-2-oxo-3-pyrimidin-5-yl-1,2-dihydro-[1,7]naphthyridine-6-carbonyl)-amino]-propionic acid | 18.0 |
| 155 | 3-{[1-Benzyl-3-(2-dimethylamino-pyrimidin-5-yl)-5-hydroxy-2-oxo-1,2-dihydro-[1,7]naphthyridine-6-carbonyl]-amino}-propionic acid | 13.1 |
| 156 | 3-[(1-Cyclohexylmethyl-5-hydroxy-2-oxo-3-phenyl-1,2-dihydro-[1,7]naphthyridine-6-carbonyl)-amino]-propionic acid | 14.5 |
| 157 | 3-{[5-Hydroxy-2-oxo-3-phenyl-1-(tetrahydro-pyran-4-ylmethyl)-1,2-dihydro-[1,7]naphthyridine-6-carbonyl]-amino}-propionic acid | 14.2 |
| 158 | 3-[(5-Hydroxy-2-oxo-3-phenyl-1-thiazol-2-ylmethyl-1,2-dihydro-[1,7]naphthyridine-6-carbonyl)-amino]-propionic acid | 45.1 |
| 159 | 3-[(1-Benzyl-5-hydroxy-2-oxo-3-phenyl-8-pyrimidin-5-yl-1,2-dihydro-[1,7]naphthyridine-6-carbonyl)-amino]-propionic acid | 16.9 |
| 160 | 3-[(1-Benzyl-5-hydroxy-2-oxo-3-phenyl-8-pyrazin-2-yl-1,2-dihydro-[1,7]naphthyridine-6-carbonyl)-amino]-propionic acid | 92.6 |
| 161 | 5-[(1-Benzyl-5-hydroxy-2-oxo-3-phenyl-1,2-dihydro-[1,7]naphthyridine-6-carbonyl)-amino]-pentanoic acid | 48.4 |
| 162 | 4-[(1-Benzyl-5-hydroxy-2-oxo-3-phenyl-8-pyridin-3-yl-1,2-dihydro-[1,7]naphthyridine-6-carbonyl)-amino]-butyric acid | 19.2 |
| 163 | 5-[(1-Benzyl-5-hydroxy-2-oxo-3-phenyl-8-pyridin-3-yl-1,2-dihydro-[1,7]naphthyridine-6-carbonyl)-amino]-pentanoic acid | 200 |
| 164 | 3-[(5-Hydroxy-2-oxo-1,3-diphenyl-8-pyridin-3-yl-1,2-dihydro-[1,7]naphthyridine-6-carbonyl)-amino]-propionic acid | 29.0 |

TABLE V-continued

| No. | Name | HIF PH2 IC$_{50}$ (μM) |
|---|---|---|
| 165 | 3-[(5-Hydroxy-1-methyl-2-oxo-3-phenyl-8-pyridin-3-yl-1,2-dihydro-[1,7]naphthyridine-6-carbonyl)-amino]-propionic acid | 69.8 |
| 166 | 3-[(5-Hydroxy-2-oxo-1-phenethyl-3-phenyl-8-pyridin-3-yl-1,2-dihydro-[1,7]naphthyridine-6-carbonyl)-amino]-propionic acid | 33.0 |
| 167 | 3-[(1-Benzyl-5-hydroxy-2-oxo-3-phenyl-8-pyridin-4-yl-1,2-dihydro-[1,7]naphthyridine-6-carbonyl)-amino]-propionic acid | 18.8 |
| 168 | 3-[(1-Benzyl-5-hydroxy-2-oxo-3,8-di-pyridin-3-yl-1,2-dihydro-[1,7]naphthyridine-6-carbonyl)-amino]-propionic acid | 6.2 |
| 169 | (R)-3-{[5-Hydroxy-2-oxo-3-phenyl-1-(1-phenyl-ethyl)-1,2-dihydro-[1,7]naphthyridine-6-carbonyl]-amino}-propionic acid | 7.4 |
| 170 | (R)-4-{[5-Hydroxy-2-oxo-3-phenyl-1-(1-phenyl-ethyl)-1,2-dihydro-[1,7]naphthyridine-6-carbonyl]-amino}-butyric acid | 12.6 |
| 171 | 3-{[1-Benzyl-5-hydroxy-8-(5-methoxy-pyridin-3-yl)-2-oxo-3-phenyl-1,2-dihydro-[1,7]naphthyridine-6-carbonyl]-amino}-propionic acid | 6.9 |
| 172 | 3-{[1-Benzyl-8-(5-chloro-pyridin-3-yl)-5-hydroxy-2-oxo-3-phenyl-1,2-dihydro-[1,7]naphthyridine-6-carbonyl]-amino}-propionic acid | 4.1 |
| 173 | (S)-3-{[5-Hydroxy-2-oxo-3-phenyl-1-(1-phenyl-ethyl)-1,2-dihydro-[1,7]naphthyridine-6-carbonyl]-amino}-propionic acid | 2.9 |
| 174 | (S)-4-{[5-Hydroxy-2-oxo-3-phenyl-1-(1-phenyl-ethyl)-1,2-dihydro-[1,7]naphthyridine-6-carbonyl]-amino}-butyric acid | 4.6 |
| 175 | (S)-3-{[5-Hydroxy-2-oxo-3-phenyl-1-(1-phenyl-ethyl)-8-pyridin-3-yl-1,2-dihydro-[1,7]naphthyridine-6-carbonyl]-amino}-propionic acid | 200 |
| 176 | (R)-3-{[5-Hydroxy-2-oxo-3-phenyl-1-(1-phenyl-ethyl)-8-pyridin-3-yl-1,2-dihydro-[1,7]naphthyridine-6-carbonyl]-amino}-propionic acid | 195.5 |
| 177 | 3-{[1-Benzyl-8-(5-fluoro-pyridin-3-yl)-5-hydroxy-2-oxo-3-phenyl-1,2-dihydro-[1,7]naphthyridine-6-carbonyl]-amino}-propionic acid | 13.5 |
| 178 | 3-{[1-Benzyl-5-hydroxy-8-(2-methyl-pyridin-3-yl)-2-oxo-3-phenyl-1,2-dihydro-[1,7]naphthyridine-6-carbonyl]-amino}-propionic acid | 198.9 |
| 179 | 3-{[1-Benzyl-5-hydroxy-8-(6-methyl-pyridin-3-yl)-2-oxo-3-phenyl-1,2-dihydro-[1,7]naphthyridine-6-carbonyl]-amino}-propionic acid | 176.5 |
| 180 | 3-{[1-Benzyl-5-hydroxy-2-oxo-3-phenyl-8-(6-trifluoromethyl-pyridin-3-yl)-1,2-dihydro-[1,7]naphthyridine-6-carbonyl]-amino}-propionic acid | 106.6 |
| 181 | 3-{[1-Benzyl-5-hydroxy-8-(6-methoxy-pyridin-3-yl)-2-oxo-3-phenyl-1,2-dihydro-[1,7]naphthyridine-6-carbonyl]-amino}-propionic acid | 57.0 |
| 182 | 3-{[5-Hydroxy-2-oxo-3-phenyl-8-pyridin-3-yl-1-(tetrahydro-pyran-4-ylmethyl)-1,2-dihydro-[1,7]naphthyridine-6-carbonyl]-amino}-propionic acid | 65.3 |
| 183 | 3-[(1-Cyclohexylmethyl-5-hydroxy-2-oxo-3-phenyl-8-pyridin-3-yl-1,2-dihydro-[1,7]naphthyridine-6-carbonyl)-amino]-propionic acid | 24.2 |
| 184 | 4-[(1-Cyclohexylmethyl-5-hydroxy-2-oxo-3-phenyl-1,2-dihydro-[1,7]naphthyridine-6-carbonyl)-amino]-butyric acid | 11.5 |
| 185 | 3-{[1-Benzyl-5-hydroxy-3-(4-methoxy-phenyl)-2-oxo-8-pyridin-3-yl-1,2-dihydro-[1,7]naphthyridine-6-carbonyl]-amino}-propionic acid | 22.4 |
| 186 | 4-{[1-Benzyl-5-hydroxy-3-(4-methoxy-phenyl)-2-oxo-1,2-dihydro-[1,7]naphthyridine-6-carbonyl]-amino}-butyric acid | 19.7 |
| 187 | 3-{[1-Benzyl-5-hydroxy-3-(3-methoxy-phenyl)-2-oxo-1,2-dihydro-[1,7]naphthyridine-6-carbonyl]-amino}-propionic acid | 8.8 |
| 188 | 4-{[1-Benzyl-5-hydroxy-3-(3-methoxy-phenyl)-2-oxo-1,2-dihydro-[1,7]naphthyridine-6-carbonyl]-amino}-butyric acid | 14.2 |
| 189 | 1-[(1-Benzyl-5-hydroxy-2-oxo-3-phenyl-1,2-dihydro-[1,7]naphthyridine-6-carbonyl)-amino]-cyclopropanecarboxylic acid | 51.8 |
| 190 | 1-[(1-Benzyl-5-hydroxy-2-oxo-3-phenyl-8-pyridin-3-yl-1,2-dihydro-[1,7]naphthyridine-6-carbonyl)-amino]-cyclopropanecarboxylic acid | 55.2 |
| 191 | 3-[(1-Benzyl-5-hydroxy-2-oxo-3-phenyl-8-pyridin-3-yl-1,2-dihydro-[1,7]naphthyridine-6-carbonyl)-amino]-2,2-dimethyl-propionic acid | 200 |
| 192 | 3-{[1-Benzyl-8-(2-ethoxy-pyrimidin-5-yl)-5-hydroxy-2-oxo-3-phenyl-1,2-dihydro-[1,7]naphthyridine-6-carbonyl]-amino}-propionic acid | 28.0 |
| 193 | 3-[(1-Benzyl-5-hydroxy-2-oxo-3-phenyl-8-pyridin-2-yl-1,2-dihydro-[1,7]naphthyridine-6-carbonyl)-amino]-propionic acid | 163.8 |
| 194 | 3-[(1-Benzyl-5-hydroxy-2-oxo-3-phenyl-8-pyridazin-4-yl-1,2-dihydro-[1,7]naphthyridine-6-carbonyl)-amino]-propionic acid | 4.5 |
| 195 | 3-[(1-Benzyl-5-hydroxy-2-oxo-3-phenyl-8-thiazol-2-yl-1,2-dihydro-[1,7]naphthyridine-6-carbonyl)-amino]-propionic acid | 137.5 |
| 196 | 7-Benzyl-4-hydroxy-8-oxo-7,8-dihydro-[2,7]naphthyridine-3-carboxylic acid (3-formylamino-propyl)-amide | 0.4 |
| 197 | 7-Benzyl-4-hydroxy-8-oxo-7,8-dihydro-[2,7]naphthyridine-3-carboxylic acid (3-acetylamino-propyl)-amide | 0.8 |
| 198 | 3-[(1-Cyclohexylmethyl-5-hydroxy-2-oxo-3-phenyl-8-pyridin-4-yl-1,2-dihydro-[1,7]naphthyridine-6-carbonyl)-amino]-propionic acid | 200 |
| 199 | 3-[(5-Hydroxy-2-oxo-1,3-diphenyl-8-pyridin-4-yl-1,2-dihydro-[1,7]naphthyridine-6-carbonyl)-amino]-propionic acid | 200 |
| 200 | 3-{[1-Benzyl-5-hydroxy-8-(1-methyl-1H-pyrazol-4-yl)-2-oxo-3-phenyl-1,2-dihydro-[1,7]naphthyridine-6-carbonyl]-amino}-propionic acid | 37.1 |
| 201 | 3-[(1-Benzyl-5-hydroxy-2-oxo-3-phenyl-8-thiazol-5-yl-1,2-dihydro-[1,7]naphthyridine-6-carbonyl)-amino]-propionic acid | 31.0 |
| 202 | 3-[(1-Benzyl-5-hydroxy-2-oxo-3-phenyl-8-thiazol-4-yl-1,2-dihydro-[1,7]naphthyridine-6-carbonyl)-amino]-propionic acid | 200 |

TABLE V-continued

| No. Name | HIF PH2 IC$_{50}$ (µM) |
|---|---|
| 203 3-[(1-Benzyl-5-hydroxy-2-oxo-3-phenyl-8-pyridazin-3-yl-1,2-dihydro-[1,7]naphthyridine-6-carbonyl)-amino]-propionic acid | 200 |
| 204 3- [(1-Benzyl-5-hydroxy-2-oxo-3-phenethyl-8-pyridin-3-yl-1,2-dihydro-[1,7]naphthyridine-6-carbonyl)-amino]-propionic acid | 4.5 |
| 205 3-[(1,3-Dibenzyl-5-hydroxy-2-oxo-1,2-dihydro-[1,7]naphthyridine-6-carbonyl)-amino]-propionic acid | 36.2 |
| 206 3-[(7-Benzyl-4-hydroxy-8-oxo-l-pyridin-3-yl-7,8-dihydro-[2,7]naphthyridine-3-carbonyl)-amino]-propionic acid | 200 |
| 207 3-{[1-Cyclohexylmethyl-8-(2-ethoxy-pyrimidin-5-yl)-5-hydroxy-2-oxo-3-phenyl-1,2-dihydro-[1,7]naphthyridine-6-carbonyl]-amino}-propionic acid | 36 |
| 208 3-{[1-Benzyl-5-hydroxy-8-(2-methylsulfanyl-pyrimidin-5-yl)-2-oxo-3-phenyl-1,2-dihydro-[1,7]naphthyridine-6-carbonyl]-amino}-propionic acid | 54 |
| 209 3-{[1-Benzyl-5-hydroxy-2-oxo-3-(4-trifluoromethyl-phenyl)-1,2-dihydro-[1,7]naphthyridine-6-carbonyl]-amino}-propionic acid | 5.1 |
| 210 3-{[1-Benzyl-5-hydroxy-2-oxo-3-(2-trifluoromethyl-phenyl)-1,2-dihydro-[1,7]naphthyridine-6-carbonyl]-amino}-propionic acid | 12 |
| 211 4-{[1-Benzyl-5-hydroxy-2-oxo-3-(4-trifluoromethyl-phenyl)-1,2-dihydro-[1,7]naphthyridine-6-carbonyl]-amino}-butyric acid | 7.5 |
| 212 4-{[1-Benzyl-5-hydroxy-2-oxo-3-(3-trifluoromethyl-phenyl)-1,2-dihydro-[1,7]naphthyridine-6-carbonyl]-amino}-butyric acid | 10 |
| 213 4-{[1-Benzyl-5-hydroxy-2-oxo-3-(2-trifluoromethyl-phenyl)-1,2-dihydro-[1,7]naphthyridine-6-carbonyl]-amino}-butyric acid | 26 |
| 214 3-{[1-Benzyl-5-hydroxy-2-oxo-8-pyridin-3-yl-3-(4-trifluoromethyl-phenyl)-1,2-dihydro-[1,7]naphthyridine-6-carbonyl]-amino}-propionic acid | 17 |
| 215 3-{[1-Benzyl-5-hydroxy-2-oxo-8-pyridin-3-yl-3-(3-trifluoromethyl-phenyl)-1,2-dihydro-[1,7]naphthyridine-6-carbonyl]-amino}-propionic acid | 10 |
| 216 3-{[1-Benzyl-5-hydroxy-2-oxo-8-pyridin-3-yl-3-(2-trifluoromethyl-phenyl)-1,2-dihydro-[1,7]naphthyridine-6-carbonyl]-amino}-propionic acid | 27 |
| 217 3-[(1-Cyclopentylmethyl-5-hydroxy-2-oxo-3-phenyl-1,2-dihydro-[1,7]naphthyridine-6-carbonyl)-amino]-propionic acid | 5.5 |
| 218 4-[(1-Cyclopentylmethyl-5-hydroxy-2-oxo-3-phenyl-1,2-dihydro-[1,7]naphthyridine-6-carbonyl)-amino]-butyric acid | 8.9 |

7. Pharmaceutical Formulations and Routes of Administration

The compositions of the present disclosure can be delivered directly or in pharmaceutical compositions or medicaments along with suitable carriers or excipients, as is well known in the art. Present methods of treatment can comprise administration of an effective amount of a compound of the disclosure to a subject in need; e.g., a subject having or at risk for anemia due to, e.g., chronic renal failure, diabetes, cancer, AIDS, radiation therapy, chemotherapy, kidney dialysis, or surgery; or, e.g., a subject having or at risk for ischemia due to, e.g., myocardial infarction, congestive heart failure, cardiac cirrhosis, pulmonary insufficiency, atherosclerosis, peripheral vascular disease, or the like. In a preferred embodiment, the subject is a mammalian subject, and in a most preferred embodiment, the subject is a human subject.

An effective amount of such compound, composition, or medicament can readily be determined by routine experimentation, as can the most effective and convenient route of administration, and the most appropriate formulation. Various formulations and drug delivery systems are available in the art. See, e.g., Gennaro, A. R., ed. (1995) Remington's Pharmaceutical Sciences, supra.

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

Pharmaceutical dosage forms of a compound of the disclosure may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the disclosure to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art and include those listed in various pharmacopoeias. (See, e.g., the U.S. Pharmacopeia (USP), Japanese Pharmacopoeia (JP), European Pharmacopoeia (EP), and British pharmacopeia (BP); the U.S. Food and Drug Administration (www.fda.gov) Center for Drug Evaluation and Research (CEDR) publications, e.g., Inactive Ingredient Guide (1996); Ash and Ash, Eds. (2002) Handbook of Pharmaceutical Additives, Synapse Information Resources, Inc., Endicott N.Y.; etc.)

Pharmaceutical dosage forms of a compound of the present disclosure may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present disclosure can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms, and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present disclosure can be administered topically, such as through a skin patch, a semi-solid, or a liquid formulation, for example a gel, a (micro-) emulsion, an ointment, a solution, a (nano/micro-)suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the disclosure. Transdermal or topical administration would be preferred, for example, in situations in which local delivery with minimal systemic exposure is desired.

For administration by inhalation, or administration to the nose, the compounds for use according to the present disclosure are conveniently delivered in the form of a solution, suspension, emulsion, or semisolid aerosol from pressurized packs, or a nebuliser, usually with the use of a propellant, e.g., halogenated carbons derived from methane and ethane, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compositions formulated for parenteral administration by injection are usually sterile and can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the disclosure, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the compounds of the disclosure are well-known in the art and include water-based solutions containing a base, such as, for example, sodium hydroxide, to form an ionized compound; sucrose or sodium chloride as a tonicity agent; and a buffer, for example, a buffer that contains phosphate or histidine. Co-solvents, such as, for example, polyethylene glycols, may be added. These water-based systems are effective at dissolving compounds of the disclosure and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays. In certain embodiments, a compound of the disclosure is formulated for oral administration. An exemplary dose of a compound of the disclosure in a pharmaceutical formulation for oral administration is from about 0.5 to about 10 mg/kg body weight of subject. In some embodiments, a pharmaceutical formulation comprises from about 0.7 to about 5.0 mg/kg body weight of subject, or alternatively, from about 1.0 to about 2.5 mg/kg body weight of subject. A typical dosing regimen for oral administration would be administration of the pharmaceutical formulation for oral administration three times per week, two times per week, once per week or daily.

An effective amount or a therapeutically effective amount or dose of an agent, e.g., a compound of the disclosure, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the $ED_{50}$ with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of compound or composition administered may be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack; or glass and rubber stoppers such as in vials. The pack or dispenser device may be accompanied by instructions for administration. Compositions comprising a compound of the disclosure formulated in a compatible pharmaceutical carrier may also be prepared, placed in an appropriate container, and labeled for treatment of an indicated condition.

These and other embodiments of the present disclosure will readily occur to those of ordinary skill in the art in view of the disclosure herein and are specifically contemplated.

EXAMPLES

The disclosure is further understood by reference to the following examples, which are intended to be purely exemplary of the disclosure. The present disclosure is not limited in scope by the exemplified embodiments, which are intended as illustrations of single aspects of the disclosure only. Any methods that are functionally equivalent are within the scope of the disclosure. Various modifications of the disclosure in addition to those described herein will become apparent to those skilled in the art from the foregoing description and accompanying figure. Such modifications fall within the scope of the appended claims.

Unless otherwise stated all temperatures are in degrees Celsius (° C.). Also, in these examples and elsewhere, abbreviations have the following meanings:

μL=Microliter
μM=Micromolar
μCi=MicroCurie
Ac=Acetyl
aq=Aqueous
atm=Atmosphere
br=Broad
Bu=Butyl
δ=Chemical shift
d=Doublet
DABCO=1,4-diazabicyclo[2.2.2]octane
DCC=Dicyclohexylcarbodiimide
DCCU=Dicyclohexyl urea
DIAD=Diisopropyl azodocarboxylate
DMF=Dimethylformamide
DMSO=Dimethylsulfoxide
EDTA=Ethylenediamine tetraacetic acid
Et=Ethyl
ESI MS=Electrospray Ionization Mass Spectrometry
EtOH=Ethanol
EtOAc=Ethyl acetate
g=Gram
h=Hour
HEPES=4-(2-Hydroxyethyl)-1-piperazineethanesulfonic acid
HOBT=1-Hydroxybenzotriazole
HPLC=High-performance liquid chromatography
Hz=Hertz
L=Liter
M=Molar
m=Multiplet
M+1=Mass plus one
m/e=Mass peak
m/z=Mass to charge ratio
MeOH=Methanol
mg=Milligram
MHz=Mega Hertz
min=Minute
mL=Milliliter
mM=Millimolar
mmol=Millimole
mol=Mole
MS=Mass spectroscopy
N=Normal
NaOMe=Sodium methoxide
NBS=N-Bromosuccinimide
NMR=Nuclear magnetic resonance
Ph=Phenyl
ppm=Parts per million
Py=Pyridine
q=Quartet
rt or r.t.=Room temperature
s=Singlet
t=Triplet
TBAF=Tetrabutylammonium fluoride TFA=Trifluoroacetic acid
THF=Tetrahydrofuran
xg=Centrifugal force (gravities)

Example 1

[(1-Benzyl-5-hydroxy-2-oxo-1,2,3,4-tetrahydro-[1,7]naphthyridine-6-carbonyl)-amino]-acetic acid a) 4-(1-Benzylamino-ethylidene)-pent-2-enedioic acid dimethyl ester Benzyl amine (2.0 mL, 18.7 mmol) was dissolved in MeOH (60 mL). 3-Oxo-butyric acid methyl ester (2.4 mL, 22.4 mmol) was added and the mixture was refluxed for 2 h. The mixture was cooled slightly, and propynoic acid methyl ester (2.5 mL, 28 mmol) was added. The mixture was then refluxed for 48 h. The solvent was evaporated, and the residual oil was recrystallized with MeOH to give 3.7 g of the title compound as a pale yellow solid. $^1$H NMR (CDCl$_3$, 200 MHz): δ=10.94 (br s, 1H), 7.75 (d, 1H, J=15.4 Hz), 7.20-7.45 (m, 5H), 6.09 (d, 1H, J=15.4 Hz), 4.58 (d, 1H, J=6.2 Hz), 3.78 (s, 3H), 3.74 (s, 3H), 2.27 (s, 3H).

b) 1-Benzyl-5-bromo-2-methyl-6-oxo-1,6-dihydro-pyridine-3-carboxylic acid methyl ester MeOH (28 mL) was added to a flask containing 4-(1-benzylamino-ethylidene)-pent-2-enedioic acid dimethyl ester (1.0 g, 3.46 mmol). NaOMe solution (7 mL, 3.46 mmol, 0.5M in MeOH) and N-bromosuccinimide (0.74 g, 4.15 mmol) were added. The resulting mixture was refluxed for 1 h. After cooling to r.t., the solvent was evaporated in vacuo. The residue was partitioned between saturated NH$_4$Cl (50 mL) and CH$_2$Cl$_2$ (50 mL). The aqueous layer was extracted with additional CH$_2$Cl$_2$ and the organic layers were combined, dried over MgSO$_4$, and concentrated. The crude product was chromatographed (0-40% EtOAc/hexanes) to give 0.77 g of the title compound. MS: (+) m/z 357.95, 359.92 (M+Na, $^{79/81}$Br).

c) 1-Benzyl-5-bromo-2-bromomethyl-6-oxo-1,6-dihydro-pyridine-3-carboxylic acid methyl ester A mixture of 1-benzyl-5-bromo-2-methyl-6-oxo-1,6-dihydro-pyridine-3-carboxylic acid methyl ester (0.28 g, 0.83 mmol), N-bromosuccinimide (0.163 g, 0.92 mmol), and benzoyl peroxide (20 mg, 0.083 mmol) in CCl$_4$ (10 mL) was refluxed for 16 h. The solvent was evaporated in vacuo, and the residue was chromatographed (0-20% EtOAc/hexanes) to give 284 mg of the title compound as an amorphous solid. MS: (+) m/z 415.87 (M+1).

d) 1-Benzyl-5-bromo-2-{[methoxycarbonylmethyl-(toluene-4-sulfonyl)-amino]-methyl}-6-oxo-1,6-dihydro-pyridine-3-carboxylic acid methyl ester A mixture of 1-benzyl-5-bromo-2-bromomethyl-6-oxo-1,6-dihydro-pyridine-3-carboxylic acid methyl ester (2.87 g, 6.92 mmol), (toluene-4-sulfonylamino)-acetic acid methyl ester (1.68 g, 6.92 mmol), sodium iodide (1.96 g, 13.8 mmol) and potassium carbonate (1.91 g, 13.8 mmol) in DMF (50 mL) was stirred at r.t. for 3 days. Brine (50 mL) was added and the mixture was extracted several times with EtOAc. The organic layers were combined, washed with water, and dried over MgSO$_4$. After the solvent was evaporated in vacuo, the crude product was chromatographed (0-40% EtOAc/hexanes) to give 2.1 g of the title compound as a yellow oil. MS: (+) m/z 576.95, 578.89 (M+1, $^{79/81}$Br).

e) 1-Benzyl-3-bromo-5-hydroxy-2-oxo-1,2-dihydro-[1,7]naphthyridine-6-carboxylic acid methyl ester 1-Benzyl-5-bromo-2-{[methoxycarbonylmethyl-(toluene-4-sulfonyl)-amino]-methyl}-6-oxo-1,6-dihydro-pyridine-3-carboxylic acid methyl ester (169 mg, 0.29 mmol) was dissolved in 2 mL of MeOH. NaOMe solution (0.2 mL, 0.88 mmol, 25 wt % in MeOH) was added and the mixture was stirred for 5 h. Saturated NH$_4$Cl (10 mL) was added, followed by addition of 1M HCl until pH about 2. The resulting mixture was extracted several times with EtOAc. The organic layers were combined, dried over MgSO$_4$, and concentrated in vacuo. The crude product was purified by silica gel chromatography (0-60% EtOAc/hexanes+2% AcOH) to give 50 mg of the title compound as a yellow solid. MS: (+) m/z 388.95, 390.92 (M+1, $^{79/81}$Br).

f) 1-Benzyl-5-hydroxy-2-oxo-1,2,3,4-tetrahydro-[1,7]naphthyridine-6-carboxylic acid methyl ester A flask was charged with EtOH (10 mL) and 10% palladium on carbon (200 mg). A solution of 1-benzyl-3-bromo-5-hydroxy-2-oxo-1,2-dihydro-[1,7]naphthyridine-6-carboxylic acid methyl ester (150 mg, 0.39 mmol) in EtOAc (40 mL) and sodium acetate (47 mg, 0.58 mmol) were added, and the resulting mixture was stirred under H$_2$ atmosphere for 16 h. The mixture was filtered, and the filtrate was concentrated in vacuo. The residue was chromatographed (0-60% EtOAc/hexanes+2% AcOH) to give 76 mg of the title compound as a white solid. MS: (+) m/z 325.11 (M+1).

g) [(1-Benzyl-5-hydroxy-2-oxo-1,2,3,4-tetrahydro-[1,7]naphthyridine-6-carbonyl)-amino]acetic acid A mixture of 1-benzyl-5-hydroxy-2-oxo-1,2,3,4-tetrahydro-[1,7]naphthyridine-6-carboxylic acid methyl ester (76 mg, 0.24 mmol), glycine (1.74 g, 23.1 mmol) and NaOMe solution (34 mL, 17.1 mmol, 0.5M in MeOH) was refluxed for 16 h. After the mixture was cooled to r.t., the solvent was evaporated in vacuo. The residue was dissolved in saturated NaHCO$_3$ and washed with ether. The aqueous layer was acidified to pH 1 with 4M HCl, and the resulting mixture was extracted with EtOAc. The organic layer was dried over MgSO$_4$ and concentrated to give 67 mg of the title compound as a white solid. MS: (+) m/z 356.11 (M+1).

Example 2

[(1-Benzyl-5-hydroxy-3-methyl-2-oxo-1,2-dihydro-[1,7]naphthyridine-6-carbonyl)-amino]-acetic acid a) 1-Benzyl-5-hydroxy-3-methyl-2-oxo-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (204 mg, 0.52 mmol), tetramethyltin (0.22 mL, 1.57 mmol), and PdCl$_2$(PPh$_3$)$_2$ (74 mg, 0.10 mmol) in 5 mL of DMF was heated at 120° C. for 1 h under N$_2$ atmosphere. Additional tetramethyltin (0.22 mL, 1.57 mmol) was added and the mixture was heated for 1 h at the same temperature. The mixture was cooled to r.t. and diluted with brine (10 mL) and EtOAc (40 mL). The aqueous layer was extracted with additional EtOAc, and the combined organic layer was washed with water and dried over MgSO$_4$. After the solvent was evaporated in vacuo, the crude residue was chromatographed (0-60% EtOAc/hexanes+2% AcOH) to give 125 mg of the title compound as a pale yellow solid. MS: (+) m/z 325.05 (M+1).

b) [(1-Benzyl-5-hydroxy-3-methyl-2-oxo-1,2-dihydro-[1,7]naphthyridine-6-carbonyl)-amino]-acetic acid A mixture of 1-benzyl-5-hydroxy-3-methyl-2-oxo-1,2-dihydro-[1,7]naphthyridine-6-carboxylic acid methyl ester (125 mg, 0.39 mmol), glycine (1.94 g, 25.8 mmol) and NaOMe solution (39 mL, 19.3 mmol, 0.5M in MeOH) was refluxed for 16 h. After the mixture was cooled to r.t., the solvent was evaporated in vacuo. The residue was dissolved in saturated NaHCO$_3$ and washed with ether. The aqueous layer was acidified to pH 2 with 4M HCl, and the resulting mixture was extracted with EtOAc. The organic layer was dried over MgSO$_4$ and concentrated to give 99 mg of the title compound as an off-white solid. MS: (+) m/z 368.08 (M+1).

Example 3

[(1,3-Dibenzyl-5-hydroxy-2-oxo-1,2-dihydro-[1,7]naphthyridine-6-carbonyl)-amino]-acetic acid a) 1,3-Dibenzyl-5-hydroxy-2-oxo-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (800 mg, 2.06 mmol), benzylzinc bromide (10.3 mL, 5.14 mmol, 0.5 M in THF), and Pd(PPh$_3$)$_4$ (238 mg, 0.206 mmol) in THF (20 mL) was refluxed under nitrogen atmosphere for 16 h. After the mixture was cooled to r.t., 1 M HCl and EtOAc were added. The aqueous layer was extracted with additional EtOAc, and the combined organic layer was dried over MgSO$_4$. After evaporating the solvent in vacuo, the crude product was chromatographed (0-40% EtOAc/hexanes+2% AcOH) to give 470 mg of the title compound as a yellow solid. MS: (+) m/z 401.12 (M+1).

b) [(1,3-Dibenzyl-5-hydroxy-2-oxo-1,2-dihydro-[1,7]naphthyridine-6-carbonyl)-amino]acetic acid A mixture of 1,3-dibenzyl-5-hydroxy-2-oxo-1,2-dihydro-[1,7]naphthyridine-6-carboxylic acid methyl ester (75 mg, 0.19 mmol), glycine (1.87 g, 24.9 mmol) and NaOMe solution (37.5 mL, 18.8 mmol, 0.5M in MeOH) was refluxed for 16 h. After the mixture was cooled to r.t., the solvent was evaporated in vacuo. The residue was dissolved in saturated NaHCO$_3$ and washed with ether. The aqueous layer was acidified to pH 2 with 4M HCl, and the resulting mixture was extracted with EtOAc. The organic layer was dried over MgSO$_4$ and concentrated. The crude product was further purified by silica gel chromatography (20-100% EtOAc/hexanes+2% AcOH) to give 32 mg of the title compound as an off-white solid. MS: (+) m/z 444.11 (M+1).

Example 4

[(1-Benzyl-5-hydroxy-2-oxo-3-phenyl-1,2-dihydro-[1,7]naphthyridine-6-carbonyl)-amino]-acetic acid a) 1-Benzyl-5-hydroxy-2-oxo-3-phenyl-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (200 mg, 0.51 mmol), PhSnBu$_3$ (0.2 mL, 0.62 mmol), and PdCl$_2$(PPh$_3$)$_2$ (72 mg, 0.10 mmol) in DMF (5 mL) was heated at 120° C. under nitrogen atmosphere for 2 h. After the mixture was cooled to r.t., brine (10 mL) and EtOAc (40 mL) were added. 1M HCl was added with stirring until pH was about 2. The aqueous layer was extracted with additional EtOAc and the organic layers were combined, washed with water, and dried over MgSO$_4$. After evaporating the solvent in vacuo, the crude product was chromatographed (0-55% EtOAc/hexanes+2% AcOH) to give 162 mg of the title compound as a yellow solid. MS: (+) m/z 387.10 (M+1).

b) [(1-Benzyl-5-hydroxy-2-oxo-3-phenyl-1,2-dihydro-[1,7]naphthyridine-6-carbonyl)-amino]-acetic acid A mixture of 1-benzyl-5-hydroxy-2-oxo-3-phenyl-1,2-dihydro-[1,7]naphthyridine-6-carboxylic acid methyl ester (162 mg, 0.42 mmol), glycine (2.11 g, 28 mmol) and NaOMe solution (42 mL, 21 mmol, 0.5M in MeOH) was refluxed for 32 h. After the mixture was cooled to r.t., the solvent was evaporated in vacuo. The residue was dissolved in saturated NaHCO$_3$ and washed with ether. The aqueous layer was acidified to pH 2 with 4M HCl, and the resulting mixture was extracted with EtOAc. The organic layer was dried over MgSO$_4$ and concentrated. The crude product was further purified by silica gel chromatography (20-100% EtOAc/hexanes+2% AcOH) to give 131 mg of the title compound. MS: (+) m/z 430.08 (M+1).

Example 5

[(1-Benzyl-5-hydroxy-3,8-dimethyl-2-oxo-1,2-dihydro-[1,7]naphthyridine-6-carbonyl)-amino]-acetic acid a) 1-Benzyl-8-bromo-5-hydroxy-3-methyl-2-oxo-1,2-dihydro-[1,7]naphthyridine-6-carboxylic acid methyl ester A mixture of 1-benzyl-5-hydroxy-3-methyl-2-oxo-1,2-dihydro-[1,7]naphthyridine-6-carboxylic acid methyl ester (0.62 g, 1.9 mmol) and N-bromosuccinimide (0.36 g, 2.01 mmol) was refluxed for 3 h. After the mixture was cooled to r.t., solvent was evaporated in vacuo. The residue was chromatographed (0-30% EtOAc/hexanes+2% AcOH) to give 493 mg of the title compound as a pale yellow solid. MS: (+) m/z 402.98, 404.86 (M+1, $^{79/81}$Br)

b) 1-Benzyl-5-hydroxy-3,8-dimethyl-2-oxo-1,2-dihydro-[1,7]naphthyridine-6-carboxylic acid methyl ester A mixture of 1-benzyl-8-bromo-5-hydroxy-3-methyl-2-oxo-1,2-dihydro-[1,7]naphthyridine-6-carboxylic acid methyl ester (162 mg, 0.40 mmol), tetramethyltin (0.3 mL, 2.0 mmol) and PdCl$_2$(PPh$_3$)$_2$ (56 mg, 0.08 mmol) in 5 mL of DMF was heated at 120° C. under nitrogen atmosphere for 1 h. After the mixture was cooled to r.t., brine (10 mL) and EtOAc (40 mL) was added. 1M HCl was added until pH was about 3. The aqueous layer was extracted with additional EtOAc and the combined organic layer was washed with water and dried over MgSO$_4$. After evaporating the solvent in vacuo, the residue was chromatographed (0-50% EtOAc/hexanes+2% AcOH) to give 145 mg of the title compound as a white solid. MS: (+) m/z 339.11 (M+1).

c) [(1-Benzyl-5-hydroxy-3,8-dimethyl-2-oxo-1,2-dihydro-[1,7]naphthyridine-6-carbonyl)-amino]-acetic acid A mixture of 1-benzyl-5-hydroxy-3,8-dimethyl-2-oxo-1,2-dihydro-[1,7]naphthyridine-6-carboxylic acid methyl ester (145 mg, 0.43 mmol), glycine (3.22 g, 43 mmol) and NaOMe solution (68 mL, 34 mmol, 0.5M in MeOH) was refluxed for 16 h. After the mixture was cooled to r.t., the solvent was evaporated in vacuo. The residue was dissolved in saturated NaHCO$_3$ and washed with ether. The aqueous layer was acidified to pH 2 with 4M HCl, and the resulting mixture was extracted with EtOAc. The organic layer was dried over MgSO$_4$ and concentrated to give 108 mg of the title compound as a white solid. MS: (+) m/z 382.08 (M+1).

Example 6

[(1-Benzyl-8-cyano-5-hydroxy-3-methyl-2-oxo-1,2-dihydro-[1,7]naphthyridine-6-carbonyl)-amino]-acetic acid a) 1-Benzyl-8-cyano-5-hydroxy-3-methyl-2-oxo-1,2-dihydro-[1,7]naphthyridine-6-carboxylic acid methyl ester A mixture of 1-benzyl-8-bromo-5-hydroxy-3-methyl-2-oxo-1,2-dihydro-[1,7]naphthyridine-6-carboxylic acid methyl ester (164 mg, 0.41 mmol) and CuCN (73 mg, 0.82 mmol) was refluxed for 35 min under nitrogen atmosphere. After the mixture was cooled to r.t., CH$_2$Cl$_2$ (100 mL) was added. 4M HCl was added with stirring until no more solid was present. The aqueous layer was extracted with additional CH$_2$Cl$_2$, and the combined organic layer was dried over MgSO$_4$ and concentrated in vacuo. The crude product was purified by silica gel chromatography (0-100% EtOAc/hexanes+2% AcOH) to give 100 mg of the title compound as a white solid. MS: (+) m/z 350.06 (M+1).

b) [(1-Benzyl-8-cyano-5-hydroxy-3-methyl-2-oxo-1,2-dihydro-[1,7]naphthyridine-6-carbonyl)-amino]-acetic acid A mixture of 1-benzyl-8-cyano-5-hydroxy-3-methyl-2-oxo-1,2-dihydro-[1,7]naphthyridine-6-carboxylic acid methyl ester (100 mg, 0.29 mmol), glycine (2.86 g, 38 mmol) and NaOMe solution (57 mL, 29 mmol, 0.5M in MeOH) was refluxed for 16 h. After the mixture was cooled to r.t., the solvent was evaporated in vacuo. The residue was dissolved in saturated NaHCO$_3$ and washed with ether. The aqueous layer was acidified to pH 2 with 4M HCl, and the resulting mixture was extracted with EtOAc. The organic layer was dried over MgSO$_4$ and concentrated to give 77 mg of the title compound as a white solid. MS: (+) m/z 382.08 (M+1).

Example 7

[(1-Benzyl-5-hydroxy-2-oxo-1,2-dihydro-[1,7]naphthyridine-6-carbonyl)-amino]acetic acid a) 1-Benzyl-2-methyl-6-oxo-1,6-dihydro-pyridine-3-carboxylic acid methyl ester A mixture of 4-(1-benzylamino-ethylidene)-pent-2-enedioic acid dimethyl ester (3 g, 10.4 mmol), triethylamine (1.5 mL, Et$_3$N) and MeOH (200 mL) was refluxed for 23 h. NaOMe solution (0.12 mL, 0.52 mmol, 25 wt % in MeOH) was added, and the mixture was refluxed for 16 h. The mixture was cooled to r.t. and concentrated in vacuo. The residue was partitioned between saturated NH$_4$Cl (100 mL) and CH$_2$Cl$_2$ (100 mL). 1M HCl was added until pH was about 1. The aqueous layer was extracted with additional CH$_2$Cl$_2$, and the combined organic layer was dried over MgSO$_4$ and concentrated to give 2.64 g of the title compound as a white solid. MS: (+) m/z 258.13 (M+1).

b) 1-Benzyl-2-bromomethyl-6-oxo-1,6-dihydro-pyridine-3-carboxylic acid methyl ester A mixture of 1-benzyl-2-methyl-6-oxo-1,6-dihydro-pyridine-3-carboxylic acid methyl ester (2.64 g, 10.3 mmol), N-bromosuccinimide (2.01 g, 11.3 mmol), and benzoyl peroxide (250 mg, 1.03 mmol) in CCl$_4$ (100 mL) was refluxed for 16 h. The solvent was evaporated in vacuo, and the residue was chromatographed (0-40% EtOAc/hexanes) to give 2.4 g of the title compound as a viscous oil. MS: (+) m/z 335.92, 337.89 (M+1, $^{79/81}$Br)

c) 1-Benzyl-2-{[methoxycarbonylmethyl-(toluene-4-sulfonyl)-amino]-methyl}-6-oxo-1,6-dihydro-pyridine-3-carboxylic acid methyl ester A mixture of 1-benzyl-2-bromomethyl-6-oxo-1,6-dihydro-pyridine-3-carboxylic acid methyl ester (2.4 g, 7.14 mmol), (toluene-4-sulfonylamino)-acetic acid methyl ester (1.74 g, 7.14 mmol), sodium iodide (2.14 g, 14.3 mmol) and potassium carbonate (1.97 g, 14.3 mmol) in DMF (45 mL) was stirred at r.t. for 16 h. Brine (100 mL) and EtOAc (100 mL) were added and the aqueous layer was extracted several times with EtOAc. The organic layers were combined, washed with water, and dried over MgSO$_4$. After the solvent was evaporated in vacuo, the crude product was chromatographed (0-75% EtOAc/hexanes) to give 1.95 g of the title compound as a yellow oil. MS: (+) m/z 499.06 (M+1).

d) 1-Benzyl-5-hydroxy-2-oxo-1,2-dihydro-[1,7]naphthyridine-6-carboxylic acid methyl ester 1-Benzyl-2-{[methoxycarbonylmethyl-(toluene-4-sulfonyl)-amino]-methyl}-6-oxo-1,6-dihydro-pyridine-3-carboxylic acid methyl ester (2 g, 4.02 mmol) was dissolved in 60 mL of MeOH. NaOMe solution (3 mL, 12.5 mmol, 25 wt % in MeOH) was added and the mixture was stirred for 16 h. Saturated NH$_4$Cl (100 mL) was added, followed by addition of 1M HCl until pH about 2. The resulting mixture was extracted several times with CH$_2$Cl$_2$. The organic layers were combined, dried over MgSO$_4$, and concentrated in vacuo. The crude product was purified by silica gel chromatography (0-60% EtOAc/hexanes+2% AcOH) to give 1.04 g of the title compound as a white solid. MS: (+) m/z 311.05 (M+1).

e) [(1-Benzyl-5-hydroxy-2-oxo-1,2-dihydro-[1,7]naphthyridine-6-carbonyl)-amino]-acetic acid A mixture of 1-benzyl-5-hydroxy-2-oxo-1,2-dihydro-[1,7]naphthyridine-6-carboxylic acid methyl ester (100 mg, 0.32 mmol) and sodium glycinate (626 mg, 6.45 mmol) in 2-methoxyethanol (10 mL) was refluxed for 2 h. The solvent was evaporated in vacuo, and the residue was dissolved in saturated NaHCO$_3$. The aqueous phase was washed with ether, and then acidified to pH about 2 with 4M HCl. The resulting suspension was extracted with EtOAc. The organic layer was dried over MgSO$_4$ and concentrated to give 84 mg of the title compound as a pale yellow solid. MS: (+) m/z 354.02 (M+1).

Example 8

[(1-Benzyl-5-hydroxy-8-methyl-2-oxo-1,2,3,4-tetrahydro-[1,7]naphthyridine-6-carbonyl)-amino]-acetic acid a) 1-Benzyl-8-bromo-5-hydroxy-2-oxo-1,2,3,4-tetrahydro-[1,7]naphthyridine-6-carboxylic acid methyl ester A mixture of 1-benzyl-5-hydroxy-2-oxo-1,2,3,4-tetrahydro-[1,7]naphthyridine-6-carboxylic acid methyl ester (300 mg, 0.96 mmol) and N-bromosuccinimide (180 mg, 1.01 mmol) in CH$_2$Cl$_2$ (3 mL) was refluxed for 3 h. After the mixture was cooled to r.t., solvent was evaporated in vacuo, and the residue was chromatographed (0-30% EtOAc/hexanes+2% AcOH) to give 296 mg of the title compound. MS: (+) m/z 390.98, 392.88 (M+H, $^{79/81}$Br)

b) 1-Benzyl-5-hydroxy-8-methyl-2-oxo-1,2,3,4-tetrahydro-[1,7]naphthyridine-6-carboxylic acid methyl ester A mixture of 1-benzyl-8-bromo-5-hydroxy-2-oxo-1,2,3,4-tetrahydro-[1,7]naphthyridine-6-carboxylic acid methyl ester (145 mg, 0.37 mmol), tetramethyltin (0.3 mL, 1.85 mmol), and PdCl$_2$(PPh$_3$)$_2$ (52 mg, 0.074 mmol) in DMF (5 mL) was heated at 120° C. under nitrogen atmosphere for 2 h. After the mixture was cooled to r.t., EtOAc (50 mL) and brine (10 mL) were added. 1M HCl was added until pH about 3. The aqueous layer was extracted with additional EtOAc, and the organic layers were combined and washed with water and dried over MgSO$_4$. After the solvent was evaporated in vacuo, the crude product was chromatographed (0-60% EtOAc/hexanes+2% AcOH) to give 96 mg of the title compound. MS: (+) m/z 327.11 (M+1).

c) [(1-Benzyl-5-hydroxy-8-methyl-2-oxo-1,2,3,4-tetrahydro-[1,7]naphthyridine-6-carbonyl)-amino]-acetic acid A mixture of 1-benzyl-5-hydroxy-8-methyl-2-oxo-1,2,3,4-tetrahydro-[1,7]naphthyridine-6-carboxylic acid methyl ester (96 mg, 0.29 mmol), glycine (2.94 g, 39 mmol) and NaOMe solution (59 mL, 29 mmol, 0.5 M in MeOH) was refluxed for 16 h. After the mixture was cooled to r.t., solvent was evaporated in vacuo. The residue was dissolved in saturated NaHCO$_3$ and washed with ether. The aqueous layer was acidified to pH about 3 with 4M HCl and extracted with EtOAc. The organic layer was dried over MgSO$_4$ and concentrated to give 100 mg of the title compound as an off-white solid. MS: (+) m/z 370.05 (M+1).

Example 9

[(1-Benzyl-8-cyano-5-hydroxy-2-oxo-1,2,3,4-tetrahydro-[1,7]naphthyridine-6-carbonyl)-amino]-acetic acid a) 1-Benzyl-8-cyano-5-hydroxy-2-oxo-1,2,3,4-tetrahydro-[1,7]naphthyridine-6-carboxylic acid methyl ester A mixture of 1-benzyl-8-bromo-5-hydroxy-2-oxo-1,2,3,4-tetrahydro-[1,7]naphthyridine-6-carboxylic acid methyl ester (140 mg, 0.36 mmol) and CuCN (64 mg, 0.72 mmol) in DMF (5 mL) was refluxed for 30 min. After the mixture was cooled to r.t., CH$_2$Cl$_2$ (50 mL) was added. 4M HCl was added with stirring until no solid was present. The aqueous layer was extracted with additional CH$_2$Cl$_2$, and the organic layers were combined and dried over MgSO$_4$. After evaporating the solvent in vacuo, the crude residue was chromatographed (20-100 EtOAc/hexanes+2% AcOH) to give 75 mg of the title compound. MS: (+) m/z 338.03 (M+1).

b) [(1-Benzyl-8-cyano-5-hydroxy-2-oxo-1,2,3,4-tetrahydro-[1,7]naphthyridine-6-carbonyl)-amino]-acetic acid A mixture of 1-benzyl-8-cyano-5-hydroxy-2-oxo-1,2,3,4-tetrahydro-[1,7]naphthyridine-6-carboxylic acid methyl ester (102 mg, 0.30 mmol), glycine (3.02 g, 40 mmol) and NaOMe solution (61 mL, 30 mmol, 0.5 M in MeOH) was refluxed for 16 h. After the mixture was cooled to r.t., solvent was evaporated in vacuo. The residue was dissolved in saturated NaHCO$_3$ and washed with ether. The aqueous layer was acidified to pH about 2 with 4M HCl and extracted with EtOAc. The organic layer was dried over MgSO$_4$ and concentrated to give 80 mg of the title compound as an off-white solid. MS: (+) m/z 381.13 (M+1).

Example 10

[(1-Benzyl-5-hydroxy-3-methyl-2-oxo-8-pyridin-3-yl-1,2-dihydro-[1,7]naphthyridine-6-carbonyl)-amino]-acetic acid a) 1-Benzyl-5-hydroxy-3-methyl-2-oxo-8-pyridin-3-yl-1,2-dihydro-[1,7]naphthyridine-6-carboxylic acid methyl ester A mixture of 1-benzyl-8-bromo-5-hydroxy-3-methyl-2-oxo-1,2-dihydro-[1,7]naphthyridine-6-carboxylic acid methyl ester (170 mg, 0.42 mmol), 3-tributylstannanyl-pyridine (0.2 mL, 0.63 mmol), and PdCl$_2$(PPh$_3$)$_2$ (59 mg, 0.084 mmol) in 5 mL of DMF was heated at 120° C. for 2 h under nitrogen atmosphere. After the mixture was cooled to r.t., EtOAc (50 mL) and brine (10 mL) were added. 1M HCl was added with stirring until pH was about 3. The aqueous layer was extracted with additional EtOAc, and the combined organic layer was dried over MgSO$_4$ and concentrated. The crude product was purified by silica gel chromatography (20-100% EtOAc/hexanes+2% AcOH) to give 95 mg of the title compound. MS: (+) m/z 402.14 (M+1).

b) [(1-Benzyl-5-hydroxy-3-methyl-2-oxo-8-pyridin-3-yl-1,2-dihydro-[1,7]naphthyridine-6-carbonyl)-amino]-acetic acid A mixture of 1-benzyl-5-hydroxy-3-methyl-2-oxo-8-pyridin-3-yl-1,2-dihydro-[1,7]naphthyridine-6-carboxylic acid methyl ester (95 mg, 0.24 mmol), glycine (2.85 g, 38 mmol) and NaOMe solution (57 mL, 28 mmol, 0.5 M in MeOH) was refluxed for 16 h. After the mixture was cooled to r.t., the solvent was evaporated in vacuo. The residue was dissolved in saturated NaHCO$_3$ and washed with ether. The aqueous layer was acidified to pH 3 with 4 M HCl, and the resulting mixture was extracted with EtOAc. The organic layer was dried over MgSO$_4$ and concentrated to give 71 mg of the title compound as a yellow solid. MS: (+) m/z 445.11 (M+1).

Example 11

[(1-Benzyl-5-hydroxy-2-oxo-3-phenethyl-1,2-dihydro-[1,7]naphthyridine-6-carbonyl)-amino]-acetic acid a) 1-Benzyl-5-hydroxy-2-oxo-3-phenylethynyl-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (500 mg, 1.29 mmol), tributyl-phenylethynyl-stannane (0.54 mL, 1.54 mmol), and $PdCl_2(PPh_3)_2$ (180 mg, 0.26 mmol) in 10 mL of DMF was heated at 120° C. for 2 h under $N_2$ atmosphere. The mixture was cooled to r.t. and diluted with brine (10 mL) and EtOAc (40 mL). 1M HCl was added until pH was about 3. The aqueous layer was extracted with additional EtOAc, and the combined organic layer was washed with water and dried over $MgSO_4$. After the solvent was evaporated in vacuo, the crude residue was chromatographed (0-60% EtOAc/hexanes+2% AcOH) to give 450 mg of the title compound as a yellow solid. MS: (+) m/z 411.11 (M+1).

b) 1-Benzyl-5-hydroxy-2-oxo-3-phenethyl-1,2-dihydro-[1,7]naphthyridine-6-carboxylic acid methyl ester A flask was charged with 10% palladium on carbon (100 mg), EtOH (10 mL), and a solution of 1-benzyl-5-hydroxy-2-oxo-3-phenylethynyl-1,2-dihydro-[1,7]naphthyridine-6-carboxylic acid methyl ester (250 mg, 0.61 mmol) in 10 mL of EtOAc/MeOH (1:1). The mixture was placed under $H_2$ atmosphere and stirred for 16 h. After removal of Pd/C by filtration, the solution was concentrated in vacuo. The residue was purified by silica gel chromatography (0-60% EtOAc/hexanes+2% AcOH) to give 150 mg of the title compound as an off-white solid. MS: (+) m/z 415.12 (M+1).

c) [(1-Benzyl-5-hydroxy-2-oxo-3-phenethyl-1,2-dihydro-[1,7]naphthyridine-6-carbonyl)-amino]-acetic acid A mixture of 1-benzyl-5-hydroxy-2-oxo-3-phenethyl-1,2-dihydro-[1,7]naphthyridine-6-carboxylic acid methyl ester (53 mg, 0.13 mmol), glycine (2.06 g, 27.5 mmol) and NaOMe solution (41 mL, 20.5 mmol, 0.5 M in MeOH) was refluxed for 16 h. After the mixture was cooled to r.t., the solvent was evaporated in vacuo. The residue was dissolved in saturated $NaHCO_3$ and washed with ether. The aqueous layer was acidified to pH 2 with 4 M HCl, and the resulting mixture was extracted with EtOAc. The organic layer was dried over $MgSO_4$ and concentrated to give 53 mg of the title compound. MS: (+) m/z 458.10 (M+1).

Example 12

[(1-Benzyl-5-hydroxy-8-methyl-2-oxo-3-phenyl-1,2-dihydro-[1,7]naphthyridine-6-carbonyl)-amino]-acetic acid a) 1-Benzyl-8-bromo-5-hydroxy-2-oxo-3-phenyl-1,2-dihydro-[1,7]naphthyridine-6-carboxylic acid methyl ester A mixture of 1-benzyl-5-hydroxy-2-oxo-3-phenyl-1,2-dihydro-[1,7]naphthyridine-6-carboxylic acid methyl ester (600 mg, 1.55 mmol) and N-bromosuccinimide (291 mg, 1.63 mmol) in $CH_2Cl_2$ (4.2 mL) was refluxed for 3 h. After the mixture was cooled to r.t., the solvent was evaporated in vacuo. The residue was purified by silica gel chromatography (0-60% EtOAc/hexanes+2% AcOH) to give 560 mg of the title compound as a yellow solid. MS: (+) m/z 464.97, 466.94 (M+H, $^{79/81}Br$)

b) 1-Benzyl-5-hydroxy-8-methyl-2-oxo-3-phenyl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (105 mg, 0.23 mmol), tetramethyltin (0.2 mL, 1.13 mmol) and $PdCl_2(PPh_3)_2$ (32 mg, 0.045 mmol) in 5 mL of DMF was heated at 120° C. for 2 h under nitrogen atmosphere. After the mixture was cooled to r.t., EtOAc (50 mL) and brine (10 mL) were added. 1M HCl was added with stirring until pH was about 2. The aqueous layer was extracted with additional EtOAc, and the combined organic layer was washed with water and dried over $MgSO_4$. After evaporating the solvent in vacuo, the crude product was chromatographed (0-40% EtOAc/hexanes+2% AcOH) to give 58 mg of the title compound. MS: (+) m/z 401.12 (M+1).

c) [(1-Benzyl-5-hydroxy-8-methyl-2-oxo-3-phenyl-1,2-dihydro-[1,7]naphthyridine-6-carbonyl)-amino]-acetic acid A mixture of 1-benzyl-5-hydroxy-8-methyl-2-oxo-3-phenyl-1,2-dihydro-[1,7]naphthyridine-6-carboxylic acid methyl ester (58 mg, 0.15 mmol), glycine (2.61 g, 35 mmol) and NaOMe solution (52 mL, 26 mmol, 0.5 M in MeOH) was refluxed for 16 h. After the mixture was cooled to r.t., the solvent was evaporated in vacuo. The residue was dissolved in saturated $NaHCO_3$ and washed with ether. The aqueous layer was acidified to pH 2 with 4 M HCl, and the resulting mixture was extracted with EtOAc. The organic layer was dried over $MgSO_4$ and concentrated to give 39 mg of the title compound as a yellow solid. MS: (+) m/z 444.15 (M+1).

Example 13

[(1-Benzyl-5-hydroxy-2-oxo-3,8-diphenyl-1,2-dihydro-[1,7]naphthyridine-6-carbonyl)-amino]-acetic acid a) 1-Benzyl-5-hydroxy-2-oxo-3,8-diphenyl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (115 mg, 0.25 mmol), phenyltributyltin (0.1 mL, 0.30 mmol) and $PdCl_2(PPh_3)_2$ (35 mg, 0.05 mmol) in 5 mL of DMF was heated at 120° C. for 2 h under nitrogen atmosphere. After the mixture was cooled to r.t., EtOAc (50 mL) and brine (10 mL) were added. 1M HCl was added with stirring until pH was about 3. The aqueous layer was extracted with additional EtOAc, and the combined organic layer was washed with water and dried over $MgSO_4$. After evaporating the solvent in vacuo, the crude product was chromatographed (0-50% EtOAc/hexanes) to give 70 mg of the title compound. MS: (+) m/z 463.13 (M+1).

b) [(1-Benzyl-5-hydroxy-2-oxo-3,8-diphenyl-1,2-dihydro-[1,7]naphthyridine-6-carbonyl)-amino]-acetic acid A mixture of 1-benzyl-5-hydroxy-2-oxo-3,8-diphenyl-1,2-dihydro-[1,7]naphthyridine-6-carboxylic acid methyl ester (70 mg, 0.15 mmol), glycine (2.73 g, 36 mmol) and NaOMe solution (55 mL, 27 mmol, 0.5 M in MeOH) was refluxed for 16 h. After the mixture was cooled to r.t., the solvent was evaporated in vacuo. The residue was dissolved in saturated NaHCO$_3$ and washed with ether. The aqueous layer was acidified with 4 M HCl, and the resulting mixture was extracted with EtOAc. The organic layer was dried over MgSO$_4$ and concentrated. The solid obtained was further purified by silica gel chromatography (0-70% EtOAc/hexanes+2% AcOH) to give 36 mg of the title compound. MS: (+) m/z 506.13 (M+1).

Example 14

[(1-Benzyl-8-cyano-5-hydroxy-2-oxo-3-phenyl-1,2-dihydro-[1,7]naphthyridine-6-carbonyl)-amino]-acetic acid a) 1-Benzyl-8-cyano-5-hydroxy-2-oxo-3-phenyl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (200 mg, 0.43 mmol) and CuCN (77 mg, 0.86 mmol) in 5 mL of DMF was refluxed for 40 min, then cooled to r.t., and poured into a mixture of water and CH$_2$Cl$_2$. 4M HCl was added with vigorous stirring until no more solid was present. The aqueous layer was extracted with additional CH$_2$Cl$_2$ and the combined organic layer was dried over MgSO$_4$. After evaporating the solvent in vacuo, the crude product was chromatographed (0-40% EtOAc/hexanes+2% AcOH) to give 140 mg of the title compound. MS: (+) m/z 412.12 (M+1).

b) [(1-Benzyl-8-cyano-5-hydroxy-2-oxo-3-phenyl-1,2-dihydro-[1,7]naphthyridine-6-carbonyl)-amino]-acetic acid A mixture of 1-benzyl-8-cyano-5-hydroxy-2-oxo-3-phenyl-1,2-dihydro-[1,7]naphthyridine-6-carboxylic acid methyl ester (70 mg, 0.17 mmol), glycine (3.07 g, 41 mmol) and NaOMe solution (61 mL, 31 mmol, 0.5 M in MeOH) was refluxed for 16 h. After the mixture was cooled to r.t., the solvent was evaporated in vacuo. The residue was dissolved in saturated NaHCO$_3$ and washed with ether. The aqueous layer was acidified with 4 M HCl to pH about 3, and the resulting mixture was extracted with EtOAc. The organic layer was dried over MgSO$_4$ and concentrated to give 62 mg of the title compound. MS: (+) m/z 455.11 (M+1).

Example 15

3-[(1-Benzyl-8-cyano-5-hydroxy-2-oxo-3-phenyl-1,2-dihydro-[1,7]naphthyridine-6-carbonyl)-amino]-propionic acid A mixture of 1-benzyl-8-cyano-5-hydroxy-2-oxo-3-phenyl-1,2-dihydro-[1,7]naphthyridine-6-carboxylic acid methyl ester (70 mg, 0.17 mmol), beta-alanine (3.64 g, 41 mmol) and NaOMe solution (61 mL, 31 mmol, 0.5 M in MeOH) was refluxed for 16 h. After the mixture was cooled to r.t., the solvent was evaporated in vacuo. The residue was dissolved in saturated NaHCO$_3$ and washed with ether. The aqueous layer was acidified with 4 M HCl to pH about 3, and the resulting mixture was extracted with EtOAc. The organic layer was dried over MgSO$_4$ and concentrated to give 65 mg of the title compound. MS: (+) m/z 469.13 (M+1).

Example 16

[(1-Benzyl-5-hydroxy-2-oxo-3-phenyl-8-pyridin-3-yl-1,2-dihydro-[1,7]naphthyridine-6-carbonyl)-amino]-acetic acid a) 1-Benzyl-5-hydroxy-2-oxo-3-phenyl-8-pyridin-3-yl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (104 mg, 0.22 mmol), 3-tributylstannanyl-pyridine (0.11 mL, 0.34 mmol) and PdCl$_2$(PPh$_3$)$_2$ (31 mg, 0.045 mmol) in 5 mL of DMF was heated at 120° C. for 2 h under nitrogen atmosphere. After the mixture was cooled to r.t., EtOAc (50 mL) and brine (10 mL) were added. 1M HCl was added with stirring until pH was about 3. The aqueous layer was extracted with additional EtOAc, and the combined organic layer was washed with water and dried over MgSO$_4$. After evaporating the solvent in vacuo, the crude product was chromatographed (20-100% EtOAc/hexanes+2% AcOH) to give 64 mg of the title compound. MS: (+) m/z 464.15 (M+1).

b) [(1-Benzyl-5-hydroxy-2-oxo-3-phenyl-8-pyridin-3-yl-1,2-dihydro-[1,7]naphthyridine-6-carbonyl)-amino]-acetic acid A mixture of 1-benzyl-5-hydroxy-2-oxo-3-phenyl-8-pyridin-3-yl-1,2-dihydro-[1,7]naphthyridine-6-carboxylic acid methyl ester (64 mg, 0.14 mmol), glycine (3.42 g, 46 mmol) and NaOMe solution (69 mL, 35 mmol, 0.5 M in MeOH) was refluxed for 16 h. After the mixture was cooled to r.t., the solvent was evaporated in vacuo. The residue was dissolved in saturated NaHCO$_3$ and washed with ether. The aqueous layer was acidified to pH about 3, and the resulting mixture was extracted with EtOAc. The organic layer was dried over MgSO$_4$ and concentrated. The crude product obtained was further purified by silica gel chromatography (0-10% MeOH/EtOAc) to give 25 mg of the title compound. MS: (+) m/z 507.14 (M+1).

Example 17

[(1,3-Dibenzyl-8-cyano-5-hydroxy-2-oxo-1,2-dihydro-[1,7]naphthyridine-6-carbonyl)-amino]-acetic acid a) 1,3-Dibenzyl-8-bromo-5-hydroxy-2-oxo-1,2-dihydro-[1,7]naphthyridine-6-carboxylic acid methyl ester A mixture of 1,3-dibenzyl-5-hydroxy-2-oxo-1,2-dihydro-[1,7]naphthyridine-6-carboxylic acid methyl ester (470 mg, 1.18 mmol) and N-bromosuccinimide (220 mg, 1.23 mmol) was refluxed for 3 h. After the mixture was cooled to r.t., solvent was evaporated in vacuo. The residue was chromatographed (0-30% EtOAc/hexanes+2% AcOH) to give 451 mg of the title compound. MS: (+) m/z 479.06, 480.88 (M+1, $^{79/81}$Br)

b) 1,3-Dibenzyl-8-cyano-5-hydroxy-2-oxo-1,2-dihydro-[1,7]naphthyridine-6-carboxylic acid methyl ester A mixture of 1,3-dibenzyl-8-bromo-5-hydroxy-2-oxo-1,2-dihydro-[1,7]naphthyridine-6-carboxylic acid methyl ester (114 mg, 0.24 mmol) and CuCN (43 mg, 0.48 mmol) in 5 mL of DMF was refluxed for 40 min. After the mixture was cooled to r.t., it was poured into a mixture of water and CH$_2$Cl$_2$. 4M HCl was added with vigorous stirring until both layers became homogeneous. The aqueous layer was extracted with additional CH$_2$Cl$_2$, and the combined organic layer was washed with water and dried over MgSO$_4$. After evaporating the solvent in vacuo, the crude product was chromatographed (0-50% EtOAc/hexanes+2% AcOH) to give 53 mg of the title compound. MS: (+) m/z 426.14 (M−1).

c) [(1,3-Dibenzyl-8-cyano-5-hydroxy-2-oxo-1,2-dihydro-[1,7]naphthyridine-6-carbonyl)-amino]-acetic acid A mixture of 1,3-dibenzyl-8-cyano-5-hydroxy-2-oxo-1,2-dihydro-[1,7]naphthyridine-6-carboxylic acid methyl ester (30 mg, 0.071 mmol), glycine (2.82 g, 37.6 mmol) and NaOMe solution (56 mL, 28.2 mmol, 0.5 M in MeOH) was refluxed for 16 h. After the mixture was cooled to r.t., the solvent was evaporated in vacuo. The residue was dissolved in saturated NaHCO$_3$ and washed with ether. The aqueous layer was acidified to pH 2 with 4M HCl, and the resulting mixture was extracted with EtOAc. The organic layer was dried over MgSO$_4$ and concentrated to give 31 mg of the title compound. MS: (−) m/z 467.10 (M−1).

Example 18

3-[(1,3-Dibenzyl-8-cyano-5-hydroxy-2-oxo-1,2-dihydro-[1,7]naphthyridine-6-carbonyl)-amino]-propionic acid A mixture of 1,3-dibenzyl-8-cyano-5-hydroxy-2-oxo-1,2-dihydro-[1,7]naphthyridine-6-carboxylic acid methyl ester (23 mg, 0.054 mmol), β-alanine (2.57 g, 28.8 mmol) and NaOMe solution (43 mL, 21.6 mmol, 0.5 M in MeOH) was refluxed for 16 h. After the mixture was cooled to r.t., the solvent was evaporated in vacuo. The residue was dissolved in saturated NaHCO$_3$ and washed with ether. The aqueous layer was acidified to pH 2 with 4M HCl, and the resulting mixture was extracted with EtOAc. The organic layer was dried over MgSO$_4$ and concentrated to give 34 mg of the title compound. MS: (−) m/z 481.13 (M−1).

Example 19

[(1,3-Dibenzyl-5-hydroxy-8-methyl-2-oxo-1,2-dihydro-[1,7]naphthyridine-6-carbonyl)-amino]-acetic acid a) 1,3-Dibenzyl-5-hydroxy-8-methyl-2-oxo-1,2-dihydro-[1,7]naphthyridine-6-carboxylic acid methyl ester A mixture of 1,3-dibenzyl-8-bromo-5-hydroxy-2-oxo-1,2-dihydro-[1,7]naphthyridine-6-carboxylic acid methyl ester (150 mg, 0.31 mmol), tetramethyltin (0.22 mL, 1.57 mmol) and PdCl$_2$(PPh$_3$)$_2$ (44 mg, 0.063 mmol) in 5 mL of DMF was heated at 120° C. for 2 h under nitrogen atmosphere. After the mixture was cooled to r.t., EtOAc (50 mL) and brine (10 mL) were added. 1M HCl was added with stirring until pH was about 2. The aqueous layer was extracted with additional EtOAc, and the combined organic layer was washed with water and dried over MgSO$_4$. After evaporating the solvent in vacuo, the crude product was chromatographed (0-40% EtOAc/hexanes+2% AcOH) to give 80 mg of the title compound. MS: (+) m/z 415.12 (M+1).

b) [(1,3-Dibenzyl-5-hydroxy-8-methyl-2-oxo-1,2-dihydro-[1,7]naphthyridine-6-carbonyl)-amino]-acetic acid A mixture of 1,3-dibenzyl-5-hydroxy-8-methyl-2-oxo-1,2-dihydro-[1,7]naphthyridine-6-carboxylic acid methyl ester (40 mg, 0.097 mmol), glycine (2.90 g, 38.6 mmol) and NaOMe solution (58 mL, 29 mmol, 0.5 M in MeOH) was refluxed for 16 h. After the mixture was cooled to r.t., the solvent was evaporated in vacuo. The residue was dissolved in saturated NaHCO$_3$ and washed with ether. The aqueous layer was acidified to pH about 2, and the resulting mixture was extracted with EtOAc. The organic layer was dried over MgSO$_4$ and concentrated. The residue was further purified by silica gel chromatography (0-60% EtOAc/hexanes+2% AcOH) to give 17 mg of the title compound MS: (+) m/z 458.17 (M+1).

Example 20

3-[(1,3-Dibenzyl-5-hydroxy-8-methyl-2-oxo-1,2-dihydro-[1,7]naphthyridine-6-carbonyl)-amino]-propionic acid A mixture of 1,3-dibenzyl-5-hydroxy-8-methyl-2-oxo-1,2-dihydro-[1,7]naphthyridine-6-carboxylic acid methyl ester (40 mg, 0.097 mmol), β-alanine (3.44 g, 38.6 mmol) and NaOMe solution (58 mL, 29 mmol, 0.5 M in MeOH) was refluxed for 16 h. After the mixture was cooled to r.t., the solvent was evaporated in vacuo. The residue was dissolved in saturated NaHCO$_3$ and washed with ether. The aqueous layer was acidified to pH 2, and the resulting mixture was extracted with EtOAc. The organic layer was dried over MgSO$_4$ and concentrated. The residue was further purified by silica gel chromatography (0-60% EtOAc/hexanes+2% AcOH) to give 12 mg of the title compound. MS: (+) m/z 472.18 (M+1).

Example 21

[(1,3-Dibenzyl-5-hydroxy-2-oxo-8-pyridin-3-yl-1,2-dihydro-[1,7]naphthyridine-6-carbonyl)-amino]-acetic acid a) 1,3-Dibenzyl-5-hydroxy-2-oxo-8-pyridin-3-yl-1,2-dihydro-[1,7]naphthyridine-6-carboxylic acid methyl ester A mixture of 1,3-dibenzyl-8-bromo-5-hydroxy-2-oxo-1,2-dihydro-[1,7]naphthyridine-6-carboxylic acid methyl ester (105 mg, 0.22 mmol), 3-tributylstannanyl-pyridine (0.1 mL, 0.33 mmol) and PdCl$_2$(PPh$_3$)$_2$ (30 mg, 0.044 mmol) in 5 mL of DMF was heated at 120° C. for 2 h under nitrogen atmosphere. After the mixture was cooled to r.t., EtOAc (50 mL) and brine (10 mL) were added. 1M HCl was added with stirring until pH was about 3. The aqueous layer was extracted with additional EtOAc, and the combined organic layer was washed with water and dried over MgSO$_4$. After evaporating the solvent in vacuo, the crude product was chromatographed (0-80% EtOAc/hexanes+2% AcOH) to give 48 mg of the title compound. MS: (+) m/z 478.16 (M+1).

b) [(1,3-Dibenzyl-5-hydroxy-2-oxo-8-pyridin-3-yl-1,2-dihydro-[1,7]naphthyridine-6-carbonyl)-amino]-acetic acid A mixture of 1,3-dibenzyl-5-hydroxy-2-oxo-8-pyridin-3-yl-1,2-dihydro-[1,7]naphthyridine-6-carboxylic acid methyl ester (34 mg, 0.071 mmol), glycine (2.85 g, 38 mmol) and NaOMe solution (57 mL, 29 mmol, 0.5 M in MeOH) was refluxed for 16 h. After the mixture was cooled to r.t., the solvent was evaporated in vacuo. The residue was dissolved in saturated NaHCO$_3$ and washed with ether. The aqueous layer was acidified to pH about 3, and the resulting mixture was extracted with EtOAc. The organic layer was dried over MgSO$_4$ and concentrated. The residue was further purified by silica gel chromatography (0-80% EtOAc/hexanes+2% AcOH) to give 20 mg of the title compound MS: (+) m/z 521.17 (M+1).

Example 22

3-[(1,3-Dibenzyl-5-hydroxy-2-oxo-8-pyridin-3-yl-1,2-dihydro-[1,7]naphthyridine-6-carbonyl)-amino]-propionic acid A mixture of 1,3-dibenzyl-5-hydroxy-2-oxo-8-pyridin-3-yl-1,2-dihydro-[1,7]naphthyridine-6-carboxylic acid methyl ester (24 mg, 0.050 mmol), β-alanine (2.39 g, 26.8 mmol) and NaOMe solution (40 mL, 20 mmol, 0.5 M in MeOH) was refluxed for 16 h. After the mixture was cooled to r.t., the solvent was evaporated in vacuo. The residue was dissolved in saturated NaHCO$_3$ and washed with ether. The aqueous layer was acidified to pH about 3, and the resulting mixture was extracted with EtOAc. The organic layer was dried over MgSO$_4$ and concentrated. The residue was further purified by silica gel chromatography (0-80% EtOAc/hexanes+2% AcOH) to give 20 mg of the title compound. MS: (+) m/z 535.21 (M+1).

Example 23

4-[(1-Benzyl-8-cyano-5-hydroxy-2-oxo-3-phenyl-1,2-dihydro-[1,7]naphthyridine-6-carbonyl)-amino]-butyric acid A mixture of 1-benzyl-8-cyano-5-hydroxy-2-oxo-3-phenyl-1,2-dihydro-[1,7]naphthyridine-6-carboxylic acid methyl ester (45 mg, 0.11 mmol), 4-aminobutyric acid (3.76 g, 36.5 mmol) and NaOMe solution (54 mL, 27.4 mmol, 0.5 M in MeOH) was refluxed for 16 h. After the mixture was cooled to r.t., the solvent was evaporated in vacuo. The residue was partitioned between water and EtOAc. 1M HCl was added with vigorous stirring until pH was about 1. The organic layer was dried over MgSO$_4$ and concentrated. The crude was chromatographed (0-60% EtOAc/hexanes+2% AcOH) to give 35 mg of the title compound. MS: (+) m/z 483.16 (M+1).

Example 24

5-[(1-Benzyl-8-cyano-5-hydroxy-2-oxo-3-phenyl-1,2-dihydro-[1,7]naphthyridine-6-carbonyl)-amino]-pentanoic acid A mixture of 1-benzyl-8-cyano-5-hydroxy-2-oxo-3-phenyl-1,2-dihydro-[1,7]naphthyridine-6-carboxylic acid methyl ester (47 mg, 0.11 mmol), 5-aminovaleric acid (4.46 g, 38.1 mmol) and NaOMe solution (57 mL, 28.6 mmol, 0.5 M in MeOH) was refluxed for 16 h. After the mixture was cooled to r.t., the solvent was evaporated in vacuo. The residue was partitioned between water and EtOAc. 1M HCl was added with vigorous stirring until pH was about 1. The organic layer was dried over MgSO$_4$ and concentrated. The crude was chromatographed (0-60% EtOAc/hexanes+2% AcOH) to give 50 mg of the title compound as a brown oil. MS: (+) m/z 497.17 (M+1).

Example 25

3-[(1-Benzyl-8-cyano-5-hydroxy-2-oxo-3-phenyl-1,2-dihydro-[1,7]naphthyridine-6-carbonyl)-amino]-2,2-dimethyl-propionic acid a) 3-[(1-Benzyl-8-cyano-5-hydroxy-2-oxo-3-phenyl-1,2-dihydro-[1,7]naphthyridine-6-carbonyl)-amino]-2,2-dimethyl-propionic acid methyl ester A mixture of 1-benzyl-8-cyano-5-hydroxy-2-oxo-3-phenyl-1,2-dihydro-[1,7]naphthyridine-6-carboxylic acid methyl ester (52 mg, 0.127 mmol) and 3-amino-2,2-dimethyl-propionic acid methyl ester (83 mg, 0.633 mmol) in MeOH (3 mL) was heated to 150° C. for 1 h in a CEM microwave reactor. The solvent was evaporated in vacuo and the residue was chromatographed (0-40% EtOAc/hexanes) to give 63 mg of the title compound as a yellow oil. MS: (+) m/z 511.22 (M+1).

b) 3-[(1-Benzyl-8-cyano-5-hydroxy-2-oxo-3-phenyl-1,2-dihydro-[1,7]naphthyridine-6-carbonyl)-amino]-2,2-dimethyl-propionic acid A mixture of 3-[(1-benzyl-8-cyano-5-hydroxy-2-oxo-3-phenyl-1,2-dihydro-[1,7]naphthyridine-6-carbonyl)-amino]-2,2-dimethyl-propionic acid methyl ester (50 mg, 0.098 mmol), 2M NaOH (3 mL) and MeOH (3 mL) was stirred at r.t. for 1 h. 1M HCl was added to acidify the mixture, and the resulting suspension was extracted with EtOAc. The organic layer was dried over MgSO$_4$ and concentrated. The crude product was chromatographed (0-30% EtOAc/hexanes+2% AcOH) to give 26 mg of the title compound. MS: (+) m/z 497.15 (M+1).

Example 26

[(7-Benzyl-4-hydroxy-8-oxo-7,8-dihydro-[2,7]naphthyridine-3-carbonyl)-amino]-acetic acid a) 3-Ethoxycarbonyl-2-methoxycarbonyl-but-2-enoic acid methyl ester A mixture of ZnCl$_2$ (53 g, 388 mmol) in acetic anhydride (120 mL) was stirred at r.t. for 2 h. The resulting solution was decanted, and to this solution was added ethyl pyruvate (25 g, 215 mmol) and dimethyl malonate (25 mL, 215 mmol). The resulting mixture was heated at 100° C. for 1 h, then left standing at r.t. for 16 h. Ether (300 mL) was added and the mixture was washed with ice water (5×300 mL) and saturated NaHCO$_3$ (2×300 mL). The organic layer was dried over MgSO$_4$ and concentrated to give a dark brown oil, which was distilled under reduced pressure to give 34.1 g of the title compound as an orange oil. $^1$H NMR (CDCl$_3$, 200 MHz): δ=4.26 (q, 2H, J=7.0 Hz), 3.82 (s, 3H), 3.79 (s, 3H), 2.22 (s, 3H), 1.32 (t, 3H, J=7.2 Hz).

b) 5-Dimethylamino-3-ethoxycarbonyl-2-methoxy-carbonyl-penta-2,4-dienoic acid methyl ester A mixture of 3-ethoxycarbonyl-2-methoxycarbonyl-but-2-enoic acid methyl ester (10 g, 43.5 mmol), dimethylformamide dimethyl acetal (6.1 mL, 45.7 mmol) and DMF (8 mL) was heated at 80° C. for 3 h. The slightly cooled solution was poured into 100 mL of benzene, and the resulting mixture was washed several times with water. The organic layer was dried over $MgSO_4$ and concentrated to give a dark yellow solid, which was recrystallized from $CCl_4$ to give 10.6 g of the title compound as a bright yellow solid. $^1$H NMR ($CDCl_3$, 200 MHz): δ=6.77 (d, 1H, J=12.8 Hz), 5.74 (d, 1H, J=13.2 Hz), 4.34 (q, 2H, J=7.0 Hz), 3.80 (s, 3H), 3.71 (s, 3H), 2.97 (br s, 6H), 1.36 (t, 3H, J=7.0 Hz).

c) 1-Benzyl-2-oxo-1,2-dihydro-pyridine-3,4-dicarboxylic acid 4-ethyl ester 3-methyl ester A mixture of 5-dimethylamino-3-ethoxycarbonyl-2-methoxycarbonyl-penta-2,4-dienoic acid methyl ester (5 g, 17.5 mmol) and benzylamine (2 mL, 18.4 mmol) in EtOH (30 mL) was refluxed for 5 h. The mixture was cooled to r.t., concentrated in vacuo, and taken up in ether. The solution was washed with 1M HCl and water, and then dried over $MgSO_4$. Evaporation of the solvent in vacuo afforded 5.77 g of the title compound as a viscous orange oil. MS: (+) m/z 338.06 (M+Na).

d) 1-Benzyl-2-oxo-1,2-dihydro-pyridine-3,4-dicarboxylic acid 4-ethyl ester

A solution of 1-benzyl-2-oxo-1,2-dihydro-pyridine-3,4-dicarboxylic acid 4-ethyl ester 3-methyl ester (5.77 g, 18.3 mmol) in 10 mL of pyridine was added to a refluxing mixture of LiI (9.8 g, 73.3 mmol) and 70 mL of pyridine. The resulting mixture was refluxed for 1 h. After the mixture was cooled to r.t., solvent was evaporated in vacuo. The residue was taken up in water and acidified with 6M HCl. The resulting suspension was extracted several times with $CHCl_3$, and the organic layers were combined and dried over $MgSO_4$. After solvent was evaporated in vacuo, the crude product was chromatographed (100% EtOAc) to give 3.3 g of the title compound as a yellow solid. $^1$H NMR ($CDCl_3$, 200 MHz): δ=14.26 (s, 1H), 7.65 (d, 1H, J=7.0 Hz), 7.22-7.50 (m, 5H), 6.41 (d, 1H, J=6.8 Hz), 5.26 (s, 2H), 4.44 (q, 2H, J=7.6 Hz), 1.38 (t, 3H, J=7.0 Hz).

e) 1-Benzyl-3-bromomethyl-2-oxo-1,2-dihydro-pyridine-4-carboxylic acid ethyl ester 1-Benzyl-2-oxo-1,2-dihydro-pyridine-3,4-dicarboxylic acid 4-ethyl ester (581 mg, 1.93 mmol) was dissolved in 15 mL of $CH_2Cl_2$. Oxalyl chloride (1.7 mL, 19.3 mmol) and DMF (2 drops) were added, and the mixture was stirred for 2.5 h. Solvent and excess oxalyl chloride were removed by evaporation in vacuo, and to the residue was added a solution of $NaCNBH_3$ (250 mg, 3.86 mmol) in THF (15 mL). The resulting suspension was stirred at r.t. for 16 h. The reaction mixture was cooled in an ice bath, and then poured into a pre-cooled, vigorously stirring pH 4.9 phosphate buffer (100 mL). The resulting mixture was extracted several times with benzene, and the combined organic layer was washed with ice-cold water and dried over $MgSO_4$. Evaporation of the solvent at reduced pressure gave a viscous oil, which was dissolved in 10 mL of $CH_2Cl_2$. The solution was cooled in at ice bath, and triphenylphosphine (759 mg, 2.90 mmol) and carbon tetrabromide (960 mg, 2.90 mmol) were added. The mixture was then stirred at r.t. for 16 h. Solvent was evaporated in vacuo, and the residue was purified by silica gel chromatography (0-40% EtOAc/hexanes) to give 270 mg of the title compound as a yellow oil. $^1$H NMR ($CDCl_3$, 200 MHz): δ=7.15-7.42 (m, 6H), 6.51 (d, 1H, J=7.2 Hz), 5.18 (s, 2H), 4.90 (s, 2H), 4.41 (q, 2H, J=7.0 Hz), 1.43 (t, 3H, J=7.0 Hz).

f) 1-Benzyl-3-{[methoxycarbonylmethyl-(toluene-4-sulfonyl)-amino]-methyl}-2-oxo-1,2-dihydro-pyridine-4-carboxylic acid ethyl ester A mixture of 1-benzyl-3-bromomethyl-2-oxo-1,2-dihydro-pyridine-4-carboxylic acid ethyl ester (270 mg, 0.77 mmol), (toluene-4-sulfonylamino)-acetic acid methyl ester (210 mg, 0.85 mmol), sodium iodide (219 mg, 1.54 mmol) and potassium carbonate (213 mg, 1.54 mmol) in DMF (7 mL) was stirred at r.t. for 16 h. EtOAc (40 mL) and brine (10 mL) were added, and the aqueous layer was extracted with additional EtOAc. The organic layers were combined, washed with water and brine, and dried over $MgSO_4$. After evaporating the solvent in vacuo, the crude product was chromatographed (0-70% EtOAc/hexanes) to give 232 mg of the title compound as a yellow oil. MS: (+) m/z 513.19 (M+1).

g) 7-Benzyl-4-hydroxy-8-oxo-7,8-dihydro-[2,7]naphthyridine-3-carboxylic acid methyl ester 1-Benzyl-3-{[methoxycarbonylmethyl-(toluene-4-sulfonyl)-amino]-methyl}-2-oxo-1,2-dihydro-pyridine-4-carboxylic acid ethyl ester (232 mg, 0.45 mmol) was dissolved in MeOH (10 mL). NaOMe solution (0.32 mL, 1.36 mmol, 25 wt % in MeOH) was added, and the mixture was stirred overnight. Brine (20 mL) was added, followed by 1M HCl until pH was about 4. The resulting suspension was extracted with $CH_2Cl_2$. The organic layer was dried over $MgSO_4$ and concentrated. The residue was chromatographed (5-60% EtOAc/hexanes+2% AcOH) to give 119 mg of the title compound as a yellow solid. MS: (+) m/z 311.13 (M+1).

h) [(7-Benzyl-4-hydroxy-8-oxo-7,8-dihydro-[2,7]naphthyridine-3-carbonyl)-amino]acetic acid A mixture of 7-benzyl-4-hydroxy-8-oxo-7,8-dihydro-[2,7]naphthyridine-3-carboxylic acid methyl ester (60 mg, 0.19 mmol), glycine (726 mg, 9.68 mmol) and NaOMe solution (14.5 mL, 7.26 mmol, 0.5 M in MeOH) was refluxed for 16 h. Solvent was evaporated in vacuo, and the residue was partitioned between water (50 mL) and EtOAc (50 mL). 1 M HCl was added with vigorous stirring until pH was about 2. The organic layer was dried over $MgSO_4$ and concentrated. The crude product was purified by silica gel chromatography (20-100% EtOAc/hexanes) to give 49 mg of the title compound as a light yellow solid. MS: (+) m/z 354.07 (M+1).

Example 27

3-[(7-Benzyl-4-hydroxy-8-oxo-7,8-dihydro-[2,7]naphthyridine-3-carbonyl)-amino]-propionic acid A mixture of 7-benzyl-4-hydroxy-8-oxo-7,8-dihydro-[2,7]naphthyridine-3-carboxylic acid methyl ester (60 mg, 0.19 mmol), β-alanine (862 mg, 9.68 mmol) and NaOMe solution (14.5 mL, 7.26 mmol, 0.5 M in MeOH) was refluxed for 16 h. Solvent was evaporated in vacuo, and the residue was partitioned between water (50 mL) and EtOAc (50 mL). 1 M HCl was added with vigorous stirring until pH was about 2. The organic layer was dried over MgSO$_4$ and concentrated. The crude product was purified by silica gel chromatography (10-80% EtOAc/hexanes+2% AcOH) to give 46 mg of the title compound as a light yellow solid. MS: (+) m/z 368.08 (M+1).

Example 28

3-[(7-Benzyl-4-hydroxy-8-oxo-7,8-dihydro-[2,7] naphthyridine-3-carbonyl)-amino]-2,2-dimethyl-propionic acid A mixture of 7-benzyl-4-hydroxy-8-oxo-7,8-dihydro-[2,7]naphthyridine-3-carboxylic acid methyl ester (40 mg, 0.13 mmol), 3-Amino-2,2-dimethyl-propionic acid TFA salt (120 mg, 0.52 mmol) and NaOMe (56 mg, 1.03 mmol) in EtOH (2 mL) was heated at 150° C. for 6 h in a CEM microwave reactor. Solvent was evaporated in vacuo, and the residue was partitioned between water and EtOAc. 1 M HCl was added with vigorous stirring until pH was about 2. The organic layer was dried over MgSO$_4$ and concentrated. The crude product was purified by silica gel chromatography (0-40% EtOAc/hexanes+2% AcOH) to give 32 mg of the title compound as a yellow solid. MS: (+) m/z 396.15 (M+1).

Example 29

4-[(7-Benzyl-4-hydroxy-8-oxo-7,8-dihydro-[2,7] naphthyridine-3-carbonyl)-amino]-butyric acid A mixture of 7-benzyl-4-hydroxy-8-oxo-7,8-dihydro-[2,7]naphthyridine-3-carboxylic acid methyl ester (50 mg, 0.16 mmol), 4-aminobutyric acid (832 mg, 8.06 mmol) and NaOMe solution (12 mL, 6.05 mmol, 0.5 M in MeOH) was refluxed for 48 h. Solvent was evaporated in vacuo, and the residue was partitioned between water and EtOAc. 1 M HCl was added with vigorous stirring until pH was about 2. The organic layer was dried over MgSO$_4$ and concentrated. The crude product was purified by silica gel chromatography (5-60% EtOAc/hexanes+2% AcOH) to give 31 mg of the title compound as a light yellow solid. MS: (+) m/z 382.01 (M+1).

Example 30

5-[(7-Benzyl-4-hydroxy-8-oxo-7,8-dihydro-[2,7] naphthyridine-3-carbonyl)-amino]-pentanoic acid A mixture of 7-benzyl-4-hydroxy-8-oxo-7,8-dihydro-[2,7]naphthyridine-3-carboxylic acid methyl ester (50 mg, 0.16 mmol), 5-aminovaleric acid (945 mg, 8.06 mmol) and NaOMe solution (12 mL, 6.05 mmol, 0.5 M in MeOH) was refluxed for 48 h. Solvent was evaporated in vacuo, and the residue was partitioned between water and EtOAc. 1 M HCl was added with vigorous stirring until pH was about 2. The organic layer was dried over MgSO$_4$ and concentrated. The crude product was purified by silica gel chromatography (5-60% EtOAc/hexanes+2% AcOH) to give 44 mg of the title compound as a light yellow solid. MS: (+) m/z 396.08 (M+1).

Example 31

7-Benzyl-4-hydroxy-8-oxo-7,8-dihydro-[2,7]naph-thyridine-3-carboxylic acid (pyridin-4-ylmethyl)-amide A mixture of 7-benzyl-4-hydroxy-8-oxo-7,8-dihydro-[2,7]naphthyridine-3-carboxylic acid methyl ester (40 mg, 0.13 mmol) and 4-(aminomethyl)-pyridine (0.050 mL, 0.45 mmol) in 2 mL of EtOH was heated at 79° C. for 4 h. Acetic acid (0.1 mL) and water (3 mL) were added, and the resulting suspension was allowed to come to r.t. The solid was isolated by filtration and dried under high vacuum to afford 33 mg of the title compound as a light yellow solid. MS: (+) m/z 386.40 (M+1).

Example 32

7-Benzyl-4-hydroxy-8-oxo-7,8-dihydro-[2,7]naph-thyridine-3-carboxylic acid methylamide A mixture of 7-benzyl-4-hydroxy-8-oxo-7,8-dihydro-[2,7]naphthyridine-3-carboxylic acid methyl ester (40 mg, 0.13 mmol) and methylamine (0.65 mL, 1.3 mmol, 2 M in THF) in 2 mL of EtOH was heated in a sealed tube at 80° C. for 4 h. After cooling to r.t., acetic acid (0.3 mL) and water (3 mL) were added. The resulting suspension was filtered and the solid isolated was washed with water and dried under high vacuum to afford 29 mg of the title compound. MS: (+) m/z 309.97 (M+1).

Example 33

7-Benzyl-4-hydroxy-8-oxo-7,8-dihydro-[2,7]naph-thyridine-3-carboxylic acid

A mixture of 7-benzyl-4-hydroxy-8-oxo-7,8-dihydro-[2,7]naphthyridine-3-carboxylic acid methyl ester (40 mg, 0.13 mmol), 2M NaOH (2 mL), MeOH (2 mL) and THF (1 mL) was stirred at r.t. for 4 h. 1 M HCl was added until pH was about 2, and the resulting mixture was cooled in an ice bath for 30 min. The precipitate formed was collected by filtration and dried under high vacuum to afford 23 mg of the title compound as a yellow solid. MS: (+) m/z 297.00 (M+1).

Example 34

7-Benzyl-4-hydroxy-8-oxo-7,8-dihydro-[2,7]naph-thyridine-3-carboxylic acid dimethylamide A mixture of 7-benzyl-4-hydroxy-8-oxo-7,8-dihydro-[2,7]naphthyridine-3-carboxylic acid methyl ester (40 mg, 0.13 mmol) and dimethylamine (0.23 mL, 1.3 mmol, 5.6 M in EtOH) in 2 mL of EtOH was heated in a sealed tube at 80° C. for 4 h. After cooling to r.t., water (3 mL) was added. The resulting suspension was filtered dried under high vacuum to afford a crude solid, which was purified by silica gel chromatography (5-40% EtOAc/hexanes+2% AcOH) to give 12 mg of the title compound. MS: (+) m/z 324.03 (M+1).

Example 35

7-Benzyl-4-hydroxy-8-oxo-7,8-dihydro-[2,7]naph-thyridine-3-carboxylic acid amide A mixture of 7-benzyl-4-hydroxy-8-oxo-7,8-dihydro-[2,7]naphthyridine-3-carboxylic acid methyl ester (40 mg, 0.13 mmol) and ammonia (10 mL, 7 M in MeOH) was stirred at r.t. for 16 h. The solvent was evaporated in vacuo, and the residue was purified by silica gel chromatography (5-60% EtOAc/ hexanes+2% AcOH) to give 18 mg of the title compound as a light yellow solid. MS: (+) m/z 296.06 (M+1).

Example 36

7-Benzyl-4-hydroxy-8-oxo-7,8-dihydro-[2,7]naphthyridine-3-carboxylic acid propylamide A mixture of 7-benzyl-4-hydroxy-8-oxo-7,8-dihydro-[2,7]naphthyridine-3-carboxylic acid methyl ester (35 mg, 0.11 mmol) and n-propylamine (0.1 mL, 1.1 mmol) in 2 mL of EtOH was heated in a sealed tube at 80° C. for 4 h. After cooling to r.t., acetic acid (0.1 mL) and water (3 mL) were added. The mixture was extracted several times with EtOAc. The combined organic layer was dried over $MgSO_4$ and concentrated. The crude product was chromatographed (5-35% EtOAc/hexanes) to give 19 mg of the title compound. MS: (+) m/z 338.02 (M+1).

Example 37

7-Benzyl-4-hydroxy-8-oxo-7,8-dihydro-[2,7]naphthyridine-3-carboxylic acid cyclopropylamide A mixture of 7-benzyl-4-hydroxy-8-oxo-7,8-dihydro-[2,7]naphthyridine-3-carboxylic acid methyl ester (35 mg, 0.11 mmol) and cyclopropylamine (0.080 mL, 1.1 mmol) in 2 mL of EtOH was heated in a sealed tube at 80° C. for 4 h. After cooling to r.t., acetic acid (0.1 mL) and water (3 mL) were added. The resulting suspension was filtered and the solid isolated was dried under high vacuum to afford 17 mg of the title compound. MS: (+) m/z 336.00 (M+1).

Example 38

7-Benzyl-1-cyano-4-hydroxy-8-oxo-7,8-dihydro-[2,7]naphthyridine-3-carboxylic acid methylamide a) 7-Benzyl-4-hydroxy-1-iodo-8-oxo-7,8-dihydro-[2,7]naphthyridine-3-carboxylic acid methyl ester A mixture of 7-benzyl-4-hydroxy-8-oxo-7,8-dihydro-[2,7]naphthyridine-3-carboxylic acid methyl ester (150 mg, 0.48 mmol) and bis(2,4,6-trimethylpyridine)iodine(I) hexafluorophosphate (1.24 g, 2.42 mmol) in 5 mL of $CH_2Cl_2$ was stirred for 16 h at r.t. The mixture was diluted with 30 mL of $CH_2Cl_2$ and washed with 5% sodium thiosulfate and 1 M HCl. The organic layer was dried over $MgSO_4$ and concentrated. The crude product was purified by silica gel chromatography (20-100% $CH_2Cl_2$/hexanes+2% AcOH) to give 136 mg of the title compound as an off-white solid. MS: (+) m/z 436.82 (M+1).

b) 7-Benzyl-1-cyano-4-hydroxy-8-oxo-7,8-dihydro-[2,7]naphthyridine-3-carboxylic acid methyl ester A mixture of 7-benzyl-4-hydroxy-1-iodo-8-oxo-7,8-dihydro-[2,7]naphthyridine-3-carboxylic acid methyl ester (136 mg, 0.31 mmol) and CuCN (56 mg, 0.62 mmol) in 5 mL of DMF was refluxed for 8 min. The mixture was cooled to r.t. and poured into a mixture of water and $CH_2Cl_2$. 4 M HCl was added to the mixture with vigorous stirring until no solid was present. The aqueous layer was extracted with additional $CH_2Cl_2$, and the combined organic layer was dried over $MgSO_4$ and concentrated. The crude product was chromatographed (0-10% EtOAc/$CH_2Cl_2$) to give 88 mg of the title compound. MS: (+) m/z 336.00 (M+1).

c) 7-Benzyl-1-cyano-4-hydroxy-8-oxo-7,8-dihydro-[2,7]naphthyridine-3-carboxylic acid methylamide A mixture of 7-benzyl-1-cyano-4-hydroxy-8-oxo-7,8-dihydro-[2,7]naphthyridine-3-carboxylic acid methyl ester (26 mg, 0.078 mmol) and methylamine (1 mL, 2M in THF) in 2 mL of EtOH was heated in a sealed tube at 80° C. for 4 h. After the mixture was cooled to r.t., solvent was evaporated in vacuo. The residue was chromatographed (0-10% EtOAc/$CH_2Cl_2$+1% AcOH) to give 18 mg of the title compound as a white solid. MS: (+) m/z 335.02 (M+1).

Example 39

7-Benzyl-1-cyano-4-hydroxy-8-oxo-7,8-dihydro-[2,7]naphthyridine-3-carboxylic acid cyclopropylamide A mixture of 7-benzyl-1-cyano-4-hydroxy-8-oxo-7,8-dihydro-[2,7]naphthyridine-3-carboxylic acid methyl ester (27 mg, 0.081 mmol) and cyclopropylamine (0.060 mL, 0.81 mmol) in 2 mL of EtOH was heated in a sealed tube at 80° C. for 4 h. After cooling to r.t., water (3 mL) were added. The mixture was extracted with EtOAc. The organic layer was dried over $MgSO_4$ and concentrated. The crude product was chromatographed (0-15% EtOAc/$CH_2Cl_2$) to give 18 mg of the title compound as a white solid. MS: (−) m/z 358.99 (M−1).

Example 40

1-Benzyl-8-cyano-5-hydroxy-2-oxo-3-phenyl-1,2-dihydro-[1,7]naphthyridine-6-carboxylic acid (pyridin-4-ylmethyl)-amide A mixture of 1-benzyl-8-cyano-5-hydroxy-2-oxo-3-phenyl-1,2-dihydro-[1,7]naphthyridine-6-carboxylic acid methyl ester (35 mg, 0.085 mmol) and 4-(aminomethyl)-pyridine (0.030 mL, 0.30 mmol) in 2 mL of EtOH was refluxed for 16 h. AcOH (0.1 mL) and water (4 mL) were added, and the resulting precipitate was isolated by filtration. The crude solid was purified by silica gel chromatography (0-45% EtOAc/$CH_2Cl_2$+1% AcOH) to give 18 mg of the title compound as an off-white solid. MS: (+) m/z 488.13 (M+1).

Example 41

1-Benzyl-8-cyano-5-hydroxy-2-oxo-3-phenyl-1,2-dihydro-[1,7]naphthyridine-6-carboxylic acid methylamide A mixture of 1-benzyl-8-cyano-5-hydroxy-2-oxo-3-phenyl-1,2-dihydro-[1,7]naphthyridine-6-carboxylic acid methyl ester (35 mg, 0.085 mmol) and methylamine (1 mL, 2M in THF) in 2 mL of EtOH was heated in a sealed tube at 80° C. for 4 h. After cooling to r.t., 3 mL of water was added. The resulting suspension was filtered, and the crude solid was purified by silica gel chromatography (0-20% EtOAc/$CH_2Cl_2$+1% AcOH) to give 13 mg of the title compound as a white solid. MS: (+) m/z 411.01 (M+1).

Example 42

(R)-2-[(1-Benzyl-8-cyano-5-hydroxy-2-oxo-3-phenyl-1,2-dihydro-[1,7]naphthyridine-6-carbonyl)-amino]-3-phenyl-propionic acid A mixture of 1-benzyl-8-cyano-5-hydroxy-2-oxo-3-phenyl-1,2-dihydro-[1,7]naphthyridine-6-carboxylic acid methyl ester (30 mg, 0.073 mmol), D-phenylalanine (241 mg, 1.46 mmol), and NaOMe (59 mg, 1.09 mmol) in 2-methoxyethanol (10 mL) was refluxed for 3 h. After the mixture was cooled to r.t., solvent was evaporated in vacuo. The residue was partitioned between EtOAc and water. 1 M HCl was added with vigorous stirring until pH was about 2. The organic layer was dried over $MgSO_4$ and concentrated. The residue was chromatographed (5-40% EtOAc/hexanes+2% AcOH) to give 40 mg of the title compound. MS: (+) m/z 545.06 (M+1).

Example 43

(S)-2-[(1-Benzyl-8-cyano-5-hydroxy-2-oxo-3-phenyl-1,2-dihydro-[1,7]naphthyridine-6-carbonyl)-amino]-3-phenyl-propionic acid A mixture of 1-benzyl-8-cyano-5-hydroxy-2-oxo-3-phenyl-1,2-dihydro-[1,7]naphthyridine-6-carboxylic acid methyl ester (30 mg, 0.073 mmol), L-phenylalanine (241 mg, 1.46 mmol), and NaOMe (59 mg, 1.09 mmol) in 2-methoxyethanol (10 mL) was refluxed for 3 h. After the mixture was cooled to r.t., solvent was evaporated in vacuo. The residue was partitioned between EtOAc and water. 1 M HCl was added with vigorous stirring until pH was about 2. The organic layer was dried over $MgSO_4$ and concentrated. The residue was chromatographed (5-40% EtOAc/hexanes+2% AcOH) to give 37 mg of the title compound. MS: (+) m/z 544.99 (M+1).

Example 44

[(7-Benzyl-4-hydroxy-1-methyl-8-oxo-7,8-dihydro-[2,7]naphthyridine-3-carbonyl)-amino]-acetic acid a) 7-Benzyl-4-hydroxy-1-methyl-8-oxo-7,8-dihydro-[2,7]naphthyridine-3-carboxylic acid methyl ester A mixture of 7-benzyl-4-hydroxy-1-iodo-8-oxo-7,8-dihydro-[2,7]naphthyridine-3-carboxylic acid methyl ester (117 mg, 0.27 mmol), tetramethyltin (0.2 mL, 1.34 mmol), and $PdCl_2(PPh_3)_2$ (38 mg, 0.054 mmol) in 5 mL of DMF was heated at 120° C. for 2 h under nitrogen atmosphere. After the mixture was cooled to r.t., EtOAc and brine were added. 1 M HCl was added with stirring until pH about 3. The aqueous layer was extracted with additional EtOAc, and the combined organic layer was dried over $MgSO_4$ and concentrated. The crude product was chromatographed (5-35% EtOAc/hexanes) to give 51 mg of the title compound. MS: (+) m/z 325.09 (M+1).

b) [(7-Benzyl-4-hydroxy-1-methyl-8-oxo-7,8-dihydro-[2,7]naphthyridine-3-carbonyl)-amino]-acetic acid A mixture of 7-benzyl-4-hydroxy-1-methyl-8-oxo-7,8-dihydro-[2,7]naphthyridine-3-carboxylic acid methyl ester (25 mg, 0.077 mmol), glycine (770 mg, 10.3 mmol) and NaOMe solution (15 mL, 7.7 mmol, 0.5 M in MeOH) was refluxed for 16 h. After the mixture was cooled to r.t., solvent was evaporated in vacuo. The residue was partitioned between water and EtOAc. 1 M HCl was added with vigorous stirring until pH was about 2. The organic layer was dried over $MgSO_4$ and concentrated. The crude was chromatographed (5-70% EtOAc/hexanes+2% AcOH) to give 21 mg of the title compound as a pale yellow solid. MS: (+) m/z 367.98 (M+1).

Example 45

{[7-Benzyl-1-(5-fluoro-pyridin-3-yl)-4-hydroxy-8-oxo-7,8-dihydro-[2,7]naphthyridine-3-carbonyl]-amino}-acetic acid a) 7-Benzyl-1-(5-fluoro-pyridin-3-yl)-4-hydroxy-8-oxo-7,8-dihydro-[2,7]naphthyridine-3-carboxylic acid methyl ester A mixture of 7-benzyl-4-hydroxy-1-iodo-8-oxo-7,8-dihydro-[2,7]naphthyridine-3-carboxylic acid methyl ester (117 mg, 0.27 mmol), 5-fluoropyridine-3-boronic acid (45 mg, 0.32 mmol), $Cs_2CO_3$ (175 mg, 0.54 mmol) and $Pd(PPh_3)_4$ (31 mg, 0.027 mmol) in 5 mL of DMF was heated at 100° C. for 16 h under $N_2$ atmosphere. After the mixture was cooled to r.t., EtOAc (50 mL) and brine (10 mL) were added. 1 M HCl was added with stirring until pH was about 4. The aqueous layer was extracted with additional EtOAc, and the combined organic layer was dried over $MgSO_4$ and concentrated. The crude product was purified by silica gel chromatography (5-70% EtOAc/hexanes) to give 61 mg of the title compound. MS: (+) m/z 405.97 (M+1).

b) {[7-Benzyl-1-(5-fluoro-pyridin-3-yl)-4-hydroxy-8-oxo-7,8-dihydro-[2,7]naphthyridine-3-carbonyl]-amino}-acetic acid A mixture of 7-benzyl-1-(5-fluoro-pyridin-3-yl)-4-hydroxy-8-oxo-7,8-dihydro-[2,7]naphthyridine-3-carboxylic acid methyl ester (30 mg, 0.074 mmol), glycine (740 mg, 9.9 mmol) and NaOMe solution (15 mL, 7.4 mmol, 0.5 M in MeOH) was refluxed for 16 h. After the mixture was cooled to r.t., solvent was evaporated in vacuo. The residue was partitioned between water and EtOAc. 1 M HCl was added with vigorous stirring until pH was about 3-4. The organic layer was dried over $MgSO_4$ and concentrated. The crude was chromatographed (20-100% EtOAc/hexanes+2% AcOH) to give 19 mg of the title compound as a white solid. MS: (+) m/z 448.95 (M+1).

Example 46

[(7-Benzyl-4-hydroxy-8-oxo-1-phenyl-7,8-dihydro-[2,7]naphthyridine-3-carbonyl)-amino]-acetic acid a) 7-Benzyl-4-hydroxy-8-oxo-1-phenyl-7,8-dihydro-[2,7]naphthyridine-3-carboxylic acid methyl ester A mixture of 7-benzyl-4-hydroxy-1-iodo-8-oxo-7,8-dihydro-[2,7]naphthyridine-3-carboxylic acid methyl ester (117 mg, 0.27 mmol), phenyltributyltin (0.11 mL, 0.32 mmol), and $PdCl_2(PPh_3)_2$ (38 mg, 0.054 mmol) in 5 mL of DMF was heated at 120° C. for 2 h under $N_2$ atmosphere. After the mixture was cooled to r.t., EtOAc (30 mL) and brine (10 mL) were added. 1 M HCl was added with stirring until pH was about 3. The aqueous layer was extracted with additional EtOAc, and the combined organic layer was dried over $MgSO_4$ and concentrated. The crude product was purified by silica gel chromatography (5-35% EtOAc/hexanes) to give 58 mg of the title compound. MS: (+) m/z 387.07 (M+1).

b) [(7-Benzyl-4-hydroxy-8-oxo-1-phenyl-7,8-dihydro-[2,7]naphthyridine-3-carbonyl)-amino]-acetic acid A mixture of 7-benzyl-4-hydroxy-8-oxo-1-phenyl-7,8-dihydro-[2,7]naphthyridine-3-carboxylic acid methyl ester (29 mg, 0.075 mmol), glycine (750 mg, 10 mmol) and NaOMe solution (15 mL, 7.5 mmol, 0.5 M in MeOH) was refluxed for 16 h. After the mixture was cooled to r.t., solvent was evaporated in vacuo. The residue was partitioned between water and EtOAc. 1 M HCl was added with vigorous stirring until pH was about 2. The organic layer was dried over $MgSO_4$ and concentrated. The crude was chromatographed (5-70% EtOAc/hexanes+2% AcOH) to give 24 mg of the title compound as a pale yellow solid. MS: (+) m/z 429.99 (M+1).

Example 47

[(7-Benzyl-1-cyano-4-hydroxy-8-oxo-7,8-dihydro-[2,7]naphthyridine-3-carbonyl)-amino]-acetic acid A mixture of 7-benzyl-1-cyano-4-hydroxy-8-oxo-7,8-dihydro-[2,7]naphthyridine-3-carboxylic acid methyl ester (25 mg, 0.075 mmol), glycine (745 mg, 9.9 mmol) and NaOMe solution (15 mL, 7.5 mmol, 0.5 M in MeOH) was refluxed for 16 h. After the mixture was cooled to r.t., solvent was evaporated in vacuo. The residue was partitioned between EtOAc (50 mL) and water (30 mL). 1 M HCl was added with vigorous stirring until pH was about 2. The aqueous layer was extracted with additional EtOAc, and the combined organic layer was dried over $MgSO_4$ and concentrated. The crude product was chromatographed (20-100% EtOAc/hexanes+2% AcOH) to give 19 mg of the title compound as an off-white solid. MS: (+) m/z 378.95 (M+1).

Example 48

7-Benzyl-1-cyano-4-hydroxy-8-oxo-7,8-dihydro-[2,7]naphthyridine-3-carboxylic acid (pyridin-4-ylmethyl)-amide A mixture of 7-benzyl-1-cyano-4-hydroxy-8-oxo-7,8-dihydro-[2,7]naphthyridine-3-carboxylic acid methyl ester (35 mg, 0.104 mmol) and 4-(aminomethyl)-pyridine (0.040 mL, 0.366 mmol) in 2 mL of EtOH was refluxed for 16 h. Acetic acid (0.1 mL) and water (3 mL) were added, and the mixture was allowed to come to r.t. The resulting precipitate was filtered, washed with 5 mL of water/MeOH (1:1), and dried under high vacuum to afford 15 mg of the title compound as a gray solid. MS: (+) m/z 412.20 (M+1).

Example 49

3-[(7-Benzyl-1-cyano-4-hydroxy-8-oxo-7,8-dihydro-[2,7]naphthyridine-3-carbonyl)-amino]-propionic acid A mixture of 7-benzyl-1-cyano-4-hydroxy-8-oxo-7,8-dihydro-[2,7]naphthyridine-3-carboxylic acid methyl ester (30 mg, 0.090 mmol), β-alanine (1.06 g, 11.9 mmol) and NaOMe solution (18 mL, 8.96 mmol, 0.5 M in MeOH) was refluxed for 16 h. After the mixture was cooled to r.t., solvent was evaporated in vacuo. The residue was partitioned between EtOAc and water. 1 M HCl was added with vigorous stirring until pH was about 2. The organic layer was dried over $MgSO_4$ and concentrated. The crude residue was dissolved in saturated $NaHCO_3$ and washed with ether. 1 M HCl was added to the aqueous layer until pH was about 1, and the resulting precipitate was isolated by filtration to give 21 mg of the title compound as a white solid. MS: (+) m/z 393.00 (M+1).

Example 50

3-[(7-Benzyl-1-cyano-4-hydroxy-8-oxo-7,8-dihydro-[2,7]naphthyridine-3-carbonyl)-amino]-2,2-dimethyl-propionic acid A mixture of 7-benzyl-1-cyano-4-hydroxy-8-oxo-7,8-dihydro-[2,7]naphthyridine-3-carboxylic acid methyl ester (30 mg, 0.090 mmol), 3-amino-2,2-dimethyl-propionic acid TFA salt (83 mg, 0.36 mmol) and NaOMe (39 mg, 0.72 mmol) in 2 mL of EtOH was heated at 150° C. for 3 h in a CEM microwave reactor. The solvent was evaporated in vacuo, and the residue was partitioned between EtOAc and water. 1 M HCl was added with vigorous stirring until pH was about 2. The organic layer was dried over $MgSO_4$ and concentrated. The residue was chromatographed (5-40% EtOAc/hexanes+2% AcOH) to give a crude solid. The solid was dissolved in saturated $NaHCO_3$ and washed with ether. 1 M HCl was added to the aqueous layer until pH was about 2, and the resulting suspension was extracted with EtOAc. The organic layer was dried over $MgSO_4$ and concentrated to give 24 mg of the title compound. MS: (+) m/z 421.02 (M+1).

Example 51

(R)-2-[(7-Benzyl-1-cyano-4-hydroxy-8-oxo-7,8-dihydro-[2,7]naphthyridine-3-carbonyl)-amino]-3-phenyl-propionic acid A mixture of 7-benzyl-1-cyano-4-hydroxy-8-oxo-7,8-dihydro-[2,7]naphthyridine-3-carboxylic acid methyl ester (30 mg, 0.090 mmol), D-phenylalanine (296 mg, 1.8 mmol) and NaOMe (73 mg, 1.3 mmol) in 2-methoxyethanol (10 mL) was refluxed for 3 h. After the mixture was cooled to r.t., solvent was evaporated in vacuo. The residue was partitioned between EtOAc and water. 1 M HCl was added with vigorous stilling until pH was about 2. The organic layer was dried over $MgSO_4$ and concentrated. The residue was chromatographed (5-60% EtOAc/hexanes+2% AcOH) to give a crude solid. The solid was dissolved in saturated $NaHCO_3$ and washed with ether. 1 M HCl was added to the aqueous layer until pH was about 1, and the resulting precipitate was isolated by filtration to give 21 mg of the title compound as an off-white solid. MS: (+) m/z 469.02 (M+1).

Example 52

5-[(7-Benzyl-1-cyano-4-hydroxy-8-oxo-7,8-dihydro-[2,7]naphthyridine-3-carbonyl)-amino]-pentanoic acid A mixture of 7-benzyl-1-cyano-4-hydroxy-8-oxo-7,8-dihydro-[2,7]naphthyridine-3-carboxylic acid methyl ester (30 mg, 0.090 mmol), 5-aminovaleric acid (525 mg, 4.5 mmol) and NaOMe solution (6.7 mL, 3.36 mmol, 0.5 M in MeOH) was refluxed for 48 h. After the mixture was cooled to r.t., solvent was evaporated in vacuo. The residue was partitioned between EtOAc and water. 1 M HCl was added with vigorous stilling until pH was about 2. The organic layer was dried over MgSO$_4$ and concentrated. The residue was chromatographed (20-100% EtOAc/hexanes+2% AcOH) to give a crude solid. The solid was dissolved in EtOAc and washed several times with 1 M HCl. The organic layer was dried over MgSO$_4$ and concentrated. The residue was taken up in saturated NaHCO$_3$ and washed with ether. The aqueous layer was acidified to pH 1 with 4 M HCl, and the resulting precipitate was isolated by filtration to give 18 mg of the title compound as an off-white solid. MS: (−) m/z 418.94 (M−1).

Example 53

[(6-Benzyl-4-hydroxy-5-oxo-5,6-dihydro-[2,6]naphthyridine-3-carbonyl)-amino]-acetic acid a) 2-Ethoxycarbonyl-3-methoxycarbonyl-but-2-enoic acid ethyl ester A mixture of ZnCl$_2$ (42 g, 308 mmol) in acetic anhydride (100 mL) was stirred at r.t. for 2 h. The resulting solution was decanted, and to this solution was added methyl pyruvate (15.5 mL, 171 mmol) and diethyl malonate (26 mL, 171 mmol). The resulting mixture was heated at 100° C. for 1 h, then left standing at r.t. for 16 h. Ether (250 mL) was added and the mixture was washed with ice water and saturated NaHCO$_3$. The organic layer was dried over MgSO$_4$ and concentrated to give a dark brown oil, which was distilled under reduced pressure to give 32.3 g of the title compound as a yellow oil. $^1$H NMR (CDCl$_3$, 200 MHz): δ=4.15-4.40 (m, 4H), 3.78 (s, 3H), 2.20 (s, 3H), 1.20-1.40 (m, 6H).

b) 5-Dimethylamino-2-ethoxycarbonyl-3-methoxycarbonyl-penta-2,4-dienoic acid ethyl ester A mixture of 2-ethoxycarbonyl-3-methoxycarbonyl-but-2-enoic acid ethyl ester (15 g, 61.5 mmol), dimethylformamide diethyl acetal (11.1 mL, 64.5 mmol) and DMF (15 mL) was heated at 80° C. for 5 h. After the mixture was cooled, 200 mL of benzene was added, and the resulting mixture was washed several times with 1 M HCl and water. The organic layer was dried over MgSO$_4$ and concentrated to give an orange solid, which was recrystallized from hexanes/CCl$_4$ to give 8.1 g of the title compound as a bright yellow solid. $^1$H NMR (CDCl$_3$, 200 MHz): δ=6.70 (d, 1H, J=13.2 Hz), 5.66 (d, 1H, J=13.4 Hz), 4.10-4.40 (m, 4H), 3.88 (s, 3H), 2.96 (br s, 6H), 1.20-1.40 (m, 6H).

c) 1-Benzyl-2-oxo-1,2-dihydro-pyridine-3,4-dicarboxylic acid 3-ethyl ester 4-methyl ester A mixture of 5-dimethylamino-2-ethoxycarbonyl-3-methoxycarbonyl-penta-2,4-dienoic acid ethyl ester (5 g, 16.7 mmol) and benzylamine (1.9 mL, 17.6 mmol) in MeOH (30 mL) was refluxed for 5 h. The mixture was cooled to r.t., concentrated in vacuo, and taken up in ether. The solution was washed with 1 M HCl and water, and then dried over MgSO$_4$. Evaporation of the solvent in vacuo afforded 4.1 g of the title compound as a dark brown oil. $^1$H NMR (CDCl$_3$, 200 MHz): δ=7.20-7.40 (m, 6H), 6.56 (d, 1H, J=7.0 Hz), 5.15 (s, 2H), 4.42 (q, 2H, J=7.4 Hz), 3.88 (s, 3H), 1.40 (t, 3H, J=7.0 Hz).

d) 1-Benzyl-2-oxo-1,2-dihydro-pyridine-3,4-dicarboxylic acid 3-ethyl ester

A solution of 1-benzyl-2-oxo-1,2-dihydro-pyridine-3,4-dicarboxylic acid 3-ethyl ester 4-methyl ester (4.1 g, 13 mmol) in 10 mL of pyridine was added to a refluxing mixture of LiI (7.0 g, 52 mmol) and 50 mL of pyridine. The resulting mixture was refluxed for 1 h. After the mixture was cooled to r.t., solvent was evaporated in vacuo. The residue was taken up in water (150 mL) and acidified to pH about 2 with 6M HCl. The resulting suspension was extracted several times with CHCl$_3$, and the organic layers were combined and dried over MgSO$_4$. After solvent was evaporated in vacuo, the crude product was chromatographed (100% EtOAc) to give 1.8 g of the title compound as a yellow solid. $^1$H NMR (CDCl$_3$, 200 MHz): δ=7.20-7.45 (m, 6H), 6.61 (d, 1H, J=7.0 Hz), 5.16 (s, 2H), 4.41 (q, 2H, J=7.4 Hz), 1.37 (t, 3H, J=6.2 Hz).

e) 1-Benzyl-4-bromomethyl-2-oxo-1,2-dihydro-pyridine-3-carboxylic acid ethyl ester 1-Benzyl-2-oxo-1,2-dihydro-pyridine-3,4-dicarboxylic acid 3-ethyl ester (1.8 g, 5.98 mmol) was dissolved in 50 mL of CH$_2$Cl$_2$. Oxalyl chloride (5.2 mL, 59.8 mmol) and DMF (2 drops) were added, and the mixture was stirred for 3 h. Solvent and excess oxalyl chloride were removed by evaporation in vacuo, and to the residue was added a solution of NaCNBH$_3$ (750 mg, 12 mmol) in THF (40 mL). The resulting suspension was stirred at r.t. for 16 h. The reaction mixture was cooled in an ice bath, and then poured into a pre-cooled, vigorously stirring pH 4.9 phosphate buffer (300 mL). The resulting mixture was extracted several times with benzene, and the combined organic layer was washed with ice-cold water and dried over MgSO$_4$. Evaporation of the solvent at reduced pressure gave a yellow oil, which was dissolved in 30 mL of CH$_2$Cl$_2$. The solution was cooled in at ice bath, and triphenylphosphine (1.64 g, 6.27 mmol) and carbon tetrabromide (2.08 g, 6.27 mmol) were added. The mixture was then stirred at r.t. for 16 h. Solvent was evaporated in vacuo, and the residue was purified by silica gel chromatography (0-60% EtOAc/hexanes) to give 860 mg of the title compound as an orange oil. $^1$H NMR (CDCl$_3$, 200 MHz): δ=7.20-7.45 (m, 6H), 6.20 (d, 1H, J=7.0 Hz), 5.12 (s, 2H), 4.43 (q, 2H, J=7.0 Hz), 4.28 (s, 2H), 1.42 (t, 3H, J=7.0 Hz).

f) 1-Benzyl-4-{[methoxycarbonylmethyl-(toluene-4-sulfonyl)-amino]-methyl}-2-oxo-1,2-dihydro-pyridine-3-carboxylic acid ethyl ester A mixture of 1-benzyl-4-bromomethyl-2-oxo-1,2-dihydro-pyridine-3-carboxylic acid ethyl ester (860 mg, 2.46 mmol), (toluene-4-sulfonylamino)-acetic acid methyl ester (660 mg, 2.70 mmol), sodium iodide (740 mg, 4.91 mmol) and potassium carbonate (680 mg, 4.91 mmol) in DMF (20 mL) was stirred at r.t. for 16 h. Brine (50 mL) were added, and the mixture was extracted with EtOAc. The organic layers were combined, washed with water, and dried over MgSO$_4$. After evaporating the solvent in vacuo, the crude product was chromatographed (0-70% EtOAc/hexanes) to give 940 mg of the title compound. MS: (+) m/z 512.97 (M+1).

g) 6-Benzyl-4-hydroxy-5-oxo-5,6-dihydro-[2,6]naphthyridine-3-carboxylic acid methyl ester 1-Benzyl-4-{[methoxycarbonylmethyl-(toluene-4-sulfonyl)-amino]-methyl}-2-oxo-1,2-dihydro-pyridine-3-carboxylic acid ethyl ester (0.94 g, 1.84 mmol) was dissolved in MeOH (40 mL) and cooled in an ice bath. NaOMe solution (1.3 mL, 5.51 mmol, 25 wt % in MeOH) was added, and the mixture was stirred overnight. The mixture was placed in an ice bath, and 1 M HCl was added until pH was about 3-4. The resulting suspension was extracted with CH$_2$Cl$_2$. The organic layer was dried over MgSO₄ and concentrated. The residue was chromatographed (5-90% EtOAc/hexanes+2% AcOH) to give 183 mg of the title compound as an orange solid. MS: (−) m/z 309.01 (M−1).

h) [(6-Benzyl-4-hydroxy-5-oxo-5,6-dihydro-[2,6]naphthyridine-3-carbonyl)-amino]acetic acid A mixture of 6-benzyl-4-hydroxy-5-oxo-5,6-dihydro-[2,6]naphthyridine-3-carboxylic acid methyl ester (25 mg, 0.081 mmol), glycine (805 mg, 10.7 mmol) and NaOMe solution (16 mL, 8.06 mmol, 0.5 M in MeOH) was refluxed for 16 h. Solvent was evaporated in vacuo, and the residue was partitioned between water and EtOAc. 1 M HCl was added with vigorous stirring until pH was about 2. The organic layer was dried over MgSO₄ and concentrated. The crude solid was dissolved in saturated NaHCO₃ and washed with ether. The aqueous layer was acidified to pH about 2 with 4 M HCl, and then extracted with EtOAc. The organic layer was dried over MgSO₄ and concentrated to give 20 mg of the title compound as a yellow solid. MS: (+)

Example 54

3-[(6-Benzyl-4-hydroxy-5-oxo-5,6-dihydro-[2,6]naphthyridine-3-carbonyl)-amino]-propionic acid A mixture of 6-benzyl-4-hydroxy-5-oxo-5,6-dihydro-[2,6]naphthyridine-3-carboxylic acid methyl ester (25 mg, 0.081 mmol), β-alanine (956 mg, 10.7 mmol) and NaOMe solution (16 mL, 8.06 mmol, 0.5 M in MeOH) was refluxed for 16 h. Solvent was evaporated in vacuo, and the residue was partitioned between water and EtOAc. 1 M HCl was added with vigorous stirring until pH was about 2. The organic layer was dried over MgSO₄ and concentrated. The crude solid was dissolved in saturated NaHCO₃ and washed with ether. The aqueous layer was acidified to pH about 2 with 4 M HCl, and then extracted with EtOAc. The organic layer was dried over MgSO₄ and concentrated to give 20 mg of the title compound. MS: (+) m/z 368.00 (M+1).

Example 55

[(6-Benzyl-1-cyano-4-hydroxy-5-oxo-5,6-dihydro-[2,6]naphthyridine-3-carbonyl)-amino]-acetic acid a) 6-Benzyl-4-hydroxy-1-iodo-5-oxo-5,6-dihydro-[2,6]naphthyridine-3-carboxylic acid methyl ester A mixture of 6-benzyl-4-hydroxy-5-oxo-5,6-dihydro-[2,6]naphthyridine-3-carboxylic acid methyl ester (130 mg, 0.42 mmol) and bis(2,4,6-trimethylpyridine)iodine(I) hexafluorophosphate (1.08 g, 2.10 mmol) in 5 mL of CH₂Cl₂ was stirred at r.t. for 16 h. The mixture was diluted with CH₂Cl₂ (50 mL) and washed with dilute sodium bisulfite and 1 M HCl. The organic layer was dried over MgSO₄ and concentrated to give 180 mg of the title compound as a pale yellow solid. $^1$H NMR (CDCl₃, 200 MHz): δ=13.56 (s, 1H), 7.20-7.50 (m, 6H), 6.77 (d, 1H, J=7.4 Hz), 5.30 (s, 2H), 3.99 (s, 3H).

b) 6-Benzyl-1-cyano-4-hydroxy-5-oxo-5,6-dihydro-[2,6]naphthyridine-3-carboxylic acid methyl ester A mixture of 6-benzyl-4-hydroxy-1-iodo-5-oxo-5,6-dihydro-[2,6]naphthyridine-3-carboxylic acid methyl ester (180 mg, 0.41 mmol) and CuCN (74 mg, 0.83 mmol) in 5 mL of DMF was refluxed for 8 min. The reaction mixture was cooled to r.t. and poured into a stirring mixture of 1% NH₄OH solution and CH₂Cl₂. 4 M HCl was then added with vigorous stirring until no more solid was present. The aqueous layer was extracted with additional CH₂Cl₂, and the combined organic layer was dried over MgSO₄ and concentrated. The crude was chromatographed (0-15% CH₂Cl₂/EtOAc+1% AcOH) to give 81 mg of the title compound as a pale yellow solid. MS: (−) m/z 334.00 (M−1).

c) [(6-Benzyl-1-cyano-4-hydroxy-5-oxo-5,6-dihydro-[2,6]naphthyridine-3-carbonyl)-amino]-acetic acid A mixture of 6-benzyl-1-cyano-4-hydroxy-5-oxo-5,6-dihydro-[2,6]naphthyridine-3-carboxylic acid methyl ester (27 mg, 0.081 mmol), glycine (805 mg, 10.7 mmol), and NaOMe solution (16 mL, 8.06 mmol, 0.5 M in MeOH) was refluxed for 16 h. After the mixture was cooled to r.t., solvent was evaporated in vacuo. The residue was partitioned between EtOAc and water. 1 M HCl was added with vigorous stirring until pH was about 1. The aqueous layer was extracted with additional EtOAc, and the combined organic layer was dried over MgSO₄ and concentrated. The crude residue was dissolved in saturated NaHCO₃ and washed with ether. The aqueous layer was acidified to pH about 1 with 4 M HCl and extracted with EtOAc. The organic layer was dried over MgSO₄ and concentrated to give 33 mg of the title compound. MS: (+) m/z 379.00 (M+1).

Example 56

(S)-2-[(7-Benzyl-1-cyano-4-hydroxy-8-oxo-7,8-dihydro-[2,7]naphthyridine-3-carbonyl)-amino]-3-phenyl-propionic acid A mixture of 7-benzyl-1-cyano-4-hydroxy-8-oxo-7,8-dihydro-[2,7]naphthyridine-3-carboxylic acid methyl ester (30 mg, 0.090 mmol), L-phenylalanine (296 mg, 1.8 mmol) and NaOMe (73 mg, 1.3 mmol) in 2-methoxyethanol (10 mL) was refluxed for 3 h. After the mixture was cooled to r.t., solvent was evaporated in vacuo. The residue was partitioned between EtOAc and water. 1 M HCl was added with vigorous stilling until pH was about 2. The organic layer was dried over MgSO₄ and concentrated. The residue was chromatographed (5-60% EtOAc/hexanes+2% AcOH) to give a crude solid. The solid was dissolved in saturated NaHCO₃ and washed with ether. 1 M HCl was added to the aqueous layer until pH was about 1, and the resulting precipitate was isolated by filtration to give 25 mg of the title compound as an off-white solid. MS: (+) m/z 469.26 (M+1).

Example 57

(S)-2-[(7-Benzyl-1-cyano-4-hydroxy-8-oxo-7,8-dihydro-[2,7]naphthyridine-3-carbonyl)-amino]-propionic acid A mixture of 7-benzyl-1-cyano-4-hydroxy-8-oxo-7,8-dihydro-[2,7]naphthyridine-3-carboxylic acid methyl ester (30 mg, 0.090 mmol), L-alanine (1061 mg, 11.9 mmol) and NaOMe solution (18 mL, 9 mmol, 0.5 M in MeOH) was refluxed for 48 h. After the mixture was cooled to r.t., solvent was evaporated in vacuo. The residue was partitioned between EtOAc and water. 1 M HCl was added with vigorous stirring until pH was about 2. The organic layer was dried over MgSO₄ and concentrated to give a crude solid. The solid was dissolved in saturated NaHCO₃ and washed with ether. 4 M HCl was added to the aqueous layer until pH was about 1, and the resulting precipitate was isolated by filtration to give 25 mg of the title compound as an off-white solid. MS: (+) m/z 393.25 (M+1).

Example 58

(R)-2-[(7-Benzyl-1-cyano-4-hydroxy-8-oxo-7,8-dihydro-[2,7]naphthyridine-3-carbonyl)-amino]-propionic acid A mixture of 7-benzyl-1-cyano-4-hydroxy-8-oxo-7,8-dihydro-[2,7]naphthyridine-3-carboxylic acid methyl ester (30 mg, 0.090 mmol), D-alanine (1061 mg, 11.9 mmol) and NaOMe solution (18 mL, 9 mmol, 0.5 M in MeOH) was refluxed for 48 h. After the mixture was cooled to r.t., solvent was evaporated in vacuo. The residue was partitioned between EtOAc and water. 1 M HCl was added with vigorous stirring until pH was about 2. The organic layer was dried over MgSO₄ and concentrated to give a crude solid. The solid was dissolved in saturated NaHCO₃ and washed with ether. 4 M HCl was added to the aqueous layer until pH was about 1, and the resulting precipitate was isolated by filtration to give 23 mg of the title compound as an off-white solid. MS: (+) m/z 393.25 (M+1).

Example 59

7-Benzyl-1-cyano-4-hydroxy-8-oxo-7,8-dihydro-[2,7]naphthyridine-3-carboxylic acid (2-morpholin-4-yl-ethyl)-amide A mixture of 7-benzyl-1-cyano-4-hydroxy-8-oxo-7,8-dihydro-[2,7]naphthyridine-3-carboxylic acid methyl ester (25 mg, 0.075 mmol) and 2-morpholin-4-yl-ethylamine (0.034 mL, 0.26 mmol) in EtOH (2 mL) was refluxed for 16 h. After the mixture was cooled to r.t., AcOH (0.1 mL) and water (5 mL) were added. The resulting mixture was extracted with EtOAc, and the organic layer was dried over MgSO₄ and concentrated. The crude product was purified by chromatography (0-10% MeOH/CH₂Cl₂) to give 18 mg of the title compound. MS: (+) m/z 434.34 (M+1).

Example 60

7-Benzyl-1-cyano-4-hydroxy-8-oxo-7,8-dihydro-[2,7]naphthyridine-3-carboxylic acid (pyridazin-4-ylmethyl)-amide A mixture of 7-benzyl-1-cyano-4-hydroxy-8-oxo-7,8-dihydro-[2,7]naphthyridine-3-carboxylic acid methyl ester (25 mg, 0.075 mmol) and pyridazin-4-yl-methylamine (29 mg, 0.26 mmol) in EtOH (2 mL) was refluxed for 16 h. AcOH (0.1 mL) and water (2 mL) were added, and the mixture was allowed to come to r.t. The resulting suspension was filtered and the solid was washed with 5 mL of MeOH/H₂O (1:1). The solid was dried under vacuum to give 22 mg of the title compound. MS: (+) m/z 413.30 (M+1).

Example 61

{2-[(7-Benzyl-1-cyano-4-hydroxy-8-oxo-7,8-dihydro-[2,7]naphthyridine-3-carbonyl)-amino]-ethoxy}-acetic acid A mixture of 7-benzyl-1-cyano-4-hydroxy-8-oxo-7,8-dihydro-[2,7]naphthyridine-3-carboxylic acid methyl ester (25 mg, 0.075 mmol), (2-amino-ethoxy)-acetic acid (60 mg, 0.50 mmol), and NaOMe (20 mg, 0.37 mmol) in EtOH (5 mL) was refluxed for 16 h, then heated at 150° C. in a microwave reactor for 2 h. Solvent was evaporated in vacuo, and the residue was partitioned between EtOAc and water. 1 M HCl was added with vigorous stilling until pH about 2, and the organic layer was dried over MgSO₄ and concentrated. The crude product was purified by chromatography (5-80% EtOAc/hexanes+2% AcOH) to give 4 mg of the title compound as a pale yellow solid. MS: (+) m/z 423.19 (M+1).

Example 62

1-{[(7-Benzyl-1-cyano-4-hydroxy-8-oxo-7,8-dihydro-[2,7]naphthyridine-3-carbonyl)-amino]-methyl}-cyclobutanecarboxylic acid a) 1-{[(7-Benzyl-1-cyano-4-hydroxy-8-oxo-7,8-dihydro-[2,7]naphthyridine-3-carbonyl)-amino]-methyl}-cyclobutanecarboxylic acid tert-butyl ester A mixture of 7-benzyl-1-cyano-4-hydroxy-8-oxo-7,8-dihydro-[2,7]naphthyridine-3-carboxylic acid methyl ester (25 mg, 0.075 mmol) and 1-aminomethyl-cyclobutanecarboxylic acid tert-butyl ester (55 mg, 0.30 mmol) in EtOH (2 mL) was heated at 140° C. in a microwave reactor for 2 h. Solvent was evaporated in vacuo, and the residue was purified by chromatography (0-30% EtOAc/hexanes+2% AcOH) to give 32 mg of the title compound as a viscous oil. MS: (+) m/z 489.33 (M+1).

b) 1-{[(7-Benzyl-1-cyano-4-hydroxy-8-oxo-7,8-dihydro-[2,7]naphthyridine-3-carbonyl)-amino]-methyl}-cyclobutanecarboxylic acid 1-{[(7-Benzyl-1-cyano-4-hydroxy-8-oxo-7,8-dihydro-[2,7]naphthyridine-3-carbonyl)-amino]-methyl}-cyclobutanecarboxylic acid tert-butyl ester (32 mg, 0.066 mmol) was dissolved in 2 mL of CH₂Cl₂. Trifluoroacetic acid (0.4 mL) was added, and the mixture was stirred at r.t. for 2 h. The mixture was concentrated in vacuo, and the residue was dissolved in saturated NaHCO₃. The aqueous solution was washed with ether, and then acidified to pH about 1 with 4 M HCl to give a white suspension. The solid was isolated by filtration and dried under vacuum to give 22 mg of the title compound as an off-white solid. MS: (+) m/z 433.35 (M+1).

Example 63

7-(2,4-Dimethoxy-benzyl)-4-hydroxy-8-oxo-7,8-dihydro-[2,7]naphthyridine-3-carboxylic acid methylamide a) 1-(2,4-Dimethoxy-benzyl)-2-oxo-1,2-dihydropyridine-3,4-dicarboxylic acid 4-ethyl ester 3-methyl ester A mixture of 5-dimethylamino-3-ethoxycarbonyl-2-methoxycarbonyl-penta-2,4-dienoic acid methyl ester (14.7 g, 51.7 mmol) and 2,4-dimethoxybenzylamine (8.2 mL, 54.3 mmol) in EtOH (90 mL) was refluxed for 5 h. The mixture was cooled to r.t., concentrated in vacuo, and the residual oil was partitioned between ether and 1 M HCl. The aqueous layer was extracted with additional ether, and the organic layers were combined, washed with water, and dried over MgSO₄. Evaporation of the solvent in vacuo afforded 18.4 g of the title compound as a viscous orange oil. MS: (+) m/z 398.23 (M+Na).

b) 1-(2,4-Dimethoxy-benzyl)-2-oxo-1,2-dihydro-pyridine-3,4-dicarboxylic acid 4-ethyl ester A solution of 1-(2,4-dimethoxy-benzyl)-2-oxo-1,2-dihydro-pyridine-3,4-dicarboxylic acid 4-ethyl ester 3-methyl ester (18.4 g, 49.0 mmol) in 30 mL of pyridine was added to a refluxing mixture of LiI (26.2 g, 196 mmol) in 190 mL of pyridine. The resulting mixture was refluxed for 1 h. After the mixture was cooled to r.t., solvent was evaporated in vacuo. The residue was dissolved in water (200 mL) and acidified with 6M HCl to pH about 2. The resulting precipitate was collected by filtration. The crude product was purified by chromatography (100% EtOAc) to give 13.2 g of the title compound. MS: (+) m/z 384.29 (M+Na).

c) 3-Bromomethyl-1-(2,4-dimethoxy-benzyl)-2-oxo-1,2-dihydro-pyridine-4-carboxylic acid ethyl ester 1-(2,4-Dimethoxy-benzyl)-2-oxo-1,2-dihydro-pyridine-3,4-dicarboxylic acid 4-ethyl ester (13.2 g, 36.5 mmol) was dissolved in 280 mL of CH₂Cl₂. Oxalyl chloride (32 mL, 365 mmol) and DMF (3 drops) were added, and the mixture was stirred for 3 h. Solvent and excess oxalyl chloride were removed by evaporation in vacuo, and to the residue was added a solution of NaCNBH₃ (4.6 g, 73 mmol) in THF (250 mL). The resulting yellow suspension was stirred at r.t. for 16 h. The reaction mixture was cooled in an ice bath, and then poured into a pre-cooled, vigorously stirring pH 4.9 phosphate buffer (900 mL). The resulting mixture was extracted several times with benzene, and the combined organic layer was washed with ice-cold water and dried over MgSO₄. Evaporation of the solvent at reduced pressure gave a viscous oil, which was dissolved in 260 mL of CH₂Cl₂. The solution was cooled in at ice bath, and triphenylphosphine (10.5 g, 39.9 mmol) and carbon tetrabromide (13.2 g, 39.9 mmol) were added. The mixture was then stirred at r.t. for 16 h. Solvent was evaporated in vacuo, and the residue was purified by silica gel chromatography (0-60% EtOAc/hexanes) to give 4.43 g of the title compound as a light yellow solid. ¹H NMR (CDCl₃, 200 MHz): δ=7.35-7.50 (m, 2H), 6.40-6.55 (m, 3H), 5.07 (s, 2H), 4.87 (s, 2H), 4.39 (q, 2H, J=7.0 Hz), 3.81 (s, 3H), 3.80 (s, 3H), 1.41 (t, 3H, J=7.0 Hz).

d) 1-(2,4-Dimethoxy-benzyl)-3-{[methoxycarbonyl-methyl-(toluene-4-sulfonyl)-amino]-methyl}-2-oxo-1,2-dihydro-pyridine-4-carboxylic acid ethyl ester A mixture of 3-bromomethyl-1-(2,4-dimethoxy-benzyl)-2-oxo-1,2-dihydro-pyridine-4-carboxylic acid ethyl ester (4.43 g, 10.8 mmol), (toluene-4-sulfonylamino)-acetic acid methyl ester (2.89 mg, 11.9 mmol), sodium iodide (3.24 g, 21.6 mmol) and potassium carbonate (2.99 g, 21.6 mmol) in DMF (95 mL) was stirred at r.t. for 16 h. Brine (150 mL) was added, and the resulting suspension was extracted with EtOAc. The organic layer was washed with water and dried over MgSO₄. After evaporating the solvent in vacuo, the crude product was purified by chromatography (0-80% EtOAc/hexanes) to give 4.2 g of the title compound. MS: (+) m/z 595.32 (M+Na).

e) 7-(2,4-Dimethoxy-benzyl)-4-hydroxy-8-oxo-7,8-dihydro-[2,7]naphthyridine-3-carboxylic acid methyl ester 1-(2,4-Dimethoxy-benzyl)-3-{[methoxycarbonylmethyl-(toluene-4-sulfonyl)-amino]-methyl}-2-oxo-1,2-dihydro-pyridine-4-carboxylic acid ethyl ester (4.2 g, 7.34 mmol) was dissolved in MeOH (160 mL). NaOMe solution (5 mL, 22 mmol, 25 wt % in MeOH) was added, and the mixture was stirred overnight. 1 M HCl was added to acidify the mixture, and the resulting suspension was extracted with CH₂Cl₂. The organic layer was dried over MgSO₄ and concentrated. The residue was chromatographed (5-80% EtOAc/hexanes+2% AcOH) to give 2.45 g of the title compound as a yellow solid. MS: (+) m/z 371.28 (M+1).

f) 7-(2,4-Dimethoxy-benzyl)-4-hydroxy-8-oxo-7,8-dihydro-[2,7]naphthyridine-3-carboxylic acid methylamide A mixture of 7-(2,4-dimethoxy-benzyl)-4-hydroxy-8-oxo-7,8-dihydro-[2,7]naphthyridine-3-carboxylic acid methyl ester (20 mg, 0.054 mmol) and methylamine (0.8 mL, 2M in THF) in EtOH (2 mL) was heated in a sealed tube at 80° C. for 16 h. After cooling the mixture to r.t., water (2 mL) was added. The resulting precipitate was isolated by filtration, washed with cold MeOH/H₂O (5 mL, 1:1), and dried under vacuum to give 9 mg of the title compound. MS: (+) m/z 370.28 (M+1).

Example 64

{[7-(2,4-Dimethoxy-benzyl)-4-hydroxy-8-oxo-7,8-dihydro-[2,7]naphthyridine-3-carbonyl]-amino}-acetic acid A mixture of 7-(2,4-dimethoxy-benzyl)-4-hydroxy-8-oxo-7,8-dihydro-[2,7]naphthyridine-3-carboxylic acid methyl ester (25 mg, 0.068 mmol), glycine (675 mg, 8.9 mmol) and NaOMe solution (13.5 mL, 6.8 mmol, 0.5 M in MeOH) was refluxed for 16 h. Solvent was evaporated in vacuo, and the residue was dissolved in saturated NaHCO₃ and washed with ether. The aqueous layer was acidified with 4 M HCl to pH about 1, and the resulting precipitate was isolated by filtration. The crude solid was further purified by silica gel chromatography (10-90% EtOAc/hexanes+2% AcOH) to give 12 mg of the title compound as a light yellow solid. MS: (+) m/z 414.31 (M+1).

Example 65

3-{[7-(2,4-Dimethoxy-benzyl)-4-hydroxy-8-oxo-7,8-dihydro-[2,7]naphthyridine-3-carbonyl]-amino}-propionic acid A mixture of 7-(2,4-dimethoxy-benzyl)-4-hydroxy-8-oxo-7,8-dihydro-[2,7]naphthyridine-3-carboxylic acid methyl ester (25 mg, 0.068 mmol), β-alanine (801 mg, 9.0 mmol) and NaOMe solution (13.5 mL, 6.8 mmol, 0.5 M in MeOH) was refluxed for 16 h. Solvent was evaporated in vacuo, and the residue was dissolved in saturated NaHCO3 and washed with ether. The aqueous layer was acidified with 4 M HCl to pH about 1, and the resulting precipitate was isolated by filtration. The crude solid was further purified by silica gel chromatography (5-60% EtOAc/hexanes+2% AcOH) to give 14 mg of the title compound as a light yellow solid. MS: (+) m/z 428.31 (M+1).

Example 66

7-(2,4-Dimethoxy-benzyl)-4-hydroxy-8-oxo-5,6,7,8-tetrahydro-[2,7]naphthyridine-3-carboxylic acid methylamide a) 7-(2,4-Dimethoxy-benzyl)-4-hydroxy-8-oxo-5,6,7,8-tetrahydro-[2,7]naphthyridine-3-carboxylic acid methyl ester A round bottom flask was charged with 10% palladium on carbon (50 mg) and EtOH (5 mL). 7-(2,4-Dimethoxy-benzyl)-4-hydroxy-8-oxo-7,8-dihydro-[2,7]naphthyridine-3-carboxylic acid methyl ester (20 mg, 0.054 mmol) dissolved in EtOAc/THF (10 mL, 1:1) was added, and the mixture was stirred under $H_2$ atmosphere (1 atm) for 16 h. The mixture was filtered and the filtrate was concentrated in vacuo. The residue was purified by silica gel chromatography (5-80% EtOAc/hexanes+2% AcOH) to give 15 mg of the title compound. MS: (+) m/z 373.33 (M+H).

b) 7-(2,4-Dimethoxy-benzyl)-4-hydroxy-8-oxo-5,6,7,8-tetrahydro-[2,7]naphthyridine-3-carboxylic acid methylamide A mixture of 7-(2,4-dimethoxy-benzyl)-4-hydroxy-8-oxo-5,6,7,8-tetrahydro-[2,7]naphthyridine-3-carboxylic acid methyl ester (15 mg, 0.040 mmol) and methylamine (0.8 mL, 2M in THF) in EtOH (2 mL) was heated at 80° C. in a sealed tube for 4 h. After the mixture was cooled to r.t., solvent was evaporated in vacuo. The residue was purified by silica gel chromatography (5-80% EtOAc/hexanes+2% AcOH) to give 12 mg of the title compound as a light yellow solid. MS: (+) m/z 372.27 (M+1).

Example 67

{[7-(2,4-Dimethoxy-benzyl)-4-hydroxy-8-oxo-5,6,7,8-tetrahydro-[2,7]naphthyridine-3-carbonyl]amino}-acetic acid A mixture of 7-(2,4-dimethoxy-benzyl)-4-hydroxy-8-oxo-5,6,7,8-tetrahydro-[2,7]naphthyridine-3-carboxylic acid methyl ester (19 mg, 0.051 mmol), glycine (510 mg, 6.79 mmol), and NaOMe solution (10 mL, 5.11, 0.5 M in MeOH) was refluxed for 16 h. After the mixture was cooled to r.t., solvent was evaporated in vacuo. The residue was partitioned between EtOAc and water, and 1 M HCl was added with vigorous stirring until pH about 1. The organic layer was dried over $MgSO_4$ and concentrated. The crude was first purified by silica gel chromatography (5-80% EtOAc/hexanes+2% AcOH), and the product isolated was then dissolved in saturated $NaHCO_3$. The aqueous solution was washed with ether, acidified to pH about 1 with 4 M HCl, and the resulting precipitate was collected by filtration and dried under vacuum to give 7.8 mg of the title compound. MS: (+) m/z 416.27 (M+1).

Example 68

3-{[7-(2,4-Dimethoxy-benzyl)-4-hydroxy-8-oxo-5,6,7,8-tetrahydro-[2,7]naphthyridine-3-carbonyl]amino}-propionic acid A mixture of 7-(2,4-dimethoxy-benzyl)-4-hydroxy-8-oxo-5,6,7,8-tetrahydro-[2,7]naphthyridine-3-carboxylic acid methyl ester (19 mg, 0.051 mmol), β-alanine (605 mg, 6.79 mmol), and NaOMe solution (10 mL, 5.11, 0.5 M in MeOH) was refluxed for 16 h. After the mixture was cooled to r.t., solvent was evaporated in vacuo. The residue was partitioned between EtOAc and water, and 1 M HCl was added with vigorous stirring until pH about 1. The organic layer was dried over $MgSO_4$ and concentrated. The crude was first purified by silica gel chromatography (5-80% EtOAc/hexanes+2% AcOH), and the product isolated was then dissolved in saturated $NaHCO_3$. The aqueous solution was washed with ether, acidified to pH about 1 with 4 M HCl, and the resulting precipitate was collected by filtration and dried under vacuum to give 7.3 mg of the title compound. MS: (+) m/z 430.27 (M+1).

Example 69

[(1-Benzyl-8-hydroxy-2-oxo-1,2-dihydro-[1,6]naphthyridine-7-carbonyl)-amino]acetic acid a) 3-Methyl-pyridine-2-carboxylic acid ethyl ester 3-Methyl-pyridine-2-carboxylic acid (1 g, 7.29 mmol) was dissolved in EtOH (50 mL) and cooled to −20° C. Thionyl chloride (1.1 mL, 14.6 mmol) was added, and the resulting white suspension was refluxed for 5 h, then concentrated to dryness. Water (10 mL) was added and solid $Na_2CO_3$ was added to neutralize the solution. The resulting mixture was extracted with ether. The organic layer was dried over $MgSO_4$, and the solvent was removed by distillation to give 1.25 g of the title compound as an oil. $^1H$ NMR ($CDCl_3$, 200 MHz): δ=8.54 (d, 1H, J=3.9 Hz), 7.59 (d, 1H, J=7.8 Hz), 7.26-7.40 (m, 1H), 4.45 (q, 2H, J=7.0 Hz), 2.59 (s, 3H), 1.45 (t, 3H, J=7.0 Hz).

b) 3-Methyl-pyridine-N-oxide-2-carboxylic acid ethyl ester

3-Methyl-pyridine-2-carboxylic acid ethyl ester (1.25 g, 7.58 mmol) was dissolved in $CH_2Cl_2$ (75 mL). M-CBPA (2.55 g, 11.4 mmol) was added, and the mixture was stirred at r.t. for 16 h. The mixture was washed with 5% sodium bisulfite and saturated $NaHCO_3$, and the organic layer was dried over $MgSO_4$. After evaporating the solvent in vacuo, the crude was purified by silica chromatography (0-30% MeOH/EtOAc) to give 680 mg of the title compound. MS: (+) m/z 182.28 (M+1).

c) 6-Chloro-3-methyl-pyridine-2-carboxylic acid ethyl ester

3-Methyl-pyridine-N-oxide-2-carboxylic acid ethyl ester (680 mg, 3.76 mmol) was dissolved in DMF (30 mL) and cooled in ice bath. $POCl_3$ (0.42 mL, 4.51 mmol) was added, and the mixture was stirred at 0° C. for 1 h, and then at r.t. for 16 h. The mixture was neutralized with saturated $NaHCO_3$, and extracted with $CH_2Cl_2$. The organic layer was dried over $MgSO_4$ and concentrated in vacuo. The crude product was purified by silica gel chromatography (0-5% MeOH/$CH_2Cl_2$) to give 650 mg of the title compound as a viscous oil. MS: (+) m/z 200.20 (M+1).

d) 3-Methyl-6-oxo-1,6-dihydro-pyridine-2-carboxylic acid ethyl ester

A mixture of 6-chloro-3-methyl-pyridine-2-carboxylic acid ethyl ester (650 mg, 3.26 mmol), dichloroacetic acid (5 mL) and water (0.5 mL) was refluxed for 1 h. After cooling to r.t., the mixture was neutralized with saturated NaHCO$_3$ and extracted with CH$_2$Cl$_2$. The organic layer was dried over MgSO$_4$ and concentrated in vacuo. The crude product was purified by silica gel chromatography (0-10% MeOH/ CH$_2$Cl$_2$) to give 230 mg of the title compound as a white solid. MS: (+) m/z 182.25 (M+1).

e) 1-Benzyl-3-methyl-6-oxo-1,6-dihydro-pyridine-2-carboxylic acid ethyl ester

A flask was charged with 3-methyl-6-oxo-1,6-dihydro-pyridine-2-carboxylic acid ethyl ester (230 mg, 1.27 mmol), toluene (6.4 mL) and water (0.064 mL). K$_2$CO$_3$ (351 mg, 2.54 mmol), LiBr (221 mg, 2.54 mmol), tetrabutylammonium bromide (41 mg, 0.127 mmol), and benzyl bromide (0.23 mL, 1.91 mmol) were added, and the resulting suspension was heated at 80° C. for 40 min. The mixture was allowed to come to r.t., diluted with CH$_2$Cl$_2$, and filtered. The filtrate was concentrated in vacuo, and the residue was chromatographed (0-10% MeOH/CH$_2$Cl$_2$) to give 158 mg of the title compound as a viscous oil. MS: (+) m/z 272.31 (M+1).

f) 1-Benzyl-3-bromomethyl-6-oxo-1,6-dihydro-pyridine-2-carboxylic acid ethyl ester A mixture of 1-benzyl-3-methyl-6-oxo-1,6-dihydro-pyridine-2-carboxylic acid ethyl ester (158 mg, 0.58 mmol), N-bromosuccinimide (114 mg, 0.64 mmol) and benzoyl peroxide (14 mg, 0.058 mmol) in CCl$_4$ (6 mL) was refluxed for 16 h. After cooling to r.t., solvent was evaporated in vacuo. The residue was chromatographed (0-35% EtOAc/hexanes) to give 147 mg of the title compound. $^1$H NMR (CDCl$_3$, 200 MHz): δ=7.10-7.40 (m, 6H), 6.72 (d, 1H, J=9.2 Hz), 5.32 (s, 2H), 4.24, (s, 2H), 4.19 (q, 2H, J=7.0 Hz), 1.16 (t, 3H, J=7.0 Hz).

g) 1-Benzyl-3-{[methoxycarbonylmethyl-(toluene-4-sulfonyl)-amino]-methyl}-6-oxo-1,6-dihydro-pyridine-2-carboxylic acid ethyl ester A mixture of 1-benzyl-3-bromomethyl-6-oxo-1,6-dihydro-pyridine-2-carboxylic acid ethyl ester (147 mg, 0.42 mmol), (toluene-4-sulfonylamino)-acetic acid methyl ester (112 mg, 0.46 mmol), sodium iodide (126 mg, 0.84 mmol) and potassium carbonate (116 mg, 0.84 mmol) in DMF (4 mL) was stirred at r.t. for 16 h. Brine (20 mL) were added, and the mixture was extracted with EtOAc. The organic layers were combined, washed with water, and dried over MgSO$_4$. After evaporating the solvent in vacuo, the crude product was purified by silica gel chromatography (0-60% EtOAc/hexanes) to give 140 mg of the title compound. MS: (+) m/z 513.34 (M+1).

h) 1-Benzyl-8-hydroxy-2-oxo-1,2-dihydro-[1,6] naphthyridine-7-carboxylic acid methyl ester 1-Benzyl-3-{[methoxycarbonylmethyl-(toluene-4-sulfonyl)-amino]-methyl}-6-oxo-1,6-dihydro-pyridine-2-carboxylic acid ethyl ester (0.14 g, 0.27 mmol) was dissolved in MeOH (10 mL) and cooled in an ice bath. NaOMe solution (0.2 mL, 0.82 mmol, 25 wt % in MeOH) was added, and the mixture was stirred overnight. The mixture was placed in an ice bath, and 1 M HCl was added until pH was about 3. The resulting mixture was extracted with CH$_2$Cl$_2$. The organic layer was dried over MgSO$_4$ and concentrated. The residue was chromatographed (10-90% EtOAc/hexanes+2% AcOH) to give 76 mg of the title compound. MS: (–) m/z 311.30 (M+1).

i) [(1-Benzyl-8-hydroxy-2-oxo-1,2-dihydro-[7,6] naphthyridine-7-carbonyl)-amino]-acetic acid A mixture of 1-benzyl-8-hydroxy-2-oxo-1,2-dihydro-[1,6]naphthyridine-7-carboxylic acid methyl ester (19 mg, 0.061 mmol), glycine (612 mg, 8.15 mmol) and NaOMe solution (12.3 mL, 6.113 mmol, 0.5 M in MeOH) was refluxed for 16 h. Solvent was evaporated in vacuo, and the residue was dissolved in saturated NaHCO$_3$ and washed several times with ether. The aqueous layer was acidified to pH about 1 with 4 M HCl, and the resulting precipitate was collected by filtration and dried to give 15 mg of the title compound as an off-white solid. MS: (+) m/z 354.27 (M+1).

Example 70

3-[(1-Benzyl-8-hydroxy-2-oxo-1,2-dihydro-[1,6] naphthyridine-7-carbonyl)-amino]-propionic acid A mixture of 1-benzyl-8-hydroxy-2-oxo-1,2-dihydro-[1, 6]naphthyridine-7-carboxylic acid methyl ester (19 mg, 0.061 mmol), β-alanine (726 mg, 8.15 mmol) and NaOMe solution (12.3 mL, 6.113 mmol, 0.5 M in MeOH) was refluxed for 16 h. Solvent was evaporated in vacuo, and the residue was dissolved in saturated NaHCO$_3$ and washed several times with ether. The aqueous layer was acidified to pH about 1 with 4 M HCl, and the resulting precipitate was collected by filtration and dried to give 12 mg of the title compound as a pale pink solid. MS: (+) m/z 368.33 (M+1).

Example 71

3-[(1-Benzyl-8-hydroxy-2-oxo-1,2-dihydro-[1,6] naphthyridine-7-carbonyl)-amino]-2,2-dimethyl-propionic acid A mixture of 1-benzyl-8-hydroxy-2-oxo-1,2-dihydro-[1, 6]naphthyridine-7-carboxylic acid methyl ester (19 mg, 0.061 mmol), 3-amino-2,2-dimethyl-propionic acid TFA salt (71 mg, 0.31 mmol) and NaOMe (33 mg, 0.61 mmol) in 2 mL of EtOH was heated at 150° C. in a microwave reactor for 6 h. Solvent was evaporated in vacuo, and the residue was partitioned between water and EtOAc. 1 M was added with vigorous stirring until pH about 1. The organic layer was dried over MgSO$_4$ and concentrated in vacuo. The crude product was purified by silica gel chromatography (5-60% EtOAc/ hexanes+2% AcOH). The product isolated was then dissolved in saturated NaHCO$_3$ and washed several times with ether. The aqueous layer was acidified to pH about 1 with 4 M HCl, and the resulting precipitate was collected by filtration and dried to give 6.7 mg of the title compound. MS: (+) m/z 396.30 (M+1).

Example 72

1-Benzyl-8-hydroxy-2-oxo-1,2-dihydro-[1,6]naphthyridine-7-carboxylic acid (pyridin-4-ylmethyl)-amide A mixture of 1-benzyl-8-hydroxy-2-oxo-1,2-dihydro-[1, 6]naphthyridine-7-carboxylic acid methyl ester (19 mg, 0.061 mmol) and pyridin-4-yl-methylamine (0.022 mL, 0.21 mmol) in 2 mL of EtOH was heated at 150° C. in a microwave reactor for 6 h. AcOH (0.1 mL) and water (10 mL) were added, and the cloudy mixture was extracted with EtOAc. The organic layer was dried over MgSO$_4$ and concentrated in vacuo. The crude product was purified by silica gel chromatography (0-5% MeOH/CH$_2$Cl$_2$) to give 17 mg of the title compound. MS: (+) m/z 387.40 (M+1).

Example 73

7-Benzyl-1-cyano-4-hydroxy-8-oxo-7,8-dihydro-[2,7]naphthyridine-3-carboxylic acid (3-propylcarbamoyl-propyl)-amide a) 4-[(7-Benzyl-1-cyano-4-hydroxy-8-oxo-7,8-dihydro-[2,7]naphthyridine-3-carbonyl)-amino]-butyric acid A mixture of 7-benzyl-1-cyano-4-hydroxy-8-oxo-7,8-dihydro-[2,7]naphthyridine-3-carboxylic acid methyl ester (30 mg, 0.090 mmol), 4-aminobutyric acid (185 mg, 1.79 mmol) and NaOMe solution (2.7 mL, 1.34 mmol, 0.5 M in MeOH) was refluxed for 24 h. After the mixture was cooled to r.t., solvent was evaporated in vacuo. The residue was partitioned between EtOAc and water. 1 M HCl was added with vigorous stirring until pH was about 1. The organic layer was dried over MgSO$_4$ and concentrated to give 32 mg of the title compound as an off-white solid. MS: (+) m/z 407.31 (M+1).

b) 7-Benzyl-1-cyano-4-hydroxy-8-oxo-7,8-dihydro-[2,7]naphthyridine-3-carboxylic acid (3-propylcarbamoyl-propyl)-amide A mixture of 4-[(7-benzyl-1-cyano-4-hydroxy-8-oxo-7,8-dihydro-[2,7]naphthyridine-3-carbonyl)-amino]-butyric acid (30 mg, 0.074 mmol) and triethylamine (0.015 mL, 0.11 mmol) in CH$_2$Cl$_2$ (3 mL) was cooled in an ice bath. Isobutyl chloroformate (0.014 mL, 0.11 mmol) was added, and the mixture was stirred at 0° C. for 10 min. Propylamine (0.1 mL) was then added, and the mixture was slowly warmed to r.t. and stirred for 16 h. The mixture was diluted with CH$_2$Cl$_2$ (30 mL) and washed with 1 M HCl. The organic layer was dried over MgSO$_4$ and concentrated. The crude product was purified twice by silica gel chromatography (0-30% EtOAc/CH$_2$Cl$_2$, then 10-80% EtOAc/hexanes+2% AcOH) to give 23 mg of the title compound as a white solid. MS: (+) m/z 448.35 (M+1).

Example 74

3-[(4-Hydroxy-8-oxo-7,8-dihydro-[2,7]naphthyridine-3-carbonyl)-amino]-propionic acid a) 4-Hydroxy-8-oxo-7,8-dihydro-[2,7]naphthyridine-3-carboxylic acid methyl ester 7-(2,4-dimethoxy-benzyl)-4-hydroxy-8-oxo-7,8-dihydro-[2,7]naphthyridine-3-carboxylic acid methyl ester (60 mg, 0.162 mmol) in TFA (3 mL) was refluxed for 16 h. Solvent was evaporated in vacuo, and the residue was partitioned between CH$_2$Cl$_2$ and saturated NaHCO$_3$. The aqueous layer was extracted with 10% MeOH/CH$_2$Cl$_2$ until the layers were free of solid. The organic layers were combined, dried over MgSO$_4$, and concentrated in vacuo. The crude product was purified by silica gel chromatography (0-10% MeOH/CH$_2$Cl$_2$) to give 22 mg of the title compound as a pale brown solid. MS: (+) m/z 221.25 (M+1).

b) 3-[(4-Hydroxy-8-oxo-7,8-dihydro-[2,7]naphthyridine-3-carbonyl)-amino]-propionic acid A mixture of 4-hydroxy-8-oxo-7,8-dihydro-[2,7]naphthyridine-3-carboxylic acid methyl ester (17 mg, 0.077 mmol), β-alanine (138 mg, 1.55 mmol) and NaOMe solution (2.3 mL, 1.16 mmol, 0.5 M in MeOH) was refluxed for 16 h. Solvent was evaporated in vacuo, and the residue was dissolved in saturated NaHCO$_3$ and washed several times with ether. The aqueous layer was acidified with 4 M HCl to pH about 1, and the resulting mixture was extracted with EtOAc. The organic layer was dried over MgSO$_4$ and concentrated to give 19 mg of the title compound as an off-white solid. MS: (+) m/z 278.21 (M+1).

Example 75

1-Benzyl-8-hydroxy-2-oxo-1,2-dihydro-[1,6]naphthyridine-7-carboxylic acid methylamide A mixture of 1-benzyl-8-hydroxy-2-oxo-1,2-dihydro-[1,6]naphthyridine-7-carboxylic acid methyl ester (15 mg, 0.048 mmol) and methylamine (1 mL, 2 M in THF) in 2 mL of EtOH was heated in a sealed tube at 80° C. for 16 h. Solvent was evaporated in vacuo, and the residue was purified by silica gel chromatography (0-5% MeOH/CH$_2$Cl$_2$) to give 9.1 mg of the title compound as a pale yellow solid. MS: (+) m/z 310.27 (M+1).

Example 76

7-(2,4-Dimethoxy-benzyl)-4-hydroxy-8-oxo-7,8-dihydro-[2,7]naphthyridine-3-carboxylic acid phenethyl-amide A mixture of 7-(2,4-dimethoxy-benzyl)-4-hydroxy-8-oxo-7,8-dihydro-[2,7]naphthyridine-3-carboxylic acid methyl ester (15 mg, 0.041 mmol) and phenethylamine (0.020 mL, 0.142 mmol) in EtOH (2 mL) was refluxed for 16 h. After cooling the mixture to r.t., AcOH (0.1 mL) and water (2 mL) were added. The resulting precipitate was isolated by filtration, washed with cold MeOH/H$_2$O (5 mL, 1:1), and purified by silica gel chromatography (0-2% MeOH/CH$_2$Cl$_2$) to give 13 mg of the title compound. MS: (+) m/z 460.36 (M+1).

Example 77

7-(2,4-Dimethoxy-benzyl)-4-hydroxy-8-oxo-7,8-dihydro-[2,7]naphthyridine-3-carboxylic acid (2-methoxy-ethyl)-amide A mixture of 7-(2,4-dimethoxy-benzyl)-4-hydroxy-8-oxo-7,8-dihydro-[2,7]naphthyridine-3-carboxylic acid methyl ester (15 mg, 0.041 mmol) and 2-methoxyethylamine (0.012 mL, 0.14 mmol) in EtOH (2 mL) was refluxed for 16 h. After cooling the mixture to r.t., AcOH (0.1 mL) and water (2 mL) were added. The resulting precipitate was isolated by filtration, washed with cold MeOH/H$_2$O (5 mL, 1:1), and dried under vacuum to give 9 mg of the title compound. MS: (+) m/z 414.36 (M+1).

Example 78

7-(2,4-Dimethoxy-benzyl)-4-hydroxy-8-oxo-7,8-dihydro-[2,7]naphthyridine-3-carboxylic acid 4-fluoro-benzylamide A mixture of 7-(2,4-dimethoxy-benzyl)-4-hydroxy-8-oxo-7,8-dihydro-[2,7]naphthyridine-3-carboxylic acid methyl ester (15 mg, 0.041 mmol) and 4-fluorobenzylamine (0.020 mL, 0.14 mmol) in EtOH (2 mL) was refluxed for 16 h. After cooling the mixture to r.t., AcOH (0.1 mL) and water (2 mL) were added. The resulting precipitate was isolated by filtration, washed with cold MeOH/H$_2$O (5 mL, 1:1), and purified by silica gel chromatography (0-2% MeOH/CH$_2$Cl$_2$) to give 15 mg of the title compound. MS: (+) m/z 464.35 (M+1).

Example 79

1-Benzyl-5-cyano-8-hydroxy-2-oxo-1,2-dihydro-[1,6]naphthyridine-7-carboxylic acid methylamide a) 1-Benzyl-8-hydroxy-5-iodo-2-oxo-1,2-dihydro-[1,6]naphthyridine-7-carboxylic acid methyl ester A mixture of 1-benzyl-8-hydroxy-2-oxo-1,2-dihydro-[1,6]naphthyridine-7-carboxylic acid methyl ester (200 mg, 0.645 mmol) and bis(2,4,6-trimethylpyridine)iodine(I) hexafluorophosphate (0.83 g, 1.61 mmol) in 10 mL of CH$_2$Cl$_2$ was stirred at r.t. for 16 h. The mixture was diluted with CH$_2$Cl$_2$ and washed with dilute NaHSO$_3$ and 1 M HCl. The organic layer was dried over MgSO$_4$ and concentrated. The residue was purified by silica gel chromatography (100% CH$_2$Cl$_2$) to give 113 mg of the title compound as a pale yellow solid. MS: (+) m/z 437.13 (M+1).

b) 1-Benzyl-5-cyano-8-hydroxy-2-oxo-1,2-dihydro-[7,6]naphthyridine-7-carboxylic acid methyl ester A mixture of 1-benzyl-8-hydroxy-5-iodo-2-oxo-1,2-dihydro-[1,6]naphthyridine-7-carboxylic acid methyl ester (113 mg, 0.26 mmol) and CuCN (46 mg, 0.52 mmol) in DMF (3 mL) was heated at 120° C. for 8 min. After cooling to r.t., CH$_2$Cl$_2$ (50 mL) and 4 M HCl (50 mL) were added. The mixture was stirred vigorously until no more solid was present. The aqueous layer was extracted with additional CH$_2$Cl$_2$, and organic layers were combined, washed with water, and dried over MgSO$_4$. After evaporating the solvent, the crude product was purified by silica gel chromatography (100% CH$_2$Cl$_2$) to give 54 mg of the title compound. MS: (−) m/z 334.30 (M−1).

c) 1-Benzyl-5-cyano-8-hydroxy-2-oxo-1,2-dihydro-[1,6]naphthyridine-7-carboxylic acid methylamide A mixture of 1-benzyl-5-cyano-8-hydroxy-2-oxo-1,2-dihydro-[1,6]naphthyridine-7-carboxylic acid methyl ester (18 mg, 0.054 mmol) and methylamine (1 mL, 2M in THF) in EtOH (2 mL) was heated in a sealed tube at 80° C. for 16 h. After cooling to r.t., mixture was concentrated in vacuo. The residue was purified by silica gel chromatography (0-2% MeOH/CH$_2$Cl$_2$) to give 10 mg of the title compound. MS: (−) m/z 333.30 (M−1).

Example 80

{[1-Benzyl-5-(5-fluoro-pyridin-3-yl)-8-hydroxy-2-oxo-1,2-dihydro-[1,6]naphthyridine-7-carbonyl]-amino}-acetic acid a) 1-Benzyl-5-bromo-8-hydroxy-2-oxo-1,2-dihydro-[1,6]naphthyridine-7-carboxylic acid methyl ester A mixture of 1-benzyl-8-hydroxy-2-oxo-1,2-dihydro-[1,6]naphthyridine-7-carboxylic acid methyl ester (50 mg, 0.16 mmol) and N-bromosuccinimide (30 mg, 0.17 mmol) in 0.5 mL of CH$_2$Cl$_2$ was refluxed for 3 h. Solvent was evaporated, and the residue was purified by silica gel chromatography (0-5% MeOH/CH$_2$Cl$_2$) to give 26 mg of the title compound as a pale yellow solid. MS: (+) m/z 387.14, 389.13 (M-1, $^{79/81}$Br).

b) 1-Benzyl-5-(5-fluoro-pyridin-3-yl)-8-hydroxy-2-oxo-1,2-dihydro-[1,6]naphthyridine-7-carboxylic acid methyl ester A mixture of 1-benzyl-5-bromo-8-hydroxy-2-oxo-1,2-dihydro-[1,6]naphthyridine-7-carboxylic acid methyl ester (70 mg, 0.18 mmol), 5-fluoro-pyridine-3-boronic acid (30 mg, 0.22 mmol), Pd(PPh$_3$)$_4$ (21 mg, 0.018 mmol) and Cs$_2$CO$_3$ (117 mg, 0.36 mmol) in DMF (4 mL) was heated at 100° C. for 16 h under nitrogen atmosphere. After cooling to r.t., EtOAc (50 mL) and brine (10 mL) were added. 1 M HCl was added until pH about 4. The aqueous layer was extracted with additional EtOAc, and the organic layers were combined, washed with water, and dried over MgSO$_4$. After evaporating the solvent, the crude product was purified by silica gel chromatography (0-70% EtOAc/hexanes+2% AcOH) to give 45 mg of the title compound. MS: (+) m/z 406.33 (M+1).

c) {[1-Benzyl-5-(5-fluoro-pyridin-3-yl)-8-hydroxy-2-oxo-1,2-dihydro-[7,6]naphthyridine-7-carbonyl]-amino}-acetic acid A mixture of 1-benzyl-5-(5-fluoro-pyridin-3-yl)-8-hydroxy-2-oxo-1,2-dihydro-[1,6]naphthyridine-7-carboxylic acid methyl ester (23 mg, 0.056 mmol), glycine (417 mg, 5.6 mmol) and NaOMe solution (9 mL, 4.4 mmol) was refluxed for 16 h. After cooling to r.t., solvent was evaporated. The residue was partitioned between EtOAc and water. 1 M HCl was added with vigorous stilling until pH about 3. The organic layer was dried over MgSO$_4$ and concentrated. The crude product was purified by silica gel chromatography (0-60% EtOAc/hexanes+2% AcOH). The product isolated was then dissolved in saturated NaHCO$_3$ and washed several times with ether. The aqueous layer was acidified to pH about 2 with 4 M HCl, and the resulting precipitate was isolated by filtration to give 10 mg of the title compound. MS: (+) m/z 449.34 (M+1).

Example 81

3-{[1-Benzyl-5-(5-fluoro-pyridin-3-yl)-8-hydroxy-2-oxo-1,2-dihydro-[1,6]naphthyridine-7-carbonyl]amino}-propionic acid A mixture of 1-benzyl-5-(5-fluoro-pyridin-3-yl)-8-hydroxy-2-oxo-1,2-dihydro-[1,6]naphthyridine-7-carboxylic acid methyl ester (23 mg, 0.056 mmol), β-alanine (495 mg, 5.6 mmol) and NaOMe solution (9 mL, 4.4 mmol) was refluxed for 16 h. After cooling to r.t., solvent was evaporated. The residue was partitioned between EtOAc and water. 1 M HCl was added with vigorous stilling until pH about 3. The organic layer was dried over MgSO$_4$ and concentrated. The crude product was purified by silica gel chromatography (0-40% EtOAc/hexanes+2% AcOH). The product isolated was then dissolved in saturated NaHCO$_3$ and washed several times with ether. The aqueous layer was acidified to pH about 2 with 4 M HCl, and the resulting precipitate was isolated by filtration to give 10 mg of the title compound. MS: (+) m/z 463.35 (M+1).

Example 82

1-Benzyl-8-hydroxy-2-oxo-1,2-dihydro-[1,6]naphthyridine-7-carboxylic acid (1H-tetrazol-5-ylmethyl)-amide A mixture of 1-benzyl-8-hydroxy-2-oxo-1,2-dihydro-[1,6]naphthyridine-7-carboxylic acid methyl ester (30 mg, 0.097 mmol), (1H-tetrazol-5-yl)-methylamine (29 mg, 0.29 mmol), and NaOMe (13 mg, 0.24 mmol) in 2 mL of EtOH was heated at 140° C. for 6 h in a microwave reactor. Solvent was evaporated in vacuo, and the residue was partitioned between EtOAc and water. 1 M HCl was added with vigorous stirring until pH about 2. The aqueous layer was extracted with additional EtOAc, and the organic layers were combined and dried over $MgSO_4$. After evaporating the solvent, the crude product was purified by silica gel chromatography (40-100% EtOAc/$CH_2Cl_2$+1% AcOH). The product isolated was then dissolved in saturated $NaHCO_3$ and washed with ether. The aqueous layer was acidified to pH about 2 with 4 M HCl, and the resulting precipitate was isolated by filtration to give 9.6 mg of the title compound. MS: (+) m/z 378.31 (M+1).

Example 83

1-Benzyl-5-hydroxy-2-oxo-3-phenyl-1,2-dihydro-[1,7]naphthyridine-6-carboxylic acid methylamide A mixture of 1-benzyl-5-hydroxy-2-oxo-3-phenyl-1,2-dihydro-[1,7]naphthyridine-6-carboxylic acid methyl ester (15 mg, 0.039 mmol) and methylamine (1 mL, 2 M in THF) in EtOH (2 mL) was heated in a sealed tube at 80° C. for 16 h. Solvent was evaporated in vacuo, and the residue was chromatographed (0-5% MeOH/$CH_2Cl_2$) to give 4.9 mg of the title compound as a pale yellow solid. MS: (+) m/z 386.21 (M+1).

Example 84

3-[(1-Benzyl-5-hydroxy-2-oxo-3-phenyl-1,2-dihydro-[1,7]naphthyridine-6-carbonyl)-amino]-propionic acid A mixture of 1-benzyl-5-hydroxy-2-oxo-3-phenyl-1,2-dihydro-[1,7]naphthyridine-6-carboxylic acid methyl ester (30 mg, 0.078 mmol), β-alanine (692 mg, 7.8 mmol), and NaOMe solution (12 mL, 5.8 mmol, 0.5 M in MeOH) was refluxed for 16 h. After cooling to r.t., solvent was evaporated in vacuo. The residue was partitioned between EtOAc and water. 1 M HCl was added with vigorous stirring until pH about 2. The organic layer was dried over $MgSO_4$ and concentrated. The crude product was purified by silica gel chromatography (0-30% EtOAc/$CH_2Cl_2$+1% AcOH). The product isolated was then dissolved in saturated $NaHCO_3$ and washed with ether. The aqueous layer was acidified to pH about 2 with 4 M HCl, and the resulting precipitate was isolated by filtration to give 7.7 mg of the title compound. MS: (+) m/z 444.37 (M+1).

Example 85

{2-[(7-Benzyl-4-hydroxy-8-oxo-7,8-dihydro-[2,7]naphthyridine-3-carbonyl)-amino]-ethoxy}-acetic acid A mixture of 7-benzyl-4-hydroxy-8-oxo-7,8-dihydro-[2,7]naphthyridine-3-carboxylic acid methyl ester (20 mg, 0.065 mmol), (2-amino-ethoxy)-acetic acid (39 mg, 0.32 mmol), and NaOMe (14 mg, 0.26 mmol) in MeOH (2 mL) was heated at 140° C. in a microwave reactor for 6 h. Solvent was evaporated in vacuo, and the residue was partitioned between EtOAc and water. 1 M HCl was added with vigorous stirring until pH about 1, and the organic layer was dried over $MgSO_4$ and concentrated. The crude product was purified by chromatography (0-2% MeOH/EtOAc+1% AcOH) to give a yellow solid. The solid was then dissolved in saturated $NaHCO_3$ and washed several times with ether. The aqueous layer was acidified to pH about 1 with 4 M HCl, and the resulting precipitate was collected by filtration and dried to give 8.3 mg of the title compound as an off-white solid. MS: (+) m/z 398.29 (M+1).

Example 86

7-Benzyl-4-hydroxy-8-oxo-7,8-dihydro-[2,7]naphthyridine-3-carboxylic acid (1H-tetrazol-5-ylmethyl)-amide A mixture of 7-benzyl-4-hydroxy-8-oxo-7,8-dihydro-[2,7]naphthyridine-3-carboxylic acid methyl ester (30 mg, 0.097 mmol), (1H-tetrazol-5-yl)-methylamine (29 mg, 0.29 mmol), and NaOMe (13 mg, 0.24 mmol) in EtOH (2 mL) was heated at 140° C. in a microwave reactor for 6 h.

Solvent was evaporated in vacuo, and the residue was partitioned between EtOAc and water. 1 M HCl was added with vigorous stirring until pH about 2, and the organic layer was dried over $MgSO_4$ and concentrated. The crude product was purified by chromatography (50-100% $CH_2Cl_2$/EtOAc+1% AcOH) to give 15 mg of the title compound. MS: (+) m/z 378.31 (M+1).

Example 87

3-{[7-Benzyl-1-(5-fluoro-pyridin-3-yl)-4-hydroxy-8-oxo-7,8-dihydro-[2,7]naphthyridine-3-carbonyl]amino}-propionic acid A mixture of 7-benzyl-1-(5-fluoro-pyridin-3-yl)-4-hydroxy-8-oxo-7,8-dihydro-[2,7]naphthyridine-3-carboxylic acid methyl ester (17 mg, 0.042 mmol), β-alanine (374 mg, 4.19 mmol) and NaOMe solution (6.3 mL, 3.15 mmol, 0.5 M in MeOH) was refluxed for 16 h. After the mixture was cooled to r.t., solvent was evaporated in vacuo. The residue was partitioned between water and EtOAc. 1 M HCl was added with vigorous stirring until pH was about 3. The organic layer was dried over $MgSO_4$ and concentrated. The crude product was purified by silica gel chromatography (0-40% EtOAc/$CH_2Cl_2$+1% AcOH) to give 9 mg of the title compound. MS: (+) m/z 463.35 (M+1).

Example 88

3-{[7-Benzyl-1-(5-fluoro-pyridin-3-yl)-4-hydroxy-8-oxo-7,8-dihydro-[2,7]naphthyridine-3-carbonyl]amino}-2,2-dimethyl-propionic acid A mixture of 7-benzyl-1-(5-fluoro-pyridin-3-yl)-4-hydroxy-8-oxo-7,8-dihydro-[2,7]naphthyridine-3-carboxylic acid methyl ester (17 mg, 0.042 mmol), 3-amino-2,2-dimethyl-propionic acid TFA salt (39 mg, 0.17 mmol), and NaOMe (18 mg, 0.34 mmol) in EtOH (2 mL) was heated at 140° C. for 6 h in a microwave reactor. After the mixture was cooled to r.t., solvent was evaporated in vacuo. The residue was partitioned between water and EtOAc. 1 M HCl was added with vigorous stirring until pH was about 2. The organic layer was dried over MgSO$_4$ and concentrated. The crude product was purified by silica gel chromatography (0-40% EtOAc/CH$_2$Cl$_2$+1% AcOH). The product was then dissolved in saturated NaHCO$_3$ and washed several times with ether. The aqueous layer was acidified to pH about 2, and the resulting precipitate was isolated by filtration to give 7 mg of the title compound. MS: (+) m/z 491.37 (M+1).

Example 89

7-Benzyl-4-hydroxy-8-oxo-7,8-dihydro-[2,7]naphthyridine-3-carboxylic acid [2-(3-isopropyl-ureido)-ethyl]amide a) {2-[(7-Benzyl-4-hydroxy-8-oxo-7,8-dihydro-[2,7]naphthyridine-3-carbonyl)-amino]-ethyl}-carbamic acid tert-butyl ester A mixture of 7-benzyl-4-hydroxy-8-oxo-7,8-dihydro-[2,7]naphthyridine-3-carboxylic acid methyl ester (100 mg, 0.32 mmol) and (2-amino-ethyl)-carbamic acid tert-butyl ester (62 mg, 0.39 mmol) in EtOH (9 mL) was refluxed for 16 h. After cooling to r.t., AcOH (0.2 mL) was added, and the mixture was concentrated in vacuo. The residue was partitioned between water and EtOAc. The aqueous layer was extracted with additional EtOAc, and the organic layers were combined and washed with 0.1 M HCl and brine. The organic layer was dried over MgSO$_4$ and concentrated. The crude product was purified by silica gel chromatography (0-5% MeOH/CH$_2$Cl$_2$) to give 113 mg of the title compound as an off-white solid. MS: (−) m/z 437.33 (M−1).

b) 7-Benzyl-4-hydroxy-8-oxo-7,8-dihydro-[2,7]naphthyridine-3-carboxylic acid [2-(3-isopropyl-ureido)-ethyl]-amide {2-[(7-Benzyl-4-hydroxy-8-oxo-7,8-dihydro-[2,7]naphthyridine-3-carbonyl)-amino]-ethyl}-carbamic acid tert-butyl ester (38 mg, 0.087 mmol) was dissolved in CH$_2$Cl$_2$ (1.5 mL). Trifluoroacetic acid (1 mL) was added, and the mixture was stirred at r.t. for 2 h. Solvent and excess TFA were removed in vacuo. To the residue were added CH$_2$Cl$_2$ (2 mL), triethylamine (0.030 mL, 0.19 mmol), and isopropyl isocyanate (0.010 mL, 0.10 mmol), and the resulting mixture was stirred at r.t. for 16 h. 1 M HCl and EtOAc were added, and the aqueous layer was extracted with additional EtOAc. The organic layers were combined and concentrated to dryness. The residue was washed with CH$_2$Cl$_2$, isolated by filtration, and dried to give 17 mg of the title compound as a white solid. MS: (+) m/z 424.35 (M+1).

Example 90

7-Benzyl-4-hydroxy-8-oxo-7,8-dihydro-[2,7]naphthyridine-3-carboxylic acid (2-sulfamoyl-ethyl)-amide A mixture of 7-benzyl-4-hydroxy-8-oxo-7,8-dihydro-[2,7]naphthyridine-3-carboxylic acid methyl ester (30 mg, 0.097 mmol), 2-amino-ethanesulfonic acid amide HCl salt (24 mg, 0.19 mmol), and NaOMe (9.9 mg, 0.18 mmol) in EtOH (2 mL) was heated at 140° C. for 6 h in a microwave reactor. Solvent was evaporated in vacuo, and the residue was partitioned between 1 M HCl and EtOAc. The aqueous layer was extracted with additional EtOAc, and the organic layers were combined and dried over MgSO$_4$. After evaporating the solvent, the crude product was purified by silica gel chromatography (0-10% MeOH/CH$_2$Cl$_2$) to give 21 mg of the title compound. MS: (+) m/z 403.25 (M+1).

Example 91

7-Benzyl-4-hydroxy-8-oxo-7,8-dihydro-[2,7]naphthyridine-3-carboxylic acid [2-(2,2,2-trifluoro-acetylamino)-ethyl]-amide {2-[(7-Benzyl-4-hydroxy-8-oxo-7,8-dihydro-[2,7]naphthyridine-3-carbonyl)-amino]-ethyl}-carbamic acid tert-butyl ester (30 mg, 0.068 mmol) was dissolved in CH$_2$Cl$_2$ (1.5 mL). Trifluoroacetic acid (1 mL) was added, and the mixture was stirred at r.t. for 2 h. Solvent and excess TFA were removed in vacuo. To the residue were added THF (3 mL), triethylamine (0.050 mL, 0.34 mmol), and ethyl trifluoroacetate (2 mL), and the mixture was refluxed for 48 h. After cooling to r.t., the mixture was concentrated to dryness. The residue was partitioned between EtOAc and water, and pH was adjusted to about 4 with 1 M HCl. The organic layer was dried over MgSO$_4$ and concentrated. The crude product was purified by silica gel chromatography (0-5% MeOH/CH$_2$Cl$_2$) to give 12 mg of the title compound as a pale yellow solid. MS: (+) m/z 435.31 (M+1).

Example 92

7-Benzyl-4-hydroxy-8-oxo-7,8-dihydro-[2,7]naphthyridine-3-carboxylic acid (2-acetylamino-ethyl)-amide A mixture of 7-benzyl-4-hydroxy-8-oxo-7,8-dihydro-[2,7]naphthyridine-3-carboxylic acid methyl ester (20 mg, 0.065 mmol) and N-(2-amino-ethyl)-acetamide (20 mg, 0.19 mmol), in EtOH (2 mL) was refluxed for 16 h. After cooling to r.t., AcOH (0.1 mL) and water (20 mL) were added. The resulting cloudy solution was extracted with EtOAc. The organic layer was dried over MgSO$_4$ and concentrated. The crude product was purified by silica gel chromatography (0-10% MeOH/CH$_2$Cl$_2$) to give 13 mg of the title compound as an off-white solid. MS: (+) m/z 381.34 (M+1).

Example 93

[(1-Benzyl-5-cyano-8-hydroxy-2-oxo-1,2-dihydro-[1,6]naphthyridine-7-carbonyl)-amino]-acetic acid A mixture of 1-benzyl-5-cyano-8-hydroxy-2-oxo-1,2-dihydro-[1,6]naphthyridine-7-carboxylic acid methyl ester (20 mg, 0.060 mmol), glycine (448 mg, 6.0 mmol) and NaOMe solution (9.6 mL, 4.8 mmol, 0.5 M in MeOH) was refluxed for 16 h. After the mixture was cooled to r.t., solvent was evaporated in vacuo. The residue was partitioned between EtOAc and water. 1 M HCl was added with vigorous stirring until pH about 2. The organic layer was dried over MgSO$_4$ and concentrated. The residue was taken up in saturated NaHCO$_3$ and washed several times with ether. The aqueous layer was acidified to pH about 2 with 4 M HCl, and the resulting precipitate was isolated by filtration to give 15 mg of the title compound as a pale pink solid. MS: (−) m/z 377.31 (M−1).

Example 94

3-[(1-Benzyl-5-cyano-8-hydroxy-2-oxo-1,2-dihydro-[1,6]naphthyridine-7-carbonyl)-amino]-propionic acid A mixture of 1-benzyl-5-cyano-8-hydroxy-2-oxo-1,2-dihydro-[1,6]naphthyridine-7-carboxylic acid methyl ester (20 mg, 0.060 mmol), β-alanine (532 mg, 6.0 mmol) and NaOMe solution (9.6 mL, 4.8 mmol, 0.5 M in MeOH) was refluxed for 16 h. After the mixture was cooled to r.t., solvent was evaporated in vacuo. The residue was partitioned between EtOAc and water. 1 M HCl was added with vigorous stirring until pH about 2. The organic layer was dried over MgSO$_4$ and concentrated. The residue was taken up in saturated NaHCO$_3$ and washed several times with ether. The aqueous layer was acidified to pH about 2 with 4 M HCl, and the resulting precipitate was isolated by filtration to give 12 mg of the title compound as a pale pink solid. MS: (−) m/z 391.35 (M−1).

Example 95

1-Benzyl-5-cyano-8-hydroxy-2-oxo-1,2-dihydro-[1,6]naphthyridine-7-carboxylic acid (2-acetylamino-ethyl)-amide A mixture of 1-benzyl-5-cyano-8-hydroxy-2-oxo-1,2-dihydro-[1,6]naphthyridine-7-carboxylic acid methyl ester (20 mg, 0.060 mmol) and N-(2-amino-ethyl)-acetamide (20 mg, 0.18 mmol) in EtOH (3 mL) was refluxed for 16 h. After cooling to r.t., AcOH (0.1 mL), water (15 mL) and EtOAc (20 mL) were added. The aqueous layer was extracted with additional EtOAc, and the organic layers were combined, dried over MgSO$_4$, and concentrated. The crude product was purified by silica gel chromatography (0-5% MeOH/CH$_2$Cl$_2$) to give 8.7 mg of the title compound as a light yellow solid. MS: (−) m/z 404.32 (M−1).

Example 96

1-Benzyl-8-hydroxy-2-oxo-1,2-dihydro-[1,6]naphthyridine-7-carboxylic acid (2-acetylamino-ethyl)-amide A mixture of 1-benzyl-8-hydroxy-2-oxo-1,2-dihydro-[1,6]naphthyridine-7-carboxylic acid methyl ester (20 mg, 0.065 mmol) and N-(2-amino-ethyl)-acetamide (20 mg, 0.19 mmol) in EtOH (3 mL) was refluxed for 16 h. After cooling to r.t., AcOH (0.1 mL), water (15 mL) and EtOAc (20 mL) were added. The aqueous layer was extracted with additional EtOAc, and the organic layers were combined, dried over MgSO$_4$, and concentrated. The crude product was purified by silica gel chromatography (0-7% MeOH/CH$_2$Cl$_2$) to give 16 mg of the title compound as a light yellow solid. MS: (+) m/z 381.34 (M+1).

Example 97

7-Benzyl-4-hydroxy-8-oxo-7,8-dihydro-[2,7]naphthyridine-3-carboxylic acid {2-[methyl-(2,2,2-trifluoro-acetyl)-amino]ethyl}-amide a) {2-[(7-Benzyl-4-hydroxy-8-oxo-7,8-dihydro-[2,7]naphthyridine-3-carbonyl)-amino]-ethyl}-methyl-carbamic acid tert-butyl ester A mixture of 7-benzyl-4-hydroxy-8-oxo-7,8-dihydro-[2,7]naphthyridine-3-carboxylic acid methyl ester (100 mg, 0.32 mmol) and (2-amino-ethyl)-methyl-carbamic acid tert-butyl ester (67 mg, 0.39 mmol) in EtOH (9 mL) was refluxed for 16 h. After cooling to r.t., the mixture was concentrated in vacuo. The residue was dissolved in EtOAc and washed with 0.1 M HCl. The organic layer was dried over MgSO$_4$ and concentrated. The crude product was purified by silica gel chromatography (0-2% MeOH/CH$_2$Cl$_2$) to give 141 mg of the title compound. MS: (−) m/z 451.37 (M−1).

b) 7-Benzyl-4-hydroxy-8-oxo-7,8-dihydro-[2,7]naphthyridine-3-carboxylic acid {2-[methyl-(2,2,2-trifluoro-acetyl)-amino]-ethyl}-amide {2-[(7-Benzyl-4-hydroxy-8-oxo-7,8-dihydro-[2,7]naphthyridine-3-carbonyl)-amino]-ethyl}-methyl-carbamic acid tert-butyl ester (25 mg, 0.055 mmol) was dissolved in CH$_2$Cl$_2$ (1.5 mL). Trifluoroacetic acid (1 mL) was added, and the mixture was stirred at r.t. for 2 h. Solvent and excess TFA were removed in vacuo. To the residue were added THF (3 mL), triethylamine (0.040 mL, 0.28 mmol), and ethyl trifluoroacetate (2 mL), and the resulting mixture was refluxed for 16 h. The mixture was concentrated to dryness, and the residue was dissolved in EtOAc and washed with 1 M HCl. The organic layers were dried over MgSO$_4$ and concentrated. The crude product was purified by silica gel chromatography (0-5% MeOH/CH$_2$Cl$_2$) to give 5.4 mg of the title compound as a white solid. MS: (+) m/z 449.29 (M+1).

Example 98

7-Benzyl-4-hydroxy-8-oxo-7,8-dihydro-[2,7]naphthyridine-3-carboxylic acid [2-(3-isopropyl-1-methyl-ureido)-ethyl]amide {2-[(7-Benzyl-4-hydroxy-8-oxo-7,8-dihydro-[2,7]naphthyridine-3-carbonyl)-amino]-ethyl}-methyl-carbamic acid tert-butyl ester (25 mg, 0.055 mmol) was dissolved in CH$_2$Cl$_2$ (2 mL). Trifluoroacetic acid (1 mL) was added, and the mixture was stirred at r.t. for 1 h. Solvent and excess TFA were removed in vacuo. To the residue were added CH$_2$Cl$_2$ (2 mL), triethylamine (0.040 mL), and isopropyl isocyanate (0.040 mL), and the resulting mixture was stirred for 16 h. EtOAc was added to dilute the mixture, and the solution washed with 1 M HCl. The organic layers were dried over MgSO$_4$ and concentrated. The crude product was purified by silica gel chromatography (0-5% MeOH/CH$_2$Cl$_2$) to give 17 mg of the title compound. MS: (+) m/z 438.40 (M+1).

Example 99

{2-[(7-Benzyl-4-hydroxy-8-oxo-7,8-dihydro-[2,7]naphthyridine-3-carbonyl)-amino]ethyl}-methyl-carbamic acid methyl ester {2-[(7-Benzyl-4-hydroxy-8-oxo-7,8-dihydro-[2,7]naphthyridine-3-carbonyl)-amino]-ethyl}-methyl-carbamic acid tert-butyl ester (25 mg, 0.055 mmol) was dissolved in CH$_2$Cl$_2$ (2 mL). Trifluoroacetic acid (1 mL) was added, and the mixture was stirred at r.t. for 1 h. Solvent and excess TFA were removed in vacuo. To the residue were added CH$_2$Cl$_2$ (2 mL), pyridine (0.072 mL, 0.88 mmol), and methyl chloroformate (0.034 mL, 0.44 mmol), and the resulting mixture was stirred for 16 h. The mixture was diluted with CH$_2$Cl$_2$ and washed with 1 M HCl. The organic layer was dried over MgSO$_4$ and concentrated. The crude product was dissolved in 5 mL of 0.5 M NaOMe solution and refluxed for 1 h. After cooling to r.t., the mixture was acidified to pH about 2 and extracted with EtOAc. The combined organic layer was dried over MgSO$_4$ and concentrated. The residue was chromatographed (0-5% MeOH/CH$_2$Cl$_2$) to give the desired product and an impurity. The crude product was then treated with a mixture of 1 M NaOH and MeOH (1:1 v/v) for 16 h at r.t. The mixture was acidified to pH about 2 and extracted with EtOAc. The organic layer was dried over MgSO₄, concentrated, and the crude product was purified by chromatography (0-5% MeOH/CH₂Cl₂) to give 6.3 mg of the title compound. MS: (+) m/z 411.25 (M+1).

Example 100

7-Benzyl-4-hydroxy-8-oxo-7,8-dihydro-[2,7]naphthyridine-3-carboxylic acid [2-(methanesulfonyl-methyl-amino)-ethyl]-amide A mixture of 7-benzyl-4-hydroxy-8-oxo-7,8-dihydro-[2,7]naphthyridine-3-carboxylic acid methyl ester (25 mg, 0.081 mmol), N-(2-amino-ethyl)-N-methyl-methanesulfonamide HCl salt (61 mg, 0.32 mmol), and NaOMe (17 mg, 0.32 mmol) in EtOH (2 mL) was heated at 140° C. for 6 h in a microwave reactor. The mixture was concentrated in vacuo, and the residue was partitioned between EtOAc and 0.1 M HCl. The organic layer was dried over MgSO₄ and concentrated. The crude product was purified by silica gel chromatography (0-5% MeOH/CH₂Cl₂) to give 22 mg of the title compound as an off-white solid. MS: (+) m/z 431.28 (M+1).

Example 101

7-Benzyl-4-hydroxy-8-oxo-7,8-dihydro-[2,7]naphthyridine-3-carboxylic acid (2-methanesulfonylamino-ethyl)-amide (2-Methanesulfonylamino-ethyl)-carbamic acid tert-butyl ester (77 mg, 0.32 mmol) was dissolved in CH₂Cl₂ (2 mL). Trifluoroacetic acid (1 mL) was added, and the mixture was stirred at r.t. for 2 h. Solvent and excess TFA were removed by evaporation, and the residue was taken up in EtOH (2 mL). NaOMe was added with vigorous stirring until pH about 8. The resulting cloudy solution was transferred to a microwave vial containing 7-benzyl-4-hydroxy-8-oxo-7,8-dihydro-[2,7]naphthyridine-3-carboxylic acid methyl ester (25 mg, 0.081 mmol), and the mixture was heated at 140° C. for 6 h in a microwave reactor. The mixture was diluted with EtOAc and washed with 0.1 M HCl. The organic layer was dried over MgSO₄ and concentrated. The crude product was purified by silica gel chromatography (0-5% MeOH/CH₂Cl₂) to give 20 mg of the title compound as an off-white solid. MS: (+) m/z 417.30 (M+1).

Example 102

7-Benzyl-4-hydroxy-8-oxo-7,8-dihydro-[2,7]naphthyridine-3-carboxylic acid [3-(2,2,2-trifluoro-acetylamino)-propyl]-amide a) {3-[(7-Benzyl-4-hydroxy-8-oxo-7,8-dihydro-[2,7]naphthyridine-3-carbonyl)-amino]propyl}-carbamic acid tert-butyl ester A mixture of 7-benzyl-4-hydroxy-8-oxo-7,8-dihydro-[2,7]naphthyridine-3-carboxylic acid methyl ester (100 mg, 0.32 mmol) and (3-amino-propyl)-carbamic acid tert-butyl ester (67 mg, 0.39 mmol) in EtOH (8 mL) was refluxed for 16 h. After cooling to r.t., mixture was diluted with EtOAc and washed with a pH 3 aqueous solution until the washes became acidic. The organic layer was dried over MgSO₄ and concentrated. The crude product was purified by silica gel chromatography (0-5% MeOH/CH₂Cl₂) to give 80 mg of the title compound as a pale yellow solid. MS: (−) m/z 451.37 (M−1).

b) 7-Benzyl-4-hydroxy-8-oxo-7,8-dihydro-[2,7]naphthyridine-3-carboxylic acid [3-(2,2,2-trifluoro-acetylamino)-propyl]-amide {3-[(7-Benzyl-4-hydroxy-8-oxo-7,8-dihydro-[2,7]naphthyridine-3-carbonyl)-amino]-propyl}-carbamic acid tert-butyl ester (27 mg, 0.060 mmol) was dissolved in CH₂Cl₂ (2 mL). Trifluoroacetic acid (1 mL) was added, and the mixture was stirred at r.t. for 1 h. Solvent and excess TFA were removed in vacuo. To the residue were added THF (3 mL), triethylamine (0.050 mL), and ethyl trifluoroacetate (2 mL), and the resulting mixture was refluxed for 16 h. After cooling to r.t., mixture was concentrated to dryness. 0.1 M HCl and EtOAc were added, and the aqueous layer was extracted with additional EtOAc. The organic layers were combined, dried over MgSO₄, and concentrated. The crude product was purified by silica gel chromatography (0-5% MeOH/CH₂Cl₂) to give 16.4 mg of the title compound as a pale yellow solid. MS: (+) m/z 449.23 (M+1).

Example 103

7-Benzyl-4-hydroxy-8-oxo-7,8-dihydro-[2,7]naphthyridine-3-carboxylic acid [3-(3-isopropyl-ureido)-propyl]-amide {3-[(7-Benzyl-4-hydroxy-8-oxo-7,8-dihydro-[2,7]naphthyridine-3-carbonyl)-amino]-propyl}-carbamic acid tert-butyl ester (27 mg, 0.060 mmol) was dissolved in CH₂Cl₂ (2 mL). Trifluoroacetic acid (1 mL) was added, and the mixture was stirred at r.t. for 1 h. Solvent and excess TFA were removed in vacuo. To the residue were added CH₂Cl₂ (2 mL), triethylamine (0.050 mL), and isopropyl isocyanate (0.050 mL), and the resulting mixture was stirred for 16 h. 0.1 M HCl and EtOAc were added, and the aqueous layer was extracted with additional EtOAc. The organic layers were combined, dried over MgSO₄, and concentrated. The crude product was purified by silica gel chromatography (0-5% MeOH/CH₂Cl₂) to give 17.4 mg of the title compound as a pale yellow solid. MS: (+) m/z 460.31 (M+Na).

Example 104

7-Benzyl-4-hydroxy-8-oxo-7,8-dihydro-[2,7]naphthyridine-3-carboxylic acid (3-ureido-propyl)-amide {3-[(7-Benzyl-4-hydroxy-8-oxo-7,8-dihydro-[2,7]naphthyridine-3-carbonyl)-amino]-propyl}-carbamic acid tert-butyl ester (26 mg, 0.058 mmol) was dissolved in CH₂Cl₂ (2 mL).

Trifluoroacetic acid (1 mL) was added, and the mixture was stirred at r.t. for 1 h. Solvent and excess TFA were removed in vacuo. To the residue were added CH₂Cl₂ (3 mL), triethylamine (0.080 mL, 0.58 mmol), and trimethylsilyl isocyanate (0.050 mL, 0.29 mmol), and the resulting mixture was stirred for 16 h. The mixture was diluted with EtOAc and washed with 0.1 M HCl. The organic layer was dried over MgSO₄ and concentrated. The crude product was purified by silica gel chromatography (0-10% MeOH/CH$_2$Cl$_2$) to give 9.3 mg of the title compound. MS: (+) m/z 418.31 (M+Na).

Example 105

1-Benzyl-8-hydroxy-2-oxo-1,2-dihydro-[1,6]naph-thyridine-7-carboxylic acid [2-(methanesulfonyl-methyl-amino)-ethyl]amide A mixture of 1-benzyl-8-hydroxy-2-oxo-1,2-dihydro-[1,6]naphthyridine-7-carboxylic acid methyl ester (25 mg, 0.081 mmol), N-(2-amino-ethyl)-N-methyl-methane-sulfonamide HCl salt (61 mg, 0.32 mmol), and NaOMe (17 mg, 0.32 mmol) in EtOH (3 mL) was heated at 140° C. for 6 h in a microwave reactor. The mixture was concentrated to dryness, and the residue was partitioned between EtOAc and 0.1 M HCl. The organic layer was dried over MgSO$_4$, and concentrated. The crude product was purified by silica gel chromatography (0-5% MeOH/CH$_2$Cl$_2$) to give 19 mg of the title compound as a white solid. MS: (+) m/z 431.34 (M+1).

Example 106

1-Benzyl-5-cyano-8-hydroxy-2-oxo-1,2-dihydro-[1,6]naphthyridine-7-carboxylic acid (2-sulfamoyl-ethyl)-amide A mixture of 1-benzyl-5-cyano-8-hydroxy-2-oxo-1,2-dihydro-[1,6]naphthyridine-7-carboxylic acid methyl ester (20 mg, 0.060 mmol), 2-amino-ethanesulfonic acid amide HCl salt (30 mg, 0.24 mmol), and NaOMe (13 mg, 0.23 mmol) in EtOH (2 mL) was heated at 140° C. for 6 h in a microwave reactor. The mixture was concentrated to dryness, and the residue was partitioned between EtOAc and water. 1 M HCl was added with vigorous stirring until pH about 1, and the aqueous layer was extracted with additional EtOAc. The organic layers were combined, dried over MgSO$_4$, and concentrated. The crude product was first purified by column chromatography (0-5% MeOH/CH$_2$Cl$_2$), then by preparative TLC (10% MeOH/CH$_2$Cl$_2$) to give 5.8 mg of the title compound. MS: (−) m/z 426.24 (M−1).

Example 107

1-Benzyl-5-hydroxy-2-oxo-3-phenyl-1,2-dihydro-[1,7]naphthyridine-6-carboxylic acid (2-acetylamino-ethyl)-amide A mixture of 1-benzyl-5-hydroxy-2-oxo-3-phenyl-1,2-dihydro-[1,7]naphthyridine-6-carboxylic acid methyl ester (25 mg, 0.065 mmol) and N-(2-amino-ethyl)-acetamide in EtOH (3 mL) was refluxed for 48 h. After cooling to r.t., AcOH (0.1 mL) was added, and solvent was evaporated in vacuo. The residue was purified by silica gel chromatography (0-3% MeOH/CH$_2$Cl$_2$) to give 12 mg of the title compound as a light yellow solid. MS: (+) m/z 457.35 (M+1).

Example 108

1-Benzyl-5-hydroxy-2-oxo-3-phenyl-1,2-dihydro-[1,7]naphthyridine-6-carboxylic acid [2-(methanesulfo-nyl-methyl-amino)-ethyl]-amide A mixture of 1-benzyl-5-hydroxy-2-oxo-3-phenyl-1,2-dihydro-[1,7]naphthyridine-6-carboxylic acid methyl ester (25 mg, 0.065 mmol), N-(2-amino-ethyl)-N-methyl-methane-sulfonamide HCl salt (49 mg, 0.26 mmol), and NaOMe (14 mg, 0.26 mmol) in EtOH (3 mL) was heated at 140° C. for 6 h in a microwave reactor. Solvent was evaporated in vacuo, and the residue was partitioned between EtOAc and 0.1 M HCl. The aqueous layer was extracted with additional EtOAc, and the organic layers were combined and dried over MgSO$_4$. After evaporating the solvent, the residue was purified by silica gel chromatography (0-3% MeOH/CH$_2$Cl$_2$) to give 11.4 mg of the title compound as a light yellow solid. MS: (+) m/z 507.36 (M+1).

Example 109

1-Benzyl-5-hydroxy-2-oxo-3-phenyl-1,2-dihydro-[1,7]naphthyridine-6-carboxylic acid [2-(2,2,2-trif-luoro-acetylamino)-ethyl]-amide a) {2-[(1-Benzyl-5-hydroxy-2-oxo-3-phenyl-1,2-dihydro-[1,7]naphthyridine-6-carbonyl)-amino]-ethyl}-carbamic acid tert-butyl ester A mixture of 1-benzyl-5-hydroxy-2-oxo-3-phenyl-1,2-dihydro-[1,7]naphthyridine-6-carboxylic acid methyl ester (60 mg, 0.16 mmol) and (2-amino-ethyl)-carbamic acid tert-butyl ester (75 mg, 0.47 mmol) was refluxed for 48 h. After cooling to r.t., AcOH (0.2 mL) was added, and the mixture was concentrated to dryness. The residue was dissolved in EtOAc and washed with 0.1 M HCl, saturated NaHCO$_3$, and brine. The organic layer was dried over MgSO$_4$ and concentrated to give 88 mg of the title compound as a pale yellow solid. MS: (+) m/z 515.30 (M+1).

b) 1-Benzyl-5-hydroxy-2-oxo-3-phenyl-1,2-dihydro-[1,7]naphthyridine-6-carboxylic acid [2-(2,2,2-trif-luoro-acetylamino)-ethyl]amide {2-[(1-Benzyl-5-hydroxy-2-oxo-3-phenyl-1,2-dihydro-[1,7]naphthyridine-6-carbonyl)-amino]ethyl}-carbamic acid tert-butyl ester (25 mg, 0.049 mmol) was dissolved in CH$_2$Cl$_2$ (2 mL). Trifluoroacetic acid (1 mL) was added, and the mixture was stirred for 2 h. Solvent and excess TFA was removed by evaporation, and to the residue were added THF (3 mL), triethylamine (0.034 mL, 0.24 mmol), and ethyl trifluoroac-etate (2 mL). The resulting mixture was refluxed overnight, then concentrated to dryness. The residue was dissolved in EtOAc and washed with 0.1 M HCl. The organic layer was dried over MgSO$_4$ and concentrated, and the crude product was purified by silica gel chromatography (0-5% MeOH/CH$_2$Cl$_2$) to give 12.7 mg of the title compound as a light yellow solid. MS: (+) m/z 511.33 (M+1).

Example 110

1-Benzyl-5-hydroxy-2-oxo-3-phenyl-1,2-dihydro-[1,7]naphthyridine-6-carboxylic acid [2-(3-ethyl-ure-ido)-ethyl]-amide {2-[(1-Benzyl-5-hydroxy-2-oxo-3-phenyl-1,2-dihydro-[1,7]naphthyridine-6-carbonyl)-amino]ethyl}-carbamic acid tert-butyl ester (25 mg, 0.049 mmol) was dissolved in CH$_2$Cl$_2$ (2 mL). Trifluoroacetic acid (1 mL) was added, and the mixture was stirred for 2 h. Solvent and excess TFA was removed by evaporation, and to the residue were added CH$_2$Cl$_2$ (3 mL), triethylamine (0.068 mL, 0.49 mmol), and ethyl isocyanate (17 mg, 0.24 mmol). The resulting mixture was stirred overnight. EtOAc (50 mL) and 0.1 M HCl (20 mL) were added, and the aqueous layer was extracted with additional EtOAc. The organic layers were combined, dried over MgSO$_4$ and concentrated. The crude product was purified by silica gel chromatography (0-8% MeOH/CH$_2$Cl$_2$) to give 17 mg of the title compound as a pale yellow solid. MS: (+) m/z 486.39 (M+1).

Example 111

1-Benzyl-8-hydroxy-2-oxo-1,2-dihydro-[1,6]naphthyridine-7-carboxylic acid (2-methanesulfonylamino-ethyl)-amide (2-Methanesulfonylamino-ethyl)-carbamic acid tert-butyl ester (77 mg, 0.32 mmol) was dissolved in CH$_2$Cl$_2$ (2 mL). Trifluoroacetic acid (1 mL) was added, and the mixture was stirred at r.t. for 2 h. Solvent and excess TFA were removed by evaporation, and the residue was taken up in EtOH (2 mL). NaOMe was added with vigorous stirring until pH about 8. The resulting cloudy solution was transferred to a microwave vial containing 1-benzyl-8-hydroxy-2-oxo-1,2-dihydro-[1,6]naphthyridine-7-carboxylic acid methyl ester (25 mg, 0.081 mmol), and the mixture was heated at 140° C. for 6 h in a microwave reactor. The mixture was diluted with EtOAc and washed with 0.1 M HCl. The organic layer was dried over MgSO$_4$ and concentrated. The crude product was first purified by column chromatography (0-5% MeOH/CH$_2$Cl$_2$), then by preparative TLC (10% MeOH/CH$_2$Cl$_2$) to give 2.7 mg of the title compound as an off-white solid. MS: (+) m/z 417.30 (M+1).

Example 112

3-[(1-Benzyl-8-hydroxy-5-methyl-2-oxo-1,2-dihydro-[1,6]naphthyridine-7-carbonyl)-amino]-propionic acid a) 1-Benzyl-8-hydroxy-5-methyl-2-oxo-1,2-dihydro-[1,6]naphthyridine-7-carboxylic acid methyl ester A mixture of 1-benzyl-8-hydroxy-5-iodo-2-oxo-1,2-dihydro-[1,6]naphthyridine-7-carboxylic acid methyl ester (86 mg, 0.197 mmol), tetramethyltin (0.14 mL, 0.99 mmol) and PdCl$_2$(PPh$_3$)$_2$ (28 mg, 0.039 mmol) in DMF (4 mL) was heated at 120° C. for 2 h under N$_2$ atmosphere. After cooling to r.t., EtOAc (50 mL) and brine (10 mL) were added. 1 M HCl was added until pH about 2-3. The aqueous layer was extracted with additional EtOAc, and the organic layers were combined, dried over MgSO$_4$, and concentrated. The crude product was purified by silica gel chromatography (0-3% MeOH/CH$_2$Cl$_2$) to give 18 mg of the title compound as a white solid. MS: (+) m/z 325.28 (M+1).

b) 3-[(1-Benzyl-8-hydroxy-5-methyl-2-oxo-1,2-dihydro-[1,6]naphthyridine-7-carbonyl)-amino]-propionic acid A mixture of 1-benzyl-8-hydroxy-5-methyl-2-oxo-1,2-dihydro-[1,6]naphthyridine-7-carboxylic acid methyl ester (18 mg, 0.056 mmol), β-alanine (494 mg, 5.6 mmol) and NaOMe solution (8.9 mL, 4.4 mmol, 0.5 M in MeOH) was refluxed for 16 h. After cooling to r.t., mixture was concentrated in vacuo. The residue was partitioned between EtOAc and water. 1 M HCl was added with vigorous stirring until pH about 2. The organic layer was dried over MgSO$_4$ and concentrated. The crude product was purified by silica gel chromatography (0-10% MeOH/CH$_2$Cl$_2$) to give 11.4 mg of the title compound. MS: (+) m/z 382.28 (M+1).

Example 113

1-Benzyl-5-hydroxy-2-oxo-3-phenyl-1,2-dihydro-[1,7]naphthyridine-6-carboxylic acid (1H-tetrazol-5-ylmethyl)-amide A mixture of 1-benzyl-5-hydroxy-2-oxo-3-phenyl-1,2-dihydro-[1,7]naphthyridine-6-carboxylic acid methyl ester (30 mg, 0.078 mmol), (1H-tetrazol-5-yl)-methylamine (31 mg, 0.31 mmol), and NaOMe (15 mg, 0.27 mmol) in EtOH (2 mL) was heated at 140° C. for 6 h in a microwave reactor. Solvent was evaporated in vacuo, and the residue was partitioned between EtOAc and water. 1 M HCl was added with vigorous stirring until pH about 2. The organic layer was dried over MgSO$_4$ and concentrated. The crude product was purified by silica gel chromatography (0-20% MeOH/CH$_2$Cl$_2$) to give 11.2 mg of the title compound as a yellow solid. MS: (+) m/z 454.33 (M+1).

Example 114

3-[(1-Benzyl-5-hydroxy-2-oxo-3-phenyl-1,2-dihydro-[1,7]naphthyridine-6-carbonyl)-amino]-2,2-dimethyl-propionic acid a) 3-[(1-Benzyl-5-hydroxy-2-oxo-3-phenyl-1,2-dihydro-[1,7]naphthyridine-6-carbonyl)-amino]-2,2-dimethyl-propionic acid tert-butyl ester A mixture of 1-benzyl-5-hydroxy-2-oxo-3-phenyl-1,2-dihydro-[1,7]naphthyridine-6-carboxylic acid methyl ester (30 mg, 0.078 mmol) and 3-amino-2,2-dimethyl-propionic acid tert-butyl ester (40 mg, 0.233 mmol) in EtOH (2 mL) was heated at 140° C. for 6 h in a microwave reactor. Solvent was evaporated in vacuo, and the residue was purified by silica gel chromatography (0-15% EtOAc/hexanes+2% AcOH) to give 22 mg of the title compound as a yellow oil. $^1$H NMR (CDCl$_3$, 200 MHz): δ=13.2 (s, 1H), 8.35 (s, 1H), 8.28 (t, 1H, J=6.2 Hz), 8.18 (s, 1H), 7.75-7.90 (m, 2H), 7.20-7.60 (m, 8H), 5.65 (s, 2H), 3.50 (d, 2H, J=6.6 Hz), 1.47 (s, 9H), 1.21 (s, 6H).

b) 3-[(1-Benzyl-5-hydroxy-2-oxo-3-phenyl-1,2-dihydro-[1,7]naphthyridine-6-carbonyl)-amino]-2,2-dimethyl-propionic acid Trifluoroacetic acid (2 mL) was added to a mixture of 3-[(1-benzyl-5-hydroxy-2-oxo-3-phenyl-1,2-dihydro-[1,7]naphthyridine-6-carbonyl)-amino]-2,2-dimethyl-propionic acid tert-butyl ester (22 mg, 0.042 mmol) and CH$_2$Cl$_2$ (3 mL), and the resulting mixture was stirred for 2 h. Solvent was evaporated in vacuo, and the residue was dissolved in saturated NaHCO$_3$ and washed several times with ether. The aqueous layer was acidified to pH about 2 and extracted with EtOAc. The organic layer was dried over MgSO$_4$ and concentrated to give 11.8 mg of the title compound as a light yellow solid. MS: (+) m/z 472.34 (M+1).

Example 115

7-Benzyl-4-hydroxy-8-oxo-7,8-dihydro-[2,7]naphthyridine-3-carboxylic acid [2-(formyl-methylamino)-ethyl]-amide {2-[(7-Benzyl-4-hydroxy-8-oxo-7,8-dihydro-[2,7]naphthyridine-3-carbonyl)-amino]-ethyl}-methyl-carbamic acid tert-butyl ester (65 mg, 0.14 mmol) was dissolved in CH$_2$Cl$_2$ (2 mL). Trifluoroacetic acid (1 mL) was added, and the mixture was stirred at r.t. for 2 h. Solvent and excess TFA were removed in vacuo. To the residue were added THF (5 mL), triethylamine (0.1 mL, 0.72 mmol), and ethyl formate (5 mL), and the resulting mixture was refluxed for 4 days. Mixture was concentrated in vacuo, and the residue was purified by silica gel chromatography (0-5% MeOH/CH$_2$Cl$_2$) to give 35 mg of the title compound as a light yellow solid. MS: (+) m/z 381.34 (M+1).

Example 116

7-Benzyl-4-hydroxy-8-oxo-7,8-dihydro-[2,7]naph-thyridine-3-carboxylic acid [2-(acetyl-methyl-amino)-ethyl]-amide {2-[(7-Benzyl-4-hydroxy-8-oxo-7,8-dihydro-[2,7]naph-thyridine-3-carbonyl)-amino]-ethyl}-methyl-carbamic acid tert-butyl ester (65 mg, 0.14 mmol) was dissolved in CH$_2$Cl$_2$ (2 mL). Trifluoroacetic acid (1 mL) was added, and the mixture was stirred at r.t. for 2 h. Solvent and excess TFA were removed in vacuo. To the residue were added CH$_2$Cl$_2$ (3 mL), triethylamine (0.2 mL, 1.4 mmol), and acetic anhydride (0.070 mL, 0.72 mmol), and the resulting mixture was stirred for 16 h. The mixture was diluted with CH$_2$Cl$_2$ (50 mL) and washed with 0.1 M HCl, saturated NaHCO$_3$ and brine. The organic layer was dried over MgSO$_4$ and concentrated. The crude product was dissolved in MeOH (3 mL) and treated with 2.9 mL of 0.5 M NaOMe solution. After stirring for 1 h at r.t., 1 M HCl was added to acidify the mixture. The resulting suspension was extracted with EtOAc, and the organic layer was dried over MgSO$_4$ and concentrated. The crude product was purified by silica gel chromatography (0-5% MeOH/CH$_2$Cl$_2$) to give 32 mg of the title compound. MS: (+) m/z 395.32 (M+1).

Example 117

1-Benzyl-5-hydroxy-2-oxo-3-phenyl-1,2-dihydro-[1,7]naphthyridine-6-carboxylic acid (2-formylamino-ethyl)-amide {2-[(1-Benzyl-5-hydroxy-2-oxo-3-phenyl-1,2-dihydro-[1,7]naphthyridine-6-carbonyl)-amino]ethyl}-carbamic acid tert-butyl ester (35 mg, 0.068 mmol) was dissolved in CH$_2$Cl$_2$ (2 mL). Trifluoroacetic acid (1 mL) was added, and the mixture was stirred for 2 h. Solvent and excess TFA was removed by evaporation, and to the residue were added THF (3 mL), triethylamine (0.050 mL, 0.34 mmol), and ethyl formate (3 mL). The resulting mixture was refluxed for 4 days. After cooling to r.t., solvent was evaporated. The residue was partitioned between EtOAc and 0.1 M HCl. The aqueous layer was extracted with additional EtOAc, and the organic layers were combined, dried over MgSO$_4$ and concentrated. The crude product was purified by silica gel chromatography (0-5% MeOH/CH$_2$Cl$_2$) to give 11.4 mg of the title compound as a light yellow solid. MS: (+) m/z 443.37 (M+1)

Example 118

3-[(1-Benzyl-5-hydroxy-2-oxo-3-phenyl-8-pyridin-3-yl-1,2-dihydro-[1,7]naphthyridine-6-carbonyl)-amino]-propionic acid A mixture of 1-benzyl-5-hydroxy-2-oxo-3-phenyl-8-pyridin-3-yl-1,2-dihydro-[1,7]naphthyridine-6-carboxylic acid methyl ester (35 mg, 0.076 mmol), β-alanine (896 mg, 10.1 mmol) and NaOMe solution (15 mL, 7.6 mmol, 0.5 M in MeOH) was refluxed for 16 h. After the mixture was cooled to r.t., the solvent was evaporated in vacuo. The residue was dissolved in water and washed several times with ether. The aqueous layer was acidified to pH about 3 with 4 M HCl, and the resulting precipitate was collected by filtration and dried to give 29 mg of the title compound as a pale yellow solid. MS: (+) m/z 521.34 (M+1).

Example 119

3-[(1-Benzyl-5-hydroxy-2-oxo-3,8-diphenyl-1,2-dihydro-[1,7]naphthyridine-6-carbonyl)-amino]-propionic acid A mixture of 1-benzyl-5-hydroxy-2-oxo-3,8-diphenyl-1,2-dihydro-[1,7]naphthyridine-6-carboxylic acid methyl ester (23 mg, 0.050 mmol), β-alanine (444 mg, 5.0 mmol) and NaOMe solution (8 mL, 3.7 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH about 2. The organic layer was dried over MgSO$_4$ and concentrated. The crude product was purified by silica gel chromatography (5-60% EtOAc/hexanes+2% AcOH) to give 24 mg of the title compound as a yellow solid. MS: (+) m/z 520.34 (M+1).

Example 120

3-[(1-Benzyl-5-hydroxy-8-methyl-2-oxo-3-phenyl-1,2-dihydro-[1,7]naphthyridine-6-carbonyl)-amino]-propionic acid A mixture of 1-benzyl-5-hydroxy-8-methyl-2-oxo-3-phenyl-1,2-dihydro-[1,7]naphthyridine-6-carboxylic acid methyl ester (30 mg, 0.075 mmol), β-alanine (668 mg, 7.5 mmol) and NaOMe solution (11 mL, 5.6 mmol, 0.5 M in MeOH) was refluxed for 16 h. After the mixture was cooled to r.t., the solvent was evaporated in vacuo. The residue was dissolved in water washed several times with ether. The aqueous layer was acidified to pH 2 with 4 M HCl, and the resulting precipitate was collected by filtration and dried to give 9 mg of the title compound. MS: (+) m/z 458.36 (M+1).

Example 121

3-[(1-Benzyl-5-hydroxy-2-oxo-3-phenyl-1,2,3,4-tetrahydro-[1,7]naphthyridine-6-carbonyl)-amino]-propionic acid a) 1-Benzyl-5-hydroxy-2-oxo-3-phenyl-1,2,3,4-tetrahydro-[1,7]naphthyridine-6-carboxylic acid methyl ester To a mixture of 10% Pd/C (50 mg) and EtOH (5 mL) was added a solution of 1-benzyl-5-hydroxy-2-oxo-3-phenyl-1,2-dihydro-[1,7]naphthyridine-6-carboxylic acid methyl ester (40 mg, 0.104 mmol) in 5 mL of THF. The resulting mixture was placed under H$_2$ (35 psi) for 5 days. The mixture was filtered through a pad of Celite and the filtrate was concentrated. The residue was purified by silica gel chromatography (0-50% EtOAc/hexanes+2% AcOH) to give 22 mg of the title compound as a white solid. MS: (+) m/z 389.34 (M+1).

b) 3-[(1-Benzyl-5-hydroxy-2-oxo-3-phenyl-1,2,3,4-tetrahydro-[1,7]naphthyridine-6-carbonyl)-amino]-propionic acid A mixture of 1-benzyl-5-hydroxy-2-oxo-3-phenyl-1,2,3,4-tetrahydro-[1,7]naphthyridine-6-carboxylic acid methyl ester (22 mg, 0.057 mmol), β-alanine (657 mg, 7.4 mmol) and NaOMe solution (11 mL, 5.7 mmol, 0.5 M in MeOH) was refluxed for 48 h. After the mixture was cooled to r.t., the solvent was evaporated in vacuo. The residue was partitioned between EtOAc and water. 1 M HCl was added with vigorous stirring until pH about 2. The aqueous layer was extracted with additional EtOAc, and the organic layers were combined, dried over MgSO₄, and concentrated. The residue was dissolved in saturated NaHCO₃ and washed several times with ether. The aqueous layer was acidified to pH 2 with 4 M HCl, and the resulting precipitate was collected by filtration to give 12.4 mg of the title compound as a white solid. MS: (+) m/z 446.40 (M+1).

Example 122

3-[(1-Benzyl-5-hydroxy-2-oxo-1,2-dihydro-[1,7]naphthyridine-6-carbonyl)-amino]-propionic acid A mixture of 1-benzyl-5-hydroxy-2-oxo-1,2-dihydro-[1,7]naphthyridine-6-carboxylic acid methyl ester (40 mg, 0.13 mmol), β-alanine (920 mg, 10.3 mmol) and NaOMe solution (15 mL, 7.7 mmol, 0.5 M in MeOH) was refluxed for 16 h. The solvent was evaporated in vacuo, and the residue was dissolved in water and washed several times with ether. The aqueous layer was acidified to pH about 2 with 4 M HCl, and the resulting precipitate was collected by filtration and dried to give 33 mg of the title compound as an off-white solid. MS: (+) m/z 368.24 (M+1).

Example 123

3-[(1-Benzyl-5-hydroxy-2-oxo-3-phenethyl-1,2-dihydro-[1,7]naphthyridine-6-carbonyl)-amino]-propionic acid A mixture of 1-benzyl-5-hydroxy-2-oxo-3-phenethyl-1,2-dihydro-[1,7]naphthyridine-6-carboxylic acid methyl ester (40 mg, 0.097 mmol), β-alanine (861 mg, 9.7 mmol) and NaOMe solution (15 mL, 7.7 mmol, 0.5 M in MeOH) was refluxed for 16 h. After the mixture was cooled to r.t., the solvent was evaporated in vacuo. The residue was dissolved in water and washed several times with ether. The aqueous layer was acidified to pH about 2 with 4 M HCl, and the resulting precipitate was collected by filtration and dried to give 30 mg of the title compound as an off-white solid. MS: (+) m/z 472.41 (M+1).

Example 124

3-[(1-Benzyl-5-hydroxy-2-oxo-3-pyridin-3-yl-1,2-dihydro-[1,7]naphthyridine-6-carbonyl)-amino]-propionic acid a) 1-Benzyl-5-hydroxy-2-oxo-3-pyridin-3-yl-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (70 mg, 0.18 mmol), 3-(tributylstannyl)pyridine (0.086 mL, 0.27 mmol), and PdCl₂(PPh₃)₂ (25 mg, 0.036 mmol) in DMF (5 mL) was heated at 120° C. under nitrogen atmosphere for 2 h. After the mixture was cooled to r.t., brine (10 mL) and EtOAc (50 mL) were added. 1 M HCl was added with stirring until pH was about 3-4. The aqueous layer was extracted with additional EtOAc and the organic layers were combined, washed with water, and dried over MgSO₄. After evaporating the solvent in vacuo, the crude product was purified twice by silica gel chromatography (0-5% MeOH/CH₂Cl₂, then 20-100% EtOAc/hexanes+2% AcOH) to give 35 mg of the title compound as an off-white solid. MS: (+) m/z 388.26 (M+1).

b) 3-[(1-Benzyl-5-hydroxy-2-oxo-3-pyridin-3-yl-1,2-dihydro-[1,7]naphthyridine-6-carbonyl)-amino]-propionic acid A mixture of 1-benzyl-5-hydroxy-2-oxo-3-pyridin-3-yl-1,2-dihydro-[1,7]naphthyridine-6-carboxylic acid methyl ester (35 mg, 0.090 mmol), β-alanine (806 mg, 9.0 mmol) and NaOMe solution (13.6 mL, 6.78 mmol, 0.5 M in MeOH) was refluxed for 16 h. After the mixture was cooled to r.t., the solvent was evaporated in vacuo. The residue was dissolved in water and washed several times with ether. The aqueous layer was acidified to pH about 3-4 with 1 M HCl, and the resulting precipitate was isolated by filtration to give 19 mg of the title compound. MS: (+) m/z 445.33 (M+1).

Example 125

3-[(1-Benzyl-5-hydroxy-2-oxo-3-pyridin-2-yl-1,2-dihydro-[1,7]naphthyridine-6-carbonyl)-amino]-propionic acid a) 1-Benzyl-5-hydroxy-2-oxo-3-pyridin-2-yl-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (70 mg, 0.18 mmol), 2-(tributylstannyl)pyridine (99 mg, 0.27 mmol), and PdCl₂(PPh₃)₂ (25 mg, 0.036 mmol) in DMF (5 mL) was heated at 120° C. under nitrogen atmosphere for 3 h. After the mixture was cooled to r.t., brine (10 mL) and EtOAc (50 mL) were added. 1 M HCl was added with stirring until pH was about 3-4. The aqueous layer was extracted with additional EtOAc and the organic layers were combined, washed with water, and dried over MgSO₄. After evaporating the solvent in vacuo, the crude product was purified by silica gel chromatography (20-100% EtOAc/hexanes+2% AcOH) to give 25 mg of the title compound. MS: (+) m/z 388.33 (M+1).

b) 3-[(1-Benzyl-5-hydroxy-2-oxo-3-pyridin-2-yl-1,2-dihydro-[1,7]naphthyridine-6-carbonyl)-amino]-propionic acid A mixture of 1-benzyl-5-hydroxy-2-oxo-3-pyridin-2-yl-1,2-dihydro-[1,7]naphthyridine-6-carboxylic acid methyl ester (25 mg, 0.065 mmol), β-alanine (863 mg, 9.69 mmol) and NaOMe solution (15.5 mL, 7.75 mmol, 0.5 M in MeOH) was refluxed for 16 h. After the mixture was cooled to r.t., the solvent was evaporated in vacuo. The residue was dissolved in water and washed several times with ether. The aqueous layer was acidified to pH about 3-4 with 1 M HCl, and the resulting precipitate was isolated by filtration to give 9 mg of the title compound. MS: (+) m/z 445.33 (M+1).

Example 126

4-[(1-Benzyl-5-hydroxy-2-oxo-3-phenyl-1,2-dihydro-[1,7]naphthyridine-6-carbonyl)-amino]-butyric acid a) 1-Benzyl-5-hydroxy-2-oxo-3-phenyl-1,2-dihydro-[1,7]naphthyridine-6-carboxylic acid A mixture of 1-benzyl-5-hydroxy-2-oxo-3-phenyl-1,2-dihydro-[1,7]naphthyridine-6-carboxylic acid methyl ester (35 mg, 0.091 mmol), 2 M aq. NaOH (3 mL), THF (3 mL) and MeOH (3 mL) was stirred at r.t. for 16 h. The mixture was concentrated to one-third of its original volume, and then placed in an ice bath. 1 M HCl was added with stirring until pH about 2, and the resulting mixture was extracted with EtOAc. The organic layer was washed with brine and dried over MgSO$_4$. Solvent was evaporated in vacuo to give 35 mg of the title compound as a yellow solid. MS: (+) m/z 373.28 (M+1).

b) 4-[(1-Benzyl-5-hydroxy-2-oxo-3-phenyl-1,2-dihydro-[1,7]naphthyridine-6-carbonyl)-amino]-butyric acid ethyl ester 1-Benzyl-5-hydroxy-2-oxo-3-phenyl-1,2-dihydro-[1,7] naphthyridine-6-carboxylic acid (35 mg, 0.094 mmol) and HOBt (13 mg, 0.094 mmol) were added to 2 mL of CH$_2$Cl$_2$. EDC (25 mg, 0.13 mmol) was added, and the mixture was stirred for 10 min. 4-Amino-butyric acid ethyl ester HCl salt (16 mg, 0.094 mmol) and Hunig's base (0.033 mL, 0.19 mmol) were then added, and the mixture was stirred for 16 h. The mixture was diluted with EtOAc (40 mL) and washed with 0.1 M HCl and brine. The organic layer was dried over MgSO$_4$ and concentrated. The crude product was purified by silica gel chromatography (0-40% EtOAc/hexanes+2% AcOH) to give 13 mg of the title compound. MS: (+) m/z 486.39 (M+1).

c) 4-[(1-Benzyl-5-hydroxy-2-oxo-3-phenyl-1,2-dihydro-[1,7]naphthyridine-6-carbonyl)-amino]-butyric acid A mixture of 4-[(1-benzyl-5-hydroxy-2-oxo-3-phenyl-1,2-dihydro-[1,7]naphthyridine-6-carbonyl)-amino]-butyric acid ethyl ester (38 mg, 0.078 mmol), 2M aq. NaOH (4 mL), THF (4 mL) and MeOH (4 mL) was stirred at r.t. for 16 h. Solvent was evaporated in vacuo to one-third of its original volume, and the mixture was placed in an ice bath. 1 M HCl was added until pH about 2, and the resulting precipitate was collected by filtration and dried to give 27 mg of the title compound as a pale yellow solid. MS: (+) m/z 458.36 (M+1).

Example 127

3-[(1-Benzyl-5-hydroxy-3-methyl-2-oxo-1,2-dihydro-[1,7]naphthyridine-6-carbonyl)-amino]-propionic acid A mixture of 1-benzyl-5-hydroxy-3-methyl-2-oxo-1,2-dihydro-[1,7]naphthyridine-6-carboxylic acid methyl ester (36 mg, 0.11 mmol), β-alanine (990 mg, 11 mmol) and NaOMe solution (16.6 mL, 8.3 mmol, 0.5 M in MeOH) was refluxed for 16 h. After the mixture was cooled to r.t., the solvent was evaporated in vacuo. The residue was dissolved in water and washed several times with ether. The aqueous layer was acidified to pH about 1 with 1 M HCl, and the resulting precipitate was isolated by filtration and dried to give 14 mg of the title compound as a pale yellow solid. MS: (+) m/z 382.22 (M+1).

Example 128

3-[(1-Benzyl-5-hydroxy-2-oxo-3-thiophen-2-yl-1,2-dihydro-[1,7]naphthyridine-6-carbonyl)-amino]-propionic acid a) 1-Benzyl-5-hydroxy-2-oxo-3-thiophen-2-yl-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (70 mg, 0.18 mmol), tributyl-thiophen-2-yl-stannane (0.070 mL, 0.22 mmol), and PdCl$_2$(PPh$_3$)$_2$ (25 mg, 0.036 mmol) in DMF (4 mL) was heated at 120° C. under nitrogen atmosphere for 2 h. After the mixture was cooled to r.t., brine (10 mL) and EtOAc (40 mL) were added. 1 M HCl was added with stirring until pH was about 3. The aqueous layer was extracted with additional EtOAc and the organic layers were combined, washed with water, and dried over MgSO$_4$. After evaporating the solvent in vacuo, the crude product was purified by silica gel chromatography (0-50% EtOAc/hexanes+2% AcOH) to give 30 mg of the title compound. MS: (+) m/z 393.24 (M+1).

b) 3-[(1-Benzyl-5-hydroxy-2-oxo-3-thiophen-2-yl-1,2-dihydro-[1,7]naphthyridine-6-carbonyl)-amino]-propionic acid A mixture of 1-benzyl-5-hydroxy-2-oxo-3-thiophen-2-yl-1,2-dihydro-[1,7]naphthyridine-6-carboxylic acid methyl ester (30 mg, 0.077 mmol), β-alanine (886 mg, 9.9 mmol) and NaOMe solution (15 mL, 7.7 mmol, 0.5 M in MeOH) was refluxed for 16 h. After the mixture was cooled to r.t., the solvent was evaporated in vacuo. The residue was dissolved in water and washed several times with ether. The aqueous layer was acidified to pH 1 with 1 M HCl, and the resulting precipitate was isolated by filtration to give 20 mg of the title compound as a brown solid. MS: (+) m/z 450.24 (M+1).

Example 129

3-[(1-Benzyl-5-hydroxy-2-oxo-3-pyridin-4-yl-1,2-dihydro-[1,7]naphthyridine-6-carbonyl)-amino]-propionic acid a) 1-Benzyl-5-hydroxy-2-oxo-3-pyridin-4-yl-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (70 mg, 0.18 mmol), 4-(tributylstannyl)pyridine (99 mg, 0.27 mmol), and PdCl$_2$(PPh$_3$)$_2$ (25 mg, 0.036 mmol) in DMF (4 mL) was heated at 120° C. under nitrogen atmosphere for 3 h. After the mixture was cooled to r.t., brine (10 mL) and EtOAc (40 mL) were added. 1 M HCl was added with stirring until pH was about 3-4. The aqueous layer was extracted with additional EtOAc and the organic layers were combined, washed with water, and dried over MgSO$_4$. After evaporating the solvent in vacuo, the crude product was purified by silica gel chromatography (20-100% EtOAc/hexanes+2% AcOH) to give 29 mg of the title compound. MS: (+) m/z 388.33 (M+1).

b) 3-[(1-Benzyl-5-hydroxy-2-oxo-3-pyridin-4-yl-1,2-dihydro-[1,7]naphthyridine-6-carbonyl)-amino]-propionic acid A mixture of 1-benzyl-5-hydroxy-2-oxo-3-pyridin-4-yl-1,2-dihydro-[1,7]naphthyridine-6-carboxylic acid methyl ester (29 mg, 0.075 mmol), β-alanine (868 mg, 9.7 mmol) and NaOMe solution (15 mL, 7.5 mmol, 0.5 M in MeOH) was refluxed for 16 h. After the mixture was cooled to r.t., the solvent was evaporated in vacuo. The residue was dissolved in water and washed several times with ether. The aqueous layer was acidified to pH about 3-4 with 1 M HCl, and the resulting precipitate was isolated by filtration to give 28 mg of the title compound as a bright yellow solid. MS: (+) m/z 445.26 (M+1).

Example 130

1-Benzyl-5-hydroxy-2-oxo-3-phenyl-1,2-dihydro-[1,7]naphthyridine-6-carboxylic acid (2-methanesulfonylamino-ethyl)-amide (2-Methanesulfonylamino-ethyl)-carbamic acid tert-butyl ester (94 mg, 0.38 mmol) was dissolved in $CH_2Cl_2$ (2 mL). Trifluoroacetic acid (1 mL) was added, and the mixture was stirred at r.t. for 2 h. Solvent and excess TFA were removed by evaporation, and the residue was taken up in EtOH (3 mL). NaOMe was added with vigorous stirring until pH was about 8. The resulting mixture was transferred to a microwave vial containing 1-benzyl-5-hydroxy-2-oxo-3-phenyl-1,2-dihydro-[1,7]naphthyridine-6-carboxylic acid methyl ester (38 mg, 0.098 mmol), and the mixture was heated at 140° C. for 6 h in a microwave reactor. The solvent was evaporated, and the residue was partitioned between EtOAc and 0.1 M HCl. The organic layer was dried over $MgSO_4$ and concentrated. The crude product was purified by silica gel chromatography (0-5% $MeOH/CH_2Cl_2$) to give 16 mg of the title compound. MS: (+) m/z 493.32 (M+1).

Example 131

1-Benzyl-8-cyano-5-hydroxy-2-oxo-3-phenyl-1,2-dihydro-[1,7]naphthyridine-6-carboxylic acid [2-(methanesulfonyl-methyl-amino)-ethyl]-amide A mixture of 1-benzyl-8-cyano-5-hydroxy-2-oxo-3-phenyl-1,2-dihydro-[1,7]naphthyridine-6-carboxylic acid methyl ester (25 mg, 0.061 mmol), N-(2-amino-ethyl)-N-methyl-methanesulfonamide HCl salt (57 mg, 0.30 mmol), and NaOMe (16 mg, 0.30 mmol) in EtOH (3 mL) was heated at 140° C. for 6 h in a microwave reactor. Solvent was evaporated in vacuo, and the residue was partitioned between EtOAc and 0.1 M HCl. The organic layer was dried over $MgSO_4$ and concentrated. The residue was purified by silica gel chromatography (0-3% $MeOH/CH_2Cl_2$) to give 22 mg of the title compound as a light yellow solid. MS: (+) m/z 532.11 (M+1).

Example 132

1-Benzyl-5-hydroxy-8-methyl-2-oxo-3-phenyl-1,2-dihydro-[1,7]naphthyridine-6-carboxylic acid [2-(methanesulfonyl-methyl-amino)-ethyl]-amide A mixture of 1-benzyl-5-hydroxy-8-methyl-2-oxo-3-phenyl-1,2-dihydro-[1,7]naphthyridine-6-carboxylic acid methyl ester (35 mg, 0.088 mmol), N-(2-amino-ethyl)-N-methyl-methanesulfonamide HCl salt (83 mg, 0.44 mmol), and NaOMe (24 mg, 0.44 mmol) in EtOH (3 mL) was heated at 140° C. for 6 h in a microwave reactor. Solvent was evaporated in vacuo, and the residue was partitioned between EtOAc and 0.1 M HCl. The organic layer was dried over $MgSO_4$ and concentrated. The residue was purified twice by silica gel chromatography (first eluted with 0-2.5% $MeOH/CH_2Cl_2$, then with 15-100% EtOAc/hexanes+2% AcOH) to give 16 mg of the title compound as an off-white solid. MS: (+) m/z 521.28 (M+1).

Example 133

1-Benzyl-5-hydroxy-2-oxo-3,8-diphenyl-1,2-dihydro-[1,7]naphthyridine-6-carboxylic acid [2-(methanesulfonyl-methyl-amino)-ethyl]amide A mixture of 1-benzyl-5-hydroxy-2-oxo-3,8-diphenyl-1,2-dihydro-[1,7]naphthyridine-6-carboxylic acid methyl ester (39 mg, 0.084 mmol), N-(2-amino-ethyl)-N-methyl-methanesulfonamide HCl salt (80 mg, 0.42 mmol), and NaOMe (23 mg, 0.42 mmol) in EtOH (3 mL) was heated at 140° C. for 6 h in a microwave reactor. Solvent was evaporated in vacuo, and the residue was partitioned between EtOAc and 0.1 M HCl. The organic layer was washed with brine and dried over $MgSO_4$. After evaporating the solvent, the residue was purified by silica gel chromatography (10-100% EtOAc/hexanes+2% AcOH) to give 24 mg of the title compound as a light yellow solid. MS: (+) m/z 583.32 (M+1).

Example 134

1-Benzyl-5-hydroxy-2-oxo-3-phenyl-8-pyridin-3-yl-1,2-dihydro-[1,7]naphthyridine-6-carboxylic acid [2-(methanesulfonyl-methyl-amino)-ethyl]amide A mixture of 1-benzyl-5-hydroxy-2-oxo-3-phenyl-8-pyridin-3-yl-1,2-dihydro-[1,7]naphthyridine-6-carboxylic acid methyl ester (38.5 mg, 0.083 mmol), N-(2-amino-ethyl)-N-methyl-methanesulfonamide HCl salt (78 mg, 0.42 mmol), and NaOMe (22 mg, 0.42 mmol) in EtOH (3 mL) was heated at 140° C. for 6 h in a microwave reactor. Solvent was evaporated in vacuo, and the residue was partitioned between EtOAc and water. 1 M HCl was added until pH was about 3. The aqueous layer was extracted with additional EtOAc, and the combined organic layer was dried over $MgSO_4$ and concentrated. The residue was purified by silica gel chromatography (0-10% $MeOH/CH_2Cl_2$) to give 26 mg of the title compound. MS: (+) m/z 584.26 (M+1).

Example 135

3-[(5-Hydroxy-2-oxo-1-phenethyl-3-phenyl-1,2-dihydro-[1,7]naphthyridine-6-carbonyl)-amino]-propionic acid a) 4-(1-Phenethylamino-ethylidene)-pent-2-enedioic acid dimethyl ester Phenethylamine (5.0 mL, 39.7 mmol) was dissolved in MeOH (130 mL). 3-Oxo-butyric acid methyl ester (5.1 mL, 47.6 mmol) was added, and the mixture was refluxed for 3 h. To the reaction mixture was added propynoic acid methyl ester (5.3 mL, 59.5 mmol), and the resulting mixture was then refluxed for 2 days. The solvent was evaporated, and the crude solid was recrystallized from MeOH to give 9.14 g of the title compound as a light orange solid. MS: (+) m/z 326.23 (M+Na).

b) 5-Bromo-2-methyl-6-oxo-1-phenethyl-1,6-dihydro-pyridine-3-carboxylic acid methyl ester MeOH (220 mL) was added to a flask containing 4-(1-phenethylamino-ethylidene)-pent-2-enedioic acid dimethyl ester (7.0 g, 23.1 mmol). NaOMe solution (5.3 mL, 23.1 mmol, 4.375 M in MeOH) and N-bromosuccinimide (4.93 g, 27.7 mmol) were added, and the resulting mixture was refluxed for 1 h. After cooling to r.t., the solvent was evaporated in vacuo. The residue was partitioned between saturated NH$_4$Cl (200 mL) and CH$_2$Cl$_2$ (200 mL). The aqueous layer was extracted with additional CH$_2$Cl$_2$ and the organic layers were combined, dried over MgSO$_4$, and concentrated. The crude product was chromatographed (0-40% EtOAc/hexanes) to give 5.75 g of the title compound as a pale yellow solid. MS: (+) m/z 372.14, 374.16 (M+Na, $^{79/81}$Br).

c) 5-Bromo-2-bromomethyl-6-oxo-1-phenethyl-1,6-dihydro-pyridine-3-carboxylic acid methyl ester A mixture of 5-bromo-2-methyl-6-oxo-1-phenethyl-1,6-dihydro-pyridine-3-carboxylic acid methyl ester (1 g, 2.86 mmol), N-bromosuccinimide (0.56 g, 3.14 mmol), and benzoyl peroxide (70 mg, 0.286 mmol) in CCl$_4$ (25 mL) was refluxed for 16 h. The solvent was evaporated in vacuo, and the residue was chromatographed (0-25% EtOAc/hexanes) to give 320 mg of the title compound as a tan solid. MS: (+) m/z 452.06 (M+Na).

d) 5-Bromo-2-{[methoxycarbonylmethyl-(toluene-4-sulfonyl)-amino]-methyl}-6-oxo-1-phenethyl-1,6-dihydro-pyridine-3-carboxylic acid methyl ester A mixture of 5-bromo-2-bromomethyl-6-oxo-1-phenethyl-1,6-dihydro-pyridine-3-carboxylic acid methyl ester (320 mg, 0.746 mmol), (toluene-4-sulfonylamino)-acetic acid methyl ester (200 mg, 0.821 mmol), sodium iodide (212 mg, 1.49 mmol) and potassium carbonate (206 mg, 1.49 mmol) in DMF (7 mL) was stirred at r.t. for 16 h. Brine (50 mL) was added and the mixture was extracted with EtOAc. The organic layer was washed with water and dried over MgSO$_4$. After the solvent was evaporated in vacuo, the crude product was chromatographed (0-60% EtOAc/hexanes) to give 371 mg of the title compound. MS: (+) m/z 591.13, 593.08 (M+1, $^{79/81}$Br).

e) 3-Bromo-5-hydroxy-2-oxo-1-phenethyl-1,2-dihydro-[1,7]naphthyridine-6-carboxylic acid methyl ester 5-Bromo-2-{[methoxycarbonylmethyl-(toluene-4-sulfonyl)-amino]-methyl}-6-oxo-1-phenethyl-1,6-dihydro-pyridine-3-carboxylic acid methyl ester (371 mg, 0.628 mmol) was dissolved in 10 mL of MeOH and placed in ice bath. NaOMe solution (0.43 mL, 1.88 mmol, 25 wt % in MeOH) was added and the mixture was stirred for 16 h at r.t. 1 M HCl was added to acidify the mixture, followed by addition of 50 mL of brine. The resulting suspension was extracted with CH$_2$Cl$_2$. The organic layer was dried over MgSO$_4$ and concentrated. The crude product was purified twice by silica gel chromatography (first eluted with 5-60% EtOAc/hexanes+ 2% AcOH, then with 0-20% EtOAc/CH$_2$Cl$_2$) to give 166 mg of the title compound. MS: (+) m/z 403.13, 405.14 (M+1, $^{79/81}$Br).

f) 5-Hydroxy-2-oxo-1-phenethyl-3-phenyl-1,2-dihydro-[1,7]naphthyridine-6-carboxylic acid methyl ester A mixture of 3-bromo-5-hydroxy-2-oxo-1-phenethyl-1,2-dihydro-[1,7]naphthyridine-6-carboxylic acid methyl ester (166 mg, 0.41 mmol), PhSnBu$_3$ (0.16 mL, 0.49 mmol), and PdCl$_2$(PPh$_3$)$_2$ (58 mg, 0.082 mmol) in DMF (4 mL) was heated at 120° C. under nitrogen atmosphere for 2 h. After the mixture was cooled to r.t., brine (10 mL) and EtOAc (50 mL) were added. The aqueous layer was extracted with additional EtOAc and the organic layers were combined, washed with water, and dried over MgSO$_4$. After evaporating the solvent in vacuo, the crude product was chromatographed (0-40% EtOAc/hexanes+2% AcOH) to give 151 mg of the title compound as a light yellow solid. MS: (+) m/z 401.30 (M+1).

g) 3-[(5-Hydroxy-2-oxo-1-phenethyl-3-phenyl-1,2-dihydro-[1,7]naphthyridine-6-carbonyl)-amino]-propionic acid A mixture of 5-hydroxy-2-oxo-1-phenethyl-3-phenyl-1,2-dihydro-[1,7]naphthyridine-6-carboxylic acid methyl ester (30 mg, 0.075 mmol), β-alanine (668 mg, 7.5 mmol) and NaOMe solution (12 mL, 6 mmol, 0.5 M in MeOH) was refluxed for 16 h. After the mixture was cooled to r.t., the solvent was evaporated in vacuo. The residue was dissolved in saturated NaHCO$_3$ and washed several times with ether. The aqueous layer was acidified to pH 2 with 6 M HCl, and the resulting precipitate was isolated by filtration to give 27 mg of the title compound as a yellow solid. MS: (+) m/z 458.30 (M+1).

Example 136

3-[(5-Hydroxy-2-oxo-1,3-diphenyl-1,2-dihydro-[1,7]naphthyridine-6-carbonyl)-amino]-propionic acid a) 3-Phenylamino-but-2-enoic acid ethyl ester

A mixture of 3-oxo-butyric acid ethyl ester (7 mL, 53.7 mmol), aniline (5 g, 53.7 mmol), acetic acid (0.060 mL) and 4 Å molecular sieves (5 g) in EtOH (20 mL) was refluxed for 5 h. After cooling to r.t., the mixture was filtered. EtOAc was added to rinse the solids, and the filtrate was concentrated to give a reddish oil, which was purified by silica gel chromatography (0-10% EtOAc/hexanes) to give 7 g of the title compound as a pale yellow oil. $^1$H NMR (CDCl$_3$, 200 MHz): δ=10.38 (br s, 1H), 7.00-7.40 (m, 5H), 4.69 (s, 1H), 4.15 (q, 2H, J=7.0 Hz), 2.00 (s, 3H), 1.29 (t, 3H, J=7.0 Hz).

b) 4-(1-Phenylamino-ethylidene)-pent-2-enedioic acid 5-ethyl ester 1-methyl ester A mixture of 3-phenylamino-but-2-enoic acid ethyl ester (7 g, 34.1 mmol) and propynoic acid methyl ester (4.6 mL, 51.2 mmol) in MeOH (114 mL) was refluxed for 48 h. The solvent was evaporated, and the crude oil was purified by silica gel chromatography (0-20% EtOAc/hexanes) to give 5.88 g of the title compound as an orange oil. MS: (+) m/z 290.27 (M+1).

c) 5-Bromo-2-methyl-6-oxo-1-phenyl-1,6-dihydro-pyridine-3-carboxylic acid methyl ester MeOH (200 mL) was added to a flask containing 4-(1-phenylamino-ethylidene)-pent-2-enedioic acid 5-ethyl ester 1-methyl ester (5.88 g, 20.3 mmol). NaOMe solution (4.7 mL, 20.3 mmol, 4.375 M in MeOH) and N-bromosuccinimide (4.35 g, 24.4 mmol) were added, and the resulting mixture was refluxed for 1 h. After cooling to r.t., the solvent was evaporated in vacuo. The residue was partitioned between saturated $NH_4Cl$ and $CH_2Cl_2$. The aqueous layer was extracted with additional $CH_2Cl_2$ and the organic layers were combined, dried over $MgSO_4$, and concentrated. The crude product was chromatographed (0-45% EtOAc/hexanes) to give 2.51 g of the title compound (containing about 14% of the corresponding ethyl ester) as a yellow solid. MS: (+) m/z 343.93, 346.07 (M+Na, $^{79/81}Br$).

d) 5-Bromo-2-bromomethyl-6-oxo-1-phenyl-1,6-dihydro-pyridine-3-carboxylic acid methyl ester A mixture of 5-bromo-2-methyl-6-oxo-1-phenyl-1,6-dihydro-pyridine-3-carboxylic acid methyl ester (2.51 g, 7.8 mmol), N-bromosuccinimide (1.53 g, 8.6 mmol), and benzoyl peroxide (189 mg, 0.78 mmol) in $CCl_4$ (60 mL) was refluxed for 16 h. After cooling to r.t., the solvent was evaporated in vacuo, and the residue was chromatographed (0-20% EtOAc/hexanes) to give 2.82 g of the title compound. MS: (+) m/z 402.06 (M+1)

e) 5-Bromo-2-{[methoxycarbonylmethyl-(toluene-4-sulfonyl)-amino]-methyl}-6-oxo-1-phenyl-1,6-dihydro-pyridine-3-carboxylic acid methyl ester A mixture of 5-bromo-2-bromomethyl-6-oxo-1-phenyl-1,6-dihydro-pyridine-3-carboxylic acid methyl ester (2.82 g, 7.03 mmol), (toluene-4-sulfonylamino)-acetic acid methyl ester (1.71 g, 7.03 mmol), sodium iodide (2 g, 14.1 mmol) and potassium carbonate (1.94 g, 14.1 mmol) in DMF (60 mL) was stirred at r.t. for 48 h. Brine (120 mL) was added and the mixture was extracted with EtOAc. The organic layer was washed with water and dried over $MgSO_4$. After the solvent was evaporated in vacuo, the crude product was chromatographed (0-60% EtOAc/hexanes) to give 2.67 g of the title compound. MS: (+) m/z 585.21, 587.10 (M+Na, $^{79/81}Br$).

f) 3-Bromo-5-hydroxy-2-oxo-1-phenyl-1,2-dihydro-[1,7]naphthyridine-6-carboxylic acid methyl ester 5-Bromo-2-{[methoxycarbonylmethyl-(toluene-4-sulfonyl)-amino]-methyl}-6-oxo-1-phenyl-1,6-dihydro-pyridine-3-carboxylic acid methyl ester (2.67 g, 4.74 mmol) was dissolved in 80 mL of MeOH and placed in ice bath. NaOMe solution (3.3 mL, 14.2 mmol, 4.375 M in MeOH) was added and the mixture was stirred for 16 h at r.t. 1 M HCl was added to acidify the mixture, followed by addition of 100 mL of brine. The resulting suspension was extracted with $CH_2Cl_2$. The organic layer was dried over $MgSO_4$ and concentrated. The crude product was purified by silica gel chromatography (0-20% EtOAc/$CH_2Cl_2$) to give 1.54 g of the title compound as a light yellow solid. MS: (−) m/z 373.15, 375.16 (M-1, $^{79/81}Br$).

g) 5-Hydroxy-2-oxo-1,3-diphenyl-1,2-dihydro-[1,7] naphthyridine-6-carboxylic acid methyl ester A mixture of 3-bromo-5-hydroxy-2-oxo-1-phenyl-1,2-dihydro-[1,7]naphthyridine-6-carboxylic acid methyl ester (300 mg, 0.8 mmol), $PhSnBu_3$ (0.31 mL, 0.96 mmol), and $PdCl_2(PPh_3)_2$ (112 mg, 0.16 mmol) in DMF (8 mL) was heated at 120° C. under nitrogen atmosphere for 2 h. After the mixture was cooled to r.t., brine (10 mL) and EtOAc (50 mL) were added. The aqueous layer was extracted with additional EtOAc and the organic layers were combined, washed with water, and dried over $MgSO_4$. After evaporating the solvent in vacuo, the crude product was chromatographed (0-50% EtOAc/hexanes+2% AcOH) to give 195 mg of the title compound as a light yellow solid. MS: (−) m/z 371.32 (M−1).

h) 3-[(5-Hydroxy-2-oxo-1,3-diphenyl-1,2-dihydro-[1,7]naphthyridine-6-carbonyl)-amino]-propionic acid A mixture of 5-hydroxy-2-oxo-1,3-diphenyl-1,2-dihydro-[1,7]naphthyridine-6-carboxylic acid methyl ester (30 mg, 0.081 mmol), β-alanine (431 mg, 4.84 mmol) and NaOMe solution (8 mL, 4.03 mmol, 0.5 M in MeOH) was refluxed for 16 h. After the mixture was cooled to r.t., the solvent was evaporated in vacuo. The residue was dissolved in water and washed several times with ether. The aqueous layer was acidified to pH 2 with 4 M HCl, and the resulting precipitate was isolated by filtration to give 30 mg of the title compound as a light yellow solid. MS: (+) m/z 430.27 (M+1).

Example 137

3-[(3-Benzyl-5-hydroxy-2-oxo-1-phenyl-1,2-dihydro-[1,7]naphthyridine-6-carbonyl)-amino]-propionic acid a) 3-Benzyl-5-hydroxy-2-oxo-1-phenyl-1,2-dihydro-[1,7]naphthyridine-6-carboxylic acid methyl ester A mixture of 3-bromo-5-hydroxy-2-oxo-1-phenyl-1,2-dihydro-[1,7]naphthyridine-6-carboxylic acid methyl ester (120 mg, 0.323 mmol), benzylzinc bromide solution (1.6 mL, 0.806 mmol, 0.5 M in THF), and $Pd(PPh_3)_4$ (37 mg, 0.0323 mmol) in THF (6 mL) was refluxed under nitrogen atmosphere for 16 h. After the mixture was cooled to r.t., saturated $NH_4Cl$ and EtOAc were added. The aqueous layer was extracted with additional EtOAc, and the organic layers were combined and dried over $MgSO_4$. After evaporating the solvent in vacuo, the crude product was dissolved in a mixture of EtOAc/EtOH (1:1). To the resulting mixture were added 50 mg of 10% Pd/C and 50 mg of sodium acetate. The mixture was placed under $H_2$ atmosphere for 1 h, then filtered through a pad of Celite. The filtrate was concentrated, and the residue was chromatographed (0-50% EtOAc/hexanes+2% AcOH) to give 25 mg of the title compound. MS: (+) m/z 387.32 (M+1).

b) 3-[(3-Benzyl-5-hydroxy-2-oxo-1-phenyl-1,2-dihydro-[1,7]naphthyridine-6-carbonyl)-amino]-propionic acid A mixture of 3-benzyl-5-hydroxy-2-oxo-1-phenyl-1,2-dihydro-[1,7]naphthyridine-6-carboxylic acid methyl ester (25 mg, 0.065 mmol), β-alanine (767 mg, 8.6 mmol) and NaOMe solution (13 mL, 6.5 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 2. The organic layer was dried over $MgSO_4$ and concentrated. The crude product was dissolved in saturated $NaHCO_3$ and washed several times with ether. The aqueous layer was acidified to pH about 2, and the resulting precipitate was isolated by filtration to give 13 mg of the title compound. MS: (+) m/z 444.25 (M+1).

Example 138

3-[(5-Hydroxy-1-methyl-2-oxo-3-phenyl-1,2-dihydro-[1,7]naphthyridine-6-carbonyl)-amino]-propionic acid a) 4-(1-Methylamino-ethylidene)-pent-2-enedioic acid dimethyl ester Methylamine (20 mL, 40 mmol, 2 M in THF) was dissolved in MeOH (130 mL). 3-Oxo-butyric acid methyl ester (5.7 mL, 48 mmol) was added, and the mixture was heated at 90° C. for 3 h in a sealed tube. After cooling the mixture to r.t., propynoic acid methyl ester (5.3 mL, 60 mmol) was added. The resulting mixture was then refluxed for 48 h. After cooling to r.t., the solvent was evaporated, and the crude residue was purified by silica gel chromatography (0-50% EtOAc/hexanes) to give 0.97 g of the title compound as a light yellow solid. $^1$H NMR (CDCl$_3$, 200 MHz): δ=10.55 (br s, 1H), 7.75 (d, 1H, J=15.4 Hz), 6.06 (d, 1H, J=15.4 Hz), 3.75 (s, 3H), 3.72 (s, 3H), 3.04 (d, 3H, J=4.8 Hz), 2.26 (s, 3H).

b) 5-Bromo-1,2-dimethyl-6-oxo-1,6-dihydro-pyridine-3-carboxylic acid methyl ester MeOH (45 mL) was added to a flask containing 4-(1-methylamino-ethylidene)-pent-2-enedioic acid dimethyl ester (0.97 g, 4.55 mmol). NaOMe solution (1.04 mL, 4.55 mmol, 4.375 M in MeOH) and N-bromosuccinimide (0.97 g, 5.46 mmol) were added, and the resulting mixture was refluxed for 1 h. After cooling to r.t., the solvent was evaporated in vacuo. The residue was partitioned between saturated NH$_4$Cl and CH$_2$Cl$_2$. The aqueous layer was extracted with additional CH$_2$Cl$_2$ and the organic layers were combined, dried over MgSO$_4$, and concentrated. The crude product was chromatographed (0-50% EtOAc/hexanes) to give 540 mg of the title compound. MS: (+) m/z 260.22, 262.18 (M+Na, $^{79/81}$Br).

c) 5-Bromo-2-bromomethyl-1-methyl-6-oxo-1,6-dihydro-pyridine-3-carboxylic acid methyl ester A mixture of 5-bromo-1,2-dimethyl-6-oxo-1,6-dihydro-pyridine-3-carboxylic acid methyl ester (540 mg, 2.08 mmol), N-bromosuccinimide (388 mg, 2.18 mmol), and benzoyl peroxide (50 mg, 0.208 mmol) in CCl$_4$ (20 mL) was refluxed for 16 h. The solvent was evaporated in vacuo, and the residue was chromatographed (0-50% EtOAc/hexanes) to give 363 mg of the title compound. MS: (+) m/z 340.02 (M+1).

d) 5-Bromo-2-{[methoxycarbonylmethyl-(toluene-4-sulfonyl)-amino]-methyl}-1-methyl-6-oxo-1,6-dihydro-pyridine-3-carboxylic acid methyl ester A mixture of 5-bromo-2-bromomethyl-1-methyl-6-oxo-1,6-dihydro-pyridine-3-carboxylic acid methyl ester (363 mg, 1.07 mmol), (toluene-4-sulfonylamino)-acetic acid methyl ester (260 mg, 1.07 mmol), sodium iodide (321 mg, 2.14 mmol) and potassium carbonate (296 mg, 2.14 mmol) in DMF (10 mL) was stirred at r.t. for 16 h. Brine (30 mL) was added and the mixture was extracted with EtOAc. The organic layer was washed with water and dried over MgSO$_4$. After the solvent was evaporated in vacuo, the crude product was chromatographed (0-70% EtOAc/hexanes) to give 292 mg of the title compound. MS: (+) m/z 501.13, 503.08 (M+1, $^{79/81}$Br).

e) 3-Bromo-5-hydroxy-1-methyl-2-oxo-1,2-dihydro-[1,7]naphthyridine-6-carboxylic acid methyl ester 5-Bromo-2-{[methoxycarbonylmethyl-(toluene-4-sulfonyl)-amino]-methyl}-1-methyl-6-oxo-1,6-dihydro-pyridine-3-carboxylic acid methyl ester (292 mg, 0.58 mmol) was dissolved in 10 mL of MeOH and placed in ice bath. NaOMe solution (0.4 mL, 1.75 mmol, 4.375 M in MeOH) was added and the mixture was stirred for 16 h at r.t. 0.1 M HCl was added to acidify the mixture, and the resulting suspension was extracted with CH$_2$Cl$_2$. The organic layer was dried over MgSO$_4$ and concentrated. The crude product was purified by silica gel chromatography (0-5% MeOH/CH$_2$Cl$_2$) to give 150 mg of the title compound as an off-white solid. MS: (+) m/z 313.13, 315.14 (M+1, $^{79/81}$Br).

f) 5-Hydroxy-1-methyl-2-oxo-3-phenyl-1,2-dihydro-[1,7]naphthyridine-6-carboxylic acid methyl ester A mixture of 3-bromo-5-hydroxy-1-methyl-2-oxo-1,2-dihydro-[1,7]naphthyridine-6-carboxylic acid methyl ester (60 mg, 0.19 mmol), PhSnBu$_3$ (0.075 mL, 0.23 mmol), and PdCl$_2$(PPh$_3$)$_2$ (27 mg, 0.038 mmol) in DMF (3 mL) was heated at 120° C. under nitrogen atmosphere for 2 h. After the mixture was cooled to r.t., brine and EtOAc were added. 1 M HCl was added until pH was about 2. The aqueous layer was extracted with additional EtOAc and the organic layers were combined, washed with water, and dried over MgSO$_4$. After evaporating the solvent in vacuo, the crude product was chromatographed (0-60% EtOAc/hexanes+2% AcOH) to give 35 mg of the title compound. MS: (+) m/z 311.24 (M+1).

g) 3-[(5-Hydroxy-1-methyl-2-oxo-3-phenyl-1,2-dihydro-[1,7]naphthyridine-6-carbonyl)-amino]-propionic acid A mixture of 5-hydroxy-1-methyl-2-oxo-3-phenyl-1,2-dihydro-[1,7]naphthyridine-6-carboxylic acid methyl ester (35 mg, 0.11 mmol), β-alanine (805 mg, 9.0 mmol) and NaOMe solution (13.5 mL, 6.8 mmol, 0.5 M in MeOH) was refluxed for 48 h. After the mixture was cooled to r.t., the solvent was evaporated in vacuo. The residue was partitioned between EtOAc and water. 1 M HCl was added with vigorous stirring until pH was about 1. The organic layer was dried over MgSO$_4$ and concentrated. The residue was dissolved in saturated NaHCO$_3$ and washed several times with ether. The aqueous layer was acidified to pH 2 with 6 M HCl, and the resulting suspension was extracted with CH$_2$Cl$_2$. The organic layer was dried over MgSO$_4$ and concentrated to give 30 mg of the title compound as a light yellow solid. MS: (−) m/z 366.28 (M-1).

Example 139

3-{[1-Benzyl-3-(4-cyano-phenyl)-5-hydroxy-2-oxo-1,2-dihydro-[1,7]naphthyridine-6-carbonyl]-amino}-propionic acid a) 1-Benzyl-3-(4-cyano-phenyl)-5-hydroxy-2-oxo-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (80 mg, 0.206 mmol), 4-cyanophenylboronic acid (45 mg, 0.308 mmol), $K_3PO_4$ (87 mg, 0.411 mmol), $H_2O$ (7.4 mg, 0.411 mmol), SPhos (5.1 mg, 0.0123 mmol) and Pd(OAc)$_2$ (4.2 mg, 0.00617 mmol) in toluene (3 mL) was heated at 100° C. under nitrogen atmosphere for 16 h. After the mixture was cooled to r.t., brine (10 mL) and EtOAc (20 mL) were added. 1 M HCl was added with stirring until pH was about 3, and the organic layer was dried over MgSO$_4$ and concentrated. The crude product was purified by silica gel chromatography (0-60% EtOAc/hexanes+2% AcOH) to give 40 mg of the title compound. MS: (+) m/z 412.26 (M+1).

b) 3-{[1-Benzyl-3-(4-cyano-phenyl)-5-hydroxy-2-oxo-1,2-dihydro-[1,7]naphthyridine-6-carbonyl]-amino}-propionic acid A mixture of 1-benzyl-3-(4-cyano-phenyl)-5-hydroxy-2-oxo-1,2-dihydro-[1,7]-naphthyridine-6-carboxylic acid methyl ester (40 mg, 0.097 mmol), β-alanine (694 mg, 7.8 mmol) and NaOMe solution (11.7 mL, 5.8 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 2. The organic layer was dried over MgSO$_4$ and concentrated. The crude solid obtained was dissolved in saturated NaHCO$_3$ and washed several times with ether. The aqueous layer was acidified to pH about 2, and the resulting precipitate was isolated by filtration to give 27 mg of the title compound. MS: (−) m/z 467.24 (M−1).

Example 140

3-{[1-Benzyl-5-hydroxy-3-(4-methoxy-phenyl)-2-oxo-1,2-dihydro-[1,7]naphthyridine-6-carbonyl]-amino}-propionic acid a) 1-Benzyl-5-hydroxy-3-(4-methoxy-phenyl)-2-oxo-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (60 mg, 0.15 mmol), 4-methoxyphenylboronic acid (35 mg, 0.23 mmol), $K_3PO_4$ (65 mg, 0.31 mmol), SPhos (3.2 mg, 0.0077 mmol) and Pd(OAc)$_2$ (3.1 mg, 0.0046 mmol) in toluene (3 mL) was heated at 100° C. under nitrogen atmosphere for 16 h. After the mixture was cooled to r.t., brine and EtOAc were added. 1 M HCl was added with stirring until pH was about 3, and the aqueous layer extracted with additional EtOAc. The organic layers were combined, dried over MgSO$_4$ and concentrated. The crude product was purified by silica gel chromatography (0-60% EtOAc/hexanes+2% AcOH) to give 13 mg of the title compound. MS: (+) m/z 417.30 (M+1).

b) 3-{[1-Benzyl-5-hydroxy-3-(4-methoxy-phenyl)-2-oxo-1,2-dihydro-[1,7]naphthyridine-6-carbonyl]-amino}-propionic acid A mixture of 1-benzyl-5-hydroxy-3-(4-methoxy-phenyl)-2-oxo-1,2-dihydro-[1,7]naphthyridine-6-carboxylic acid methyl ester (30 mg, 0.072 mmol), β-alanine (854 mg, 9.6 mmol) and NaOMe solution (14.4 mL, 7.2 mmol, 0.5 M in MeOH) was refluxed for 16 h. After the mixture was cooled to r.t., the solvent was evaporated in vacuo. The residue was dissolved in saturated NaHCO$_3$ and washed several times with ether. The aqueous layer was acidified to pH about 2 with 6 M HCl, and the resulting precipitate was isolated by filtration to give 25 mg of the title compound. MS: (+) m/z 474.30 (M+1).

Example 141

3-[(1-Benzyl-5-hydroxy-2-oxo-3-thiazol-2-yl-1,2-dihydro-[1,7]naphthyridine-6-carbonyl)-amino]-propionic acid a) 1-Benzyl-5-hydroxy-2-oxo-3-thiazol-2-yl-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (80 mg, 0.21 mmol), 2-tributylstannanyl-thiazole (0.1 mL, 0.31 mmol), and PdCl$_2$(PPh$_3$)$_2$ (29 mg, 0.041 mmol) in DMF (4 mL) was heated at 120° C. under nitrogen atmosphere for 2 h. After the mixture was cooled to r.t., brine (10 mL) and EtOAc (20 mL) were added. 1 M HCl was added with stirring until pH was about 3-4, and the organic layer was washed with water and dried over MgSO$_4$. After evaporating the solvent, the crude product was purified by silica gel chromatography (0-60% EtOAc/hexanes+2% AcOH) to give 28 mg of the title compound. MS: (+) m/z 394.25 (M+1).

b) 3-[(1-Benzyl-5-hydroxy-2-oxo-3-thiazol-2-yl-1,2-dihydro-[1,7]naphthyridine-6-carbonyl)-amino]-propionic acid A mixture of 1-benzyl-5-hydroxy-2-oxo-3-thiazol-2-yl-1,2-dihydro-[1,7]naphthyridine-6-carboxylic acid methyl ester (28 mg, 0.071 mmol), β-alanine (844 mg, 9.5 mmol) and NaOMe solution (14 mL, 7.1 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3. The organic layer was dried over MgSO$_4$ and concentrated. The crude solid was dissolved in saturated NaHCO$_3$ and washed several times with ether. The aqueous layer was acidified to pH about 3 with 6 M HCl, and the resulting precipitate was isolated by filtration to give 6.4 mg of the title compound. MS: (+) m/z 451.18 (M+1).

Example 142

(R)-3-[(1-Benzyl-5-hydroxy-2-oxo-3-phenyl-1,2-dihydro-[1,7]naphthyridine-6-carbonyl)-amino]-butyric acid A mixture of 1-benzyl-5-hydroxy-2-oxo-3-phenyl-1,2-dihydro-[1,7]naphthyridine-6-carboxylic acid methyl ester (35 mg, 0.090 mmol), (R)-3-amino-butyric acid (94 mg, 0.90 mmol) and NaOMe (39 mg, 0.73 mmol) in 2-methoxyethanol (10 mL) was refluxed for 3 h. After the mixture was cooled to r.t., the solvent was evaporated in vacuo. The residue was dissolved in saturated NaHCO$_3$ and washed with ether. The aqueous layer was acidified to pH about 2 with 6 M HCl, and the resulting precipitate was isolated by filtration to give 28 mg of the title compound as a yellow solid. MS: (+) m/z 458.30 (M+1).

Example 143

3-{[5-Hydroxy-1-(4-methoxy-benzyl)-2-oxo-3-phenyl-1,2-dihydro-[1,7]naphthyridine-6-carbonyl]-amino}-propionic acid a) 4-[1-(4-Methoxy-benzylamino)-ethylidene]-pent-2-enedioic acid dimethyl ester A mixture of 4-methoxybenzyl amine (3 g, 21.9 mmol) and 3-oxo-butyric acid methyl ester (2.83 mL, 26.2 mmol) in MeOH (80 mL) was refluxed for 2 h. Propynoic acid methyl ester (2.92 mL, 32.8 mmol) was added, and the resulting mixture was refluxed for 48 h. After cooling to r.t., the solvent was evaporated, and the crude residue was recrystallized from MeOH to give 5 g of the title compound as a yellow solid. $^1$H NMR (CDCl$_3$, 200 MHz): δ=10.87 (br s, 1H), 7.76 (d, 1H, J=15.4 Hz), 7.18 (d, 2H, J=8.8 Hz), 6.89 (d, 2H, J=8.8 Hz), 6.09 (d, 1H, J=15.4 Hz), 4.50 (d, 2H, J=5.8 Hz), 3.80 (s, 3H), 3.77 (s, 3H), 3.73 (s, 3H), 2.27 (s, 3H).

b) 5-Bromo-1-(4-methoxy-benzyl)-2-methyl-6-oxo-1,6-dihydro-pyridine-3-carboxylic acid methyl ester MeOH (120 mL) was added to a flask containing 4-[1-(4-methoxy-benzylamino)-ethylidene]-pent-2-enedioic acid dimethyl ester (5 g, 15.7 mmol). NaOMe solution (3.6 mL, 15.7 mmol, 4.375 M in MeOH) and N-bromosuccinimide (3.35 g, 18.8 mmol) were added, and the resulting mixture was refluxed for 1 h. After cooling to r.t., the solvent was evaporated in vacuo. The residue was partitioned between saturated NH$_4$Cl and CH$_2$Cl$_2$. The aqueous layer was extracted with additional CH$_2$Cl$_2$ and the organic layers were combined, dried over MgSO$_4$, and concentrated. The crude product was chromatographed (0-50% EtOAc/hexanes) to give 3.5 g of the title compound. MS: (+) m/z 388.14, 390.15 (M+Na, $^{79/81}$Br).

c) 5-Bromo-2-bromomethyl-1-(4-methoxy-benzyl)-6-oxo-1,6-dihydro-pyridine-3-carboxylic acid methyl ester A mixture of 5-bromo-1-(4-methoxy-benzyl)-2-methyl-6-oxo-1,6-dihydro-pyridine-3-carboxylic acid methyl ester (3.5 g, 9.6 mmol), N-bromosuccinimide (1.87 g, 10.5 mmol), and benzoyl peroxide (231 mg, 0.96 mmol) in CCl$_4$ (90 mL) was refluxed for 16 h. The solvent was evaporated in vacuo, and the residue was chromatographed (0-25% EtOAc/hexanes) to give 2.55 g of the title compound. MS: (+) m/z 468.00 (M+Na).

d) 5-Bromo-1-(4-methoxy-benzyl)-2-{[methoxycarbonylmethyl-(toluene-4-sulfonyl)-amino]-methyl}-6-oxo-1,6-dihydro-pyridine-3-carboxylic acid methyl ester A mixture of 5-bromo-2-bromomethyl-1-(4-methoxy-benzyl)-6-oxo-1,6-dihydro-pyridine-3-carboxylic acid methyl ester (2.55 g, 5.73 mmol), (toluene-4-sulfonylamino)-acetic acid methyl ester (1.32 g, 5.44 mmol), sodium iodide (1.72 g, 11.5 mmol) and potassium carbonate (1.58 g, 11.5 mmol) in DMF (50 mL) was stirred at r.t. for 16 h. Brine (100 mL) was added and the mixture was extracted with EtOAc. The organic layer was washed with water and dried over MgSO$_4$. After the solvent was evaporated in vacuo, the crude product was chromatographed (0-60% EtOAc/hexanes) to give 2.03 g of the title compound as a viscous oil. MS: (+) m/z 629.17, 631.06 (M+Na, $^{79/81}$Br).

e) 3-Bromo-5-hydroxy-1-(4-methoxy-benzyl)-2-oxo-1,2-dihydro-[1,7]naphthyridine-6-carboxylic acid methyl ester 5-Bromo-1-(4-methoxy-benzyl)-2-{[methoxycarbonylmethyl-(toluene-4-sulfonyl)-amino]-methyl}-6-oxo-1,6-dihydro-pyridine-3-carboxylic acid methyl ester (2.03 g, 3.34 mmol) was dissolved in 80 mL of MeOH and placed in ice bath. NaOMe solution (2.3 mL, 10.0 mmol, 4.375 M in MeOH) was added and the mixture was stirred for 16 h at r.t. 0.1 M HCl was added to acidify the mixture, and the resulting suspension was extracted with CH$_2$Cl$_2$. The organic layer was dried over MgSO$_4$ and concentrated. The crude product was purified by silica gel chromatography (0-20% EtOAc/CH$_2$Cl$_2$) to give 1.02 g of the title compound as an off-white solid. MS: (+) m/z 419.19, 421.14 (M+1, $^{79/81}$Br).

f) 5-Hydroxy-1-(4-methoxy-benzyl)-2-oxo-3-phenyl-1,2-dihydro-[1,7]naphthyridine-6-carboxylic acid methyl ester A mixture of 3-bromo-5-hydroxy-1-(4-methoxy-benzyl)-2-oxo-1,2-dihydro-[1,7]naphthyridine-6-carboxylic acid methyl ester (180 mg, 0.43 mmol), PhSnBu$_3$ (0.17 mL, 0.52 mmol), and PdCl$_2$(PPh$_3$)$_2$ (60 mg, 0.086 mmol) in DMF (5 mL) was heated at 120° C. under nitrogen atmosphere for 2 h. After the mixture was cooled to r.t., brine (10 mL) and EtOAc (20 mL) were added. 0.1 M HCl was added until pH was about 3. The aqueous layer was extracted with additional EtOAc and the organic layers were combined, washed with water, and dried over MgSO$_4$. After evaporating the solvent in vacuo, the crude product was chromatographed (0-60% EtOAc/hexanes+2% AcOH) to give 140 mg of the title compound as a light yellow solid. MS: (+) m/z 417.30 (M+1).

g) 3-{[5-Hydroxy-1-(4-methoxy-benzyl)-2-oxo-3-phenyl-1,2-dihydro-[1,7]naphthyridine-6-carbonyl]-amino}-propionic acid A mixture of 5-hydroxy-1-(4-methoxy-benzyl)-2-oxo-3-phenyl-1,2-dihydro-[1,7]naphthyridine-6-carboxylic acid methyl ester (35 mg, 0.084 mmol), β-alanine (750 mg, 8.4 mmol) and NaOMe solution (13 mL, 6.3 mmol, 0.5 M in MeOH) was refluxed for 16 h. After the mixture was cooled to r.t., the solvent was evaporated in vacuo. The residue was dissolved in saturated NaHCO$_3$ and washed several times with ether. The aqueous layer was acidified to pH 2 with 6 M HCl, and the resulting precipitate was isolated by filtration to give 31 mg of the title compound as a yellow solid. MS: (+) m/z 474.30 (M+1).

Example 144

3-{[1-(4-Cyano-benzyl)-5-hydroxy-2-oxo-3-phenyl-1,2-dihydro-[1,7]naphthyridine-6-carbonyl]-amino}-propionic acid a) 4-[1-(4-Cyano-benzylamino)-ethylidene]-pent-2-enedioic acid dimethyl ester A mixture of 4-cyanobenzyl amine (3 g, 22.7 mmol) and 3-oxo-butyric acid methyl ester (2.94 mL, 27.2 mmol) in MeOH (80 mL) was refluxed for 2 h. Propynoic acid methyl ester (3.03 mL, 34 mmol) was added, and the resulting mixture was refluxed for 48 h. After cooling to r.t., the solvent was evaporated, and the crude residue was recrystallized from MeOH to give 3.35 g of the title compound as a light yellow solid. $^1$H NMR (CDCl$_3$, 200 MHz): δ=10.97 (br s, 1H), 7.72 (d, 1H, J=15.4 Hz), 7.67 (d, 2H, J=8.8 Hz), 7.37 (d, 2H, J=8.4 Hz), 6.11 (d, 1H, J=15.8 Hz), 4.63 (d, 2H, J=6.0 Hz), 3.79 (s, 3H), 3.73 (s, 3H), 2.21 (s, 3H).

b) 5-Bromo-1-(4-cyano-benzyl)-2-methyl-6-oxo-1,6-dihydro-pyridine-3-carboxylic acid methyl ester MeOH (90 mL) was added to a flask containing 4-[1-(4-cyano-benzylamino)-ethylidene]-pent-2-enedioic acid dimethyl ester (3.35 g, 10.7 mmol). NaOMe solution (2.44 mL, 10.7 mmol, 4.375 M in MeOH) and N-bromosuccinimide (2.28 g, 12.8 mmol) were added, and the resulting mixture was refluxed for 1 h. After cooling to r.t., the solvent was evaporated in vacuo. Saturated NH$_4$Cl (120 mL) was added, and the resulting mixture was extracted with CH$_2$Cl$_2$. The organic layer was dried over MgSO$_4$ and concentrated. The crude product was chromatographed (0-40% EtOAc/hexanes) to give 2.05 g of the title compound. MS: (+) m/z 361.18, 363.14 (M+Na, $^{79/81}$Br).

c) 5-Bromo-2-bromomethyl-1-(4-cyano-benzyl)-6-oxo-1,6-dihydro-pyridine-3-carboxylic acid methyl ester A mixture of 5-bromo-1-(4-cyano-benzyl)-2-methyl-6-oxo-1,6-dihydro-pyridine-3-carboxylic acid methyl ester (2.05 g, 5.68 mmol), N-bromosuccinimide (1.11 g, 6.25 mmol), and benzoyl peroxide (0.14 g, 0.568 mmol) in CCl$_4$ (60 mL) was refluxed for 16 h. The solvent was evaporated in vacuo, and the residue was chromatographed (0-45% EtOAc/hexanes) to give 2.27 g of the title compound as a white solid. $^1$H NMR (CDCl$_3$, 200 MHz): δ=8.42 (s, 1H), 7.65 (d, 2H, J=8.2 Hz), 7.20-7.40 (m, 2H), 5.69 (br s, 2H), 4.87 (br s, 2H), 3.91 (s, 3H).

d) 5-Bromo-1-(4-cyano-benzyl)-2-{[methoxycarbonylmethyl-(toluene-4-sulfonyl)-amino]-methyl}-6-oxo-1,6-dihydro-pyridine-3-carboxylic acid methyl ester A mixture of 5-bromo-2-bromomethyl-1-(4-cyano-benzyl)-6-oxo-1,6-dihydro-pyridine-3-carboxylic acid methyl ester (2.27 g, 5.16 mmol), (toluene-4-sulfonylamino)-acetic acid methyl ester (1.23 g, 5.06 mmol), sodium iodide (1.55 g, 10.3 mmol) and potassium carbonate (1.43 g, 10.3 mmol) in DMF (40 mL) was stirred at r.t. for 16 h. Brine (100 mL) and EtOAc (150 mL) were added, and the resulting mixture was extracted with EtOAc. The organic layers were combined, washed with water and dried over MgSO$_4$. After the solvent was evaporated in vacuo, the crude product was chromatographed (0-80% EtOAc/hexanes) to give 2 g of the title compound. MS: (+) m/z 602.09, 604.04 (M+1, $^{79/81}$Br).

e) 3-Bromo-1-(4-cyano-benzyl)-5-hydroxy-2-oxo-1,2-dihydro-[1,7]naphthyridine-6-carboxylic acid methyl ester 5-Bromo-1-(4-cyano-benzyl)-2-{[methoxycarbonylmethyl-(toluene-4-sulfonyl)-amino]-methyl}-6-oxo-1,6-dihydro-pyridine-3-carboxylic acid methyl ester (2 g, 3.32 mmol) was dissolved in 60 mL of MeOH and placed in ice bath. NaOMe solution (2.3 mL, 9.97 mmol, 4.375 M in MeOH) was added and the mixture was stirred for 16 h at r.t. 1 M HCl was added to acidify the mixture, and the resulting suspension was extracted with CH$_2$Cl$_2$. The organic layer was dried over MgSO$_4$ and concentrated. The crude product was purified by silica gel chromatography (0-20% EtOAc/CH$_2$Cl$_2$) to give 1 g of the title compound. MS: (−) m/z 412.07, 414.02 (M-1, $^{79/81}$Br).

f) 1-(4-Cyano-benzyl)-5-hydroxy-2-oxo-3-phenyl-1,2-dihydro-[1,7]naphthyridine-6-carboxylic acid methyl ester A mixture of 3-bromo-1-(4-cyano-benzyl)-5-hydroxy-2-oxo-1,2-dihydro-[1,7]naphthyridine-6-carboxylic acid methyl ester (100 mg, 0.24 mmol), PhSnBu$_3$ (0.1 mL, 0.29 mmol), and PdCl$_2$(PPh$_3$)$_2$ (34 mg, 0.048 mmol) in DMF (5 mL) was heated at 120° C. under nitrogen atmosphere for 2 h. After the mixture was cooled to r.t., brine (5 mL) and EtOAc (15 mL) were added. 1 M HCl was added until pH was about 3. The aqueous layer was extracted with additional EtOAc and the organic layers were combined, washed with water, and dried over MgSO$_4$. After evaporating the solvent in vacuo, the crude product was chromatographed (0-80% EtOAc/hexanes+2% AcOH) to give 40 mg of the title compound. MS: (+) m/z 412.26 (M+1).

g) 3-{[1-(4-Cyano-benzyl)-5-hydroxy-2-oxo-3-phenyl-1,2-dihydro-[1,7]naphthyridine-6-carbonyl]-amino}-propionic acid A mixture of 1-(4-cyano-benzyl)-5-hydroxy-2-oxo-3-phenyl-1,2-dihydro-[1,7]naphthyridine-6-carboxylic acid methyl ester (40 mg, 0.097 mmol), β-alanine (694 mg, 7.9 mmol) and NaOMe solution (12 mL, 5.8 mmol, 0.5 M in MeOH) was refluxed for 16 h. After the mixture was cooled to r.t., the solvent was evaporated in vacuo. The residue was dissolved in saturated NaHCO$_3$ and washed several times with ether. The aqueous layer was acidified to pH 2 with 6 M HCl, and the resulting precipitate was isolated by filtration to give 31 mg of the title compound as a brown solid. MS: (−) m/z 467.24 (M−1).

Example 145

3-[(1-Benzyl-5-hydroxy-2-oxo-3-pyrazin-2-yl-1,2-dihydro-[1,7]naphthyridine-6-carbonyl)-amino]-propionic acid a) 1-Benzyl-5-hydroxy-2-oxo-3-pyrazin-2-yl-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (80 mg, 0.21 mmol), 2-tributylstannanyl-pyrazine (0.078 mL, 0.25 mmol), and PdCl$_2$(PPh$_3$)$_2$ (29 mg, 0.041 mmol) in DMF (4 mL) was heated at 120° C. under nitrogen atmosphere for 2 h. After the mixture was cooled to r.t., brine (10 mL) and EtOAc (20 mL) were added. 1 M HCl was added with stirring until pH was about 3-4, and the organic layer was washed with water and brine, and dried over MgSO$_4$. After evaporating the solvent, the crude product was purified by silica gel chromatography (20-100% EtOAc/hexanes+2% AcOH) to give 40 mg of the title compound as a light yellow solid. MS: (+) m/z 389.27 (M+1).

b) 3-[(1-Benzyl-5-hydroxy-2-oxo-3-pyrazin-2-yl-1, 2-dihydro-[1,7]naphthyridine-6-carbonyl)-amino]-propionic acid A mixture of 1-benzyl-5-hydroxy-2-oxo-3-pyrazin-2-yl-1, 2-dihydro-[1,7]naphthyridine-6-carboxylic acid methyl ester (40 mg, 0.10 mmol), β-alanine (735 mg, 8.25 mmol) and NaOMe solution (12.4 mL, 6.19 mmol, 0.5 M in MeOH) was refluxed for 16 h. After the mixture was cooled to r.t., the solvent was evaporated in vacuo. The residue was partitioned between EtOAc and water. 1 M HCl was added with vigorous stilling until pH was about 2. The organic layer was dried over MgSO$_4$ and concentrated. The crude solid was dissolved in saturated NaHCO$_3$ and washed several times with ether. The aqueous layer was acidified to pH about 1 with 6 M HCl, and the resulting precipitate was isolated by filtration to give 28 mg of the title compound as a light yellow solid. MS: (+) m/z 446.27 (M+1).

Example 146

3-{[1-Benzyl-5-hydroxy-3-(4-methane sulfonyl-phenyl)-2-oxo-1,2-dihydro-[1,7]naphthyridine-6-carbonyl]amino}-propionic acid a) 1-Benzyl-5-hydroxy-3-(4-methanesulfonyl-phenyl)-2-oxo-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (80 mg, 0.21 mmol), 4-methanesulfonyl-phenylboronic acid (62 mg, 0.31 mmol), K$_3$PO$_4$ (87 mg, 0.41 mmol), H$_2$O (7.4 mg, 0.41 mmol), SPhos (4.2 mg, 0.010 mmol) and Pd(OAc)$_2$ (4.2 mg, 0.0062 mmol) in toluene (5 mL) was heated at 100° C. under nitrogen atmosphere for 16 h. After the mixture was cooled to r.t., water (10 mL) and EtOAc (15 mL) were added. 1 M HCl was added with stirring until pH was about 2-3, and the organic layer was dried over MgSO$_4$ and concentrated. The crude product was purified by silica gel chromatography (10-100% EtOAc/hexanes+2% AcOH) to give 27 mg of the title compound. MS: (+) m/z 465.23 (M+1).

b) 3-{[1-Benzyl-5-hydroxy-3-(4-methanesulfonyl-phenyl)-2-oxo-1,2-dihydro-[1,7]naphthyridine-6-carbonyl]-amino}-propionic acid A mixture of 1-benzyl-5-hydroxy-3-(4-methanesulfonyl-phenyl)-2-oxo-1,2-dihydro-[1,7]naphthyridine-6-carboxylic acid methyl ester (27 mg, 0.058 mmol), β-alanine (689 mg, 7.7 mmol) and NaOMe solution (12 mL, 5.8 mmol, 0.5 M in MeOH) was refluxed for 16 h. After the mixture was cooled to r.t., the solvent was evaporated in vacuo. The residue was dissolved in saturated NaHCO$_3$ and washed several times with ether. The aqueous layer was acidified to pH about 2 with 6 M HCl, and the resulting precipitate was isolated by filtration to give 19 mg of the title compound as a yellow solid. MS: (+) m/z 522.23 (M+1).

Example 147

3-{[1-Benzyl-5-hydroxy-2-oxo-3-(3-trifluoromethyl-phenyl)-1,2-dihydro-[1,7]naphthyridine-6-carbonyl]amino}-propionic acid a) 1-Benzyl-5-hydroxy-2-oxo-3-(3-trifluoromethyl-phenyl)-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (80 mg, 0.21 mmol), tributyl-(3-trifluoromethyl-phenyl)-stannane (134 mg, 0.31 mmol), and PdCl$_2$(PPh$_3$)$_2$ (29 mg, 0.041 mmol) in DMF (5 mL) was heated at 120° C. under nitrogen atmosphere for 2 h. After the mixture was cooled to r.t., brine and EtOAc were added. 1 M HCl was added until pH was about 3. The aqueous layer was extracted with additional EtOAc, and the organic layers were combined, washed with water, and dried over MgSO$_4$. After evaporating the solvent, the crude product was purified by silica gel chromatography (0-60% EtOAc/hexanes+2% AcOH) to give 55 mg of the title compound. MS: (+) m/z 455.28 (M+1).

b) 3-{[1-Benzyl-5-hydroxy-2-oxo-3-(3-trifluoromethyl-phenyl)-1,2-dihydro-[1,7]naphthyridine-6-carbonyl]-amino}-propionic acid A mixture of 1-benzyl-5-hydroxy-2-oxo-3-(3-trifluoromethyl-phenyl)-1,2-dihydro-[1,7]naphthyridine-6-carboxylic acid methyl ester (55 mg, 0.12 mmol), β-alanine (863 mg, 9.7 mmol) and NaOMe solution (14.5 mL, 7.3 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3. The organic layer was washed with brine, dried over MgSO$_4$, and concentrated. The crude solid was dissolved in saturated NaHCO$_3$ and washed several times with ether. The aqueous layer was acidified to pH about 3 with 6 M HCl, and the resulting precipitate was isolated by filtration to give 46 mg of the title compound. MS: (+) m/z 512.27 (M+1).

Example 148

3-{[1-Benzyl-5-hydroxy-3-(4-morpholin-4-yl-phenyl)-2-oxo-1,2-dihydro-[1,7]naphthyridine-6-carbonyl]-amino}-propionic acid a) 1-Benzyl-5-hydroxy-3-(4-morpholin-4-yl-phenyl)-2-oxo-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (80 mg, 0.21 mmol), 4-(4-tributylstannanyl-phenyl)-morpholine (0.12 mL, 0.31 mmol), and PdCl$_2$(PPh$_3$)$_2$ (29 mg, 0.041 mmol) in DMF (5 mL) was heated at 120° C. under nitrogen atmosphere for 2 h. After the mixture was cooled to r.t., brine (10 mL) and EtOAc (20 mL) were added. 1 M HCl was added until pH was about 3-4. The aqueous layer was extracted with additional EtOAc, and the organic layers were combined, washed with water, and dried over MgSO$_4$. After evaporating the solvent, the crude product was purified by silica gel chromatography (5-70% EtOAc/hexanes+2% AcOH) to give 44 mg of the title compound. MS: (+) m/z 472.34 (M+1).

b) 3-{[1-Benzyl-5-hydroxy-3-(4-morpholin-4-yl-phenyl)-2-oxo-1,2-dihydro-[1,7]naphthyridine-6-carbonyl]-amino}-propionic acid A mixture of 1-benzyl-5-hydroxy-3-(4-morpholin-4-yl-phenyl)-2-oxo-1,2-dihydro-[1,7]naphthyridine-6-carboxylic acid methyl ester (44 mg, 0.093 mmol), β-alanine (666 mg, 7.5 mmol) and NaOMe solution (11 mL, 5.6 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The organic layer was washed with brine, dried over MgSO$_4$, and concentrated. The crude solid was dissolved in saturated NaHCO$_3$ and washed several times with ether. The aqueous layer was acidified to pH about 3-4 with 6 M HCl, and the resulting precipitate was isolated by filtration to give 32 mg of the title compound. MS: (+) m/z 529.34 (M+1).

Example 149

3-[(3-Benzo[1,2,5]oxadiazol-5-yl-1-benzyl-5-hydroxy-2-oxo-1,2-dihydro-[1,7]naphthyridine-6-carbonyl)-amino]-propionic acid a) 3-Benzo[1,2,5]oxadiazol-5-yl-1-benzyl-5-hydroxy-2-oxo-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (80 mg, 0.21 mmol), benzo[1,2,5]oxadiazole-5-boronic acid (51 mg, 0.31 mmol), K$_3$PO$_4$ (87 mg, 0.41 mmol), H$_2$O (7.4 mg, 0.41 mmol), SPhos (4.2 mg, 0.010 mmol) and Pd(OAc)$_2$ (4.2 mg, 0.0062 mmol) in toluene (5 mL) was heated at 100° C. under nitrogen atmosphere for 16 h. After the mixture was cooled to r.t., brine and EtOAc were added. 1 M HCl was added with stirring until pH was about 3, and the organic layer was dried over MgSO$_4$ and concentrated. The crude product was first purified by silica gel chromatography (0-60% EtOAc/hexanes+1% AcOH), then by preparative TLC (20% EtOAc/CH$_2$Cl$_2$) to give 33 mg of the title compound. MS: (+) m/z 429.27 (M+1).

b) 3-[(3-Benzo[1,2,5]oxadiazol-5-yl-1-benzyl-5-hydroxy-2-oxo-1,2-dihydro-[1,7]naphthyridine-6-carbonyl)-amino]-propionic acid A mixture of 3-benzo[1,2,5]oxadiazol-5-yl-1-benzyl-5-hydroxy-2-oxo-1,2-dihydro-[1,7]naphthyridine-6-carboxylic acid methyl ester (33 mg, 0.077 mmol), β-alanine (687 mg, 7.7 mmol) and NaOMe solution (12 mL, 6.2 mmol, 0.5 M in MeOH) was refluxed for 16 h. After stirring the mixture for another 24 h at r.t., the solvent was evaporated in vacuo. The residue was partitioned between EtOAc and water. 1 M HCl was added with vigorous stirring until pH was about 3-4. The organic layer was washed with brine, dried over MgSO$_4$ and concentrated. The crude solid was dissolved in saturated NaHCO$_3$ and washed several times with ether. The aqueous layer was acidified to pH about 2 with 6 M HCl, and the resulting precipitate was isolated by filtration to give 23 mg of the title compound as a brown solid. MS: (+) m/z 486.26 (M+1).

Example 150

3-{[1-Benzyl-3-(5-fluoro-2-methoxy-phenyl)-5-hydroxy-2-oxo-1,2-dihydro-[1,7]naphthyridine-6-carbonyl]amino}-propionic acid a) 1-Benzyl-3-(5-fluoro-2-methoxy-phenyl)-5-hydroxy-2-oxo-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (80 mg, 0.21 mmol), tributyl-(5-fluoro-2-methoxy-phenyl)-stannane (128 mg, 0.31 mmol), and PdCl$_2$(PPh$_3$)$_2$ (29 mg, 0.041 mmol) in DMF (5 mL) was heated at 120° C. under nitrogen atmosphere for 2 h. After the mixture was cooled to r.t., brine and EtOAc were added. 1 M HCl was added until pH was about 3. The aqueous layer was extracted with additional EtOAc, and the organic layers were combined, washed with water, and dried over MgSO$_4$. After evaporating the solvent, the crude product was first purified by silica gel chromatography (0-60% EtOAc/hexanes+1% AcOH), then by preparative TLC (20% EtOAc/CH$_2$Cl$_2$) to give 27 mg of the title compound. MS: (+) m/z 435.31 (M+1).

b) 3-{[1-Benzyl-3-(5-fluoro-2-methoxy-phenyl)-5-hydroxy-2-oxo-1,2-dihydro-[1,7]naphthyridine-6-carbonyl]-amino}-propionic acid A mixture of 1-benzyl-3-(5-fluoro-2-methoxy-phenyl)-5-hydroxy-2-oxo-1,2-dihydro-[1,7]naphthyridine-6-carboxylic acid methyl ester (27 mg, 0.062 mmol), β-alanine (737 mg, 8.3 mmol) and NaOMe solution (12 mL, 6.2 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 2. The organic layer was washed with brine, dried over MgSO$_4$, and concentrated. The crude solid was dissolved in saturated NaHCO$_3$ and washed several times with ether. The aqueous layer was acidified to pH about 2 with 6 M HCl, and the resulting precipitate was isolated by filtration to give 23 mg of the title compound as a white solid. MS: (+) m/z 492.25 (M+1).

Example 151

3-{[1-Benzyl-5-hydroxy-2-oxo-3-(4-trifluoromethoxy-phenyl)-1,2-dihydro-[1,7]naphthyridine-6-carbonyl]amino}-propionic acid a) 1-Benzyl-5-hydroxy-2-oxo-3-(4-trifluoromethoxy-phenyl)-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (80 mg, 0.21 mmol), 4-trifluoromethoxy-phenylboronic acid (64 mg, 0.31 mmol), K$_3$PO$_4$ (87 mg, 0.41 mmol), H$_2$O (7.4 mg, 0.41 mmol), SPhos (4.2 mg, 0.010 mmol) and Pd(OAc)$_2$ (4.2 mg, 0.0062 mmol) in toluene (5 mL) was heated at 100° C. under nitrogen atmosphere for 16 h. After the mixture was cooled to r.t., water (10 mL) and EtOAc (30 mL) were added. 1 M HCl was added with stirring until pH was about 2, and the organic layer was washed with brine, dried over MgSO$_4$, and concentrated. The crude product was purified by silica gel chromatography (5% EtOAc/CH$_2$Cl$_2$) to give 36 mg of the title compound. MS: (+) m/z 471.27 (M+1).

b) 3-{[1-Benzyl-5-hydroxy-2-oxo-3-(4-trifluoromethoxy-phenyl)-1,2-dihydro-[1,7]naphthyridine-6-carbonyl]-amino}-propionic acid A mixture of 1-benzyl-5-hydroxy-2-oxo-3-(4-trifluoromethoxy-phenyl)-1,2-dihydro-[1,7]naphthyridine-6-carboxylic acid methyl ester (36 mg, 0.077 mmol), β-alanine (682 mg, 7.7 mmol) and NaOMe solution (12 mL, 6.1 mmol, 0.5 M in MeOH) was refluxed for 16 h. After cooling to r.t., the solvent was evaporated in vacuo. The residue was partitioned between EtOAc and water. 1 M HCl was added with vigorous stilling until pH was about 2. The organic layer was washed with brine, dried over MgSO$_4$ and concentrated. The crude solid was dissolved in saturated NaHCO$_3$ and washed several times with ether. The aqueous layer was acidified to pH about 3 with 6 M HCl, and the resulting precipitate was isolated by filtration to give 21 mg of the title compound as a yellow solid. MS: (+) m/z 528.27 (M+1).

Example 152

(R)-2-[(1-Benzyl-5-hydroxy-2-oxo-3-phenyl-1,2-dihydro-[1,7]naphthyridine-6-carbonyl)-amino]-3-phenyl-propionic acid A mixture of 1-benzyl-5-hydroxy-2-oxo-3-phenyl-1,2-dihydro-[1,7]naphthyridine-6-carboxylic acid methyl ester (60 mg, 0.16 mmol), D-phenylalanine (514 mg, 3.1 mmol), and NaOMe (126 mg, 2.3 mmol) in 2-methoxyethanol (10 mL) was refluxed for 2 h. After the mixture was cooled to r.t., solvent was evaporated in vacuo. The residue was partitioned between EtOAc and water. 1 M HCl was added with vigorous stirring until pH was about 3. The organic layer was dried over $MgSO_4$ and concentrated. The residue was purified by silica gel chromatography (0-60% EtOAc/hexanes+1% AcOH). The product isolated was dissolved in saturated $NaHCO_3$ and washed several times with ether. The aqueous layer was acidified to pH about 3 with 6 M HCl, and the resulting precipitate was isolated by filtration to give 36 mg of the title compound as a dull yellow solid. MS: (+) m/z 520.27 (M+1).

Example 153

3-{[1-Benzyl-5-hydroxy-3-(1-methyl-1H-pyrazol-4-yl)-2-oxo-1,2-dihydro-[1,7]naphthyridine-6-carbonyl]amino}-propionic acid a) 1-Benzyl-5-hydroxy-3-(1-methyl-1H-pyrazol-4-yl)-2-oxo-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (80 mg, 0.21 mmol), 1-methyl-4-tributylstannanyl-1H-pyrazole (0.1 mL, 0.31 mmol), and $PdCl_2(PPh_3)_2$ (29 mg, 0.041 mmol) in DMF (5 mL) was heated at 120° C. under nitrogen atmosphere for 2 h. After the mixture was cooled to r.t., water and EtOAc were added. 1 M HCl was added until pH was about 4. The aqueous layer was extracted with additional EtOAc, and the organic layers were combined, washed with water, and dried over $MgSO_4$. After evaporating the solvent, the crude product was purified by silica gel chromatography (50% EtOAc/$CH_2Cl_2$, then 100% EtOAc+1% AcOH) to give 44 mg of the title compound. MS: (+) m/z 391.29 (M+1).

b) 3-{[1-Benzyl-5-hydroxy-3-(1-methyl-1H-pyrazol-4-yl)-2-oxo-1,2-dihydro-[1,7]naphthyridine-6-carbonyl]-amino}-propionic acid A mixture of 1-benzyl-5-hydroxy-3-(1-methyl-1H-pyrazol-4-yl)-2-oxo-1,2-dihydro-[1,7]naphthyridine-6-carboxylic acid methyl ester (44 mg, 0.11 mmol), β-alanine (804 mg, 9.0 mmol) and NaOMe solution (13 mL, 6.8 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 4. The organic layer was dried over $MgSO_4$ and concentrated. The crude solid was dissolved in saturated $NaHCO_3$ and washed several times with ether. The aqueous layer was acidified to pH about 4 with 6 M HCl, and the resulting precipitate was isolated by filtration to give 31 mg of the title compound as a yellow solid. MS: (+) m/z 448.29 (M+1).

Example 154

3-[(1-Benzyl-5-hydroxy-2-oxo-3-pyrimidin-5-yl-1,2-dihydro-[1,7]naphthyridine-6-carbonyl)-amino]-propionic acid a) 1-Benzyl-5-hydroxy-2-oxo-3-pyrimidin-5-yl-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (80 mg, 0.21 mmol), 5-tributylstannanyl-pyrimidine (0.1 mL, 0.31 mmol), and $PdCl_2(PPh_3)_2$ (29 mg, 0.041 mmol) in DMF (5 mL) was heated at 120° C. under nitrogen atmosphere for 2 h. After the mixture was cooled to r.t., brine and EtOAc were added. 1 M HCl was added until pH was about 4. The aqueous layer was extracted with additional EtOAc, and the organic layers were combined, washed with water, and dried over $MgSO_4$. After evaporating the solvent, the crude product was purified by silica gel chromatography (90% EtOAc/hexanes+1% AcOH) to give 58 mg of the title compound. MS: (+) m/z 389.27 (M+1).

b) 3-[(1-Benzyl-5-hydroxy-2-oxo-3-pyrimidin-5-yl-1,2-dihydro-[1,7]naphthyridine-6-carbonyl)-amino]-propionic acid A mixture of 1-benzyl-5-hydroxy-2-oxo-3-pyrimidin-5-yl-1,2-dihydro-[1,7]naphthyridine-6-carboxylic acid methyl ester (58 mg, 0.15 mmol), β-alanine (706 mg, 7.9 mmol) and NaOMe solution (12 mL, 6.0 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 4. The organic layer was dried over $MgSO_4$ and concentrated. The crude solid was dissolved in saturated $NaHCO_3$ and washed several times with ether. The aqueous layer was acidified to pH about 4 with 6 M HCl, and the resulting precipitate was isolated by filtration to give 44 mg of the title compound. MS: (+) m/z 446.27 (M+1).

Example 155

3-{[1-Benzyl-3-(2-dimethylamino-pyrimidin-5-yl)-5-hydroxy-2-oxo-1,2-dihydro-[1,7]naphthyridine-6-carbonyl]amino}-propionic acid a) 1-Benzyl-3-(2-dimethylamino-pyrimidin-5-yl)-5-hydroxy-2-oxo-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (80 mg, 0.21 mmol), 2-dimethylaminopyrimidine-5-boronic acid (52 mg, 0.31 mmol), $K_3PO_4$ (87 mg, 0.41 mmol), $H_2O$ (7.4 mg, 0.41 mmol), SPhos (4.2 mg, 0.010 mmol) and $Pd(OAc)_2$ (4.2 mg, 0.0062 mmol) in toluene (5 mL) was heated at 105° C. under nitrogen atmosphere for 16 h. After the mixture was cooled to r.t., brine (10 mL) and EtOAc (20 mL) were added. 1 M HCl was added with stirring until pH was about 3-4, and the organic layer was dried over $MgSO_4$ and concentrated. The crude product was purified by silica gel chromatography (10-100% EtOAc/hexanes+2% AcOH) to give 29 mg of the title compound as a bright yellow solid. MS: (+) m/z 432.29 (M+1).

b) 3-{[1-Benzyl-3-(2-dimethylamino-pyrimidin-5-yl)-5-hydroxy-2-oxo-1,2-dihydro-[1,7]naphthyridine-6-carbonyl]-amino}-propionic acid methyl ester A mixture of 1-benzyl-3-(2-dimethylamino-pyrimidin-5-yl)-5-hydroxy-2-oxo-1,2-dihydro-[1,7]naphthyridine-6-carboxylic acid methyl ester (30 mg, 0.07 mmol), 2 M NaOH (4 mL, THF (4 mL) and MeOH (4 mL) was stirred at r.t. for 16 h. The resulting mixture was concentrated to dryness, and diluted with water (5 mL). 1 M HCl was added until pH was about 4, and the resulting precipitate was isolated by filtration and dried under high vacuum. The crude solid was dissolved in $CH_2Cl_2$, and HOBt (12 mg, 0.09 mmol) and EDC (23 mg, 0.12 mmol) were added. The resulting mixture was stirred for 10 min. β-Alanine methyl ester HCl salt (13 mg, 0.09 mmol) and Hunig's base (0.030 mL, 0.21 mmol) were then added, and the mixture was stirred for 20 h. The solvent was evaporated in vacuo, and the residue was purified by silica gel chromatography (5-80% EtOAc/hexanes+1% AcOH) to give 30 mg of the title compound as a pale yellow solid. MS: (+) m/z 503.33 (M+1).

c) 3-{[1-Benzyl-3-(2-dimethylamino-pyrimidin-5-yl)-5-hydroxy-2-oxo-1,2-dihydro-[1,7]naphthyridine-6-carbonyl]-amino}-propionic acid A mixture of 3-{[1-benzyl-3-(2-dimethylamino-pyrimidin-5-yl)-5-hydroxy-2-oxo-1,2-dihydro-[1,7]naphthyridine-6-carbonyl]-amino}-propionic acid methyl ester (30 mg, 0.060 mmol), 2 M NaOH (2 mL), THF (2 mL) and MeOH (2 mL) was stirred at r.t. overnight. The mixture was concentrated to approximately one-third of its original volume. 1 M HCl was added until pH was about 4, and the resulting suspension was extracted with EtOAc. The organic layer was dried over $MgSO_4$ and concentrated. The residue was dissolved in saturated $NaHCO_3$ and washed several times with ether. The aqueous layer was acidified to pH about 4 with 6 M HCl, and the resulting precipitate was isolated by filtration to give 16 mg of the title compound as a pale yellow solid. MS: (+) m/z 489.29 (M+1).

Example 156

3-[(1-Cyclohexylmethyl-5-hydroxy-2-oxo-3-phenyl-1,2-dihydro-[1,7]naphthyridine-6-carbonyl)-amino]-propionic acid a) 4-[1-(Cyclohexylmethyl-amino)-ethylidene]-pent-2-enedioic acid dimethyl ester A mixture of cyclohexanemethylamine (3 g, 26.5 mmol) and 3-oxo-butyric acid methyl ester (3.5 mL, 31.8 mmol) in MeOH (100 mL) was refluxed for 2 h. Propynoic acid methyl ester (3.6 mL, 39.8 mmol) was added, and the resulting mixture was refluxed for 2 days. After cooling to r.t., the solvent was evaporated, and the crude oil was recrystallized from MeOH to give 6.3 g of the title compound as a light tan solid. $^1$H NMR ($CDCl_3$, 200 MHz): δ=10.73 (br s, 1H), 7.76 (d, 1H, J=15.4 Hz), 6.06 (d, 1H, J=15.4 Hz), 3.77 (s, 3H), 3.72 (s, 3H), 3.18 (t, 2H, J=6.2 Hz), 2.25 (s, 3H), 0.80-1.90 (m, 11H).

b) 5-Bromo-1-cyclohexylmethyl-2-methyl-6-oxo-1,6-dihydro-pyridine-3-carboxylic acid methyl ester MeOH (200 mL) was added to a flask containing 4-[1-(cyclohexylmethyl-amino)-ethylidene]-pent-2-enedioic acid dimethyl ester (6.3 g, 21.4 mmol). NaOMe solution (4.9 mL, 21.4 mmol, 4.375 M in MeOH) and N-bromosuccinimide (4.56 g, 25.6 mmol) were added, and the resulting mixture was refluxed for 1 h. After cooling to r.t., the solvent was evaporated in vacuo. Saturated $NH_4Cl$ was added, and the resulting mixture was extracted with $CH_2Cl_2$. The organic layer was dried over $MgSO_4$ and concentrated. The crude product was chromatographed (20% EtOAc/hexanes) to give 4.95 g of the title compound. MS: (+) m/z 364.21, 366.16 (M+Na, $^{79/81}$Br).

c) 5-Bromo-2-bromomethyl-1-cyclohexylmethyl-6-oxo-1,6-dihydro-pyridine-3-carboxylic acid methyl ester A mixture of 5-bromo-1-cyclohexylmethyl-2-methyl-6-oxo-1,6-dihydro-pyridine-3-carboxylic acid methyl ester (4.95 g, 14.5 mmol), N-bromosuccinimide (2.83 g, 15.9 mmol), and benzoyl peroxide (0.35 g, 1.45 mmol) in $CCl_4$ (140 mL) was refluxed for 16 h. The solvent was evaporated in vacuo, and the residue was chromatographed (10% EtOAc/hexanes) to give 4.49 g of the title compound as a white solid. MS: (+) m/z 422.09 (M+1).

d) 5-Bromo-1-cyclohexylmethyl-2-{[methoxycarbonylmethyl-(toluene-4-sulfonyl)-amino]-methyl}-6-oxo-1,6-dihydro-pyridine-3-carboxylic acid methyl ester A mixture of 5-bromo-2-bromomethyl-1-cyclohexylmethyl-6-oxo-1,6-dihydro-pyridine-3-carboxylic acid methyl ester (4.49 g, 10.7 mmol), (toluene-4-sulfonylamino)-acetic acid methyl ester (2.46 g, 10.1 mmol), sodium iodide (3.19 g, 21.3 mmol) and potassium carbonate (2.95 g, 21.3 mmol) in DMF (70 mL) was stirred at r.t. for 16 h. Brine (120 mL) was added, and the resulting suspension was extracted with EtOAc. The organic layer was washed with water and dried over $MgSO_4$. After the solvent was evaporated in vacuo, the crude product was chromatographed (60% EtOAc/hexanes) to give 4.67 g of the title compound as a yellow viscous oil. MS: (+) m/z 583.19, 585.14 (M+1, $^{79/81}$Br).

e) 3-Bromo-1-cyclohexylmethyl-5-hydroxy-2-oxo-1,2-dihydro-[1,7]naphthyridine-6-carboxylic acid methyl ester 5-Bromo-1-cyclohexylmethyl-2-{[methoxycarbonylmethyl-(toluene-4-sulfonyl)-amino]-methyl}-6-oxo-1,6-dihydro-pyridine-3-carboxylic acid methyl ester (4.67 g, 8.01 mmol) was dissolved in 150 mL of MeOH and placed in ice bath. NaOMe solution (5.5 mL, 24 mmol, 4.375 M in MeOH) was added and the mixture was stirred for 16 h at r.t. 1 M HCl was added to acidify the mixture, and the resulting suspension was extracted with $CH_2Cl_2$. The organic layer was dried over $MgSO_4$ and concentrated. The crude product was purified by silica gel chromatography (4% EtOAc/$CH_2Cl_2$) to give 2.41 g of the title compound as an off-white solid. MS: (+) m/z 395.19, 397.21 (M+1, $^{79/81}$Br).

f) 1-Cyclohexylmethyl-5-hydroxy-2-oxo-3-phenyl-1,2-dihydro-[1,7]naphthyridine-6-carboxylic acid methyl ester A mixture of 3-bromo-1-cyclohexylmethyl-5-hydroxy-2-oxo-1,2-dihydro-[1,7]naphthyridine-6-carboxylic acid methyl ester (100 mg, 0.25 mmol), $PhSnBu_3$ (0.1 mL, 0.30 mmol), and $PdCl_2(PPh_3)_2$ (36 mg, 0.051 mmol) in DMF (5 mL) was heated at 120° C. under nitrogen atmosphere for 2 h. After the mixture was cooled to r.t., water and EtOAc were added. 1 M HCl was added until pH was about 3-4. The aqueous layer was extracted with additional EtOAc and the organic layers were combined, washed with water, and dried over MgSO$_4$. After evaporating the solvent in vacuo, the crude product was chromatographed (5% EtOAc/CH$_2$Cl$_2$) to give 71 mg of the title compound. MS: (+) m/z 393.37 (M+1).

g) 3-[(1-Cyclohexylmethyl-5-hydroxy-2-oxo-3-phenyl-1,2-dihydro-[1,7]naphthyridine-6-carbonyl)-amino]-propionic acid A mixture of 1-cyclohexylmethyl-5-hydroxy-2-oxo-3-phenyl-1,2-dihydro-[1,7]naphthyridine-6-carboxylic acid methyl ester (35 mg, 0.089 mmol), β-alanine (795 mg, 8.9 mmol) and NaOMe solution (13 mL, 6.7 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 2. The organic layer was dried over MgSO$_4$ and concentrated. The crude product was dissolved in saturated NaHCO$_3$ and washed several times with ether. The aqueous layer was acidified to pH about 2 with 6 M HCl, and the resulting precipitate was isolated by filtration to give 25 mg of the title compound as a light yellow solid. MS: (+) m/z 450.30 (M+1).

Example 157

3-{[5-Hydroxy-2-oxo-3-phenyl-1-(tetrahydro-pyran-4-ylmethyl)-1,2-dihydro-[1,7]naphthyridine-6-carbonyl]amino}-propionic acid a) 4-{1-[(Tetrahydro-pyran-4-ylmethyl)-amino]-ethylidene}-pent-2-enedioic acid dimethyl ester A mixture of 4-aminomethyltetrahydropyran (1.02 g, 8.9 mmol) and 3-oxo-butyric acid methyl ester (1.15 mL, 10.6 mmol) in MeOH (40 mL) was refluxed for 2 h. Propynoic acid methyl ester (1.2 mL, 13.3 mmol) was added, and the resulting mixture was refluxed for 48 h. After cooling to r.t., the solvent was evaporated, and the crude oil was recrystallized from MeOH to give 2.39 g of the title compound as an off-white solid. MS: (+) m/z 298.33 (M+1).

b) 5-Bromo-2-methyl-6-oxo-1-(tetrahydro-pyran-4-ylmethyl)-1,6-dihydro-pyridine-3-carboxylic acid methyl ester MeOH (70 mL) was added to a flask containing 4-{1-[(tetrahydro-pyran-4-ylmethyl)-amino]-ethylidene}-pent-2-enedioic acid dimethyl ester (2.39 g, 8.05 mmol). NaOMe solution (1.8 mL, 8.05 mmol, 4.375 M in MeOH) and N-bromosuccinimide (1.72 g, 9.66 mmol) were added, and the resulting mixture was refluxed for 1 h. After cooling to r.t., the solvent was evaporated in vacuo. Saturated NH$_4$Cl was added, and the resulting mixture was extracted with CH$_2$Cl$_2$. The organic layer was dried over MgSO$_4$ and concentrated. The crude product was chromatographed (0-50% EtOAc/hexanes) to give 906 mg of the title compound. MS: (+) m/z 366.16, 368.17 (M+Na, $^{79/81}$Br).

c) 5-Bromo-2-bromomethyl-6-oxo-1-(tetrahydro-pyran-4-ylmethyl)-1,6-dihydro-pyridine-3-carboxylic acid methyl ester A mixture of 5-bromo-2-methyl-6-oxo-1-(tetrahydro-pyran-4-ylmethyl)-1,6-dihydro-pyridine-3-carboxylic acid methyl ester (0.906 g, 2.63 mmol), N-bromosuccinimide (0.516 g, 2.89 mmol), and benzoyl peroxide (64 mg, 0.26 mmol) in CCl$_4$ (30 mL) was refluxed for 16 h. The solvent was evaporated in vacuo, and the residue was chromatographed (0-60% EtOAc/hexanes) to give 511 mg of the title compound. MS: (+) m/z 424.10 (M+1).

d) 5-Bromo-2-{[methoxycarbonylmethyl-(toluene-4-sulfonyl)-amino]-methyl}-6-oxo-1-(tetrahydro-pyran-4-ylmethyl)-1,6-dihydro-pyridine-3-carboxylic acid methyl ester A mixture of 5-bromo-2-bromomethyl-6-oxo-1-(tetrahydro-pyran-4-ylmethyl)-1,6-dihydro-pyridine-3-carboxylic acid methyl ester (511 mg, 1.21 mmol), (toluene-4-sulfonylamino)-acetic acid methyl ester (279 mg, 1.15 mmol), sodium iodide (362 mg, 2.42 mmol) and potassium carbonate (334 mg, 2.42 mmol) in DMF (10 mL) was stirred at r.t. for 16 h. Brine (50 mL) was added, and the resulting mixture was extracted with EtOAc. The organic layer was washed with water and brine, and dried over MgSO$_4$. After the solvent was evaporated in vacuo, the crude product was chromatographed (0-80% EtOAc/hexanes) to give 411 mg of the title compound. MS: (+) m/z 607.12, 609.08 (M+Na, $^{79/81}$Br).

e) 3-Bromo-5-hydroxy-2-oxo-1-(tetrahydro-pyran-4-ylmethyl)-1,2-dihydro-[1,7]naphthyridine-6-carboxylic acid methyl ester 5-Bromo-2-{[methoxycarbonylmethyl-(toluene-4-sulfonyl)-amino]-methyl}-6-oxo-1-(tetrahydro-pyran-4-ylmethyl)-1,6-dihydro-pyridine-3-carboxylic acid methyl ester (411 mg, 0.70 mmol) was dissolved in 15 mL of MeOH and placed in ice bath. NaOMe solution (0.5 mL, 2.11 mmol, 4.375 M in MeOH) was added and the mixture was stirred for 16 h at r.t. 1 M HCl was added to acidify the mixture, and brine was added until precipitate appeared. The resulting suspension was extracted with CH$_2$Cl$_2$. The organic layer was dried over MgSO$_4$ and concentrated. The crude product was purified by silica gel chromatography (0-4% MeOH/CH$_2$Cl$_2$) to give 200 mg of the title compound as a light yellow solid. MS: (+) m/z 397.21, 399.16 (M+1, $^{79/81}$Br).

f) 5-Hydroxy-2-oxo-3-phenyl-1-(tetrahydro-pyran-4-ylmethyl)-1,2-dihydro-[1,7]naphthyridine-6-carboxylic acid methyl ester A mixture of 3-bromo-5-hydroxy-2-oxo-1-(tetrahydro-pyran-4-ylmethyl)-1,2-dihydro-[1,7]naphthyridine-6-carboxylic acid methyl ester (70 mg, 0.18 mmol), PhSnBu$_3$ (0.070 mL, 0.21 mmol), and PdCl$_2$(PPh$_3$)$_2$ (25 mg, 0.035 mmol) in DMF (3 mL) was heated at 125° C. under nitrogen atmosphere for 2 h. After the mixture was cooled to r.t., brine (10 mL) and EtOAc (20 mL) were added. 1 M HCl was added with stirring until pH was about 2. The aqueous layer was extracted with EtOAc, and the organic layers were combined, washed with water, and dried over MgSO$_4$. After evaporating the solvent in vacuo, the crude product was purified twice by silica gel chromatography (0-4% MeOH/CH$_2$Cl$_2$, then 15-100% EtOAc/hexanes+1% AcOH) to give 50 mg of the title compound as a light yellow solid. MS: (+) m/z 395.26 (M+1).

g) 3-{[5-Hydroxy-2-oxo-3-phenyl-1-(tetrahydro-pyran-4-ylmethyl)-1,2-dihydro-[1,7]naphthyridine-6-carbonyl]amino}-propionic acid A mixture of 5-hydroxy-2-oxo-3-phenyl-1-(tetrahydro-pyran-4-ylmethyl)-1,2-dihydro-[1,7]naphthyridine-6-carboxylic acid methyl ester (50 mg, 0.13 mmol), β-alanine (678 mg, 7.6 mmol) and NaOMe solution (11 mL, 5.7 mmol, 0.5 M in MeOH) was refluxed for 16 h. After the mixture was cooled to r.t., the solvent was evaporated in vacuo. The residue was partitioned between EtOAc and water. 1 M HCl was added until pH was about 4. The aqueous layer was extracted with additional EtOAc, and the organic layers were combined, dried over MgSO$_4$ and concentrated. The crude product was dissolved in saturated NaHCO$_3$ and washed several times with ether. The aqueous layer was acidified to pH about 3, and the resulting precipitate was isolated by filtration. The solid isolated was purified twice by silica gel chromatography (0-15% MeOH/CH$_2$Cl$_2$, then 5-70% EtOAc/hexanes+1% AcOH) to give 7.7 mg of the title compound as a light yellow solid. MS: (+) m/z 452.32 (M+1).

Example 158

3-[(5-Hydroxy-2-oxo-3-phenyl-1-thiazol-2-ylmethyl-1,2-dihydro-[1,7]naphthyridine-6-carbonyl)-amino]-propionic acid a) 4-{1-[(Thiazol-2-ylmethyl)-amino]ethylidene}-pent-2-enedioic acid dimethyl ester A mixture of 4-aminomethylthiazole (1.13 g, 9.91 mmol) and 3-oxo-butyric acid methyl ester (1.3 mL, 11.9 mmol) in MeOH (50 mL) was refluxed for 2.5 h. Propynoic acid methyl ester (1.4 mL, 14.9 mmol) was added, and the resulting mixture was refluxed for 48 h. After cooling to r.t., the solvent was evaporated. The crude oil was purified by silica gel chromatography (0-80% EtOAc/hexanes) to give 2.12 g of the title compound as a yellow solid. MS: (+) m/z 297.26 (M+1).

b) 5-Bromo-2-methyl-6-oxo-1-thiazol-2-ylmethyl-1,6-dihydro-pyridine-3-carboxylic acid methyl ester MeOH (60 mL) was added to a flask containing 4-{1-[(thiazol-2-ylmethyl)-amino]-ethylidene}-pent-2-enedioic acid dimethyl ester (2.12 g, 7.16 mmol). NaOMe solution (1.64 mL, 7.16 mmol, 4.375 M in MeOH) and N-bromosuccinimide (1.53 g, 8.59 mmol) were added, and the resulting mixture was refluxed for 1 h. After cooling to r.t., the solvent was evaporated in vacuo. Saturated NH$_4$Cl was added, and the resulting mixture was extracted with CH$_2$Cl$_2$. The organic layer was dried over MgSO$_4$ and concentrated. The crude product was chromatographed (0-80% EtOAc/hexanes) to give 551 mg of the title compound as a yellow solid. MS: (+) m/z 343.11, 345.12 (M+1, $^{79/81}$Br).

c) 5-Bromo-2-bromomethyl-6-oxo-1-thiazol-2-ylmethyl-1,6-dihydro-pyridine-3-carboxylic acid methyl ester A mixture of 5-bromo-2-methyl-6-oxo-1-thiazol-2-ylmethyl-1,6-dihydro-pyridine-3-carboxylic acid methyl ester (0.551 g, 1.61 mmol), N-bromosuccinimide (0.315 g, 1.77 mmol), and benzoyl peroxide (39 mg, 0.161 mmol) in CCl$_4$ (20 mL) was refluxed for 16 h. The solvent was evaporated in vacuo, and the residue was chromatographed (0-60% EtOAc/hexanes) to give 100 mg of the title compound as a orange viscous oil. MS: (+) m/z 423.03 (M+1).

d) 5-Bromo-2-{[methoxycarbonylmethyl-(toluene-4-sulfonyl)-amino]-methyl}-6-oxo-1-thiazol-2-ylmethyl-1,6-dihydro-pyridine-3-carboxylic acid methyl ester A mixture of 5-bromo-2-bromomethyl-6-oxo-1-thiazol-2-ylmethyl-1,6-dihydro-pyridine-3-carboxylic acid methyl ester (100 mg, 0.24 mmol), (toluene-4-sulfonylamino)-acetic acid methyl ester (58 mg, 0.24 mmol), sodium iodide (71 mg, 0.47 mmol) and potassium carbonate (66 mg, 0.47 mmol) in DMF (5 mL) was stirred at r.t. for 16 h. Brine was added, and the resulting mixture was extracted with EtOAc. The organic layer was washed with water and brine, and dried over MgSO$_4$. After the solvent was evaporated in vacuo, the crude product was chromatographed (0-60% EtOAc/hexanes) to give 41 mg of the title compound as a viscous oil. MS: (+) m/z 584.14, 586.09 (M+1, $^{79/81}$Br).

e) 3-Bromo-5-hydroxy-2-oxo-1-thiazol-2-ylmethyl-1,2-dihydro-[1,7]naphthyridine-6-carboxylic acid methyl ester 5-Bromo-2-{[methoxycarbonylmethyl-(toluene-4-sulfonyl)-amino]-methyl}-6-oxo-1-thiazol-2-ylmethyl-1,6-dihydro-pyridine-3-carboxylic acid methyl ester (41 mg, 0.070 mmol) was dissolved in 5 mL of MeOH. NaOMe solution (0.050 mL, 0.21 mmol, 4.375 M in MeOH) was added and the mixture was stirred for 16 h at r.t. 1 M HCl was added to acidify the mixture, followed by addition of brine (10 mL), and the resulting mixture was extracted with CH$_2$Cl$_2$. The organic layer was dried over MgSO$_4$ and concentrated. The crude product was purified by silica gel chromatography (0-3% MeOH/CH$_2$Cl$_2$) to give 28.6 mg of the title compound. MS: (+) m/z 396.07, 398.03 (M+1, $^{79/81}$Br).

f) 5-Hydroxy-2-oxo-3-phenyl-1-thiazol-2-ylmethyl-1,2-dihydro-[1,7]naphthyridine-6-carboxylic acid methyl ester A mixture of 3-bromo-5-hydroxy-2-oxo-1-thiazol-2-ylmethyl-1,2-dihydro-[1,7]naphthyridine-6-carboxylic acid methyl ester (29 mg, 0.072 mmol), PhSnBu$_3$ (0.030 mL, 0.087 mmol), and PdCl$_2$(PPh$_3$)$_2$ (10 mg, 0.014 mmol) in DMF (3 mL) was heated at 120° C. under nitrogen atmosphere for 2 h. After the mixture was cooled to r.t., brine and EtOAc were added. 1 M HCl was added with stirring until pH was about 4. The aqueous layer was extracted with EtOAc, and the organic layers were combined, washed with water, and dried over MgSO$_4$. After evaporating the solvent in vacuo, the crude product was purified by silica gel chromatography (5-80% EtOAc/hexanes+1% AcOH) to give 16 mg of the title compound. MS: (+) m/z 394.25 (M+1).

g) 3-[(5-Hydroxy-2-oxo-3-phenyl-1-thiazol-2-ylmethyl-1,2-dihydro-[1,7]naphthyridine-6-carbonyl)-amino]-propionic acid A mixture of 5-hydroxy-2-oxo-3-phenyl-1-thiazol-2-ylmethyl-1,2-dihydro-[1,7]naphthyridine-6-carboxylic acid methyl ester (16 mg, 0.041 mmol), β-alanine (472 mg, 5.3 mmol) and NaOMe solution (8 mL, 4.1 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 4. The aqueous layer was extracted with additional EtOAc, and the organic layers were combined, dried over MgSO$_4$ and concentrated. The residue was dissolved in saturated NaHCO$_3$ and washed several times with ether. The aqueous layer was acidified to pH about 3 with 6 M HCl, and the resulting precipitate was isolated by filtration to give 6.8 mg of the title compound as a light brown solid. MS: (+) m/z 451.18 (M+1).

Example 159

3-[(1-Benzyl-5-hydroxy-2-oxo-3-phenyl-8-pyrimidin-5-yl-1,2-dihydro-[1,7]naphthyridine-6-carbonyl)-amino]-propionic acid a) 1-Benzyl-5-hydroxy-2-oxo-3-phenyl-8-pyrimidin-5-yl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (60 mg, 0.13 mmol), 5-tributylstannanyl-pyrimidine (71 mg, 0.19 mmol) and PdCl$_2$(PPh$_3$)$_2$ (18 mg, 0.026 mmol) in 3 mL of DMF was heated at 120° C. for 2 h under nitrogen atmosphere. After the mixture was cooled to r.t., EtOAc and brine were added. 1 M HCl was added with stirring until pH was about 4. The aqueous layer was extracted with additional EtOAc, and the combined organic layer was washed with water and dried over MgSO$_4$. After evaporating the solvent in vacuo, the crude product was chromatographed (10-100% EtOAc/hexanes+1% AcOH) to give 35 mg of the title compound. MS: (+) m/z 465.29 (M+1).

b) 3-[(1-Benzyl-5-hydroxy-2-oxo-3-phenyl-8-pyrimidin-5-yl-1,2-dihydro-[1,7]naphthyridine-6-carbonyl)-amino]-propionic acid A mixture of 1-benzyl-5-hydroxy-2-oxo-3-phenyl-8-pyrimidin-5-yl-1,2-dihydro-[1,7]naphthyridine-6-carboxylic acid methyl ester (35 mg, 0.075 mmol), β-alanine (672 mg, 7.54 mmol) and NaOMe solution (11 mL, 5.66 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 4. The aqueous layer was extracted with additional EtOAc, and the organic layers were combined, dried over MgSO$_4$ and concentrated. The residue was dissolved in saturated NaHCO$_3$ and washed several times with ether. The aqueous layer was acidified to pH about 4, and the resulting precipitate was isolated by filtration to give 17 mg of the title compound as a yellow solid. MS: (+) m/z 522.23 (M+1).

Example 160

3-[(1-Benzyl-5-hydroxy-2-oxo-3-phenyl-8-pyrazin-2-yl-1,2-dihydro-[1,7]naphthyridine-6-carbonyl)-amino]-propionic acid a) 1-Benzyl-5-hydroxy-2-oxo-3-phenyl-8-pyrazin-2-yl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (60 mg, 0.13 mmol), 2-tributylstannanyl-pyrazine (0.061 mL, 0.19 mmol) and PdCl$_2$(PPh$_3$)$_2$ (18 mg, 0.026 mmol) in 3 mL of DMF was heated at 120° C. for 2 h under nitrogen atmosphere. After the mixture was cooled to r.t., EtOAc and brine were added. 1 M HCl was added with stirring until pH was about 4. The aqueous layer was extracted with additional EtOAc, and the combined organic layer was washed with water and dried over MgSO$_4$. After evaporating the solvent in vacuo, the crude product was chromatographed (5-80% EtOAc/hexanes+1% AcOH) to give 40 mg of the title compound. MS: (+) m/z 465.35 (M+1).

b) 3-[(1-Benzyl-5-hydroxy-2-oxo-3-phenyl-8-pyrazin-2-yl-1,2-dihydro-[1,7]naphthyridine-6-carbonyl)-amino]-propionic acid A mixture of 1-benzyl-5-hydroxy-2-oxo-3-phenyl-8-pyrazin-2-yl-1,2-dihydro-[1,7]naphthyridine-6-carboxylic acid methyl ester (40 mg, 0.086 mmol), β-alanine (768 mg, 8.62 mmol) and NaOMe solution (13 mL, 6.47 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 4. The aqueous layer was extracted with additional EtOAc, and the organic layers were combined, dried over MgSO$_4$ and concentrated. The residue was dissolved in saturated NaHCO$_3$ and washed several times with ether. The aqueous layer was acidified to pH about 4, and the resulting precipitate was isolated by filtration to give 33 mg of the title compound as a light yellow solid. MS: (+) m/z 522.29 (M+1).

Example 161

5-[(1-Benzyl-5-hydroxy-2-oxo-3-phenyl-1,2-dihydro-[1,7]naphthyridine-6-carbonyl)-amino]-pentanoic acid A mixture of 1-benzyl-5-hydroxy-2-oxo-3-phenyl-1,2-dihydro-[1,7]naphthyridine-6-carboxylic acid methyl ester (60 mg, 0.16 mmol), 5-aminovaleric acid (909 mg, 7.8 mmol), and NaOMe solution (12 mL, 6.2 mmol) was refluxed for 16 h. After the mixture was cooled to r.t., solvent was evaporated in vacuo. The residue was partitioned between EtOAc and water. 1 M HCl was added with vigorous stirring until pH was about 3. The aqueous layer was extracted with additional EtOAc, and the organic layers were combined, dried over MgSO$_4$ and concentrated. The residue was purified by silica gel chromatography (5-60% EtOAc/hexanes+1% AcOH). The product isolated was dissolved in saturated NaHCO$_3$ and washed several times with ether. The aqueous layer was acidified to pH about 3 with 6 M HCl, and the resulting precipitate was isolated by filtration to give 24 mg of the title compound as a pale yellow solid. MS: (+) m/z 472.34 (M+1).

Example 162

4-[(1-Benzyl-5-hydroxy-2-oxo-3-phenyl-8-pyridin-3-yl-1,2-dihydro-[1,7]naphthyridine-6-carbonyl)-amino]-butyric acid A mixture of 1-benzyl-5-hydroxy-2-oxo-3-phenyl-8-pyridin-3-yl-1,2-dihydro-[1,7]naphthyridine-6-carboxylic acid methyl ester (35 mg, 0.076 mmol), 4-aminobutyric acid (624 mg, 6.05 mmol), and NaOMe solution (9 mL, 4.54 mmol) was refluxed for 16 h. After the mixture was cooled to r.t., solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over MgSO$_4$ and concentrated. The residue was dissolved in saturated NaHCO$_3$ and washed several times with ether. The aqueous layer was acidified to pH about 3-4 with 6 M HCl, and the resulting precipitate was isolated by filtration to give 17 mg of the title compound. MS: (+) m/z 535.33 (M+1).

Example 163

5-[(1-Benzyl-5-hydroxy-2-oxo-3-phenyl-8-pyridin-3-yl-1,2-dihydro-[1,7]naphthyridine-6-carbonyl)-amino]-pentanoic acid A mixture of 1-benzyl-5-hydroxy-2-oxo-3-phenyl-8-pyridin-3-yl-1,2-dihydro-[1,7]naphthyridine-6-carboxylic acid methyl ester (45 mg, 0.097 mmol), 5-aminovaleric acid (740 mg, 6.32 mmol), and NaOMe solution (10 mL, 4.86 mmol) was refluxed for 16 h. After the mixture was cooled to r.t., solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over MgSO$_4$ and concentrated. The residue was purified by silica gel chromatography (5-80% EtOAc/hexanes+1% AcOH). The product isolated was dissolved in saturated NaHCO$_3$ and washed several times with ether. The aqueous layer was acidified to pH about 3-4 with 6 M HCl, and the resulting precipitate was isolated by filtration to give 19 mg of the title compound. MS: (+) m/z 549.31 (M+1).

Example 164

3-[(5-Hydroxy-2-oxo-1,3-diphenyl-8-pyridin-3-yl-1,2-dihydro-[1,7]naphthyridine-6-carbonyl)-amino]-propionic acid a) 8-Bromo-5-hydroxy-2-oxo-1,3-diphenyl-1,2-dihydro-[1,7]naphthyridine-6-carboxylic acid methyl ester A mixture of 5-hydroxy-2-oxo-1,3-diphenyl-1,2-dihydro-[1,7]naphthyridine-6-carboxylic acid methyl ester (138 mg, 0.37 mmol) and N-bromosuccinimide (73 mg, 0.41 mmol) in CH$_2$Cl$_2$ (1.5 mL) was refluxed for 3.5 h. Solvent was evaporated in vacuo, and the residue was purified twice by silica gel chromatography (0-100% EtOAc/hexanes+1% AcOH, then 30-100% CH$_2$Cl$_2$/hexanes) to give 114 mg of the title compound as a pale yellow solid. MS: (+) m/z 451.25, 453.01 (M+1, $^{79/81}$Br).

b) 5-Hydroxy-2-oxo-1,3-diphenyl-8-pyridin-3-yl-1,2-dihydro-[1,7]naphthyridine-6-carboxylic acid methyl ester A mixture of 8-bromo-5-hydroxy-2-oxo-1,3-diphenyl-1,2-dihydro-[1,7]naphthyridine-6-carboxylic acid methyl ester (60 mg, 0.13 mmol), 3-tributylstannanyl-pyridine (0.064 mL, 0.20 mmol) and PdCl$_2$(PPh$_3$)$_2$ (19 mg, 0.027 mmol) in 3 mL of DMF was heated at 120° C. for 2 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and dried over MgSO$_4$. After evaporating the solvent in vacuo, the crude product was chromatographed (15-100% EtOAc/hexanes+1% AcOH) to give 34 mg of the title compound as a pale yellow solid. MS: (+) m/z 450.30 (M+1).

c) 3-[(5-Hydroxy-2-oxo-1,3-diphenyl-8-pyridin-3-yl-1,2-dihydro-[1,7]naphthyridine-6-carbonyl)-amino]-propionic acid A mixture of 5-hydroxy-2-oxo-1,3-diphenyl-8-pyridin-3-yl-1,2-dihydro-[1,7]naphthyridine-6-carboxylic acid methyl ester (34 mg, 0.076 mmol), β-alanine (675 mg, 7.6 mmol) and NaOMe solution (11 mL, 5.7 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over MgSO$_4$ and concentrated. The residue was dissolved in saturated NaHCO$_3$ and washed several times with ether. The aqueous layer was acidified to pH about 3-4 with 6 M HCl, and the resulting precipitate was isolated by filtration to give 25 mg of the title compound. MS: (+) m/z 507.30 (M+1).

Example 165

3-[(5-Hydroxy-1-methyl-2-oxo-3-phenyl-8-pyridin-3-yl-1,2-dihydro-[1,7]naphthyridine-6-carbonyl)-amino]-propionic acid a) 8-Bromo-5-hydroxy-1-methyl-2-oxo-3-phenyl-1,2-dihydro-[1,7]naphthyridine-6-carboxylic acid methyl ester A mixture of 5-hydroxy-1-methyl-2-oxo-3-phenyl-1,2-dihydro-[1,7]naphthyridine-6-carboxylic acid methyl ester (67 mg, 0.216 mmol) and N-bromosuccinimide (42 mg, 0.238 mmol) in CH$_2$Cl$_2$ (1 mL) was refluxed for 3 h. Solvent was evaporated in vacuo, and the residue was purified by silica gel chromatography (5-40% EtOAc/hexanes+1% AcOH) to give 69 mg of the title compound as a yellow solid. MS: (−) m/z 387.13, 389.15 (M-1, $^{79/81}$Br).

b) 5-Hydroxy-1-methyl-2-oxo-3-phenyl-8-pyridin-3-yl-1,2-dihydro-[1,7]naphthyridine-6-carboxylic acid methyl ester A mixture of 8-bromo-5-hydroxy-1-methyl-2-oxo-3-phenyl-1,2-dihydro-[1,7]naphthyridine-6-carboxylic acid methyl ester (69 mg, 0.18 mmol), 3-tributylstannanyl-pyridine (0.085 mL, 0.27 mmol) and PdCl$_2$(PPh$_3$)$_2$ (25 mg, 0.035 mmol) in 3 mL of DMF was heated at 120° C. for 2 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and dried over MgSO$_4$. After evaporating the solvent in vacuo, the crude product was purified sequentially by flash chromatography (15-100% EtOAc/hexanes+1% AcOH), preparative TLC (5% MeOH/CH$_2$Cl$_2$), and flash chromatography (0-2% MeOH/CH$_2$Cl$_2$) to give 34 mg of the title compound. MS: (+) m/z 388.39 (M+1).

c) 3-[(5-Hydroxy-1-methyl-2-oxo-3-phenyl-8-pyridin-3-yl-1,2-dihydro-[1,7]naphthyridine-6-carbonyl)-amino]-propionic acid A mixture of 5-hydroxy-1-methyl-2-oxo-3-phenyl-8-pyridin-3-yl-1,2-dihydro-[1,7]naphthyridine-6-carboxylic acid methyl ester (34 mg, 0.088 mmol), β-alanine (626 mg, 7.03 mmol) and NaOMe solution (10.5 mL, 5.3 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over MgSO$_4$ and concentrated.

The residue was dissolved in saturated NaHCO$_3$ and washed several times with ether. The aqueous layer was acidified to pH about 3-4 with 6 M HCl, and the resulting precipitate was isolated by filtration to give 26 mg of the title compound as an off-white solid. MS: (+) m/z 445.26 (M+1).

Example 166

3-[(5-Hydroxy-2-oxo-1-phenethyl-3-phenyl-8-pyridin-3-yl-1,2-dihydro-[1,7]naphthyridine-6-carbonyl)-amino]-propionic acid a) 8-Bromo-5-hydroxy-2-oxo-1-phenethyl-3-phenyl-1,2-dihydro-[1,7]naphthyridine-6-carboxylic acid methyl ester A mixture of 5-hydroxy-2-oxo-1-phenethyl-3-phenyl-1,2-dihydro-[1,7]naphthyridine-6-carboxylic acid methyl ester (57 mg, 0.14 mmol) and N-bromosuccinimide (27 mg, 0.15 mmol) in CH$_2$Cl$_2$ (0.8 mL) was refluxed for 3 h. Solvent was evaporated in vacuo, and the residue was purified by silica gel chromatography (5-40% EtOAc/hexanes) to give 54 mg of the title compound as a light yellow solid. MS: (−) m/z 477.13, 479.08 (M-1, $^{79/81}$Br).

b) 5-Hydroxy-2-oxo-1-phenethyl-3-phenyl-8-pyridin-3-yl-1,2-dihydro-[1,7]naphthyridine-6-carboxylic acid methyl ester A mixture of 8-bromo-5-hydroxy-2-oxo-1-phenethyl-3-phenyl-1,2-dihydro-[1,7]naphthyridine-6-carboxylic acid methyl ester (54 mg, 0.11 mmol), 3-tributylstannanyl-pyridine (0.054 mL, 0.17 mmol) and PdCl$_2$(PPh$_3$)$_2$ (16 mg, 0.023 mmol) in 3 mL of DMF was heated at 120° C. for 2 h under nitrogen atmosphere. After the mixture was cooled to r.t., EtOAc and water were added. 1 M HCl was added with stirring until pH was about 3-4. The aqueous layer was extracted with additional EtOAc, and the combined organic layer was washed with water and dried over MgSO$_4$. After evaporating the solvent in vacuo, the crude product was purified by silica gel chromatography (10-90% EtOAc/hexanes) to give 30 mg of the title compound as a yellow solid. MS: (+) m/z 478.39 (M+1).

c) 3-[(5-Hydroxy-2-oxo-1-phenethyl-3-phenyl-8-pyridin-3-yl-1,2-dihydro-[1,7]naphthyridine-6-carbonyl)-amino]-propionic acid A mixture of 5-hydroxy-2-oxo-1-phenethyl-3-phenyl-8-pyridin-3-yl-1,2-dihydro-[1,7]naphthyridine-6-carboxylic acid methyl ester (30 mg, 0.063 mmol), β-alanine (560 mg, 6.3 mmol) and NaOMe solution (10 mL, 5.0 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over MgSO$_4$ and concentrated. The residue was dissolved in saturated NaHCO$_3$ and washed several times with ether. The aqueous layer was acidified to pH about 3-4 and the resulting precipitate was isolated by filtration. The crude solid was purified by silica gel chromatography (10-85% EtOAc/hexanes+1% AcOH). The product isolated was dissolved in saturated NaHCO$_3$ and washed several times with ether. The aqueous layer was acidified to pH about 3-4, and the resulting precipitate was isolated by filtration to give 14 mg of the title compound. MS: (+) m/z 535.33 (M+1).

Example 167

3-[(1-Benzyl-5-hydroxy-2-oxo-3-phenyl-8-pyridin-4-yl-1,2-dihydro-[1,7]naphthyridine-6-carbonyl)-amino]-propionic acid a) 1-Benzyl-5-hydroxy-2-oxo-3-phenyl-8-pyridin-4-yl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (100 mg, 0.22 mmol), 4-tributylstannanyl-pyridine (119 mg, 0.32 mmol) and PdCl$_2$(PPh$_3$)$_2$ (30 mg, 0.043 mmol) in 5 mL of DMF was heated at 120° C. for 3 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and dried over MgSO$_4$. After evaporating the solvent in vacuo, the crude product was purified sequentially by flash chromatography (20-100% EtOAc/hexanes+1% AcOH) and preparative TLC (100% EtOAc+1% AcOH) to give 36 mg of the title compound. MS: (+) m/z 464.35 (M+1).

b) 3-[(1-Benzyl-5-hydroxy-2-oxo-3-phenyl-8-pyridin-4-yl-1,2-dihydro-[1,7]naphthyridine-6-carbonyl)-amino]-propionic acid A mixture of 1-benzyl-5-hydroxy-2-oxo-3-phenyl-8-pyridin-4-yl-1,2-dihydro-[1,7]naphthyridine-6-carboxylic acid methyl ester (36 mg, 0.078 mmol), β-alanine (693 mg, 7.8 mmol) and NaOMe solution (11.7 mL, 5.8 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over MgSO$_4$ and concentrated. The crude product was purified by silica gel chromatography (20-100% EtOAc/hexanes+1% AcOH). The product isolated was dissolved in saturated NaHCO$_3$ and washed several times with ether. The aqueous layer was acidified to pH about 3-4, and the resulting precipitate was isolated by filtration to give 14 mg of the title compound as a light yellow solid. MS: (+) m/z 521.34 (M+1).

Example 168

3-[(1-Benzyl-5-hydroxy-2-oxo-3,8-di-pyridin-3-yl-1,2-dihydro-[1,7]naphthyridine-6-carbonyl)-amino]-propionic acid a) 1-Benzyl-8-bromo-5-hydroxy-2-oxo-3-pyridin-3-yl-1,2-dihydro-[1,7]naphthyridine-6-carboxylic acid methyl ester A mixture of 1-benzyl-5-hydroxy-2-oxo-3-pyridin-3-yl-1,2-dihydro-[1,7]naphthyridine-6-carboxylic acid methyl ester (65 mg, 0.17 mmol) and N-bromosuccinimide (31 mg, 0.18 mmol) in CH$_2$Cl$_2$ (0.8 mL) was refluxed for 3 h. Solvent was evaporated in vacuo, and the residue was purified by silica gel chromatography (10-80% EtOAc/hexanes+1% AcOH) to give 40 mg of the title compound. MS: (+) m/z 466.17, 468.12 (M+1, $^{79/81}$Br).

b) 1-Benzyl-5-hydroxy-2-oxo-3,8-di-pyridin-3-yl-1,2-dihydro-[1,7]naphthyridine-6-carboxylic acid methyl ester A mixture of 1-benzyl-8-bromo-5-hydroxy-2-oxo-3-pyridin-3-yl-1,2-dihydro-[1,7]naphthyridine-6-carboxylic acid methyl ester (40 mg, 0.086 mmol), 3-tributylstannanyl-pyridine (0.040 mL, 0.13 mmol) and PdCl$_2$(PPh$_3$)$_2$ (12 mg, 0.017 mmol) in 3 mL of DMF was heated at 120° C. for 3 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and dried over MgSO$_4$. After evaporating the solvent in vacuo, the crude product was purified by silica gel chromatography (0-10% MeOH/EtOAc) to give 18 mg of the title compound. MS: (+) m/z 465.35 (M+1).

c) 3-[(1-Benzyl-5-hydroxy-2-oxo-3,8-di-pyridin-3-yl-1,2-dihydro-[1,7]naphthyridine-6-carbonyl)-amino]-propionic acid A mixture of 1-benzyl-5-hydroxy-2-oxo-3,8-di-pyridin-3-yl-1,2-dihydro-[1,7]naphthyridine-6-carboxylic acid methyl ester (18 mg, 0.039 mmol), β-alanine (553 mg, 6.21 mmol) and NaOMe solution (9 mL, 4.66 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over MgSO$_4$ and concentrated. The residue was dissolved in saturated NaHCO$_3$ and washed several times with ether. The aqueous layer was acidified to pH about 3-4, and the resulting precipitate was isolated by filtration to give 6.8 mg of the title compound as a light yellow solid. MS: (+) m/z 522.29 (M+1).

Example 169

(R)-3-{[5-Hydroxy-2-oxo-3-phenyl-1-(1-phenyl-ethyl)-1,2-dihydro-[1,7]naphthyridine-6-carbonyl]-amino}-propionic acid a) (R)-4-[7-(1-Phenyl-ethylamino)-ethylidene]pent-2-enedioic acid dimethyl ester A mixture of (R)-1-phenyl-ethylamine (3 g, 24.8 mmol) and 3-oxo-butyric acid methyl ester (3.2 mL, 29.7 mmol) in MeOH (100 mL) was refluxed for 3 h. Propynoic acid methyl ester (3.3 mL, 37.1 mmol) was added, and the resulting mixture was refluxed for 2 days. After cooling to r.t., the solvent was evaporated, and the crude oil was recrystallized from MeOH to give 5.56 g of the title compound as a pale orange solid. MS: (+) m/z 304.31 (M+1).

b) (R)-5-Bromo-2-methyl-6-oxo-1-(1-phenyl-ethyl)-1,6-dihydro-pyridine-3-carboxylic acid methyl ester MeOH (170 mL) was added to a flask containing (R)-4-[1-(1-phenyl-ethylamino)-ethylidene]-pent-2-enedioic acid dimethyl ester (5.56 g, 18.3 mmol). NaOMe solution (4.2 mL, 18.3 mmol, 4.375 M in MeOH) and N-bromosuccinimide (3.92 g, 22 mmol) were added, and the resulting mixture was refluxed for 7 h. After cooling to r.t., the solvent was evaporated in vacuo. Saturated NH$_4$Cl was added, and the resulting mixture was extracted with CH$_2$Cl$_2$. The organic layer was dried over MgSO$_4$ and concentrated. The crude product was chromatographed (0-25% EtOAc/hexanes) to give 3.32 g of the title compound as an off-white solid. MS: (+) m/z 372.20, 374.16 (M+Na, $^{79/81}$Br).

c) (R)-5-Bromo-2-bromomethyl-6-oxo-1-(1-phenyl-ethyl)-1,6-dihydro-pyridine-3-carboxylic acid methyl ester A mixture of (R)-5-bromo-2-methyl-6-oxo-1-(1-phenyl-ethyl)-1,6-dihydro-pyridine-3-carboxylic acid methyl ester (3.32 g, 9.5 mmol), N-bromosuccinimide (1.86 g, 10.4 mmol), and benzoyl peroxide (0.23 g, 0.95 mmol) in CCl$_4$ (100 mL) was refluxed for 16 h. The solvent was evaporated in vacuo, and the residue was chromatographed (0-25% EtOAc/hexanes) to give 3.48 g of the title compound as a white solid. MS: (+) m/z 452.06 (M+Na).

d) (R)-5-Bromo-2-{[methoxycarbonylmethyl-(toluene-4-sulfonyl)-amino]-methyl}-6-oxo-1-(1-phenyl-ethyl)-1,6-dihydro-pyridine-3-carboxylic acid methyl ester A mixture of (R)-5-bromo-2-bromomethyl-6-oxo-1-(1-phenyl-ethyl)-1,6-dihydro-pyridine-3-carboxylic acid methyl ester (3.48 g, 8.11 mmol), (toluene-4-sulfonylamino)-acetic acid methyl ester (1.87 g, 7.71 mmol), sodium iodide (2.43 g, 16.2 mmol) and potassium carbonate (2.24 g, 16.2 mmol) in DMF (50 mL) was stirred at r.t. for 16 h. Brine (100 mL) was added, and the resulting suspension was extracted with EtOAc. The organic layer was washed with water and brine, and dried over MgSO$_4$. After the solvent was evaporated in vacuo, the crude product was chromatographed (0-50% EtOAc/hexanes) to give 3.5 g of the title compound as a yellow viscous oil. MS: (+) m/z 613, 615 (M+Na, $^{79/81}$Br).

e) (R)-3-Bromo-5-hydroxy-2-oxo-1-(1-phenyl-ethyl)-1,2-dihydro-[1,7]naphthyridine-6-carboxylic acid methyl ester (R)-5-Bromo-2-{[methoxycarbonylmethyl-(toluene-4-sulfonyl)-amino]-methyl}-6-oxo-1-(1-phenyl-ethyl)-1,6-dihydro-pyridine-3-carboxylic acid methyl ester (3.5 g, 5.92 mmol) was dissolved in 120 mL of MeOH and placed in ice bath. NaOMe solution (4.1 mL, 17.8 mmol, 4.375 M in MeOH) was added and the mixture was stirred for 16 h at r.t. 1 M HCl was added to acidify the mixture, and the resulting suspension was extracted with CH$_2$Cl$_2$. The organic layer was dried over MgSO$_4$ and concentrated. The crude product was purified by silica gel chromatography (30-100% CH$_2$Cl$_2$/hexanes) to give 2.13 g of the title compound as a yellow solid. MS: (−) m/z 401.18, 403.19 (M−1, $^{79/81}$Br).

f) (R)-5-Hydroxy-2-oxo-3-phenyl-1-(1-phenyl-ethyl)-1,2-dihydro-[1,7]naphthyridine-6-carboxylic acid methyl ester A mixture of (R)-3-bromo-5-hydroxy-2-oxo-1-(1-phenyl-ethyl)-1,2-dihydro-[1,7]naphthyridine-6-carboxylic acid methyl ester (500 mg, 1.24 mmol), PhSnBu$_3$ (0.49 mL, 1.49 mmol), and PdCl$_2$(PPh$_3$)$_2$ (174 mg, 0.25 mmol) in DMF (10 mL) was heated at 120° C. under nitrogen atmosphere for 2 h. After the mixture was cooled to r.t., brine and EtOAc were added. 1 M HCl was added until pH was about 3. The aqueous layer was extracted with additional EtOAc and the organic layers were combined, washed with water, and dried over MgSO$_4$. After evaporating the solvent in vacuo, the crude product was chromatographed (5-35% EtOAc/hexanes+1% AcOH) to give 313 mg of the title compound as a yellow solid. MS: (+) m/z 401.36 (M+1).

g) (R)-3-{[5-Hydroxy-2-oxo-3-phenyl-1-(1-phenyl-ethyl)-1,2-dihydro-[1,7]naphthyridine-6-carbonyl]-amino}-propionic acid A mixture of (R)-5-hydroxy-2-oxo-3-phenyl-1-(1-phenyl-ethyl)-1,2-dihydro-[1,7]naphthyridine-6-carboxylic acid methyl ester (30 mg, 0.075 mmol), β-alanine (535 mg, 6.0 mmol) and NaOMe solution (9 mL, 4.5 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3. The aqueous layer was extracted with additional EtOAc, and the organic layers were combined, dried over MgSO$_4$ and concentrated. The crude product was dissolved in saturated NaHCO$_3$ and washed several times with ether. The aqueous layer was acidified to pH about 3, and the resulting precipitate was isolated by filtration to give 22 mg of the title compound. MS: (+) m/z 458.36 (M+1).

Example 170

(R)-4-{[5-Hydroxy-2-oxo-3-phenyl-1-(1-phenyl-ethyl)-1,2-dihydro-[1,7]naphthyridine-6-carbonyl]-amino}-butyric acid A mixture of (R)-5-hydroxy-2-oxo-3-phenyl-1-(1-phenyl-ethyl)-1,2-dihydro-[1,7]naphthyridine-6-carboxylic acid methyl ester (40 mg, 0.1 mmol), 4-aminobutyric acid (670 mg, 6.5 mmol) and NaOMe solution (10 mL, 5.0 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over MgSO$_4$ and concentrated. The residue was purified by silica gel chromatography (10-80% EtOAc/hexanes+1% AcOH). The product isolated was dissolved in saturated NaHCO$_3$ and washed several times with ether. The aqueous layer was acidified to pH about 3, and the resulting precipitate was isolated by filtration to give 18 mg of the title compound. MS: (+) m/z 472.34 (M+1).

Example 171

3-{[1-Benzyl-5-hydroxy-8-(5-methoxy-pyridin-3-yl)-2-oxo-3-phenyl-1,2-dihydro-[1,7]naphthyridine-6-carbonyl]amino}-propionic acid a) 1-Benzyl-5-hydroxy-8-(5-methoxy-pyridin-3-yl)-2-oxo-3-phenyl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (70 mg, 0.15 mmol), 3-methoxy-5-tributylstannanyl-pyridine (90 mg, 0.23 mmol) and PdCl$_2$(PPh$_3$)$_2$ (21 mg, 0.030 mmol) in 3 mL of DMF was heated at 120° C. for 3 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and dried over MgSO$_4$. After evaporating the solvent in vacuo, the crude product was chromatographed (10-85% EtOAc/hexanes+1% AcOH) to give 45 mg of the title compound as a light yellow solid. MS: (+) m/z 494.51 (M+1).

b) 3-{[1-Benzyl-5-hydroxy-8-(5-methoxy-pyridin-3-yl)-2-oxo-3-phenyl-1,2-dihydro-[1,7]naphthyridine-6-carbonyl]amino}-propionic acid A mixture of 1-benzyl-5-hydroxy-8-(5-methoxy-pyridin-3-yl)-2-oxo-3-phenyl-1,2-dihydro-[1,7]naphthyridine-6-carboxylic acid methyl ester (45 mg, 0.091 mmol), β-alanine (651 mg, 7.30 mmol) and NaOMe solution (11 mL, 5.48 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The organic layer was dried over MgSO$_4$ and concentrated. The residue was dissolved in saturated NaHCO$_3$ and washed several times with ether. The aqueous layer was acidified to pH about 3-4 with 6 M HCl, and the resulting precipitate was isolated by filtration to give 35 mg of the title compound as a light tan solid. MS: (+) m/z 551.32 (M+1).

Example 172

3-{[1-Benzyl-8-(5-chloro-pyridin-3-yl)-5-hydroxy-2-oxo-3-phenyl-1,2-dihydro-[1,7]naphthyridine-6-carbonyl]amino}-propionic acid a) 1-Benzyl-8-(5-chloro-pyridin-3-yl)-5-hydroxy-2-oxo-3-phenyl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (80 mg, 0.17 mmol), 3-chloro-5-tributylstannanyl-pyridine (104 mg, 0.26 mmol) and PdCl$_2$(PPh$_3$)$_2$ (24 mg, 0.034 mmol) in 4 mL of DMF was heated at 120° C. for 3 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and dried over MgSO$_4$. After evaporating the solvent in vacuo, the crude product was chromatographed (0-15% EtOAc/CH$_2$Cl$_2$) to give 38 mg of the title compound. MS: (+) m/z 498.29 (M+1).

b) 3-{[1-Benzyl-8-(5-chloro-pyridin-3-yl)-5-hydroxy-2-oxo-3-phenyl-1,2-dihydro-[1,7]naphthyridine-6-carbonyl]amino}-propionic acid A mixture of 1-benzyl-8-(5-chloro-pyridin-3-yl)-5-hydroxy-2-oxo-3-phenyl-1,2-dihydro-[1,7]naphthyridine-6-carboxylic acid methyl ester (38 mg, 0.076 mmol), β-alanine (681 mg, 7.6 mmol) and NaOMe solution (11 mL, 5.7 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over MgSO$_4$ and concentrated. The residue was purified by silica gel chromatography (5-100% EtOAc/hexanes+1% AcOH). The product isolated was dissolved in saturated NaHCO$_3$ and washed several times with ether. The aqueous layer was acidified to pH about 3-4 with 6 M HCl, and the resulting precipitate was isolated by filtration to give 12 mg of the title compound as an off-white solid. MS: (+) m/z 555.23 (M+1).

Example 173

(S)-3-{[5-Hydroxy-2-oxo-3-phenyl-1-(1-phenylethyl)-1,2-dihydro-[1,7]naphthyridine-6-carbonyl]-amino}-propionic acid a) (S)-4-[1-(1-Phenyl-ethylamino)-ethylidene]-pent-2-enedioic acid dimethyl ester A mixture of (S)-1-phenyl-ethylamine (3 g, 24.8 mmol) and 3-oxo-butyric acid methyl ester (3.2 mL, 29.7 mmol) in MeOH (100 mL) was refluxed for 2 h. Propynoic acid methyl ester (3.3 mL, 37.1 mmol) was added, and the resulting mixture was refluxed for 2 days. After cooling to r.t., the solvent was evaporated, and the crude solid was recrystallized from MeOH to give 4.8 g of the title compound as a pale orange solid. MS: (+) m/z 326.29 (M+Na).

b) (S)-5-Bromo-2-methyl-6-oxo-1-(1-phenyl-ethyl)-1,6-dihydro-pyridine-3-carboxylic acid methyl ester MeOH (150 mL) was added to a flask containing (S)-4-[1-(1-phenyl-ethylamino)-ethylidene]-pent-2-enedioic acid dimethyl ester (4.81 g, 15.9 mmol). NaOMe solution (3.6 mL, 15.9 mmol, 4.375 M in MeOH) and N-bromosuccinimide (3.4 g, 19 mmol) were added, and the resulting mixture was refluxed for 6 h. After cooling to r.t., the solvent was evaporated in vacuo. Saturated NH$_4$Cl (100 mL) was added, and the resulting mixture was extracted with CH$_2$Cl$_2$. The organic layer was dried over MgSO$_4$ and concentrated. The crude product was chromatographed (0-25% EtOAc/hexanes) to give 2.34 g of the title compound as a yellow solid. MS: (+) m/z 372.20, 374.16 (M+Na, $^{79/81}$Br).

c) (S)-5-Bromo-2-bromomethyl-6-oxo-1-(1-phenyl-ethyl)-1,6-dihydro-pyridine-3-carboxylic acid methyl ester A mixture of (S)-5-bromo-2-methyl-6-oxo-1-(1-phenyl-ethyl)-1,6-dihydro-pyridine-3-carboxylic acid methyl ester (2.34 g, 6.69 mmol), N-bromosuccinimide (1.31 g, 7.35 mmol), and benzoyl peroxide (0.16 g, 0.669 mmol) in CCl$_4$ (70 mL) was refluxed for 16 h. After cooling the mixture to r.t., the precipitate was removed by filtration. The filtrate was evaporated in vacuo, and the residue was chromatographed (0-25% EtOAc/hexanes) to give 2.67 g of the title compound as a white solid. MS: (+) m/z 452.06 (M+Na).

d) (S)-5-Bromo-2-{[methoxycarbonylmethyl-(toluene-4-sulfonyl)-amino]-methyl}-6-oxo-1-(1-phenyl-ethyl)-1,6-dihydro-pyridine-3-carboxylic acid methyl ester A mixture of (S)-5-bromo-2-bromomethyl-6-oxo-1-(1-phenyl-ethyl)-1,6-dihydro-pyridine-3-carboxylic acid methyl ester (2.67 g, 6.22 mmol), (toluene-4-sulfonylamino)-acetic acid methyl ester (1.44 g, 5.91 mmol), sodium iodide (1.87 g, 12.4 mmol) and potassium carbonate (1.72 g, 12.4 mmol) in DMF (60 mL) was stirred at r.t. for 16 h. Brine (100 mL) was added, and the resulting suspension was extracted with EtOAc. The organic layer was washed with water and brine, and dried over MgSO$_4$. After the solvent was evaporated in vacuo, the crude product was chromatographed (0-50% EtOAc/hexanes) to give 2.26 g of the title compound as a viscous oil. MS: (+) m/z 613, 615 (M+Na, $^{79/81}$Br).

e) (S)-3-Bromo-5-hydroxy-2-oxo-1-(1-phenyl-ethyl)-1,2-dihydro-[1,7]naphthyridine-6-carboxylic acid methyl ester (S)-5-Bromo-2-{[methoxycarbonylmethyl-(toluene-4-sulfonyl)-amino]-methyl}-6-oxo-1-(1-phenyl-ethyl)-1,6-dihydro-pyridine-3-carboxylic acid methyl ester (2.26 g, 3.82 mmol) was dissolved in 80 mL of MeOH and placed in ice bath. NaOMe solution (2.6 mL, 11.5 mmol, 4.375 M in MeOH) was added and the mixture was stirred for 16 h at r.t. 1 M HCl was added to acidify the mixture, and the resulting suspension was extracted with CH$_2$Cl$_2$. The organic layer was dried over MgSO$_4$ and concentrated. The crude product was purified by silica gel chromatography (30-100% CH$_2$Cl$_2$/hexanes) to give 1.01 g of the title compound as a pale yellow solid. MS: (−) m/z 401.24, 403.19 (M−1, $^{79/81}$Br).

f) (S)-5-Hydroxy-2-oxo-3-phenyl-1-(1-phenyl-ethyl)-1,2-dihydro-[1,7]naphthyridine-6-carboxylic acid methyl ester A mixture of (S)-3-bromo-5-hydroxy-2-oxo-1-(1-phenyl-ethyl)-1,2-dihydro-[1,7]naphthyridine-6-carboxylic acid methyl ester (350 mg, 0.87 mmol), PhSnBu$_3$ (0.34 mL, 1.04 mmol), and PdCl$_2$(PPh$_3$)$_2$ (122 mg, 0.17 mmol) in DMF (8 mL) was heated at 120° C. under nitrogen atmosphere for 2 h. After the mixture was cooled to r.t., brine and EtOAc were added. 1 M HCl was added until pH was about 2-3. The aqueous layer was extracted with additional EtOAc and the organic layers were combined, washed with water and brine, and dried over MgSO$_4$. After evaporating the solvent in vacuo, the crude product was chromatographed (0-35% EtOAc/hexanes+1% AcOH) to give 256 mg of the title compound as a yellow solid. MS: (+) m/z 401.36 (M+1).

g) (S)-3-{[5-Hydroxy-2-oxo-3-phenyl-1-(1-phenyl-ethyl)-1,2-dihydro-[1,7]naphthyridine-6-carbonyl]-amino}-propionic acid A mixture of (S)-5-hydroxy-2-oxo-3-phenyl-1-(1-phenyl-ethyl)-1,2-dihydro-[1,7]naphthyridine-6-carboxylic acid methyl ester (30 mg, 0.075 mmol), β-alanine (535 mg, 6.0 mmol) and NaOMe solution (9 mL, 4.5 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3. The aqueous layer was extracted with additional EtOAc, and the organic layers were combined, dried over MgSO$_4$ and concentrated. The crude product was dissolved in saturated NaHCO$_3$ and washed several times with ether. The aqueous layer was acidified to pH about 3 with 6 M HCl, and the resulting precipitate was isolated by filtration to give 26 mg of the title compound. MS: (+) m/z 458.36 (M+1).

Example 174

(S)-4-{[5-Hydroxy-2-oxo-3-phenyl-1-(1-phenyl-ethyl)-1,2-dihydro-[1,7]naphthyridine-6-carbonyl]-amino}-butyric acid A mixture of (S)-5-hydroxy-2-oxo-3-phenyl-1-(1-phenyl-ethyl)-1,2-dihydro-[1,7]naphthyridine-6-carboxylic acid methyl ester (40 mg, 0.1 mmol), 4-aminobutyric acid (825 mg, 8.0 mmol) and NaOMe solution (12 mL, 6.0 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3. The aqueous layer was extracted with additional EtOAc, and the organic layers were combined, dried over $MgSO_4$ and concentrated. The residue was purified by silica gel chromatography (5-60% EtOAc/hexanes+1% AcOH). The product isolated was dissolved in saturated $NaHCO_3$ and washed several times with ether. The aqueous layer was acidified to pH about 3 with 6 M HCl, and the resulting precipitate was isolated by filtration to give 17 mg of the title compound. MS: (+) m/z 472.34 (M+1).

Example 175

(S)-3-{[5-Hydroxy-2-oxo-3-phenyl-1-(1-phenyl-ethyl)-8-pyridin-3-yl-1,2-dihydro-[1,7]naphthyridine-6-carbonyl]amino}-propionic acid a) (S)-8-Bromo-5-hydroxy-2-oxo-3-phenyl-1-(1-phenyl-ethyl)-1,2-dihydro-[1,7]naphthyridine-6-carboxylic acid methyl ester A mixture of (S)-5-hydroxy-2-oxo-3-phenyl-1-(1-phenyl-ethyl)-1,2-dihydro-[1,7]naphthyridine-6-carboxylic acid methyl ester (100 mg, 0.25 mmol) and N-bromosuccinimide (49 mg, 0.275 mmol) in $CH_2Cl_2$ (1 mL) was refluxed for 3 h. Solvent was evaporated in vacuo, and the residue was purified by silica gel chromatography (5-20% EtOAc/hexanes+1% AcOH) to give 78 mg of the title compound. MS: (−) m/z 477.19, 479.21 (M-1, $^{79/81}$Br).

b) (S)-5-Hydroxy-2-oxo-3-phenyl-1-(1-phenyl-ethyl)-8-pyridin-3-yl-1,2-dihydro-[1,7]naphthyridine-6-carboxylic acid methyl ester A mixture of (S)-8-bromo-5-hydroxy-2-oxo-3-phenyl-1-(1-phenyl-ethyl)-1,2-dihydro-[1,7]naphthyridine-6-carboxylic acid methyl ester (78 mg, 0.16 mmol), 3-tributylstannanyl-pyridine (0.078 mL, 0.24 mmol) and $PdCl_2(PPh_3)_2$ (23 mg, 0.033 mmol) in 4 mL of DMF was heated at 120° C. for 3 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and dried over $MgSO_4$. After evaporating the solvent in vacuo, the crude product was purified by silica gel chromatography (5-90% EtOAc/hexanes+1% AcOH) to give 30 mg of the title compound. MS: (+) m/z 478.39 (M+1).

c) (S)-3-{[5-Hydroxy-2-oxo-3-phenyl-1-(1-phenyl-ethyl)-8-pyridin-3-yl-1,2-dihydro-[1,7]naphthyridine-6-carbonyl]amino}-propionic acid A mixture of (S)-5-hydroxy-2-oxo-3-phenyl-1-(1-phenyl-ethyl)-8-pyridin-3-yl-1,2-dihydro-[1,7]naphthyridine-6-carboxylic acid methyl ester (30 mg, 0.063 mmol), β-alanine (672 mg, 7.5 mmol) and NaOMe solution (11 mL, 5.7 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over $MgSO_4$ and concentrated. The residue was purified by silica gel chromatography (10-100% EtOAc/hexanes+1% AcOH). The product isolated was dissolved in saturated $NaHCO_3$ and washed several times with ether. The aqueous layer was acidified to pH about 3-4 with 6 M HCl, and the resulting precipitate was isolated by filtration to give 16 mg of the title compound. MS: (+) m/z 535.39 (M+1).

Example 176

(R)-3-{[5-Hydroxy-2-oxo-3-phenyl-1-(1-phenyl-ethyl)-8-pyridin-3-yl-1,2-dihydro-[1,7]naphthyridine-6-carbonyl]amino}-propionic acid a) (R)-8-Bromo-5-hydroxy-2-oxo-3-phenyl-1-(1-phenyl-ethyl)-1,2-dihydro-[1,7]naphthyridine-6-carboxylic acid methyl ester A mixture of (R)-5-hydroxy-2-oxo-3-phenyl-1-(1-phenyl-ethyl)-1,2-dihydro-[1,7]naphthyridine-6-carboxylic acid methyl ester (90 mg, 0.225 mmol) and N-bromosuccinimide (44 mg, 0.248 mmol) in $CH_2Cl_2$ (1 mL) was refluxed for 3 h. Solvent was evaporated in vacuo, and the residue was purified by silica gel chromatography (5-20% EtOAc/hexanes+1% AcOH) to give 73 mg of the title compound as a yellow solid. MS: (−) m/z 477.19, 479.15 (M-1, $^{79/81}$Br).

b) (R)-5-Hydroxy-2-oxo-3-phenyl-1-(1-phenyl-ethyl)-8-pyridin-3-yl-1,2-dihydro-[1,7]naphthyridine-6-carboxylic acid methyl ester A mixture of (R)-8-bromo-5-hydroxy-2-oxo-3-phenyl-1-(1-phenyl-ethyl)-1,2-dihydro-[1,7]naphthyridine-6-carboxylic acid methyl ester (73 mg, 0.15 mmol), 3-tributylstannanyl-pyridine (0.073 mL, 0.23 mmol) and $PdCl_2(PPh_3)_2$ (21 mg, 0.030 mmol) in 4 mL of DMF was heated at 120° C. for 3 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and dried over $MgSO_4$. After evaporating the solvent in vacuo, the crude product was purified by silica gel chromatography (5-90% EtOAc/hexanes+1% AcOH) to give 30 mg of the title compound as a brown oil. MS: (+) m/z 478.39 (M+1).

c) (R)-3-{[5-Hydroxy-2-oxo-3-phenyl-1-(1-phenyl-ethyl)-8-pyridin-3-yl-1,2-dihydro-[1,7]naphthyridine-6-carbonyl]-amino}-propionic acid A mixture of (R)-5-hydroxy-2-oxo-3-phenyl-1-(1-phenyl-ethyl)-8-pyridin-3-yl-1,2-dihydro-[1,7]naphthyridine-6-carboxylic acid methyl ester (30 mg, 0.063 mmol), β-alanine (560 mg, 6.3 mmol) and NaOMe solution (9.5 mL, 4.7 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over $MgSO_4$ and concentrated. The residue was dissolved in saturated $NaHCO_3$ and washed several times with ether. The aqueous layer was acidified to pH about 3-4 with 6 M HCl, and the resulting precipitate was isolated by filtration. The crude solid was purified by silica gel chromatography (10-100% EtOAc/hexanes+1% AcOH). The product isolated was dissolved in satu-

Example 177

3-{[1-Benzyl-8-(5-fluoro-pyridin-3-yl)-5-hydroxy-2-oxo-3-phenyl-1,2-dihydro-[1,7]naphthyridine-6-carbonyl]amino}-propionic acid a) 1-Benzyl-8-(5-fluoro-pyridin-3-yl)-5-hydroxy-2-oxo-3-phenyl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (70 mg, 0.15 mmol), 3-fluoro-5-tributylstannanyl-pyridine (87 mg, 0.23 mmol) and $PdCl_2(PPh_3)_2$ (21 mg, 0.030 mmol) in 3 mL of DMF was heated at 120° C. for 4 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and dried over $MgSO_4$. After evaporating the solvent in vacuo, the crude product was chromatographed (0-20% EtOAc/$CH_2Cl_2$) to give 32 mg of the title compound. MS: (+) m/z 482.30 (M+1).

b) 3-{[1-Benzyl-8-(5-fluoro-pyridin-3-yl)-5-hydroxy-2-oxo-3-phenyl-1,2-dihydro-[1,7]naphthyridine-6-carbonyl]-amino}-propionic acid A mixture of 1-benzyl-8-(5-fluoro-pyridin-3-yl)-5-hydroxy-2-oxo-3-phenyl-1,2-dihydro-[1,7]naphthyridine-6-carboxylic acid methyl ester (32 mg, 0.067 mmol), β-alanine (593 mg, 6.7 mmol) and NaOMe solution (10 mL, 5.0 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over $MgSO_4$ and concentrated. The residue was dissolved in saturated $NaHCO_3$ and washed several times with ether. The aqueous layer was acidified to pH about 3-4 with 6 M HCl, and the resulting precipitate was isolated by filtration. The crude solid was purified by silica gel chromatography (5-80% EtOAc/hexanes+1% AcOH). The product isolated was dissolved in saturated $NaHCO_3$ and washed several times with ether. The aqueous layer was acidified to pH about 3-4 with 6 M HCl, and the resulting precipitate was isolated by filtration to give 14 mg of the title compound as a light yellow solid. MS: (+) m/z 539.29 (M+1).

Example 178

3-{[1-Benzyl-5-hydroxy-8-(2-methyl-pyridin-3-yl)-2-oxo-3-phenyl-1,2-dihydro-[1,7]naphthyridine-6-carbonyl]amino}-propionic acid a) 1-Benzyl-5-hydroxy-8-(2-methyl-pyridin-3-yl)-2-oxo-3-phenyl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (80 mg, 0.17 mmol), 2-methyl-3-tributylstannanyl-pyridine (103 mg, 0.26 mmol) and $PdCl_2(PPh_3)_2$ (24 mg, 0.034 mmol) in 4 mL of DMF was heated at 120° C. for 3 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and dried over $MgSO_4$. After evaporating the solvent in vacuo, the crude product was chromatographed (5-90% EtOAc/hexanes+1% AcOH) to give 28 mg of the title compound. MS: (+) m/z 478.39 (M+1).

b) 3-{[1-Benzyl-5-hydroxy-8-(2-methyl-pyridin-3-yl)-2-oxo-3-phenyl-1,2-dihydro-[1,7]naphthyridine-6-carbonyl]-amino}-propionic acid A mixture of 1-benzyl-5-hydroxy-8-(2-methyl-pyridin-3-yl)-2-oxo-3-phenyl-1,2-dihydro-[1,7]naphthyridine-6-carboxylic acid methyl ester (28 mg, 0.059 mmol), β-alanine (628 mg, 7.0 mmol) and NaOMe solution (10.5 mL, 5.3 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over $MgSO_4$ and concentrated. The residue was dissolved in saturated $NaHCO_3$ and washed several times with ether. The aqueous layer was acidified to pH about 3-4, and the resulting precipitate was isolated by filtration to give 20 mg of the title compound. MS: (+) m/z 535.51 (M+1).

Example 179

3-{[1-Benzyl-5-hydroxy-8-(6-methyl-pyridin-3-yl)-2-oxo-3-phenyl-1,2-dihydro-[1,7]naphthyridine-6-carbonyl]amino}-propionic acid a) 1-Benzyl-5-hydroxy-8-(6-methyl-pyridin-3-yl)-2-oxo-3-phenyl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (70 mg, 0.15 mmol), 2-methyl-5-tributylstannanyl-pyridine (86 mg, 0.23 mmol) and $PdCl_2(PPh_3)_2$ (21 mg, 0.030 mmol) in 4 mL of DMF was heated at 120° C. for 3 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and dried over $MgSO_4$. After evaporating the solvent in vacuo, the crude product was chromatographed (10-90% EtOAc/hexanes+1% AcOH) to give 40 mg of the title compound as a white solid. MS: (+) m/z 478.45 (M+1).

b) 3-{[1-Benzyl-5-hydroxy-8-(6-methyl-pyridin-3-yl)-2-oxo-3-phenyl-1,2-dihydro-[1,7]naphthyridine-6-carbonyl]amino}-propionic acid A mixture of 1-benzyl-5-hydroxy-8-(6-methyl-pyridin-3-yl)-2-oxo-3-phenyl-1,2-dihydro-[1,7]naphthyridine-6-carboxylic acid methyl ester (40 mg, 0.084 mmol), β-alanine (600 mg, 6.7 mmol) and NaOMe solution (10 mL, 5.0 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over MgSO$_4$ and concentrated. The residue was dissolved in saturated NaHCO$_3$ and washed several times with ether. The aqueous layer was acidified to pH about 3-4, and the resulting precipitate was isolated by filtration. The crude solid was purified by silica gel chromatography (10-100% EtOAc/hexanes+1% AcOH). The product isolated was dissolved in saturated NaHCO$_3$ and washed several times with ether. The aqueous layer was acidified to pH about 3-4, and the resulting precipitate was isolated by filtration to give 4.8 mg of the title compound. MS: (+) m/z 535.33 (M+1).

Example 180

3-{[1-Benzyl-5-hydroxy-2-oxo-3-phenyl-8-(6-trifluoromethyl-pyridin-3-yl)-1,2-dihydro-[1,7]naphthyridine-6-carbonyl]amino}-propionic acid a) 1-Benzyl-5-hydroxy-2-oxo-3-phenyl-8-(6-trifluoromethyl-pyridin-3-yl)-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (70 mg, 0.15 mmol), 5-tributylstannanyl-2-trifluoromethyl-pyridine (98 mg, 0.23 mmol) and PdCl$_2$(PPh$_3$)$_2$ (21 mg, 0.030 mmol) in 4 mL of DMF was heated at 120° C. for 3 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and dried over MgSO$_4$. After evaporating the solvent in vacuo, the crude product was chromatographed (2-30% EtOAc/hexanes+1% AcOH) to give 67 mg of the title compound. MS: (+) m/z 532.30 (M+1).

b) 3-{[1-Benzyl-5-hydroxy-2-oxo-3-phenyl-8-(6-trifluoromethyl-pyridin-3-yl)-1,2-dihydro-[1,7]naphthyridine-6-carbonyl]-amino}-propionic acid A mixture of 1-benzyl-5-hydroxy-2-oxo-3-phenyl-8-(6-trifluoromethyl-pyridin-3-yl)-1,2-dihydro-[1,7]naphthyridine-6-carboxylic acid methyl ester (67 mg, 0.13 mmol), β-alanine (674 mg, 7.6 mmol) and NaOMe solution (11 mL, 5.7 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over MgSO$_4$ and concentrated. The residue was dissolved in saturated NaHCO$_3$ and washed several times with ether. The aqueous layer was acidified to pH about 3-4, and the resulting precipitate was isolated by filtration. The crude solid was purified by silica gel chromatography (5-50% EtOAc/hexanes+1% AcOH). The product isolated was dissolved in saturated NaHCO$_3$ and washed several times with ether. The aqueous layer was acidified to pH about 3-4, and the resulting precipitate was isolated by filtration to give 32 mg of the title compound as an off-white solid. MS: (+) m/z 589.30 (M+1).

Example 181

3-{[1-Benzyl-5-hydroxy-8-(6-methoxy-pyridin-3-yl)-2-oxo-3-phenyl-1,2-dihydro-[1,7]naphthyridine-6-carbonyl]amino}-propionic acid a) 1-Benzyl-5-hydroxy-8-(6-methoxy-pyridin-3-yl)-2-oxo-3-phenyl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (70 mg, 0.15 mmol), 2-methoxy-5-tributylstannanyl-pyridine (90 mg, 0.23 mmol) and PdCl$_2$(PPh$_3$)$_2$ (21 mg, 0.030 mmol) in 4 mL of DMF was heated at 120° C. for 2 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and dried over MgSO$_4$. After evaporating the solvent in vacuo, the crude product was chromatographed (5-35% EtOAc/hexanes+1% AcOH) to give 67 mg of the title compound. MS: (+) m/z 494.39 (M+1).

b) 3-{[1-Benzyl-5-hydroxy-8-(6-methoxy-pyridin-3-yl)-2-oxo-3-phenyl-1,2-dihydro-[1,7]naphthyridine-6-carbonyl]-amino}-propionic acid A mixture of 1-benzyl-5-hydroxy-8-(6-methoxy-pyridin-3-yl)-2-oxo-3-phenyl-1,2-dihydro-[1,7]naphthyridine-6-carboxylic acid methyl ester (67 mg, 0.14 mmol), β-alanine (726 mg, 8.2 mmol) and NaOMe solution (12 mL, 6.1 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over MgSO$_4$ and concentrated. The residue was dissolved in saturated NaHCO$_3$ and washed several times with ether. The aqueous layer was acidified to pH about 3-4, and the resulting precipitate was isolated by filtration to give 53 mg of the title compound as a light yellow solid. MS: (+) m/z 551.39 (M+1).

Example 182

3-{[5-Hydroxy-2-oxo-3-phenyl-8-pyridin-3-yl-1-(tetrahydro-pyran-4-ylmethyl)-1,2-dihydro-[1,7]naphthyridine-6-carbonyl]amino}-propionic acid a) 8-Bromo-5-hydroxy-2-oxo-3-phenyl-1-(tetrahydro-pyran-4-ylmethyl)-1,2-dihydro-[1,7]naphthyridine-6-carboxylic acid methyl ester A mixture of 5-hydroxy-2-oxo-3-phenyl-1-(tetrahydropyran-4-ylmethyl)-1,2-dihydro-[1,7]naphthyridine-6-carboxylic acid methyl ester (109 mg, 0.277 mmol) and N-bromosuccinimide (54 mg, 0.304 mmol) in CH$_2$Cl$_2$ (1 mL) was refluxed for 3 h. Solvent was evaporated in vacuo, and the residue was purified by silica gel chromatography (5-40% EtOAc/hexanes+1% AcOH) to give 91 mg of the title compound as a light yellow solid. MS: (+) m/z 473.29, 475.18 (M+1, [79/81]Br).

b) 5-Hydroxy-2-oxo-3-phenyl-8-pyridin-3-yl-1-(tetrahydro-pyran-4-ylmethyl)-1,2-dihydro-[1,7]naphthyridine-6-carboxylic acid methyl ester A mixture of 8-bromo-5-hydroxy-2-oxo-3-phenyl-1-(tetrahydro-pyran-4-ylmethyl)-1,2-dihydro-[1,7]naphthyridine- 6-carboxylic acid methyl ester (91 mg, 0.19 mmol), 3-tributylstannanyl-pyridine (0.092 mL, 0.29 mmol) and PdCl$_2$(PPh$_3$)$_2$ (27 mg, 0.038 mmol) in 4 mL of DMF was heated at 120° C. for 3 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and dried over MgSO$_4$. After evaporating the solvent in vacuo, the crude product was purified sequentially by flash chromatography (10-100% EtOAc/hexanes+1% AcOH) and preparative TLC (5% MeOH/CH$_2$Cl$_2$) to give 36 mg of the title compound. MS: (+) m/z 472.41 (M+1).

c) 3-{[5-Hydroxy-2-oxo-3-phenyl-8-pyridin-3-yl-1-(tetrahydro-pyran-4-ylmethyl)-1,2-dihydro-[1,7]naphthyridine-6-carbonyl]-amino}-propionic acid A mixture of 5-hydroxy-2-oxo-3-phenyl-8-pyridin-3-yl-1-(tetrahydro-pyran-4-ylmethyl)-1,2-dihydro-[1,7]naphthyridine-6-carboxylic acid methyl ester (36 mg, 0.076 mmol), β-alanine (545 mg, 6.1 mmol) and NaOMe solution (9 mL, 4.6 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over MgSO$_4$ and concentrated. The residue was dissolved in saturated NaHCO$_3$ and washed several times with ether. The aqueous layer was acidified to pH about 3-4, and the resulting precipitate was isolated by filtration to give 7.8 mg of the title compound as a pale brown solid. MS: (+) m/z 529.41 (M+1).

Example 183

3-[(1-Cyclohexylmethyl-5-hydroxy-2-oxo-3-phenyl-8-pyridin-3-yl-1,2-dihydro-[1,7]naphthyridine-6-carbonyl)-amino]-propionic acid a) 8-Bromo-1-cyclohexylmethyl-5-hydroxy-2-oxo-3-phenyl-1,2-dihydro-[1,7]naphthyridine-6-carboxylic acid methyl ester A mixture of 1-cyclohexylmethyl-5-hydroxy-2-oxo-3-phenyl-1,2-dihydro-[1,7]naphthyridine-6-carboxylic acid methyl ester (81 mg, 0.21 mmol) and N-bromosuccinimide (40 mg, 0.23 mmol) in CH$_2$Cl$_2$ (0.8 mL) was refluxed for 3 h. Solvent was evaporated in vacuo, and the residue was purified by silica gel chromatography (5-15% EtOAc/hexanes+1% AcOH) to give 62 mg of the title compound as a light yellow solid. MS: (−) m/z 469.20, 471.15 (M-1, $^{79/81}$Br).

b) 1-Cyclohexylmethyl-5-hydroxy-2-oxo-3-phenyl-8-pyridin-3-yl-1,2-dihydro-[1,7]naphthyridine-6-carboxylic acid methyl ester A mixture of 8-bromo-1-cyclohexylmethyl-5-hydroxy-2-oxo-3-phenyl-1,2-dihydro-[1,7]naphthyridine-6-carboxylic acid methyl ester (62 mg, 0.13 mmol), 3-tributylstannanyl-pyridine (0.063 mL, 0.20 mmol) and PdCl$_2$(PPh$_3$)$_2$ (18 mg, 0.026 mmol) in 3 mL of DMF was heated at 120° C. for 3 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and dried over MgSO$_4$. After evaporating the solvent in vacuo, the crude product was purified by silica gel chromatography (5-70% EtOAc/hexanes+1% AcOH) to give 41 mg of the title compound. MS: (+) m/z 470.39 (M+1).

c) 3-[(1-Cyclohexylmethyl-5-hydroxy-2-oxo-3-phenyl-8-pyridin-3-yl-1,2-dihydro-[1,7]naphthyridine-6-carbonyl)-amino]-propionic acid A mixture of 1-cyclohexylmethyl-5-hydroxy-2-oxo-3-phenyl-8-pyridin-3-yl-1,2-dihydro-[1,7]naphthyridine-6-carboxylic acid methyl ester (41 mg, 0.087 mmol), β-alanine (623 mg, 7.0 mmol) and NaOMe solution (10 mL, 5.2 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over MgSO$_4$ and concentrated. The residue was dissolved in saturated NaHCO$_3$ and washed several times with ether. The aqueous layer was acidified to pH about 3-4, and the resulting precipitate was isolated by filtration. The crude solid was purified by silica gel chromatography (5-90% EtOAc/hexanes+1% AcOH). The product isolated was dissolved in saturated NaHCO$_3$ and washed several times with ether. The aqueous layer was acidified to pH about 3-4, and the resulting precipitate was isolated by filtration to give 10 mg of the title compound as a white solid. MS: (+) m/z 527.45 (M+1).

Example 184

4-[(1-Cyclohexylmethyl-5-hydroxy-2-oxo-3-phenyl-1,2-dihydro-[1,7]naphthyridine-6-carbonyl)-amino]-butyric acid a) 4-[(1-Cyclohexylmethyl-5-hydroxy-2-oxo-3-phenyl-1,2-dihydro-[1,7]naphthyridine-6-carbonyl)-amino]-butyric acid ethyl ester A mixture of 1-cyclohexylmethyl-5-hydroxy-2-oxo-3-phenyl-1,2-dihydro-[1,7]naphthyridine-6-carboxylic acid methyl ester (60 mg, 0.15 mmol), 2 M NaOH (3 mL), MeOH (3 mL) and THF (3 mL) was stirred at r.t. overnight, then concentrated to approximately one-third of its original volume. 1 M HCl was added to acidify the mixture, and the resulting suspension was extracted with EtOAc. The organic layer was dried over MgSO$_4$ and concentrated. To the residue were then added HOBt (33 mg, 0.24 mmol), CH$_2$Cl$_2$ (3 mL), and EDC (53 mg, 0.28 mmol), and the resulting mixture was stirred for 10 min. 4-Amino-butyric acid ethyl ester HCl salt (41 mg, 0.24 mmol) and Hunig's base (0.1 mL, 0.56 mmol) were added, and the mixture was stirred for 48 h. The mixture was diluted with EtOAc and washed with 0.1 M HCl. The organic layer was dried over MgSO$_4$ and concentrated. The crude product was purified by silica gel chromatography (5-30% EtOAc/hexanes+1% AcOH) to give 39 mg of the title compound. MS: (+) m/z 492.44 (M+1).

b) 4-[(1-Cyclohexylmethyl-5-hydroxy-2-oxo-3-phenyl-1,2-dihydro-[1,7]naphthyridine-6-carbonyl)-amino]-butyric acid A mixture of 4-[(1-cyclohexylmethyl-5-hydroxy-2-oxo-3-phenyl-1,2-dihydro-[1,7]naphthyridine-6-carbonyl)-amino]-butyric acid ethyl ester (39 mg, 0.079 mmol), 2 M NaOH (3 mL), MeOH (3 mL) and THF (3 mL) was stirred at r.t. for 16 h, then concentrated to approximately one-third of its original volume. 1 M HCl was added to acidify the mixture, and the resulting suspension was extracted with EtOAc. The organic layer was dried over $MgSO_4$ and concentrated. The crude product was purified by silica gel chromatography (5-60% EtOAc/hexanes+1% AcOH). The product isolated was dissolved in saturated $NaHCO_3$ and washed several times with ether. The aqueous layer was acidified to pH about 3 with 6 M HCl, and the resulting precipitate was isolated by filtration to give 18 mg of the title compound. MS: (+) m/z 464.41 (M+1).

Example 185

3-{[1-Benzyl-5-hydroxy-3-(4-methoxy-phenyl)-2-oxo-8-pyridin-3-yl-1,2-dihydro-[1,7]naphthyridine-6-carbonyl]amino}-propionic acid a) 1-Benzyl-8-bromo-5-hydroxy-3-(4-methoxy-phenyl)-2-oxo-1,2-dihydro-[1,7]naphthyridine-6-carboxylic acid methyl ester A mixture of 1-benzyl-5-hydroxy-3-(4-methoxy-phenyl)-2-oxo-1,2-dihydro-[1,7]naphthyridine-6-carboxylic acid methyl ester (93 mg, 0.22 mmol) and N-bromosuccinimide (44 mg, 0.25 mmol) in $CH_2Cl_2$ (0.8 mL) was refluxed for 3 h. Solvent was evaporated in vacuo, and the residue was purified by silica gel chromatography (5-30% EtOAc/hexanes+1% AcOH) to give 76 mg of the title compound as a yellow solid. MS: (+) m/z 495.21, 497.10 (M+1, $^{79/81}Br$).

b) 1-Benzyl-5-hydroxy-3-(4-methoxy-phenyl)-2-oxo-8-pyridin-3-yl-1,2-dihydro-[1,7]naphthyridine-6-carboxylic acid methyl ester A mixture of 1-benzyl-8-bromo-5-hydroxy-3-(4-methoxy-phenyl)-2-oxo-1,2-dihydro-[1,7]naphthyridine-6-carboxylic acid methyl ester (76 mg, 0.15 mmol), 3-tributylstannanyl-pyridine (0.074 mL, 0.23 mmol) and $PdCl_2(PPh_3)_2$ (22 mg, 0.031 mmol) in 4 mL of DMF was heated at 120° C. for 3 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and dried over $MgSO_4$. After evaporating the solvent in vacuo, the crude product was purified by silica gel chromatography (10-100% EtOAc/hexanes+1% AcOH) to give 44 mg of the title compound. MS: (+) m/z 494.39 (M+1).

c) 3-{[1-Benzyl-5-hydroxy-3-(4-methoxy-phenyl)-2-oxo-8-pyridin-3-yl-1,2-dihydro-[1,7]naphthyridine-6-carbonyl]-amino}-propionic acid A mixture of 1-benzyl-5-hydroxy-3-(4-methoxy-phenyl)-2-oxo-8-pyridin-3-yl-1,2-dihydro-[1,7]naphthyridine-6-carboxylic acid methyl ester (44 mg, 0.089 mmol), β-alanine (636 mg, 7.1 mmol) and NaOMe solution (10.7 mL, 5.4 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over $MgSO_4$ and concentrated. The residue was dissolved in saturated $NaHCO_3$ and washed several times with ether. The aqueous layer was acidified to pH about 3-4, and the resulting precipitate was isolated by filtration to give 34 mg of the title compound as a yellow solid. MS: (+) m/z 551.39 (M+1).

Example 186

4-{[1-Benzyl-5-hydroxy-3-(4-methoxy-phenyl)-2-oxo-1,2-dihydro-[1,7]naphthyridine-6-carbonyl]-amino}-butyric acid a) 4-{[1-Benzyl-5-hydroxy-3-(4-methoxy-phenyl)-2-oxo-1,2-dihydro-[1,7]naphthyridine-6-carbonyl]-amino}-butyric acid ethyl ester A mixture of 1-benzyl-5-hydroxy-3-(4-methoxy-phenyl)-2-oxo-1,2-dihydro-[1,7]naphthyridine-6-carboxylic acid methyl ester (51 mg, 0.123 mmol), 2 M NaOH (3 mL), MeOH (3 mL) and THF (3 mL) was stirred at r.t. overnight, then concentrated to approximately one-third of its original volume. 1 M HCl was added to acidify the mixture, and the resulting suspension was extracted with EtOAc. The organic layer was dried over $MgSO_4$ and concentrated. To the residue were then added HOBt (27 mg, 0.20 mmol), $CH_2Cl_2$ (3 mL), and EDC (42 mg, 0.22 mmol), and the resulting mixture was stirred for 10 min. 4-Amino-butyric acid ethyl ester HCl salt (33 mg, 0.20 mmol) and Hunig's base (0.080 mL, 0.44 mmol) were added, and the mixture was stirred overnight. The mixture was diluted with EtOAc and washed with 0.1 M HCl. The organic layer was dried over $MgSO_4$ and concentrated. The crude product was purified by silica gel chromatography (5-45% EtOAc/hexanes+1% AcOH) to give 20 mg of the title compound. MS: (+) m/z 516.37 (M+1).

b) 4-{[1-Benzyl-5-hydroxy-3-(4-methoxy-phenyl)-2-oxo-1,2-dihydro-[1,7]naphthyridine-6-carbonyl]-amino}-butyric acid A mixture of 4-{[1-benzyl-5-hydroxy-3-(4-methoxy-phenyl)-2-oxo-1,2-dihydro-[1,7]naphthyridine-6-carbonyl]-amino}-butyric acid ethyl ester (20 mg, 0.039 mmol), 2 M NaOH (3 mL), MeOH (3 mL) and THF (3 mL) was stirred at r.t. for 16 h, then concentrated to approximately one-third of its original volume. 1 M HCl was added to acidify the mixture, and the resulting suspension was extracted with EtOAc. The organic layer was dried over $MgSO_4$ and concentrated. The residue was dissolved in saturated $NaHCO_3$ and washes several times with ether. The aqueous layer was acidified to pH about 3, and the resulting precipitate was isolated by filtration. The crude solid was purified by silica gel chromatography (5-80% EtOAc/hexanes+1% AcOH). The product isolated was dissolved in saturated $NaHCO_3$ and washed several times with ether. The aqueous layer was acidified to pH about 3 with 6 M HCl, and the resulting precipitate was isolated by filtration to give 3.5 mg of the title compound. MS: (+) m/z 488.34 (M+1).

Example 187

3-{[1-Benzyl-5-hydroxy-3-(3-methoxy-phenyl)-2-oxo-1,2-dihydro-[1,7]naphthyridine-6-carbonyl]-amino}-propionic acid a) 1-Benzyl-5-hydroxy-3-(3-methoxy-phenyl)-2-oxo-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (220 mg, 0.57 mmol), 3-methoxyphenylboronic acid (129 mg, 0.85 mmol), $K_3PO_4$ (240 mg, 1.13 mmol), $H_2O$ (20 mg, 1.13 mmol), SPhos (12 mg, 0.028 mmol) and Pd(OAc)$_2$ (11 mg, 0.017 mmol) in toluene (10 mL) was heated at 100° C. under nitrogen atmosphere for 16 h. After the mixture was cooled to r.t., brine (15 mL) and EtOAc (30 mL) were added. 1 M HCl was added with stirring until pH was about 3, and the aqueous layer extracted with additional EtOAc. The organic layers were combined, dried over MgSO$_4$ and concentrated. The crude product was purified by silica gel chromatography (5-60% EtOAc/hexanes+1% AcOH) to give 189 mg of the title compound as a yellow solid. MS: (+) m/z 417.36 (M+1).

b) 3-{[1-Benzyl-5-hydroxy-3-(3-methoxy-phenyl)-2-oxo-1,2-dihydro-[1,7]naphthyridine-6-carbonyl]-amino}-propionic acid A mixture of 1-benzyl-5-hydroxy-3-(3-methoxy-phenyl)-2-oxo-1,2-dihydro-[1,7]naphthyridine-6-carboxylic acid methyl ester (35 mg, 0.084 mmol), β-alanine (600 mg, 6.7 mmol) and NaOMe solution (10 mL, 5.0 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3. The aqueous layer was extracted with additional EtOAc, and the organic layers were combined, dried over MgSO$_4$ and concentrated. The residue was dissolved in saturated NaHCO$_3$ and washed several times with ether. The aqueous layer was acidified to pH about 3, and the resulting precipitate was isolated by filtration to give 30 mg of the title compound as a yellow solid. MS: (+) m/z 474.36 (M+1).

Example 188

4-{[1-Benzyl-5-hydroxy-3-(3-methoxy-phenyl)-2-oxo-1,2-dihydro-[1,7]naphthyridine-6-carbonyl]-amino}-butyric acid a) 4-{[1-Benzyl-5-hydroxy-3-(3-methoxy-phenyl)-2-oxo-1,2-dihydro-[1,7]naphthyridine-6-carbonyl]-amino}-butyric acid ethyl ester A mixture of 1-benzyl-5-hydroxy-3-(3-methoxy-phenyl)-2-oxo-1,2-dihydro-[1,7]naphthyridine-6-carboxylic acid methyl ester (60 mg, 0.14 mmol), 2 M NaOH (3 mL), MeOH (3 mL) and THF (3 mL) was stirred at r.t. overnight, then concentrated to approximately one-third of its original volume. 1 M HCl was added to acidify the mixture, and the resulting suspension was extracted with EtOAc. The organic layer was dried over MgSO$_4$ and concentrated. To the residue were then added HOBt (32 mg, 0.23 mmol), CH$_2$Cl$_2$ (3 mL), and EDC (50 mg, 0.26 mmol), and the resulting mixture was stirred for 10 min. 4-Amino-butyric acid ethyl ester HCl salt (39 mg, 0.23 mmol) and Hunig's base (0.1 mL, 0.52 mmol) were added, and the mixture was stirred for 48 h. The mixture was diluted with EtOAc and washed with 0.1 M HCl. The organic layer was dried over MgSO$_4$ and concentrated. The crude product was purified by silica gel chromatography (5-50% EtOAc/hexanes+1% AcOH) to give 38 mg of the title compound. MS: (+) m/z 516.37 (M+1).

b) 4-{[1-Benzyl-5-hydroxy-3-(3-methoxy-phenyl)-2-oxo-1,2-dihydro-[1,7]naphthyridine-6-carbonyl]-amino}-butyric acid A mixture of 4-{[1-benzyl-5-hydroxy-3-(3-methoxy-phenyl)-2-oxo-1,2-dihydro-[1,7]naphthyridine-6-carbonyl]-amino}-butyric acid ethyl ester (38 mg, 0.074 mmol), 2 M NaOH (3 mL), MeOH (3 mL) and THF (3 mL) was stirred at r.t. for 16 h, then concentrated to approximately one-third of its original volume. 1 M HCl was added to acidify the mixture, and the resulting suspension was extracted with EtOAc. The organic layer was dried over MgSO$_4$ and concentrated. The residue was dissolved in saturated NaHCO$_3$ and washes several times with ether. The aqueous layer was acidified to pH about 3, and the resulting precipitate was isolated by filtration to give 24 mg of the title compound as a yellow solid. MS: (+) m/z 488.40 (M+1).

Example 189

1-[(1-Benzyl-5-hydroxy-2-oxo-3-phenyl-1,2-dihydro-[1,7]naphthyridine-6-carbonyl)-amino]-cyclopropanecarboxylic acid a) 1-[(1-Benzyl-5-hydroxy-2-oxo-3-phenyl-1,2-dihydro-[1,7]naphthyridine-6-carbonyl)-amino]-cyclopropanecarboxylic acid ethyl ester A mixture of 1-benzyl-5-hydroxy-2-oxo-3-phenyl-1,2-dihydro-[1,7]naphthyridine-6-carboxylic acid methyl ester (60 mg, 0.16 mmol), 2 M NaOH (3 mL), MeOH (3 mL) and THF (3 mL) was stirred at r.t. overnight, then concentrated to approximately one-third of its original volume. 1 M HCl was added to acidify the mixture, and the resulting suspension was extracted with EtOAc. The organic layer was dried over MgSO$_4$ and concentrated. To the residue were then added HOBt (34 mg, 0.25 mmol), CH$_2$Cl$_2$ (3 mL), and EDC (54 mg, 0.28 mmol), and the resulting mixture was stirred for 10 min. 1-Amino-cyclopropanecarboxylic acid ethyl ester HCl salt (41 mg, 0.25 mmol) and Hunig's base (0.1 mL, 0.56 mmol) were added, and the mixture was stirred for 48 h. The mixture was diluted with EtOAc and washed with 0.1 M HCl. The organic layer was dried over MgSO$_4$ and concentrated. The crude product was purified by silica gel chromatography (5-45% EtOAc/hexanes+1% AcOH) to give 40 mg of the title compound. MS: (+) m/z 484.37 (M+1).

b) 1-[(1-Benzyl-5-hydroxy-2-oxo-3-phenyl-1,2-dihydro-[1,7]naphthyridine-6-carbonyl)-amino]-cyclopropanecarboxylic acid A mixture of 1-[(1-benzyl-5-hydroxy-2-oxo-3-phenyl-1,2-dihydro-[1,7]naphthyridine-6-carbonyl)-amino]-cyclopropanecarboxylic acid ethyl ester (40 mg, 0.083 mmol), 2 M NaOH (3 mL), MeOH (3 mL) and THF (3 mL) was stirred at r.t. for 16 h, then concentrated to approximately one-third of its original volume. 1 M HCl was added to acidify the mixture, and the resulting suspension was extracted with EtOAc. The organic layer was dried over MgSO$_4$ and concentrated. The residue was dissolved in saturated NaHCO$_3$ and washes several times with ether. The aqueous layer was acidified to pH about 3, and the resulting precipitate was isolated by filtration. The crude solid was purified by silica gel chromatography (5-60% EtOAc/hexanes+1% AcOH). The product isolated was dissolved in saturated NaHCO$_3$ and washed several times with ether. The aqueous layer was acidified to pH about 3, and the resulting precipitate was isolated by filtration to give 15 mg of the title compound. MS: (+) m/z 456.35 (M+1).

Example 190

1-[(1-Benzyl-5-hydroxy-2-oxo-3-phenyl-8-pyridin-3-yl-1,2-dihydro-[1,7]naphthyridine-6-carbonyl)-amino]-cyclopropanecarboxylic acid a) 1-[(1-Benzyl-5-hydroxy-2-oxo-3-phenyl-8-pyridin-3-yl-1,2-dihydro-[1,7]naphthyridine-6-carbonyl)-amino]-cyclopropanecarboxylic acid ethyl ester A mixture of 1-benzyl-5-hydroxy-2-oxo-3-phenyl-8-pyridin-3-yl-1,2-dihydro-[1,7]naphthyridine-6-carboxylic acid methyl ester (105 mg, 0.23 mmol), 2 M NaOH (3 mL), MeOH (3 mL) and THF (3 mL) was stirred at r.t. overnight, then concentrated to approximately one-third of its original volume. 1 M HCl was added to acidify the mixture, and the resulting suspension was extracted with EtOAc. The organic layer was dried over MgSO$_4$ and concentrated to give 105 mg of 1-benzyl-5-hydroxy-2-oxo-3-phenyl-8-pyridin-3-yl-1,2-dihydro-[1,7]naphthyridine-6-carboxylic acid as a light orange solid, which was immediately used in the next step without purification.

A mixture of 1-benzyl-5-hydroxy-2-oxo-3-phenyl-8-pyridin-3-yl-1,2-dihydro-[1,7]naphthyridine-6-carboxylic acid (53 mg, 0.118 mmol) and HOBt (26 mg, 0.189 mmol) was dissolved in CH$_2$Cl$_2$ (3 mL). EDC (41 mg, 0.212 mmol) was added, and the resulting mixture was stirred for 10 min. 1-Amino-cyclopropanecarboxylic acid ethyl ester HCl salt (31 mg, 0.189 mmol) and Hunig's base (0.075 mL, 0.425 mmol) were added, and the mixture was stirred overnight. The mixture was diluted with EtOAc and brine, and 1 M HCl was added until pH was about 3-4. The aqueous layer was extracted with additional EtOAc, and the organic layers were combined, dried over MgSO$_4$ and concentrated. The crude product was purified by silica gel chromatography (5-80% EtOAc/hexanes+1% AcOH) to give 24 mg of the title compound. MS: (+) m/z 561.40 (M+1).

b) 1-[(1-Benzyl-5-hydroxy-2-oxo-3-phenyl-8-pyridin-3-yl-1,2-dihydro-[1,7]naphthyridine-6-carbonyl)-amino]-cyclopropanecarboxylic acid A mixture of 1-[(1-benzyl-5-hydroxy-2-oxo-3-phenyl-8-pyridin-3-yl-1,2-dihydro-[1,7]naphthyridine-6-carbonyl)-amino]-cyclopropanecarboxylic acid ethyl ester (24 mg, 0.043 mmol), 2 M NaOH (3 mL), MeOH (3 mL) and THF (3 mL) was stirred at r.t. for 16 h, then concentrated to approximately one-third of its original volume. 1 M HCl was added to acidify the mixture, and the resulting suspension was extracted with EtOAc. The organic layer was dried over MgSO$_4$ and concentrated. The crude product was purified by silica gel chromatography (10-100% EtOAc/hexanes+1% AcOH). The product isolated was dissolved in saturated NaHCO$_3$ and washed several times with ether. The aqueous layer was acidified to pH about 3-4, and the resulting precipitate was isolated by filtration to give 13 mg of the title compound as a light yellow solid. MS: (+) m/z 533.37 (M+1).

Example 191

3-[(1-Benzyl-5-hydroxy-2-oxo-3-phenyl-8-pyridin-3-yl-1,2-dihydro-[1,7]naphthyridine-6-carbonyl)-amino]-2,2-dimethyl-propionic acid a) 3-[(1-Benzyl-5-hydroxy-2-oxo-3-phenyl-8-pyridin-3-yl-1,2-dihydro-[1,7]naphthyridine-6-carbonyl)-amino]-2,2-dimethyl-propionic acid ethyl ester A mixture of 1-benzyl-5-hydroxy-2-oxo-3-phenyl-8-pyridin-3-yl-1,2-dihydro-[1,7]naphthyridine-6-carboxylic acid (53 mg, 0.118 mmol) and HOBt (26 mg, 0.189 mmol) was dissolved in CH$_2$Cl$_2$ (3 mL). EDC (41 mg, 0.212 mmol) was added, and the resulting mixture was stirred for 10 min. 3-Amino-2,2-dimethyl-propionic acid ethyl ester HCl salt (34 mg, 0.189 mmol) and Hunig's base (0.075 mL, 0.425 mmol) were added, and the mixture was stirred overnight. The mixture was diluted with EtOAc and brine, and 1 M HCl was added until pH was about 3-4. The aqueous layer was extracted with additional EtOAc, and the organic layers were combined, dried over MgSO$_4$ and concentrated. The crude product was purified by silica gel chromatography (5-60% EtOAc/hexanes+1% AcOH) to give 30 mg of the title compound. MS: (+) m/z 577.40 (M+1).

b) 3-[(1-Benzyl-5-hydroxy-2-oxo-3-phenyl-8-pyridin-3-yl-1,2-dihydro-[1,7]naphthyridine-6-carbonyl)-amino]-2,2-dimethyl-propionic acid A mixture of 3-[(1-benzyl-5-hydroxy-2-oxo-3-phenyl-8-pyridin-3-yl-1,2-dihydro-[1,7]naphthyridine-6-carbonyl)-amino]-2,2-dimethyl-propionic acid ethyl ester (30 mg, 0.052 mmol), 2 M NaOH (3 mL), MeOH (3 mL) and THF (3 mL) was stirred at r.t. for 16 h, then concentrated to approximately one-third of its original volume. 1 M HCl was added to acidify the mixture, and the resulting suspension was extracted with EtOAc. The organic layer was dried over MgSO$_4$ and concentrated. The crude product was purified by silica gel chromatography (5-60% EtOAc/hexanes+1% AcOH). The product isolated was dissolved in saturated NaHCO$_3$ and washed several times with ether. The aqueous layer was acidified to pH about 3-4, and the resulting precipitate was isolated by filtration to give 8.4 mg of the title compound as a light yellow solid. MS: (+) m/z 549.56 (M+1).

Example 192

3-{[1-Benzyl-8-(2-ethoxy-pyrimidin-5-yl)-5-hydroxy-2-oxo-3-phenyl-1,2-dihydro-[1,7]naphthyridine-6-carbonyl]amino}-propionic acid a) 1-Benzyl-8-(2-ethoxy-pyrimidin-5-yl)-5-hydroxy-2-oxo-3-phenyl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (80 mg, 0.17 mmol), 2-ethoxy-5-tributylstannanyl-pyrimidine (107 mg, 0.26 mmol) and PdCl$_2$(PPh$_3$)$_2$ (24 mg, 0.034 mmol) in 4 mL of DMF was heated at 120° C. for 2 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and brine, and dried over MgSO$_4$. After evaporating the solvent in vacuo, the crude product was chromatographed (0-15% EtOAc/CH$_2$Cl$_2$) to give 58 mg of the title compound. MS: (+) m/z 509.44 (M+1).

b) 3-{[1-Benzyl-8-(2-ethoxy-pyrimidin-5-yl)-5-hydroxy-2-oxo-3-phenyl-1,2-dihydro-[1,7]naphthyridine-6-carbonyl]-amino}-propionic acid A mixture of 1-benzyl-8-(2-ethoxy-pyrimidin-5-yl)-5-hydroxy-2-oxo-3-phenyl-1,2-dihydro-[1,7]naphthyridine-6-carboxylic acid methyl ester (58 mg, 0.11 mmol), β-alanine (818 mg, 9.13 mmol) and NaOMe solution (13.7 mL, 6.85 mmol, 0.5 M in MeOH) was refluxed for 16 h. After the

Example 193

3-[(1-Benzyl-5-hydroxy-2-oxo-3-phenyl-8-pyridin-2-yl-1,2-dihydro-[1,7]naphthyridine-6-carbonyl)-amino]-propionic acid a) 1-Benzyl-5-hydroxy-2-oxo-3-phenyl-8-pyridin-2-yl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (170 mg, 0.37 mmol), 2-tributylstannanyl-pyridine (202 mg, 0.55 mmol) and PdCl$_2$(PPh$_3$)$_2$ (51 mg, 0.073 mmol) in 8 mL of DMF was heated at 120° C. for 2 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and dried over MgSO$_4$. After evaporating the solvent in vacuo, the crude product was purified twice by silica gel chromatography (5-70% EtOAc/hexanes+1% AcOH, then 0-10% EtOAc/CH$_2$Cl$_2$) to give 80 mg of the title compound. MS: (+) m/z 464.41 (M+1).

b) 3-[(1-Benzyl-5-hydroxy-2-oxo-3-phenyl-8-pyridin-2-yl-1,2-dihydro-[1,7]naphthyridine-6-carbonyl)-amino]-propionic acid methyl ester A mixture of 1-benzyl-5-hydroxy-2-oxo-3-phenyl-8-pyridin-2-yl-1,2-dihydro-[1,7]naphthyridine-6-carboxylic acid methyl ester (80 mg, 0.17 mmol), 2 M NaOH (3 mL), MeOH (3 mL) and THF (3 mL) was stirred at r.t. for 16 h. The mixture was concentrated to approximately one-third of its original volume, and then acidified to pH about 3-4. The resulting suspension was extracted with EtOAc. The organic layer was dried over MgSO$_4$ and concentrated. To the residue were then added HOBt (37 mg, 0.28 mmol), CH$_2$Cl$_2$ (3 mL), and EDC (60 mg, 0.31 mmol), and the resulting mixture was stirred for 10 min. β-Alanine methyl ester HCl salt (39 mg, 0.28 mmol) and Hunig's base (0.11 mL, 0.62 mmol) were added, and the mixture was stirred for 48 h. The mixture was diluted with EtOAc and water, and acidified to pH about 3-4. The organic layer was dried over MgSO$_4$ and concentrated. The crude product was purified by silica gel chromatography (5-70% EtOAc/hexanes+1% AcOH) to give 62 mg of the title compound. MS: (+) m/z 535.58 (M+1).

c) 3-[(1-Benzyl-5-hydroxy-2-oxo-3-phenyl-8-pyridin-2-yl-1,2-dihydro-[1,7]naphthyridine-6-carbonyl)-amino]-propionic acid A mixture of 3-[(1-benzyl-5-hydroxy-2-oxo-3-phenyl-8-pyridin-2-yl-1,2-dihydro-[1,7]naphthyridine-6-carbonyl)-amino]-propionic acid methyl ester (62 mg, 0.116 mmol), 2 M NaOH (3 mL), MeOH (3 mL) and THF (3 mL) was stirred at r.t. for 16 h, then concentrated to approximately one-third of its original volume. 1 M HCl was added until pH was about 3-4, and the resulting suspension was extracted with EtOAc. The organic layer was dried over MgSO$_4$ and concentrated. The crude product was purified twice by silica gel chromatography (100% EtOAc, then 10-60% EtOAc/hexanes+1% AcOH). The product isolated was dissolved in saturated NaHCO$_3$ and washed several times with ether. The aqueous layer was acidified to pH about 3-4, and the resulting precipitate was isolated by filtration to give 18 mg of the title compound. MS: (+) m/z 521.41 (M+1).

Example 194

3-[(1-Benzyl-5-hydroxy-2-oxo-3-phenyl-8-pyridazin-4-yl-1,2-dihydro-[1,7]naphthyridine-6-carbonyl)-amino]-propionic acid a) 1-Benzyl-5-hydroxy-2-oxo-3-phenyl-8-pyridazin-4-yl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (70 mg, 0.15 mmol), 4-tributylstannanyl-pyridazine (83 mg, 0.23 mmol) and PdCl$_2$(PPh$_3$)$_2$ (21 mg, 0.030 mmol) in 4 mL of DMF was heated at 120° C. for 2 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and brine, and dried over MgSO$_4$. After evaporating the solvent in vacuo, the crude product was chromatographed (10-100% EtOAc/hexanes+1% AcOH) to give 28 mg of the title compound. MS: (+) m/z 465.42 (M+1).

b) 3-[(1-Benzyl-5-hydroxy-2-oxo-3-phenyl-8-pyridazin-4-yl-1,2-dihydro-[1,7]naphthyridine-6-carbonyl)-amino]-propionic acid A mixture of 1-benzyl-5-hydroxy-2-oxo-3-phenyl-8-pyridazin-4-yl-1,2-dihydro-[1,7]naphthyridine-6-carboxylic acid methyl ester (30 mg, 0.065 mmol), β-alanine (576 mg, 6.5 mmol) and NaOMe solution (10 mL, 5.2 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over MgSO$_4$ and concentrated. The crude product was purified by silica gel chromatography (15-100% EtOAc/hexanes+1% AcOH). The product isolated was dissolved in saturated NaHCO$_3$ and washed several times with ether. The aqueous layer was acidified to pH about 3-4 with 6 M HCl, and the resulting precipitate was isolated by filtration to give 15 mg of the title compound. MS: (+) m/z 522.35 (M+1).

Example 195

3-[(1-Benzyl-5-hydroxy-2-oxo-3-phenyl-8-thiazol-2-yl-1,2-dihydro-[1,7]naphthyridine-6-carbonyl)-amino]-propionic acid a) 1-Benzyl-5-hydroxy-2-oxo-3-phenyl-8-thiazol-2-yl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (70 mg, 0.15 mmol), 2-tributylstannanyl-thiazole (84 mg, 0.23 mmol) and $PdCl_2(PPh_3)_2$ (21 mg, 0.030 mmol) in 4 mL of DMF was heated at 120° C. for 2 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and brine, and dried over $MgSO_4$. After evaporating the solvent in vacuo, the crude product was purified by silica gel chromatography (5-30% EtOAc/hexanes+1% AcOH) to give 33 mg of the title compound. MS: (+) m/z 470.33 (M+1).

b) 3-[(1-Benzyl-5-hydroxy-2-oxo-3-phenyl-8-thiazol-2-yl-1,2-dihydro-[1,7]naphthyridine-6-carbonyl)-amino]-propionic acid methyl ester A mixture of 1-benzyl-5-hydroxy-2-oxo-3-phenyl-8-thiazol-2-yl-1,2-dihydro-[1,7]naphthyridine-6-carboxylic acid methyl ester (64 mg, 0.14 mmol), 2 M NaOH (3 mL), MeOH (3 mL) and THF (3 mL) was stirred at r.t. overnight. The mixture was concentrated to approximately one-third of its original volume, and then acidified to pH about 3 with 1 M HCl. The resulting suspension was extracted with EtOAc. The organic layer was dried over $MgSO_4$ and concentrated. To the residue were then added HOBt (30 mg, 0.22 mmol), $CH_2Cl_2$ (3 mL), and EDC (47 mg, 0.25 mmol), and the resulting mixture was stirred for 10 min. β-Alanine methyl ester HCl salt (31 mg, 0.22 mmol) and Hunig's base (0.1 mL, 0.49 mmol) were added, and the mixture was stirred for 16 h. The mixture was concentrated in vacuo, and the residue was purified by silica gel chromatography (5-40% EtOAc/hexanes+1% AcOH) to give 28 mg of the title compound. MS: (+) m/z 541.31 (M+1).

c) 3-[(1-Benzyl-5-hydroxy-2-oxo-3-phenyl-8-thiazol-2-yl-1,2-dihydro-[1,7]naphthyridine-6-carbonyl)-amino]-propionic acid A mixture of 3-[(1-benzyl-5-hydroxy-2-oxo-3-phenyl-8-thiazol-2-yl-1,2-dihydro-[1,7]naphthyridine-6-carbonyl)-amino]-propionic acid methyl ester (28 mg, 0.052 mmol), 2 M NaOH (3 mL), MeOH (3 mL) and THF (3 mL) was stirred at r.t. for 16 h, then concentrated to approximately one-third of its original volume. 1 M HCl was added until pH was about 3-4, and the resulting suspension was extracted with EtOAc. The organic layer was dried over $MgSO_4$ and concentrated. The crude product was purified by silica gel chromatography (5-60% EtOAc/hexanes+1% AcOH). The product isolated was dissolved in saturated $NaHCO_3$ and washed several times with ether. The aqueous layer was acidified to pH about 3-4 with 6 M HCl, and the resulting precipitate was isolated by filtration to give 11 mg of the title compound. MS: (+) m/z 527.33 (M+1).

Example 196

7-Benzyl-4-hydroxy-8-oxo-7,8-dihydro-[2,7]naphthyridine-3-carboxylic acid (3-formylamino-propyl)-amide {3-[(7-Benzyl-4-hydroxy-8-oxo-7,8-dihydro-[2,7]naphthyridine-3-carbonyl)-amino]-propyl}-carbamic acid tert-butyl ester (81 mg, 0.18 mmol) was dissolved in $CH_2Cl_2$ (2 mL). Trifluoroacetic acid (1 mL) was added, and the mixture was stirred at r.t. for 2 h. Solvent and excess TFA were removed in vacuo. To the residue were added THF (5 mL), triethylamine (0.12 mL, 0.90 mmol), and ethyl formate (5 mL), and the resulting mixture was refluxed for 4 days. The mixture was concentrated to dryness, and the residue was purified by silica gel chromatography (0-5% MeOH/$CH_2Cl_2$) to give 46 mg of the title compound as an off-white solid. MS: (+) m/z 381.37 (M+1).

Example 197

7-Benzyl-4-hydroxy-8-oxo-7,8-dihydro-[2,7]naphthyridine-3-carboxylic acid (3-acetylamino-propyl)-amide {3-[(7-Benzyl-4-hydroxy-8-oxo-7,8-dihydro-[2,7]naphthyridine-3-carbonyl)-amino]-propyl}-carbamic acid tert-butyl ester (81 mg, 0.18 mmol) was dissolved in $CH_2Cl_2$ (2 mL). Trifluoroacetic acid (1 mL) was added, and the mixture was stirred at r.t. for 2 h. Solvent and excess TFA were removed in vacuo. To the residue were added $CH_2Cl_2$ (3 mL), triethylamine (0.25 mL, 1.79 mmol), and acetic anhydride (0.085 mL, 0.90 mmol), and the resulting mixture was stirred at r.t. for 16 h. The mixture was concentrated to dryness, and the residue was dissolved in MeOH (3.6 mL) and treated with NaOMe (3.6 mL, 1.79 mmol, 0.5 M in MeOH) for 1 h at r.t. 1 M HCl was added until pH was about 3-4, and the mixture was extracted with EtOAc. The organic layer was dried over $MgSO_4$ and concentrated. The crude product was purified by silica gel chromatography (0-5% MeOH/$CH_2Cl_2$) to give 37 mg of the title compound as an off-white solid. MS: (+) m/z 395.38 (M+1).

Example 198

3-[(1-Cyclohexylmethyl-5-hydroxy-2-oxo-3-phenyl-8-pyridin-4-yl-1,2-dihydro-[1,7]naphthyridine-6-carbonyl)-amino]-propionic acid a) 1-Cyclohexylmethyl-5-hydroxy-2-oxo-3-phenyl-8-pyridin-4-yl-1,2-dihydro-[1,7]naphthyridine-6-carboxylic acid methyl ester A mixture of 8-bromo-1-cyclohexylmethyl-5-hydroxy-2-oxo-3-phenyl-1,2-dihydro-[1,7]naphthyridine-6-carboxylic acid methyl ester (124 mg, 0.26 mmol), 4-tributylstannanyl-pyridine (145 mg, 0.39 mmol) and $PdCl_2(PPh_3)_2$ (37 mg, 0.053 mmol) in 5 mL of DMF was heated at 120° C. for 3.5 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and brine, and dried over $MgSO_4$. After evaporating the solvent in vacuo, the crude product was purified by silica gel chromatography (5-80%

EtOAc/hexanes+1% AcOH) to give 46 mg of the title compound. MS: (+) m/z 470.45 (M+1).

b) 3-[(1-Cyclohexylmethyl-5-hydroxy-2-oxo-3-phenyl-8-pyridin-4-yl-1,2-dihydro-[1,7]naphthyridine-6-carbonyl)-amino]-propionic acid A mixture of 1-cyclohexylmethyl-5-hydroxy-2-oxo-3-phenyl-8-pyridin-4-yl-1,2-dihydro-[1,7]naphthyridine-6-carboxylic acid methyl ester (46 mg, 0.098 mmol), β-alanine (699 mg, 7.8 mmol) and NaOMe solution (11.8 mL, 5.9 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over MgSO$_4$ and concentrated. The crude product was purified by silica gel chromatography (5-100% EtOAc/hexanes+1% AcOH). The product isolated was dissolved in saturated NaHCO$_3$ and washed several times with ether. The aqueous layer was acidified to pH about 3-4, and the resulting precipitate was isolated by filtration to give 5 mg of the title compound. MS: (+) m/z 527.45 (M+1).

Example 199

3-[(5-Hydroxy-2-oxo-1,3-diphenyl-8-pyridin-4-yl-1,2-dihydro-[1,7]naphthyridine-6-carbonyl)-amino]-propionic acid a) 5-Hydroxy-2-oxo-1,3-diphenyl-8-pyridin-4-yl-1,2-dihydro-[1,7]naphthyridine-6-carboxylic acid methyl ester A mixture of 8-bromo-5-hydroxy-2-oxo-1,3-diphenyl-1,2-dihydro-[1,7]naphthyridine-6-carboxylic acid methyl ester (126 mg, 0.28 mmol), 4-tributylstannanyl-pyridine (154 mg, 0.42 mmol) and PdCl$_2$(PPh$_3$)$_2$ (39 mg, 0.056 mmol) in 6 mL of DMF was heated at 120° C. for 2 h under nitrogen atmosphere. After the mixture was cooled to r.t., EtOAc and water were added. 1 M HCl was added with stirring until pH was about 3-4. The aqueous layer was extracted with additional EtOAc, and the combined organic layer was dried over MgSO$_4$. After evaporating the solvent in vacuo, the crude product was chromatographed (5-100% EtOAc/hexanes+1% AcOH) to give 40 mg of the title compound. MS: (+) m/z 450.36 (M+1).

b) 3-[(5-Hydroxy-2-oxo-1,3-diphenyl-8-pyridin-4-yl-1,2-dihydro-[1,7]naphthyridine-6-carbonyl)-amino]-propionic acid A mixture of 5-hydroxy-2-oxo-1,3-diphenyl-8-pyridin-4-yl-1,2-dihydro-[1,7]naphthyridine-6-carboxylic acid methyl ester (40 mg, 0.089 mmol), β-alanine (635 mg, 7.13 mmol) and NaOMe solution (10.7 mL, 5.35 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over MgSO$_4$ and concentrated. The crude product was purified by silica gel chromatography (10-100% EtOAc/hexanes+1% AcOH). The product isolated was dissolved in saturated NaHCO$_3$ and washed several times with ether. The aqueous layer was acidified to pH about 3-4, and the resulting precipitate was isolated by filtration to give 6 mg of the title compound as a white solid. MS: (+) m/z 507.49 (M+1).

Example 200

3-{[1-Benzyl-5-hydroxy-8-(1-methyl-1H-pyrazol-4-yl)-2-oxo-3-phenyl-1,2-dihydro-[1,7]naphthyridine-6-carbonyl]amino}-propionic acid a) 1-Benzyl-5-hydroxy-8-(1-methyl-1H-pyrazol-4-yl)-2-oxo-3-phenyl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (100 mg, 0.22 mmol), 1-methyl-4-tributylstannanyl-1H-pyrazole (0.105 mL, 0.32 mmol) and PdCl$_2$(PPh$_3$)$_2$ (30 mg, 0.043 mmol) in 5 mL of DMF was heated at 120° C. for 2 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and brine, and dried over MgSO$_4$. After evaporating the solvent in vacuo, the crude product was chromatographed (5-100% EtOAc/hexanes+1% AcOH) to give 52 mg of the title compound. MS: (+) m/z 467.37 (M+1).

b) 3-{[1-Benzyl-5-hydroxy-8-(1-methyl-1H-pyrazol-4-yl)-2-oxo-3-phenyl-1,2-dihydro-[1,7]naphthyridine-6-carbonyl]amino}-propionic acid A mixture of 1-benzyl-5-hydroxy-8-(1-methyl-1H-pyrazol-4-yl)-2-oxo-3-phenyl-1,2-dihydro-[1,7]naphthyridine-6-carboxylic acid methyl ester (52 mg, 0.11 mmol), β-alanine (596 mg, 6.7 mmol) and NaOMe solution (10 mL, 5.0 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over MgSO$_4$ and concentrated. The crude product was purified by silica gel chromatography (5-100% EtOAc/hexanes+1% AcOH). The product isolated was dissolved in saturated NaHCO$_3$ and washed several times with ether. The aqueous layer was acidified to pH about 3-4, and the resulting precipitate was isolated by filtration to give 26 mg of the title compound. MS: (+) m/z 524.37 (M+1).

Example 201

3-[(1-Benzyl-5-hydroxy-2-oxo-3-phenyl-8-thiazol-5-yl-1,2-dihydro-[1,7]naphthyridine-6-carbonyl)-amino]-propionic acid a) 1-Benzyl-5-hydroxy-2-oxo-3-phenyl-8-thiazol-5-yl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (100 mg, 0.22 mmol), 5-tributylstannanyl-thiazole (121 mg, 0.32 mmol) and PdCl$_2$(PPh$_3$)$_2$ (30 mg, 0.043 mmol) in 5 mL of DMF was heated at 120° C. for 2 h under nitrogen atmosphere. After the mixture was cooled to r.t., EtOAc and brine were added. 1 M HCl was added with stirring until pH was about 3-4. The aqueous layer was extracted with additional EtOAc, and the combined organic layer was washed with water and brine, and dried over MgSO$_4$. After evaporating the solvent in vacuo, the crude product was purified twice by silica gel chromatography (0-50% EtOAc/CH$_2$Cl$_2$, then 5-60% EtOAc/hexanes+1% AcOH) to give 61 mg of the title compound. MS: (+) m/z 470.39 (M+1).

b) 3-[(1-Benzyl-5-hydroxy-2-oxo-3-phenyl-8-thiazol-5-yl-1,2-dihydro-[1,7]naphthyridine-6-carbonyl)-amino]-propionic acid A mixture of 1-benzyl-5-hydroxy-2-oxo-3-phenyl-8-thiazol-5-yl-1,2-dihydro-[1,7]naphthyridine-6-carboxylic acid methyl ester (61 mg, 0.13 mmol), β-alanine (695 mg, 7.8 mmol) and NaOMe solution (11.7 mL, 5.9 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over MgSO$_4$ and concentrated. The crude product was purified by silica gel chromatography (5-70% EtOAc/hexanes+1% AcOH). The product isolated was dissolved in saturated NaHCO$_3$ and washed several times with ether. The aqueous layer was acidified to pH about 3-4, and the resulting precipitate was isolated by filtration to give 28 mg of the title compound. MS: (+) m/z 527.33 (M+1).

Example 202

3-[(1-Benzyl-5-hydroxy-2-oxo-3-phenyl-8-thiazol-4-yl-1,2-dihydro-[1,7]naphthyridine-6-carbonyl)-amino]-propionic acid a) 1-Benzyl-5-hydroxy-2-oxo-3-phenyl-8-thiazol-4-yl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (100 mg, 0.22 mmol), 4-tributylstannanyl-thiazole (121 mg, 0.32 mmol) and PdCl$_2$(PPh$_3$)$_2$ (30 mg, 0.043 mmol) in 5 mL of DMF was heated at 120° C. for 2 h under nitrogen atmosphere. After the mixture was cooled to r.t., EtOAc and water were added. 1 M HCl was added with stirring until pH was about 3-4. The aqueous layer was extracted with additional EtOAc, and the combined organic layer was washed with water and dried over MgSO$_4$. After evaporating the solvent in vacuo, the crude product was purified twice by silica gel chromatography (0-40% EtOAc/CH$_2$Cl$_2$, then 5-30% EtOAc/hexanes+1% AcOH) to give 64 mg of the title compound. MS: (+) m/z 470.33 (M+1).

b) 3-[(1-Benzyl-5-hydroxy-2-oxo-3-phenyl-8-thiazol-4-yl-1,2-dihydro-[1,7]naphthyridine-6-carbonyl)-amino]-propionic acid methyl ester A mixture of 1-benzyl-5-hydroxy-2-oxo-3-phenyl-8-thiazol-4-yl-1,2-dihydro-[1,7]naphthyridine-6-carboxylic acid methyl ester (64 mg, 0.14 mmol), 2 M NaOH (3 mL), MeOH (3 mL) and THF (3 mL) was stirred at r.t. overnight. The mixture was concentrated to approximately one-third of its original volume, and the resulting mixture was acidified to pH about 3-4 and extracted with EtOAc. The organic layer was dried over MgSO$_4$ and concentrated. To the residue were then added HOBt (30 mg, 0.22 mmol), CH$_2$Cl$_2$ (3 mL), and EDC (47 mg, 0.25 mmol), and the resulting mixture was stirred for 10 min. β-Alanine methyl ester HCl salt (31 mg, 0.22 mmol) and Hunig's base (0.1 mL, 0.49 mmol) were added, and the mixture was stirred for 16 h. EtOAc (30 mL) was added, and the mixture was washed with 0.1 M HCl. The organic layer was dried over MgSO$_4$ and concentrated. The residue was purified by silica gel chromatography (5-70% EtOAc/hexanes+1% AcOH) to give 24 mg of the title compound. MS: (+) m/z 541.31 (M+1).

c) 3-[(1-Benzyl-5-hydroxy-2-oxo-3-phenyl-8-thiazol-4-yl-1,2-dihydro-[1,7]naphthyridine-6-carbonyl)-amino]-propionic acid A mixture of 3-[(1-benzyl-5-hydroxy-2-oxo-3-phenyl-8-thiazol-4-yl-1,2-dihydro-[1,7]naphthyridine-6-carbonyl)-amino]-propionic acid methyl ester (24 mg, 0.044 mmol), 2 M NaOH (3 mL), MeOH (3 mL) and THF (3 mL) was stirred at r.t. for 16 h, then concentrated to approximately one-third of its original volume. 1 M HCl was added until pH was about 3-4, and the resulting suspension was extracted with EtOAc. The organic layer was dried over MgSO$_4$ and concentrated. The crude product was purified by silica gel chromatography (10-100% EtOAc/hexanes+1% AcOH). The product isolated was dissolved in saturated NaHCO$_3$ and washed several times with ether. The aqueous layer was acidified to pH about 3-4, and the resulting precipitate was isolated by filtration to give 13 mg of the title compound. MS: (+) m/z 527.33 (M+1).

Example 203

3-[(1-Benzyl-5-hydroxy-2-oxo-3-phenyl-8-pyridazin-3-yl-1,2-dihydro-[1,7]naphthyridine-6-carbonyl)-amino]-propionic acid a) 1-Benzyl-5-hydroxy-2-oxo-3-phenyl-8-pyridazin-3-yl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (100 mg, 0.22 mmol), 3-tributylstannanyl-pyridazine (119 mg, 0.32 mmol) and PdCl$_2$(PPh$_3$)$_2$ (30 mg, 0.043 mmol) in 5 mL of DMF was heated at 120° C. for 2 h under nitrogen atmosphere. After the mixture was cooled to r.t., EtOAc and water were added. 1 M HCl was added with stirring until pH was about 3-4. The aqueous layer was extracted with additional EtOAc, and the combined organic layer was washed with water and brine, and dried over MgSO$_4$. After evaporating the solvent in vacuo, the crude product was dissolved in anhydrous MeOH (40 mL). Concentrated H$_2$SO$_4$ (10 drops) was added, and the mixture was refluxed overnight. After cooling to r.t., pH of the mixture was adjusted to about 3-4, and the mixture was extracted with EtOAc. The organic layer was dried over MgSO$_4$ and concentrated. The crude product was purified by silica gel chromatography (5-100% EtOAc/hexanes+1% AcOH) to give 18 mg of the title compound as a light brown solid. MS: (+) m/z 465.35 (M+1).

b) 3-[(1-Benzyl-5-hydroxy-2-oxo-3-phenyl-8-pyridazin-3-yl-1,2-dihydro-[1,7]naphthyridine-6-carbonyl)-amino]-propionic acid A mixture of 1-benzyl-5-hydroxy-2-oxo-3-phenyl-8-pyridazin-3-yl-1,2-dihydro-[1,7]naphthyridine-6-carboxylic acid methyl ester (45 mg, 0.097 mmol), β-alanine (864 mg, 9.7 mmol) and NaOMe solution (15.5 mL, 7.8 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over $MgSO_4$ and concentrated. The crude product was purified by silica gel chromatography (20-100% EtOAc/hexanes+1% AcOH). The product isolated was dissolved in saturated $NaHCO_3$ and washed several times with ether. The aqueous layer was acidified to pH about 3-4, and the resulting precipitate was isolated by filtration to give 14 mg of the title compound as a yellow solid. MS: (+) m/z 522.35 (M+1).

Example 204

3-[(1-Benzyl-5-hydroxy-2-oxo-3-phenethyl-8-pyridin-3-yl-1,2-dihydro-[1,7]naphthyridine-6-carbonyl)-amino]-propionic acid a) 1-Benzyl-8-bromo-5-hydroxy-2-oxo-3-phenethyl-1,2-dihydro-[1,7]naphthyridine-6-carboxylic acid methyl ester A mixture of 1-benzyl-5-hydroxy-2-oxo-3-phenethyl-1,2-dihydro-[1,7]naphthyridine-6-carboxylic acid methyl ester (78 mg, 0.19 mmol) and N-bromosuccinimide (37 mg, 0.21 mmol) in $CH_2Cl_2$ (0.7 mL) was refluxed for 3 h. Solvent was evaporated in vacuo, and the residue was purified by silica gel chromatography (5-20% EtOAc/hexanes+1% AcOH) to give 77 mg of the title compound as a light yellow solid. MS: (+) m/z 493.25, 495.14 (M+1, $^{79/81}$Br).

b) 1-Benzyl-5-hydroxy-2-oxo-3-phenethyl-8-pyridin-3-yl-1,2-dihydro-[1,7]naphthyridine-6-carboxylic acid methyl ester A mixture of 1-benzyl-8-bromo-5-hydroxy-2-oxo-3-phenethyl-1,2-dihydro-[1,7]naphthyridine-6-carboxylic acid methyl ester (77 mg, 0.16 mmol), 3-tributylstannanyl-pyridine (0.075 mL, 0.23 mmol) and $PdCl_2(PPh_3)_2$ (22 mg, 0.031 mmol) in 4 mL of DMF was heated at 120° C. for 3 h under nitrogen atmosphere. After the mixture was cooled to r.t., EtOAc and water were added. 1 M HCl was added with stirring until pH was about 3-4. The aqueous layer was extracted with additional EtOAc, and the combined organic layer was washed with water and dried over $MgSO_4$. After evaporating the solvent in vacuo, the crude product was purified by silica gel chromatography (5-100% EtOAc/hexanes+ 1% AcOH) to give 42 mg of the title compound as a yellow oil. MS: (+) m/z 492.56 (M+1).

c) 3-[(1-Benzyl-5-hydroxy-2-oxo-3-phenethyl-8-pyridin-3-yl-1,2-dihydro-[1,7]naphthyridine-6-carbonyl)-amino]-propionic acid A mixture of 1-benzyl-5-hydroxy-2-oxo-3-phenethyl-8-pyridin-3-yl-1,2-dihydro-[1,7]naphthyridine-6-carboxylic acid methyl ester (42 mg, 0.086 mmol), β-alanine (610 mg, 6.8 mmol) and NaOMe solution (10 mL, 5.1 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3. The aqueous layer was extracted with additional EtOAc, and the organic layers were combined, dried over $MgSO_4$ and concentrated. The residue was purified by silica gel chromatography (10-100% EtOAc/hexanes+1% AcOH). The product isolated was dissolved in saturated $NaHCO_3$ and washed several times with ether. The aqueous layer was acidified to pH about 3, and the resulting precipitate was isolated by filtration to give 24 mg of the title compound as a light yellow solid. MS: (+) m/z 549.50 (M+1).

Example 205

3-[(1,3-Dibenzyl-5-hydroxy-2-oxo-1,2-dihydro-[1,7]naphthyridine-6-carbonyl)-amino]-propionic acid A mixture of 1,3-dibenzyl-5-hydroxy-2-oxo-1,2-dihydro-[1,7]naphthyridine-6-carboxylic acid methyl ester (35 mg, 0.088 mmol), β-alanine (624 mg, 7.0 mmol) and NaOMe solution (10.5 mL, 5.3 mmol, 0.5 M in MeOH) was refluxed for 16 h. After the mixture was cooled to r.t., the solvent was evaporated in vacuo. The residue was partitioned between EtOAc and water. 1 M HCl was added until pH was about 3. The aqueous layer was extracted with additional EtOAc, and the organic layers were combined, dried over $MgSO_4$ and concentrated. The residue was purified by silica gel chromatography (5-50% EtOAc/hexanes+1% AcOH). The product isolated was dissolved in saturated $NaHCO_3$ and washed several times with ether. The aqueous layer was acidified to pH about 3, and the resulting precipitate was isolated by filtration to give 22 mg of the title compound as a light yellow solid. MS: (+) m/z 458.36 (M+1).

Example 206

3-[(7-Benzyl-4-hydroxy-8-oxo-1-pyridin-3-yl-7,8-dihydro-[2,7]naphthyridine-3-carbonyl)-amino]-propionic acid a) 7-Benzyl-4-hydroxy-8-oxo-1-pyridin-3-yl-7,8-dihydro-[2,7]naphthyridine-3-carboxylic acid methyl ester A mixture of 7-benzyl-4-hydroxy-1-iodo-8-oxo-7,8-dihydro-[2,7]naphthyridine-3-carboxylic acid methyl ester (105 mg, 0.24 mmol), 3-tributylstannanyl-pyridine (133 mg, 0.36 mmol), and $PdCl_2(PPh_3)_2$ (34 mg, 0.048 mmol) in 5 mL of DMF was heated at 120° C. for 2 h under $N_2$ atmosphere. After the mixture was cooled to r.t., EtOAc and water were added. 1 M HCl was added until pH was about 3-4. The aqueous layer was extracted with additional EtOAc, and the combined organic layer was washed with water, dried over $MgSO_4$ and concentrated. The crude product was purified by silica gel chromatography (5-100% EtOAc/hexanes+1% AcOH) to give 24 mg of the title compound. MS: (+) m/z 388.33 (M+1).

b) 3-[(7-Benzyl-4-hydroxy-8-oxo-1-pyridin-3-yl-7,8-dihydro-[2,7]naphthyridine-3-carbonyl)-amino]-propionic acid A mixture of 7-benzyl-4-hydroxy-8-oxo-1-pyridin-3-yl-7,8-dihydro-[2,7]naphthyridine-3-carboxylic acid methyl ester (24 mg, 0.062 mmol), β-alanine (552 mg, 6.2 mmol) and NaOMe solution (10 mL, 5.0 mmol, 0.5 M in MeOH) was refluxed for 16 h. After the mixture was cooled to r.t., solvent was evaporated in vacuo. The residue was partitioned between water and EtOAc. 1 M HCl was added until pH was about 3-4. The aqueous layer was extracted with additional EtOAc, and the organic layers were combined and concentrated to dryness. The residue was dissolved in saturated NaHCO$_3$ and washed several times with ether. The aqueous layer was acidified to pH about 3-4, and the resulting precipitate was isolated by filtration to give 12 mg of the title compound as a light yellow solid. MS: (+) m/z 445.39 (M+1).

Example 207

3-{[1-Cyclohexylmethyl-8-(2-ethoxy-pyrimidin-5-yl)-5-hydroxy-2-oxo-3-phenyl-1,2-dihydro-[1,7]naphthyridine-6-carbonyl]amino}-propionic acid a) 1-Cyclohexylmethyl-8-(2-ethoxy-pyrimidin-5-yl)-5-hydroxy-2-oxo-3-phenyl-1,2-dihydro-[1,7]naphthyridine-6-carboxylic acid methyl ester A mixture of 8-bromo-1-cyclohexylmethyl-5-hydroxy-2-oxo-3-phenyl-1,2-dihydro-[1,7]naphthyridine-6-carboxylic acid methyl ester (80 mg, 0.17 mmol), 2-ethoxy-5-tributylstannanyl-pyrimidine (105 mg, 0.25 mmol) and PdCl$_2$(PPh$_3$)$_2$ (24 mg, 0.034 mmol) in 4 mL of DMF was heated at 120° C. for 2 h under nitrogen atmosphere. After the mixture was cooled to r.t., EtOAc and brine were added. 1 M HCl was added until pH was about 3. The aqueous layer was extracted with additional EtOAc, and the combined organic layer was washed with water and dried over MgSO$_4$. After evaporating the solvent in vacuo, the crude product was purified by silica gel chromatography (5-35% EtOAc/hexanes+1% AcOH) to give 35 mg of the title compound. MS: (+) m/z 515.36 (M+1).

b) 3-{[1-Cyclohexylmethyl-8-(2-ethoxy-pyrimidin-5-yl)-5-hydroxy-2-oxo-3-phenyl-1,2-dihydro-[1,7]naphthyridine-6-carbonyl]-amino}-propionic acid A mixture of 1-cyclohexylmethyl-8-(2-ethoxy-pyrimidin-5-yl)-5-hydroxy-2-oxo-3-phenyl-1,2-dihydro-[1,7]naphthyridine-6-carboxylic acid methyl ester (35 mg, 0.068 mmol), β-alanine (607 mg, 6.8 mmol) and NaOMe solution (11 mL, 5.4 mmol, 0.5 M in MeOH) was refluxed for 16 h. After the mixture was cooled to r.t., the solvent was evaporated in vacuo. The residue was partitioned between EtOAc and water. 1 M HCl was added until pH was about 3-4. The aqueous layer was extracted with additional EtOAc, and the organic layers were combined, dried over MgSO$_4$ and concentrated. The crude product was purified by silica gel chromatography (5-40% EtOAc/hexanes+1% AcOH). The product isolated was dissolved in saturated NaHCO$_3$ and washed several times with ether. The aqueous layer was acidified to pH about 3-4, and the resulting precipitate was isolated by filtration to give 15 mg of the title compound. MS: (+) m/z 572.36 (M+1).

Example 208

3-{[1-Benzyl-5-hydroxy-8-(2-methylsulfanyl-pyrimidin-5-yl)-2-oxo-3-phenyl-1,2-dihydro-[1,7]naphthyridine-6-carbonyl]amino}-propionic acid a) 1-Benzyl-5-hydroxy-8-(2-methylsulfanyl-pyrimidin-5-yl)-2-oxo-3-phenyl-1,2-dihydro-[1,7]naphthyridine-6-carboxylic acid methyl ester A mixture of 1-benzyl-8-bromo-5-hydroxy-2-oxo-3-phenyl-1,2-dihydro-[1,7]naphthyridine-6-carboxylic acid methyl ester (80 mg, 0.17 mmol), 2-methylsulfanyl-5-tributylstannanyl-pyrimidine (143 mg, 0.34 mmol) and PdCl$_2$(PPh$_3$)$_2$ (24 mg, 0.034 mmol) in 4 mL of DMF was heated at 120° C. for 2 h under nitrogen atmosphere. After the mixture was cooled to r.t., EtOAc and brine were added. 1 M HCl was added until pH was about 3-4. The aqueous layer was extracted with additional EtOAc, and the combined organic layer was washed with water and brine, and dried over MgSO$_4$. After evaporating the solvent in vacuo, the crude product was purified twice by silica gel chromatography (0-5% EtOAc/CH$_2$Cl$_2$, then 5-50% EtOAc/hexanes+1% AcOH) to give 34 mg of the title compound. MS: (+) m/z 511.33 (M+1).

b) 3-{[1-Benzyl-5-hydroxy-8-(2-methylsulfanyl-pyrimidin-5-yl)-2-oxo-3-phenyl-1,2-dihydro-[1,7]naphthyridine-6-carbonyl]-amino}-propionic acid A mixture of 1-benzyl-5-hydroxy-8-(2-methylsulfanyl-pyrimidin-5-yl)-2-oxo-3-phenyl-1,2-dihydro-[1,7]naphthyridine-6-carboxylic acid methyl ester (34 mg, 0.067 mmol), β-alanine (594 mg, 6.7 mmol) and NaOMe solution (10.7 mL, 5.3 mmol, 0.5 M in MeOH) was refluxed for 16 h. After the mixture was cooled to r.t., the solvent was evaporated in vacuo. The residue was partitioned between EtOAc and water. 1 M HCl was added until pH was about 3-4. The aqueous layer was extracted with additional EtOAc, and the organic layers were combined, dried over MgSO$_4$ and concentrated. The crude product was purified by silica gel chromatography (5-60% EtOAc/hexanes+1% AcOH). The product isolated was dissolved in saturated NaHCO$_3$ and washed several times with ether. The aqueous layer was acidified to pH about 3, and the resulting precipitate was isolated by filtration to give 16 mg of the title compound as an off-white solid. MS: (+) m/z 568.33 (M+1).

Example 209

3-{[1-Benzyl-5-hydroxy-2-oxo-3-(4-trifluoromethyl-phenyl)-1,2-dihydro-[1,7]naphthyridine-6-carbonyl]amino}-propionic acid a) 1-Benzyl-5-hydroxy-2-oxo-3-(4-trifluoromethyl-phenyl)-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (220 mg, 0.57 mmol), 4-(trifluoromethyl)phenylboronic acid (161 mg, 0.85 mmol), K$_3$PO$_4$ (240 mg, 1.13 mmol), H$_2$O (20 mg, 1.13 mmol), SPhos (12 mg, 0.028 mmol) and Pd(OAc)$_2$ (12 mg, 0.017 mmol) in toluene (10 mL) was heated at 105° C. under nitrogen atmosphere for 20 h. After the mixture was cooled to r.t., water and EtOAc were added. 1 M HCl was added until pH was about 3, and the aqueous layer was extracted with additional EtOAc. The organic layers were combined, dried over MgSO$_4$ and concentrated. The crude product was purified by silica gel chromatography (5-50% EtOAc/hexanes+1% AcOH) to give 169 mg of the title compound as a yellow solid. MS: (+) m/z 455.34 (M+1).

b) 3-{[1-Benzyl-5-hydroxy-2-oxo-3-(4-trifluoromethyl-phenyl)-1,2-dihydro-[1,7]naphthyridine-6-carbonyl]-amino}-propionic acid A mixture of 1-benzyl-5-hydroxy-2-oxo-3-(4-trifluoromethyl-phenyl)-1,2-dihydro-[1,7]naphthyridine-6-carboxylic acid methyl ester (30 mg, 0.066 mmol), β-alanine (589 mg, 6.6 mmol) and NaOMe solution (10.6 mL, 5.3 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 2. The aqueous layer was extracted with additional EtOAc, and the organic layers were combined, dried over $MgSO_4$ and concentrated. The crude product was purified by silica gel chromatography (5-50% EtOAc/hexanes+1% AcOH). The product isolated was dissolved in saturated $NaHCO_3$ and washed several times with ether. The aqueous layer was acidified to pH about 2, and the resulting precipitate was isolated by filtration to give 15 mg of the title compound as a light yellow solid. MS: (+) m/z 512.34 (M+1).

Example 210

3-{[1-Benzyl-5-hydroxy-2-oxo-3-(2-trifluoromethyl-phenyl)-1,2-dihydro-[1,7]naphthyridine-6-carbonyl]-amino}-propionic acid a) 1-Benzyl-5-hydroxy-2-oxo-3-(2-trifluoromethyl-phenyl)-1,2-dihydro-[1,7]naphthyridine-6-carboxylic acid methyl ester A mixture of 1-benzyl-3-bromo-5-hydroxy-2-oxo-1,2-dihydro-[1,7]naphthyridine-6-carboxylic acid methyl ester (100 mg, 0.26 mmol), 2-(trifluoromethyl)phenylboronic acid (73 mg, 0.39 mmol), $K_3PO_4$ (109 mg, 0.51 mmol), $H_2O$ (9.3 mg, 0.51 mmol), SPhos (5.3 mg, 0.013 mmol) and $Pd(OAc)_2$ (5.2 mg, 0.0077 mmol) in toluene (5 mL) was heated at 100° C. under nitrogen atmosphere for 20 h. After the mixture was cooled to r.t., water and EtOAc were added. 1 M HCl was added until pH was about 2, and the aqueous layer was extracted with additional EtOAc. The organic layers were combined, dried over $MgSO_4$ and concentrated. The crude product was purified by silica gel chromatography (5-50% EtOAc/hexanes+1% AcOH) to give 36 mg of the title compound. MS: (+) m/z 455.28 (M+1).

b) 3-{[1-Benzyl-5-hydroxy-2-oxo-3-(2-trifluoromethyl-phenyl)-1,2-dihydro-[1,7]naphthyridine-6-carbonyl]-amino}-propionic acid A mixture of 1-benzyl-5-hydroxy-2-oxo-3-(2-trifluoromethyl-phenyl)-1,2-dihydro-[1,7]naphthyridine-6-carboxylic acid methyl ester (27 mg, 0.059 mmol), β-alanine (530 mg, 5.9 mmol) and NaOMe solution (9.6 mL, 4.8 mmol, 0.5 M in MeOH) was refluxed for 16 h. After the mixture was cooled to r.t., the solvent was evaporated in vacuo. The residue was partitioned between EtOAc and water. 1 M HCl was added until pH was about 3. The aqueous layer was extracted with additional EtOAc, and the organic layers were combined, dried over $MgSO_4$ and concentrated. The crude product was purified by silica gel chromatography (5-60% EtOAc/hexanes+1% AcOH). The product isolated was dissolved in saturated $NaHCO_3$ and washed several times with ether. The aqueous layer was acidified to pH about 3, and the resulting precipitate was isolated by filtration to give 16 mg of the title compound. MS: (+) m/z 512.27 (M+1).

Example 211

4-{[1-Benzyl-5-hydroxy-2-oxo-3-(4-trifluoromethyl-phenyl)-1,2-dihydro-[1,7]naphthyridine-6-carbonyl]-amino}-butyric acid A mixture of 1-benzyl-5-hydroxy-2-oxo-3-(4-trifluoromethyl-phenyl)-1,2-dihydro-[1,7]naphthyridine-6-carboxylic acid methyl ester (40 mg, 0.088 mmol), 4-aminobutyric acid (726 mg, 7.0 mmol) and NaOMe solution (10.6 mL, 5.3 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 2. The aqueous layer was extracted with additional EtOAc, and the organic layers were combined, dried over $MgSO_4$ and concentrated. The crude product was purified by silica gel chromatography (5-50% EtOAc/hexanes+1% AcOH). The product isolated was dissolved in saturated $NaHCO_3$ and washed several times with ether. The aqueous layer was acidified to pH about 2, and the resulting precipitate was isolated by filtration to give 15.5 mg of the title compound as a light yellow solid. MS: (+) m/z 526.26 (M+1).

Example 212

4-{[1-Benzyl-5-hydroxy-2-oxo-3-(3-trifluoromethyl-phenyl)-1,2-dihydro-[1,7]naphthyridine-6-carbonyl]-amino}-butyric acid A mixture of 1-benzyl-5-hydroxy-2-oxo-3-(3-trifluoromethyl-phenyl)-1,2-dihydro-[1,7]naphthyridine-6-carboxylic acid methyl ester (40 mg, 0.088 mmol), 4-aminobutyric acid (726 mg, 7.0 mmol) and NaOMe solution (10.6 mL, 5.3 mmol, 0.5 M in MeOH) was refluxed for 16 h. After the mixture was cooled to r.t., the solvent was evaporated in vacuo. The residue was partitioned between EtOAc and water. 1 M HCl was added until pH was about 3. The aqueous layer was extracted with additional EtOAc, and the organic layers were combined, dried over $MgSO_4$ and concentrated. The crude product was purified by silica gel chromatography (5-50% EtOAc/hexanes+1% AcOH). The product isolated was dissolved in saturated $NaHCO_3$ and washed several times with ether. The aqueous layer was acidified to pH about 2, and the resulting precipitate was isolated by filtration to give 18 mg of the title compound. MS: (+) m/z 526.32 (M+1).

Example 213

4-{[1-Benzyl-5-hydroxy-2-oxo-3-(2-trifluoromethyl-phenyl)-1,2-dihydro-[1,7]naphthyridine-6-carbonyl] amino}-butyric acid A mixture of 1-benzyl-5-hydroxy-2-oxo-3-(2-trifluoromethyl-phenyl)-1,2-dihydro-[1,7]naphthyridine-6-carboxylic acid methyl ester (36 mg, 0.079 mmol), 4-aminobutyric acid (653 mg, 6.34 mmol) and NaOMe solution (9.5 mL, 4.76 mmol, 0.5 M in MeOH) was refluxed for 16 h. After the mixture was cooled to r.t., the solvent was evaporated in vacuo. The residue was partitioned between EtOAc and water. 1 M HCl was added until pH was about 3. The aqueous layer was extracted with additional EtOAc, and the organic layers were combined, dried over $MgSO_4$ and concentrated. The crude product was purified by silica gel chromatography (5-50% EtOAc/hexanes+1% AcOH). The product isolated was dissolved in saturated $NaHCO_3$ and washed several times with ether. The aqueous layer was acidified to pH about 3, and the resulting precipitate was isolated by filtration to give 16 mg of the title compound. MS: (+) m/z 526.32 (M+1).

Example 214

3-{[1-Benzyl-5-hydroxy-2-oxo-8-pyridin-3-yl-3-(4-trifluoromethyl-phenyl)-1,2-dihydro-[1,7]naphthyridine-6-carbonyl]amino}-propionic acid a) 1-Benzyl-8-bromo-5-hydroxy-2-oxo-3-(4-trifluoromethyl-phenyl)-1,2-dihydro-[1,7]naphthyridine-6-carboxylic acid methyl ester A mixture of 1-benzyl-5-hydroxy-2-oxo-3-(4-trifluoromethyl-phenyl)-1,2-dihydro-[1,7]naphthyridine-6-carboxylic acid methyl ester (99 mg, 0.22 mmol) and N-bromosuccinimide (43 mg, 0.24 mmol) in $CH_2Cl_2$ (0.8 mL) was refluxed for 3 h. Solvent was evaporated in vacuo, and the residue was purified by silica gel chromatography (5-20% EtOAc/hexanes+1% AcOH) to give 76 mg of the title compound as a yellow solid. MS: (−) m/z 531.23, 533.18 (M-1, $^{79/81}$Br).

b) 1-Benzyl-5-hydroxy-2-oxo-8-pyridin-3-yl-3-(4-trifluoromethyl-phenyl)-1,2-dihydro-[1,7]naphthyridine-6-carboxylic acid methyl ester A mixture of 1-benzyl-8-bromo-5-hydroxy-2-oxo-3-(4-trifluoromethyl-phenyl)-1,2-dihydro-[1,7]naphthyridine-6-carboxylic acid methyl ester (76 mg, 0.14 mmol), 3-tributylstannanyl-pyridine (0.068 mL, 0.21 mmol) and $PdCl_2(PPh_3)_2$ (20 mg, 0.029 mmol) in 4 mL of DMF was heated at 120° C. for 2.5 h under nitrogen atmosphere. After the mixture was cooled to r.t., EtOAc and water were added. 1 M HCl was added with stirring until pH was about 3-4. The aqueous layer was extracted with additional EtOAc, and the combined organic layer was washed with water and brine and dried over $MgSO_4$. After evaporating the solvent in vacuo, the crude product was purified by silica gel chromatography (5-100% EtOAc/hexanes+1% AcOH) to give 32 mg of the title compound as a tan solid. MS: (+) m/z 532.30 (M+1).

c) 3-{[1-Benzyl-5-hydroxy-2-oxo-8-pyridin-3-yl-3-(4-trifluoromethyl-phenyl)-1,2-dihydro-[1,7]naphthyridine-6-carbonyl]-amino}-propionic acid A mixture of 1-benzyl-5-hydroxy-2-oxo-8-pyridin-3-yl-3-(4-trifluoromethyl-phenyl)-1,2-dihydro-[1,7]naphthyridine-6-carboxylic acid methyl ester (32 mg, 0.060 mmol), β-alanine (537 mg, 6.0 mmol) and NaOMe solution (9.6 mL, 4.8 mmol, 0.5 M in MeOH) was refluxed for 16 h. After the mixture was cooled to r.t., the solvent was evaporated in vacuo. The residue was partitioned between EtOAc and water. 1 M HCl was added until pH was about 3. The aqueous layer was extracted with additional EtOAc, and the organic layers were combined, dried over $MgSO_4$ and concentrated. The residue was purified by silica gel chromatography (10-100% EtOAc/hexanes+1% AcOH). The product isolated was dissolved in saturated $NaHCO_3$ and washed several times with ether. The aqueous layer was acidified to pH about 3, and the resulting precipitate was isolated by filtration to give 18 mg of the title compound. MS: (+) m/z 589.36 (M+1).

Example 215

3-{[1-Benzyl-5-hydroxy-2-oxo-8-pyridin-3-yl-3-(3-trifluoromethyl-phenyl)-1,2-dihydro-[1,7]naphthyridine-6-carbonyl]amino}-propionic acid a) 1-Benzyl-8-bromo-5-hydroxy-2-oxo-3-(3-trifluoromethyl-phenyl)-1,2-dihydro-[1,7]naphthyridine-6-carboxylic acid methyl ester A mixture of 1-benzyl-5-hydroxy-2-oxo-3-(3-trifluoromethyl-phenyl)-1,2-dihydro-[1,7]naphthyridine-6-carboxylic acid methyl ester (115 mg, 0.25 mmol) and N-bromosuccinimide (50 mg, 0.28 mmol) in $CH_2Cl_2$ (1 mL) was refluxed for 3 h. Solvent was evaporated in vacuo, and the residue was purified by silica gel chromatography (5-20% EtOAc/hexanes+1% AcOH) to give 76 mg of the title compound as a yellow solid. MS: (−) m/z 531.17, 533.12 (M-1, $^{79/81}$Br).

b) 1-Benzyl-5-hydroxy-2-oxo-8-pyridin-3-yl-3-(3-trifluoromethyl-phenyl)-1,2-dihydro-[1,7]naphthyridine-6-carboxylic acid methyl ester A mixture of 1-benzyl-8-bromo-5-hydroxy-2-oxo-3-(3-trifluoromethyl-phenyl)-1,2-dihydro-[1,7]naphthyridine-6-carboxylic acid methyl ester (76 mg, 0.14 mmol), 3-tributylstannanyl-pyridine (0.070 mL, 0.21 mmol) and $PdCl_2(PPh_3)_2$ (20 mg, 0.029 mmol) in 4 mL of DMF was heated at 120° C. for 2 h under nitrogen atmosphere. After the mixture was cooled to r.t., EtOAc and water were added. 1 M HCl was added until pH was about 3. The aqueous layer was extracted with additional EtOAc, and the combined organic layer was washed with water and brine, and dried over $MgSO_4$. After evaporating the solvent in vacuo, the crude product was purified by silica gel chromatography (5-95% EtOAc/hexanes+1% AcOH) to give 29 mg of the title compound. MS: (+) m/z 532.30 (M+1).

c) 3-{[1-Benzyl-5-hydroxy-2-oxo-8-pyridin-3-yl-3-(3-trifluoromethyl-phenyl)-1,2-dihydro-[1,7]naphthyridine-6-carbonyl]-amino}-propionic acid A mixture of 1-benzyl-5-hydroxy-2-oxo-8-pyridin-3-yl-3-(3-trifluoromethyl-phenyl)-1,2-dihydro-[1,7]naphthyridine-6-carboxylic acid methyl ester (29 mg, 0.055 mmol), β-alanine (487 mg, 5.5 mmol) and NaOMe solution (8.8 mL, 4.4 mmol, 0.5 M in MeOH) was refluxed for 16 h. After the mixture was cooled to r.t., the solvent was evaporated in vacuo. The residue was partitioned between EtOAc and water. 1 M HCl was added until pH was about 3-4. The aqueous layer was extracted with additional EtOAc, and the organic layers were combined, dried over $MgSO_4$ and concentrated. The residue was purified by silica gel chromatography (10-100% EtOAc/hexanes+1% AcOH). The product isolated was dissolved in saturated $NaHCO_3$ and washed several times with ether. The aqueous layer was acidified to pH about 3-4, and the resulting precipitate was isolated by filtration to give 13 mg of the title compound. MS: (+) m/z 589.24 (M+1).

Example 216

3-{[1-Benzyl-5-hydroxy-2-oxo-8-pyridin-3-yl-3-(2-trifluoromethyl-phenyl)-1,2-dihydro-[1,7]naphthyridine-6-carbonyl]amino}-propionic acid a) 1-Benzyl-8-bromo-5-hydroxy-2-oxo-3-(2-trifluoromethyl-phenyl)-1,2-dihydro-[1,7]naphthyridine-6-carboxylic acid methyl ester A mixture of 1-benzyl-5-hydroxy-2-oxo-3-(2-trifluoromethyl-phenyl)-1,2-dihydro-[1,7]naphthyridine-6-carboxylic acid methyl ester (85 mg, 0.19 mmol) and N-bromosuccinimide (37 mg, 0.21 mmol) in $CH_2Cl_2$ (0.8 mL) was refluxed for 3 h. Solvent was evaporated in vacuo, and the residue was purified by silica gel chromatography (5-30% EtOAc/hexanes+1% AcOH) to give 80 mg of the title compound as a yellow solid. MS: (−) m/z 531.17, 533.12 (M-1, $^{79/81}$Br).

b) 1-Benzyl-5-hydroxy-2-oxo-8-pyridin-3-yl-3-(2-trifluoromethyl-phenyl)-1,2-dihydro-[1,7]naphthyridine-6-carboxylic acid methyl ester A mixture of 1-benzyl-8-bromo-5-hydroxy-2-oxo-3-(2-trifluoromethyl-phenyl)-1,2-dihydro-[1,7]naphthyridine-6-carboxylic acid methyl ester (80 mg, 0.15 mmol), 3-tributylstannanyl-pyridine (0.072 mL, 0.23 mmol) and $PdCl_2(PPh_3)_2$ (21 mg, 0.030 mmol) in 4 mL of DMF was heated at 120° C. for 2 h under nitrogen atmosphere. After the mixture was cooled to r.t., EtOAc and brine were added. 1 M HCl was added until pH was about 3. The aqueous layer was extracted with additional EtOAc, and the combined organic layer was washed with water and dried over $MgSO_4$. After evaporating the solvent in vacuo, the crude product was purified by silica gel chromatography (5-100% EtOAc/hexanes+1% AcOH) to give 30 mg of the title compound. MS: (+) m/z 532.37 (M+1).

c) 3-{[1-Benzyl-5-hydroxy-2-oxo-8-pyridin-3-yl-3-(2-trifluoromethyl-phenyl)-1,2-dihydro-[1,7]naphthyridine-6-carbonyl]-amino}-propionic acid A mixture of 1-benzyl-5-hydroxy-2-oxo-8-pyridin-3-yl-3-(2-trifluoromethyl-phenyl)-1,2-dihydro-[1,7]naphthyridine-6-carboxylic acid methyl ester (30 mg, 0.056 mmol), β-alanine (503 mg, 5.6 mmol) and NaOMe solution (9 mL, 4.5 mmol, 0.5 M in MeOH) was refluxed for 16 h. After the mixture was cooled to r.t., the solvent was evaporated in vacuo. The residue was partitioned between EtOAc and water. 1 M HCl was added until pH was about 3-4. The aqueous layer was extracted with additional EtOAc, and the organic layers were combined, dried over $MgSO_4$ and concentrated. The residue was purified by silica gel chromatography (15-100% EtOAc/hexanes+1% AcOH). The product isolated was dissolved in saturated $NaHCO_3$ and washed several times with ether. The aqueous layer was acidified to pH about 3, and the resulting precipitate was isolated by filtration to give 23 mg of the title compound as a light tan solid. MS: (+) m/z 589.30 (M+1).

Example 217

3-[(1-Cyclopentylmethyl-5-hydroxy-2-oxo-3-phenyl-1,2-dihydro-[1,7]naphthyridine-6-carbonyl)-amino]-propionic acid a) 4-[1-(Cyclopentylmethyl-amino)-ethylidene]-pent-2-enedioic acid dimethyl ester A mixture of cyclopentanemethylamine (4.52 g, 45.7 mmol) and 3-oxo-butyric acid methyl ester (5.9 mL, 54.8 mmol) in MeOH (170 mL) was refluxed for 2 h. Propynoic acid methyl ester (6.1 mL, 68.5 mmol) was added, and the resulting mixture was refluxed for 2 days. After cooling to r.t., the solvent was evaporated, and the residue was recrystallized from MeOH to give 7.17 g of the title compound as a light tan solid. MS: (+) m/z 282.33 (M+1).

b) 5-Bromo-1-cyclopentylmethyl-2-methyl-6-oxo-1,6-dihydro-pyridine-3-carboxylic acid methyl ester MeOH (240 mL) was added to a flask containing 4-[1-(cyclopentylmethyl-amino)-ethylidene]-pent-2-enedioic acid dimethyl ester (7.2 g, 25.6 mmol). NaOMe solution (5.9 mL, 25.6 mmol, 4.375 M in MeOH) and N-bromosuccinimide (5.5 g, 30.7 mmol) were added, and the resulting mixture was refluxed for 1 h. After cooling to r.t., the solvent was evaporated in vacuo. Saturated $NH_4Cl$ was added, and the resulting mixture was extracted with $CH_2Cl_2$. The organic layer was dried over $MgSO_4$ and concentrated. The crude product was chromatographed (0-25% EtOAc/hexanes) to give 4.46 g of the title compound. MS: (+) m/z 350.22, 352.24 (M+Na, $^{79/81}$Br).

c) 5-Bromo-2-bromomethyl-1-cyclopentylmethyl-6-oxo-1,6-dihydro-pyridine-3-carboxylic acid methyl ester A mixture of 5-bromo-1-cyclopentylmethyl-2-methyl-6-oxo-1,6-dihydro-pyridine-3-carboxylic acid methyl ester (4.46 g, 13.6 mmol), N-bromosuccinimide (2.66 g, 15.0 mmol), and benzoyl peroxide (0.33 g, 1.36 mmol) in $CCl_4$ (130 mL) was refluxed for 16 h. The resulting suspension was filtered, and the filtrate was evaporated in vacuo. The residue was purified by silica gel chromatography (0-25% EtOAc/hexanes) to give 2.5 g of the title compound. MS: (+) m/z 408.10 (M+1).

d) 5-Bromo-1-cyclopentylmethyl-2-{[methoxycarbonylmethyl-(toluene-4-sulfonyl)-amino]-methyl}-6-oxo-1,6-dihydro-pyridine-3-carboxylic acid methyl ester A mixture of 5-bromo-2-bromomethyl-1-cyclopentylmethyl-6-oxo-1,6-dihydro-pyridine-3-carboxylic acid methyl ester (2.5 g, 6.14 mmol), (toluene-4-sulfonylamino)-acetic acid methyl ester (1.42 g, 5.84 mmol), sodium iodide (1.84 g, 12.3 mmol) and potassium carbonate (1.70 g, 12.3 mmol) in DMF (40 mL) was stirred at r.t. for 16 h. Water was added, and the resulting suspension was extracted with EtOAc. The organic layer was washed with water and brine, and dried over $MgSO_4$. After the solvent was evaporated in vacuo, the crude product was purified by silica gel chromatography (5-60% EtOAc/hexanes) to give 2.76 g of the title compound. MS: (+) m/z 591.19, 593.14 (M+Na, $^{79/81}$Br).

e) 3-Bromo-1-cyclopentylmethyl-5-hydroxy-2-oxo-1,2-dihydro-[1,7]naphthyridine-6-carboxylic acid methyl ester 5-Bromo-1-cyclopentylmethyl-2-{[methoxycarbonylmethyl-(toluene-4-sulfonyl)-amino]-methyl}-6-oxo-1,6-dihydro-pyridine-3-carboxylic acid methyl ester (2.76 g, 4.85 mmol) was dissolved in 90 mL of MeOH and placed in ice bath. NaOMe solution (3.3 mL, 14.6 mmol, 4.375 M in MeOH) was added and the mixture was stirred for 16 h at r.t. 1 M HCl was added to acidify the mixture, and the resulting suspension was extracted with $CH_2Cl_2$. The organic layer was dried over $MgSO_4$ and concentrated. The crude product was purified by silica gel chromatography (0-5% EtOAc/$CH_2Cl_2$) to give 1.61 g of the title compound as an off-white solid. MS: (+) m/z 381.21, 383.16 (M+1, $^{79/81}$Br).

f) 1-Cyclopentylmethyl-5-hydroxy-2-oxo-3-phenyl-1,2-dihydro-[1,7]naphthyridine-6-carboxylic acid methyl ester A mixture of 3-bromo-1-cyclopentylmethyl-5-hydroxy-2-oxo-1,2-dihydro-[1,7]naphthyridine-6-carboxylic acid methyl ester (300 mg, 0.79 mmol), $PhSnBu_3$ (0.31 mL, 0.94 mmol), and $PdCl_2(PPh_3)_2$ (111 mg, 0.16 mmol) in DMF (15 mL) was heated at 120° C. under nitrogen atmosphere for 3 h. After the mixture was cooled to r.t., brine and EtOAc were added. 1 M HCl was added until pH was about 2-3. The aqueous layer was extracted with additional EtOAc and the organic layers were combined, washed with water and brine, and dried over MgSO$_4$. After evaporating the solvent in vacuo, the crude product was chromatographed (3-35% EtOAc/hexanes+1% AcOH) to give 227 mg of the title compound as a yellow solid. MS: (+) m/z 379.38 (M+1).

g) 3-[(1-Cyclopentylmethyl-5-hydroxy-2-oxo-3-phenyl-1,2-dihydro-[1,7]naphthyridine-6-carbonyl)-amino]-propionic acid A mixture of 1-cyclopentylmethyl-5-hydroxy-2-oxo-3-phenyl-1,2-dihydro-[1,7]naphthyridine-6-carboxylic acid methyl ester (35 mg, 0.093 mmol), β-alanine (660 mg, 7.4 mmol) and NaOMe solution (11 mL, 5.6 mmol, 0.5 M in MeOH) was refluxed for 16 h. After the mixture was cooled to r.t., the solvent was evaporated in vacuo. The residue was partitioned between EtOAc and water. 1 M HCl was added until pH was about 3. The aqueous layer was extracted with additional EtOAc, and the organic layers were combined, dried over MgSO$_4$ and concentrated. The residue was purified by silica gel chromatography (5-40% EtOAc/hexanes+1% AcOH). The product isolated was dissolved in saturated NaHCO$_3$ and washed several times with ether. The aqueous layer was acidified to pH about 3, and the resulting precipitate was isolated by filtration to give 20 mg of the title compound as a yellow solid. MS: (+) m/z 436.38 (M+1).

Example 218

4-[(1-Cyclopentylmethyl-5-hydroxy-2-oxo-3-phenyl-1,2-dihydro-[1,7]naphthyridine-6-carbonyl)-amino]-butyric acid A mixture of 1-cyclopentylmethyl-5-hydroxy-2-oxo-3-phenyl-1,2-dihydro-[1,7]naphthyridine-6-carboxylic acid methyl ester (45 mg, 0.12 mmol), 4-aminobutyric acid (736 mg, 7.1 mmol) and NaOMe solution (10.7 mL, 5.4 mmol, 0.5 M in MeOH) was refluxed for 16 h. After the mixture was cooled to r.t., the solvent was evaporated in vacuo. The residue was partitioned between EtOAc and water. 1 M HCl was added until pH was about 2-3. The aqueous layer was extracted with additional EtOAc, and the organic layers were combined, dried over MgSO$_4$ and concentrated. The residue was purified by silica gel chromatography (5-40% EtOAc/hexanes+1% AcOH). The product isolated was dissolved in saturated NaHCO$_3$ and washed several times with ether. The aqueous layer was acidified to pH about 3, and the resulting precipitate was isolated by filtration to give 22 mg of the title compound as a yellow solid. MS: (+) m/z 450.36 (M+1).

Example 219

3-[(1-Cyclopentylmethyl-5-hydroxy-2-oxo-3-phenyl-8-pyridin-3-yl-1,2-dihydro-[1,7]naphthyridine-6-carbonyl)-amino]-propionic acid a) 8-Bromo-1-cyclopentylmethyl-5-hydroxy-2-oxo-3-phenyl-1,2-dihydro-[1,7]naphthyridine-6-carboxylic acid methyl ester A mixture of 1-cyclopentylmethyl-5-hydroxy-2-oxo-3-phenyl-1,2-dihydro-[1,7]naphthyridine-6-carboxylic acid methyl ester (147 mg, 0.39 mmol) and N-bromosuccinimide (76 mg, 0.43 mmol) in CH$_2$Cl$_2$ (1.5 mL) was refluxed for 3 h. Solvent was evaporated in vacuo and the residue was purified by silica gel chromatography (5-15% EtOAc/hexanes+1% AcOH) to give 127 mg of the title compound as a yellow solid. MS: (−) m/z 455.21, 457.17 (M-1, $^{79/81}$Br).

b) 1-Cyclopentylmethyl-5-hydroxy-2-oxo-3-phenyl-8-pyridin-3-yl-1,2-dihydro-[1,7]naphthyridine-6-carboxylic acid methyl ester A mixture of 8-bromo-1-cyclopentylmethyl-5-hydroxy-2-oxo-3-phenyl-1,2-dihydro-[1,7]naphthyridine-6-carboxylic acid methyl ester (66 mg, 0.14 mmol), 3-tributylstannanyl-pyridine (0.069 mL, 0.22 mmol) and PdCl$_2$(PPh$_3$)$_2$ (20 mg, 0.029 mmol) in 4 mL of DMF was heated at 120° C. for 2.5 h under nitrogen atmosphere. After the mixture was cooled to r.t., EtOAc and brine were added. 1 M HCl was added with stirring until pH was about 3. The aqueous layer was extracted with additional EtOAc, and the combined organic layer was washed with water and brine, and dried over MgSO$_4$. After evaporating the solvent in vacuo, the crude product was purified by silica gel chromatography (5-90% EtOAc/hexanes+1% AcOH) to give 38 mg of the title compound. MS: (+) m/z 456.41 (M+1).

c) 3-[(1-Cyclopentylmethyl-5-hydroxy-2-oxo-3-phenyl-8-pyridin-3-yl-1,2-dihydro-[1,7]naphthyridine-6-carbonyl)-amino]-propionic acid A mixture of 1-cyclopentylmethyl-5-hydroxy-2-oxo-3-phenyl-8-pyridin-3-yl-1,2-dihydro-[1,7]naphthyridine-6-carboxylic acid methyl ester (38 mg, 0.084 mmol), β-alanine (595 mg, 6.7 mmol) and NaOMe solution (10 mL, 5.0 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 3-4. The aqueous layer was extracted with additional EtOAc, and the organic layers were combined, dried over MgSO$_4$ and concentrated. The residue was purified by silica gel chromatography (5-90% EtOAc/hexanes+1% AcOH). The product isolated was dissolved in saturated NaHCO$_3$ and washed several times with ether. The aqueous layer was acidified to pH about 3-4, and the resulting precipitate was isolated by filtration to give 15 mg of the title compound as a pale yellow solid. MS: (+) m/z 513.47 (M+1).

Example 220

1-[(7-Benzyl-4-hydroxy-8-oxo-7,8-dihydro-[2,7]naphthyridine-3-carbonyl)-amino]-cyclopropanecarboxylic acid a) 1-[(7-Benzyl-4-hydroxy-8-oxo-7,8-dihydro-[2,7]naphthyridine-3-carbonyl)-amino]-cyclopropanecarboxylic acid ethyl ester A mixture of 7-benzyl-4-hydroxy-8-oxo-7,8-dihydro-[2,7]naphthyridine-3-carboxylic acid methyl ester (53 mg, 0.17 mmol), 2 M NaOH (3 mL), MeOH (3 mL) and THF (3 mL) was stirred at r.t. for 16 h, then concentrated to dryness. The residue was dissolved in water and acidified to pH about 2 with 1 M HCl. The resulting precipitate was isolated by filtration. To the crude solid were added CH$_2$Cl$_2$ (3 mL), HOBt (29 mg, 0.22 mmol), and EDC (47 mg, 0.24 mmol), and the resulting mixture was stirred for 10 min. 1-Amino-cyclopropanecarboxylic acid ethyl ester HCl salt (36 mg, 0.22 mmol) and Hunig's base (0.086 mL, 0.49 mmol) were added, and the mixture was stirred for 16 h. The mixture was diluted with EtOAc and brine, and 1 M HCl was added until pH was about 2. The aqueous layer was extracted with additional EtOAc, and the organic layers were combined, dried over MgSO$_4$ and concentrated. The crude product was purified by silica gel chromatography (5-40% EtOAc/hexanes+1% AcOH) to give 23 mg of the title compound. MS: (+) m/z 408.29 (M+1).

b) 1-[(7-Benzyl-4-hydroxy-8-oxo-7,8-dihydro-[2,7]naphthyridine-3-carbonyl)-amino]-cyclopropanecarboxylic acid A mixture of 1-[(7-benzyl-4-hydroxy-8-oxo-7,8-dihydro-[2,7]naphthyridine-3-carbonyl)-amino]-cyclopropanecarboxylic acid ethyl ester (23 mg, 0.057 mmol), 2 M NaOH (3 mL), MeOH (3 mL) and THF (3 mL) was stirred at r.t. for 16 h, then concentrated to approximately one-third of its original volume. 1 M HCl was added to acidify the mixture to pH about 2, and the resulting suspension was extracted with EtOAc. The organic layer was dried over MgSO$_4$ and concentrated. The crude product was purified by silica gel chromatography (5-50% EtOAc/hexanes+1% AcOH). The product isolated was dissolved in saturated NaHCO$_3$ and washed several times with ether. The aqueous layer was acidified to pH about 2, and the resulting precipitate was isolated by filtration to give 9 mg of the title compound as a yellow solid. MS: (+) m/z 380.27 (M+1).

Example 221

3-{[1-(2-Ethyl-butyl)-5-hydroxy-2-oxo-3-phenyl-1,2-dihydro-[1,7]naphthyridine-6-carbonyl]amino}-propionic acid a) 4-[1-(2-Ethyl-butylamino)-ethylidene]pent-2-enedioic acid dimethyl ester A mixture of 2-ethyl-butylamine (4.5 g, 44.6 mmol) and 3-oxo-butyric acid methyl ester (5.8 mL, 53.5 mmol) in MeOH (170 mL) was refluxed for 2 h. Propynoic acid methyl ester (6 mL, 66.8 mmol) was added, and the resulting mixture was refluxed for 2 days. After cooling to r.t., the solvent was evaporated. The residue was purified by silica gel chromatography (0-30% EtOAc/hexanes) to give 7.32 g of the title compound as an orange oil. MS: (+) m/z 284.35 (M+1).

b) 5-Bromo-1-(2-ethyl-butyl)-2-methyl-6-oxo-1,6-dihydro-pyridine-3-carboxylic acid methyl ester MeOH (240 mL) was added to a flask containing 4-[1-(2-ethyl-butylamino)-ethylidene]-pent-2-enedioic acid dimethyl ester (7.32 g, 25.9 mmol). NaOMe solution (5.9 mL, 25.9 mmol, 4.375 M in MeOH) and N-bromosuccinimide (5.52 g, 31.0 mmol) were added, and the resulting mixture was refluxed for 1 h. After cooling to r.t., the solvent was evaporated in vacuo. Saturated NH$_4$Cl was added, and the resulting mixture was extracted with CH$_2$Cl$_2$. The organic layer was dried over MgSO$_4$ and concentrated. The crude product was chromatographed (0-25% EtOAc/hexanes) to give 5.72 g of the title compound. MS: (+) m/z 352.18, 354.19 (M+Na, $^{79/81}$Br).

c) 5-Bromo-2-bromomethyl-1-(2-ethyl-butyl)-6-oxo-1,6-dihydro-pyridine-3-carboxylic acid methyl ester A mixture of 5-bromo-1-(2-ethyl-butyl)-2-methyl-6-oxo-1,6-dihydro-pyridine-3-carboxylic acid methyl ester (5.72 g, 17.3 mmol), N-bromosuccinimide (3.39 g, 19.1 mmol), and benzoyl peroxide (0.42 g, 1.73 mmol) in CCl$_4$ (170 mL) was refluxed for 16 h. The resulting suspension was filtered, and the filtrate was evaporated in vacuo. The residue was purified by silica gel chromatography (0-20% EtOAc/hexanes) to give 4.9 g of the title compound as a yellow viscous oil. MS: (+) m/z 432.10 (M+Na).

d) 5-Bromo-1-(2-ethyl-butyl)-2-{[methoxycarbonyl-methyl-(toluene-4-sulfonyl)-amino]-methyl}-6-oxo-1,6-dihydro-pyridine-3-carboxylic acid methyl ester A mixture of 5-bromo-2-bromomethyl-1-(2-ethyl-butyl)-6-oxo-1,6-dihydro-pyridine-3-carboxylic acid methyl ester (4.9 g, 12.0 mmol), (toluene-4-sulfonylamino)-acetic acid methyl ester (2.62 g, 10.8 mmol), sodium iodide (3.6 g, 24.0 mmol) and potassium carbonate (3.3 g, 24.0 mmol) in DMF (75 mL) was stirred at r.t. for 16 h. Brine was added, and the resulting mixture was extracted with EtOAc. The organic layer was washed with water and dried over MgSO$_4$. After the solvent was evaporated in vacuo, the crude product was purified by silica gel chromatography (5-60% EtOAc/hexanes) to give 4.89 g of the title compound. MS: (+) m/z 571.22, 573.11 (M+H, $^{79/81}$Br).

e) 3-Bromo-1-(2-ethyl-butyl)-5-hydroxy-2-oxo-1,2-dihydro-[1,7]naphthyridine-6-carboxylic acid methyl ester 5-Bromo-1-(2-ethyl-butyl)-2-{[methoxycarbonylmethyl-(toluene-4-sulfonyl)-amino]-methyl}-6-oxo-1,6-dihydro-pyridine-3-carboxylic acid methyl ester (4.89 g, 8.6 mmol) was dissolved in 170 mL of MeOH and placed in ice bath. NaOMe solution (6 mL, 25.7 mmol, 4.375 M in MeOH) was added and the mixture was stirred for 16 h at r.t. 1 M HCl was added to acidify the mixture, followed by addition of brine, and the resulting suspension was extracted with CH$_2$Cl$_2$. The organic layer was dried over MgSO$_4$ and concentrated. The crude product was purified by silica gel chromatography (0-5% EtOAc/CH$_2$Cl$_2$) to give 3.1 g of the title compound as an off-white solid. MS: (+) m/z 383.23, 385.18 (M+1, $^{79/81}$Br).

f) 1-(2-Ethyl-butyl)-5-hydroxy-2-oxo-3-phenyl-1,2-dihydro-[1,7]naphthyridine-6-carboxylic acid methyl ester A mixture of 3-bromo-1-(2-ethyl-butyl)-5-hydroxy-2-oxo-1,2-dihydro-[1,7]naphthyridine-6-carboxylic acid methyl ester (500 mg, 1.3 mmol), PhSnBu$_3$ (0.51 mL, 1.6 mmol), and PdCl$_2$(PPh$_3$)$_2$ (183 mg, 0.26 mmol) in DMF (25 mL) was heated at 120° C. under nitrogen atmosphere for 3 h. After the mixture was cooled to r.t., brine and EtOAc were added. 1 M HCl was added until pH was about 3. The aqueous layer was extracted with additional EtOAc and the organic layers were combined, washed with water and brine, and dried over MgSO$_4$. After evaporating the solvent in vacuo, the crude product was chromatographed (3-35% EtOAc/hexanes+1% AcOH) to give 280 mg of the title compound as a yellow solid. MS: (+) m/z 381.34 (M+1).

g) 3-{[1-(2-Ethyl-butyl)-5-hydroxy-2-oxo-3-phenyl-1,2-dihydro-[1,7]naphthyridine-6-carbonyl]-amino}-propionic acid A mixture of 1-(2-ethyl-butyl)-5-hydroxy-2-oxo-3-phenyl-1,2-dihydro-[1,7]naphthyridine-6-carboxylic acid methyl ester (35 mg, 0.092 mmol), β-alanine (492 mg, 5.5 mmol) and NaOMe solution (8.3 mL, 4.1 mmol, 0.5 M in MeOH) was refluxed for 16 h. After the mixture was cooled to r.t., the solvent was evaporated in vacuo. The residue was partitioned between EtOAc and water. 1 M HCl was added with vigorous stirring until pH was about 2. The aqueous layer was extracted with additional EtOAc, and the organic layers were combined, dried over $MgSO_4$ and concentrated. The residue was purified by silica gel chromatography (5-40% EtOAc/hexanes+1% AcOH). The product isolated was dissolved in saturated $NaHCO_3$ and washed several times with ether. The aqueous layer was acidified to pH about 3, and the resulting precipitate was isolated by filtration to give 8 mg of the title compound as a yellow solid. MS: (+) m/z 438.33 (M+1).

Example 222

4-{[1-(2-Ethyl-butyl)-5-hydroxy-2-oxo-3-phenyl-1,2-dihydro-[1,7]naphthyridine-6-carbonyl]-amino}-butyric acid A mixture of 1-(2-ethyl-butyl)-5-hydroxy-2-oxo-3-phenyl-1,2-dihydro-[1,7]naphthyridine-6-carboxylic acid methyl ester (45 mg, 0.12 mmol), 4-aminobutyric acid (732 mg, 7.1 mmol) and NaOMe solution (10.7 mL, 5.3 mmol, 0.5 M in MeOH) was refluxed for 16 h. After the mixture was cooled to r.t., the solvent was evaporated in vacuo. The residue was partitioned between EtOAc and water. 1 M HCl was added until pH was about 2. The aqueous layer was extracted with additional EtOAc, and the organic layers were combined, dried over $MgSO_4$ and concentrated. The residue was purified by silica gel chromatography (5-40% EtOAc/hexanes+1% AcOH). The product isolated was dissolved in saturated $NaHCO_3$ and washed several times with ether. The aqueous layer was acidified to pH about 3, and the resulting precipitate was isolated by filtration to give 19 mg of the title compound as a yellow solid. MS: (+) m/z 452.32 (M+1).

Example 223

3-{[1-(2-Ethyl-butyl)-5-hydroxy-2-oxo-3-phenyl-8-pyridin-3-yl-1,2-dihydro-[1,7]naphthyridine-6-carbonyl]amino}-propionic acid a) 8-Bromo-1-(2-ethyl-butyl)-5-hydroxy-2-oxo-3-phenyl-1,2-dihydro-[1,7]naphthyridine-6-carboxylic acid methyl ester A mixture of 1-(2-ethyl-butyl)-5-hydroxy-2-oxo-3-phenyl-1,2-dihydro-[1,7]naphthyridine-6-carboxylic acid methyl ester (200 mg, 0.53 mmol) and N-bromosuccinimide (103 mg, 0.58 mmol) in $CH_2Cl_2$ (2 mL) was refluxed for 3 h. Solvent was evaporated in vacuo, and the residue was purified by silica gel chromatography (3-15% EtOAc/hexanes+1% AcOH) to give 156 mg of the title compound as a yellow solid. MS: (+) m/z 459.31, 461.13 (M+1, $^{79/81}$Br).

b) 1-(2-Ethyl-butyl)-5-hydroxy-2-oxo-3-phenyl-8-pyridin-3-yl-1,2-dihydro-[1,7]naphthyridine-6-carboxylic acid methyl ester A mixture of 8-bromo-1-(2-ethyl-butyl)-5-hydroxy-2-oxo-3-phenyl-1,2-dihydro-[1,7]naphthyridine-6-carboxylic acid methyl ester (64 mg, 0.139 mmol), 3-tributylstannanyl-pyridine (0.070 mL, 0.209 mmol) and $PdCl_2(PPh_3)_2$ (20 mg, 0.028 mmol) in 3 mL of DMF was heated at 120° C. for 2.5 h under nitrogen atmosphere. After the mixture was cooled to r.t., EtOAc and brine were added. 1 M HCl was added until pH was about 3-4. The aqueous layer was extracted with additional EtOAc, and the combined organic layer was washed with water and dried over $MgSO_4$. After evaporating the solvent in vacuo, the crude product was purified by silica gel chromatography (5-90% EtOAc/hexanes+1% AcOH) to give 30 mg of the title compound. MS: (+) m/z 458.49 (M+1).

c) 3-{[1-(2-Ethyl-butyl)-5-hydroxy-2-oxo-3-phenyl-8-pyridin-3-yl-1,2-dihydro-[1,7]naphthyridine-6-carbonyl]-amino}-propionic acid A mixture of 1-(2-ethyl-butyl)-5-hydroxy-2-oxo-3-phenyl-8-pyridin-3-yl-1,2-dihydro-[1,7]naphthyridine-6-carboxylic acid methyl ester (30 mg, 0.066 mmol), β-alanine (585 mg, 6.6 mmol) and NaOMe solution (10 mL, 4.9 mmol, 0.5 M in MeOH) was refluxed for 16 h. After the mixture was cooled to r.t., the solvent was evaporated in vacuo. The residue was partitioned between EtOAc and water. 1 M HCl was added until pH was about 3-4. The aqueous layer was extracted with additional EtOAc, and the organic layers were combined, dried over $MgSO_4$ and concentrated. The residue was purified by silica gel chromatography (5-90% EtOAc/hexanes+1% AcOH). The product isolated was dissolved in saturated $NaHCO_3$ and washed several times with ether. The aqueous layer was acidified to pH about 3, and the resulting precipitate was isolated by filtration to give 13 mg of the title compound as an off-white solid. MS: (+) m/z 515.36 (M+1).

Example 224

3-{[1-(2-Ethyl-butyl)-5-hydroxy-2-oxo-3-phenyl-8-pyridin-4-yl-1,2-dihydro-[1,7]naphthyridine-6-carbonyl]amino}-propionic acid a) 1-(2-Ethyl-butyl)-5-hydroxy-2-oxo-3-phenyl-8-pyridin-4-yl-1,2-dihydro-[1,7]naphthyridine-6-carboxylic acid methyl ester A mixture of 8-bromo-1-(2-ethyl-butyl)-5-hydroxy-2-oxo-3-phenyl-1,2-dihydro-[1,7]naphthyridine-6-carboxylic acid methyl ester (89 mg, 0.19 mmol), 4-tributylstannanyl-pyridine (107 mg, 0.29 mmol) and $PdCl_2(PPh_3)_2$ (27 mg, 0.039 mmol) in 4 mL of DMF was heated at 120° C. for 2.5 h under nitrogen atmosphere. After the mixture was cooled to r.t., EtOAc and brine were added. 1 M HCl was added until pH was about 3-4. The aqueous layer was extracted with additional EtOAc, and the combined organic layer was washed with water and dried over $MgSO_4$. After evaporating the solvent in vacuo, the crude product was purified by silica gel chromatography (5-90% EtOAc/hexanes+1% AcOH) to give 30 mg of the title compound. MS: (+) m/z 458.43 (M+1).

b) 3-{[1-(2-Ethyl-butyl)-5-hydroxy-2-oxo-3-phenyl-8-pyridin-4-yl-1,2-dihydro-[1,7]naphthyridine-6-carbonyl]-amino}-propionic acid A mixture of 1-(2-ethyl-butyl)-5-hydroxy-2-oxo-3-phenyl-8-pyridin-4-yl-1,2-dihydro-[1,7]naphthyridine-6-carboxylic acid methyl ester (30 mg, 0.066 mmol), β-alanine (585 mg, 6.6 mmol) and NaOMe solution (10 mL, 4.9 mmol, 0.5 M in MeOH) was refluxed for 16 h. After the mixture was cooled to r.t., the solvent was evaporated in vacuo. The residue was partitioned between EtOAc and water. 1 M HCl was added until pH was about 3-4. The aqueous layer was extracted with additional EtOAc, and the organic layers were combined, dried over $MgSO_4$ and concentrated. The residue was purified by silica gel chromatography (5-90% EtOAc/hexanes+1% AcOH). The product isolated was dissolved in saturated NaHCO$_3$ and washed several times with ether. The aqueous layer was acidified to pH about 3, and the resulting precipitate was isolated by filtration to give 14 mg of the title compound as an off-white solid. MS: (+) m/z 515.36 (M+1).

Example 225

3-{[(1-Benzyl-5-hydroxy-2-oxo-3-phenyl-1,2-dihydro-[1,7]naphthyridine-6-carbonyl)-amino]-methyl}-benzoic acid A mixture of 1-benzyl-5-hydroxy-2-oxo-3-phenyl-1,2-dihydro-[1,7]naphthyridine-6-carboxylic acid methyl ester (63 mg, 0.16 mmol), 3-aminomethyl-benzoic acid HCl salt (306 mg, 1.6 mmol) and NaOMe (167 mg, 3.1 mmol) in EtOH (6 mL) was heated at 150° C. in a microwave reactor for 6 h. The solvent was evaporated, and the residue was partitioned between EtOAc and water. 1 M HCl was added until pH was about 2. The organic layer was dried over MgSO$_4$ and concentrated. The residue was dissolved in a 1:1 mixture of THF and MeOH (6 mL). 2 M NaOH (3 mL) was added, and the mixture was stirred at r.t. for 16 h. The mixture was concentrated to approximately one-third of its original volume, and 1 M HCl was added until pH was about 2. The resulting mixture was extracted with EtOAc. The organic layer was dried over MgSO$_4$ and concentrated. The crude product was purified by silica gel chromatography (5-50% EtOAc/hexanes+1% AcOH). The product isolated was dissolved in saturated NaHCO$_3$ and washed several times with ether. The aqueous layer was acidified to pH about 2, and the resulting precipitate was isolated by filtration to give 14 mg of the title compound as a yellow solid. MS: (+) m/z 506.29 (M+1).

Example 226

{1-[(1-Benzyl-5-hydroxy-2-oxo-3-phenyl-8-pyridin-3-yl-1,2-dihydro-[1,7]naphthyridine-6-carbonyl)-amino]-cyclopropyl}-acetic acid a) {1-[(1-Benzyl-5-hydroxy-2-oxo-3-phenyl-8-pyridin-3-yl-1,2-dihydro-[1,7]naphthyridine-6-carbonyl)-amino]-cyclopropyl}-acetic acid methyl ester A mixture of 1-benzyl-5-hydroxy-2-oxo-3-phenyl-8-pyridin-3-yl-1,2-dihydro-[1,7]naphthyridine-6-carboxylic acid methyl ester (80 mg, 0.17 mmol), 2 M NaOH (3 mL), MeOH (3 mL) and THF (3 mL) was stirred at r.t. for 16 h, then concentrated to approximately one-third of its original volume. 1 M HCl was added until pH was about 3-4, and the resulting suspension was extracted with EtOAc. The organic layer was dried over MgSO$_4$ and concentrated to give 68 mg of 1-benzyl-5-hydroxy-2-oxo-3-phenyl-8-pyridin-3-yl-1,2-dihydro-[1,7]naphthyridine-6-carboxylic acid as a yellow solid, which was immediately used in the next step without purification.

A mixture of 1-benzyl-5-hydroxy-2-oxo-3-phenyl-8-pyridin-3-yl-1,2-dihydro-[1,7]naphthyridine-6-carboxylic acid (68 mg, 0.15 mmol) and HOBt (33 mg, 0.24 mmol) was dissolved in CH$_2$Cl$_2$ (3 mL). EDC (52 mg, 0.27 mmol) was added, and the resulting mixture was stirred for 10 min. (1-Amino-cyclopropyl)-acetic acid methyl ester HCl salt (40 mg, 0.24 mmol) and Hunig's base (0.1 mL, 0.55 mmol) were added, and the mixture was stirred for 16 h. The mixture was diluted with EtOAc and washed with 0.1 M HCl. The organic layer was dried over MgSO$_4$ and concentrated. The crude product was purified by silica gel chromatography (5-90% EtOAc/hexanes+1% AcOH) to give 5 mg of the title compound as a yellow solid. MS: (+) m/z 561.34 (M+1).

b) {1-[(1-Benzyl-5-hydroxy-2-oxo-3-phenyl-8-pyridin-3-yl-1,2-dihydro-[1,7]naphthyridine-6-carbonyl)-amino]cyclopropyl}-acetic acid A mixture of {1-[(1-benzyl-5-hydroxy-2-oxo-3-phenyl-8-pyridin-3-yl-1,2-dihydro-[1,7]naphthyridine-6-carbonyl)-amino]-cyclopropyl}-acetic acid methyl ester (5 mg, 0.0089 mmol), 2 M NaOH (3 mL), MeOH (3 mL) and THF (3 mL) was stirred at r.t. for 2 days, then concentrated to approximately one-third of its original volume. 1 M HCl was added until pH was about 3, and the resulting suspension was extracted with EtOAc. The organic layer was dried over MgSO$_4$ and concentrated. The crude product was purified by silica gel chromatography (5-90% EtOAc/hexanes+1% AcOH). The product isolated was dissolved in saturated NaHCO$_3$ and washed several times with ether. The aqueous layer was acidified to pH about 3, and the resulting suspension was extracted with CH$_2$Cl$_2$. The organic layer was dried over MgSO$_4$ and concentrated to give 2.3 mg of the title compound as a yellow solid. MS: (+) m/z 547.35 (M+1).

Example 227

Production of Endogenous Erythropoietin In Vitro

The disclosure provides methods for producing endogenous erythropoietin using in vitro cell culture technologies. In particular embodiments, cells derived from animal tissues, preferably human tissues, capable of expressing erythropoietin when stimulated by compounds of the disclosure are cultured for the in vitro production of endogenous proteins. Cells contemplated for use in such methods include, but are not limited to, cells derived from hepatic, hematopoietic, renal, and neural tissues.

Cell culture techniques are generally available in the art and include any method that maintains cell viability and facilitates expression of endogenous proteins. Cells are typically cultured in a growth medium optimized for cell growth, viability, and protein production. Cells may be in suspension or attached to a substrate, and medium may be supplied in batch feed or continuous flow-through regimens. Compounds of the disclosure are added to the culture medium at levels that stimulate erythropoietin production without compromising cell viability. Erythropoietin produced by the cells is secreted into the culture medium. The medium is then collected and the erythopoietin is purified using methods known to those of skill in the art. (See, e.g., Lai et al. (1987) U.S. Pat. No. 4,667,016; and Egrie (1985) U.S. Pat. No. 4,558,006.)

In a particular embodiment, human cells derived from hepatocarcinoma (Hep3B) tissue (see, e.g., American Type Culture Collection, Manassas Va.) are seeded into 35 mm culture dishes and grown at 37° C., 20% O$_2$, 5% CO$_2$ in Minimal Essential Medium (MEM), Earle's balanced salt solution (Mediatech Inc., Herndon Va.), 2 mM L-glutamine, 0.1 mM non-essential amino acids, 1 mM sodium pyruvate, and 10% FBS. When cell layers reach confluence, the media is replaced with OPTI-MEM media (Invitrogen Life Technologies, Carlsbad Calif.) and cell layers are incubated for approximately 24 hours in 20% O$_2$, 5% CO$_2$ at 37° C. A compound of the disclosure or 1% DMSO (negative control) is then added to existing media and incubation is continued overnight.

Following incubation, the conditioned media is collected from cell cultures and analyzed for erythropoietin expression using a QUANTIKINE immunoassay (R&D Systems, Inc., Minneapolis Minn.) according to the manufacturer's instructions. Thus, compounds of the disclosure can be rapidly tested for increased erythropoietin expression in vitro in cells derived from tissues that normally produce erythropoietin in animals.

What is claimed is:

1. A method of treating, anemia, the method comprising administering to a patient in need thereof a therapeutically effective amount of a compound represented by Formula Ia:

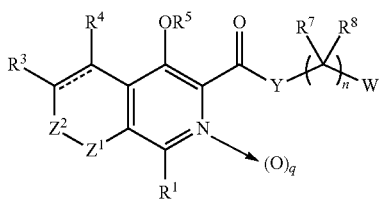

wherein
q is 0 or 1;
$R^1$ is selected from the group consisting of hydrogen, cyano, halo, hydroxy, alkoxy, amino, acyloxy, aminoacyl, alkyl, cycloalkyl, cycloalkoxy, aryl, aryloxy, heterocycloalkyl, heteroaryloxy, and heteroaryl;
one of $Z^1$ or $Z^2$ is —$NR^2$— and the other of $Z^1$ or $Z^2$ is —C(O)—;
$R^2$ is selected from the group consisting of hydrogen, alkyl, cycloalkyl, aryl, heterocycloalkyl, and heteroaryl;
$R^3$ and $R^4$ are each independently selected from the group consisting of hydrogen, alkyl, alkoxy, amino, acyloxy, aminoacyl, cycloalkyl, cycloalkoxy, aryl, aryloxy, heterocycloalkyl, heteroaryloxy, and heteroaryl;
— is a single or a double bond;
Y is —$NR^6$— or —O—;
n is 1, 2, 3, 4, 5, or 6;
$R^5$ is selected from the group consisting of hydrogen, acyl, sulfonyl, aminoacyl, oxycarbonyl, alkyl, cycloalkyl, aryl, heterocycloalkyl, and heteroaryl;
$R^6$ is selected from the group consisting of hydrogen, alkyl, cycloalkyl, aryl, heterocycloalkyl, and heteroaryl;
$R^7$ and $R^8$ are each independently selected from the group consisting of hydrogen, alkyl, cycloalkyl, aryl, heterocycloalkyl, and heteroaryl; or $R^7$ and $R^8$ together with the carbon atom to which they are attached form a cycloalkyl, or heterocycloalkyl;
W is selected from the group consisting of $R^9$, —C(O)$OR^9$, —C(O)$NR^6R^9$, —$NR^6C(O)R^9$, —$NR^6C(O)OR^9$, —$NR^6C(O)NR^6R^9$, —$NR^6S(O)_2R^9$, —$S(O)_2NR^6R^9$, —$NR^6R^9$ and —$OR^9$; and
$R^9$ is selected from the group consisting of hydrogen, alkyl, cycloalkyl, aryl, heterocycloalkyl, and heteroaryl; and
further wherein each alkyl, alkoxy, amino, acyloxy, aminoacyl, cycloalkyl, cycloalkoxy, aryl, aryloxy, heterocycloalkyl, heteroaryloxy, and heteroaryl described above for $R^1$, $R^2$, $R^3$, $R^4$, $R^6$, $R^7$, $R^8$ and $R^9$ can be optionally substituted with from 1 to 3 $R^{10}$,
wherein each $R^{10}$ is independently selected from the group consisting of alkyl, alkoxy, haloalkyl, haloalkoxy, acyl, acylamino, acyloxy, amino, aminoacyl, aminocarbonylamino, aminothiocarbonylamino, aminocarbonyloxy, aryl, aryloxy, aryloxyaryl, cyano, halogen, hydroxyl, nitro, oxo, thioxo, carboxyl, carboxyl ester, cycloalkyl, thio, alkylthio, arylthio, cycloalkylthio, heteroarylthio, heterocyclicthio, sulfonyl, heteroaryl, heterocyclic, cycloalkoxy, heteroaryloxy, heterocyclyloxy, oxycarbonylamino, oxythiocarbonylamino, —$OS(O)_2$-alkyl, —$OS(O)_2$-aryl, —$OS(O)_2$-heteroaryl, —$OS(O)_2$-heterocyclic, —$OSO_2$—$NR^{40}R^{40}$, —$NR^{40}S(O)_2$—$NR^{40}$-alkyl, —$NR^{40}S(O)_2$—$NR^{40}$-aryl, —$NR^{40}S(O)_2$—$NR^{40}$-heteroaryl, and —$NR^{40}S(O)_2$—$NR^{40}$-heterocyclic, where each $R^{40}$ is independently hydrogen or alkyl; and further wherein each alkyl, alkoxy, aryl, aryloxy, aryloxyaryl, cycloalkyl, alkylthio, arylthio, cycloalkylthio, heteroarylthio, heterocyclicthio, heteroaryl, heterocyclic, cycloalkoxy, heteroaryloxy, or heterocyclyloxy may be additionally substituted with from 1-3 substituents independently alkyl, alkoxy, haloalkyl, haloalkoxy, or halogen;
or a pharmaceutically acceptable salt, single stereoisomer, mixture of stereoisomers, ester, tautomer or prodrug thereof.

2. The method of claim 1, wherein the compound is represented by Formula IIa:

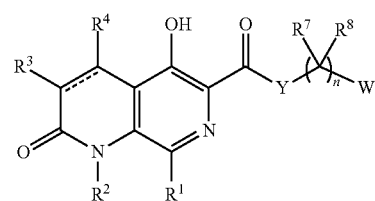

wherein
$R^1$ is selected from the group consisting of hydrogen, cyano, halo, hydroxy, alkoxy, amino, acyloxy, aminoacyl, alkyl, cycloalkyl, cycloalkoxy, aryl, aryloxy, heterocycloalkyl, heteroaryloxy, and heteroaryl;
$R^2$ is selected from the group consisting of hydrogen, alkyl, cycloalkyl, aryl, heterocycloalkyl, and heteroaryl;
— is a single or a double bond;
$R^3$ and $R^4$ are each independently selected from the group consisting of hydrogen, alkyl, alkoxy, amino, acyloxy, aminoacyl, cycloalkyl, cycloalkoxy, aryl, aryloxy, heterocycloalkyl, heteroaryloxy, and heteroaryl;
Y is —$NR^6$— or —O—;
n is 1, 2, 3, 4, 5, or 6;
$R^6$ is selected from the group consisting of hydrogen, alkyl, cycloalkyl, aryl, heterocycloalkyl, and heteroaryl;
$R^7$ and $R^8$ are each independently selected from the group consisting of hydrogen, alkyl, cycloalkyl, aryl, heterocycloalkyl, and heteroaryl; or $R^7$ and $R^8$ together with the carbon atom to which they are attached form a cycloalkyl, or heterocycloalkyl;
W is selected from the group consisting of $R^9$, —C(O)$OR^9$, —C(O)$NR^6R^9$, —$NR^6C(O)R^9$, —$NR^6C(O)OR^9$, —$NR^6C(O)NR^6R^9$, —$NR^6S(O)_2R^9$, —$S(O)_2NR^6R^9$, —$NR^6R^9$ and —$OR^9$; and
$R^9$ is selected from the group consisting of hydrogen, alkyl, cycloalkyl, aryl, heterocycloalkyl, and heteroaryl;
further wherein each alkyl, alkoxy, amino, acyloxy, aminoacyl, cycloalkyl, cycloalkoxy, aryl, aryloxy, heterocycloalkyl, heteroaryloxy, and heteroaryl described above for $R^1$, $R^2$, $R^3$, $R^4$, $R^6$, $R^7$, $R^8$ and $R^9$ can be optionally substituted with from 1 to 3 $R^{10}$, wherein each $R^{10}$ is independently selected from the group consisting of alkyl, alkoxy, haloalkyl, haloalkoxy, acyl, acylamino, acyloxy, amino, aminoacyl, aminocarbonylamino, aminothiocarbonylamino, aminocarbonyloxy, aryl, aryloxy, aryloxyaryl, cyano, halogen, hydroxyl, nitro, oxo, thioxo, carboxyl, carboxyl ester, cycloalkyl, thio, alkylthio, arylthio, cycloalkylthio, heteroarylthio, heterocyclicthio, sulfonyl, heteroaryl, heterocyclic, cycloalkoxy, heteroaryloxy, heterocyclyloxy, oxycarbonylamino, oxythiocarbonylamino, —OS(O)$_2$-alkyl, —OS(O)$_2$-aryl, —OS(O)$_2$-heteroaryl, —OS(O)$_2$-heterocyclic, —OSO$_2$—NR$^{40}$R$^{40}$, —NR$^{40}$S(O)$_2$—NR$^{40}$-alkyl, —NR$^{40}$S(O)$_2$—NR$^{40}$-aryl, —NR$^{40}$S(O)$_2$—NR$^{40}$-heteroaryl, and —NR$^{40}$S(O)$_2$—NR-heterocyclic, where each $R^{40}$ is independently hydrogen or alkyl; and further wherein each alkyl, alkoxy, aryl, aryloxy, aryloxyaryl, cycloalkyl, alkylthio, arylthio, cycloalkylthio, heteroarylthio, heterocyclicthio, heteroaryl, heterocyclic, cycloalkoxy, heteroaryloxy, or heterocyclyloxy may be additionally substituted with from 1-3 substituents independently alkyl, alkoxy, haloalkyl, haloalkoxy, or halogen;

or a pharmaceutically acceptable salt, single stereoisomer, mixture of stereoisomers, ester, tautomer or prodrug thereof.

3. The method of claim 1, wherein the compound is represented by Formula IIb:

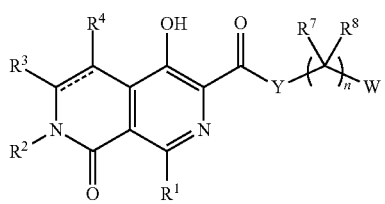

IIb wherein
- $R^1$ is selected from the group consisting of hydrogen, cyano, halo, hydroxy, alkoxy, amino, acyloxy, aminoacyl, alkyl, cycloalkyl, cycloalkoxy, aryl, aryloxy, heterocycloalkyl, heteroaryloxy, and heteroaryl;
- $R^2$ is selected from the group consisting of hydrogen, alkyl, cycloalkyl, aryl, heterocycloalkyl, and heteroaryl;
- — is a single or a double bond;
- $R^3$ and $R^4$ are each independently selected from the group consisting of hydrogen, alkyl, alkoxy, amino, acyloxy, aminoacyl, cycloalkyl, cycloalkoxy, aryl, aryloxy, heterocycloalkyl, heteroaryloxy, and heteroaryl;
- Y is —NR$^6$— or —O—;
- n is 1, 2, 3, 4, 5, or 6;
- $R^6$ is selected from the group consisting of hydrogen, alkyl, cycloalkyl, aryl, heterocycloalkyl, and heteroaryl;
- $R^7$ and $R^8$ are each independently selected from the group consisting of hydrogen, alkyl, cycloalkyl, aryl, heterocycloalkyl, and heteroaryl; or $R^7$ and $R^8$ together with the carbon atom to which they are attached form a cycloalkyl, or heterocycloalkyl;
- W is selected from the group consisting of $R^9$, —C(O)OR$^9$, —C(O)NR$^6$R$^9$, —NR$^6$C(O)R$^9$, —NR$^6$C(O)OR$^9$, —NR$^6$C(O)NR$^6$R$^9$, —NR$^6$S(O)$_2$R$^9$, —S(O)$_2$NR$^6$R$^9$, —NR$^6$R$^9$ and —OR$^9$; and
- $R^9$ is selected from the group consisting of hydrogen, alkyl, cycloalkyl, aryl, heterocycloalkyl, and heteroaryl;

further wherein each alkyl, alkoxy, amino, acyloxy, aminoacyl, cycloalkyl, cycloalkoxy, aryl, aryloxy, heterocycloalkyl, heteroaryloxy, and heteroaryl described above for $R^1$, $R^2$, $R^3$, $R^4$, $R^6$, $R^7$, $R^8$ and $R^9$ can be optionally substituted with from 1 to 3 $R^{10}$, wherein each $R^{10}$ is independently selected from the group consisting of alkyl, alkoxy, haloalkyl, haloalkoxy, acyl, acylamino, acyloxy, amino, aminoacyl, aminocarbonylamino, aminothiocarbonylamino, aminocarbonyloxy, aryl, aryloxy, aryloxyaryl, cyano, halogen, hydroxyl, nitro, oxo, thioxo, carboxyl, carboxyl ester, cycloalkyl, thio, alkylthio, arylthio, cycloalkylthio, heteroarylthio, heterocyclicthio, sulfonyl, heteroaryl, heterocyclic, cycloalkoxy, heteroaryloxy, heterocyclyloxy, oxycarbonylamino, oxythiocarbonylamino, —OS(O)$_2$-alkyl, —OS(O)$_2$-aryl, —OS(O)$_2$-heteroaryl, —OS(O)$_2$-heterocyclic, —OSO$_2$—NR$^{40}$R$^{40}$, —NR$^{40}$S(O)$_{2-NR}{}^{40}$-alkyl, —NR$^{40}$S(O)$_2$—NR$^{40}$-aryl, —NR$^{40}$S(O)$_2$—NR$^{40}$-heteroaryl, and —NR$^{40}$S(O)$_{2-NR}{}^{40}$-heterocyclic, where each $R^{40}$ is independently hydrogen or alkyl; and further wherein each alkyl, alkoxy, aryl, aryloxy, aryloxyaryl, cycloalkyl, alkylthio, arylthio, cycloalkylthio, heteroarylthio, heterocyclicthio, heteroaryl, heterocyclic, cycloalkoxy, heteroaryloxy, or heterocyclyloxy may be additionally substituted with from 1-3 substituents independently alkyl, alkoxy, haloalkyl, haloalkoxy, or halogen;

or a pharmaceutically acceptable salt, single stereoisomer, mixture of stereoisomers, ester, tautomer or prodrug thereof.

4. The method of claim 1, wherein

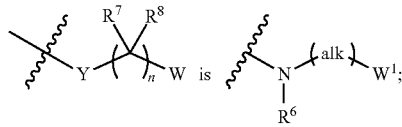

alk is optionally substituted $C_1$-$C_6$ alkylene;
$W^1$ is —C(O)OR$^9$, —NR$^6$C(O)R$^9$, —NR$^6$C(O)NR$^6$R$^9$, or —NR$^6$S(O)$_2$R$^9$; and
each $R^6$ is independently hydrogen or alkyl.

5. The method of claim 1, wherein

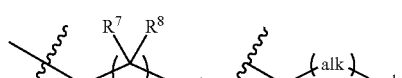

alk is optionally substituted $C_1$-$C_6$ alkylene;
$W^1$ is $R^9$; and
$R^6$ is hydrogen or alkyl.

6. The method of claim 1, wherein q is 0.

7. The method of claim 1, wherein $R^1$ is selected from the group consisting of hydrogen, cyano, optionally substituted alkyl, optionally substituted aryl, and optionally substituted heteroaryl.

8. The method of claim 1, wherein $Z^1$ is —NR$^2$—, and $Z^2$ is —C(O)—.

9. The method of claim 1, wherein $Z^1$ is, —C(O)—, and $Z^2$ is —NR$^2$—.

10. The method of claim 1, wherein $R^2$ is selected from the group consisting of hydrogen, and optionally substituted alkyl.

11. The method of claim 1, wherein --- is a single bond.

12. The method of claim 1, wherein --- is a double bond.

13. The method of claim 1, wherein $R^3$ and $R^4$ are each independently selected from the group consisting of hydrogen, optionally substituted alkyl, optionally substituted cycloalkyl, optionally substituted aryl, optionally substituted heterocycloalkyl, and optionally substituted heteroaryl.

14. The method of claim 1, wherein Y is —$NR^6$—, and $R^6$ is hydrogen or optionally substituted alkyl.

15. The method of claim 1, wherein Y is —O—.

16. The method of claim 1, wherein $R^5$ and $R^6$ are each independently selected from the group consisting of hydrogen, and optionally substituted alkyl.

17. The method of claim 1, wherein $R^7$ and $R^8$ are each independently selected from the group consisting of hydrogen, and optionally substituted alkyl; or $R^7$ and $R^8$ together with the carbon atom to which they are attached form an optionally substituted cycloalkyl.

18. The method of claim 1, wherein W is $R^9$ or —C(O)$OR^9$.

19. The method of claim 1, wherein $R^9$ is hydrogen.

20. The method of claim 1, wherein
q is 0;
$R^1$ is selected from the group consisting of hydrogen, cyano, optionally substituted alkyl, optionally substituted aryl, and optionally substituted heteroaryl;
$R^3$ and $R^4$ are each independently selected from the group consisting of hydrogen, optionally substituted alkyl, optionally substituted cycloalkyl, optionally substituted aryl, optionally substituted heterocycloalkyl, and optionally substituted heteroaryl;
$R^5$ is selected from the group consisting of hydrogen, and optionally substituted alkyl; and
$R^6$, when present, is selected from the group consisting of hydrogen, and optionally substituted alkyl.

21. The method of claim 1, wherein
q is 0;
$R^1$ is selected from the group consisting of hydrogen, cyano, optionally substituted alkyl, optionally substituted aryl, and optionally substituted heteroaryl;
$R^2$ is substituted alkyl;
$R^3$ and $R^4$ are each independently selected from the group consisting of hydrogen, optionally substituted alkyl, optionally substituted cycloalkyl, optionally substituted aryl, optionally substituted heterocycloalkyl, and optionally substituted heteroaryl;
Y is —O— or —$NR^6$—; and
$R^5$ and $R^6$ are hydrogen.

22. The method of claim 1, wherein
q is 0;
$R^1$ is selected from the group consisting of hydrogen, cyano, optionally substituted alkyl, optionally substituted aryl, and optionally substituted heteroaryl;
$R^2$ is substituted alkyl;
$R^3$ and $R^4$ are each independently selected from the group consisting of hydrogen, optionally substituted alkyl, optionally substituted cycloalkyl, optionally substituted aryl, optionally substituted heterocycloalkyl, and optionally substituted heteroaryl;
Y is —O— or —$NR^6$—;
$R^5$ and $R^6$ are hydrogen;
$R^7$ and $R^8$ are each independently selected from the group consisting of hydrogen, and optionally substituted alkyl; or $R^7$ and $R^8$ together with the carbon atom to which they are attached form an optionally substituted cycloalkyl; and
W is $R^9$ or —C(O)$OR^9$.

23. The method of claim 1, wherein
q is 0;
$R^1$ is selected from the group consisting of hydrogen, cyano, optionally substituted alkyl, optionally substituted aryl, and optionally substituted heteroaryl;
$R^2$ is substituted alkyl;
$R^3$ and $R^4$ are each independently selected from the group consisting of hydrogen, optionally substituted alkyl, optionally substituted cycloalkyl, optionally substituted aryl, optionally substituted heterocycloalkyl, and optionally substituted heteroaryl;
Y is —O— or —$NR^6$—;
$R^5$ and $R^6$ are hydrogen;
$R^7$ and $R^8$ are each independently selected from the group consisting of hydrogen, optionally substituted alkyl; $R^7$ and $R^8$ together with the carbon atom to which they are attached form an optionally substituted cycloalkyl;
W is —C(O)$OR^9$; and
$R^9$ is hydrogen.

24. A method of treating, anemia, the method comprising administering to a patient in need thereof a therapeutically effective amount of a compound selected from the group consisting of [(1-benzyl-5-hydroxy-2-oxo-1,2,3,4-tetrahydro-[1,7]naphthyridine-6-carbonyl)-amino]-acetic acid; [(1-benzyl-5-hydroxy-3-methyl-2-oxo-1,2-dihydro-[1,7]naphthyridine-6-carbonyl)-amino]-acetic acid; [(1,3-dibenzyl-5-hydroxy-2-oxo-1,2-dihydro-[1,7]naphthyridine-6-carbonyl)-amino]-acetic acid; [(1-benzyl-5-hydroxy-2-oxo-3-phenyl-1,2-dihydro-[1,7]naphthyridine-6-carbonyl)-amino]-acetic acid; [(1-benzyl-5-hydroxy-3,8-dimethyl-2-oxo-1,2-dihydro-[1,7]naphthyridine-6-carbonyl)-amino]-acetic acid; [(1-benzyl-8-cyano-5-hydroxy-3-methyl-2-oxo-1,2-dihydro-[1,7]naphthyridine-6-carbonyl)-amino]-acetic acid; [(1-benzyl-5-hydroxy-2-oxo-1,2-dihydro-[1,7]naphthyridine-6-carbonyl)-amino]-acetic acid; [(1-benzyl-5-hydroxy-8-methyl-2-oxo-1,2,3,4-tetrahydro-[1,7]naphthyridine-6-carbonyl)-amino]-acetic acid; [(1-benzyl-8-cyano-5-hydroxy-2-oxo-1,2,3,4-tetrahydro-[1,7]naphthyridine-6-carbonyl)-amino]-acetic acid; [(1-benzyl-5-hydroxy-3-methyl-2-oxo-8-pyridin-3-yl-1,2-dihydro-[1,7]naphthyridine-6-carbonyl)-amino]-acetic acid; [(1-benzyl-5-hydroxy-2-oxo-3-phenethyl-1,2-dihydro-[1,7]naphthyridine-6-carbonyl)-amino]-acetic acid; [(1-benzyl-5-hydroxy-8-methyl-2-oxo-3-phenyl-1,2-dihydro-[1,7]naphthyridine-6-carbonyl)-amino]-acetic acid; [(1-benzyl-5-hydroxy-2-oxo-3,8-diphenyl-1,2-dihydro-[1,7]naphthyridine-6-carbonyl)-amino]-acetic acid; [(1-benzyl-8-cyano-5-hydroxy-2-oxo-3-phenyl-1,2-dihydro-[1,7]naphthyridine-6-carbonyl)-amino]-acetic acid; 3-[(1-benzyl-8-cyano-5-hydroxy-2-oxo-3-phenyl-1,2-dihydro-[1,7]naphthyridine-6-carbonyl)-amino]-propionic acid; [(1-benzyl-5-hydroxy-2-oxo-3-phenyl-8-pyridin-3-yl-1,2-dihydro-[1,7]naphthyridine-6-carbonyl)-amino]-acetic acid; [(1,3-dibenzyl-8-cyano-5-hydroxy-2-oxo-1,2-dihydro-[1,7]naphthyridine-6-carbonyl)-amino]-acetic acid; 3-[(1,3-dibenzyl-8-cyano-5-hydroxy-2-oxo-1,2-dihydro-[1,7]naphthyridine-6-carbonyl)-amino]-propionic acid; [(1,3-dibenzyl-5-hydroxy-8-methyl-2-oxo-1,2-dihydro-[1,7]naphthyridine-6-carbonyl)-amino]-acetic acid; 3-[(1,3-dibenzyl-5-hydroxy-8-methyl-2-oxo-1,2-dihydro-[1,7]naphthyridine-6-carbonyl)-amino]-propionic acid; [(1,3-dibenzyl-5-hydroxy-2-oxo-8-pyridin-3-yl-1,2-dihydro-[1,7]naphthyridine-6-carbonyl)-amino]-acetic acid; 3-[(1,3-dibenzyl-5-hydroxy-2-oxo-8-pyridin-3-yl-1,2-dihydro-[1,7]naphthyridine-6-carbonyl)-amino]-propionic acid; 4-[(1-benzyl-8-cyano-5-hydroxy-2-oxo-3-phenyl-1,2-dihydro-[1,7]naphthyridine-6-carbonyl)-amino]-butyric acid; 5-[(1- benzyl-8-cyano-5-hydroxy-2-oxo-3-phenyl-1,2-dihydro-[1,7]naphthyridine-6-carbonyl)-amino]-pentanoic acid; 3-[(1-benzyl-8-cyano-5-hydroxy-2-oxo-3-phenyl-1,2-dihydro-[1,7]naphthyridine-6-carbonyl)-amino]-2,2-dimethyl-propionic acid; [(7-benzyl-4-hydroxy-8-oxo-7,8-dihydro-[2,7]naphthyridine-3-carbonyl)-amino]-acetic acid; 3-[(7-benzyl-4-hydroxy-8-oxo-7,8-dihydro-[2,7]naphthyridine-3-carbonyl)-amino]-propionic acid; 3-[(7-benzyl-4-hydroxy-8-oxo-7,8-dihydro-[2,7]naphthyridine-3-carbonyl)-amino]-2,2-dimethyl-propionic acid; 4-[(7-benzyl-4-hydroxy-8-oxo-7,8-dihydro-[2,7]naphthyridine-3-carbonyl)-amino]-butyric acid; 5-[(7-benzyl-4-hydroxy-8-oxo-7,8-dihydro-[2,7]naphthyridine-3-carbonyl)-amino]-pentanoic acid; 7-benzyl-4-hydroxy-8-oxo-7,8-dihydro-[2,7]naphthyridine-3-carboxylic acid (pyridin-4-ylmethyl)-amide; 7-benzyl-4-hydroxy-8-oxo-7,8-dihydro-[2,7]naphthyridine-3-carboxylic acid methylamide; 7-benzyl-4-hydroxy-8-oxo-7,8-dihydro-[2,7]naphthyridine-3-carboxylic acid; 7-benzyl-4-hydroxy-8-oxo-7,8-dihydro-[2,7]naphthyridine-3-carboxylic acid dimethylamide; 7-benzyl-4-hydroxy-8-oxo-7,8-dihydro-[2,7]naphthyridine-3-carboxylic acid amide; 7-benzyl-4-hydroxy-8-oxo-7,8-dihydro-[2,7]naphthyridine-3-carboxylic acid propylamide; 7-benzyl-4-hydroxy-8-oxo-7,8-dihydro-[2,7]naphthyridine-3-carboxylic acid cyclopropylamide; 1-benzyl-8-cyano-5-hydroxy-2-oxo-3-phenyl-1,2-dihydro-[1,7]naphthyridine-6-carboxylic acid (pyridin-4-ylmethyl)-amide; (R)-2-[(1-benzyl-8-cyano-5-hydroxy-2-oxo-3-phenyl-1,2-dihydro-[1,7]naphthyridine-6-carbonyl)-amino]-3-phenyl-propionic acid; (S)-2-[(1-benzyl-8-cyano-5-hydroxy-2-oxo-3-phenyl-1,2-dihydro-[1,7]naphthyridine-6-carbonyl)-amino]-3-phenyl-propionic acid; [(7-benzyl-4-hydroxy-1-methyl-8-oxo-7,8-dihydro-[2,7]naphthyridine-3-carbonyl)-amino]-acetic acid; {7-benzyl-1-(5-fluoro-pyridin-3-yl)-4-hydroxy-8-oxo-7,8-dihydro-[2,7]naphthyridine-3-carbonyl]-amino}-acetic acid; [(7-benzyl-4-hydroxy-8-oxo-1-phenyl-7,8-dihydro-[2,7]naphthyridine-3-carbonyl)-amino]-acetic acid; [(7-benzyl-1-cyano-4-hydroxy-8-oxo-7,8-dihydro-[2,7]naphthyridine-3-carbonyl)-amino]-acetic acid; 7-benzyl-1-cyano-4-hydroxy-8-oxo-7,8-dihydro-[2,7]naphthyridine-3-carboxylic acid (pyridin-4-ylmethyl)-amide; 3-[(7-benzyl-1-cyano-4-hydroxy-8-oxo-7,8-dihydro-[2,7]naphthyridine-3-carbonyl)-amino]-propionic acid; 3-[(7-benzyl-1-cyano-4-hydroxy-8-oxo-7,8-dihydro-[2,7]naphthyridine-3-carbonyl)-amino]-2,2-dimethyl-propionic acid; (R)-2-[(7-benzyl-1-cyano-4-hydroxy-8-oxo-7,8-dihydro-[2,7]naphthyridine-3-carbonyl)-amino]-3-phenyl-propionic acid; 5-[(7-benzyl-1-cyano-4-hydroxy-8-oxo-7,8-dihydro-[2,7]naphthyridine-3-carbonyl)-amino]-pentanoic acid; (S)-2-[(7-benzyl-1-cyano-4-hydroxy-8-oxo-7,8-dihydro-[2,7]naphthyridine-3-carbonyl)-amino]-3-phenyl-propionic acid; (S)-2-[(7-benzyl-1-cyano-4-hydroxy-8-oxo-7,8-dihydro-[2,7]naphthyridine-3-carbonyl)-amino]-propionic acid; (R)-2-[(7-benzyl-1-cyano-4-hydroxy-8-oxo-7,8-dihydro-[2,7]naphthyridine-3-carbonyl)-amino]-propionic acid; 7-benzyl-1-cyano-4-hydroxy-8-oxo-7,8-dihydro-[2,7]naphthyridine-3-carboxylic acid (2-morpholin-4-yl-ethyl)-amide; 7-benzyl-1-cyano-4-hydroxy-8-oxo-7,8-dihydro-[2,7]naphthyridine-3-carboxylic acid (pyridazin-4-ylmethyl)-amide; {2-[(7-benzyl-1-cyano-4-hydroxy-8-oxo-7,8-dihydro-[2,7]naphthyridine-3-carbonyl)-amino]-ethoxy}-acetic acid; 1-{[(7-benzyl-1-cyano-4-hydroxy-8-oxo-7,8-dihydro-[2,7]naphthyridine-3-carbonyl)-amino]-methyl}-cyclobutanecarboxylic acid; 7-(2,4-dimethoxy-benzyl)-4-hydroxy-8-oxo-7,8-dihydro-[2,7]naphthyridine-3-carboxylic acid methylamide; {[7-(2,4-dimethoxy-benzyl)-4-hydroxy-8-oxo-7,8-dihydro-[2,7]naphthyridine-3-carbonyl]-amino}-acetic acid; 3-{[7-(2,4-dimethoxy-benzyl)-4-hydroxy-8-oxo-7,8-dihydro-[2,7]naphthyridine-3-carbonyl]-amino}-propionic acid; 7-(2,4-dimethoxy-benzyl)-4-hydroxy-8-oxo-5,6,7,8-tetrahydro-[2,7]naphthyridine-3-carboxylic acid methylamide; {[7-(2,4-dimethoxy-benzyl)-4-hydroxy-8-oxo-5,6,7,8-tetrahydro-[2,7]naphthyridine-3-carbonyl]-amino}-acetic acid; 3-{[7-(2,4-dimethoxy-benzyl)-4-hydroxy-8-oxo-5,6,7,8-tetrahydro-[2,7]naphthyridine-3-carbonyl]-amino}-propionic acid; 7-benzyl-1-cyano-4-hydroxy-8-oxo-7,8-dihydro-[2,7]naphthyridine-3-carboxylic acid (3-propylcarbamoyl-propyl)-amide; 3-[(4-hydroxy-8-oxo-7,8-dihydro-[2,7]naphthyridine-3-carbonyl)-amino]-propionic acid; 7-(2,4-dimethoxy-benzyl)-4-hydroxy-8-oxo-7,8-dihydro-[2,7]naphthyridine-3-carboxylic acid phenethyl-amide; 7-(2,4-dimethoxy-benzyl)-4-hydroxy-8-oxo-7,8-dihydro-[2,7]naphthyridine-3-carboxylic acid (2-methoxy-ethyl)-amide; 7-(2,4-dimethoxy-benzyl)-4-hydroxy-8-oxo-7,8-dihydro-[2,7]naphthyridine-3-carboxylic acid 4-fluoro-benzylamide; 1-benzyl-5-hydroxy-2-oxo-3-phenyl-1,2-dihydro-[1,7]naphthyridine-6-carboxylic acid methylamide; 3-[(1-benzyl-5-hydroxy-2-oxo-3-phenyl-1,2-dihydro-[1,7]naphthyridine-6-carbonyl)-amino]-propionic acid; {2-[(7-benzyl-4-hydroxy-8-oxo-7,8-dihydro-[2,7]naphthyridine-3-carbonyl)-amino]-ethoxy}-acetic acid; 7-benzyl-4-hydroxy-8-oxo-7,8-dihydro-[2,7]naphthyridine-3-carboxylic acid (1H-tetrazol-5-ylmethyl)-amide; 3-{[7-benzyl-1-(5-fluoro-pyridin-3-yl)-4-hydroxy-8-oxo-7,8-dihydro-[2,7]naphthyridine-3-carbonyl]-amino}-propionic acid; 3-{[7-benzyl-1-(5-fluoro-pyridin-3-yl)-4-hydroxy-8-oxo-7,8-dihydro-[2,7]naphthyridine-3-carbonyl]-amino}-2,2-dimethyl-propionic acid; 7-benzyl-4-hydroxy-8-oxo-7,8-dihydro-[2,7]naphthyridine-3-carboxylic acid [2-(3-isopropyl-ureido)-ethyl]-amide; 7-benzyl-4-hydroxy-8-oxo-7,8-dihydro-[2,7]naphthyridine-3-carboxylic acid (2-sulfamoyl-ethyl)-amide; 7-benzyl-4-hydroxy-8-oxo-7,8-dihydro-[2,7]naphthyridine-3-carboxylic acid [2-(2,2,2-trifluoro-acetylamino)-ethyl]-amide; 7-benzyl-4-hydroxy-8-oxo-7,8-dihydro-[2,7]naphthyridine-3-carboxylic acid (2-acetylamino-ethyl)-amide; 7-benzyl-4-hydroxy-8-oxo-7,8-dihydro-[2,7]naphthyridine-3-carboxylic acid {2-[methyl-(2,2,2-trifluoro-acetyl)-amino]-ethyl}-amide; 7-benzyl-4-hydroxy-8-oxo-7,8-dihydro-[2,7]naphthyridine-3-carboxylic acid [2-(3-isopropyl-1-methyl-ureido)-ethyl]-amide; {2-[(7-benzyl-4-hydroxy-8-oxo-7,8-dihydro-[2,7]naphthyridine-3-carbonyl)-amino]-ethyl}-methyl-carbamic acid methyl ester; 7-benzyl-4-hydroxy-8-oxo-7,8-dihydro-[2,7]naphthyridine-3-carboxylic acid [2-(methanesulfonyl-methyl-amino)-ethyl]-amide; 7-benzyl-4-hydroxy-8-oxo-7,8-dihydro-[2,7]naphthyridine-3-carboxylic acid (2-methanesulfonylamino-ethyl)-amide; 7-benzyl-4-hydroxy-8-oxo-7,8-dihydro-[2,7]naphthyridine-3-carboxylic acid [3-(2,2,2-trifluoro-acetylamino)-propyl]-amide; 7-benzyl-4-hydroxy-8-oxo-7,8-dihydro-[2,7]naphthyridine-3-carboxylic acid [3-(3-isopropyl-ureido)-propyl]-amide; 7-benzyl-4-hydroxy-8-oxo-7,8-dihydro-[2,7]naphthyridine-3-carboxylic acid (3-ureido-propyl)-amide; 1-benzyl-5-hydroxy-2-oxo-3-phenyl-1,2-dihydro-[1,7]naphthyridine-6-carboxylic acid (2-acetylamino-ethyl)-amide; 1-benzyl-5-hydroxy-2-oxo-3-phenyl-1,2-dihydro-[1,7]naphthyridine-6-carboxylic acid [2-(methanesulfonyl-methyl-amino)-ethyl]-amide; 1-benzyl-5-hydroxy-2-oxo-3-phenyl-1,2-dihydro-[1,7]naphthyridine-6-carboxylic acid [2-(2,2,2-trifluoro-acetylamino)-ethyl]-amide; 1-benzyl-5-hydroxy-2-oxo-3-phenyl-1,2-dihydro-[1,7]naphthyridine-6-carboxylic acid [2-(3-ethyl-ureido)-ethyl]-amide; 1-benzyl-5-hydroxy-2-oxo-3-phenyl-1,2-dihydro-[1,7]naphthyridine-6-carboxylic acid (1H- tetrazol-5-ylmethyl)-amide; 3-[(1-benzyl-5-hydroxy-2-oxo-3-phenyl-1,2-dihydro-[1,7]naphthyridine-6-carbonyl)-amino]-2,2-dimethyl-propionic acid; 7-benzyl-4-hydroxy-8-oxo-7,8-dihydro-[2,7]naphthyridine-3-carboxylic acid [2-(formyl-methyl-amino)-ethyl]-amide; 7-benzyl-4-hydroxy-8-oxo-7,8-dihydro-[2,7]naphthyridine-3-carboxylic acid [2-(acetyl-methyl-amino)-ethyl]-amide; 1-benzyl-5-hydroxy-2-oxo-3-phenyl-1,2-dihydro-[1,7]naphthyridine-6-carboxylic acid (2-formylamino-ethyl)-amide; 3-[(1-benzyl-5-hydroxy-2-oxo-3-phenyl-8-pyridin-3-yl-1,2-dihydro-[1,7]naphthyridine-6-carbonyl)-amino]-propionic acid; 3-[(1-benzyl-5-hydroxy-2-oxo-3,8-diphenyl-1,2-dihydro-[1,7]naphthyridine-6-carbonyl)-amino]-propionic acid; 3-[(1-benzyl-5-hydroxy-8-methyl-2-oxo-3-phenyl-1,2-dihydro-[1,7]naphthyridine-6-carbonyl)-amino]-propionic acid; 3-[(1-benzyl-5-hydroxy-2-oxo-3-phenyl-1,2,3,4-tetrahydro-[1,7]naphthyridine-6-carbonyl)-amino]-propionic acid; 3-[(1-benzyl-5-hydroxy-2-oxo-1,2-dihydro-[1,7]naphthyridine-6-carbonyl)-amino]-propionic acid; 3-[(1-benzyl-5-hydroxy-2-oxo-3-phenethyl-1,2-dihydro-[1,7]naphthyridine-6-carbonyl)-amino]-propionic acid; 3-[(1-benzyl-5-hydroxy-2-oxo-3-pyridin-3-yl-1,2-dihydro-[1,7]naphthyridine-6-carbonyl)-amino]-propionic acid; 3-[(1-benzyl-5-hydroxy-2-oxo-3-pyridin-2-yl-1,2-dihydro-[1,7]naphthyridine-6-carbonyl)-amino]-propionic acid; 4-[(1-benzyl-5-hydroxy-2-oxo-3-phenyl-1,2-dihydro-[1,7]naphthyridine-6-carbonyl)-amino]-butyric acid; 3-[(1-benzyl-5-hydroxy-3-methyl-2-oxo-1,2-dihydro-[1,7]naphthyridine-6-carbonyl)-amino]-propionic acid; 3-[(1-benzyl-5-hydroxy-2-oxo-3-thiophen-2-yl-1,2-dihydro-[1,7]naphthyridine-6-carbonyl)-amino]-propionic acid; 7-benzyl-1-cyano-4-hydroxy-8-oxo-7,8-dihydro-[2,7]naphthyridine-3-carboxylic acid methylamide; 7-benzyl-1-cyano-4-hydroxy-8-oxo-7,8-dihydro-[2,7]naphthyridine-3-carboxylic acid cyclopropylamide; 1-benzyl-8-cyano-5-hydroxy-2-oxo-3-phenyl-1,2-dihydro-[1,7]naphthyridine-6-carboxylic acid methylamide; 3-[(1-benzyl-5-hydroxy-2-oxo-3-pyridin-4-yl-1,2-dihydro-[1,7]naphthyridine-6-carbonyl)-amino]-propionic acid; 1-benzyl-5-hydroxy-2-oxo-3-phenyl-1,2-dihydro-[1,7]naphthyridine-6-carboxylic acid (2-methanesulfonylamino-ethyl)-amide; 1-benzyl-8-cyano-5-hydroxy-2-oxo-3-phenyl-1,2-dihydro-[1,7]naphthyridine-6-carboxylic acid [2-(methanesulfonyl-methyl-amino)-ethyl]-amide; 1-benzyl-5-hydroxy-8-methyl-2-oxo-3-phenyl-1,2-dihydro-[1,7]naphthyridine-6-carboxylic acid [2-(methanesulfonyl-methyl-amino)-ethyl]-amide; 1-benzyl-5-hydroxy-2-oxo-3,8-diphenyl-1,2-dihydro-[1,7]naphthyridine-6-carboxylic acid [2-(methanesulfonyl-methyl-amino)-ethyl]-amide; 1-benzyl-5-hydroxy-2-oxo-3-phenyl-8-pyridin-3-yl-1,2-dihydro-[1,7]naphthyridine-6-carboxylic acid [2-(methanesulfonyl-methyl-amino)-ethyl]-amide; 3-[(5-hydroxy-2-oxo-1-phenethyl-3-phenyl-1,2-dihydro-[1,7]naphthyridine-6-carbonyl)-amino]-propionic acid; 3-[(5-hydroxy-2-oxo-1,3-diphenyl-1,2-dihydro-[1,7]naphthyridine-6-carbonyl)-amino]-propionic acid; 3-[(3-benzyl-5-hydroxy-2-oxo-1-phenyl-1,2-dihydro-[1,7]naphthyridine-6-carbonyl)-amino]-propionic acid; 3-[(5-hydroxy-1-methyl-2-oxo-3-phenyl-1,2-dihydro-[1,7]naphthyridine-6-carbonyl)-amino]-propionic acid; 3-{[1-benzyl-3-(4-cyano-phenyl)-5-hydroxy-2-oxo-1,2-dihydro-[1,7]naphthyridine-6-carbonyl]-amino}-propionic acid; 3-{[1-benzyl-5-hydroxy-3-(4-methoxy-phenyl)-2-oxo-1,2-dihydro-[1,7]naphthyridine-6-carbonyl]-amino}-propionic acid; 3-[(1-benzyl-5-hydroxy-2-oxo-3-thiazol-2-yl-1,2-dihydro-[1,7]naphthyridine-6-carbonyl)-amino]-propionic acid; (R)-3-[(1-benzyl-5-hydroxy-2-oxo-3-phenyl-1,2-dihydro-[1,7]naphthyridine-6-carbonyl)-amino]-butyric acid; 3-{[5-hydroxy-1-(4-methoxy-benzyl)-2-oxo-3-phenyl-1,2-dihydro-[1,7]naphthyridine-6-carbonyl]-amino}-propionic acid; 3-{[1-(4-cyano-benzyl)-5-hydroxy-2-oxo-3-phenyl-1,2-dihydro-[1,7]naphthyridine-6-carbonyl]-amino}-propionic acid; 3-[(1-benzyl-5-hydroxy-2-oxo-3-pyrazin-2-yl-1,2-dihydro-[1,7]naphthyridine-6-carbonyl)-amino]-propionic acid; 3-{[1-benzyl-5-hydroxy-3-(4-methanesulfonyl-phenyl)-2-oxo-1,2-dihydro-[1,7]naphthyridine-6-carbonyl]-amino}-propionic acid; 3-{[1-benzyl-5-hydroxy-2-oxo-3-(3-trifluoromethyl-phenyl)-1,2-dihydro-[1,7]naphthyridine-6-carbonyl]-amino}-propionic acid; 3-{[1-benzyl-5-hydroxy-3-(4-morpholin-4-yl-phenyl)-2-oxo-1,2-dihydro-[1,7]naphthyridine-6-carbonyl]-amino}-propionic acid; 3-[(3-benzo[1,2,5]oxadiazol-5-yl-1-benzyl-5-hydroxy-2-oxo-1,2-dihydro-[1,7]naphthyridine-6-carbonyl)-amino]-propionic acid; 3-{[1-benzyl-3-(5-fluoro-2-methoxy-phenyl)-5-hydroxy-2-oxo-1,2-dihydro-[1,7]naphthyridine-6-carbonyl]-amino}-propionic acid; 3-{[1-benzyl-5-hydroxy-2-oxo-3-(4-trifluoromethoxy-phenyl)-1,2-dihydro-[1,7]naphthyridine-6-carbonyl]-amino}-propionic acid; (R)-2-[(1-benzyl-5-hydroxy-2-oxo-3-phenyl-1,2-dihydro-[1,7]naphthyridine-6-carbonyl)-amino]-3-phenyl-propionic acid; 3-{[1-benzyl-5-hydroxy-3-(1-methyl-1h-pyrazol-4-yl)-2-oxo-1,2-dihydro-[1,7]naphthyridine-6-carbonyl]-amino}-propionic acid; 3-[(1-benzyl-5-hydroxy-2-oxo-3-pyrimidin-5-yl-1,2-dihydro-[1,7]naphthyridine-6-carbonyl)-amino]-propionic acid; 3-{[1-benzyl-3-(2-dimethylamino-pyrimidin-5-yl)-5-hydroxy-2-oxo-1,2-dihydro-[1,7]naphthyridine-6-carbonyl]-amino}-propionic acid; 3-[(1-cyclohexylmethyl-5-hydroxy-2-oxo-3-phenyl-1,2-dihydro-[1,7]naphthyridine-6-carbonyl)-amino]-propionic acid; 3-{[5-hydroxy-2-oxo-3-phenyl-1-(tetrahydro-pyran-4-ylmethyl)-1,2-dihydro-[1,7]naphthyridine-6-carbonyl]-amino}-propionic acid; 3-[(5-hydroxy-2-oxo-3-phenyl-1-thiazol-2-ylmethyl-1,2-dihydro-[1,7]naphthyridine-6-carbonyl)-amino]-propionic acid; 3-[(1-benzyl-5-hydroxy-2-oxo-3-phenyl-8-pyrimidin-5-yl-1,2-dihydro-[1,7]naphthyridine-6-carbonyl)-amino]-propionic acid; 3-[(1-benzyl-5-hydroxy-2-oxo-3-phenyl-8-pyrazin-2-yl-1,2-dihydro-[1,7]naphthyridine-6-carbonyl)-amino]-propionic acid; 5-[(1-benzyl-5-hydroxy-2-oxo-3-phenyl-1,2-dihydro-[1,7]naphthyridine-6-carbonyl)-amino]-pentanoic acid; 4-[(1-benzyl-5-hydroxy-2-oxo-3-phenyl-8-pyridin-3-yl-1,2-dihydro-[1,7]naphthyridine-6-carbonyl)-amino]-butyric acid; 5-[(1-benzyl-5-hydroxy-2-oxo-3-phenyl-8-pyridin-3-yl-1,2-dihydro-[1,7]naphthyridine-6-carbonyl)-amino]-pentanoic acid; 3-[(5-hydroxy-2-oxo-1,3-diphenyl-8-pyridin-3-yl-1,2-dihydro-[1,7]naphthyridine-6-carbonyl)-amino]-propionic acid; 3-[(5-hydroxy-1-methyl-2-oxo-3-phenyl-8-pyridin-3-yl-1,2-dihydro-[1,7]naphthyridine-6-carbonyl)-amino]-propionic acid; 3-[(5-hydroxy-2-oxo-1-phenethyl-3-phenyl-8-pyridin-3-yl-1,2-dihydro-[1,7]naphthyridine-6-carbonyl)-amino]-propionic acid; 3-[(1-benzyl-5-hydroxy-2-oxo-3-phenyl-8-pyridin-4-yl-1,2-dihydro-[1,7]naphthyridine-6-carbonyl)-amino]-propionic acid; 3-[(1-benzyl-5-hydroxy-2-oxo-3,8-di-pyridin-3-yl-1,2-dihydro-[1,7]naphthyridine-6-carbonyl)-amino]-propionic acid; (R)-3-{[5-hydroxy-2-oxo-3-phenyl-1-(1-phenyl-ethyl)-1,2-dihydro-[1,7]naphthyridine-6-carbonyl]-amino}-propionic acid; (R)-4-{[5-hydroxy-2-oxo-3-phenyl-1-(1-phenyl-ethyl)-1,2-dihydro-[1,7]naphthyridine-6-carbonyl]-amino}-butyric acid; 3-{[1-benzyl-5-hydroxy-8-(5-methoxy-pyridin-3-yl)-2-oxo-3-phenyl-1,2-dihydro-[1,7]naphthyridine-6-carbonyl]-amino}-propionic acid; 3-{[1-benzyl-8-(5-chloro-pyridin-3-yl)-5-hydroxy-2-oxo-3-phenyl-1,2-dihydro-[1,7]naphthyridine-6-carbonyl]-amino}-propionic acid; (S)-3-{[5-hydroxy-2-oxo-3-phenyl-1-(1-phenylethyl)-1,2-dihydro-[1,7]naphthyridine-6-carbonyl]-amino}-propionic acid; (S)-4-{[5-hydroxy-2-oxo-3-phenyl-1-(1-phenyl-ethyl)-1,2-dihydro-[1,7]naphthyridine-6-carbonyl]-amino}-butyric acid; (S)-3-{[5-hydroxy-2-oxo-3-phenyl-1-(1-phenyl-ethyl)-8-pyridin-3-yl-1,2-dihydro-[1,7]naphthyridine-6-carbonyl]-amino}-propionic acid; (R)-3-{[5-hydroxy-2-oxo-3-phenyl-1-(1-phenyl-ethyl)-8-pyridin-3-yl-1,2-dihydro-[1,7]naphthyridine-6-carbonyl]-amino}-propionic acid; 3-{[1-benzyl-8-(5-fluoro-pyridin-3-yl)-5-hydroxy-2-oxo-3-phenyl-1,2-dihydro-[1,7]naphthyridine-6-carbonyl]-amino}-propionic acid; 3-{[1-benzyl-5-hydroxy-8-(2-methyl-pyridin-3-yl)-2-oxo-3-phenyl-1,2-dihydro-[1,7]naphthyridine-6-carbonyl]-amino}-propionic acid; 3-{[1-benzyl-5-hydroxy-8-(6-methyl-pyridin-3-yl)-2-oxo-3-phenyl-1,2-dihydro-[1,7]naphthyridine-6-carbonyl]-amino}-propionic acid; 3-{[1-benzyl-5-hydroxy-2-oxo-3-phenyl-8-(6-trifluoromethyl-pyridin-3-yl)-1,2-dihydro-[1,7]naphthyridine-6-carbonyl]-amino}-propionic acid; 3-{[1-benzyl-5-hydroxy-8-(6-methoxy-pyridin-3-yl)-2-oxo-3-phenyl-1,2-dihydro-[1,7]naphthyridine-6-carbonyl]-amino}-propionic acid; 3-{[5-hydroxy-2-oxo-3-phenyl-8-pyridin-3-yl-1-(tetrahydro-pyran-4-ylmethyl)-1,2-dihydro-[1,7]naphthyridine-6-carbonyl]-amino}-propionic acid; 3-[(1-cyclohexylmethyl-5-hydroxy-2-oxo-3-phenyl-8-pyridin-3-yl-1,2-dihydro-[1,7]naphthyridine-6-carbonyl)-amino]-propionic acid; 4-[(1-cyclohexylmethyl-5-hydroxy-2-oxo-3-phenyl-1,2-dihydro-[1,7]naphthyridine-6-carbonyl)-amino]-butyric acid; 3-{[1-benzyl-5-hydroxy-3-(4-methoxy-phenyl)-2-oxo-8-pyridin-3-yl-1,2-dihydro-[1,7]naphthyridine-6-carbonyl]-amino}-propionic acid; 4-{[1-benzyl-5-hydroxy-3-(4-methoxy-phenyl)-2-oxo-1,2-dihydro-[1,7]naphthyridine-6-carbonyl]-amino}-butyric acid; 3-{[1-benzyl-5-hydroxy-3-(3-methoxy-phenyl)-2-oxo-1,2-dihydro-[1,7]naphthyridine-6-carbonyl]-amino}-propionic acid; 4-{[1-benzyl-5-hydroxy-3-(3-methoxy-phenyl)-2-oxo-1,2-dihydro-[1,7]naphthyridine-6-carbonyl]-amino}-butyric acid; 1-[(1-benzyl-5-hydroxy-2-oxo-3-phenyl-1,2-dihydro-[1,7]naphthyridine-6-carbonyl)-amino]-cyclopropanecarboxylic acid; 1-[(1-benzyl-5-hydroxy-2-oxo-3-phenyl-8-pyridin-3-yl-1,2-dihydro-[1,7]naphthyridine-6-carbonyl)-amino]-cyclopropanecarboxylic acid; 3-[(1-benzyl-5-hydroxy-2-oxo-3-phenyl-8-pyridin-3-yl-1,2-dihydro-[1,7]naphthyridine-6-carbonyl)-amino]-2,2-dimethyl-propionic acid; 3-{[1-benzyl-8-(2-ethoxy-pyrimidin-5-yl)-5-hydroxy-2-oxo-3-phenyl-1,2-dihydro-[1,7]naphthyridine-6-carbonyl]-amino}-propionic acid; 3-[(1-benzyl-5-hydroxy-2-oxo-3-phenyl-8-pyridin-2-yl-1,2-dihydro-[1,7]naphthyridine-6-carbonyl)-amino]-propionic acid; 3-[(1-benzyl-5-hydroxy-2-oxo-3-phenyl-8-pyridazin-4-yl-1,2-dihydro-[1,7]naphthyridine-6-carbonyl)-amino]-propionic acid; 3-[(1-benzyl-5-hydroxy-2-oxo-3-phenyl-8-thiazol-2-yl-1,2-dihydro-[1,7]naphthyridine-6-carbonyl)-amino]-propionic acid; 7-benzyl-4-hydroxy-8-oxo-7,8-dihydro-[2,7]naphthyridine-3-carboxylic acid (3-formylamino-propyl)-amide; 7-benzyl-4-hydroxy-8-oxo-7,8-dihydro-[2,7]naphthyridine-3-carboxylic acid (3-acetylamino-propyl)-amide; 3-[(1-cyclohexylmethyl-5-hydroxy-2-oxo-3-phenyl-8-pyridin-4-yl-1,2-dihydro-[1,7]naphthyridine-6-carbonyl)-amino]-propionic acid; 3-[(5-hydroxy-2-oxo-1,3-diphenyl-8-pyridin-4-yl-1,2-dihydro-[1,7]naphthyridine-6-carbonyl)-amino]-propionic acid; 3-{[1-benzyl-5-hydroxy-8-(1-methyl-1h-pyrazol-4-yl)-2-oxo-3-phenyl-1,2-dihydro-[1,7]naphthyridine-6-carbonyl]-amino}-propionic acid; 3-[(1-benzyl-5-hydroxy-2-oxo-3-phenyl-8-thiazol-5-yl-1,2-dihydro-[1,7]naphthyridine-6-carbonyl]-amino]-propionic acid; 3-[(1-benzyl-5-hydroxy-2-oxo-3-phenyl-8-thiazol-4-yl-1,2-dihydro-[1,7]naphthyridine-6-carbonyl)-amino]-propionic acid; 3-[(1-benzyl-5-hydroxy-2-oxo-3-phenyl-8-pyridazin-3-yl-1,2-dihydro-[1,7]naphthyridine-6-carbonyl)-amino]-propionic acid; 3-[(1-benzyl-5-hydroxy-2-oxo-3-phenethyl-8-pyridin-3-yl-1,2-dihydro-[1,7]naphthyridine-6-carbonyl)-amino]-propionic acid; 3-[(1,3-dibenzyl-5-hydroxy-2-oxo-1,2-dihydro-[1,7]naphthyridine-6-carbonyl)-amino]-propionic acid; 3-[(7-benzyl-4-hydroxy-8-oxo-1-pyridin-3-yl-7,8-dihydro-[2,7]naphthyridine-3-carbonyl)-amino]-propionic acid; 3-{[1-cyclohexylmethyl-8-(2-ethoxy-pyrimidin-5-yl)-5-hydroxy-2-oxo-3-phenyl-1,2-dihydro-[1,7]naphthyridine-6-carbonyl]-amino}-propionic acid; 3-{[1-benzyl-5-hydroxy-8-(2-methylsulfanyl-pyrimidin-5-yl)-2-oxo-3-phenyl-1,2-dihydro-[1,7]naphthyridine-6-carbonyl]-amino}-propionic acid; 3-{[1-benzyl-5-hydroxy-2-oxo-3-(4-trifluoromethyl-phenyl)-1,2-dihydro-[1,7]naphthyridine-6-carbonyl]-amino}-propionic acid; 3-{[1-benzyl-5-hydroxy-2-oxo-3-(2-trifluoromethyl-phenyl)-1,2-dihydro-[1,7]naphthyridine-6-carbonyl]-amino}-propionic acid; 4-{[1-benzyl-5-hydroxy-2-oxo-3-(4-trifluoromethyl-phenyl)-1,2-dihydro-[1,7]naphthyridine-6-carbonyl]-amino}-butyric acid; 4-{[1-benzyl-5-hydroxy-2-oxo-3-(3-trifluoromethyl-phenyl)-1,2-dihydro-[1,7]naphthyridine-6-carbonyl]-amino}-butyric acid; 4-{[1-benzyl-5-hydroxy-2-oxo-3-(2-trifluoromethyl-phenyl)-1,2-dihydro-[1,7]naphthyridine-6-carbonyl]-amino}-butyric acid; 3-{[1-benzyl-5-hydroxy-2-oxo-8-pyridin-3-yl-3-(4-trifluoromethyl-phenyl)-1,2-dihydro-[1,7]naphthyridine-6-carbonyl]-amino}-propionic acid; 3-{[1-benzyl-5-hydroxy-2-oxo-8-pyridin-3-yl-3-(3-trifluoromethyl-phenyl)-1,2-dihydro-[1,7]naphthyridine-6-carbonyl]-amino}-propionic acid; 3-{[1-benzyl-5-hydroxy-2-oxo-8-pyridin-3-yl-3-(2-trifluoromethyl-phenyl)-1,2-dihydro-[1,7]naphthyridine-6-carbonyl]-amino}-propionic acid; 3-[(1-cyclopentylmethyl-5-hydroxy-2-oxo-3-phenyl-1,2-dihydro-[1,7]naphthyridine-6-carbonyl)-amino]-propionic acid; 4-[(1-cyclopentylmethyl-5-hydroxy-2-oxo-3-phenyl-1,2-dihydro-[1,7]naphthyridine-6-carbonyl)-amino]-butyric acid; 3-[(1-cyclopentylmethyl-5-hydroxy-2-oxo-3-phenyl-8-pyridin-3-yl-1,2-dihydro-[1,7]naphthyridine-6-carbonyl)-amino]-propionic acid; 1-[(7-benzyl-4-hydroxy-8-oxo-7,8-dihydro-[2,7]naphthyridine-3-carbonyl)-amino]-cyclopropanecarboxylic acid; 3-{[1-(2-ethyl-butyl)-5-hydroxy-2-oxo-3-phenyl-1,2-dihydro-[1,7]naphthyridine-6-carbonyl]-amino}-propionic acid; 4-{[1-(2-ethyl-butyl)-5-hydroxy-2-oxo-3-phenyl-1,2-dihydro-[1,7]naphthyridine-6-carbonyl]-amino}-butyric acid; 3-{[1-(2-ethyl-butyl)-5-hydroxy-2-oxo-3-phenyl-8-pyridin-3-yl-1,2-dihydro-[1,7]naphthyridine-6-carbonyl]-amino}-propionic acid; 3-{[1-(2-ethyl-butyl)-5-hydroxy-2-oxo-3-phenyl-8-pyridin-4-yl-1,2-dihydro-[1,7]naphthyridine-6-carbonyl]-amino}-propionic acid; 3-{[(1-benzyl-5-hydroxy-2-oxo-3-phenyl-1,2-dihydro-[1,7]naphthyridine-6-carbonyl)-amino]-methyl}-benzoic acid; and {1-[(1-benzyl-5-hydroxy-2-oxo-3-phenyl-8-pyridin-3-yl-1,2-dihydro-[1,7]naphthyridine-6-carbonyl)-amino]-cyclopropyl}-acetic acid; or a pharmaceutically acceptable salt, single stereoisomer, mixture of stereoisomers, ester, tautomer, or prodrug thereof.

25. The method of claim 1, wherein the compound is administered in a pharmaceutical composition further comprising at least one additional therapeutic agent selected from the group consisting of vitamin B 12, folic acid, ferrous sulfate, recombinant human erythropoietin, and an erythropoiesis stimulating agent (ESA).

26. A method of inhibiting the activity of a HIF hydroxylase, the method comprising bringing into contact the HIF hydroxylase and an inhibitory-effective amount of a compound of Formula Ia:

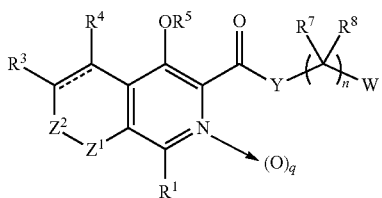

Ia wherein
q is 0 or 1;
R¹ is selected from the group consisting of hydrogen, cyano, halo, hydroxy, alkoxy, amino, acyloxy, aminoacyl, alkyl, cycloalkyl, cycloalkoxy, aryl, aryloxy, heterocycloalkyl, heteroaryloxy, and heteroaryl;
one of $Z^1$ or $Z^2$ is —$NR^2$— and the other of $Z^1$ or $Z^2$ is —C(O)—;
$R^2$ is selected from the group consisting of hydrogen, alkyl, cycloalkyl, aryl, heterocycloalkyl, and heteroaryl;
$R^3$ and $R^4$ are each independently selected from the group consisting of hydrogen, alkyl, alkoxy, amino, acyloxy, aminoacyl, cycloalkyl, cycloalkoxy, aryl, aryloxy, heterocycloalkyl, heteroaryloxy, and heteroaryl;
— is a single or a double bond;
Y is —$NR^6$— or —O—;
n is 1, 2, 3, 4, 5, or 6;
$R^5$ is selected from the group consisting of hydrogen, acyl, sulfonyl, aminoacyl, oxycarbonyl, alkyl, cycloalkyl, aryl, heterocycloalkyl, and heteroaryl;
$R^6$ is selected from the group consisting of hydrogen, alkyl, cycloalkyl, aryl, heterocycloalkyl, and heteroaryl;
$R^7$ and $R^8$ are each independently selected from the group consisting of hydrogen, alkyl, cycloalkyl, aryl, heterocycloalkyl, and heteroaryl; or $R^7$ and $R^8$ together with the carbon atom to which they are attached form a cycloalkyl, or heterocycloalkyl;
W is selected from the group consisting of $R^9$, —C(O)$OR^9$, —C(O)$NR^6R^9$, —$NR^6$C(O)$R^9$, —$NR^6$C(O)$OR^9$, —$NR^6$C(O)$NR^6R^9$, —$NR^6$S(O)$_2R^9$, —S(O)$_2NR^6R^9$, —$NR^6R^9$ and —$OR^9$; and
$R^9$ is selected from the group consisting of hydrogen, alkyl, cycloalkyl, aryl, heterocycloalkyl, and heteroaryl; and
further wherein each alkyl, alkoxy, amino, acyloxy, aminoacyl, cycloalkyl, cycloalkoxy, aryl, aryloxy, heterocycloalkyl, heteroaryloxy, and heteroaryl described above for $R^1$, $R^2$, $R^3$, $R^4$, $R^6$, $R^7$, $R^8$ and $R^9$ can be optionally substituted with from 1 to 3 $R^{10}$,
wherein each $R^{10}$ is independently selected from the group consisting of alkyl, alkoxy, haloalkyl, haloalkoxy, acyl, acylamino, acyloxy, amino, aminoacyl, aminocarbonylamino, aminothiocarbonylamino, aminocarbonyloxy, aryl, aryloxy, aryloxyaryl, cyano, halogen, hydroxyl, nitro, oxo, thioxo, carboxyl, carboxyl ester, cycloalkyl, thio, alkylthio, arylthio, cycloalkylthio, heteroarylthio, heterocyclicthio, sulfonyl, heteroaryl, heterocyclic, cycloalkoxy, heteroaryloxy, heterocyclyloxy, oxycarbonylamino, oxythiocarbonylamino, —OS(O)$_2$-alkyl, —OS(O)$_2$-aryl, —OS(O)$_2$-heteroaryl, —OS(O)$_2$-heterocyclic, —OSO$_2$—$NR^{40}R^{40}$, —$NR^{40}$S(O)$_2$—$NR^{40}$-alkyl, —$NR^{40}$S(O)$_2$—$NR^{40}$-aryl, —$NR^{40}$S(O)$_2$—$NR^{40}$-heteroaryl, and —$NR^{40}$S(O)$_2$—$NR^{40}$-heterocyclic, where each $R^{40}$ is independently hydrogen or alkyl; and further wherein each alkyl, alkoxy, aryl, aryloxy, aryloxyaryl, cycloalkyl, alkylthio, arylthio, cycloalkylthio, heteroarylthio, heterocyclicthio, heteroaryl, heterocyclic, cycloalkoxy, heteroaryloxy, or heterocyclyloxy may be additionally substituted with from 1-3 substituents independently alkyl, alkoxy, haloalkyl, haloalkoxy, or halogen;
or a pharmaceutically acceptable salt, single stereoisomer, mixture of stereoisomers, ester, tautomer or prodrug thereof.

27. The method of claim 26, wherein the HIF hydroxylase enzyme is an asparaginyl hydroxylase.

28. The method of claim 27, wherein the asparaginyl hydroxylase is factor inhibiting HIF.

29. The method of claim 26, wherein the HIF hydroxylase enzyme is a prolyl hydroxylase.

30. The method of claim 29, wherein the prolyl hydroxylase is selected from the group consisting of human EGLN1, EGLN2, and EGLN3.

* * * * *